US011697814B2

(12) United States Patent
Collard et al.

(10) Patent No.: US 11,697,814 B2
(45) Date of Patent: Jul. 11, 2023

(54) TREATMENT OF TUMOR SUPPRESSOR GENE RELATED DISEASES BY INHIBITION OF NATURAL ANTISENSE TRANSCRIPT TO THE GENE

(71) Applicant: CuRNA, Inc., Miami, FL (US)

(72) Inventors: Joseph Collard, Delray Beach, FL (US); Olga Khorkova Sherman, Tequesta, FL (US)

(73) Assignee: CuRNA, Inc., Miami, FL (US)

( * ) Notice: Subject to any disclaimer, the term of this patent is extended or adjusted under 35 U.S.C. 154(b) by 0 days.

(21) Appl. No.: 16/437,224

(22) Filed: Jun. 11, 2019

(65) Prior Publication Data

US 2019/0309303 A1 Oct. 10, 2019

Related U.S. Application Data

(60) Division of application No. 14/533,371, filed on Nov. 5, 2014, now Pat. No. 10,358,646, which is a continuation of application No. 13/133,039, filed as application No. PCT/US2009/066654 on Dec. 3, 2009, now abandoned.

(60) Provisional application No. 61/166,381, filed on Apr. 3, 2009, provisional application No. 61/157,249, filed on Mar. 4, 2009, provisional application No. 61/154,594, filed on Feb. 23, 2009, provisional application No. 61/119,973, filed on Dec. 4, 2008.

(51) Int. Cl.

| | |
|---|---|
| ***C12N 15/11*** | (2006.01) |
| ***C12N 15/113*** | (2010.01) |
| ***A61K 31/712*** | (2006.01) |
| ***C12Q 1/6886*** | (2018.01) |

(52) U.S. Cl.

CPC ........ *C12N 15/1137* (2013.01); *A61K 31/712* (2013.01); *C12N 15/1135* (2013.01); *C12Q 1/6886* (2013.01); *C12N 2310/11* (2013.01); *C12N 2310/14* (2013.01); *C12N 2310/315* (2013.01); *C12Q 2600/158* (2013.01)

(58) Field of Classification Search

CPC .......... C12N 15/1137; C12N 2310/315; C12N 2310/11; A61K 31/712; C12Q 1/6886

See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,754,065 | A | 6/1988 | Levenson et al. |
| 4,800,159 | A | 1/1989 | Mullis et al. |
| 5,034,506 | A | 7/1991 | Summerton et al. |
| 5,138,045 | A | 8/1992 | Cook et al. |
| 5,218,105 | A | 6/1993 | Cook et al. |
| 5,288,512 | A | 2/1994 | Seiden |
| 5,288,514 | A | 2/1994 | Ellman |
| 5,319,080 | A | 6/1994 | Leumann |
| 5,393,878 | A | 2/1995 | Leumann |
| 5,432,272 | A | 7/1995 | Benner |
| 5,457,189 | A | 10/1995 | Crooke et al. |
| 5,459,255 | A | 10/1995 | Cook et al. |
| 5,474,796 | A | 12/1995 | Brennan |
| 5,491,084 | A | 2/1996 | Chalfie et al. |
| 5,506,337 | A | 4/1996 | Summerton et al. |
| 5,519,134 | A | 5/1996 | Acevedo et al. |
| 5,525,735 | A | 6/1996 | Gallop et al. |
| 5,539,083 | A | 7/1996 | Cook et al. |
| 5,549,974 | A | 8/1996 | Holmes |
| 5,569,588 | A | 10/1996 | Ashby et al. |
| 5,576,302 | A | 11/1996 | Cook et al. |
| 5,593,853 | A | 1/1997 | Chen et al. |
| 5,605,662 | A | 2/1997 | Heller et al. |
| 5,661,134 | A | 8/1997 | Cook et al. |
| 5,708,161 | A | 1/1998 | Reese |
| 5,739,119 | A | 4/1998 | Galli et al. |
| 5,739,311 | A | 4/1998 | Lackey et al. |
| 5,756,710 | A | 5/1998 | Stein et al. |
| 5,849,902 | A | 12/1998 | Arrow et al. |
| 5,891,725 | A | 4/1999 | Soreq et al. |
| 5,902,880 | A | 5/1999 | Thompson |
| 5,908,779 | A | 6/1999 | Carmichael et al. |
| 5,965,721 | A | 10/1999 | Cook et al. |
| 5,985,663 | A | 11/1999 | Bennett et al. |
| 6,005,095 | A | 12/1999 | Capaccioli et al. |
| 6,013,639 | A | 1/2000 | Peyman et al. |
| 6,013,786 | A | 1/2000 | Chen et al. |

(Continued)

FOREIGN PATENT DOCUMENTS

| | | |
|---|---|---|
| CA | 2686933 | 4/2008 |
| CA | 2686933 A1 | 10/2008 |

(Continued)

OTHER PUBLICATIONS

Machine translation of WO 03/025177 A2, 2003, pp. 1-6 (Year: 2003).*

Barak, et al., "A β-Arrestin/Green Fluorescent Protein Biosensor for Detecting G Protein-Coupled Receptor Activation," J. Biol. Chem. 272:27497-27500 (1997).

Boutla, A., et al., "Short 5'-phosphorylated double-stranded RNAs induce RNA interference in *Drosophila*," Curr. Biol. 11:1776-1780 (2001).

Boyd-Kimball, et al., "Proteomic Identification of Proteins Specifically Oxidized by Intracerebral Injection of Amyloid β-Peptide (1-42) into Rat Brain: Implications for Alzheimer's Disease," Neuroscience 132, 313-324 (2005).

(Continued)

*Primary Examiner* — Ekaterina Poliakova-Georgantas

(74) *Attorney, Agent, or Firm* — Goodwin Procter LLP

(57) ABSTRACT

The present invention relates to antisense oligonucleotides that modulate the expression of and/or function of Tumor Suppressor genes, in particular, by targeting natural antisense polynucleotides of Tumor Suppressor genes. The invention also relates to the identification of these antisense oligonucleotides and their use in treating diseases and disorders associated with the expression of Tumor Suppressor genes.

14 Claims, 88 Drawing Sheets

Specification includes a Sequence Listing.

(56) References Cited

U.S. PATENT DOCUMENTS 6,034,233 A 3/2000 Ecker et al.
6,100,090 A 8/2000 Monia et al.
6,140,492 A 10/2000 Morelli et al.
6,147,200 A 11/2000 Manoharan et al.
6,165,712 A 12/2000 Foulkes et al.
6,165,990 A 12/2000 Singh et al.
6,175,409 B1 1/2001 Nielsen et al.
6,221,587 B1 4/2001 Ecker et al.
6,239,265 B1 5/2001 Cook
6,242,589 B1 6/2001 Cook et al.
6,268,490 B1 7/2001 Imanishi et al.
6,303,374 B1 10/2001 Zhang et al.
6,307,040 B1 10/2001 Cook et al.
6,316,198 B1 11/2001 Skouv et al.
6,335,434 B1 1/2002 Guzaev et al.
6,376,541 B1 4/2002 Nixon et al.
6,403,566 B1 6/2002 Wang
6,444,464 B1 9/2002 Wyatt
6,451,991 B1 9/2002 Martin et al.
6,525,191 B1 2/2003 Ramasamy
6,528,262 B1 3/2003 Gilad et al.
6,528,631 B1 3/2003 Cook et al.
6,617,122 B1 9/2003 Hayden et al.
6,617,442 B1 9/2003 Crooke et al.
6,630,315 B1 10/2003 Miwa et al.
6,639,059 B1 10/2003 Kochkine et al.
6,656,730 B1 12/2003 Manoharan
6,667,337 B2 12/2003 Wilson
6,670,461 B1 12/2003 Wengel et al.
6,710,174 B2 3/2004 Bennett et al.
6,734,291 B2 5/2004 Kochkine et al.
6,762,169 B1 7/2004 Manoharan
6,794,499 B2 9/2004 Wengel et al.
6,833,361 B2 12/2004 Hong et al.
6,861,514 B2 3/2005 Cook et al.
6,867,294 B1 3/2005 Sanghvi et al.
6,936,467 B2 8/2005 Kmiec et al.
6,936,593 B1 8/2005 Agrawal et al.
6,977,295 B2 12/2005 Belotserkovskii et al.
6,986,988 B2 1/2006 Gilad et al.
7,034,133 B2 4/2006 Wengel et al.
7,034,145 B2 4/2006 Shen et al.
7,053,195 B1 5/2006 Goff
7,053,199 B2 5/2006 Imanishi et al.
7,053,207 B2 5/2006 Wengel
7,060,809 B2 6/2006 Wengel et al.
7,084,125 B2 8/2006 Wengel
7,087,589 B2 8/2006 Jacobson et al.
7,125,982 B1 10/2006 Frayne
7,144,995 B2 12/2006 Wise et al.
7,144,999 B2 12/2006 Ward et al.
7,148,204 B2 12/2006 Bennett et al.
7,153,954 B2 12/2006 Koch et al.
7,169,916 B2 1/2007 Krotz et al.
7,199,107 B2 4/2007 Dobie et al.
7,202,357 B2 4/2007 Crooke et al.
7,217,572 B2 5/2007 Ward et al.
7,220,549 B2 5/2007 Buzby
7,226,785 B2 6/2007 Kmiec et al.
7,229,974 B2 6/2007 Peyman et al.
7,229,976 B2 6/2007 Dobie et al.
7,235,534 B2 6/2007 Tanguay et al.
7,235,653 B2 6/2007 Bennett et al.
7,238,858 B2 7/2007 Marraccini et al.
7,276,599 B2 10/2007 Moore et al.
7,285,288 B1 10/2007 Tormo et al.
7,297,786 B2 11/2007 McCray et al.
7,314,750 B2 * 1/2008 Zhou .................... C12Q 1/6883
435/287.2
7,314,923 B2 1/2008 Kaneko et al.
7,320,965 B2 1/2008 Sah et al.
7,321,828 B2 1/2008 Cowsert et al.
7,335,764 B2 2/2008 Crooke et al.
7,335,765 B2 2/2008 Kaneko et al.
7,339,051 B2 3/2008 Crooke et al.
7,371,833 B1 5/2008 Weiss
7,399,845 B2 7/2008 Seth et al.
7,402,434 B2 7/2008 Newman et al.
7,402,574 B2 7/2008 Iversen et al.
7,420,050 B2 9/2008 Park et al.
7,423,142 B2 9/2008 Vornlocher
7,425,545 B2 9/2008 Crooke et al.
7,427,675 B2 9/2008 Capaldi et al.
7,456,154 B2 11/2008 Soreq et al.
7,462,642 B2 12/2008 Wang et al.
7,468,431 B2 12/2008 Bhanot et al.
7,510,830 B2 3/2009 Baguley et al.
7,541,344 B2 6/2009 Bhat et al.
7,547,684 B2 6/2009 Seth et al.
7,569,575 B2 8/2009 Sorensen et al.
7,569,686 B1 8/2009 Bhat et al.
7,572,582 B2 8/2009 Wengel et al.
7,582,745 B2 9/2009 Sah et al.
7,585,893 B2 9/2009 Baguley et al.
7,589,190 B2 9/2009 Westergaard et al.
7,598,227 B2 10/2009 Crooke et al.
7,605,251 B2 10/2009 Tan et al.
7,622,453 B2 11/2009 Frieden et al.
7,662,948 B2 2/2010 Kurreck et al.
7,666,854 B2 2/2010 Seth et al.
7,674,895 B2 3/2010 Reich et al.
7,687,617 B2 3/2010 Thrue et al.
7,691,995 B2 4/2010 Zamore et al.
7,695,902 B2 4/2010 Crooke
7,696,345 B2 4/2010 Allerson et al.
7,709,456 B2 5/2010 Corey et al.
7,709,630 B2 5/2010 Gaarde et al.
7,713,738 B2 5/2010 Hansen et al.
7,718,629 B2 5/2010 Bamcrot et al.
7,723,508 B2 5/2010 Crooke et al.
7,732,422 B2 6/2010 Gleave et al.
7,732,590 B2 6/2010 Bhanot et al.
7,737,264 B2 6/2010 Thrue et al.
7,737,265 B2 6/2010 Akinc et al.
7,741,305 B2 6/2010 Crooke et al.
7,741,309 B2 6/2010 Hansen et al.
7,741,457 B2 6/2010 Seth et al.
7,745,609 B2 6/2010 Bennett et al.
7,749,978 B2 7/2010 Sah et al.
10,358,646 B2 7/2019 Collard et al.
2003/0139359 A1 7/2003 Dobie
2003/0144239 A1 7/2003 Agami et al.
2003/0186920 A1 10/2003 Sirois
2003/0191075 A1 10/2003 Cook et al.
2003/0228597 A1 12/2003 Cowsert et al.
2003/0228618 A1 12/2003 Levanon et al.
2003/0233670 A1 12/2003 Edgerton et al.
2004/0006031 A1 1/2004 Dean et al.
2004/0033480 A1 2/2004 Wong
2004/0101858 A1 5/2004 Ward et al.
2004/0137423 A1 7/2004 Hayden et al.
2004/0138155 A1 7/2004 Baird et al.
2004/0161777 A1 8/2004 Baker
2004/0175803 A1 9/2004 Meritet et al.
2004/0180336 A1 9/2004 Gilad et al.
2004/0254137 A1 12/2004 Ackermann et al.
2005/0009771 A1 1/2005 Levanon et al.
2005/0026160 A1 2/2005 Allerson et al.
2005/0113326 A1 5/2005 Siwkowski et al.
2005/0143357 A1 6/2005 Pousette et al.
2005/0153286 A1 7/2005 Clements
2005/0215504 A1 9/2005 Bennett et al.
2005/0221354 A1 * 10/2005 Mounts ................ C12Q 1/6876
435/287.2
2005/0222029 A1 10/2005 Bartel et al.
2005/0246794 A1 11/2005 Khvorova et al.
2006/0009410 A1 1/2006 Crooke et al.
2006/0088825 A1 4/2006 Hayes et al.
2006/0142196 A1 6/2006 Klein et al.
2006/0178333 A1 8/2006 Soreq et al.
2007/0009899 A1 * 1/2007 Mounts ................ C12Q 1/6883
435/6.16
2007/0082848 A1 4/2007 Alitalo et al.
2007/0111963 A1 5/2007 Corey et al.

(56) References Cited

U.S. PATENT DOCUMENTS

| | | | |
|---|---|---|---|
| 2007/0197459 | A1 | 8/2007 | Milner |
| 2007/0213274 | A1 | 9/2007 | Salonen |
| 2007/0213292 | A1 | 9/2007 | Stoffel et al. |
| 2007/0231816 | A1 | 10/2007 | Chaussabel et al. |
| 2007/0248590 | A1 | 10/2007 | Milne et al. |
| 2007/0275921 | A1 | 11/2007 | Swayze |
| 2008/0146788 | A1 | 6/2008 | Bhat et al. |
| 2008/0200664 | A1 | 8/2008 | Yang et al. |
| 2008/0221051 | A1 | 9/2008 | Becker et al. |
| 2008/0293142 | A1 | 11/2008 | Liu et al. |
| 2009/0191263 | A1 | 7/2009 | Reich et al. |
| 2009/0192106 | A1 | 7/2009 | Dobie et al. |
| 2009/0208479 | A1 | 8/2009 | Jaye et al. |
| 2009/0258925 | A1 | 10/2009 | Wahlestedt |
| 2009/0318536 | A1 | 12/2009 | Freier et al. |
| 2009/0326041 | A1 | 12/2009 | Bhanot et al. |
| 2010/0105760 | A1 | 4/2010 | Collard et al. |

FOREIGN PATENT DOCUMENTS

| | | | | |
|---|---|---|---|---|
| EP | 335451 | A3 | 3/1988 | |
| EP | 335451 | A2 | 10/1989 | |
| RU | 2174409 | C2 | 10/2001 | |
| RU | 2219241 | C2 | 12/2003 | |
| RU | 2235787 | C2 | 9/2004 | |
| WO | 1984/03564 | A1 | 9/1984 | |
| WO | WO-1984/03564 | | 9/1984 | |
| WO | 1991/19735 | A1 | 12/1991 | |
| WO | WO-1991/19735 | | 12/1991 | |
| WO | 1992/00091 | A1 | 1/1992 | |
| WO | WO-1992/00091 | | 1/1992 | |
| WO | 1992/08796 | A1 | 5/1992 | |
| WO | WO-1992/08796 | | 5/1992 | |
| WO | 9320242 | | 10/1993 | |
| WO | WO-1993/20242 | | 10/1993 | |
| WO | 1994/026887 | A1 | 11/1994 | |
| WO | WO-1994-026887 | A1 | 11/1994 | |
| WO | 1994/28143 | A1 | 12/1994 | |
| WO | WO 1994/28143 | | 12/1994 | |
| WO | 1995/015373 | A2 | 6/1995 | |
| WO | WO-1995-015373 | A2 | 6/1995 | |
| WO | 1995/22618 | A1 | 8/1995 | |
| WO | WO-1995/22618 | | 8/1995 | |
| WO | 9525116 | | 9/1995 | |
| WO | WO 1995/25116 | | 10/1995 | |
| WO | 9535505 | | 12/1995 | |
| WO | WO-1995/35505 | | 12/1995 | |
| WO | 1996/027663 | A2 | 9/1996 | |
| WO | WO-1996-027663 | A2 | 9/1996 | |
| WO | 1997/000271 | A1 | 1/1997 | |
| WO | 9739120 | A2 | 10/1997 | |
| WO | WO-1997-039120 | A1 | 10/1997 | |
| WO | 9835978 | A1 | 8/1998 | |
| WO | 1999/14226 | A2 | 3/1999 | |
| WO | WO-1999-014226 | A1 | 3/1999 | |
| WO | 1999/039352 | A1 | 8/1999 | |
| WO | WO-1999-039352 | A1 | 8/1999 | |
| WO | 1999/066946 | A1 | 12/1999 | |
| WO | 2000/57837 | A2 | 10/2000 | |
| WO | 2000/061770 | A2 | 10/2000 | |
| WO | WO-2000-057837 | A1 | 10/2000 | |
| WO | WO-2000-061770 | A2 | 10/2000 | |
| WO | 2001/000669 | A2 | 1/2001 | |
| WO | WO-2001-000669 | A2 | 1/2001 | |
| WO | 2001/21631 | A2 | 3/2001 | |
| WO | WO-2001-21631 | A2 | 3/2001 | |
| WO | 2001/22972 | A2 | 4/2001 | |
| WO | 2001/025488 | A2 | 4/2001 | |
| WO | WO-2001-025488 | A2 | 4/2001 | |
| WO | 2001/051630 | A1 | 7/2001 | |
| WO | WO-2001-051630 | A1 | 7/2001 | |
| WO | 2002/062840 | A1 | 8/2002 | |
| WO | WO-2002-062840 | A1 | 8/2002 | |
| WO | 2002/068688 | A1 | 9/2002 | |
| WO | WO-2002-068688 | A1 | 9/2002 | |
| WO | 2002/085309 | A2 | 10/2002 | |
| WO | WO-03025177 | A2 * | 3/2003 | ............ C07K 14/47 |
| WO | 2004/016255 | A1 | 2/2004 | |
| WO | WO-2004-016255 | A1 | 2/2004 | |
| WO | 2004/024079 | A2 | 3/2004 | |
| WO | WO-2004-024079 | A2 | 3/2004 | |
| WO | 2004/030750 | A1 | 4/2004 | |
| WO | WO-2004-030750 | A1 | 4/2004 | |
| WO | 2004/041838 | A1 | 5/2004 | |
| WO | WO-2004-041838 | A1 | 5/2004 | |
| WO | WO-2004044134 | A2 * | 5/2004 | ......... C12N 15/1137 |
| WO | 2004/104161 | A2 | 12/2004 | |
| WO | WO-2004-104161 | A2 | 12/2004 | |
| WO | WO-2005018534 | A2 * | 3/2005 | ......... C12N 15/1137 |
| WO | 2005/045034 | A2 | 5/2005 | |
| WO | WO-2005-045034 | A2 | 5/2005 | |
| WO | 2005/070136 | A2 | 8/2005 | |
| WO | WO-2005-070136 | A2 | 8/2005 | |
| WO | 2005/079862 | A1 | 9/2005 | |
| WO | WO-2005-079862 | A1 | 9/2005 | |
| WO | WO-2006034573 | A1 * | 4/2006 | ........... C12Q 1/6886 |
| WO | 2007/028065 | A2 | 3/2007 | |
| WO | WO-2007-028065 | A2 | 3/2007 | |
| WO | 2007/071182 | A1 | 6/2007 | |
| WO | WO-2007-071182 | A1 | 6/2007 | |
| WO | 2007/087113 | A2 | 8/2007 | |
| WO | WO-2007-087113 | A2 | 8/2007 | |
| WO | 2007/138023 | A1 | 12/2007 | |
| WO | WO-2007-138023 | A1 | 12/2007 | |
| WO | 2008/025025 | A2 | 2/2008 | |
| WO | 2008/057556 | A2 | 5/2008 | |
| WO | WO-2008-057556 | A2 | 5/2008 | |
| WO | 2008/066672 | A2 | 6/2008 | |
| WO | WO-2008-066672 | A2 | 6/2008 | |
| WO | 2008/087561 | A2 | 7/2008 | |
| WO | 2008/091703 | A2 | 7/2008 | |
| WO | WO-2008-087561 | A2 | 7/2008 | |
| WO | 2010/002984 | A1 | 1/2010 | |
| WO | WO-2010-002984 | A1 | 1/2010 | |
| WO | 2010/040571 | A2 | 4/2010 | |
| WO | WO-2010-040571 | A2 | 4/2010 | |
| WO | 2010/054364 | A1 | 5/2010 | |
| WO | 2010/058227 | A2 | 5/2010 | |
| WO | WO-2010-054364 | A1 | 5/2010 | |
| WO | WO-2010-058227 | A2 | 5/2010 | |
| WO | 2010/065787 | A2 | 6/2010 | |

OTHER PUBLICATIONS

Bright, et al., "Delivery of Macromolecules Into Adherent Cells via Electroporation for Use in Fluorescence Spectroscopic Imaging and Metabolic Studies," Cytometry 24:226-233 (1996).

Budni, J., et al., "The Involvement of BDNF, NGF and GDNF in Aging and Alzheimher's Disease," Aging and Disease, vol. 6, No. 5, pp. 331-341, (2016).

Campbell, et al., "Phosphonmate Ester Synthesis Using a modified Mitsunobu Condensation," J. Org. Chem. 59:658-660 (1994).

Cheng, J. et al., "Transcriptional maps of 10 human chromosomes at 5-nucleotide resolution," Science 308:5725:1149-1154 (2005).

Dai et al., "SIRT1 Interacts With p73 and Suppresses p73-Dependent Transcriptional Activity," J Cell Physiol 210(1):161-165 (2007).

Deng et al., "Small Interfering RNA Targeting the PINK1 Induces Apopsis in Dopaminergic Cells SH-SY5Y", Biochemical and Biophysical Research Communications, vol. 337, No. 4, pp. 1133-1138 (2005).

Faghihi, M. & Wahlestedt, C., "RNA interference is not involved in natural antiserise mediated regulation of gene expression in mammals," Genome Biol (2005).

Geller, A.I. et al., "An HSV-1 Vector Expressing Tyrosine Hydroxylase Causes Production and Release of L-DOPA from Cultured Rat Striatal Cells," J. Neurochem 64:487-496 (1995).

Geller, A.I. et al., "Long-terra increases in neurotransmitter release from neuronal cells expressing a constitutively active adenylate cyclase from a herpes simplex virus type 1 vector," PNAS U.S.A. :90:7603-7607 (1993).

(56) References Cited

OTHER PUBLICATIONS

Geller, A.I., et al., "Infection of cultured central nervous system neurons with a defective herpes simplex virus 1 vector results in stable expression of *Escherichia coli* β-galactosidase," PNAS USA 87:1149-1153 (1990).
GenBank Accession No. NM_000559, *Homo sapiens* Hemoglobin, Gamma A (HBG1), mRNA, (2008).
Giuliano, et al., "FLuorescent Protein Bioseasors: Measurement of Molecular Dynamics in Living Cells," Ann. Rev. of Biophysics and Biomolecular Structure 24:405-434 (1995).
Hagihara, et al., "Virtylogous Polypeptides: An Alternate Peptide Backbone," J. Amer. Chem. Soc. 114:6568-6571 (1992).
Haussecker, D., et al., "Dicer-Dependent Turnover of Intergenic from the Human β-Globin Gene Cluster," Molecular and Cellular Biology, vol. 25, No. 21, pp. 9724-9731, (2005).
Hobbs-DeWitt, et al., "Divesomers: An approach to nonpeptide, nonoligomeric chemical diversity," Proc. Nat. Acad. Sci. USA 90;6909-6913 (1993).
Houghton AN, Gold JS, Blachere NE, Immunity against cancer: lessons learned from melanoma,. Curr Opin Immunol 13:134-140 (2001).
International Human Genome Sequencing Consortium "Finishing the euchroinatic sequence of the human genome." Nature 431:7011:931-945 (2004).
Janowski, et al., "Inhibiting gene expression at transcription start sites in chromosomal DNA with antigene RNAs," Nature Chemical Biology, 1(4):210-222 (2005).
Kaplitt, M.G., et al., "Long-term gene expression and phenotypic correction using adeno-associated vints vectors in the mammalian brain," Nat. Genet. 8:148-154 (1994).
Kawahara & Nishikura, "Extensive adenosine-to-inosine editing detected in Alu repeats of antisense RNAs reveals scarcity of sense-antisense duplex fonnation," FEBS Lett 580:2301-2305 (2006).
Kay, et al., "Identification of enzyme inhibitors from phage-displayed combinatorial peptide libraries," Comb Chem High Throughput Screen 4:535-543 (2001).
Li et al., "Control of APP processing and Aβ generation level by BACE1 enzymatic activity and transcription," Faseb J 20; 285-292 (2006).
Rosenfeld, et al., "In Vivo Transfer of the Human Cystic Fibrosis Transmembrane Conductance Regulator Gene to the Airway Epithelium," Cell, 68:143-155 (1992).
Schena, et al., "Parallel human genuine analysis: Microarray-based expression monitoring of 1000 genes," PNAS 93:10614-10619(1996).
Shea, et al., "Synthesis, hybridization properties and antiviral activity of lipid-oligodeoxynucleotide conjugates," Nucl. Adds Res 18:3777-3783 (1990).
Shen, T., et al., "Modification of Globin Gene Expression by RNA Targeting Strategies," Experimental Hematology, vol. 35, No. 8, pp. 1209-1218, (2007).
Shimoniura, et al., "Semi-synthetic aequorin," J. of Biochemistry (Tokyo) 251:405-410 (1988).
Tamagno, et al., "The various aggregation states of β-amyloid 1-42 mediate different effects on oxidative stress, neurodegeneration, and BACE-1 expression," Free Radic Biol Med 41:202-212 (2006).
Thomas et al., "Intracellular pH Measurements in Ehrlich Ascites Tumor Cells Utilizing Spectroscopic Probes Generated in Situ," Biochemistry 18:2210-2218 (1979).
To, Ky, "Identification of Differential Gene Expressionm by High Throughput Analysis," Comb. Chem. High Throughput Screen 3:235-241 (2000).
Tong, et al., "Oxidative stress potepotentiates BACE1 gene expression," Neural Transm 112, 455-469 (2005).
Uhlman, E., "Recent advances in the medical chemistry of antisense oligonucleotide," Current Opinions in Drug Discovery & Development 3:203-213 (2000).
Vanhee-Brossolet and Vaquero, "Do natural antisense transcripts make sense in eukaryotes?" Gene 211:1-9 (1998).
Vaughn, et al., "Human Antibodies with Sub-nanomolar Affinities Isolated from a Large Non-immunized Phage Display Library," Nature Biotechnology, 141:309-314 (1996).
Walsh, et al., "The role of cell-derived oligomers of Aβ in Alzheimer's disease and avenues for therapeutic intervention," Biochem Soc Trans 33: 1087-1090 (2005).
Yamada, et al., "Endothelial Nitric-Oxide Synthase Amisense (NOS3AS) Gene Encodes an Autophagy-Related Protein (APG9-like2) Highly Expressed in Trophoblast" (2005).
Yoshigai, et al., "Characterization of Natural Antisense Transcripts Expressed from Interleukin 1β-inducible Genes in Rat Hepatocytes," HOAJ Biology 1-10 (2012).
International Search Report and Written Opinion for PCT Application No. PCT/US2010/033078 mailed Jun. 29, 2011.
PCT/US96/10287 (WO97/000271) the Regents of the University of California 1.3.97.
Galardi et al., "miR-221 and miR-222 expression affects the proliferation potential of human prostate carcinoma cell lines by targeting p27Kip1." Journal of Biological Chemistry 282, No. 32 (2007): 23716-23724.
Geller, A.I., et al., "Infection of cultured central nervous system neurons with a defective herpes simplex virus 1 vector results in stable expression of *Escherichia coli* beta-galactosidase," PNAS USA 87:1149-1153 (1990).
Telerman et al., WO 03/025177, Mar. 2003, search result attached, 31 pages.
Ausubel, Current Protocols in Molecular Biology vol. 1, 1994, 6.0.1-6.4.10.
Barak, et al., "A .beta.-Arrestin/Green Fluorescent Protein Biosensor for Detecting G Protein-Coupled Receptor Activation," J. Biol. Chem. 272:27497-27500 (1997).
Barber, et al., "Delivery of membrane-impermeant fluorescent probes into living neural cell populations by lipotransfer," Neuroscience, Letters 207:17-20 (1996).
Baum, "Solid-phase synthesis of benzodiazepines," C&EN News, Jan. 18, p. 33-34 (1993).
Bernstein, E., et al., "Role for a Bidentate Ribonuclease in the Initiation Step of RNA Interference," Nature 409:363-366 (2001).
Boutla, A., et al., "Short 5'-phosphorylated double-stranded RNAs induce RNA interference in *Drosophilia*," Curr Biol 11:1776-1780 (2001).
Boyd-Kimball, et al., "Proteomic Identification of Proteins Specifically Oxidized by Intracerebral Injection of Amyloid .beta.-Peptide (1-42) into Rat Brain: Implications for Alzheimer's Disease," Neuroscience 132, 313-324 (2005).
Brazma & Vilo, "Gene expression data analysis," FEBS Lett., 480:17-24 (2000).
Bright, et al., "Chapter 6. Fluorescence Ratio Imaging Microscopy," Methods in Cell Biology vol. 30, Taylor and Wang (eds) p. 157-192 (1989).
Bright, el al., "Delivery of Macromolecules Into Adherent Cells via Electroporation for Use in Fluorescence Spectroscopic Imaging and Metabolic Studies," Cytometry 24:226-233 (1996).
Bright, et al., "Fluorescence Ratio Imaging Microscopy: Temporal and Spatial Measurements of Cytoplasmic pH," J. Cell Biology 104:1019-1033 (1987).
Campbell, et al., "Phosphonate Ester Synthesis Using a Modified Mitsunobu Condensation," J. Org. Chem. 59:658-660 (1994).
Caplen, N. J., et al., "Specific inhibition of gene expression by small double-stranded RNAs in invertebrate and vertebrate systems," PNAS Sci. USA 98:9742-9747 (2001).
Carninci et al., "The transcriptional landscape of the mammalian genome," Science 309:1559-1563 (2005).
Carulli, et al., "High Throughput Analysis of Differential Gene Expression," J. Cell Biochem. Suppl., 3:286-296 (1998).
Celis, et al., "Gene expression profiling: monitoring transcription and translation products using DNA microarrays and proteomics," FEBS Lett. 480:2-16 (2000).
Chabala, J.C., "Solid-phase combinatorial chemistry and novel tagging methods for identifying leads," Curr Opin Biotechnol. 6:632-639 (1995).
Cech, J., "Ribozymes and Their Medical Implications," American. Med Assoc. 260:3030-3035 (1988).

(56) References Cited

OTHER PUBLICATIONS

Chen, et al., "Expression of ssDNA in Mammalian Cells," BioTechniques 34:167-171 (2003).
Chen, et al., "Analogous Organic Synthesis of Small-Compound Libraries: Validation of Combinatorial Chemistry in Small-Molecule Synthesis," J. Amer. Chem. Soc. 116:2661-2662 (1994).
Cheng, J. et al., "Transcriptional maps of 10 human chromosomes at 5-nucleolidc resolution," Science 308:5725:1149-1154 (2005).
Cho et al., "An Unnatural Biopolymer" Science 261: 1303-1305 (1993).
Christiensen, N.K. et al., "A Novel Class of Oligonucleotide Analogues Containing 2'-O,3'-C-Linked [3.2.0] Bicycloarabinonucleoside Monomers: Synthesis, Thermal Affinity Studies, and Molecular Modeling," J. Am. Chem. Soc., 120:5458-5463 (1998).
Cubitt, et al. , "Understanding, improving and using green fluorescent proteins." Trends in Biochemical Science 20:448-455 (1995).
Curiel, D. T. et al., "Adenovirus enhancement of transferrin-polylysine-mediated gene delivery," PNAS 88:8850-8854 (1991).
Dai et al., "SIRT1 Intends With p73 and Suppresses p73-Dependent Transcriptional Activity," J Cell Physiol 210(1):161-165 (2007).
Davidson, et al., "A model system for in vivo gene transfer into the central nervous system using an adenoviral vector," Nat. Genet 3:219-223 (1993).
Davis, et al., "Direct Gene Transfer into Skeletal Muscle In Vivo: Factors Affecting Efficiency of Transfer and Stability of Expression," Hum Gene Ther 4:151-159 (1993).
De Mesmaeker, et al., "Antisense Oligonucleotides," Acc. Chem. Res. 28:366-374 (1995).
Deng et al., "Small Interfering RNA Targeting the PINK1 Induces Apoptosis in Dopaminergic Cells SH-SY5Y", Biochemical and Biophysical Research Communications, vol. 337, No. 4, pp. 1133-1138 (2005).
Dixon, et al., "Anthrax," New England J. Med. 341:815-826 (1999).
Dolle, "Discovery of Enzyme inhibitors through combinatorial chemistry," Mol Divers. 2:223-236 (1997).
Dykxhoorn, D., et al., "Determinants of Specific RNA Interference-Mediated Silencing of Human ?-Globin Alleles Differing by a Single Nucleotide Polymorphism," PNAS, vol. 103, No. 15, pp. 5953-5958, {2006).
Eguchi, et al., "Antisense RNA," Annu. Rev. Biochem 60:631-652 (1991).
Eichler, et al., "Generation and utilization of synthetic combinatorial libraries," Mol Med Today 1:174-180 (1995).
Eichler, et al., "Peptide Peptidomimetic and organic synthetic combinatorial libraries," Med Res Rev 15:481-496 (1995).
Espeseth, et al., A genome wide analysis of ubiquitin ligases in APP processing identifies a novel regulator of BACE1 mRNA levels, Mol. Cell Neurosci. 33: 227-235 (2006).
Faghihi, M. & Wahlestedt, C., "RNA interference is not involved in natural antisense mediated regulation of gene expression in mammals," Genome Biol (2005), p. 1-9.
Fauchere, et al., "Peptide and nonpeptide lead discovery using robotically synthesized soluble libraries," Can J. Physiol Pharmacol 75:683-689 (1997).
Felgner and Holm, "Cationic Liposome-Mediated Transfection," Bethesda Res. Lab Focus, 11:2:21 (1989).
Fields, et al., "How many genes in the human genome?" Nature Genetics 7:345-346 (1994).
Freier & Altman, "The ups and downs of nucleic acid duplex stability: structure-stability studies on chemically-modified DNA:RNA duplexes," Nucl. Acid Res., 25:22:4429-4443 (1997).
Fuchs, et al., "Identification of Differentially Expressed Genes by Mutually Subtracted RNA Fingerprinting," Anal. Biochem., 286:91-98 (2000).
Gebeyehu, G., et al., "Novel biotinylated nucleotide-analogs for labeling and colorimetric detection of DNA," Nucl. Acids Res. 15:4513 (1987).
Seller, A.I. et al., "An HSV-1 Vector Expressing Tyrosine Hydroxylase Causes Production and Release of L-DOPA from Cultured Rat Striatal Cells," J. Neurochem 64:487-496 (1995).
Seller, A.I. et al., "Long-term increases in neurotransmitter release from neuronal cells expressing a constitutively active adenylate cyclase from a herpes simplex virus type 1 vector," PNAS U.S.A.:90:7603-7607 (1993).
Flibotte, S., et al., "Experimental Analysis of Oligonucleotide Microarray Design Criteria to Detect Deletions by Comparative Genomic Hybridization," BMC Genomics, vol. 9, No. 497, pp. 1-12, (2008).
Han, J. et al., "Selection of Antisense Oligonucleotides on the Basis of Genomic Frequency of the Target Sequence," Antisense Res Dev., vol. 4, No. 1, pp. 53-65, (1994), Abstract.
Faghihi et al., "Expression of a noncoding RNA is elevated in Alzheimer's disease and drives rapid feed-forward regulation of β-secretase." Nature medicine 14, No. 7 (2008): 723-730.
Khalil et al., "A novel RNA transcript with antiapoptotic function is silenced in fragile X syndrome." PLoS One 3, No. 1 (2008): e1486.
Farnebo, "Wrap53, a novel regulator of p53." Cell Cycle 8, No. 15 (2009): 2343-2346.
Fish et al., "Hypoxia-inducible expression of a natural cis-antisense transcript inhibits endothelial nitric-oxide synthase." Journal of Biological Chemistry 282, No. 21 (2007): 15652-15666.
Mahmoudi et al., "Wrap53, a natural p53 antisense transcript required for p53 induction upon DNA damage." Molecular cell 33, No. 4 (2009): 462-471.
Mise-Omata et al., "Transient strong reduction of PTEN expression by specific RNAi induces loss of adhesion of the cells." Biochemical and biophysical research communications 328, No. 4 (2005): 1034-1042.
Carthew et al., "Origins and mechanisms of miRNAs and siRNAs." Cell 136, No. 4 (2009): 642-655.
Garcia-Closas et al., "Common genetic variation in TP53 and its flanking genes, WDR79 and ATP1B2, and susceptibility to breast cancer" International journal of cancer 121, No. 11 (2007): 2532-2538.
PCT/US2009/066654—International Search Report, dated Aug. 4, 2010, 4 pages.
PCT/US2009/066654—International Preliminary Report on Patentability, dated Jun. 7, 2011, 6 pages.
Blanco-Aparicio et al., "PTEN, more than the AKT pathway." Carcinogenesis 28, No. 7 (2007): 1379-1386.
Chalhoub et al., "PTEN and the PI3-kinase pathway in cancer." Annual Review of Pathology: Mechanisms of Disease 4 (2009): 127-150.
El-Deiry et al., "WAF1, a potential mediator of p53 tumor suppression." Cell 75, No. 4 (1993): 817-825.
Meng et al., "Involvement of human micro-RNA in growth and response to chemotherapy in human cholangiocarcinoma cell lines" Gastroenterology 130, No. 7 (2006): 2113-2129.
Fasanaro et al., "MicroRNA-210 modulates endothelial cell response to hypoxia and inhibits the receptor tyrosine kinase ligand Ephrin-A3 " Journal of biological chemistry 283, No. 23 (2008): 15878-15883.
GenBank Accession: NM_017818.2, "*Homo sapiens* WD repeat domain 8 (WDR8), mRNA," Jun. 3, 2007, 5 pages.
GenBank Accession: AC196671.6, "Rhesus Macaque BAC CH250-243C8 ( ) complete sequence," Feb. 21, 2007, 127 pages.
GenBank Accession: AC196698.5, "Rhesus Macaque BAC CH250-329E22 ( ) complete sequence," May 1, 2007, 112 pages.
Hartmann et al., "Phosphatidylinositol 3'-kinase/AKT signaling is activated in medulloblastoma cell proliferation and is associated with reduced expression of PTEN " Clinical cancer research 12, No. 10 (2006): 3019-3027.
Ji et al., "MicroRNA expression signature and antisense-mediated depletion reveal an essential role of MicroRNA in vascular neointimal lesion formation." Circulation research 100, No. 11 (2007): 1579-1588.
Matallanas et al., "RASSF1A elicits apoptosis through an MST2 pathway directing proapoptotic transcription by the p73 tumor suppressor protein." Molecular cell 27, No. 6 (2007): 962-975.
Rosenbluth et al., "The jury is in: p73 is a tumor suppressor after all." Genes & development 22, No. 19 (2008): 2591-2595.

(56) References Cited

OTHER PUBLICATIONS

Saito et al., "Epigenetic therapy upregulates the tumor suppressor microRNA-126 and its host gene EGFL7 in human cancer cells." Biochemical and biophysical research communications 379, No. 3 (2009): 726-731.
Katayama et al., "Antisense transcription in the mammalian transcriptome." Science 309, No. 5740 (2005): 1564-1566.
GenBank Accession: BC086311.1, "*Homo sapiens* WD repeat domain 8, mRNA (cDNA clone MGC:99569 IMAGE:6427357), complete cds," Jul. 15, 2006, 4 pages.
GenBank Accession: U92436.1, "Human mutated in multiple advanced cancers protein (MMAC1) mRNA, complete cds," Apr. 1, 1997, 4 pages.
GenBank Accession: CU041290.5, "Human DNA sequence from clone XX-DSH1_15P21, complete sequence," Oct. 2, 2006, 62 pages.
GenBank Accession: CU678067.1, "Synthetic construct *Homo sapiens* gateway clone IMAGE:100018288 3' read WDR8 mRNA," Feb. 19, 2008, 3 pages.
GenBank Accession: CU678066.1, "Synthetic construct *Homo sapiens* gateway clone IMAGE:100018288 5' read WDR8 mRNA," Feb. 19, 2008, 3 pages.
GenBank Accession: AC121979.3, "Mus musculus BAG clone RP24-289L14 from chromosome 9, complete sequence," Nov. 13, 2003, 114 pages.
GenBank Accession: AC133937.3, "Mus musculus BAG clone RP24-486L5 from chromosome 5, complete sequence," Feb. 6, 2004, 137 pages.
Meng et al., "Microrna-370 regulates interleukin-6 dependent p38 map kinase signaling in human cholangiocarcinoma." In Hepatology, vol. 46, No. 4, Abstract 1218, pp. 778A, Oct. 2007.
GenBank Accession: NM000559, *Homo sapiens* Hemoglobin, Gamma A (HBG1), mRNA, (2008).
Giuliano, et al., "Fluorescent Protein Biosensors: Measurement of Molecular Dynamics in Living Cells," Ann. Rev. of Biophysics and Biomolecular Structure 24:405-434 (1995).
Giuliano, et al., "Light-Optical-Based Reagents for the Measurement and Manipulation of Ions, Metabolites, and Macromolecules in Living Cells," Methods in Neuroscience 27:1-16 (1995).
Giuliano, et al., "Determination of Intracellular pH of BALB/c-3T3 Cells Using the Fluorescence of Pyranine," Anal. Biochem 167:362-371 (1987).
Going & Gusterson, "Molecular Pathology and Future Developments," Eur. J. Cancer, 35:1895-1904 (1999).
Hagihara, et al., "Vinylogous Polypeptides: An Alternate Peptide Backbone," J. Amer. Chem. Soc. 114:6568-6571 (1992).
Haussecker, D., et al., "Dicer-Dependent Turnover of Intergenic from the Human Beta-Globin Gene Cluster," Molecular and Cellular Biology, vol. 25, No. 21, pp. 9724-9733, (2005).
Heller, et al., "Discovery and analysis of inflammatory disease-related genes using cDNA microarrays," PNAS U.S.A. 94:2150-2155 (1997).
Herdewijn P., "Heterocyclic Modifications of Oligonucleotides and Antisense Technology," Antisense & Nucleic Acid Drug Dev., 10:297-310 (2000).
Hirschmann, et al., J. Amer. Chem. Soc., 114:9217-9218 (1992).
Hobs-DeWitt, et al., "Diversomers: An approach to nonpeptide, nonoligomeric chemical diversity," Proc. Nat. Acad. Sci. USA 90:6909-6913 (1993).
Houghton AN, Gold JS, Blachere NE, Immunity against cancer: lessons learned front melanoma,. Curr Opin Immunol 13:134-140(2001).
International Human Genome Sequencing Consortium "Finishing the euchromatic sequence of the human genome." Nature 431:7011:931-945 (2004).
Janda, K.D. "Tagged versus untagged libraries: Methods for the generation and screening of combinatorial chemical libraries," PNAS 91:10779-10785 (1994).
Janowski, et al., "Inhibiting gene expression at transcription start sites in chromosomal DNA with antigene RNAs," Nature Chemical Biology, 1(4):216-222 (2005).
Jungblut, et al., "Proteomics in human disease: Cancer, heart and infectious diseases," Electrophoresis 20:2100-2110 (1999).
Jurecic & Belmont, "Long-distance DD-PCR and cDNA microarrays," Curr. Opin. Microbiol., 3:316-321 (2000).
Kabanov, et al., "A new class of antivirals; antisense oligonucleotides combined with a hydrophobic substituent effectively inhibit influenza virus reproduction and synthesis of virus-specific proteins in MDCK cells," FEBS Lett. 259:327-330 (1990).
Kaplitt, M.G., et al., "Long-term gene expression and phenotypic correction using adeno-associated virus vectors in the mammalian brain," Nat. Genet. 8:148-154 (1994).
Kapranov, P. et al., "Examples of the complex architecture of the human transcriptome revealed by RACE and high-density tiling arrays," Genome Res 15:7:987-997 (2005).
Katayama, S. et al., "Antisense Transcription in the Mammalian Transcriptome," Science 309:1564-1566 (2005).
Kawahara & Nishikura, "Extensive adenosine-to-inosine editing detected in Alu repeats of antisense RNAs reveals scarcity of sense-antisense duplex formation," FEBS Lett 580:2301-2305 (2006).
Kay, et al., "Identification or enzyme inhibitors from phage-displayed combinatorial peptide libraries," Comb Chem High Throughput Screen 4:535-543 (2001).
Kenan, et al., "Exploring molecular diversity with combinatorial shape libraries," Trends Biochem Sci 19:57-64 (1994).
Kornberg, A., DNA Replication, W.H. Freeman & Co., San Francisco, pp. 75-77, (1980).
Larson, et al., "Rapid DNA Fingerprinting of Pathogens by Flow Cytometry," Cytometry, 2000, 41:203-208 (2000).
Larsson, et al., "High-throughput protein expression of cDNA products as a tool in functional genomics," J. Biotechnology., 80:143-157 (2000).
Lebl, et al., "One-bead-one-structure combinatorial libraries" Biopolymers 37:177-198 (1995).
LeGal Lasalle et al., "An Adenovirus Vector for Gene Transfer into Neurons and Glia in teh Brain," Science 259:988-990 (1993).
Letsinger, et al., "Cholesteryl-conjugated oligonucleotides: Synthesis, properties, and activity as inhibitors of replication of human immunodeficiency virus in cell culture," PNAS 86:6553-6556 (1989).
Li et al., "Control of APP processing and A.beta. generation level by BACE1 enzymatic activity and transcription," Faseb J 20; 285-292 (2006).
Li, et al., J. Neurochem 89 1308-1312 (2004).
Liang, et al., "Parallel Synthesis and Screening of a Solid Phase Carbohydrate Library," Science 274:1520-1522 (1996).
Luther, "Role of endogenous antisense RNA in cardiac gene regulation," J. Mol. Med. 83:26-32 (2005).
Madden, et al., "Serial analysis of gene expression: from gene discovery to target identification," Drug Discov. Today 5:415-425 (2000).
Makalowska I, Lin CF, Makalowski W., "Overlapping genes in vertebrate genomes," Comput Biol. Chem 29:1:1-12 (2005).
Mannino and Gould-Fogerite, "Liposome Mediated Gene Transfer," BioTechniques 6:682-690 (1988).
Manoharan et al., "Lipidic Nucleic Acids," Tetrahedron Lett 36:3651-3654 (1995).
Manoharan, et al., "Chemical Modifications to Improve Uptake and Bioavailability of Antisense Oligonucleotides," Ann. N.Y. Acad. Scie 660:306-309 (1992).
Manoharan, et al., "Introduction of a Lipophilic Thioether in teh Minor Groove of Nucleic Acids for Antisense Applications," Bioorg. Med. Chem. Let 3:2765-2770 (1993).
Manoharan, et al., "Cholic Acid-Oligonucleotide Conjugates for Antisense Applications," Bioorg. Med. Chem. Let 4;1053 (1994).
Manoharan, et al., "Oligonucleotide Conjugates: Alteration of the Pharmacokinetic Properties of Antisense Agents," Nucleosides & Nucleotides 14:969-973 (1995).
Manoharan, M., "2'-Carbohydrate modifications in antisense oligonucleotide therapy: importance of conformation, configurationj and conjugation," Biochemica et Biophysica Acta 1489:117-139 (1999).

(56) References Cited

OTHER PUBLICATIONS

Mattick, J. S. "RNA regulation: a new genetics?" Nat. Rev. Genet 5:4:316-323 (2004).
Maurer, R.A., "Cationic Liposome-Mediated Transfection of Primary Cultures of Rat Pituitary Cells," Bethesda Res. Lab. Focus 11:2:25 (1989).
McNeil in Methods in Cell Biology vol. 29, Taylor and Wang (eds.) p. 153-173 (1989).
Morelli et al., "The antisense bcl-2-IgH transcript is an optimal target for synthetic oligonucleotides," PNAS USA 94:8150-8155 (1997).
Nielsen et al. "Sequence-Selective Recognition of DNA by Strand Displacement with a Thymine-Substituted Polyamide" Science, 254:1497-1500 (1991).
Oberhauser, et al., "Effective incorporation of 2'-O-methyl-oligoribonucleotides into liposomes and enhanced cell association through modification with thiocholesterol," Nucl. Acids Res. 20:533-538 (1992).
Petit et al., "Wild-type PINK1 Prevents Basal and Induced Neuronal Apoptosis, a Protective Effect Abrogated by Parkinson Disease-Related Mutations", Journ. BioL Chem., vol. 280, No. 40, pp. 34025-334032 (2005).
Prasanth, et al., "Regulating Gene Expression through RNA Nuclear Retention," Cell 123, 249-263 (2005).
Prashar & Weissman, "READS: A Method for Display of 3'-End Fragments of Restriction Enzyme-Digested cDNAs for Analysis of Differential Gene Expression," Methods Enzymol., 303:258-272 (1999).
Quantin, et al., "Adenovirus as an expression vector in muscle cells in vivo," PNAS 89:2581-2584 (1992).
Rosenfeld, et al., "In Vivo Transfer of the Human Cystic Fibrosis Transmembrane Conductance Regulator Gene to the Airway Epithelium," Cell, 68:143-153 (1992).
Rosok and Sioud, "Systematic identification of sense-antisense transcripts in mammalian cells," Nature Biotech. 22(1):104-108 (2004).
Saison-Behmoaras et al., "Short Modified Antisense Oligonucleotides Directed Against Ha-ras Point Mutation Induce Selective Cleavage of the mRNA and Inhibit T24 Cells Proliferation" EMBO J.,10: 1111-1118(1991).
Sanghvi, Y.S, in Crooke, S.T. and Lebleu, B., eds., Antisense Research and Applications, CRC Press, Boca Raton, 1993, p. 276-278.
Scheele et al., "The Human PINK1 Locus is Regulated and Vivo by a Non-Coding Natural Antisense RNA During Modulation of Mitochondrial Function", BMC Genomics, vol. 8, No. 1, p. 74 (2007).
Schena, et al., "Parallel human genome analysis: Microarray-based expression monitoring of 1000 genes," PNAS 93:10614-10619(1996).
Shea, et al., "Synthesis, hybridization properties and antiviral activity of lipid-oligodeoxynucleotide conjugates," Nucl. Acids Res 18:3777-3783 (1990).
Shen, T., et a!., "Modification of Globin Gene Expression by RNA Targeting Strategies," Experimental Hematology, vol. 35, No. 8,. pp. 1209-1218, (2007).
Shimomura, et al., "Semi-synthetic aequorin," J. of Biochemistry (Tokyo) 251:405-410 (1988).
Singer, et al., "Targeting BACE1 with siRNAs ameliorates Alzheimer disease neuropathology in a transgenic model," Nat Neurosci 8:1343-1349 (2005).
Southwick, et al., "Cyanine Dye Labeling Reagents-Carboxymethylindocyanine Succinimidyl Esters," Cytometry 11:418-430 (1990).
Stratford-Perricadet, et al., "Widespread Long-term Gene Transfer to Mouse Skeletal Muscles and Heart," J. Clin. Invest., 90:626-630 (1992).
Sullenger, et al., "Overexpression of TAR sequences Renders Cells Resistant to Human Immunodeficiency Virus Replication," Cell63:601-608 (1990).
Sun, et al., "Downregulation of Sirt1 by antisense oligonucleotides induces apoptosis and enhances radiations sensitization in A549 lung cancer cells," Lung Cancer 58(1):21-29 (2007).
Sutcliffe, et al., "TOGA: An automated parsing technology for analyzing expression of nearly all genes," PNAS, 97:1976-1981 (2000).
Sutton, et al., "TIGR Assembler: A New Tool for Assembling Large Shotgun Sequencing Projects," Genome Science & Tech., 1:9-19 (1995).
Svinarchuk, et al., "Inhibition of HIV proliferation in MT-4 cells by antisense oligonucleotide conjugated to lipophilic groups," Biochimie 75:49-54 (1993).
Tamagno, et al., "The various aggregation states of beta.-amyloid 1-42 mediate different effects on oxidative stress, neurodegeneration, and BASE-1 expression," Free Radio Biol Med 41:202-212 (2006).
Thakker, D.R., et al., "siRNA-mediated knockdown of the serotonin transporter in the adult mouse brain," Mol Psychiatry 10:782-789 (2005).
Thakker, et al., "Neurochemical and behavioral consequences of widespread gene knockdown in the adult mouse brain by using nonviral RNA interference," PNAS 101:17270-17275 (2004).
Thomas et al., "Intracellular pH Measurements in Ehrlich Ascites Tumor Cells Utilizing Spectroscopic Probes Generated in Situ," Biochemisiry 18:2210-2218 (1979).
Thompson, et al., "Synthesis and Applications of Small Molecule Libraries" Chem Rev 96:555-600 (1996).
To, Ky, "Identification of Differential Gene Expression by High Throughput Analysis," Comb. Chem. High Throughput Screen 3:235-241 (2000).
Tong, et al., "Oxidative stress potentiates BACE1 gene expression," Neural Transm 112, 455-469 (2005).
Toulme, J.J., "New candidates for true antisense," Nature Biotechnology 19:17-18 (2001).
Tsien in Methods in Cell Biology vol. 30 Taylor and Wang (eds) p. 127-156 (1989).
Ulhman, E., "Recent advances in the medical chemistry of antisense oligonucleotide," Current Opinions in Drug Discovery & Development 3:203-213 (2000).
Van Den Eynde BJ, "T cell defined tumor antigens," Curr Opin Immunol 9:684-693 (1997).
Van Der Bruggen, et al., "Tumor-specific shared antigenic peptides recognized by human T cells," Immunol Rev188:51-64 (2002).
Vanhee-Brossolet and Vaquera, "Do natural antisense transcripts make sense in eukaryotes?" Gene 211;1-9 (1998).
Vaughn, et al., "Human Antibodies with Sub-nanomolar Affinities Isolated from a Large Non-immunized Phage Display Library," Nature Biotechnology, 14:3:309-314 (1996).
Velculescu, et al., "Serial Analysis of Gene Expression," Science 270:484-487 (1995).
Wahlestedt, "Natural antisense and noncoding RNA transcripts as potential drug targets," Drug Discovery Today 11(11/12):503-508 (2006).
Wahlestedt, C., "Antisense oligonucleotide strategies in neuropharmacology," Trends Pharmacol Sci 15:2:42-46 (1994).
Walsh, et al., The role of cell-derived oligomers of A.beta. in Alzheimer's disease and avenues for therapeutic intervention, Biochem Soc Trans 33: 1087-1090 (2005).
Wang, B.B. et al., "Identification of a nuclear-specific cyclophilin which interacts with the proteinase inhibitor eglin c," Biochem J. 314 (Pt 1) 313-319 (1996).
Wiesenhofer et al., "Glial cell line-derived neurotrophic factor (GDNP) is a proliferation factor for rat C6 glioma cells: evidence from antisense experiments," Antisense & Nucleic Acid Drug Development 10(5);311-321 (2000).
Xue, et al., "Hypoxia and reoxygenation increased BACE1 mRNA and protein levels in human neuroblastoma SH-SY5Y cells," Neurosci Lett 405,231-235 (2006).
Yamada, et al., "Endothelial Nitric-Oxide Synthase Antisense (NOS3AS) Gene Encodes an Autophagy-Related Protein (APG9-like2) Highly Expressed in Trophoblast" (2005), p. 18283-18290.

(56) References Cited

OTHER PUBLICATIONS

Yang, et al., "Cellular and Humoral Immune Responses to Viral Antigens Create Barriers to Lung-Directed Gene Therapy with Recombinant Adenoviruses," J. Virol 69:2004-2015 (1995).
Yoshigai, et al., "Characterization of Natural Antisense Transcripts Expressed from Interleukin 1.beta.-inducible Genes in Rat Hepatocytes," HOAJ Biology; 1-10 (2012).
EP Application No. 06850393.7 Examination Report dated Oct. 18, 2011.
PCT/US2010/033078—International Search Report and Written Opinion, dated Jun. 29, 2011.
PCT/US2010/026119 Search Report and Written Opinion dated Feb. 7, 2011.
PCT/US2010/024079 Search Report and Written Opinion dated Jan. 31, 2011.
PCT/US2010/027394 Search Report and Written Opinion dated Nov. 5, 2010.
Collin R., et al., "Antisense Oligonucleotide (AON)-based Therapy for Leber Congenital Amaurosis Caused by a Frequent Mutation in CEP290," Molecular Therapy-Nucleic Acids, vol. 1, No. 14, pp. 1-7, (2012).

* cited by examiner

FIG.4

(SEQ ID NO: 1)

>gi|187828068|ref|NM_005427.2| Homo sapiens tumor protein p73 (TP73), transcript variant 1, mRNA AGGGGACGCAGCGAAACCGGGGCCCGCGCCAGGCCAGCCGGGACGGACGCCGATGCCCGGGGCTGCGACGGCTGCAG
AGCGAGCTGCCCTCGGAGGCCGGCGTGGGGAAGATGGCCCAGTCCACCGCCACCTCCCCTGATGGGGGCACCACGTT
TGAGCACCTCTGGAGCTCTCTGGAACCAGACAGCACCTACTTCGACCTTCCCCAGTCAAGCCGGGGGAATAATGAGG
TGGTGGGCGGAACGGATTCCAGCATGGACGTCTTCCACCTGGAGGGCATGACTACATCTGTCATGGCCCAGTTCAAT
CTGCTGAGCAGCACCATGGACCAGATGAGCAGCCGCGCGGCCTCGGCCAGCCCCTACACCCCAGAGCACGCCGCCAG
CGTGCCCACCCACTCGCCCTACGCACAACCCAGCTCCACCTTCGACACCATGTCGCCGGCGCCTGTCATCCCCTCCA
ACACCGACTACCCCGGACCCCACCACTTTGAGGTCACTTTCCAGCAGTCCAGCACGGCCAAGTCAGCCACCTGGACG
TACTCCCCGCTCTTGAAGAAACTCTACTGCCAGATCGCCAAGACATGCCCCATCCAGATCAAGGTGTCCACCCCGCC
ACCCCCAGGCACCGCCATCCGGGCCATGCCTGTTTACAAGAAAGCGGAGCACGTGACCGACGTCGTGAAACGCTGCC
CCAACCACGAGCTCGGGAGGGACTTCAACGAAGGACAGTCTGCTCCAGCCAGCCACCTCATCCGCGTGGAAGGCAAT
AATCTCTCGCAGTATGTGGATGACCCTGTCACCGGCAGGCAGAGCGTCGTGGTGCCCTATGAGCCACCACAGGTGGG
GACGGAATTCACCACCATCCTGTACAACTTCATGTGTAACAGCAGCTGTGTAGGGGGCATGAACCGGCGGCCCATCC
TCATCATCATCACCCTGGAGATGCGGGATGGGCAGGTGCTGGGCCGCCGGTCCTTTGAGGGCCGCATCTGCGCCTGT
CCTGGCCGCGACCGAAAAGCTGATGAGGACCACTACCGGGAGCAGCAGGCCCTGAACGAGAGCTCCGCCAAGAACGG
GGCCGCCAGCAAGCGTGCCTTCAAGCAGAGCCCCCCTGCCGTCCCCGCCCTTGGTGCCGGTGTGAAGAAGCGGCGGC
ATGGAGACGAGGACACGTACTACCTTCAGGTGCGAGGCCGGGAGAACTTTGAGATCCTGATGAAGCTGAAAGAGAGC
CTGGAGCTGATGGAGTTGGTGCCGCAGCCACTGGTGGACTCCTATCGGCAGCAGCAGCAGCTCCTACAGAGGCCGAG
TCACCTACAGCCCCCGTCCTACGGGCCGGTCCTCTCGCCCATGAACAAGGTGCACGGGGGCATGAACAAGCTGCCCT
CCGTCAACCAGCTGGTGGGCCAGCCTCCCCCGCACAGTTCGGCAGCTACACCCAACCTGGGGCCCGTGGGCCCCGGG
ATGCTCAACAACCATGGCCACGCAGTGCCAGCCAACGGCGAGATGAGCAGCAGCCACAGCGCCCAGTCCATGGTCTC
GGGGTCCCACTGCACTCCGCCACCCCCCTACCACGCCGACCCCAGCCTCGTCAGTTTTTTAACAGGATTGGGGTGTC
CAAACTGCATCGAGTATTTCACCTCCCAAGGGTTACAGAGCATTTACCACCTGCAGAACCTGACCATTGAGGACCTG
GGGGCCCTGAAGATCCCCGAGCAGTACCGCATGACCATCTGGCGGGGCCTGCAGGACCTGAAGCAGGGCCACGACTA
CAGCACCGCGCAGCAGCTGCTCCGCTCTAGCAACGCGGCCACCATCTCCATCGGCGGCTCAGGGGAACTGCAGCGCC
AGCGGGTCATGGAGGCCGTGCACTTCCGCGTGCGCCACACCATCACCATCCCCAACCGCGGCGGCCCAGGCGGCGGC
CCTGACGAGTGGGCGGACTTCGGCTTCGACCTGCCCGACTGCAAGGCCCGCAAGCAGCCCATCAAGGAGGAGTTCAC
GGAGGCCGAGATCCACTGAGGGCCTCGCCTGGCTGCAGCCTGCGCCACCGCCCAGAGACCCAAGCTGCCTCCCCTCT
CCTTCCTGTGTGTCCAAAACTGCCTCAGGAGGCAGGACCTTCGGGCTGTGCCCGGGGAAAGGCAAGGTCCGGCCCAT
CCCCAGGCACCTCACAGGCCCCAGGAAAGGCCCAGCCACCGAAGCCGCCTGTGGACAGCCTGAGTCACCTGCAGAAC
CTTCTGGAGCTGCCCTAGTGCTGGGCTTGTGGGGCGGGGGCTGGCCCACTCTCAGCCCTGCCACTGCCCCGGCGTGC
TCCATGGCAGGCGTGGGTGGGGACCGCAGCGTCGGCTCCGACTTCCAGGCTTCATCCTAGAGACTGTCATCTCCCAA
CCAGGCGAGGTCCTTCCAAAGGAAAGGATCCTCTTTGCTGATGGACTGCCAAAAGTATTTTGCGACATCTTTTGGT
TCTGGATAGTAGTGAGCAGCCAAGTGACTGTGTCTGAAACACCAGTGTATTTTCAGGGAATGTCCCTAACTGCGTCT
TGCCCGCGCCGGGGGCTGGGGACTCTCTCTGCTGGACTTGGGACTGGCCTCTGCCCCCAGCACGCTGTATTCTGCAG
GACCGCCTCCTTCCTGCCCCTAACAACAACCACAGTGTTGCTGAAATTGGAGAAAACTGGGGAGGGCGCAACCCCCC
CCAGGCGCGGGGAAGCATGTGGTACCGCCTCAGCCAGTGCCCCTCAGCCTGGCCACAGTCGCCTCTCCTCGGGGACC
CCTCAGCAGAAAGGACAGCCTGTCCTTAGAGGACTGGAAATTGTCAATATTTGATAAAATGATACCCTTTTC

FIG. 4 (Continued)

(SEQ ID NO: 2)

>hg18_knownGene_uc001akp.2 range=chr1:3558989-3640327 5'pad=0 3'pad=0 strand=+
repeatMasking=none
AGGGACGCAGCGAAACCGGGCCCGCGCCAGGCCAGCCGGACGGACCCGATGCCCGGGCTGCGACGGCTGCAGgtagg
aggcccagggccgggggcggttcggctccgcgggcgggggctggagcgcagcgctgggcaggcacctgggctcgcagctcc
gaagctgggaggtgaggggagagcgatcggggacgagctgggacaaggcgacacaggggctccctcggagttggatcggccc
ctgggacttggcgctcgcgagaggctggagcggccagagtctagcctgcgaggagacgcgggtcctgccctcagcgccggcc
gcctttggcgccaaagacagccccgcagggttccgggagggccctcctcctgctgtccccctctccacccgggctccgagg
gccgttgggagggtaaccccgggaagaggccggggtgcgggcgcgggtgcaggtggaaatcgccagcaagctcctccccgc
ccgcgcgctccctccgacctgcagggctgtgccaatcccgaggcctcagcttccctgaggagccagggcaggcccccctct
ggacagggagaaggatctgggcgggggccttgacccatggagttggttactaagcggtttcgatggtttcccgagggacagc
tccctgtggctctgagtttgtctgtcgagggctcctggcctgtctccggagcggtcccaggtagagaaagcccgtgaagaaa
tggccgggcgcggcctggagggagacacctcacgcccccttagctcctgggccgcctcctcctgcagccccctgcctttcccg
gggcttggacttggggagcgatgattacctttgctcagcttgtatttttggcctggacgctaggagataagcccatgtagtat
gcacacgtctgctacataaacaggggacagatagacgatcttcaaccagcaagggtgcagggaaaagcaatgcaccccaaac
ttctgaccagaggtcatttgctttccaaagatgctgccatctgtttattcactgtctggacatttggaaatggctcaggctca
ttaacacaatgctttggtttttgttgtttttgtttttttgttgctgtcattgctgtttatttgttcagccttagctctgggga
ggagtaaacaaagcgcgtggcctctggcacttactgagcgctgagccaccctctttggatttattcggggaaagattaaaa
agcatttcattaagaacaggacacggtgtttgaaatgttgccatatatgaatgtatgcattacgtatgtagtttttaaaata
agataaaaagttggctgggcacggtagctcacgcctgtcatccctcacagcctttgggaggccaaggtgggtggatcacctg
aggtcaggagttcgagaccagcctggccatcatggtgaaacccagtctctacttgaaatacaaaaattagctgggcatggtg
gcaggcacctgtactcccagctactcgggaggctgaggcacaagaattgcttgaacctgggatggagaggttgcagcgagct
gatatcatgccactgcactccagcctgggcaacagagcaagactctgtctcaaaaaataagatgaaataagataaaagttgg
tgtcagaggctgcagtgtggcagctgcctattgtcaatcagaggtagcctggggtgaacggaaggcggacctgagcggggct
tgtctatgcgcggggccaccagagaatggctcgggatgtgagccctgccttgcagtccttctcgtgaaagctacgcgaac
agtagctgtctccaaatcccgaaggccagtcgcatggagaagctggtctggcacagtggttaatggggtagtatggaagtca
gaatgctggggttcaaatctcctcttcccatttactccagcaagtcacttaaccacttggagcctcaggttacccatctgc
agagtcgggtaatagtagttcctgcctcagaggcttggagaacagtcagtgaggtgcgtccgaagggcttgggagagtgcc
tggcacccactcagtgtcctcacacatgatggcttcgggtcccaggtgctgttccagagctgggagagccaggagccctggg
gagagacccggctccttagtatctggtaggtatctccagggcaggagggatggcagtgaggcaggcatctgcccaaggcgtg
ggtggaagctgatggcatctgtcagaagtatgcactgggcaaggatgcctggtttagtatttatttatagggcatgcccca
cccaggtccaagaatggatttgataaactgagcacgtgtgaaaggcacggctaaagtggagagaagagaagaggctgaggc
cgagagaggagccgcacacccactccagaacccggacgaggccctgcccttgcccagcggcggtattaaccctgagattccg
agcacaccaaagtgacatcgcgtacacggtgaaccctgtgtttgcaaaaagtcagaaaaagtcttcaaaacatcctttaagg
ccaggcgccgtggcccacgcctgtaatctcagccctttgggaggccgaggtgggtggatcacttgagatcaggagttcaaga
ccagcctgggcaaaatggtgaaatcttgtccccaccaaaaatacaaaaattagccgggggtggtgtctggtgcctgtagtct
cagctactcaggaggctgaggcaggagaatcgcttgaacttgggaggcagaggttgcagtgagccgagatcaccccactgca
ctccagcccgggcaacagagcgagactctgtctcaaaaaaacacgcaaaaaatactttggtgtgtgtttcatgtaacgagc
tgccatttgcggcttgcctttgtttccagtgtgggagggctaaggcaacctttaagatatctgtatgttatttcctcg
tgatttgctttaaagcaaaaaagaaaaagctgagatgagttactaaatgacaataacgcctactttctttgaattcc
cgtgttatttgtatctgaatgtggtgaaagtttctaaatgtaatgttttatcaccagtaagtaggctgagtgatcacttac
tcctaccagtatttaatacttccatgttctgcccagattcctttaacaaatacacaaacacacttgtagctggcaacatcc
actcgtgtataatgaaaacacacaatggctttcttagaagtttgccttcttaagtgggttacacaggatgcctcgaaaatcc
ttctctgtgggtcgtgcagaaggtatttattctaaaattccctctactcagccgggcgcagtggctcacgcctgtaatcc
cagcatttgggaggctgaggcgggtggatcacgaggtcaggagatcaagaccatcctggctaacacggtgaaaccccgtct
ctactaaaaatacaaaaaattagtcgggcgtggtgcgggcacctgtagtcccagctacccaggaggctgaggcaggagaatg
gcgtgaacccggaaggcggagcttgcagtgagctgagatcacgcactacactccagcctgggcgacagagcgagactacgtc
tcaaaaaaaaaaaaaaaaatccctctgctcattggcatttgagtgtaagacagcttataccaaagtgggctcagacagaca
tatgcacatgtttacagactttctgcctgcccctggcagtccactctgtgctcagtatttctttgcaggctaaacactcgc
tcatccaaagtgctttctttcctggacaagttgcacatcacagacccaaagaagaaaaagataatccagcccaactcttgt
tttttaatgtttcctgtaataactcacatttagcccatggtggctgtgagctggtacttggctaaaaagtttacattttttt
ccctgtaatccccacaatagcccgttgaagtagatactataattatgcccatttacagatgaggaaactgaggcttcaactg
gctatttctacttgcacagggtcacacagctgcaaagtacgggagtggggactccagctatgacccacgaagctgggactgggg
ctgccaaaccatcctttgcctgggtctgccgttggctcagacacggccccagacacctaggaccgtggaacattcaggccg

FIG. 4 (Continued)

gaagggccccttcccagaacatctaagcccaggggtagagagtcccagggtgctgtgagcctggatggggaaaatggcaccttgt
attaacctcaaagcaaatttcagcatttcctctagttttgaatgtaggcagcaaactacagtcatagcagtacctgtgacct
caccagtgggaaccactgatatttttcatggtgtccggtaatagctgcagcatcttaaaaagtggtttgtgcttgtcgctccg
ttgcaattatggcggtgattagatctgctctcaggcttacgacttaatgtatgaacaaagaagcgcacatatgatcacctcc
cagttttgcttttaaatattagggtcactttgtaagtttctcaggctgctgttacaaatgaccacaaattaagtggctgg
aaacaatagagagtgttgtctcacggttgtggaggcaggaatctgaagccaggtgtgggcagggtcgggttccctcggaggc
tctgagaggggctcgcctcctgtctccctcctaggatctggggctgccggccatcctgtggttcccaggcatgcagatgc
accacccagtctctgccaccatcttgccatggccttctcctctgtgtccctgtgtgtctctcctttttgtcccttagatgg
acacctgtccttggatttcgggcccacctggaaaatccagaatgatcttatcttgagacccttacctaagtggcatctgcaa
agaccctgattccaaataacatcccattctgaggctcgttcccagaggctgcatccaacccactagagtggctatgtttcag
taactcgtgatcctgtgtattttgcttcatgtatttaaaacattctcccggacaaggcgtctgagattccccaggctgccag
aggggccatggcgcaaacggggaagaaacctggtctaagccacgccctcttttcaggacgaggatcttggaaccggacac
tgaaggtcggggttgggcacagccggggatgggcagcccccctctcccccagcacctcccgcctggcgcctcctccacagcc
cctgcatcctggaaaacagactgttccacacactccagcagctcctctacctggggactgcttgggccgcatagccccagt
tagggacagaaaccagaggtattgaacaagaagccccacccgggagaggcgagacccgggccccagccctggacctggccgtg
ggtgctacagaaggtcggggacatcggtctgcgcggaagggtctggagaggcacctctcagggagttggacagagaggaga
cgccgtcccagtggtggcctccagtgaggcctggagagaccaggtggcaggaagggccctgctggggccagagcaagggcac
ggaaggcaggtctcatggagcagggacccgtggagggacatggggacacattagggatggacagtggccggaagattccgt
gggccttggagattaaatcgggttccccaaagagcaagctgtggagaggggaagggaagttgcctccctcttccctacggg
gttcttgtcaataaacgattgacaaaagacagactcacaagagacaacagttttaaggctgtgccccgccccggaagtgcca
taaaaacaggagactcagcagtaaccagatgggagcggtgcagatgtccgtcctctgtgacagaaaggaaaggggcctggg
cttctggggagcggtagagacaaatgaggagagggtgagggaggaaacgtctgggcataaaggctgcctcgtggtgcagcta
tcagtctcatggtgagaaaatgcgtcttggcgcgcggctctcttcctggcacacagaccattactaatgaaaatgtccttta
tagatgtcaatttctttagaaaagagagtttttacttttatttagggagctgaagagctttttctgttggctggttct
cagttgcttttagctcaaagtaatcaacatgtcaacatggcatatttggggtgacgtattctggtctcctacagtcatatt
ttggggtgacgtattctggtctcctacagtcatattttggggtgacgtattctagtctcctacagtcatatttaggggtggc
gtattctggtctcctacagtcatatttggggtggcgtattctggtctcctacagtcatatttggggtggcgtattctggt
ctcctacagtcatatttggggtgacgtattctggtctcctatagtcatatttaggggtggcgtattctggtctcctacagt
catactttggggtgatgtgtcctgagccccattgtttcctagtctgaaacttccccaagaagctccacggtacagaaactgg
gtgggtgtgttgtcccataatgctttgaagaggcatttctatggaaacaaaagaaaaaaaaaaaaaagctaatcattggagct
gactaaaaaccagtttctgagcctgggggccgtggcggggcaggtttgtagatgttgggctccgagcatcttctgcggtttg
gtctctggcgatgtctgggcggcccacgcagcaacaggcgtgagggtccctcgcacctgggcttcgtggtaatctcgctgat
gagtatttcaagtcgtccagcctcagtttgcaggatttctgggcaaagggcagttttgttcttcgtgattccaataagaacg
gtgggagaaaattgaaagtgttagtttgggagttgcagccagatactggaggaaactagaaacatcaggaacccgtccagtt
tgtagacatcaatagataacaaaacccccaaagacgttaaacaggacaagaatctaatatggggcgcacaatatggctttcta
ctgaaatatatgttctttctacatcacccctctttctactaaaaataatctcagtaagattattattattattattttt
gagacagagttccactccgtcgctcaaggctagagtgtagtggcatcatctcgactcactgcaaactctgcctcccgggttc
aagtgattctcctgcctcagcctcctggagttacaggcatgcaccaccactaatttttgtattattattacttttttttagt
agagacagggtttgccatgttggccaggctggtcttgaactcctgacctcacaggatccacccacttcggcctcccaaagt
gctaggattacagacgtgagccactgtgcccagcctagtcagattaacttgtttgtaaagtaagtctagcctcattaaaatt
ggcctgattatttgcacaagtgcagcaagaatagtaagtggccagctaggctttctttaggtcagctttgctggaactttta
ataaatctcaggttaggctttcaaaagcctcttgaggctaagaagtcaagccaaggacttgatatcagacttcacctgcaat
acctatagatttgggtggattcctctttctcaaggttcccaacgtattcttgagaattactgccaaaaaatcacagtctttc
ctcaacccgtgaggctgcagaagcccttaatccaggtacaagggcaatttgtttttcctccaacgggtttcattggctcca
taaagtcaaccttagttccttaaagctactcacatctgattttatgcacatcactctcaaatatgatattccggtcaaacac
ttggtgagctaaccaacatttccagttgtttcctattacaaggcagcagattcatcttgaacttaagcaaataactctatgg
ccgtaaaaataaaaatgctaatagtttctaaattctggagagatcaggtagggagaaaagtcatcatttcaattttgcttat
aaaagtgtaatgtaccagaatgctgtaagttataaatagtttcttcatttacattctggaaattcttgccatccagtggtgt
gatcttaatgtatcagaaacctgtactggtcaaagtcttccccatgaaatcttctcgaagacacaacatttagaattatag
ttgcttgcaaaagctttcgggaaagcatcagagccaaacagttaactgtgtatgacagaaaggcttaaaatggccttggcta
aagatgtgatgacatcattacaatgtaactgatgaggaagtttggttattcctgtggtgtatactttcacataataactaga
attacaactaatatagaatgtatcagatttctaagaatttcatataatttctggaactcttatatgaatatatatccatgca
aatataactcacccagagaaggttaatcatcacttcatatttttacagtgcttccatgcaaatttagttgatcaaataagccc
aatttatttaatatctttttatttttatctaaaacaatttttcccttaacattggcaaaataatctatgtttttataaggaga
gaaaataaatcctttttgagatattccaggggccaatctaggaaatcccaaacgttaattcagggtcaaaaagacttaattta

FIG. 4 (Continued)

gagtgtgtgattttggaaagttgtcaaaatgtcaaaaggttgaaagcacttgattaaatagaatcccagatcattatgaaat
aatacttaattctcatttaatcaaagtaacaatgaaatattcaaagagaaatgcagaaagttagatagtttaaaatactctt
agatctggccaggcatggtgggtcatgcctgtaattccagcactttgagaggctgacatgagcggatcactagagcccagga
gttcgagaccagcctgggcaacatggcaaaacccgtctctaccaaaaatacaaaaattagccaggcatggtggcacatgcc
tgtaatctcagctactcgggaagctgagataggaggatcccttgaacccagggagattcatgccacagtgagctgagatcgc
accactgtactccagcctgagcaacaaactgtatatacacacacatgtatttgtgtatatatatatatatataatatgtat
tacatatatacatacactatatataatatgtattatatatatacatacactatatataatatatgtattatatatatacacg
ctatatatataatatatgtattatatatatacacacaatatatatttttttatttttatttttttatttttttattttttttttaatt
agctgggtgtggtggtgcccacctgtctcccagctactcgggaggctgaggtggcaggatcccttgaagcccaggagttgag
gctgcgatgaactatgatggtgccactgcactctagcctgggtgacagagtgagaccctgtctcaaaaaaaaaaagaactag
ttcacacccatgtttcctcctgctgccccaaattgccactctcctggagcagcccctgaaggtggagaccaggcacctgctg
gagcaggaactcttccttcaccggcttctgttggggcccccaggatcctgcagctgtggcatccacagggagtaaggccagcc
acggaggtcctttcatgtcaccaagctgcaggggaggaaaagtgacatcagacagatcaacaggagaaaacccatttaatg
atatgtccacgaatggagtcccacacggagatgaaactggggaagggccagatggcggaggcgtctgcgtcatcctcag
ctgcaggaagatacaggactgtggggctgctgcaggctgaaccagctatagcaggggagttgactggtgaatgaaggtggtt
tcgtcacgcggacatgcgtctctcaggcgatcagagttacctggagccgctctcctcccggcatagagaccttacgaatgg
aaatgtctttcatttctctcccagacaggcagctgggcagagccactcctgtgtctgcagttactcgaaataatggatatac
ccaaggcatgtttggggtggcacattctgcccctcaagccatgtttggggtggggtggcgtgtcctgagcccaacccag
gtgtcagggctatggagggacattgcaaggggcctagaggggcctctatgggccttggagatggaatcagctccccacca
ggcccaggacagacctggctggggagcgcagggaggggtccccagtgtgaggacagcatggggctgcctcttccagcagct
ccgagcgctctcagagaaaacgaaattctctttataagagaaacttgtctctggtcccatgtgttgcccttgggcactg
gcatgagtaatctgagggcgggcgctttcctcactgcagtggcatcatacagatgagggctttgctgatcattatctggaaac
agtgatcactgtcccattcacagatggggaggctgaagcctgggagatcaattcatgccaccaagatcagctgcaggccggg
ccacccatgcctgaggggagaagggcctctcttctcacgaggctggtggctgcggcacctacaaagacaggttaacaaga
ggacctctgcctatcacgagcctggtggctgcgtaccagtaatgaaagacaagttaacaagagggcgtgcaggcttatt
tacgagaagttccatgtgacacaggagccttgagaatggaacacccatcgaaccggggaactctgcatatttcctcctggg
tttgtggggtgtggacagcacggagcgtgatgaaaggatacaggcggctgggcgtggtggctcacgcctgtaatcccagcac
tttgggaggctgagtcgggcggatcactaggtcaggagatcgagactatactggctcacacggtgaaaccccatctctacta
aaaaatacaaaaaattagccaggcgtggtggcgggcgcctgtagtcccagctactcgggaggctgaggcaggagaatggcgt
gaaccaggaaggtggagcttgcagtgagccaagatcgtgcaacaatgcgagactccatctcaaaaaaaaaaaaaaaagaaaga
aagaaaggatacagacatcctgaacgggggctggggccaggtctgaaggtctgatcttcctttcttctgggtctagggca
catgagggtctgtgacctaattcagaggaaggccagagaactctttatggcctgcctcagggtgacagggagcaggagaga
gcatacctgctttccctggcttctcagatgccaccgtgccaggttttggggtagtggtatgtcttgagcccaatcagtacc
tggggtcgtggccggccccctccctccatgccacaggctctctggagaggccactgctgtatccccactgtgagctcgat
ctgagctgcctatgggaccacacctgagaaccccaagggtggcactggcagacttgaggtgcccaagtgaggctggtgcag
ccctctgcctgccagtctgggcacgggccctgggcatcgcgactcctaccttcctaccagcccagatgcagggcctgag
ccggcagggcttccacccagcccagggtgtgtcccccctacccagaggcgctgcattggataggaaggacccacctgtttccct
gcccagtaccagctggcaggccccccgtggctcagggtgcctgtgaggaggggtgggggctctaattgctcacctgctgctc
tgaggtgtcaggcagggttgggggtggcacctggggaaggctgggctgaggggcaggctgcccctcctgcaggagaggtgc
agtatttcactgggtcctttggaaagggcagggaagctcctgctcgcccgtactgcaccatttcctgtgatcttagcaatga
cttcctggctccatttttctccaccagtccgaatacatgagccagacccgcagctttctcttccacagcctcctggcctcgg
gtccacctgggtggtgcccacccgccagactggggcctggtggttgtaggggacggggagcagccttgcttcagtgtgggtc
attcctgactgtgagatggttgggggcagggttgtagagtctgtggaggcctcggctggcctcagagagggtatctc
ttctgcagaaaacccagccacccttaccagatgcggtcaggctacaaagggaagatgtgctccctctttagaggcaggtgat
tcctgtgaatccgatgaccgagataaggtgcacgattcagtgggcaaggcaactcaccatcctctctttatggtcctcgcaa
tttgcaccatgcacaatgcagggtgaagtcagccccccaaattacagaggaaagactctgcggtctttgtcagttaaacagga
gatgcaaactccaagctagttaatgagctgtgatcggccacgctcacgattcagtgcaggtctctccttcctgctatcacag
tctttgccggctgcatcatgactaccaaccagtcccctcataattacaagagtctcctgtcatgttttcttctggagcgagg
catgctccaacttgcttctgggttcttaattttgatcagggacggctccttgactaattatttggcagtaatgaggagga
cagatcgagttgtgaaagtccccccaagctttagaaggaagctgcaaattaaaaaatgaggtattggtaaacaggatgct
aattggattaatatgaaaatgatgaattctgataaaaatagcaaaatacacggttgtaagattgaggccagtataactccaa
gaattcattgtctaatgttcagctggtcagtctggtctttgaaagtattagaataacagaaagagtctactcttgacgatga
agtatacggttagtaatttatgcaaaacagaactttaaaaccggaaggacttgatatgagtggggtgcatggaaatcattcg
tattttgaagtttcataactctgacccctaggtcctttggtttgtctctcttttcttttttttttttttagacaatttct
ctctctgtcacccaggctggagtgcagtggcatgatcttggctcactgaaacctccacctcccaggttcaagcgattctcct

FIG. 4 (Continued)

gcctcagcctcctgagtggctgggattacaggcatgaaccaccgtgcccggcctttttttttttttttttttaagagaca
gaatcaccaggcaaggtggctcacacctgtaatcccagcactttgggaggccaaggcaggtggatcaccaggtcaggagttt
gagaccaacctggccaacatacagtgaaaccccatctctactaaaaatacaaaaattagctgggtatagtaattccagctac
ttgggaggctgaggcaggagaatcgcttttgaagcccaggaggcggagtttgtggtgagctgagatcgcaccattgtactcca
gcctgggcaacaagagcaaaactctgtctcaaaaaaaaaaaaaaaaaaaaaaaaaaaaagagagagagagagagagaatctcac
tctgcagcctaggctggtgtgcagtggtgcagtcacagctgaccacagcctccaactgctgggctcaggccatcctcttgcc
tgtgtcctgagtagctgtgaccatagacacacaccaccacatccagttaatttagttttgttgtttcttgctttagagaca
gggtcttgctatgtatcccacactaatgaatgtaaaatcttaaaatggtgcctggtgcagagtaagctgtgtgtttggtgggg
tgtaattatgggtcatattgacagtttcacttctgcggcatgccctcaggaactcactgatgcacacagagggacctgctgg
caaatactgaagagctgtggggagaaaggaagggtctgacagtgaaggtgggtgcgtgggcgggggctttaatggtccc
tctgctggctccctccccaccacctcctgcccacctccctggccttggctgcaggctagggtgcccttgacctcaaagagg
cctgtcctgtgtgtctcactgagcaggaacaaacggtcccagaagcccttcagctcggaagtgagtaagcattggcggtggg
gatggtgctctgagcagacgcgactcagtgccatgcgggcgtctctcccagggcggctttcagactgacccccaaacagagg
gctcagaaaagatgtttttcaatgagggacatttatggttggcaaaaaaaagtggctccccaaaggtcttcacgtcccaatc
cccagaacccgtgtctatgttatttcccatggcaaaggggacggtgattcagctatttgagatggggaggccatctggcag
gatccaggtgggtccagtgtcatcaggggggcccacaagaggggtgagagagggagctgatgatggaggcagaggttggagg
gatgcatttcagagatggaggaaagtgtcacatgccaaggaatatgcctgcggaagcaggagaggacggggaggtagggatt
gtcccagggcctccagaaccaagagaagacagggagtagggattctcccagggcccccaaagacaggaagagggggaaat
gtattctccggggtctccagaagcagccagccctgcccgcagtttggctttagctccctggtacccatctcggactctgac
ctacagaactgtaagagagtaaatttatctcattctgtgctgctcattgtgtggtcattggttacggcagccacagaaaaca
gacagtgcgcacatccgcatggtcccctctccagctcttgcctgataggcataaacgagggcagctgggcgcggtggctcac
gcttgcaatcccagcactttgggaggccgaggcgggtggatcatgaggtcagaagattgaaactatcctggcccacatggtg
aaaccccgtttctactaaaaatacaaaaaattagccaggcgtggtggcacgtgcctgtagtcccagctattcaggaggctga
ggcatgagaatcgcttgaacctgggaggcaaaggttgcagtgagccaagatggagccactgcactccagcctgggcgacaga
gagagattctgtctcaaaaaaaaaaaaaaaagaaagaaaaaaagtaaaaagaaaaaaaggaaataaacaagggcttgccctg
tagttcacatctggaccacccagcttaaaatagggcagggagttcaggaatagctttgcaacccttgtgttacggtgcaca
ggtgtgcaaaaattctccttgaactccccttcagtgtcccccagggctcatggccactgtcactctgtgctagttgctct
tcagaccagggaacagacttggccatggctatggccagggtccagctgctattgctcctcctgtcacccacccacctttgt
ctccaacaaggatgttgagaggagccaggcaccagcctccctgggttcaggtctttcctctccctcactttcctatgaact
aggggtggggaggaggagtgcctgccaggaggtcactgcagccaaggaacccaaattggtgtgcttgagaatgacccatgg
atacactttccaaagagtcacccggctgcgatgaggggccatctcccctcctggagccaacagccatgagtagctgtcacac
acatccgtgcagcacctagacacacatccgtgctgtccactccgtgctgctgcaattgtggggaggaaggtggcacagtgg
cagcgacacacacttccctctccaaaattggggcggggctcctcaaaatcctctgaccagcattaaagattcagaatttgat
attatggctgcatataatgttgaattatctgaacttgctgcacgtgtgtgtgtgtgtgtgtgtgtgtgtgtgtattgttg
gtaggaccaaaacggttaattatcagcaatttcatggtttgacctaatatttaaaagagaggttcttacctgctggaagca
tgtactggtgtattacggatgagacggtctcataggtggaatttgctgtgaaatgccccaggaaacaaaaagccagaggtca
gagtgatgagagctggggacgggtggatgggttcctgggccgttccctgtagtgctgagtgtgcttggaagtgtccacaatg
aggagtagaaacgagtacaaagctgggtggagacagccctgtcctggctgccctgagctcggccctgtcagtcgccttgagg
agggttgggggagcagggatgcagggtggcgcgtgcatgccaggtggcaggcggcaggtgctggctccaggccgtctcca
gccccagggctccaggccatgctccgcccccagctgccctgcagctccaggccggccacgctgccgcctagtttcgcaactc
caatgtcatcacctaggtgacagggacgctgctgccaccgcccgcctgcgggagccaggagccagccgagggccacttccac
ctggccccaccgaccctccgggggcccaggcttagccaaggtaggcttgggcttggctcgccctcctctcggcctgagtcggg
gggagtctccttgccaccgtgggtgcagtggctcggggggcccacctggggtgcagagagcccctctacggcctcccagga
ggcgggcttggaaatgcagtactgttcaggccagggtggggaggccttgcccacagttctcctgatgggacaagccacagctc
tggggagccatctgccccaagtggcacatcagggctcctcgtgtgaccctaggatcgggggcagaagtggctctggtaccgc
cacctccaccccttggacccaccaggagctctttccacttcctgccaaggaggcgcagagtgactgccccagcctggcacgt
ccgggggcttcccggctggggccgccatcctcagcctcacacagctgatccagaacctcccagttctccccagccccctca
ctctttgtggcccggagcctctcccggcaacagcaagccatgccccggcctccccggcactcacgcagctactcccaagc
ctgaccatgacgtggacggcaggaagggctgggcatgtcctgttccttctgcctgggtcctgcttccagggctggactccc
aggctggggaatcctcagggacccatcaaactggggacagggagggcttgtggggatttgctgtgaggagggcagagtg
tgtacgtggcagtgcctgcggacacatgtgtgcgcatatgtgaataggtgtgtccatgtgcatgtatgtgcaagtgtgttgc
tagaggtgagagggtgggtagggaaactgagtgaccagctcctccctgaagccttgggggaatgtccgagggccagggcct
ctggatcctgttcccttggctctttgcaaagtctccagcctggcctcctggatgggcatgtggctcgggggcgagaccatg
ggctcttcctggcttgctgtgtcgctctgggtgcgttttacaccactctgaggatctctctgctcatccctaaggcaggat
gatgatggggccaggggaccacatgggcacaggtaaggcagggatgatgatggggccgggggaccacatgggcacaggcttc

FIG. 4 (Continued)

tggaatgtgggtgtcgtctccctggggtcccgcagtctgaactcaagactcaagagccccatgtccaggtggggatgtaccg
gagccccttagaagtggggaagaaggccaggcgtggtggctcacatctgtaatcccagcactctgggaggctgaggcgggtg
gatcaacagaggtcaggagttcgagagcaacctggccaacatggtgaaccctgtctctactaaaaatacaaaaattagctgg
gcgtggtggcgcacacagctgtaatcccagctactgggaggctgagtcagaagaatcatttgaacctggaaggcggaggtt
gcagtgagctgagatcgtaccactgcactccagcctgggtgacagagcgagactctatctcaaaaaaaataaaataaaataa
aaaagataggaaaagaaaaagaaaaagtgaggagaaatgaggaggaagtcgagcaatttaaccccaaatggtgcttctccag
cagtcactctgttcctgtcctgacctgacctgctgggccccgccgctcaaaccaaatcatggattctgtcatcgcttcttc
acggagcacctactgtgtgccaggcgggtgctggggctgcagcgcagagagcagtcagggcttggtggtctggccccgcaaag
agtcagcatgtgaatgtctctccatgcgatgggtgctgggagggaggagccctggcaggtctggggaagaccagcgtctctt
aaatggggtgcgcgggccctgaggagtgaggcttcctgacagccgtccctcgtgggtgccatgctggtcagagtggggtct
ggctgcacagcctccctcagggctgggctggaagcacaggtcggctggcacctgtccaggtttcagggttccagggctccag
ctggaactgcctcagggatggcaggggtgggcctgtccctggagaggcgtggggtgtgggagctgggagcgtgacgggaagc
agcccctcagacctggagtagcatggagcctaggatccattgtgaccttggtggtcctgtaccctgtccagctccagttgc
tgttcctgcctctccctgacctactggctgcccaggctgccccttggccgagctccaccatggccagtgcccctccattcgc
ttgtgagtcccacaagatcacagccctgcccagggcctaggcagctcttgggctgacccagccatcgtcgggagccccttc
gtgacgggggcaaaggctggatcgttgtctgccctgcaggagccggggcctccagaggacgggctgcctggcgggaaggtgg
agctcacggagcccagcctaagccagctgtggtgcttctgagatgtgcggccctgggcaggctgctcgccctctcggggcc
tctgggaacacctggggacttcccgctgggttcctctgaggattgaatgagcttgaaaatatggaggatttggcacaggaa
tgctgggcagcaatatcagaaaggcaaccctgagagccagcggacagccactctgaggaacagcagtggctgcctctggaag
gagtgaggggtgggtggaccccgtgatcgctgcacgggggaggtcacggggctgagcggccaccactgtgcaggggaggtc
acagggctgagcggctgactccagaacaggaagggaacacgccaggagggaggattgctcactgagtcagggcgggactcag
agggacgcatgacaagttcagggagttgacagctgtctggaagggcacgtctgctcagaccgcagggtagggagtggtcagc
agggagacatgtcccactggtgcagcgggcgtgtcccagaccccttagagaaagcccagagccaggggtgaggggtatgtgt
agggtggggacatctcagagtggagcatccccaccaagggtgtccagaggagggtggccaggtggggacagcagcttgagaa
gggtcattctctcttggttggaggagtggaagtgcttctctggggaaagaaagaagattctggaggacagcacaggcacttc
caacatgggcgctggccgcacaaaggctagtgacacccggtgtgatcccttggggtagaaggggggtgtgagaggaggatcg
gagggggcagaggacagggatgtgtctgtgcagaacgaggctgtggcagctccagcgaaggcggctgcggccccatcagtca
cctgccctgctgagggcagcgctgtactcatcacctgtgaacacaggtatcgactcagacacccactctggccataagctcc
gctctgtcccagccctggaccccctcacccccatccttggcagtcggtcctctgggtcttcttcctgtgcccactgtgctgg
tctgaacctcccttagtgacagatctgctcctacccaccccgccagggtcgcccttcctctaacaggtgggctcctggcagg
aaacatcacccaagctcagcgccccagttccctgacagggccccacttccctcctgccgccaacctcgtcccccaagggcca
tgtccctgcccacccctttcaccccttcttagaggaagctcagcccatcaggccgctcatgcttctgaccccacctccaaa
ccctcctgacccgcttacccccaggagcaccgcccactccaaggcgcaagcaagctggggctggggtgcagacttctcttcc
accacccacccctcctcatacccagcctctgagggcctcacagacatacatgatttgcctccagtgggccagggttatctgtt
taccgcgttgcatgccccgggcatggagctggcaccggctgccgctgcaactgggcactacccgttccgaggacgcctcat
tccctgagagactgaggataggctggtgctctgcaaaagggtgcggagaccactgtaaaagtggggtgagacacgcgtgctg
accatgaaatggagaggcactcgaaggagccagggacccggcagccagcagaccccaccttccgccccgtgtgtgcagtt
ctgtcgctcagcctggtgcctttgggacccgggcctcattggttcttcctccactgccaccacctgatactaaataacgtc
ggtcaatggcaactcgatacggtttatggggcatccacggtgtgcccagatagaggagtgctttcgctttgatatgcgtag
agttacttcattccacctagcgcttctaggaggcactacaattatctccatttacagacaaggaaacagaggctcagaatg
ggcaagacatctatctgaggtcacacagctagagcgcggcagaggtgggctgcgtgggcagagcaggagagggaactggagt
gtgtgccccggcagtgctgggcttcagggcacgaagcggtggggcaggaatcatgtgtcttggtatgacccaaacacatatat
gacagcaagaaggcctgggcaggcagcagaggacaaggcgggcctcttggatgtctggatgtggattgggcctcaatgtacc
ggtgaagatagatggacaggcagggatttccagagaggggctttcccaggcagggtgcggggtgtggctgtgcggtgggaac
acggactggggagggggattgcagccgggcccgtgcctcccttgctcagctccaggtcaggcccagggtagagccaggctgctg
ggttcgacctccaccctgaccagctgtgtgcccatggagggctggtcttccctctctgtgcatgtctcctggttggtaacag
gtgtgtggcctcactgggccgtcgtggggtggctggaatccccgggaattagccatgctttggtgtttctacatttcacttg
gctgagtgtgaactgacccaggaagctggttggggcacccccacccacgggggtcgggcatttttggtttggtcatggcct
caaagcttctggggtgaggctcagggattccccagactgtcctgggcatctgcctcccctcccctcccgcttcccgtgggc
cacggcccaggagagagagggcagcttgctcaggcacctccagctgtccgcatatttcacacggtgcacgctacccacccgt
gggaggctgtgtttgtctttcatccccatgctgggcttccccaaactaggggagtggggcagcaggcgtgccatctgtggcg
gtgagggggctctcagccgcatcctcctcacaggccctgcggacaggccttcgtccctgccctgacctgctgacgaagc
cgtcctggcaaccctgtctgaaggacctggccccatcgtacccacagagggaggccacatggtccttagcctctgtcggag
gggcaggcaatgctggcagagggccttgcccctgagagggaggccctcctggccctcactccgggggacccctgtccttggc
cccagcctgccaagcgagagcggccctctttcttgcggtggctggaggggagagtgaggcccttggcacagagggccccag

FIG. 4 (Continued)

gaggctgggctctgatgacgccctgcaggaattccgctgggctgctgcctgggagagccgctgtctcacaagggccagcct
gcctggcttcattctggtgcgctgaccgcccgaccccctctgcccaggcggggctcttctgggttctgggtcctgggacctg
cctgagtccctgggaaaagggcacaaggggattgagacggtctcctcccacaatggcccaggtgtctcctcccacaatggcc
caggtgtctcctcccacaatggcccaggtgtctcctcccacaatggcccaggtgtctcctcccacaatggcccaggtgtctc
ctcccacaatggcccaggtgtctcctcccacaatggcccaggtgtctcctcccacaatggcccaggtgtctcctcccacaat
ggcccaggtgtctcctcccacaatggcccaggtgtctcctcccacaatggcccaggtgtctcctcccacaatggcccaggtg
tctcctcccacaatggcccaggtgtctcctcccacaatggcccaggtgtctcctcccacaatggcccaggtttctttgcca
cttcagattggaatcgttgatctgctgaaataacaggtaaatcattggtggtttgggaacccaccggaatcagaagtgcatt
gagatgtttgctttagggtggcccggggcgggtggagttcctggggctttccctcctccctgaatggaggaggacaccc
tgcacccctcctgtgatccccttaagagccagtgtccgggatggctgggccagacggggcagaggggcctgtgtctcctgc
ccaggctgagtgcggacggctcggtctcagagctccaccgagggtgggtaggtaacagcagccctgcggccagggcccctg
caggtgggagtgggtgtccccatggggagtgcctcttccagagtgggctcagtcggggtggagtgtcctggcttatcaaagg
tggttgtggagccctgtctgccccaggcctgggcagaggtggaaggggttggggaactgacgaggccttacctgtgggccca
tggccaaggaaatgtctggtctcccacctcctgtcaggtggtgaggggagaggatggggcgtcagccggagacggggttcct
agaggaggctgggtcctggcctggcctggagagataggggatgagatgggagggcaggaagggggtggtagacaaaggctgaa
cacagagagcacatagccaggcatgtggggactggggacaggggacaaggagggcacccatggggacaagagataggagag
gacagagggacaggagacggggagggacagaggatggggacaaggaggggacaggaggacggggacagggagggggacacag
aaacaggagctaggacggggacagaggatgggagaaggagaggtcaaaggacagggaacagggagggggacccatggggata
gggcagggatctatggggacaagggacagggaggggacagagaaacaggagatggggaggggacagagggatgcagacaggg
aggggatagaagatgggggctaggggacaaagggaaagggacagggaaggaacctatgggggacagggagacagggggac
agggagaggacagaggaacagggacagggaggggatgcttggggacagggagggaatgcttgggacaggcaggggacag
ggggctgtggctttcgtgggaagctatggaagacgaggccagaggggttgggcagggtgagatgagagaggctgagagcccc
tcaccggctgcggactcctcccacagggcagaggggagcattcgggtgcggccaggccatcagaggacctgggcttggctg
gagtcccagctcctcagccctcagtagctttgggccagccactgggcctcctggcctccacttgctcatctctgaactgggg
cagggttggcgtgtgagcctgaggccctgcaaagtgcctggccagcctcagctcggagccatggcacagcaccccctctccg
ccacggccccgacagctgggcgtgcgttctgctgtgggcagctgccctgagcaacgtagggtgctaagcagcatccctgtct
tgcacactagattccacagcaccctctgacccgtggaaaatgtccccacatgggaatatcctctggggtggaactgcccc
tggtgagaaccccctaggctgagacctcagaaggccctgagtcaaaccgagaagtcatcagagagccttgtttcagctccag
ggagcttgggcaggctggtttctgggccacacagtcccctccccagcccacctgtgctccgtgggtccggggaagctgtg
ggggcctaattgctggtgtgagttcctttcctgttctgagtcacacgtgtgtgggggctctccctgtggtgcagctggtaca
gcggcccctggagttgaggatccaagcaggctgaggtctgggtttgccggagggccctcggtggctggtctttgtcctgctc
ccactgctgtgggcactgtaggacttggaacgctggtcacctttccagcctggcaaaggagggggacttgtctgaggcctca
tggaagttggggcagggtcgaggtgccctgcttcctgggtgtgccagcagcctacagcctggctacagcgtaaccaggaaca
cccagcacaactgtcctttgcaactctgtgccctgacttgatggtgccagggctgggggggtgccggccagcagctccccaa
tgaccaccccaaatgctgtggccacacaaagccttccactgcaagacctgtggtaatacacactggacgcccctgttacaa
ctgagaactcatttatttcatttccttccttccctttttttttttttttttttagagttgtggtctagctctgttgcccag
actggagtgcagtggtgcaatcatggctcactgcagcctcgagcccctgggctcaagtgattctcccacctcagcaccctgc
gtggtttggactgcaggcacatgccatcacgccctcatgcccagctaatatttttttaagtttttggagagctgaggtctcc
ctgtgttgcccaggctggtctcaagcccttgggctcaagtaatcctccctccttggcctcctaaagtgttgggattacagtt
atgaaccactgcacccagcccatccctcctagactaaatcttcttagaaaaacctacacttccaataatgtatttgcatttt
atgatgttgataaaacttcctaaagatgtcttatgaaattggtctcctttccccattgatacacatgattttaaaactatt
ggcaacgtttcaaaagcaatttctgttttgtcccagaaccgtgatccccttgtgaacgaattttcaaattaaaggcaaatg
gttgggaaaattggatttaattgaaaggccatttttattagaattgacttatttttctcgccactgggatccttgcctgaaag
gcggctgtggcagagggcacatactcccctgcccagcgcagcgtccctgcacccccaacagagcttcctgttcctcatg
cccagtactcccagatgcctgcggagccagtcatcagctcaggtgtgtgaggccggttggggagcccctgcctggcgcctg
tgcctgtgagcagtgttcctgtggggccctgggaccaatgctaccagcgttggcgtttcccaggaagttgggaatcaggca
tctcgtggcttccggttcaagttcctccgtgtgctttaagtctgggcaggtttcgggtcctggttttggctaatgaggaac
ccgattcccatggggaggccggtggctgcagcagggccccgagcagtggcaaggctggccctcatgacagtgtcctcctca
ggggcctgtcccaggctcttcatgactcccctggaggcttgttaaagggcagattcctgggccctgccccagcccccactg
tggggagggtgtcctggaagatgcatctgcccagggcttccggctggtccacacgcctgcacctggaggcccactgcccac
atctcaggcaaacaggcctggggatgtttggggacccaactcctggcgtggaggaagcccctttcccacccccacatgctcct
ggtggtggcctgtcctgtgagcctggagggcggacgggtggatcggggacccacgaccacgctcgctggcctctgtcctg
tgcccaggcagggatgagaggccaagctggtgtcctgcagtgcacagtgggtgcggtcaggggatgtggaagctgggtctc
cggcaggcagaggcgcgctgacaagaagggtcgctgttcctcattcagggttcagtgggaagagagggtgtcgcttcaggg
gagttcacaggatgccgacttgaaaatacagccaacgcccatgtcccaggcataagatcacaaatcatgtttgccgaccag

FIG. 4 (Continued)

ttcctgtgagccctgagccctgcgcggagggatgccccgtgcacacctgttcacggaaccccctggacctccagtaggggtgc
ggcgggatgccgtcggctcccacgctgtctgtctccctgtccctctctctttccctctgtttctctgtctgtctctgtctgt
ctctgtctccctgtctctctccatctctctctgtctctctcccgtctctctgtctctgtctctctccatctctctgtctct
ctttgtccttgtctctccctgtctctgtctctctcactctctgtctctctttgtccttgtctctctgttttgtctctctttg
tccctgtctctctgtctctgtctctctctctttgtccttgtatctctctgtctctctttgtccctgtctctctctgcctt
tgtctctctccgtctctctttgtccctgtctctctctgcctttgtctctctccgtctctctttgtccttgtctctctgtttt
gtctctctttgtccctgtctctctgtctctgtctctgtctctctttgtccttgtatctctctgtctctctttgtccctgtct
ctctctgcctttgtctctctccgtctctctgtctctctttcctgtctctctctatctctttccctgtctctttctgtctctct
ttgtctctctctttgtccctgtctctctgtctctctttcctgtctttctctttctttgtccttgtctctctctctctgtctct
ctctttcctgtctctatccctgtctctatgtctctgtctctctttgtccttgtttctctctgtctctctgtctctgtctctct
ctgtctttgtcccaccttagccttgggagggacagctcacaggctgacagatgaggtcatgtgtcctgagcatgaggtttt
caggtctcacccacgctgtagcatgtcagagcttcgttcctttcatggccgcgtaatgttccattgcttgctggcaccaca
tctcctgtgccggccctctgctgatgggcgtctgggctatgtgcaccgttcagctaccaggaatggtgctgctgtgaaggg
agctgggatttgtcatccacctgctgtggatggcaagtccatttccatctctggactcaggtggcccatctacaaaatgaa
ggggatgcgacccagaggcctctggggcaaaaccttcccaggcttgtcctcttggatctaagggaatttctttcctccgag
tccagcccctccagtgctcctgcccttcaggaaacatgcctggaccctcacttgtgcccacccagccttggccccacatac
ctgcaccaagaggctaccctactcatactgctcagcccaaagggacccacgtggggtatgggcaagggcgggttctgctct
ccccgggggccctgtgccagcctcagctggacctgcggttctgcttcctgtcacactctccaitttaaattaacggaatgg
tgcggtccccatgcacaccctcagctccactggggttttagcccagcccaggatcggaggcctgcaagggcacacccacctg
gccacgtgatggtgaagtggggtggggcagggcaaccaaattaacttctaattctaagagccctggagcattcatcaccag
cacttacagccgtgtgacctcacacaagtcacttaacccctctgagccttggggctcctgaaaagtggatggagcggtcacg
cccacctgggagaggtggcttgggccagcaccctctaagctgcttgtcccaggccatcatggctcacggaccgcccctcagc
ctggcctgtgccacttctccagggcccggcacgtggcagccacaggcttctatcagctcccgcctgcctggggaaggacaaa
aacgacaggttccaggccatggcctgcacccccgctggccgtgggcaggtccaggcctgcctgcctgagcattgcagggcgg
tggccaagcctgtcccatagcacctcaccgaggacctggtgaggctggcccaggggagaggtcacctcagccggggctgggg
ctgtgggcagggtgggctcgggttccctgtcccctccccagctgtgctctgcctggacactgccacctcctcatgggtgt
ccagggccactgggagctgggcccagggcttctcaggggagcaatggtggagacaaagaccagcggacgggcgctggggtca
gagctctccaatccctgggtgtctcctttctcaagccgtgaccaccagcagtggccggctgcaggacagggcagcttcaag
ttcccagccttgccaggcttccctgtggccctggggtgcaggaaggagcccagctcagaaggcgagggggcgtctgtgtcc
tgcagcagtgggcacagctaggctctagcccgggggcttggctgcagcctccagcgcagccctcacacacgctgttccccaaga
tggggtgaccgggacccggagccacctccaggtcccgggcatcagggagacccaaaccctggctgcatccccaggccaaacc
cagacacaggggatcgtaacagacccacaggcctcacacacttgttccggcccaagcatccccaggcccaaacctagacacag
tggatcataacagacccacaggcctcacacgcttgtcccggcccaagcatctcaaagagtctgctctcctgaaggccctcaag
gcagccccaggagcgggtgttgctgtcacccccctcttccaaggcgacggctctgagaagctcctgcctgcccagggcaccc
cacggatgggtctgatccaggcccgcccacctccaaggcagagctgcccacctggccttcggtttccagccgcggggaacagg
gtggacgaaatgacagtggagagggcacagggaggggcaaggcgggggcacctgctccagggatgccccaggcaggcccactt
gcctgccgcccccaccgaggctgtcacaggaggacagagcacgagttcccagggtgctcaggtgtcattccttccttcctgc
agAGCGAGCTGCCCTCGGAGGCCGGCGTGGGGAAGATGGCCCAGTCCACGCCCACCTCCCCTGATGGGGGCACCACGTTTGA
GCACCTCTGGAGCTCTCTGgtgagtgcgcttggctggccagagctgggggccccctgggaggcactctgggctagcctcagc
caccttcgctgggctaactgggccagagcaggagggtggccccgggaggactctgggctagccccagccacccctcactgag
actttgggctaaacttggcaaccctcactgggattctgggctagcctcgaccacccttgctgcactaactggaccagagcag
gagaggtggctccacactagtcttgggctagccttagccaccctcatcagcttggggacagggcgggtcggaggggcagga
agagggactgctgccctaggccttccctgggatgcaggaccaaaattcagactctttctctggccagctctggagaggc
ccatggccagcagaggcccagaataacagagcccatgactggctctgcctctctggcactcacagcagccctggaatggcag
gtggaggacagagatgggatgagagggaatgggaagggcaggagacgtaggcctcaccaggagtctcaggctagccttgagc
tctgggcctgggaggtattggggtgacacccaaactggggactgacgcttctatttcctctccctgccccagGGAACCAGA
CAGCACCTACTTCGACCTTCCCCAGTCAAGCGGGGGAATAATGAGGTGGTGGGCGGAACGGATTCCAGCATGGACGTCTTC
CACCTGGAGGGCATGACTACATCTGTCATGGgtgagtgggggggctgccctctgcaagaggactggagtggggacaacaaatg
tggcctgtcctgtcttgggagcctggcagaaccaggagatagcctcttggttgtacagcttcccctgtgggtttctgaggac
acttcaaattgcaaaggagaaaatgtatcagctcatgtaactgtcaatccagagataggaatggattcaggcatggctggat
ccaggtgtaggaagggcttcaggcatggctagatccaggtgtaggaagggcttcaggcacagctagatccagatgtaggaag
ggctttggacatgggtgggtccaggtgtaggaagggctttctactggtggatccaggtatagaaagggctttgggcatggctg
tgtccaggtgcttcacagctgcctcgctcagtctcttggtctgctttcccctgcagtgactttgttttaggccgcatctcc
tctcatggtgaagagtaccaggctccaccagcatgccctatccctgtggagaggagatccctctttcccatagtccagcag
tcctgcctcccgttgatctgaatgtggtcatgggcccatctctgagccacatctgtgcctctgattggcctggcctccacca

FIG. 4 (Continued)

tcagtggaacagggtgacaatggaatggagtggggtgggcctccccaccagggacccccaaaggaagatggaggtgctgtt
tccaggagaagaggactggatagggggcaggcagggccagtgaggcctccggcacccatcttggcaggctccccattcct
gggagtctcaagccctgccccattggctgctcctctgggggaaaaggccaggctgtgggagctggtggggggccacgctcctg
cctacctctctggctgccccatagccaggcctcgactgtgccgggaggtggatggcaggtgggcaccacacgtgaggagagag
caaagatcccgacctgggaggcccagcgaggccagccgtccccgctggactcgtcagctgctcggccccgcccacaggctgg
ctgccccgccccgcctccgccgcccagggattcgtaggtggggaatttgtttgcgctgcggaaaaccagcccgaactgtggg
gatacgcggaacagcgcgtctgggcagggtcgggcctccctcacttatgctcagcccgaaagggagggaggcgatgctggg
cctctggggcctgagagcaccgggcctggccctcctcctccctcaagtccccattccaggagctggagccccttccttgcc
cctgcgcacgactgactgtctgaggcatggggtgggcggcccagccaccctgagcactggagggagtggggctgtggggc
tccagtcagaacgaacagagtgaagcggggtggggagtgtagaggtggagggccgtgttgcctgttccgtctccattgcg
gatgctgggctggcccagagccatgtggggccagagaaggcacctccttgggcagccacagtcccgggggtcaattcctcc
gaggagcccctcagcctgtatctgagggttcgacggcctgcccctgccctcccaccctgctcaggagaccgtcccagtgga
aacactcgacagtgtctgcgcgtgttctagtcccgtgttatgggtgaggaaaccgaggcagatgctgggaaagggtggctg
gggatggggccgggtagtgcaagaaagtgagactgcaacctctcccctctctcgctttggaacagttctgccggctgctctc
tggggacaagggtcctgaccccacccctccaggtccccttctggacatccgtgtcctccaatctggggagggggcaggaact
ggccgctggacccagggagggagggaggaagacccataagattgtcccctgagatccagaagccacctcccaaccccaagt
tgctcagccactcccctgcagagggcagaaggccctaagatggcacagacccaccctgtgtcgggaggaggacctggact
cagggaggcagaaggagcagttctacattcctgagtgggtggagcgtgcttgtcctccccagccccggagggttccctgagc
tccatatcggggtctggtccgagccccgcctgctggaacgtgccactccccagccacagggtgacagtgggagcctcgaac
ctccgcaaacagcaaggtggctggatctgtctggcagcgacacgcctcctcccaaagccatgtatgaaattcctaggtgcac
agctcgactcacggagatggggattccctggaatgaaggcaggcccaggcctgcgtggggagagccaagcctcattctgac
cccagggcccagcccctcacaacagtggctgctgggccaagagcatgctgtccccctaccccctgactcccatgggagcgcca
ggtacaaagacagagactccgaagggcgccaacgggtgggctcgggcagcctggcacagggcccagggcttagctgccttga
gaatggcccctggcccgctaactccaggggtcccagagtggggctggagctgaactgggggcattgttttaaagttcagcc
caggagctcagggaagctgctgtgctggggctggggacctggacccggttcagtgcggatgcggcatggggggctctgagt
gcccctggaaaactgccacctgcagctcaggggcccagttctagccccaccacgaggctggtgaccttggacaagaacac
cacacaggcccggcctcgggtcagacaggcggttctagtgccggatgtttccggggctaccgatagtcctgagttcgtggct
caggtgggggcctgcttgtggaagtggctgcacacgcacctgccccacctgcccctggcggctccctctggccacctgtc
cctgggtgttggtggcatctggctgctcccatactcagggggcgggtctgggactcatccagcaaaggggcctcagctcgggc
aggcacagtgcttgagcgcaggacactggtcctctgcagtggggcgtgccttccgcatctggggggacgtgggtctccccgaa
ccacgagcaggcagattggttcccgttggacacagggtgtctgagggatgccttagccacctgcttagcagccgtgggagac
aggcggagcaggtggtttcaagctcccacaattctctgagcctccatgtccttgctggtgaagctggggtgacaggggtag
gagcccagagcagagagccctttgggaggtggcatagactctgggatgccaggtgctgggtgctggctctgcccaaccccgt
gggcctcggacaaccctcctgccacactggcccctgcagaggaggctgagtttaggcagttcaggagagtggggtgtgggca
agagcagttgaaccctcagtgggctctagaggagtcccaggccacagacttattggggagactgtgagctctgtgtggccat
agcaggaaacagacccgtggtcactgtggccatctgactgaggtggcccagaaagtccagcaggccgaggtgggtgtggct
ggggctccgaggccaggtttgctgagctcaggacctaccccttcccttctgagctgggcaactttaaagaattacatagc
cctctgggcctcagtttcctgtctataaatggcgctactgagaggctccaagtcacccacgatgtgaggatgtccagtggtg
ccgggcccatcgggagtatgtgacaaacgctaggtgtgagggtgagggcagggaggaggccctgtgtttaagaaagctgctc
ctcggacaccagaacagcagagccaggagggcctaggataggatctgggaccagggcctgctgcctttgcctggcacagttc
ctgcctgagctgtcccgtgccttaggctctggctgtccctgaagaccctacatggctcacagggacctcactctaaaatagg
gccccgttctgcaagaggagagcaggggaagcctgtggccgggcctccccatgggctggggagggtggccgaggagcca
cagctaaaactggcccagccctgccctctcaggaccctggctggttccctgaatgaggaaggcttgacgggcttctggatg
ccacctgggtggggtctgccctggccacccccacaccgtctgggaagagctgcagaggataaagctccctcgtaggctcgca
ggctgcgaggaggcagtgtgggtgtgatggtggggcgggggtcctatcctcacccggacccacccgaggagtctctgcagtg
ctgggcctgggcttggaagcgaatccctgcccctctgagcgctagcgtcccctcggacaaaaccagcgcagggcaatgagac
ctgcggcccttgctggctctcaggatgctccacaaggagggaggacacaggagggggagaaaggagagagaggcaagtgtct
cctccctcccctcccctccactctgctccgctcccgtcctctcccctcccctctctgtccctagagcctcctccagggctgg
cccctcccctgtgcccttcctgcctctcctggcgcctttctctgacaacaggtgttgtgggcaggtgggccacagagcggg
gtctacagctggtggggcagaaggcaggctgatctaccctgggagcccggggaacccagtggcaggacagacacccgggtc
agaaccttcggacacttggggcttgagaccctagaggtcacccagataggccttggtgacttcagggagaggtattctcc
ccaggcccaggagaaggaagggcgcaggtcccgtgcatgtgtggccccaggaaagggcaggcggacagagggagaaggaca
cccctcccttccagggaggatctgtagctggaggaagggtggggtcatgcgtgggagcagggagggggctcagctcaccacg
gtcagctctgagactccagcccacccgttacccctcccagagagccccactcagcctttcctttggtgggctttcgtgac
aaagcactttggggctgcacagaagtgaacccacccagcacccaggtctcagagccttgcagcttctgcggcctcttccat

FIG. 4 (Continued)

gcggtgggatgaagcccagctgcccagcagggacccctgtgccatgagtttggccttgaactgacacatcactggcaccaggaa
acgaagtcccccctgtctgttctggcacataaccctcccactaactggttcctgaagagtgccgtggcctgcggcagcgtcg
ttcccccctgtcctgcggcccagggtcctgcggaaagtcaggcggaatcccggtgagtcagaagcagaatgaaagcagaat
ggaggacccagcagggagggaacctggaggaggcgctaagggccacgccaagggggtgtggccccagatcccctgtccctgt
ccctctgcaaggctgggccttgggaacgtttgcagaaagctgggtgccgctctggggcagaggccagtggtttgggtgcttt
tgagttggaaacgtgtagctcagccgcactgggatccccgcagcctggcccagatgctaagggtggagagatgcggggtctc
aggcacggtgccctgggcatgggtggggctcgtgctgaaggcagcctggctgtcttccttcctcacgtccttccacttggcg
ctctcctttggctatttataaaaccatcaggccggccctgtgcatgggactcgcctgagtctccttttcaatgcatcattc
cctttggcaggagaggacaccgcctacagaggctgaggatgtgccctgtgggggtcgggagcggaacccaggcccggcctcg
gccctgctctgagggtctgtccatccctggggagccccgccccccaacccaagagggggtcccaggctcagaagcagaaggcacc
ctcatccccagggcatccccgatcccagcaggagtctcctagtgctcgccctgggctctcctgcaaggaggctgctgctttc
cccagaacatccagtctgggcccagccgaccccctgcaggggggcttcccagagacgcccttcctgaacctgatctaccaga
caaaactgtctttttctcagtcgtctcctcctgagtgctgctgcccttcctgttggggggctgagatcctctgccacaggaag
agacgggcgtccaggactcacctgctgcctccggccctagggccctgagctgggctctccaggcccagcccttggggca
caacacctggaatcgtccttttcgtcctcagcccggcctgctggtggggcagggcgggtccccagggctcctcaggcagctgc
agtccaaacctcccctgccctcacccagctctgcccgctctccgggggtggggtggggagcgatgaggccctgccggct
ctcggtggggacgacagggaggaaggaagctggggagatggagacaagagaaagcaggcaggtggtttgggatttggcagga
aaaggttggaaggaaagggaaagggtctccgcatggatttctcagctccccatggatttctcagccctcgtgagagccacg
gcgccctggggactggaagtgtgggtccgcaggccccagtccccaggtttgtctgagcatagatgccctgcctgcttccagg
gggactcgggccccctctgccagggtcaactttgtacccaagacggctgaaatacaatggaaattcagacggcccaacaggga
gtggcagtcacctcaaaggcccactagacgggtgcggggcacccactgcagagcccctccctggctgtgccaaggccgtcca
cgcctgcaggggggcccactgccgggctgttcttggcaacagtggcttgtccctgttcctggggggcttggccagtgccag
ggtgggctccaaacgcacggctctgggctcttggactcaccccctgctttgggcaggcagtggaaggcaggccccacaagagc
tgctcactcccgtcacctgtctccctcggggtctagggtcgaacctcctgtgagcccctcctctccatgcagcccttggac
tggtcctggcggaccaccgagttccccgcgcaggggcaggtgcgccccacctgggtgccaagggaggcgacaccatctctc
cccttggggtggcccagccttgcctaccatgatctccagggccggggctcagccctcatgcctgggaacagaggctgcttt
acggggtgagggcctggggccccccgagccttccccaggcaggcagcatctcggaaggagccctggtgggtttaattatgga
gccgggcgctgaccggcgtccccgccctccccacgcagcctccttggtgcggtccaacacatcaccgggcaagctgaggcctg
ccccggacttggatgaatactcatgaggaataaaggggtgggccgcggggttttgttgttggattcagccagttgacagaact
aagggagatgggaaaagcgaaaatgccaacaaacggcccgcatgttccccagcatcctcggctcctgcctcactagctgcgg
agcctctcccgctcggtccacgctgccgggcggccacgacgtgaccttcccctcgggccgcccagatccatgcctcgtcc
cacgggacaccagttccctggcgtgtgcagaccccccggcgcctaccatgctgtacgtcggtgaccccgcacggcacctcgc
cacggtaggtgtgacgcgccattcataggatctcttcggggactttgcgggggattttgctgcagtgtagggttcagaggg
catccttctgcctgccttcctggcctggagtctgctgccagttggggtgagcagaggtaggaagggaggcgttgaggggcta
gaggcaggtcccaggcatggaggcaagcagattcgggctccaacagcctgtgcccacctgctgggcagggacccgcagccag
ggagaggaggccgggtccatgccgatggggctgctggtgtttctgcctcgtgctcggggtctctgatgctccttggctttg
gggctggcggcttggtccaggctcagagtttccgagctgccctgccctgccccagctgccaggagctcagtgcaccctagaa
gtcatctttgctcctgggcttgggtgtgaagctgcccccgccctcatcagggaatttgctcatttgacagcagtggcagacg
gtgcttcttgtcagccccacgggctcttctcggtgtgggtctgagctccagggccaggacctgtggcaaactgggcttgagg
cctctttgcgccaccgcccccctgcagtgggctgctggcttggaagaggggagggaagggtctgcagcttgtggttggccct
gcagcctgagccctggggacctggcctcacttccagacttgccaggtccctgggggccaggcaggcaccagctgctaattga
gaaggtggaaggctcggcacagctgctccacgtggggccgttcctcctcccagggaagcagacagctgggaccatgggtacc
tgtgccacacgggaaactcagccatgggcaggggcagcgggcagataggcagagtccaagtgccccgaagctctgctggca
ctgggatgtagaggcccaaagatctggggacggaggcctttggagccgtgggctccccaggcagtgtgaccagggtgtgtgt
gacagcgatgtgtgtgagcgtgcacatcaatgtgcatgtggcgggtgggtattggtgtgcgtgcatgtgtgtgtctaagcgt
ggatgtgcatgcaatacgcagggcgaggatatgtgcagatgtgtgtgtgtatgttatgggtgtgtgtacaggctggtgtgtgt
gtatgtacacgtgtttgcctgtgtgttgtggtgtgtgtacgtgtgagcagattggtactgcaggtgtgattgtgtgatttgg
gtgggtaggtgctcacgtgtgtccgtatgtgtgttgcgatggatacatggatgtctgtgcctgtagctgtgtgttcccaggc
aaggctttgagaagagaggcagtgtgtgtgtgtggcccagagggtgggtgagggtgtgggtgacccagccccacagcctgcc
cagatgctgggtccatgcactcgagtctggcggcacccatggcctctccacacgcctgcgtgatctttttatctgaaacccag
tgctgggactgtagcccagagcgtggaacggctacatcaggcatggggtgtccctctctcccttgtctggctgtcacccact
tgtgcattgatacatgtatccaccaacacgttgctattagaaacgcacagcaggcctgggctcctgggggctgccttgta
cccccagactctcccaggaggtgtgtgagctgggagggctatctccggctgctggaccgcctggaacccgaggtggatcc
agaagcctcgggtggagaggccagtgtcgctgcctggccagccgagaagcctggggacctggggactctagtacaatcttt
tcccttgaatggagcagatgtcaccatgtgactcaccctctcggggactccacaaggttgagtatgtggttgcgcagacg

FIG. 4 (Continued)

ccattcccgggagggggtggggaggtggagccctgctgccctggcctgcagaccctcactgcctgcaggagctgctggtgtcc
actcggctgctgctgcccggtgccctgggcgtcagcaatggccagctgtgccatcactgtttcttttacaccaaggattac
tgtggttcgttcgttcatttgtccattcattcatcccatcagcaagtgttaactgggcacgttttgtgtgttaggctgagtg
ccaggagcaggtggaggcagtgcccagagccagccatgtctccagcacctcttccctctcggggggaggtgggctaggctgg
gccatcctaatgggcggagtggtgactcagtttccctgtttctgtgccagagagagtattcatgacctcatcttactgcagg
aacgtatttttgagagagaaagtggtatttggcccaaagggttttaaacccaaagtgagcgaatagagttgtattggagttgg
tggctttgtgaggccctggttattcctatcaaagcacagtagctgctccggagcccgctgggccagcctggccctgggaaga
ggcccctgggttgcaggacactgtctgagcccccagctgggcccgccaattgcccccagcctggcacagggttccaggtgtg
ggcttggggtctgtctctctggcatctgccagctgagtctttggtcagtgacgcgctctctgagcctcagtctcctctatg
atgaggacggtgttcaccgtagctgctcggctgcggggcccaatgggagccactggttacttgctgcagatggggacgcagg
ggggcctggcctggagagctgccgcctcagcccctcctcccacaatcccacccatgcagccttagcccctcctcctgcaatc
ccagccctgcagcctcagctcctcctcccacaatcccacccatgcagcctcagcccctcctcccgcaatcccagccctgcag
cctcagcccctcctcccgcaatcccagccatgcagcctcagctcctcctcccacaatcccacccatgcagcctccgcccctc
ctcccgcaatcccagccctgcagcctcagcccctcctcccgcaatcccagccatgcagcctcagcccctcctcccgcaatc
ccagccctgcagcctcagcccctcctcccgcaatcccagccatgcagcctcagcccctcctcccgcaatcccagccatgcag
cctcagcccctcctcccgcaatcccagccctgcattctcagcccctcctcccgcaatcccagccatgcagcctcagcccctc
ctcccgcaatcccagccctgcagcctcagcccctcctcccgcaatcccacccatgcagcctcagcccctcctcccgcaatc
ccagccctgcagcctcagcccctcctcccacaatcccacccatgcagcctcagcccctcctcccgcaatcccagccatgca
gcctcagcccctcctcccgcaatcccacccatgcagcctccgcccctcctcccgcaatcccagccatgcagcctcagcccc
tcctcccgcaatcccagccctgcagcctcagcccctcctcccgcaatcccagccatgcagcctcagcccctcctcccgcaat
cccagccatgcagcctcagcccctcctcccgcaatcccagccctgcagcctcagcccctcctcccgcaatcccagccatgca
gcctcagcccctcctcccgcaatcccagccatgcagcctcagcccctcctcccgcaatcccagccctgcagcctcagcccct
cctcccgcaatcccacccatgcagcctcagcccctcctcccgcaatcccacccatgcagcctcagcccctcctcctgcaatc
ccagccatgcagcctcagcccctcctcccgcaatcccagccatgcagcctcagcccctcctcctgcaatcccagccatgcag
cctcagacccttcctcccacaatcccacccatgcagcctcagcccctcctcctgcaatcccagccatgcagcctcagcccct
cctcctgcaatcccacccatgcatcttcagcccctcctcccgcaatcccagccctgcagcctcagcccctcctcctgcaatc
ccagccatgcagcctcagcccctcctcccgcaatcccagccatgctcttcacttgcttcccacactgtccttccacatgggg
gactggataatcctgtggtggctctggccaaacaaggccacgttctgagtctgcggctcccacggactggggttgatcaatg
cccaacccgaggtggacacagagacattacccacttctgcctgtagcaaggaaggagccgatggctggatgagtggggccc
ctctagaagaggctgagcgctggagacgtcggagctgggtgctgtctacccaacacccaggagtctccctgacttcccaaatg
tccagttcatggcccttgccccccacttcctcctggggccgctgttcttcagctttagggtctcaggaggttagccagggt
gatgggagacaccccctagctctcctgcgccctctctatggagggggctggagcctgtctcgccgcagggcctgggctgtgcac
ccttgggcctggcctgttcccaccctgcccctccgcatggtgggcatccatgcgttgcgggaacgtggccacccctgtgctg
aggagcagcacggacggatctggagctttggacaccccactcccgtgcgccccatggagccagtgtccactctgttcctgc
agaaagtgaaacctctgggcaggatgggcctccaggacagggccctggggcgggggaagccaatcagtgcagcaagctgca
gttactaggcacctactctgtacgtggggctacggaaccaagggacgcagctggcagacgttctgggagggcccccggctgc
agtgctggggatagaccacagggggggcagggccaaggccaggagccgcctgcaggctggacgatccagggaatggggcagc
cccgccggtcaggtggtaccacaccgtgggattctgggcaagatttgctgatgggctggatatgagggaagggggtgggggag
accccaagtttctgccctgagattggtagaactgcagcagagcaggggtgaaaacgccgcggtcggccgtggctgtgttgg
agatgcccggcagccattgcatagctgagaaggagccgcatgcagggaggaggacgacgagcgagcagttcccaaagcccca
tgagggaggggtttccagtggtcctggggcctgaaaagtgtgaccacctggtggctcagtcctgtgtgcatcagaggaggtg
gtgggtggtggtcaggcttagggtggagtttgaaggtgaccttagaggaagagcaggggaggattccagaaagatgctgagg
ttccatttgcacccttgcaggaggctctgctgctccccaaggcaggaaaggccggcaggtctggatgtgaggtgggtaagg
agttggggccacactggcaggagcggccatgtggacactcagttgctggtgtgggcaggcaggctgtggagacgacctctag
ggagtcctgcacatgggcacttacagtcagggctctggggatctgcacggaggcagggagagacagcggctggagctgagc
actgggcactacgacatccgagacacccaagcagaggggagatgcagaggggcagcctgggaggccaggaggcacgagaggc
tggctgggagaacagaaaagggactggggcttggcaacccagaggctgctgagttcccacggtttggagagggcagggccca
actgggaatggctcatgggattgctgagcatggccaagggagccctcagcatccctctccaggccttgtgtcatgaaagaccc
cgagcagcggtggggctcaagccatgtggggccaggggagggaccagttgtcctaactggagatccagggatcagaggagcc
acccactcacccgcctgctgtgcctagtgcacgcccgcctccggcccccctgccaccctcggccagctgctatttctgtct
cctttgttctgtccccattggacctcccccagtcaccagcctaataggacctcaacttgctaaacccaaactaaacttat
cttccctgagaggggatggtgccgtgtctcagccagcaggaaatccactctcgcctttgctcaggccagagccctggaggc
actctccatgcctgaggtcctgtgaatcctgcctgcaaatgtgcctggggccctgcggggcccacctcgcacccgcggccc
acgtcgcacccgcggcccacctcgcacccactgctcagatacatctcacaattgctgcctttgctgacgcccgccctgtgtt
ctcaacacccggagccagagggagcgctttgcagcccgggcgtctctgctcagctccgaccacctctcccgctatcccctg

FIG. 4 (Continued)

ggctccgtctctccctgcacaggccctcggcccttcctctggctgcaggctctctgccctgctggtccccagcctggaaacc
ccccaggcccacccaatacctggggcagatctttccctttcctgcaggcccgccttcaccttttcccgagcccgtccttgcc
tggacgccagccctggccccctgtgcctggctctgtgtttctgagaccactttttgatcccaagccccctgcacgcttgctggct
ggtttgtttactgtcgtcagcatggagggccgggggtcgtgtctcgtgccggctgccatcttcctgcacctgggagggtgcta
ggatgtcaagcctaggaaatgggtgtgaagaggagacctgcctttgcaggagctgaccaaggccagtgcactgggcgggacc
atccgtcactcctgagcccactaactggggaggggacaggcagagcggggctgggtgattcctgagcaagcatgctgctgtc
tctctggctctggggcctctgccctctgcctcgatggccccccacagccgtcctggaccgccttctccaccttgggctcct
gctccaatgtccgcttatcaccgagggccatcggaggtggcacgccccgtgactgcctcccctccctgtaccctgcactgc
acgtgtcataattcaagttctcggctcagccacccattctcggctcagccactaatgtgtgctggaaggtgtccaggaagcc
ctgctaagcatctgtcagtgtctccagcacagcaggaggctgttacaggtggcgcctgattcacatctgcaggacaggtgga
tggatgggcagacagatgggcaggggcatgtgtgcaaggacacaggatgtcagggctgacacctgggttgggctctggggtg
ctggcagcagggttcggagagggggagagaagcgtgtgtgagctgtgccttcccctcgtcttcccgggcactcggcattctg
ggtgggagggcctggaccagcccgtttccaggtggttaaataaagtctgtgcatcctgttggccacctgcctctcatagga
gcagcacagggcctgatggggatacagcctggataccccactggggcctcccgcagacactcagggtccaggctgcccctcg
ccacaacctggaagggagggggctggtggccagccctctggaggaggcctctcagggggaggtgggctttgagcgggatccgg
gaggcaggggggcagaagctgagggacgtggagaagggtctggggggaggaggcgggcgcacgtgagtggactccggggcggt
tagcaggtggaaggcagtgagggttgaggagagggtggggcgaggcccttgcaccaggccacagtgggcggctcaaatgtgg
gtccgtggaggcccgggggcaccaggctacccggaggtcatctgaaggtcacctgggcgtgtggagggacatgcatctgcaa
ggcccccatgtggcgctaagcacagagtgggtgctgcagacgggctcagccgctgcgggcaggtgcaggcaggatagcagcg
gtggccctgggcctcgcagtcctgcagacacacgtctggggactgctcctgggggcgcgtttctccggtgtgaggtgtggaa
agttccacatggccctggcacgggattgggcaaggcctcgcctcagcccgggtgagagcagagggtgctgtgggtgagagc
acagggtgctgtgggtgagagcagagggtgctgtggatgagagcagagggtgctgtgtgcacattgtcgggagagggaggct
tccccccagccgcatgtcgaatcttgttggcatttccattcgtttaatcacgggctccgggagatgctgtgggaagtacggg
caggacggaggtcttgccctggtgggatgggctctcttcctccgaagcccaggctgcttgtcagtcactcacccctgggtga
ggttggggcccaagttcagacatgcccacgagagatcaggagtttgaggagcggcatactctcaaaaaacccacaacagtct
ggtctcaatattctccagggaacgaggacacggacctccttgttctacaagagctggggtcacagctcagagcccctgtcca
ggctggagggagaaggccaggaggccagagggaggccagctgagccctcaggagactccaggcaggcccccgatgccagactc
cagccctcaaacatgctgcctctggaaacgtctgtcacgggcacaccatgcaccatgccatggctgccagtggtggatgaa
gaagagcatgtctctgcccgtctggagctcccggttcctgtcctagttgaacagaatgaatgagagtgcggggataaatgcc
gggcgggagcagggatgctcgggcgggggcaggagctggagaggtgacaggagcgagggaggcggaggtggagctggggag
gggccagcggggcgtcaggatttcagctgacatccctactacgcttttcacgtgcctccctctctgactcggatcctaagt
gattaggatcagaggaatctctgtttccaagagaagggggactgcatggccagaccgtgggctcgggccccagtctcctgat
ctccgccaagcccagggcccccaggaagcggccccatccttgggagctgtcctggcctcagctcccaaggatggggtccctcg
ggaagctgttattgctgtctacggggcaggagctccgtctttcgagcctctgcacttgtggagacaaaggtttccgaatgag
catttgtgccccgccctccccacccacccctgccaggcccaatgcagggaccaggctgcatgtgccttccccgcctcacatct
cctccgctggaggagtcagccaaaaccgtggcctttggagatgtggccagagtcattgtgaatttgctggcaggtttctct
gttgtcatttccactaaaaatacgttccgttctggacagtaccacatctgtcccctgtcatccgatggcacggtcgtgacc
tcccatgccttgctttgcattgtgtcttaaatatcctaggctctgataaaaggcactgtggatacgggaagcgagaggagt
ggactagggggggaacagggacacaaacttgaaaaagatttatttcccatctacttgtaaaaaaaatcactcaaatgccccac
gcctgtaatcccagcactttgggaggctgaggtgggcagatcacctgaggtcaggagttcgagaccagcctggccaacatgg
tgaaaccccgtctctactaaaaatacaaaaattagccgtctgtaatcccagctactggggaggctgaggcaagataatcgct
tgaacccaggaggtggaagttgcagtgagccgagatcccaccactgcactccagcctgggcgacacagtgagacttcgtctc
aaaaaaaaaaaaagtcacttgagacggtttacacattttaaacagtcaacaggtgcaatgggaatctttaacaaaaccaca
aaatccaacttaatctgaaatagaacagaacccatgcggcgggagggtgatgatggggcccagctccctccagctcctggc
cggtgaggacaaagagtctttcaagggggctgtccccgccctccacattctgaggaaggcagcctggaccctgggcactgtct
gggcttggggctgtggccgacatggcgggcagtggcacaccgtggccacttcccccagttggatggcccgcgtggatttcag
ggtctgtttcatccaaccaagagtttctgagcgtcctgtcggtactggctatctggacacctcggggaacaggagagacccc
gacccctgtgagcacctgcccccgagagcacctgctcttcccatccgtccctgtgcccagggcttagcgactgtcctctgc
gtagtgaatctggattcccgtccctgttcctcggcgggagcctgcccagccgtcgttcctcctggctgggtttttgtgcccag
gcgtggaggtcatgcctcgtgcatgggagcttcctggacattggttccaggagggctccgggcgagagtcacttccgatga
agtctcaggttaccatacttctggaccctcttgatccccacaaccatcctacgaagtccacgttgatttcctttttggtttt
tttcgagacagagtcttgctctgtcacccaggctggagtgctgtggcgtgatctcagctcactgcaacctctgcctcccggg
ttcaagcaattctcctttgctcatcctcccaagtagctgggattacaggtgcccaccaccacgcccagctaattttttttgt
agtttagtagagacggggtttcaccatattggctaggccagtcttgaactccggacctcaggtgatccgcctgcctcgtcc
tcccaaattgctgggatgacaggcatgagccaccacgcctggccagtacatgttgatttcatccccactctgcagatgagaa

FIG. 4 (Continued)

aacgaagacctagggaggtggagcgatgggccaggttacacaggtggagctgagacttggccccaggactcctgacctcaga
gccctgcttggcccccaggtccctgggaggtctctcctgccctctcctggatgggcagagaggcctggtttccaggatgg
tggcgtaggggcatcagtagacccagaagaacctgctgttctgggatgggcagccctggccaccacttcctgcccacctgt
gggaaccccagacctcagccatcacgtccccagcttggccgacggtagatgctggtgcttggattggggtgtccagccag
tgggatggggcttcagggctgggctgagctctggcctccccacactgctccctctgctctcagacaggcaggccagggg
caggcgggaccctccacagccctcctggagggggcccagctactgggtggcctctcagtctctgaccctcatttggagca
aggtcactggcctgctgccacccccaggggcatgggtggatcaaaccagtgaggtctgggaactgtgttgatacctgtgactg
gcccaggcgagagagcagccccatttacccactgcctgctgcccacacccagccccagccccagccccagcccagagct
aatctccagcacaggtgcacccagggaggtccccaacccatccgcagggaggagagatgaggcctcctgggtgggtgcgtgg
gggctgcagtatttcccctggcagagcactcctgcccgcaacaaggccctggggcccagcagggcctggtgcgtccgcgg
cctggaggctggcgggaaggccacccgctggctctctggctcccgcgcactccttgggtcaggcccaggagccctgcacaca
catgtaggcacttgtggccgccgcgggccgggcgtgtcctaattagccccactatcttgggagctcttgttgaaagcaaaaca
aaccaaaaaagtcctggttgtgccgggttcctccccgtggcttcgggggccctctggttgtgggagacccgggctcctg
tgcaggcctgtgttaggttcagggttccctgtttcagcagcttgaccccgagcaggagccaggccccagggaaagctccttg
ccgccaggcaggaagcgaaagggaagaccagagtccccgagccaggtggagggcttgtggaggatgcctggggaggccta
aggggaggtcagagacccagaaagcccctacacttcccagatgctgcgttcccagctgcattcataactgcagctgcaaa
gcctctgccacccactggggtgtgacaggggcggtgaccacaggcagggccagcgtgcagggagagaggtcccctggaagc
aggaggagaggacagcgtccccggcagaggacaggcccagtaaccctgggaggagggggcttcagaggccccaccccg
tgtcactgagcctgaggatgagaggggaccagagggagaggccgacatcggggccctgcctgaggaaggccctgctaaggga
gcctgcctggggccctgggccacagaggacggcaccgagagggcttcaggcctgctgtccggacacttgtccactaattagg
attcccgcgtggggccgcctgccgcaagggcctggctcactcccgctgggctgtgctaggcgcagagatcctatcagctctt
ctcctcttgcctcaatgactaattccttggcaccttcctcagatcatacaagaatgtggacaagttaaaatatgaaacacgt
tgtcgtgggtctgcatcctgcttctcccaaacaagggaggcatgggctttttgccccactggctgtcctgttctcagggatg
gagcagggatgggagtcgggcaggggacctggagcctgcccttgcctgtcatcctgacctgagaagcctcagctgggcag
cccttgagccccgggatgttcttgcccgggggactcaaatgagtcaggaatgggaagtcgtgcatcctgaggccatcccc
gggcccaaaacagggaagaccttccaggaaggccaccgctggtcacctggaagagagagggcaccacggagagggggaggt
gggcaggctggcacccggtacccggtgatgggaggggcggctcatgtcccacactcactcctgggcagctggactgggga
gccgtcctgcattcgcttgttcgtttgttctgccagctcgcttgttcagcgagcctttcaagcagccacgctgtaatagggag
cacggactgagggtgtcggctccgagccgtgtgtgtaattctgcttttttctagtagccgcattcaaaaaggtggaaaggagc
tggcggaagtcatttaattatttcctgtattcacccgtaactgtgatcgtttcagcctgtaatcagtaggaaatggtgagcg
aggtgtttccgttctttccgtggtcctgagcccttggaatcggggtgcgctcacacactgggctcaggtccatccacattt
cacacacccccacccctgtgtggccagtggccaccgtatccagggtcctcgtgggttcacagtcgagtaggggagacagaagc
catggggacatgcgagcctgcccttccggagaatggctagaaagatgctcaaaccgggtgacgaaagagaacacctgaggc
ctgggcgctgctcctgcccgtgtggccagggctgacccctcggaacagtgacctctgagcccggacagggctggtgaaggt
cgtgtgcagaccacaagtgcaggcttccaggaagggcctgggccgtggtcgtaagcaggtctcagacacctcagaggcctc
ttgggcctcggtgaggagtctgggagcgggggactctggggcggggcctgggctgtgcgaccagagcctggcactgcccctt
gtcacccccacccatcacccaacctcccatgtgtgtagctgaggcaggggtccatcctctgtgccagaagcctactggcagct
cgccggtgcccagggtgacacccaaccagacaccaggaggagcaggagtagcctttctacatctttctctgagggggggcagt
ggctgcttccccagaccccctcacaatagcccaggagccaggagaggcgagggtcacccttccctgggatgttatatttgt
ttcgtttttgagacaaagtcttgccctgtctcccaggctggagggcagtggcgtgatcttggctctctgccgtctcagatt
cctgggctcaagagatcctcccgcctctgcccccccagaatgctgggattacgggcgtccccccgtgatgtttttaagctggc
accatggcttatcccacgtggcagcgtgtgggagcttccttctgtcttatggccgaggaagaggcccactgtacagacacactg
tttctttatccatttgccattcagtgaaccctgggctcctgggaaggacctgtggtgcaggaagttagggaggttgtgggga
gcgcgacagaccaggaaggaggctgcagtggtgccggagaggtgggcagggcccgtgctgcagggggtccccgttccactgg
tgggtgggctccccaggttgacagctcacagccagcttaatggtgccagatgatggcagcttcagccgaggcctcgtgccaa
gacccttgcagtggagccagggcacgggtcgcccctgacggctcaggcctgctggggctgttggctgtcctgggctggagca
cacagggagagggcctgcctggccttggtggccctgggaacagtggtgatggctctggtgagcagcagtcccctgcctcct
gcccctccggcatcccgggctgagctgcctccacgttggactgcactcagtggaggactcagtagaggactcagagaggacg
caaactctggacttgcctgggcgtccttctccatttggatgctggagggggccgggggatgcggccctcgtcagggacctcagtg
gatgtgtgtcctaggacctgcagagccgagggcctctgggtcactaaacccaaccacctctgatggagaaggctgaggtgca
ggaagggctgagcctgggagtccgggcgaggcccctgcaccctcctgtgcgggcagtgcacgtttgtttcttggattgga
ggggcaggctggtggagggaagagtgtgctcacagcacaccacagcttctctaaagagggacacagggcagaatgaccgc
ccccgcccccggcccgcctccgcctggctctgccccttcctgccctgcaatccccagttcaggtctgggggtctcagcctg
caccttgctgactgctggtgacctttgtgccgtctgctggggccgctagatcactggggtcaatcgtttccccagccccata
gctcagtttcctcatctgtaaaatggggacaatcatggtgcccaccgcaggcctggggagaggggtaatagggacaatcacg

FIG. 4 (Continued)

gtgcccgccgcaggcccggggagggggtaatagggacaatcacggtgcccgccgcaggcccggggagggggtaataggga
caatcacggtgcccgccgcaggcccggggagaggggtaatagggacaatcacggtgcccgccgcaggcccggggagagggg
gtaaaggcatttgtttgcgttgagcctcggggtcacaggaaagcgctgtttatacatgtgcagtcttcctccagcacccg
cctctggatttggaaggagggtcttcctcagcagcccaccaagtgaggtctgccctgccctggatctgagacatcgaggcca
gaccagcaccccctccctcagctggggcctccccttaagctcctggcagaggctgatccatgctggggtcccggggcgccaca
gacggtggcgcaggggacacacccacaggggttcctgttccttggtgtgtggtcctggcgggggagctggggtaggggcct
aacgagagaacccgggccagggggcagcaggggtgaggctttgccggcccctgagcgtggagcggcctttccagtcggggt
gaggccgttcaccgagagatgaggccgcccaactgggaaattgggctcagccattgaacagcagttccaccttatcccacc
acctagagggccagacctagtgagagcccggatctggtctccagcacctcagggcacccacgcacccaagcccaggtgtgc
gcaccctgcactcagggcccacttgtgcccagcccacctccccactgcctggctccctggggctggatctccccactttga
gctgtgaggtccagaccccgatgccgcccggagggtacagtgaagcccgtgtgggcatcagggcctgggagcctccccacc
cgacgcctccctccaggtgtgcagagagtctattccgcctcatcaacggctgggtggatccccagaaacctggcaccggg
aggctgatggagggggagggcgaggtgaatatgtcagtttatcccaatgcaagtagtggcctgttgggatggggagagaccc
ggggaaatatttgggatgactggagccgctggcccttaaggctcctgtaacaggacacctcctagacgggacaggacgact
gactgtgtgtgtttcccccctccctcctccccttcccgcgccagGCCCAGTTCAATCTGCTGAGCAGCACCATGGACCAGAT
GAGCAGCCGCGCGGCCTCGGCCAGCCCCTACACCCCAGAGCACGCCGCCAGCGTGCCCACCCACTCGCCCTACGCACAACCC
AGCTCCACCTTCGACACCATGTCGCCGGCGCCTGTCATCCCCTCCAACACCGACTACCCCGGACCCCACCACTTTGAGGTCA
CTTTCCAGCAGTCCAGCACGGCCAAGTCAGCCACCTGGACGgtgagttccccctagtccctgagggctgcgggctgcgggctg
cgggctggagaggaggtggctgcgttccccgcacctcaagaggtctgagctcgccccactgtctgctcggggttcccacctg
gcccgggccaggaggagcatcgggcaggaggcgggtctcagggccgggcagtctgggtgtgcccaccccctctagacgtgagt
ggccagagccagtcagcctccaaagggccacagaggggacggacttggccctgctggtgagatctctgccaagactggccag
cggctttccccatgctcaggtgggatctttggtttgaaatcctgtcctggacagaggcacgggctctgctgccaagagttgtc
tgtccgagacaggcccacagccctagggtctgcagaacctgcctcctccaggcagcgagacgcatctgcgggtgggtggatt
tgggctttgctggcactgtctctggagtgtcatttccaggaattggcatgcaccaaggagatggggtggaaccacgtgcca
agggctcaggtcctcactgcggtgcccctggagacagactggcccacggtggggatcttgctaattctgataacatcacctg
tgcacaaggccagtctcctcgagcccaggcacccatgctcagggcttgagttgagctaactcttgcacccaccaacaacgcac
agggctgactcccatcactgctccccttttacagccaaggaggctgaggctcggggagggaagtggttcgcccagagttctgc
tcatagtaagtggggggcagcccacctctgcatctgtattcctaacccactgagctgccctgcccagacagcttcaggggaggg
gtctgtcaggagggggcaaggtgaaggctgcatgaccccagccaggagtggagggcacgcaggggctgggcgggaaaagcagc
cccaagagccctccgggtctcccctcctgcaccgaggaggggcaagtgagccctgcctgggcacccaggccatggctgcag
gaggggctctatgggacacatgttggtccggcccactgggcagcgtcccctccccacgaggcccgcctccccgggcacag
ctcagtgctggccccctgaagtccatgcagggcggccgcattcccacccccgtcgggagtgctgagcaagggggcccctcag
gtttttccgctttaagaatcgggtcccactgccctgctggccatagctgcggttttcccacgctcctggagggccgaggggc
agggcggagcctaaggtagactgtcaggctctgcaggtagccggacagtcctgccgggctggtctggggtctgggttccagg
ccccgcccgccccacctgcggttgtttctgattctcactccagccacgggctcccccagctgctggctccgggctaagaga
aggctcagcccggactcgctgggcttgatgggagggggctctgtgggctgttgggctgaggggcagaggacctggcacctcc
tccgggggcctcccacctccatctggcaggcaatgccgaccccagtgctaacaccccgttttctccatttggaaattactcct
ccacgcaccttactgcacgatggagataaggatgggaagaccgtgccagggctgtggccagcacggtgcttagctcgcagca
ggaggcccatgcgttgtcttaatttgtggtggtggtgtgctggcctgggcctccccaaatgagtggttccgtggcagctgcacc
tgcctgtggggcaagggggaccaggcctatccttccacccacttggaggtctgaagccaggtcagaaagccccaaggcatc
ctcacctgcacacctccagcagcaggagcctcaccactgcttctctcccacactcaggcttgttgcctaagtccactctctc
ccctctaaggacactgacctcctgccctggggtttatgatgctggtggtttctggagagtgtctccctggagtcctggcagg
cagcttgtgggagctctgcctcccttcctcccatggtctgaggatgctgatggggtcttcaccatgcttggaatgcactgca
tgtggtctgagctgatcctcatggaaggacaggagcaacccccctctggctggcttcccccatctagggtatctgccaccc
ccaccccctgccaggtgtgtggcatcaggttcaagggacttcatggtttgtctcaactgccttgtcctgcaggacggggtg
gccttgccctgtgggatgggctggtctgctcagaccaggcatccggggctggtcagctgcaccagcgggaggggaaagctgt
gcctggtgcccagcagaggagcagtgacacctcctcgctccctccctgctgggctctgtggatgctgggcgggggggagggt
gggggggcgcgaactggggaggaaaatgctgtcgcctgcacccagggctcctcctccgaagccctgtggatccaggggtgg
gacaaaccttgataatgagattttggcacctcagctctctggggccagaacccccctccaccagggctttctttccttgccca
gggagggcaggcaagtggtcggctcacagtgcagaacggggccgccgggcagcccgcttgctcccagctctggggtcccac
catgcgggtgctgcccagccctgctgcctgtgcttgcgtccggcctctgcacgtgactcctggggctccgggcacgccagc
cggctggtaactgatagataattcatatttttctcaagtacaagtccacattggctgccgccctcctttctccccgatcagg
aaaaacaccctcaccagccccaagtgaccacagatcagacctcagatctccttgggcactgagaggtctggaggctgcggt
tcacaggtctgtgcatatgtgtgcatacacacgcatgtgcacacacacagacacagcaccctcccacatgcatgcacacacg
tggatacacaagtaccttatgcacacgcagacacatgtaaacacacaggcatgcgtgtacatgcacaggcctcccccatca

FIG. 4 (Continued)

ctgcccagggttctagtagctcccacccccatggaaacccaggaggaggaggagggcgagtcgtgggtaaccgagcagccagag
gaaggatttgtgtttagccacgagagtgtaaccagtgaccagtgacagggcaaggccggcatttggtgagagggaccctgca
tggtgagagggggtggagctgggtctgctggggtcccaatcccagagctgcccgtgagcaccttctgcttcgcccctctgcc
ctggcatcctcacctgcaaagagaggtatggcctgccagccatggtggggacaaaggagctggctcttgggacttcttaggt
cagggcagggtacctggggagcgctccacacacgtgagctctgagtgcagtgctgatggtgacaccagtgcccttctcccag
ttcaacaccctctgtgggacagtgtgggctcagagtgtgggcagagctctctgcagggcatgcatgacctggcctctgagcc
ctgctggccactcctgtcctgggagccctgcaggttggcagtggtgtggacagctggttccaggaggccctcggggcagaga
atgaacaggagttcctctagctgtcagaacagcccgacgcgatgggcatcggatgctgtgacaccccggctcagccgttctg
cccccagctcagcctcatcagggaaggtggctgtccttggtgtttgggaagtttggggacggggctctgaggtcaggcaaga
aggcagtgtggggttggaagccctggcccagcacagcatctgtgggcacctcagggcatgctgagtgacacccacccacagcc
cacgaggcaggctgccatggcaggatggtgaggacacacacaggtgcgatggccagctgccccagcattcctccagacagaa
agatggcccggacacagcccctgagtgccctccagctgctctcagactcagcgtgtgtgtgtgcgcgagagcgtgtgtatgtg
tgtgtgtgtgtgtgtgtgcgcgagagcatgtgcacacatgtttgtcttagggagagagctggctccacgggtaggaaagcccccc
gtccaggagggacatatggaaggacggccagggaagcacaaaggctctgcacgggattcctggggagaatgaggctgagtca
acactaatgggtctggagcaaccttcccagcgcctcggaggcttgcaagcaggagaataatagcggaggtgtcccaacacga
tcatggtatcaattgcattatcctaaaagtttatggaatgcatgagtggaattaataccttttactggcaccagaagcaatt
atatgtgcgtaaagctgagggaagagttctaacaatgtttattgtggagatgaaacgtggattattaggggaaacaagagta
cttagggcgaaattgcagcaattgctgatatcatgtggcgcagggatctgcagcagggacggagcttccagcaggcctgctc
tggctgtggtcagcgcctcggggctcgtggcccgagccggggttggctcttctctcttcactttctggagcagccagaggaa
ctcactcttgggccctggaggtcacagaacttagccttggaggcccccaagtgaggctggggaggccccagctctgagaccct
gggtcctgctgccccacccccacactgcctggttcttggaggagacaggagggagaacccctggggggacaggattccctcc
ataggcatgagactgttgggggagaggcatgatccaatttacgtttaggaagaatcatctatttctaggacttctttcca
gtttggggacagccctgtggacccagcatgtctgattagtagcgttggcagcagcattgcccctatgtgcagggcctcccac
actcccccatttacagatgaggaaactgaggctcccagagggcacacccaggtcacctgtcagcagagggcagagccggacc
tggcccagcagccagaccccctaaccttgcccttgcagcccgtgtggtgccccacccggcccctacaggtccctggacagg
tccccacgagcagccctgccccgccccacctctgctcccagctctgtggggcaggtccctgtgacccccaggcccccc
aggggaaccagtgataaggaggtgctgacacctcagagggacctgcctgtcctaggggagaaagccttggaccgaatgggg
tgtgggggagcccaggctgtaccttggcccccatgagccttccactgctgtctgccagtgaatcaaactgggactggggggt
ggagagctgtccctgtctgctttcactgcttggttttgttgacaaaggaaaatcccctcaagaacgctttatcactggagtgc
tccgaggctggcgagcctcatgggcgagaagccaggcagctgggcttggggacggcctctcctggtgcctccctgcccccct
ctgccttcaccctcccaggcctggcctcactgccactaactcccgttgacaggggggaaagagaggcccacaggggaggggcc
gtcccaggcttctcctggacccagtgctgacgccaagatgcggtcgtaggtgacctggaccttgggccgtgtgggactcggg
gcaaggtgggggcctcagctgggcagtgagttagtttgcttcccggtctggtgggtttctgccacccccaggccagtggtca
cttctgggatttttctgagattccaaaagttgaagccacggaccctggagacccggaccctggaggcccagcccctgcctctg
ggtagagaaggccctgagcgacctccagacctctgtccctttcccgaggagcctcaggaagaggggacagacaattccag
ggtgtcccggctggaaagaaaagcatcttctctgcactccaggcggacagcgtgaggctcagagattacgtggcggccgagg
ctggtgtcccacagccaggggttacgatggggctgcagaggccgtgagcggaacagggcatttttagggcagaaagacccttt
ggagaaggtaacagcactccaggcttcagtgaggcagaagtcagagcccatggggaaaccgcacaggggggattacctaaagc
ccagagccacccccaagggttgcaaacccacccctccccagccatgccactggagcgaggcacccagctccttgcacctggc
gttggggagacaccactctctgcaggggtcagagattcggaggccaaaattctccttcccccaggcatttcaatgaagattt
acaaagtttagcaaaaacctagattctagccaactattaccttaaaagctgaagagggacccacccccaccatgtccacagctt
actcccctccctccgctgtctccggccacctccagctgctgccaattccagcccccaaggctgtcccaggaagctgtggcca
gagactccgggactgtcctgtgagcagagggcacccactgaccctggggcacccttccaatccccacagctgacaaagccgg
gcctcaaaggctgggttaatcctggcttctcctcaaagccaccagtcaggggtgggggtgaggatggtgggggcaaggatgg
tggggggcttcctcccccaggagttaaggggccctctctgcagtgagcagagcaggcctgttgccagcctgctgggcccctcgt
gggacagctccagggcctggcccacagtcccgctagctaggtccttgccagaggccggaggagaggccaggctactggcaac
gggccctccagctggcgctgtcaaaaagcaagttgcgggcagaggaccctgcgcttggtcccggcccagggcagaggctgag
tgtggtgctttgaacactctgtgtcttcagagcggaggggcagctgctggtgggcattccggggccctctgcaagccccagc
ttttgtctctgcgggacccagggcactgccctgccaccccctctgtccccaaggccccagatggggtacctgggtcctggaat
aagagcagatggagttcctcgccctgcctgggcagctcattccttcccgggcttgggcagagtgacagtgatagtagcagcc
acagggcacccgcacgcggtctcagtgaatcaggacagcggcgacccggtggggactgggccctgagctcctcacacagcat
ctgggcagcaaagtggaggctggagctgtccaggctgggccaccccaatcccagccagacacaaggcagtctgtgtgagtctc
agtctctattgtccatggagacccatccccagcaggaccaggggcaggtgaggcccctggctgttgttccccttacccctaag
gggcttaagtccagccacggggtaagaagcccatgtcccacctgacacctctgtagtaccgtctttctggaacccggggtga
cgcctctgcagtgcccagtcttcctggaacccagggggtgacgcctctgcagtgccgtcttcctggaacccaggggtgcttaa

FIG. 4 (Continued)

```
ggcgggtctctgcctagaccccgacccccaggccccaggacccaagtcaagcccagcagtgaccaagggctgggagatggagc
ttgggggtcagacagctatggtctgggtgctggtccacccagcttagcaggcaggtttgggtcactaaacggagtgacagt
gcctgacctcccagggccaaggtcaggtgagggccccgcgcagggcaggcaccagtgggcagtggatgtggccatgagggtg
gacccaggtgccccattccctggcaggtggacagcactcactgtctccccaggtctccacaccaacagaggcagacaccttg
ggcaaacgctgcctcgcagcctcccccaacactaggccctcttatctcctctgcctgtggccctcgtctcctactggaccc
ctgggccttcactatgcactggagacaaagccaccaagtctatcctgggctcagcacatacctgcttccctccctacccg
atcatagcccaggatggagatccctagaggcagccgtgcatgggacgaggatcgagcaggctccagctcctgtggtctgggt
gcactcagtgtctcccagggagcccgcgcttccaggccgttgagagtccccgtgtggctcctgctcacctgtttaggacatg
gctcaaggtcgtggtggggcagactgcccagctcctcagggttcccacttgccctggcctgccctccccagtgagcagttt
cttgtccacagcctctggggctctagcaggcctccgtcagggctgaggatcgcttggcatctgcagaggatgtttctgcctc
tggttcatcctccatagagctcctggcctgggagcccggctggccagcatggggtgccagcagacacatctgtctcctgc
agcccccccagcccaggagctctttcacagcagcctctttcttgggcagcgctgggcctggcactggctgtggcctcacagg
cattctgaagctcgcttgggcctctcatctgcctggcccatgggctgtggatgtcctggtgagtgagccgtcactgcctcga
ccatgggagccccagcttaacaccaaggtgttctgaaacagggcgattgccacatgtgtcctttcccctccccaggctag
tggcttccctggggcagggagggaccagccctgtgacatcctgccaggcctccctgacatctgtcagagcccagcctgtgct
cccagcagctctctgagggcgacagtgactgtgcaccagtgaaggccacagcctcccacgaaggggctgtcaccaagggg
ccctgtggctgcacctgaggatacccttcctctctcagaaggagaaagggacccaggaggaccctaatccacaggctgttg
accctggctcaggcatgtgttttaggggtccatctgtgaacccacgaatttaatggaaaggttctgtggctcagccccag
gagcttttctagggagaggaagggtccagggccttggcagagggtgggctcaaagaggccgtaacccccagagaggagagag
atgcacccctaaacacacagacgcacacacaagcaagggaactggataaaagtgagcaataaaaaaaatcgtttaaaaaata
aaagccccactgcaggcccatcttccagaatctgttgcaacagattcacccacgctggttaacggtatttgcggtttgca
agatgctacacgtcccaggaaaatgacagacaagttattatcacctctccgctgtcctcctgcccaaacctgcccgtgccgg
gcacccagctgccggggagcgaggagcgggcacaaggaaattagcagcccccgctgcaccctcccctcacccacccccgca
ccagccctgccaggcccagggctcccagccaggccgggcccatgttgtactgggcgggggaggaggggaaggagaggaggg
tcggagaggagccggcagcgtggggagggatgggcacagtggcgtttgggcaaaccctttcctgcaagcaggacggtgcacg
caccctgggcaggcaagtccaggcggctccgtgtcaacagccgaagataaatacgattttatcagctggaatctgttgaaa
cacatccatctagcggttctagggaaggagaaggcaggaggggggcggcggaggggaagtgtctccacgtgacctttcctat
agaataggctccaccggagtcctcctcctcctgccgttttccacagggcaagcccaggcctgaagcctagaggcctgctg
gggagacaggaggaaggagctgggggagcgctggagccgtcctgggctcagccaccctctagaaggacctggatctctcagg
gctcccttcccttcctgtggccacctgtgtcacccacccccagatgctgccagggcaggggacatcacagacatcctcccga
ggccacccagctccggccggctgggcacctggggtccagttagtgccagggtgaggtctgccaggcatgtatgccccaaag
gccatgtgagcactgcactggggacacctgtggggaggagagccaggcccaggaccttggtggccttactggccagagggga
ggagaagtgctcacatcgcctgaggacaggggcctccttgctctccacccctgaggcctgggcctccctccgccactggccca
ggtcgaagacctgtccgttctaggccgctccacactccagtccgagcccccacttcccggggtgggtggtccggccgccgcc
tgcaccgagtaccagggacagctcccggcgcgcccaagctcctcccgggggcgggggcggggcggggcatccacagtgctccc
cgcgcctggcccccaggaccctcttgcagacgggagtccctcagacagtgcagagacgggagcacgcactgggccctgcacc
cacttcgtagcgccctggcctgggacgccccaccacgcagcttccagagcaaggatcgccacttcaccctgcccggagaccc
agagggagtggggcgggctcagcagggcgctgctgagaggccgctgcctaggtctgcgaaatgggagcactgctgaccctga
ggcccaggcgggcgggagctcaggctccgcagaggactatggccggggtgctggggcaggggcctaggggaggggctgcag
gggccaggcaggagctgtgaaaccccctcacgctgttgagactccatggggctgtcagggagcgacggctgccggggcctctg
cccgcaggcttggttgcacccagagccttactccatctgtgtccaactggctgaggagcccaggcggcctccctccccctg
agtgtctggggctccttggtggatctaatgacccccatctcaggccatgggctgtggcactagggtggaagaagcctcgggg
gactcagcccggaaagggaactgtagggaagcggggcctgtgtggctccagcccccgcaaccaacacctcctcacctggt
gctgagaataacgagggcgcagtagccactaacacctgcaggccactgtgttcccaggggacacgcagtgagtcagagatgc
aggtggagaggcttgtgcagtggctagaggcatcccagctgacgagcacaaagccaaaactgccaccccacagggccggacct
cagaggcccttctcctttgccgcccctgagactctgacctgagccacccggccggggtctgtttcaaggggggtctgccg
cgccctccctgctctgtggtttccctagggagcggctaggatggatggcatttgttgagtaccacctgtgtacctccatctg
ctacacgttactgaggagagacgagggggacagagccaggtgcctgaattccaggggggcctgtgtgctctgcacacaagagg
tgctccataaatgctcagcaatgggcagctcgccctgcaggctgccctggcctcggagaagcctggcgacacggctgccggc
cctgtgttcctctccctgctcggggcactggcagacaagagcctgccaccacctggccctcctccctctgtccccaacca
gcacagatggagaccaggcgtggtgtgtagcttcaggcaggccctttgtccaagagaccagtgcctggacacaggccactgc
aagtttgggccaagagccctccctgtctgagtctcctgagggtccgagtcccagagggtctgtgctgcgagctgttcccatg
tgccctggggggcagggctacctgcttatccttccaagtgatgctgtggggagcaaaggggcatttgtaatggtggggacac
tgtacatcagtggtcacctccagggaagccagactgacccccacaacaaggagactgctgtacttcccgctgtgcccaagcct
gcagctccgacagtccagggcaggcgcccgcacagggggtgggctgctagctctgcaaggctgtttctgctttcttttttc
```

FIG. 4 (Continued)

tctttgtgtgtgtgtgtgtgtgtgtgtgtgtgtgtgtgtgtgtgtgtgtgtgtgtgacggattctcactttgtcacccaggctggagt
gcaatggtgcgatctcggctcactgcaacctccacctcccgagttcaagcgattctcctgcctcctgcctcagcttcctgag
tagctgggactacaggcgcccgccaccttgcctggctaatatttgtatttttggtagagacagggtttcaccatattggcca
ggctggtcgaactcctgacctcagctgcctgccttggcctcccaaagtgctgggattacaggcgtgagccaccgccctcagc
ccgtttcctgctttctaaacagcgcccagcctcccctgcagggctgtgcatgatggttccttcctgtgtttaaacaggac
tggggatgggcggcttcctgcctaaggccctgtgcccaaggtggggtcgcaggcaggggcagtggagccactctggctcca
ggggctccaggtggacggaggacctaggaggggccagctctttggtatccaattcccatcctgaggaggccactgaaggacc
cccttccacttgtccctccagcccctcacacccatggcagggacagaccagcggttcctggctgggtctcattcggggagcc
caagtagctcaccagagaggggaccgctcccactgcacaggaacaagggcactcagggtgccggggacccaggccccaccca
ccatggctcgcagcctccgtcagctccatctcccctgtctctttcctttttccttcctggctttcgtgtgcctgcacctgc
caaggacctatgtggctcctgagagcccctcatgtcccttgatggccagagaggcagtactggtggccagtggggtcaggg
ggtcagggcccccctaacttccttggcaaagggaagactccacctgcagcttccctggttctgccagtagctccctgtctctg
acctcagtttccccaactgttccacggtggagtgcgatgggacattctccagggcacttgcggctgcagtgacttgtgattc
tgagtcatcgggggctggtgaggggcacagagggcatggggtggcagcagaagtcattctctgagcctgagactggggatca
ttcctgatggccctttggggagagagcatgaggactcccagcaggtgaccaggagccagacgcttgggaaatcagccagctt
ggaagtgagtggacgcccctgcagcggcctcagcggggtcactttttagaactcatgagagccggcctgggtcctcagatggg
cagccgggccctgtgaggcaaagaagctggaggcctctgcagggctggctcaggaagggtgtcatccagtcctcctgcagc
agggcccacgccagctccagacagacctattagctcctcgagtcccaagctggggatactggggctgtgagcccagaggggc
ccccagagtggccaagaccaagccacacagctcggctgctcagacttggtggccccagcaggagagggtgtcagagtcacca
gggctgctgaggccatgagaggccttcacaccaacccagagagctctctatggaagcttgaatgcatagtgggcaaccagcc
catcacacattaaccacttgctctgtgcaaatgccagagaagcctagctctggtcttaaaacagattcaatgctgcaaacc
cacctcttcaaaatgccgcagtcagggacatggcttccacaggcctggctcccagcccccgttcccgcctcactctccagc
agcccctcttgctctcctggcctttcttgtccccatccataaacctaaagcctctctgcctgactgccacggcactcaca
cccctgctgtcatggagcccaaatgacccgatggctgtggagtgggtgccagggcagctgtgcctggattcacgcctcaaag
gacagacacctggagggattcagcagaggggctgcttggggcagtcttcatctggggttgtggaagggcacccatgggga
ggacgtggctcccaatgggggtggcctggacaggggtgcagttgggaccactggtctcacccgctccctctccccactcc
agTACTCCCCGCTCTTGAAGAAACTCTACTGCCAGATCGCCAAGACATGCCCCATCCAGATCAAGGTGTCCACCCCGCCACC
CCCAGGCACCGCCATCCGGGCCATGCCTGTTTACAAGAAAGCGGAGCACGTGACCGACGTCGTGAAACGCTGCCCCAACCAC
GAGCTCGGGAGGGACTTCAACGAAGgtgagggccccagctcctctgcccacggtggcactttgcccagcatccggacagc
acagccgggggctgcctaactgggagagagtggggctgacagcatggcttagccattcccctgcggagggctttcagtgcc
tccaccagcccccatttcccagttctgagtgggacctgggggggcccatgctcctgggcaggggcaagtggtctgggcaga
gtctgaggggcagcggccttctggggccccagagatcctatgagtcatagcccctctctccagtgtgcctggcagggcctac
gggctaccccaaggattagcaggagaatcagggggcagagccactgggcaggcacccccagagcacaagggctgccagctgg
cctgagcctcacctggaagcccacaggactgggcctggtggtctcagttctgctgcgatgcacctggcacagctgggcgcct
ctctgcacctggcacaggggtgggcacctctctgcacctggcacagggctgggcacctctcttcacctggcatggggctggg
cacctttcttcacctggcatgggactgggcacctctctgcatgtgacacagaggtgggcacctggcatggggccgggcacct
ctctgcacctggcatggggctgggcacctctttgcacctggcacagggtgggcacctctgcacctagcacaggagtgggcac
ctctctgcacctggcatggggctggacacctctctgtgcctggcacagggctgggcacctctgcatctggcatggggctggg
catctctgcacctgacacggggtgggcacctctctgcacctggcatgcagctgggcacctctctgcacctggcactgggct
gggcacctctgcacctaacaggggtgggcacctttgcaggtggcacagagctgggcacctctctgtgcctggcacggggcca
gcacctctctgcacctgacatggggctgggcactttctttgaacctggcacggggctgggtacctctctgcacctgacatggg
gctgggcaccctttgaacccggcacagggctgggcacctctctgcacctagcacaggggtgggcacctctatgcacctctct
gaagtgtcgaccctcccggcagGACAGTCTGCTCCAGCCAGCCACCTCATCCGGCGTGGAAGGCAATAATCTCTCGCAGTAT
GTGGATGACCCTGTCACCGGCAGGCAGAGCGTCGTGGTGCCCTATGAGCCACCACAGgtaggccaggagccaggctgtgccc
agggccctgcagtcagctgtacgggtcgggggaggggtcccctgaggcagccctgtccctcctcagttggctgatctgcct
gcctgtcctgtcggcatctgtccagggctccctgctctgtgataagtctgtgtcggcggctccttcctcacccacaccgcc
ccactgtgcacactgctgctctgtccccacatccgcctcgggcactctcggggcctcagtgtgcccagctccatagtgggga
gtgggtctttcagccttgccctctgtttggtgcccaacactggttccggcctggggctcccagacacagggatttgggagatgg
ggaggtccccgcccatttagaccctggatttggctggggcagaaccaaaccagcaacagcgcctgaagggtggcaaattcta
caaaggggggttgagggatggtggaaagactcctaggccaggccaggggcccaggagaggtggcctgcaggaggctgaggctg
gtcagcagggtggagagccgggaggccccgctgggcaccacgtgggtgggggtgcagggga ctgggggcatataggctgg
aggggaggggacacggagaggctgggggctttgactttggccccaaaggcagcataagtttctgggacacaattctggagct
gatgtggggcccaactggtgtgaaaggctggggtaggggaaacagagggttttgaagttactgcgggatggtggggcagggg
cagaacaggaggtgaggagtgggtaccaggcccccaggggaaggcaggcaatggcaggcctctgccttccctgtacctggtt
ctgagaccaggctccatgctgtacccagccccagcctccccaccaggtccccatccctgtaccagacccccaggacaccc

FIG. 4 (Continued)

agactcctgtacccagtctccaggtcctccacaagcctctacccgtacccaggcccccttcgacgtccccatcccaccatc
ctctaagagcagccccttatgtcagcagaaccagggcccgggagggctccctgaaacccatgtcccacctcacctgcctag
gcctgccaggaaggcagagctctatcgcccctggtggctgccgtgtgacagcagttctgagaaaggccaagattttcccaa
acccctaatagctttgtatttgtccccagggtgacatgaaactgcccacattgtggtctggggacactcattgatcaacg
gtttggttcatggctgggcgcagtggctcacgcctgtaatcccagcactttgggaggccaaggcgggtggatcacttgagg
ttaggagttcaagaccagcctggccaacagggcgaaaccctgtctgtactaaaaacacaaaagttagccgagcctcgtggcg
catgcctgtaattccagctacttgggaggctgaggcaagagaatcgcttgaacccgggaggcagaagttgcagtgagccaag
atcgcgccattgcactccagcctgggggacagagagagactccgtctcaaaaaaaaaaaaaagagttttggttcatgtctca
gctgtactgcaaaatccctgggaaacaggagtgtgctgggggtgggttcgctggggacagctctggttcctctttctgccca
ggtgagcccgcagcatgcaacacacacgtagggccacaaaatctgtgcaggcacactcacacccagcatctgggcttgacct
ccagcctgtgtcagggagaaggttggggcaaacagacccacaggactctgtgctttctctgagagcagagaccaggtctgagc
cctcccagaacccagaaccagcccagtgcttggggttcagtgatcttcatgaatgggtggctggatggggtgagtgggtgga
tgggtggatggatgggggtgggtggggtggatgaatggatggatgggtaggtaggtgggtggatggatggatggataaatgg
ggtgggtgggtgagtggatgaatggatggagtggtgaatgggtgaatggatgggtgggtggacggatggatgaatagggtgg
gcggatggatggggtgggtgggtgaatggatggatgggtgggtgggtgaatggatggttgggtagagggatgttgaatggat
gggtgggtagagggatgggtagatggggtgggtggatggatggatggatagactgatattgttgaatggatgagtgggtgga
tggatgtttagatggatggatagataataaatgggggagtggatggatggatggggtgggggggtggatggatggatggata
ggatgatggatggatggatggggtgggtgtgggggtggatatgtgggtgggtgagtggatggatggagtgggtgggtgggt
ggatggatggatggattgactgatattgaatggatgggtgggtgaatggatggttggatggatggacagataatgggggag
tggatggatggatggggtggatgggtggatggatggatgggatgggtggatggatggggtgggtgtgggggtggatgtgtgg
gtggatggatggagtgggtgggtgggtgggtggatggatggatttattgatattgaatgggtgggtgggtggatggatggat
ggatttattgatattgaatggatgggtgggtggatggatggttggatggatggatagataataaatgggggagtggatgga
tggatgaatggggtgggtgggtggatggatggatggataggatggatggatgaggtgggtgtgggggtggatgtgtgggtg
ggtgggtggatggatggatggatggagtgggtggatgggtggatggatgaatggatgggttgatattgaatggatgggtggg
tggatagatgggtagataataaatgggggagtggatggatggatggatggatggggtgggtgttgggggtggacgtgtgggt
gggtggatgggtggatggatggattgatattgaatggatgggtgggtggatggatggggttggtggatgaatggatggatgg
atattgaatggatgggtaggtggatggatgggtagataataagtgggggagtggatggatggatggatggggtggatggatg
catggatagacgggtgggtggatggatggggtggatggatggatggattgattgatattgaatggatgggtgggtggatgga
tggttggatggggtgggtggatggatggggttcgtggatggatggggttggtggatggatgcatggatggatattgaatgga
tgggtaggtggatggatgggtagataataaatgggggagtggatggatggatggatagatgggtgggtggatggatggggtt
ggtggatggatggatggatggatggatgaatagataaatgggttcgatggatggatggatggacggatggatggatggatgg
ggtgggttggtggatggatgaatgagtggacagatatacaaatggcaacaactatagagcagggcatcccctgcctacgtg
gagccaggaccagacatggagctggggctgccaccttagtggattggggctgcgtgctgatgctagcccctctccctgctc
ccccatgtgcagGTGGGACGGAATTCACCACCATCCTGTACAACTTCATGTGTAACAGCAGCTGTGTAGGGGGCATGAACC
GGCGGCCCATCCTCATCATCATCACCCTGGAGATGCGGGAgtgagtcccgggcacacggggtggaggtgggacagggctggg
caggcacggccgggggagaaggggagctgtcatggagacctgcaggccaaggctagcttggggaagagactttggggtgtgc
tgctggaggaaggaaccgccccctggcctgcagggcctgcctgggcacaagctgggcctccggagggaggtgggagtccccg
gcgaggtctcagggcagcctcacagctttgagcctctgactccctctagcgggaacactcgctgccggcactgggtgctctg
tggtgaccgagggctctcaaggccggtcctgcagggtccgaggtgggtggggaaggtgggcaggttgagggtgggcagggtt
gagctcacaattctggctgtgcccacccgacagTGGGCAGGTGCTGGGCCGCCGGTCCTTTGAGGGCCGCATCTGCGCCTGT
CCTGGCCGCGACCGAAAAGCTGATGAGGACCACTACCGGGAGCAGCAGGCCCTGAACGAGAGCTCCGCCAAGAACGGGGCCG
CCAGCAAGCGTGgtgagcggccggccaggggaactggacgcgtgtgggaggagaaggggacacattggcaggacacaatgtg
agcccgcgtcccagggacagggccagtccctgaacggccccccacgcccagactcctccctgacggagcctgagagcagccc
ccatataagtcgcttgtcctgggccaagggcacctcagaggcctgggtggcaccgcaggtttgcccgtccctgtgggttgct
caccaccggacccacctggagaatcgattggccccaagggtgggcaggtctccctcctcccggaaggaggcctcaccctct
ggtcctgcctgctcacccgcctgccctgcctggccttccagCCTTCAAGCAGAGCCCCCTGCCGTCCCCGCCCTTGGTGC
CGGTGTGAAGAAGCGGCGGCATGGAGACGAGGACACGTACTACCTTCAGgtgagtgtgtgctcctgcacggcagccgggaga
cctgcctcacctctgtcgtctgctgagcccaggctgggccatggggagggactctggagaccatggtggagggggcgggagg
agcccagccctgtgtgagagggtccagagggcagaacctgcttgcaagagccagacccagcaggacccaactgcagggcattc
ctgagagtcccctcagtcccaaaaacccagcgtcatgccatttacaatgaagccatgtgtacatagcacaggtagggtggtg
cggagtgccaccagggtagaagttcagcaagaatccaggaccctaacgttggccaggacccgtggccacggccagcccccat
gagtgtgcctctcacatgtggcctccaacaggtgaattaaatcggcacaggcttggctgggagtcatcttccatgatgtgaa
ctttctgtttttttgagctccagaatgagccccagttggggtcagtggctcatgcctgtaatcccggcattttgggaggctga
ggcgggtggatcacttgagcccaggagtttgagaccaaagtgggcaacatggtgagaaccccatctctacaaaaattagctgg
gcgtggtggtggcgtgcagctgcagtcccagctactcagaagactgaggcaggaggatcacctgagggcaggaggatcgcct

FIG. 4 (Continued)

gagcccaggagtccaaggctgcagcgagctatgatgatgccactgcactctagcctagggacagagcaagacgctgtcgaa
agaaagagagagagagagacagagagacagagagagacagacttggtttctaaaaacccagtatctgttggtaggggaggaa
gagggaggcttggggccacaaggagcaggcatggttcttggggacaggatacctgcccactgagtcaggggctctggttag
acctgcttcttgggaagaggaaagaagatcaggggatcctgagcctctggggtgctggggaaccccagaaaggacagatgc
tttgccaagcccaggtcctcctgaggctgcggccacccccctcccgtggggtctggggcacgtgggcagagatctgctcct
ctgtgctcagGTGCGAGGCCGGGAGAACTTTGAGATCCTGATGAAGCTGAAAGAGAGCCTGGAGCTGATGGAGTTGGTGCCG
CAGCCACTGGTGGACTCCTATCGGCAGCAGCAGCAGCTCCTACAGAGGCCgtgagtcagccctagcccaccatcagtgtggg
gaaggaggacatggcttaacccccaggagaaggccaggaggacccagaaaccctccagaaggcatcatctgccagggacag
gcagcagggtccagagcagagcccacccccacatctcctcctccaggaagccttctagcacttggggctgccctggaccctg
ggtcatggcccttgctatgcctctgccactgaggggccttgtaaatgtctgctgagtggaaaggccaggaggggtggccaga
gtgaccatgacccaccaagaccagagtccgattccagtggcacaggtcatcccctgcctcccggccccgccatggccagtg
tccttctcaggcgcaggcccagtggccgtgcatggccatggttggggacagggaggctggggaggatgaagccactctctg
acatcagaggctccacccattcgcagcatggggcatcacgggcatgggtggtcggtgggcacgaggctgccttgcttccca
cccatgcgagccgttgcttctgagcagGAGTCACCTACAGCCCCCGTCCTACGGGCCGGTCCTCTCGCCCATGAACAAGGTG
CACGGGGGCATGAACAAGCTGCCCTCCGTCAACCAGCTGGTGGGCCAGCCTCCCCCGCACAGTTCGGCAGCTACACCCAACC
TGGGGCCCGTGGgtgagtcccttgggcagtgcgggcccacgggcagggcggggaggcccactgggggcgcctagctcaggac
acaccacccagctcgggacccagggcaggtgtctctgtggctggctccttccagcggttccaccctctgggcaggaggcgca
gccacggatagccctctctgcccactcctggctgtgggaggtggaggggggcgtggttaagagcgtggaacccacatgcatg
cactgcctcttggcaggcgagggagcttggggaaggctcttaacattacacagcctgtttccccatcagcaaatggccacag
aagtaccaggctcactccttgtgaggaataaatggtgcaagacctcatcaggggccccagcacaagccggggctccattgg
atagagtttgggcccccttcccctggaaggtcctcatgtgggcaggaccaagcatgttcccagtgccgtgagcaagcacccc
caggtgtttcctgaggccctgggatgtggccagcactccagtgccagctgcgattgcccttacaacccagtgccccgtacgc
acggtcacccccgtccctactaggcggggcgaggagacagggccccaggtgttcagcccttgctcaagcctctagctggcag
gggtgatgcccagcgtcacatcgccaggccttgggatggctccctggtgtccagaggtgtctggagcctgggtggaggctgc
acctggatgcccagcctggctgccctgatggcccacctgctctcacccagGCCCCGGATGCTCAACAACCATGGCCACG
CAGTGCCAGCCAACGGCGAGATGAGCAGCAGCCACAGCGCCCAGTCCATGGTCTCGGGGTCCCACTGCACTCCGCCACCCCC
CTACCACGCCGACCCCAGCCTCGTCAGgtgcgtgggctgccgagggcctgagcatgtgctgtcaccctgtctgttcacctct
gtccttctggccatgtcagctgccctgccccaccctgtgtgctcaccactcgcaaccctggatcagacaggcgggcggggc
agtcaggccaggagcatctgcagatgctggggaaatggtccacttagaggaaaagcacaaaaagccggggtcctccactgac
ctgtccccagctgagcacgtcccctccctgagggatgccgtggccacctgtgggctggagccacccttcggagacagcggca
gtctccgccccagccaggccactctcagagatggggctcgcgcagccctgtgctcggaagctaatgctgcttcctttctca
aattctctctgcagTTTTTTAACAGGATTGGGGTGTCCAAACTGCATCGAGTATTTCACCTCCCAAGGGTTACAGAGCATTT
ACCACCTGCAGAACCTGACCATTGAGgtaacgcccgggtggacccgctctgcagaggcagtagctggaggggccctgtcc
ggagggcaaagagccttctcttccttgctctcgtggctgggaaacttggaaaccctttcccacgggcaagcagatgcgatga
tttgactcttgagagcttaggcagatgcagccaggcacgtggctggtggcgcgggacacaggcccaggcctcgggatgctga
actggtcatttgagcctttttggactcccagcagccagtgtgcctttgatttaggggatgggctgtttccaaggcacaaag
aacagaagaatgtaaggccccgagggagtcagtccagttcagtgccatttacagagaggtcagcgccatttacacagacagg
aaaggggacctagggaaggcaagcacctggcccgaggccacacagctcttggcacccatggcagctgactgcaggcaccatg
attaaacagccacggcttgtctttgggttagagactagtggagtacaaagcctgctggtagcctaggacggtgtgaaccaca
gggcacgtcagtcaaggaagagcaagccctctggtgggaacctgcccccagccagtgccgcggcccaggtccaaggcccg
tcccagaccatccccagcctggggctgcagacagagatgagggtcagtgcgagctagggccagctgctcagcctaactgtcc
ctcgtgcagagagtggccgcgtctgtgtccactaaccgccctccccgcaacctgtccccagtgacccacgctgagccagctc
caggtcacgttaacccttgcctcccctgagtgatgtgtgtgcttggtgtggtgcccagagggtgttgggagctcaggatga
gctgggggtccactccagggggcagggacatggagaccaaggagggccctgccctgaggctgggaggcagttcctcccccag
ggccaggtagatgctcaggggctccatgtctaacactcccaggtcagggcccaggccccgcacaggccaggagtgactctg
gtgggctctcccccctcccccgtctcctgcctactctggttggggtgtaggggccagggtgtggtgtggccagacctccagg
cccagggcgacccccctgctctccctgctccactgcccctgcccctaatgcgccggcctctcgcaggacctggggggccct
gaagatccccgagcagtaccgcatgaccatctggcggggcctgcaggacctgaagcagggccacgactacagcaccgcgcag
cagctgctccgctctagcaacgcggccaccatctccatcggcggctcaggggaactgcagcgccagcgggtcatggaggccg
tgcacttccgcgtgcgccacaccatcaccatccccaacgcgcggcggcccaggcggcggcctgacgagtgggcggacttcgg
cttcgacctgcccgactgcaaggcccgcaagcagcccatcaaggaggagttcacggaggccgagatccactgagggcctcgc
ctggctgcagcctgcgccacagcccagagacccaagctgcctcccctctccttcctgtgtgtccaaaactgcctcaggaggc
aggaccttcgggctgtgcccggggaaaggcaaggtccggcccatccccaggcacctcacaggccccaggaaaggcccagcca
ccgaagccgcctgtggacagcctgagtcacctgcagaaccttctggagctgccctagtgctgggcttgtggggcgggggctg
gcccactctcagccctgccactgccccggcgtgctccatggcaggcgtgggtggggaccgcagcgtcggctccgacttccag

FIG. 4 (Continued)

gcttcatcctagagactgtcatctcccaaccaggcgaggtccttccaaaggaaaggatcctctttgctgatggactgccaaa
aagtattttgcgacatcttttggttctggatagtagtgagcagccaagtgactgtgtctgaaacaccagtgtatttcaggg
aatgtccctaactgcgtcttgcccgcgccgggggctggggactctctctgctggacttgggactggcctctgcccccagcac
gctgtattctgcaggaccgcctccttcctgcccctaacaacaaccacagtgttgctgaaattggagaaaactggggagggcg
caacccccccaggcgcggggaagcatgtggtaccgcctcagccagtgccctcagcctggccacagtcgcctctcctcggg
gaccctcagcagaaagggacagcctgtccttagaggactggaaattgtcaatatttgataaaatgatacccttttc (SEQ ID NO: 3)

>mm9_knownGene_uc008wbh.1 range=chr4:153432953-153514317 5'pad=0 3'pad=0 strand=-
repeatMasking=none
GGTCCCGCTTCGACCAAGACTCCGGCTACCAGCTTGCGGGCCCCGCGGAGGAGGAGACCCCGCTGGGCTAGCTGGGCGACG
CGCGCCAAGCGGCGGCGGGAAGGAGGCGGGAGGAGCGGGCCCAGACCCCGACTCGGGCAGAGCCAGCTGGGAGCGGGGC
GCGCGTGGGAGCCAGGGGCCCGGGTGGCCGGCCCTCCTCCCGCCACGGCTGAGTGCCCGCGCTGCCTTCCCGCCGGTCCCGC
AAGAAAGCCGCTAAGCCTGCGGCAGTCCCCTCGCCGCCGCCTCCCTGCTCCGCACCCTTATAACCCGCCGTCCCGCATCCAG
GCGAGGAGGCAACGCTGCAGCCCAGCCCTCGCCGACGCCGACGCCCGGCCCGGAGCAGgtaggcagctctgggacccgagct
agggccaggtatttcgcacgaggctccgaggctggagttcgggtgtgcggctgcccgggtgctagccgagtgaacggcccca
gggactccgcgtcagtggcaggaggggccggccggagtgaggctaggagtagaagcagttggcacctcggcaacccatggac
ctgcctcctgccccacactgtccactacaggtggcaaggagtcgccatacccggagatttctggggctcgggtctggtaatagg
ggaagttggaggtgcgtgggtatcctacctcacaaggaatgcaaatccccacctctgtaaggcagaaggcctttcaggtcc
cgctatggaagcagactaagagagaggaaagccaactagagccaaacctctatgctggtcccaaggtgtggggtcctggtgg
gttactgctgttctgtgatgagtttactgtggtgcctcaccagcctccctagtcttccaggtagagaacccgggcagcccac
actctctcctgctccactgggcagctgtcaccttctcactcttgagagatgagaacatctgtaggcacctatccacatacac
acccgtatgtgtgcgtgggcgggggcgggggggtggtggtgtcaggaaaaaagctctgacttctgagccccaagacacttgg
ttccctgtatgtgctgaggtctgttaattaattaagtgggcacttgggacctgggtcgtaacaatatttggggggaaggttgt
tgttgtttttcttcatttaaaagttaaattgtgtctgtgtgagtcgtgcacgggtcagaggacatctttaggagtcgattcc
cattttccatttatcagtctcaaagatttactcaagtggccaggataggcagcaagcacctctacctgctgagctccactg
cctcggattggtttcgtggtcgttgtttgtgttgctgtttagctctagaaaaaaaactcaacagagacaaaatgtatcctg
aatccttggtgtgttgcaaacgctgtcccggcccccccacccgcccccatcctttgatttattcaataaaaatgtaaaacatt
actttgtgaacaaaagataagtatttaacatttctcatccatgactgtatagattgtgtatgcagttttgaaaatcaggta
atcggtttcaaaggtgttgcatacccactaactagtcttgagctactggcgggcctatgggagcctgcctatcaagcacagg
taactaacgacaggatgctgagcaatgttgtccttctagcgatggctctgtggaacaggcagggcttgcccattctgatggc
caccctgtgtgacaacattctggattagaagtcagatgctgagttcaaatactctctgtgccctgggaccttgagcaagtta
cttaaatcctcagaacctcagtttacccatcttcgaaatggagtcatagcactgctttttctcaaagagcttatagaaacctg
gtcagtatgcctttgtaaacagaatggaaactgcctgaccctggctgaagaaggatatgagtgagatgcttgtgttcataga
ggtagagttatttgtataagaaagaaactggctcgggacctgtgagatggctccttgtagaagggtgcttgctgccaagggt
gatcatctgagttccatccatggaatccacaagctggattgtggatcccacattgtcttctggccatcacatgtgcactgtgg
cccacgggtgcacacatacatacaaatagaaaagtaaccaggatgctatatccaaagtccttggacaagtgctgataccaag
tgatctttttgagtcctagatttggctctgggactgggtggaccaagaaagaactcagagaagaaggccagttcctaggttt
tggagagatcatggcagtaaggcaggaatttgcctgcgacctgggtggaggctagcagcatctgtcaggagtatgtcctgtg
atgaagatgctcctgtttcatgtttatttatagagtatgcccaacccaggtcctggaatgggcttctagtgctgacacatgc
gaaggagaatagctaaagtggagatgaagaagggagacagggatgagggctaaagggagcttcatcaccctgctgatatcca
gggatgcaccaacccaaggctcctagcactccaaagttcttgtcattttgtcattgcattttaaaaagtcccatgtacat
ctcagtgagaaactatttctgtcacccaattcaagggtgatttacctcccagaagcaagcacacacacacacacaaaaaaaa
ttgcacttggtgaatggtgttggggcagggggcggagagaaatcctcaaaacactcttctgtgttccttctaagaaggaact
ttgaggcagcctttagttttcgcagaggatactttttaaatgttgctgacaacaactctacttatgagtaacagtgtggcaga
gactcctggaacccagatcattcaatcttgtttcggtttgaatgtgcagcaaagagtgtaacggatacatttagtacagcta
cagccaccttacaaacaggcaaggtcctctctatgggacccagcctgcagaacaacccgtggtccatctgcctttgtagact
ctgactctctctgtctctctctctgtctctctctctgtctctctctctctgtctctctctctctgtctctctctctgtctct

FIG. 4 (Continued)

ctctctgtctctgtctctctctctctctctctctctctctctctctctctctctctccactttatctttaaaccagtttgtt
ttccctgaacttgttgctccacagggggaggatcaaagagaagggattgcttggcaaaactattgcttatgaagtatctgcag
gaattagcacccagtgcacatactggctgtgtgctggtattaggcttaataatttaggatttttacctttgcttgtaattctc
caacatccccttgatgtaggttctgtaattatgcccatttttcagatgaggtcatggaggctttagcatgtgattcaaggggc
ctggagttgtgccatcacagtgtgggatttgagatctcagatctgacaaacagtccagggtatgggcttctgggtcgttctc
gccagtgtagctagtgctggatgtataaatataacctattaaacagagcccacaggaccctagaacccttgcacagggcattc
tgttgagaggactgtttgaggctaggtgactagaattaggcgtgatgtgaactcatgtagggagaaaagacgcatcgtaatt
tcatcagtaccgaagtgaaatttctcatcttcagtcatgagtgtataaacaaacaagtttacagtccgtggtactttataca
gtccatggtactttatacagtccgtggtgctcttctcactcattgcagttactgatctttttcactggatgtcccagcttggc
agaaagctcaaatttttgttctcatcgccaacctgaaattctgagttatgacagctgctgcttgacttgaccttgtcctaac
ccagaggtatgattgtcatagattaatgtcacttgaacactgtggccacttcattagaaccatgggtgggaccaaacaccta
caatggcagcactggagaggctggggtaaaggcatcaagaatccaagccccccacccccagggtcagctctgttgtgctgtcc
ttattatgctgaaggtcaagagcacaaaccagtagtctaatttgccactatatattctgatggccagaggctacatgtcagt
gtgtgggcaagactagttcccctcagataggaatcccctctatgttcctccaagatctggcaattctggcagctccttgccc
tgcaggtctgcctctgtcctatagtctctgactctgtgcagcatggccttctctttgctttctctgagtctaccctctttga
ttgtagtcagatgtgtggctcgtctgaggttctggggagaattccttgtatttaatttttatgtatttacaacactcctccct
gcataaggttctacagtgtcagggtcaggcaggttctgcttgccccagctgtctgtttaaacagaggctgctggggtgcttc
acaagacatcaacatggctttcgggataggagaggcatcctgaagaagtagaaagagaagggggaggtgttatcctaggacat
ctccactgaggctggagcgccggaccaaagaaacaaccctgtctgtgaaggaacaagagctctgaagacaggtctaggcaat
ggaggagacatgtggacatcagagggccagtggatgtaacacttgatggcccttgcagatggagtcaggttccccagagagt
ggcctatgagggaggaaagcagtcttcttccacctgcccagactctttgcttggtgcgtgactttgatggacattgcccaga
ttgatgggagaaaaaaaaatttttttagaaccatgggtaggaccaaacacctacaatggcaacactggagaggctggggtaa
aggcatcaagaatccaagccccccacccccagggtcagctctgttgtgctgtccaagcagggtgcagggcccactctcccaaa
tgttgcagccagtgaggggcagggatagctctcctgaacttatgaccttgtggacagctttccaactactggaagtgtggag
aggaggggcatcatctctacacccgtgccacctcatgacagacaagtggcagagtcagctattccacactcatgctctgagg
gtctgctcacccacactccacacccacgagggtcatgtccactgtgctgcctgggtgagggtgcagggcctgctctccctag
tgctgctggtgagtgatggggcaagctctccagagggcggcaaccagtgaagggagggggccagctctgcccagttcttggac
atctgctctgacaagggatatcccatgttctttaatggtaatgtgagccgtggacatcaacacccacctctgcatagccatg
aacccagctcaggctgccacctcactatggccccaggtggctggccactcacaacaggctgctcctctccatcctccagtct
ccagatccagctctcttcataatccttaagctgttccacttctctctctcccatctgaccaccacatgctcgcacattgtgg
tggctcccactgcaggctggccatgttgctggggggccctggggtgacatcctttggtccaagctgcacggccgtgagcagg
ccctgcacctcacccaggcagcacagtggacatgaccctggtgggtgtggggtgtgggtgagctgcatggcatttggcaag
tggttgtccacagcctgcctgtgctgtgctccagaggcagatctgtggatgctgtggcaggtttctgtctgcctttttccct
cctcatgtgctgcactgcaggtggctatgtgtgtctatggcctgctcatacagggtagagggcagatctatggctatctttc
cctgcccaaacattgtggcatggtggaacacagatctctgtctatcttcctcttccgtgccatgctacctagatttgattt
gatttgatttgatttgatttgatttgatttgatttgatttgatttgatgagtcctagacataaaacagctttggtca
ccaagccaggcatcgggccaggatgaacataggactatcatctgctctacccctgactgatgtaagaatggcatcaccaata
aggtgtctctttgtccattgacaggggttaaagtttttttaattggtaaattttttactatgtagctctggctagcctggaact
ctttatgtagaccaggctggcctgaaactttcagagctctacctactattctctgcctcctgagtgctgggatcaaaggcgt
gcattgcttggaatctcgaggggatgagggtgtggggcttctgcaggagaaaggcaggtctcaggagcctgaggaggaatgg
aaggtcattagcagtctccttgctatgcagatatcttctgtcagggaatgctctctctctctctctctctctctctctctct
ctctgacatttctatgtagtactgatttcctgcacaagtagcggtttctcatttttgctttaggcagttgggtggggttagg
ctttgtatgtgttgctagttctccatcgatttttggcttctagtatcaggtaacgtcaaagtggcgggttctggtttcctaca
gccccggtctgaggtgacaccatgaatcccagcagttgtccacctaacactctccaaagcaggctcacagtgcagaccttgg
tgagtgtatttcttatcacagtccactaaagagggctttatacagaccaagggcaaaacagacatgaaccattggaagaggc
tgcaaagcagtatgaactgcgagggcagggcagggcaggcacgggtagggatggagaggtctgcgggctgggccttccagtt
cttgcacagttgaggtcccaggaatgtgtgagtagccactgtcaccccctttgaaacctgcccacagcagaagcacggagc
ggggtttatgatgtgcagcctcagcctgaaggactttcgggagaagggcaggatctacgctccaaagcagaagcctgagagg

FIG. 4 (Continued)

aaattagaaccatggatttgggcagtgacagccatgcacgggagctaactagctgattcaggatcctgcccattttgtagat
gtttagtagtccagaaaggcagaagatagtagatgctagggacaaacgtagtttttctatgaaaatatgatttttctctatat
catttcttcttaaaaaacatttaggtgggggctggtgagatggctcagtgggtaagagcacccgactgctcttctgaaggtc
aggagttcaaatcccagcaacccacatggtggctcacaaccatccataacgagatctgactccctcttctggagtgtctgagg
gcacctacagtgtacttacatataataaataaataaatctaaaaaaaaaaaaaaaaaaaaaaaaaaacatttaggtgtctatttg
ttcatgtgtgtaggtgtgccagggtgcatgtacaggtcagaggtcatgtccagtgtcatctttgcttcctgcccaccttatt
gttttgagacagggtctgtctcattgactctggactcagtgattgggctggactaaccagccagggaactctggatttcctc
tgacttctgctccccagagccacgcttgcaggcatttgttgcctacagtctgttttgttttaaatttatatttattcatttc
atttttatttgcatttttgcctgcatgtatgtctgtgcaccacaagcttggcatgcctgtggaggtcagaagagggcatctga
tccccttggaactggagttacagatatttgtgaaccagcatgtgggtgctgcggactaaacccaggtcctctgcaagagcagc
aagtgctcttaaccactgagacaccctccagcccctttgctgttgttgtttaatgtggattgtttattggtattgcttttt
tttaaatgtgggttctggcatctgaacacaggtcttcacactttcctgactgagttagttatcttgctagtaaacccatttc
taccaaaggtgatcacagtaaactgatttttatttttcagaagcatgcctagtcttcctgaatgtgccctgcgtatttgcata
ggtctggtgaaattactaagtggctgtgctagtcaaataaggagcgtcagagcagatctcagaagcctgtgctggcagcgga
gccaggtcagggtcccagcatcaaaatccatctgcagagcttctcccgctagagatgcccaaagaactttaaggctggtggt
ccctctgtcagttacagtccttgtctgtgagaccatagagcccttgtaagccagggaccaaacaaagcatttttatctgtctg
tctgtctgtctgtctgtctgtctgtgtgtatgtgcacatgagcatgccacgtgcatgtgtgatggtcagaagacaatgtta
tctccttccaccatatgaattccatggatgacactcaaataatcactattggtagtaagcatgcatatacacagagccatct
tacaggccctgattcagtttctttcttatacaaataactcgacctctatggaaacaagcatctcactcatttttcccttcag
ccagggtcaggcagttccaattcagtttacaaaggttaattgaccaggtttctataacctatatatagcttctttaagtttc
tagacatttgtacccagttcaagggccctgcctttgaaatgtgtgctgggcagagtcctttctcaaatctccttgatcgaag
ctactggcagaggccgtgagaacatgggtagacagcggctaactgccagtggctggagaaatggcctgaatttgtgggactc
atcatccggtgggggtgtgtcttaaggcaactggacgtgaaaatctagatatttctgtattagagaaaaaaacaatctgtt
ttaagaaaagtttagaaggctcagtggttaagagcaccgactgctcttgcagaggacctgagttcaattcccagtacctaca
aggcagcccacaaacactgtgactccaattattctgacatccatgggcacatggtactcacactacacgctgacaacgcatt
tatacacctaaaataaaatgaatctttttttttaaaagtaactagaactactatagagaagtaggatttcttggggtatcata
taattaaataaatactcacacaagtgtgacaggattgatttttgtactttattataagggaaccattttttttttttaatcgtc
cagggttgcatctcagcctctggagtaaggattcatggagagttttgtggggccaatctgcaaaagttcagcagaaatcaga
agttaagaaaggtgatacagaacttagcattggaaagttctggaactagagctggaaagatgcctttgtgctgaagagcact
cgctgttcttccagagaaccagagttctgttcccagtggcccacaactgcctgtatgtaactccagctccaggagacctgac
accctcttccagtctctgcaggagcctgcacacacatgcaatacacatacataaaaaataataaaattaagctttaaaacat
tttttttatgaaaggaagttatcagccaggcatccccgcactcacaaaacagaggcagaggatctcttgtgagtttgaagct
gtagtggtagatacataaaaagttacaggtcagtcagggatacatagtgaaactctgtctcaaaaaatatctacaatgaatc
caatttttagacaatttgtgctcagagatgtagggcattcctgtgatcccagtacctaggatgctaaagcaaaggagaagctg
agacggaagagaaagatttggagcttgaggccagcctgggtcacacagtccaaatatatataaatatccaaatatataaaat
agtttatgccaacttgacacaggctagagtcatttgggaagagggaaccttaattttaaaaaaatgactctactgaattta
cttgtggtacattgtcttgattgatgattgaatgtgaaagggtctagctcactggaggagggccactcatgggcaggtggt
tccatggtgtaagacagcagaccaagaaaacaaaaccacaggaagcaagtcagtaagcagctttcttcatggcctctgacaa
tggtcaacatgaccactgacacagtcctttgtctctgttatggttctttctctccctcccccctccctctccctcttaaagat
ttatttattttattaatatgagtacactgtcactgtcttcaggcacaccagaaaagggcgtcagatcccattacagatggtt
gtaagccacggtgtggttgctggaaattgaacttaggaccctctggagggtcagacagtgttctcaactgctgagccatctc
tccagcccctatctctttccaactttctgtatcagttgagttttttttatccttcctcttcccccacagtctgtcttccta
cccttctttctcccttccatcccagcctcccttcctgtccttcctcccctctcccagtctaccttcttgtcctttctctccc
agccccattctaagcccccctttttttcctttcctttcctttcctttcctttcctttcctttcctttcctttcctttcctttc
ctttcctttcctttcccttccctttcccttcccttccctccccctccccctcccctctcctctcctctcttttcttcccctc
ttccctccttctccctcctctttttcttttttctgaagctgtttttcaattaaccttcaaactaaacacattctttcccttga
acctcagactttctttaccacaaaatgtccctgcatcttctcatgtagagtgggttctctttatagcttccacacacagacaa
aagaattttaactctctgtaattccaactcccagaagaaaacgaaaggtgagtacggacggacggggcaagtgtgggaacgc

FIG. 4 (Continued)

ccacccgagtgcccacagagcggtttgctagctgctcttgccaagggctggggtctggtcttgctatgcacacagtggctca
ccatcaccagtaacttctgtcccagggaatctgacattctcttctgatcctccttggacaccaggaacacacatggtacaca
tacatatatgtaggaaaacccaatcatacacataagataacaaaaaagtaaatctaaaagcattttcaaagatgtgggcagc
tatttttaaagcaggcatattatgattcctcattgtcatagaaatctttgcttcttatacttttattttttgagattcattt
aattttatagtttctaacaactgtgccttaattatgaaaacaccaggagaaattttatgaaagcatcctgttttaaaatgtt
tattttaaaagtttaggttttattattattatttacgggtatgtgtgtatgtgtgtgcttgtggggtgtgcatgtgaatgca
ggtacttccaagccagagagggtgtcacagtcctttggagctggaggtacctctccatccccagagtttcctgtttttaaac
aaggctagctattacccaacaacgtacctcctgctaatattttcagcacgtttgtatcaggaagagtcagaaaggcaaa
gcctgagagaggtatacttagttctgctcatttattgttgagatgacctgcagacactgctgtgtgcctgttagttcctggg
ttactgcaaggttagctgtcccagggttcgaacagacatggccaggaaacacaggaagagcagcagttgtatgtctgccttg
tgtttggatggcttggaagatatgtgtatgttagttaatccagtaaacgtaagctagcagcccaggcaggctaggtggtcat
gattcttctgccttgtcttctggagtgagccatgccttgatttggaactttaagaaactttccactcttgcttcatctcac
agcaaacagctctgcccaaattcagtctctggaggtgaggcccacttctgataatagagttgtgaaaaaaatcctttcaagta
ttttattatcaggttttagcccagccaaatacttaagtgtttctgaaagtactagggtctctctctctctctctctctctctc
tctctctctctctctctctctctctctctctctctccttccctccctccctccctccctccctccctccctccctccctccctt
tctcccttctctcttacttgtattggaaattcaacacccaaaccagcaagactttatgacaaccatgaatataaaatagtca
tgttcaaacagggggcgggcagcctgcagcccctgtgacccccaagttcacttttagacaggtgggtaaagactacatgggct
ctccagtctccacttgctattctatgatggatgtagggaagttcctgtgggaaggtaccctaccagcactgaccaggcatga
aggatgaaggaggacggagagcccctaatagacctggcctcttgtttatataggatcttttgagagctggggccatggtga
gccattgaactctgcctgactcaggccagcattgtgctatacccacagctgagagagggagaagaatgtctaccaatcatag
agcagagtggtcaggactcaggacaaactaaagggaggatatcatctagtttgactcataacaaaactgctctatgcagatg
tcagcctaccagaacccagagccgctaacctgggaagccagtgggcagcagccttccaggctggggttcttgtcctgaccaa
gatgctattcttcctgcaaagacagaggggaagaagccagaaatgagcatgctcatacccatagagcccagggctcagtagt
aggaacgtgtctggtgtgcctggaggctccgggctccatctcctgctgcctagaaagccagcaaggtctccgaatgagaact
gtgttccactgcattccttctaaatgagaactgcgttccactggattccttctactgagcagagtctgaaaaggtaaagaca
gtttctgttcttattccccaccaggtccaggaaggagtgtccctcagtcaaacctggtaccttttgctggcctcctgctaggt
tccaaatcctacagctgctatgatgatcccagagaaggcaggcttcagccactgaggtcccttcccagtcactaaagtataa
gggaaaaagattacatcagatagggtacagtaagttgtgcctatccatatgcacgggtgcgtacaggggaaggtggctct
tctgagtcccagagagaaaagtagctctgggtggcacagaggctaatgtagggatgtgaggggaagtgggcaaggaatatgc
agatatagcattgtgtgtgtgcatgtgtgtacatatgtgtgtgcatgtgtgtgtgtgtgtgagcaaggaatatgcagatata
acattgtgtgtgcacatgcatgtgtgcatgtgtgtacatatgtgtgtgcatgtgtgtgtatgtgagcaaggaatatgcagat
ataacatgtgtgtgtacacgtgcatgtgtgcatgtgtgtacatatgtgtgtgcatgtgtgtatgtgtgtgtgtgtgtatgtg
agcaaggaatatgcagatataacattgtgtgtgtgcacgtgcatgtgtgcctgtgtctacatatgtgtgtgcgtgtgtgtgc
atgtgagcaaggaatatgcagatataacattgtgtgtgtgcttgtggatgtggatgtgcatatttgtgtgtgtgtgtacatg
tgggcaaggaatatgcagacataactgtgtgtgtgcatgtgtgtgcatatgagtgtatgcatgtatgcatgtgtgtttacat
acatgtatgtacatgtgcgtgtgagtgcatgtgtgtgttgttcctcaggaggcatccactttttttttttttttttttttt
tgagcatgagcctctccctgaatctctccatcaggtctccatttcccatctctaccttcaaagcactgtgataacaagaaca
tactatcacgcctgtttttgttttttaaaggcgccaatatctccttaaattttagtgcatttattatttttcacatgtgcggg
tactcacatgccacagcatgcccatggtggtcaaagtacagtttttcagagttgggtctctcctgccatgtggggtctgggt
ttcaaactcaacattccaggcttggctaccaatgcctgctgagccaactcaatgactcctcacaccccacctttgaaacaca
ccttctggggatcacactcaggtcctcatgcctacaagtgtgtactgacccagccccagacgtgactttggtttgatggttg
cccagctgggacccctttcctgatgtatgtgtccttcagagctgtaccatctgctcctacacagggcagcttctccatgttc
agtgcatctgcagcctcagggtcacctggactcactcagggtgcccaacaggttgttctgcaatcatgtgtcccagtgtcct
gcagacatgtgtcatgcagttatatgttctgaatctcaatatagaccttagaactgtggctgaagaaaggggatgtggtgcc
agactcagtttgcccaaagagctagtgcaggatggagctggctggcactggcctagggcagactgaaaggtgcaaggggccc
ttgggtggtgacacctggtgttttagaccgttatgtgggttcccaggaaaacccctcttctgcaaaggaagcacttgtgtt
ttcccagtatgctatgggtacaaggatgactaacaatcatgacatttgcatggtgcttccttcaccgtagctgcacacaaag
gcccgtgctttgctctctttggcagaggtaggctttgtttcctcagtttacagatagggaggtggagggctgggaggtcatta

FIG. 4 (Continued)

tagtcacaagaggagtagagggctcagcacaaagtacgacaagtcaccgtaataaaattcaggcctgggccatgatcctaa
ctactggggaggctgaagcaggaggatccaaagcttaaagtgaccttcaagccggtcctggttgacttagtgagaccctgtt
tcaaaagggaaagtcaaaagagtctggggtgcattttggcaatacagtgtcctgggtttgacctcagagctgcggtgagagc
aacgagaaagaacagattcgcaacaggaaagttcacaatggatccagcactagctttcaattttaagaaagattttacatt
ttatgtctgttgtatggccatatgcttgtactctgtgggggggggagaaagagagagatagggagggagagagagagggag
agggagagagagaaagagagagagaaagagagagagagggagggagagagggagggacggagagagggagggagggagagag
ggagggagggtgggagagagaggaagaaggagagaggagagagagagagagagaggaagaatgagagagagaaagagagaga
gctctcttaactgctgagccatctctccagcccctcaacaatagttttattggacactaaggacttcagcgatgaagatcca
aagacctgactaactttctcccaagtttgtgtgtgtgtgtgtgtgtgtgtgtgtgtgtgcgcaaacatgtgtgcatgcatgc
tagagggagcctgcccaactgaaccattgttagaggacaagggttagaacaggaatgagtcaatcccatagtagggagggtc
tgcatccctgtgggatcctgtccccaagaacaggacacacaaggtctcatgctattcagggtcaggctgagaatttgctctt
caaggtttcgtggtatgtattccttgtatgtcatactgtgttgcgtaaggacatcttcctgcaggcatctattatacagcaa
gtgtacatgcttcttccccttggtccatttatcccttagacaagtcacttctgctttcctgtcacgtatacatatgtgat
ttttagatacatatgcaaaaacccaggaacaaaatatgagagaaaacatgtgatgctcgctttgctgagactggcttaattc
acatactacaatcatgtccgattgcctccatttcatgaaaggatgtaactttgtccttctttatggctggataaatgtat
gaccatgtatagttgtcatactttcttgtctgctcctctgctcttgggactagtgctacactgagcgctccttgatatact
atgttctacaatgtgcgttgactttggggtaggtgtccgtgggtggtatggtcacatggtagatctatttctaaagaccctc
catactgacttccatagtggtgggaatggtttgccttgcctctgttggtctgggagggcgtccttctgtccacgtccccacc
agcattggccacttctgttttcagccggtggctgagatggattctcagtatggttttgatttgcatttctcagattgcacct
tttaaatgcatgtattagctccttgtacttcctcttttgagaattgtctgctcaattccgttttaagcaccaggttgcttgt
gtgtgtgtttagtttttaaatatttgctttaggtttacgtgtgtgtgtgtgagcctgagtgtccatctgtgcaacatgtgt
ttgcaggaacccaaacataccagaaggtgtcgaatcccctggaactggagatacgggcaggtgtaagtcagctgacacaggt
tctgggaattgaactccgtcttatgcaacagcactaagtcttttgactgctgaaccacctctgtcaccctgtgtttagtttt
ttgagttctttgtatattctattatttatggcaaggaatgtttttgcctgtatgtatgtcttatgtacaccatgtgtgtgc
ctggtgcccatgaaggccagaaccagaaaagagagtgttaggtcctggaacagttacagatggttgtgagccgccgtgtggg
tgctacaggtttgaatctagctccgctggaagagcagccaatgttaacagctgaactgctgctctccagtcgcttttgtaa
ctccagatgtcaatcctctgccagactgacagccagcaatgactcccctaccctccctgagctgttcttcacccaaatagtt
gttttcatctctgtacaaagcctttgaatttctcaaagcctcatttatcaacggtcttctgccggaggaagaggctaggga
cagaaagcacggcctgcctactgctctctggagtgccatggtgccacgtgctgagctagagtgttctgagccccatcctggg
agttgtgagtcacctacctgcctccactgcaggctctcctacatccctcctgtgatctttcctgagacaccacaaaccacac
ctgagaccccgggggagaaccttacagggataccaggtacccaggaacatcatcacagcctccctacccaaccaactccagc
atagatgccttgggcatcttcttgtcaaccagggtcaggtcctggagtaggcagggcgtgggaaggagacccatgagagcgg
gctttgtcagcctgctcagggctactgtatctacgaagggctgttccagtgtccctgcccagtggcagctgccagatccctt
ccatggggacagcagggactctaattgctcacctgctgctcagagtctctgccagccctggaggtgtgtctggggaagctgt
gctaattaggcacacggtccatccttgtaggggcaataggcatagtgtcaacctttcggtgcgtccttcacagcaagtaaag
gagctccagtctcccattctgatctacatcccggaccttagggatgacgtcctagctgttgcctcattgatgtccaccttcc
agatggacactgccctgctcaagcacagacctggtgactctcagctcagctgacctatgggaagccttggtccttgtgggga
ctgaggagagcatcccaggttgggaagagagcatgtaggatctttagggtgtttccaccagcagcagaggggggcctcatag
tagagaggggtctaacttttgcagagaccacacagcggcccttgctaaatgctgtagcgccgcaaaggggagtcgagctcc
acagtgggtacgtcctggtatctgtgccgcccagatcatgaacagtaagcggcatatcttatcattcatttaccaagcctcc
attctctggggtccctgggactccttacccacacagtacagactagattcagctcctgctcgctatagaaggaggctctgctg
gtgatagtcatgtaagttagagacagcaggtccctgatctgcaagacttggattagacaatgtggccccctccttctcgcc
accactgtcctctgtctccccgtggtcaacccgccatcaacaagcctaattacaaaggcctcctggcactttttctttggag
taaggcatgctccggcttgcttctgggcccttaatttttgatcagggacacctcttcgactaatttatttgtcagtaatgagg
gaggagagatgaggttgcgaaagcgtccctgagcttatagagagaagctgcaaattaaaatacgaggcatccgtaaacaggg
cgctaattggattaattcaaaagtgatagattgggataagaacagagaggaagaccacaggcagattgaggtcagaataatt
ccaggagcgttgcccgggcttcctgtgatagatgtgagcctcaaagtccgagagctacagaaagtaaaatatgctgctgtgt
gtgcaaaacacatctgagtcactcaggcacaccaaccacccaggatgcatggccgtttcttaagccctggcactatctgacc

FIG. 4 (Continued)

cttgagtcatttttggagagaccagaactttcatatgacaacggcctttcttttcctctgttgtaatcaagccctctctattt
gttttaaggtttttaaattatatgtacgtgtgtatgtaagggtatgtgcacatgagtgggagtgcccatgaaagccagaatc
tccttgtagctgcagtcccaggcagctgcctggtatgggtgctgggagctaagctcccaagtacatgggcctatgtgcatgt
tcttgaccgctgagccatctctccaggccctcattctgatttctcttggtgctgtttagtgtttttgcattctttgaatctt
gagccacacttatgcgtgggctatctaatgtaattgaatttaaaaaaaaaaccattatgtcagaaggtgataaaaattatga
tgggaacatccccacttctgaacaggcagaggtgagctgaactttcaagataaggggaagcatctccctgtgtcccagtgag
cactgtctgtccgtggctgcttctcctggtatctcagcgaggcatcaggtttctgtagggcatttgaatcgcctcatagacc
aaatgtgccctgaccacttcccctggccacagtgatgctttatagtctggattaactctgggctactggcctcactcccagt
cttggctgacacctaggctgtgggagagctaatagcttattcatattatttagataagtagcatagtatttgagccgtgtac
gttttaaaagcatcaagtctttattcttagggtgagccttatcatataatcacaactgtgcaccatttcagttctcatggt
tcttccatggatcacactgaacagtaagtcctggctgcagaagagaattatttttgcacctgtctccaagtctattggttca
acataaacacaggcaatactcgaacccatatgttatcattccaccgaggggctcctagacacaccccagtcagcttcctgaa
tttctaaattcagaaagggaatgtggagctgggaagaaatagtatttcacttaagactttacttacccatcctgtcccattta
tccatcccatctatctacccatccaacacattctcccatccatctatccatccatccatctatccatctcttcatcccatat
gtccataaagcccatcatatctacccatccattgtttgtttaaccatctatccatccatccatctatccatctcttcatccc
atatgtccataaagcccatcatatctacccatccattgtttgttcatccatctatccatccacccatccatctatctatcca
tccatacatccatccattcatccacccatctatccttccatccatatgtccatccacccacccacccatccatcatccagtc
tatccatctacccgcctgtatatccactcacccgcccacccacccacccacccacaaaaccactataaaaacatccatctct
cattcattactgagtacctgctgcatactaggtcctgatctgggaccagacaattcaaactttatacactcactcagtcttc
accattctgtgacatcaacttgaagctgagggtttaattctgcagagcgcaggcctcttggaggtcccgggggcacaccaca
gtataagacacttcgtgtggagcacagaagccagtgtgccaaggacaccctttgctcctgttgttcaggtgtgggtggggat
gggtctggcagtgagacaagaggggccatgttggatatgcgcctcaagggaccatcatctagcaagcagggtagcttccagt
gatgccctaggcacctgctctccgaggtcactccctttaacttctggaagacggagaggacccagcccaaatgtactgaagg
cagatttgcttaggatccaggccaggcgtccatggatctctgcaaagagtgaaagtagacactgcaggggagctcggatgga
tgctctgtcaaggcagacgaagtgggcactgttccagtcatgaacctgtatgttatataaatcgacccctctgtttcctcatc
ggggaaccgaggtagaaactctttctcacggtaccagtgtaatggttgtgctatggataggtgtagacgctgaaattcatgct
tagtgagcagcatcagctagggcatgaggtgtttgtcacattctctgtgtgactcctatgtgctctcagaactcactgagtt
gaggatgagagcgccgacggcccggatggaagagtcagatgagacaaagaacaggtgctctggccaatgtcaagcaggttggg
agggcagggagtcttaactgggcctccatctgccaacctcctggccttggctgtcagccagggcagcctctgacctctgaa
gggcgtgtcctctgtttttctgagcaggagttgggcccacaaaggcagcccttcagtctcggacgtgagtaaatattgacgc
tggggctttgggggccctgacgttgccacttaagcatgatgtggatgtctctattggaagctcagagtggctgaggactga
gctagctgggcaaacctgctccctaaggcaaccacgttctaaccagccccccactccctggagttcttcctcctgcttcag
ggctaggacgaccctgatcatcctgcacaattaatcaggcaggcaacccagtgccgccacaagcagtcattacgcaggtatt
tctaagatggaagaactggttgcttagaatagctaagaggaatggaagccagtccttccagcagcctctgtggaatgggga
gacccatggtctcatatgttcagttgaaccaatttagctgtcccccccctgccatcgccacccccagtccgtgtgagaag
aggcacacgtggtttgaagccaccaagcaccacctcagctttgtattcatgagcactcgcgtgtgtgttcgttcacaagctc
tctctgctgtccatgggaatgcacagaggatatctttaaagtcagcacctagacaccatcttgggcccggtgtacagtgaca
gcagatcttcaaccttggcctcattcgagagagatgtgcagaaacacttgttgaattccccacaggattccctgcccggtgc
tgtcctgtcaccttaacagttaagctactgttgcccaccgcacagttgggcatatcttactttccaaaacattttttttaat
ttgtattccctttatccagttagtcctctcgatcctttccctccctctttacccaagcctttccaccctcagcattccccct
ttttacttatgttctttatactgacggtctaccatctccctgcctctaaaagccagctgtatgaggccactgtccctgaaat
gactaggtgtgaacagggaagattccctcatgagcatcaggggaaatcctatgatataaaaatgtctgcagtgggcgttgg
agagaccaactagccattaagagtgcatactgttctctaaagggacctgagtttggtacccacattgggcagctcaaaaacc
actctcagctccagttccgagggacccgacactccagcctccaagaggatttgcacccacatgcacatacagtcacaaatgt
tactttttaaccttaaaaatggctgcagtgggatgagaagctgggaagtttaggcctggagattcattcatagaaaggaagc
tggctctgcttccccagccaatctctgctggatgtttgtaaaccccaaatttgatgctgttaacctttgctctaccagccag
gctactccagatggctctacccggatgttgtaagcatctgatttgatgacctcatgaatttgagcaatagaaatgtctgctgg
aaatggtttaccttctagagacagggtcttactatacaaccttggccgtccctgaactcactccatacctcggaacgcaggc

FIG. 4 (Continued)

tggcctcaaactcacagagatctgccgcctctacctcccaagtgctggggttaacggtgtgccaccaccacctacccagcaag
ggctatatttttttatgctcttgctgtggactgttctccttgttacagagactggggccagcctgtaccaagacatagggttt
tgaggagacaagggaacctccccacccccagagtctgcttctgcagagcctaactggcacatgagagtttaccaatataatg
tgtattacaacaggaatatagtagggtgccctcaaaacccgtacactagtggttaagaatatgggatagaaattctgaattc
agcattctggctgttcattatcctgggtccacagcaactggagtctggtgtggtatgaacaggcaaagtagatttctgacat
ttaagagaggagttcttatctgccgccagcctatggagacctgtgttgttgagatgacggtatacaggacgtattgtgaatt
gcaggggagggcaaaaaacagggagagagatgagcccaaggtgttaaggggtccattgtaccatccttggatttagcttatg
tgcttgagaccatcaacaggggagcagacattgtagggttgccctctgagatttcacccccccagttcactttcccaggta
gtgggagcctgccccatgttggtcgccaggagtaggatcaaacacaataccgtaagcctggtagccagtccccagaccca
gggctccctgccaggctccacccactggcttggagctggccacacaggcctcccagcttccgtaacttcaatgtcatcacct
aggcaactggacgctgccgccactgccctgccactgcaagccaccacggggcctccagcacctctacccaagtctatggacc
caccccagggcccaggctcagccaaggtaggcaggggctctgcttgactctcagctctcaagtcagggttcgcttgctgtccc
ccttccccacagggcaacagcctcaaggttccatcaggataaggaaacccctccccatcaactcacctggtagcccagaagt
aaggctccatgtaagcaggcctgccacacgggcaggctggtggccgagacagtctgaagagacaccatctgtggctctggtg
gcacaaggcaacatggtatggcactttggaaagtcacatgtactgagtagtctccagggtctctctgtgcccctgtactgtg
acaggtcaggatggagacaagggattctgagatctcccaaaagtggttctggtatctccacagccttcattcctttaagcca
cctgaatttctctttattccatgtccaagagacaccaaacagctacctggatcttccaaggccatggttagtgctataagat
gttgccctacccagtgcctcttcctaactctccctccgctacttagtctcagagtctctttcatccttagcctgtgctggg
cttcccgcccctcacatggctggtgctcaacatgtctacatgcaggcctaagtgttgagagatggggcctcggtaggccctg
ttcctgatgttgtccacttgtgctgctgtcctgtgaacagggctggatgtcctaggactggcaaactatacagcgtcatatc
aggatgagatagagaaaatcctgtatagaaattattgcaatgaggccagagtgagtgagtgagtgtgtgtgtgtgtgtgt
gtgtgtgtgcgcatacacgtgaacacctcggttgtgtggtgcattgtgagccagtgtgcacacgtgggtggagaagcagagt
atcaggagtgtatgggccatacactctttgtggttttaccacgtgttctcagcaggacctagcggtggccctggagcccaa
atggctggagtattgcctgaaagagagatatctgccccagttttaaagtcaagatctcattttgtagcccaaactagaatt
cactgtgaaccccaggctggtcttggatcctgatcctcctgcctcagtctccccatggttgaaattacagacatgttttacc
atggctagttgtcttgggtttctctaatttgattggttacttccactgctggccctgttagcatacactgtatgcacaaga
ccatcatagcctgagacccatagcctgagaccctcatagcctgaaacacccatagcctgagatcctcatagcctgagacccc
catagcctgagacacccataacctgagatacccatagcctgagaccctatgcctcgagggtcttgtgcctacagtggatgct
gacaagaccagcaagaagacacagggccctgctatgtgtcacacaaagccagtgctatttccttgggtcccaaaatctgaac
tcctaagggcccaaagcccaaatgaggatatatttgcttttttcttattgttttaatttttatatgtatttattcattgtgtct
atatgtatgaaggcatgtgagcatatcctgagactgaactcacgtctttgagcttggcagctgtacatttagttgctgagcc
atctcacctagcccctggggtgtgaatggtgagtttgacctctaactgctcactcctgggtctgcccaactttccctgacc
tgcaaggccttgagatcatcatactaaccggttaattctgcctccaatgtctattcactgagcaccaaacttgtgctgtgca
cttgctgagctacatggctaagcctgtccatcctcggcattacatctgaacacacatagggttttaccctgcagcagatgc
catgatacttgggggctaggggctgtccagaaacccgaggggcaaggctctgtagctgttcccattctgagatgactagt
aagagtctatcaggcagcacagagcctttcctcatggccccagggctgagcacaagggattctgatgtgtttgacatcgaat
tctaccaggttaaaggccacctggaaccttctccaaggtagccccttggaggggtaagtgggactggtagtgcctgcgagaa
gccactttccaaattcaaaaccaaatggaagctgggccatgaggccccacaggtggctaaattacagacatagaactgttgg
gcccttggtaaccttgtccagcaatctcctgaaagccttgtgtagaccattcatgcaaggaaggtgtgatagcctacttgag
ggacaagaggctacagactccacacacaggaagagatggagggccctgaattgtggcttgttgagggttctgatgttggtca
gtccagaggtctgagggtcaggatggacactctagactccgtttctgtctgtgtcctcacttgttctacctgtccctaccac
ggcactccggtcaagtcagcttgccaggcagggatgcctaaaagctgctcatgaggcaaaaagagtttcacagaaactcact
cctggagtctggcgtgctctctaaattttccattcccgcgttagtctagtggatggatccacatgctctctttattataagt
gcctttttaagattgaattctgacatagctaaagcctttcgccagtgttccaacagtcctagaacgtctttgagctagacagt
gacattcagaatagcctctggtattacactatcaataaaagccaagtcgttcccatatacaggaatttacaatggtttagga
agtagatcgggctgtggttttagagtattgcattatttatgagatggttaagtagaacagaactccctagttagaaccatga
cttgggtgtgaaagcccttgccctaggagagtaaagacctcacacctggcttctaagactatagctgagtcacacccataca
cacgtatttacaatggcttaaggggaaggtagactattcaatagactaaaataggagctatggcaagggcacgaagcccttg

FIG. 4 (Continued)

accctggcttttaagattaagcaaatcttagatagagcccttttgatcccagttgttaacaatgaattttatcccaggtgg
ttcctgttagaccttctgtgtttacattcctctgttttatgtaagaatccagtaaccctctttgtaccttgctagtgtgtcac
ccaacttccttattgtcttttgcataaaaagtctgatgctcaatttgacattacattcagattccacacgacctctcctgtg
tgtgtctgtctgtcaattcatcctacgctttgtccacccgcgactagagacccgttccacacaaacaaaggggcccagaggg
tctatggcagttggcgccttcgaacagggacaccagagcggggttagtctttatttctttttctttcgtgtcctggatcgggc
ttgtctctgtgacttgcagtctctgcacccccacagctctgtcagggagttgggctgagtgtggaagagctagggctgcgaca
actcctgtgaagaggatgcttgccctgctgagacctgttctggctacctgtacacacagtctagacagacacccaccctgac
tacagtctcctgtctctcctgacttcagcatgagctccactctgccctcgatgtcgatggacctggtcctctttcctctcca
tccttgctggcccaaaccagtcttgccactcactcccccacccctgcctggtctcccttggaagctctcgccacattgccag
gaggggctgctcccttgaattgccctctatcaggcctggtgtacctctgaccccgcccctccaaattcacggtcccctt
attttcagccacgataacttggaggcatagggtaggagtccagactccctgggcttcctggtcctttctccctagtacccagc
cttggacatcagcacaggatgatcatccattctgcctcctagtaaccaggttacccaggatcccctcttctatacaatagga
atcaatttggtttttgagacacccagtgctagggacagtgctcagcaggcttgagaacactttcaaagagtggtgagaccac
agttgccgtgatggggcagagaccagatcaacgtatgtatgcacacgtatgtctgtctctgtccacagacgtagtttctca
ccaggccttcccctgacaagaggacccggacttgttctcttccactctgagccctatactaaagggggctgtgactttgctgtg
gtttgtcccctgctctatgcaggattgtcacctgcccgatgcttcacgctcatcctattacatcattccacagggtgggtg
tgacaatccgcagttatcacagaggacactctgtgagtgtcctctttacagaggaggacactgacactcatgtgggcatgtc
acctgccctggttcgcacagctggagaatggcagagggccatgtggccagcacaggaagagccccagcttaagtgcctagca
gggctgaatttcaggttagggaatggtggagctagaggccatatgtcccacatggccccacccatggggtgaagaaatggaag
cagaaggcaggcctgagcaggtcagcagagagtagggtcgtctttggttgtctgaacatgggcagggctttggaaatgaggg
tgtgggcttccccaggaaggtaagagtgtgtactcgaagtactatcatctccagggaggggagagtagagtgcaggggtcaa
tagctaggcactgtgtgccctgagtgagcaaataagatgcaagacacacttactctctgtatatcgaggggttcctgctgtc
ttgggtagatgcatggaggtcagcatgctacaatgttcacttccttggtcttgtctgagtttccacgtggtgccaggtgac
ttagcatggatgggaagtttggtcaactactgtctctttcaagaagcacagggaatgttgggtggcctgagggatgcaggct
agtcttcctccagccctgttcccattccctggcggatggcctgagcccaggcgagagaaggttaatgcttcacatagcacac
cctgccccacatggggcagctaaatttgtcttccttcaccagtacttggctcccccagcttggggagaaggcccacccgctgcc
atctggacatctagggcccacacctggctagggaacagaatgtcctgctgaaggatgaggttgtcttgtgagagaaggggagg
gatccagccagtttccagatggggcaggaccaagatggttgccacactggccctgaagaaggaggtacttctgcctgcatcg
ggtgggacctcagcctctgtgtagcctcctttctggaggtagcttgagggaaacaggcttccggcaccaaggcccccgatgt
ggccaggttcttgatactctgagttctgtgtctttgcccactgcccagagatacggtcatttcaggagagacactccctggcc
atgttcctgagcctggcacgccctctgcccacacaaggatctcatggtgctagagccttcatgtccgctggagggaaattca
cacagtggctgacatgggtccagagggcccctcctgtcatcaccactaatatactagttacttctgatttcaattcccctgt
ccactggaacaaattattagaagggatgacagtggagacaaacccacagtattgatcacgtcatgtagacataccataacaga
gatttcccaggccgggtaagtttctctggggatttccttgctgacccgaaaaggccttgccatagccagggggacccagtg
tcatcatgctgaagatcctgcctctcctgtgtctgggctatatgtggacagacttgctttagtttccactagggaaggtggg
tattcaggctcctagaaggtgggggtacatccccatggatggggtaccccttccagagcaggttcgggataattatgggca
tctggtatatcacaggtggcagtgaggctggggctgagcaggggtgagaggagatggggaataacaaggaaggaggtcccca
tcctgtgtgatttgaagtgttctatgtggccaagtgacatctgtgtctcctcctccagtcaggtggcagggatggggaaggaa
ggctcagactcagagctggtcaagacagaggttttcttgaggagccagcccacctctggctttaagggagaggggggcttgg
agagccaaacatttgaagtcacatgtatccaaagccgtggtgacagggcatgatggggaatgcttgggagaaggactcggc
tgagttgggagtatgtgggggccaggcaggaggttcgaaggttggtagctcttgctgggaagttgagactcgcggccacgtg
cagggtgaggtaatgggagagtcggagacttccttaggggccagaggatagaggacatccccggcaaacctgctctggtgca
agccctagctgaattacttgggcaagccccttgggtctcaaacacagtttactcatctctgaactagttgggggagcccatc
taggctgctgcgtgggcccagaagtcctgccaggagtctggttagcatccctgggctctctctctccgtggaggcccacggg
gccttccaccaccccagttttgaggatggaattgttcccagcagatgtaaatatcccatgggctcaagtccagtcagagctgcc
ggagctccgtggaggagccgcgcccgccgttggctcagtgaggagctgtgtcctccagtgaggaggcctgtcattggctcgg
tgttggctcagtggaggagccgtgccgttggctcagtgagcatgtgctatccgtgtgtgtggctttccgtttacagccttat
tctcctccgcatatcctggcaccacaggtctggctgctgtaccctgactctcatgcttgttgggactccttggggggggg

FIG. 4 (Continued)

ggcgggtagcaggtgctgaggtctgagtttggcacagaccatctttgtcagcttgctgtggtcctgtttcatgatgcaggca
ctgccaggcctggaggagatccagctcagcaaaggaggaggctcatctgaggctttgacggagctggaggcaaggctagggc
agggccagagacagcccagatccctgccatgcccacagcctgtgacctggctgctgacagagcttctgacacggcgggccag
gcggggccagccctccttggttggtgcttctccctaaagtctccctctgccgattctgggccttctatgcctctcctcacac
cacgggatgcgtgttctctctaggaaaactcaagtcttcagtaaaaactacaatctcagagccagtgagatggctcagtggg
tgaaggtgcttgctaccagttctgaaaactcgagtttgatccctgggacttacagagtaggaggagaaaactgactcccgga
agctgtcctctgacctctgagttgagcatctgcactcacaggcatgcacacacgcacaacgtgattatttctatatctgtg
cttcccaacactgattttttttgtactttccagaggacaagtagtttctcaaaactggcctctttgccatcatgacttgat
gttttaaatcactttccgtgcttatgtaatctgttcctgcggtgtctggggatcgctcctctggtggacacatctcttagct
agaggagtgtgtgggacctatagaaagggtcagtaaagagcttgccatgcatctatcaatctatcatctatctacctatct
atctacatctatatatctatctatcatctatgtttgtatgtatctatcatctatctatctataatctatcaatctatcgtct
atcagtctatcatctatgtatctatcatccatgtatctatctatgtatctatcatctatgtatatatgtatgtacctatcat
ctatctaccatctagcaataatctatcaatctatcatctatctatctaccatctatcagtctatctatccattcatttatct
tgcctctgcccctgcctctgactgtcatatgtctgtctctctataatctatctatctatctatctatctatctatctatcta
tctatctatctatctatctatccatccatccatcaactatcctatccctgcccctgactctggctctgactcttcaattat
ctctctgtctctctgtgccctccctcccttcctccctccctctttcccttttctgtctctctgaagagagagactataagtt
tataatatagtaaggttgggttaccagctgcaggaatttttgtagaaaatgggggagggtgacagggctgggtgatagtggt
ggcttccgtgaggctgtggtgctccatgagttcagagctagatgctagtaaggaccatttaaggacgtgggcaaggaggcat
gtcccagctgaaggactagaagtacagagccaaacactagcaggtggcccatgtgcctcccattaagactgttaggactcta
gcaaccagtgagggcaagataggagggtgagcagggcctgtgtccctggcaagcaggtcagaatttgatcttcagcatga
gaggtttggttggatgctccttccttgtgtgggtgcaggaggacctggtaggcaggaggtgtggaaagcagaggacttggca
aggggtcttggggcagagctgcaaactctgccaagctcctggaagtctgctgcctgcaggtagccccttcccacctcccgc
tctatttccaggcactgggcacctgccatttttttcttccctctgcttgagctggccatgtggacacaaggggtgaagaggg
acccaaatcctcccttgctttctcagtaggctgtccaccttcagatatgccgtttctggaattgggaaggcaagccagcatg
ggtgtcaacaggtggggtaaggtgtggcaggtagagttaccagcagagtactcctggtacaatctgtactgtgatacccaga
tcccatccaatccaaggctcttgctgacaacttccaaggctacatctatgatgggaatcttccaggaacatacacttggagt
cctcagcctaacaggggtctcaaagtgctcattcctatcctgagaacatcagtgggtgtggcaaaggaatttgggagacca
tctcagacagtgtggtcacagcaggactgacattcattccaggtgctgcctgccacaaatgtctttccctttttttttttt
aattaaaaaaaatgtgggccagtgaaatggctcagtgggtaagggtgattgctgccaagcctgatgacctgagttcaatcc
ctgaaccccatgtactggaaagaaagaatccactcctcacaatcaatcaatcaatcaatcaatcaatcgaccaatgtaatta
agtaaaaatttaaggaatgccctgaaattctcctaacatataactagcatttttattctaaaagtattattgttgttgtttt
gactgaccttgatctgatgagcttgcctcagccttgtcacagcagggactgcacgtgtgcaccactgctgtcttccaaacaa
catttgaagcttgaagctcagcgacttccagcgtcttaaatccccaggagaaacccctggccccatgagccttgctcgctg
ccgtagcacctcaggctggcacccccaacctgcctttgcctccctgttcggatttcctgttcagtacatgttgctcggacac
taggtggttcagcacggtcttcacagtccgtctacactgtgctgttttgaatcagcagttcgttcctggtcacagtcaaatg
tcacctaacatgtccgggtcatattgtatctggcagttcctcttctgatgtgttcccagtctctcaccctgtctggctaaag
tgaataatgtcactgcgaaggggcctggagtccattcactgtgtgacatgagccatgtcctttcccttctgagcttggcgt
agtccttgtaaaagggagaagaggaccaagtggtccctggggtaggacttctaagcatgtcctcttgggtctcagggtgtcc
accagcctggcccagctgaccagcccactctgactgcgaagagatacctccctgaccaatggctcctcaccagaaagtacca
ttccccggagctggtgaaggcagctctgtccaccttccatgctggttggccaatggcttgtcaaaaccttcatgactgtga
taaatgggaggtgggaaaaattaatccttattactggagaagagcataaattatgttaattcctgtgcttattatagttgtg
tgaccttgggcaaggcatgtaaggcctctgagcctgtcttctgagtagggcaggactgcgatatgtacagggtacttgtcct
gtgtcatcctcccttgctgactgagccccccaccccactctctacctgtgctcagctggtccccttttactggccctctcagc
ttgtgccacttctctgaggacccatggcctggcgcgtgccatctctagatgcgtgccacaaaccactatgagcagcctcctg
cctggggtcagacaaaagcgacagatctgccctgccagccctgggcaagtctggacctgtctgcttggcagtgcagagctgg
gccaagctggtttgcgggcttagaaggctgccccagggaggctgctccttaatgggcagcgggcaggtgggctggggtttcc
ctgccccacccctcccacaatttactgtgcctgagcgcccttacgctgccccgcctccagggtgactgtgagtgggcggagcc
tccgcgtgggaggctgtgctgaggaaatcgtggggaaagcggttgtgggtactagctggggctagagtgaccctgctccct

FIG. 4 (Continued)

ttatctcctttgaggagaccatccacaggtgacaactccagggcagtcctaggactttagccttagaccttggagggtgagg
accatagagggtcttgagtcccacggtaacctgcataactgtgcattacaggcatggttccagcaggggcgccctacacac
gctcttactaagaggaacggatgaagtttgagctgtctcgaagacctggcgacaagtcacagccttcccctccaacataca
caaaccaagacctggcttgacctaaccctggccgtcattgtaggtttaggacacggtgacggcagtcatggcccattctctc
aaaaaactgacccaagaccacaaagactaaattccctctccaacagcatctacccaatgtgagggcacatgcccttcttac
ccgtttctggcagcagaatccgggaatggcgtctctaaaaccaagcttgcctcagtctcacctcctggaccagagaatgag
ctgcttgggagtggtgatggtagggaggaagagaagggagctagacagggaaaagggaggcaaggggggggggagaaagca
acgtgagtggaaggacttagcacagctctggggtctccttgcacccatcataggcagccccgccgtccacttggctcgcctgg
tactgaggaaggcaggattccccaattctcagtgtcctccctcttcttccagAATGAGCGGCAGCGTTGGGGAGATGGCCCA
GACCTCTTCTTCCTCCTCCTCCACCTTCGAGCACCTGTGGAGTTCTCTgtgagtatggagaactccgcctcactgggtttgg
ttggcttagctggcttggaataaataggttgggagaggggtctgctgaggtagcagctgccttgggccatgtcctgtgtgca
tgtgaccccacagtcatggtctgtcctctggccagttctctagagggctgtgggcacagagatcatgtgtatgaagcatttc
taatagtcctgaagggcaagccgagggctggcagggattgtgggagctggaaaactccggaagtccaaggacatatggctta
tctcctgggatggacacacacacatggggtagcctgatatcctgaaccaggggagcacagcggattctggagcagatgctaa
catccagtgtccttcccctccaccccacagAGAGCCAGACAGCACCTACTTTGACCTCCCCCAGCCCAGCCAAGGGACTAG
CGAGGCATCAGGCAGCGAGGAGTCCAACATGGATGTCTTCCACCTGCAAGGCATGgtgagcggggctgcgctaaagactgga
tgttggtgataaatgcgggttggctttctccgggtggaacgaggaagcagggctttgggtagcccaccttgggtcggaagaa
aaatatgcaatgagctcatggtactgtcgattcctaggtaagaatggattcaagcatgattggacccagcggtaggaagagc
ttgggcatggctggacccaggtggttccctgggaccacttcctctttcacttgcatctctctttctctggtttttcctggg
gtacctttgttctttggaagcctcggccctcagagattgtccaacatttttgaggcccgtggagaggccaccccctcttttc
ctttgcccagaaacactgcttcttcatgttggtctgagcatacttgtttgctatgtgcctctgagctgtccctatctttctg
attggcccatgtttctatagctatctctggactggtcaggatgaagggtactaaggcaggctccttatattaggagaggaag
atgtggccagtggagacagtggtttattcctcatcttgtgcgctctttcctgggaccaagaggggtaccaagcagccagcc
tttggaatttgcctcctattgggagctcctcttggcaagaagacacagtagctgtgggattctgttcctgcctcactctctg
gctaccactgccgtgccctggtggtgccaggaactggaggaaggtgactgaagcatgcaaagggcaagtgaaggcctctgtt
cccgaggaagtccctcgaggccttctgtcctcagcatcctcccctactggaccaccaaagtgctaggatcccaaaggcgaga
gggttgggaaagcgtcaggcggggacttgttggaggaaccctgcaagcacattaaggaagagcaaagcccaagccgagttgg
cacatgtcggctgcagaggcaccagacagctgagcatgtctccagtgtagccttcctcccactagcacctgatgagccatat
gctagaggcccagggactctagaagccaagcaaagtgtgaggctaaccctacttggagggagaagcctggccactttaggc
attagtgaacaagggttgaagagacaggaggcactatgcccttactctccctctctctgtagaggtggaaggttggtcaga
gcccactgatctcccatggaactgggtgagactctctatagtggcagcccaggggtaagggtatcatcctggtgatgccc
acttctctgagctctgcctgtccagccctgatctctgccagctcaggagcctgtttcagaatagcagttcacctgtaagtgt
ccatttacaggcaagggaactgaggcagatgctgtggaaggagagcctggggcttggggaagagaatggtcctgcatcatg
gtgaggatagtccccatcctgcctgttactccgtagagacatgattctgacacccatcatctaggatatatgtgttctcca
gtatagagggataggaggtggctactaggctccagggagggagggccttacacaaagactctaaagatgcctgctttaggag
ttctggaagctgcctcccacagtctaagctacccagcttatgcctgagagggcagagtgctcagagacccccactgtgactga
aggaagaagcagggaacagccctggggccccggaggctagggatgtggtacccaccccggccccaaagatgcccaacgtaaa
cgtgttggcgggtgctcctgggtgctcacctgctggggcatgctgctcccagcaggggtaacacgggcggggctcaacacct
ccacaaacaaggggccgctttctcaggtagcaacacgccttgcagtaaagccatggacgaaattcctgggcgcacagctcag
ctcctagaagtgggaattccctggaaacaggacttcctggcctcccttctgcagggctcagctgaccctcatgcacagttct
ttcaagagacagctactggtccaacagcttcctgtatgctcagaacttccagcagtcctgacagcaaaaatcaagactcaga
gatgagtgacagatagggccatgtggcagcaatgctccagagctcatctggactgcagggaactggggtggggtgaggtct
tgcaggtgctgcaggaagttggggtgggtgggggatgcagagagcactagacattgcatgccatgaaatgaggtagatga
agtttgatctcataaattacatggtcgattacagcttattaggatggcagaggaaaggggcatccaggcaccacagggagca
tctttgagtccagggatggaggcagctatggaaatgacagtttggggtacagatgtgtgagagtggtttggggacctacaga
atccatcatcgtttcagggtgcagcccggaggaagcaatggtctgggtatagactacagagtacagactggtctgtgaatgc
tgcagacagggtagcctgcccaggcccacattcagctccacaggtgctctgctatgtccagtgtctgaagtccaggagctga
gcctgctgactcaccctgggggggggggctccaaagtctgatgggcatcagagggaggggttgtggagcactctcagaggga

FIG. 4 (Continued)

ggagttggtgagcactctcatagggaggagggtgtgcatgccatggattcacgtgttgtttgcagcggcttctaaagtgctg
ggaggttttaagagagtgcctgagtgtgtgtggtttagagttccagggctatgggaggcacagagaggaaagggccctaag
agggctgggataccagggccagctcagcgctgtgatgaggtggaagctcccaaatgctatccccatccctgagaactctagc
cccatccctagctgggtccaggacaagaaacactacccaggcatgttctcaggtcaataggcagttctggcatttgaggttc
taaggacttccagcaactccacctcctgtgttctcaggtacccctccacccccacagagccctactcagtgatgactggtg
tccagttgttcctgtgtgctggacaatcccacccaaataccaggatagtccagcaaaggtgtcatggcttaagccagcatgg
cccttgagtagatgggatatgtattctcttcaatggttccttctgtgtctaagggacctcaaacgggagattgctttctgtc
acatggaatgtcctgagcaggtctaccagctgtggtgaaccctcagaactccatgatgctcttctccccaacttaatggct
gtcagaaacggtgcagtcagtgagttcaagttctcacatgctcccgagtctccacatccttgctttgtgaagttgaggtgat
ggaaagggctagaatggagaggaccctgggagatcggtgcagcctcctgggtaccagcttgtctgcctggccttgtgcagag
gggtgggccaggcctggacatctaaccattcccgagtctcattggagtagagtgtgttgtaagattaaagcaaatgggatgg
gcaggagcggatgaaccctagtgggtctgaggagaaccctaggcatggtgagggacgcccttgtggccttagcttcctgtg
gccatgtagatggcatagcagagcctagacagttgtgataggtaaagagggaactgaaggtctctggggctcgatgtcctgg
gtttgtagccccatcctggtcttcctagttgggaggttctcaggatcctttagtctcctggatctgagtggccccatctctaa
gatggggaagtggacagatcagaagcccataagtgctgtttctcccacagggagtgacagttagctcaagggcgaaggccta
tgtttccacactgttggagactctgcacagtttgccatgcaggggcacccggactctagagctggctttgccccttggccat
tttggcttctgcatatggagctccttgctcctgcaaatggccttcagttctagctgtcctttttagattccgggtgcttcaca
gaaactccactttaaaaatggcctggagactaggtgcggtggcacgtgcttaaatcacagcccctgggtggccagtggaggt
ggatctaaagtttgaagccagcctgacctacacagagaaaccctatctcaaaagtgaaatgatcccctgcccagctagaag
agaactcagagatgcctctcccggggtgctgtgtagggtgagctgagggcccatgccaaaggctagggctagtcacagggtg
ctcagcaaggttgagaatcaatgggtgttgtcacatgtcggggacaggtcccagatcaataaggccctacccacagggtctt
gggagattgagtggagggcaaagttcacattgtgagcacgtgtgccaagaggcagtggagggcttgaccctgagggcagaa
atcccagttctcaccctccatgcccagtgtttgagcagaccttctctctgcttccctggttctccatggacccacaagaagg
tggacacccaagagccagaggccggtccagctcttcaaatacagaaaaaggacagagtgctgatggtcagcagaggaaagggg
agagaggcaggtgccctgggcggctgcaggatcactgcccttcccgcctcttcatgtcctcctccaggcctgcacctcc
cctcagatgcccctttcccgctgtttctgggcgcctttctctagcaacagctgttaggaacagatgggccgcagagggttggg
gaggtgctgcagctggctgggcagaaggtgctctgctgatctccctgtggcctgcaggggactgagccagggagtagatgcc
ctgagaccccaagggacacccaaggaaaccttgctggctttgagaaagggatcgtctctctcctgcccaagagaagcatgtg
tatgggccctgtgtatgaatccttggggcaggtaggtcaggaaggatagaccttggcagggagaatttatatcaagggaagg
gcagggcaaacggagatggagactgagttttatgtgatcctcttggggacccccagctccccacccacttccagtggtttct
gaccactcttccttggcaggctttggtagcaagagggtcgaaggtgtatagtactgaacttagctgagcccctccccagtt
ccagagtctcactgagagcccattcctctccccaactccagggtccagaggaagagggacaaagccaccagcagggacagta
tgtggtgtgtttgctcctgaatcaacacaccatacttgggcactgtagtcttgagcatgtgttgtggagagaacgccagggg
agcctgcagaacttcacttccacctcagctgtgagagctacaggagcagtcagcaaggcagagcctccagtgtgttacccc
agagaagcaggtgctgaggaccctggcactacctaggggcacggcagtggaggcagacaggcaaacacctaggaggaagc
aggagccaggctggggctgtggcagagaggagagctcagtggtgggcgtcccttccctggccagacggttcctcagggctc
acagactctcaggccaggtgcttcctctgggagtcaggtgtgagttctcacggacagtcccattctcctttccggccttaat
ccttcccttatttttctccttggggtgtttgtgaagccaacacgacaattgattgatgaggacccagagtggctgagggaca
caattccttaaacccaatctagaaacttgaaggccatctcttcagggctctctggagcagcctggccacacctacggggtg
ggagtctgtaaactcagcccttagtccccatggagggaggctgcagttgacccctggtctatctattataaatagatccctg
agcagtgtttctccaaagattgctccccaaaattagactagaaactgactttattgttcatagctgacttatgagcagtgca
cacctgtgcagccccagccatgaacatgcctctcagaccagcgtagggatcagtatgaagtagtccatctttactgcttctg
tgaattccagagctttgaacaggggctacagccactgccacagccctctgaccaagcccagatactgcaagctctctggagg
gagaaggaagctggtttggaacttggcgagaaaagggttaaacagaggactctgtcttcacaccatctctgcgtcttcttgaa
catccttagactctaaatgtgtgtgtgtgtgtgtgtgtgtgtgtgtgtgtgtgtgtgtgtggcggagggggctcaagctgtc
cttctaggaggcctagagattcagggcgatgaccctttcacaggacacgcatctgttgtggaccactatggtgacttcat
gcgtgaaccagacctgaaactcaaatgccccagacaagggcagtggtatccactgtatggtccccactaggcagatgctg
atatagagccctggctctacaaactctaccatgcctgtggtgccttctcgggtggtccttcaaaaattctctttggtggag

FIG. 4 (Continued)

tggccctgtctctgcttcctggacttagctagagccaggacaaaatgctgtctgtaaaactctgttatgggttctttggct
ccaacogccactttgggcctttgacggtagttggccgtgttctcgactctccctagcccaagcatactggtgtgtctttcc
tctactcagtccttggggtggtccctgtaggtccacgattccctggaaggaggcaggttctctcccctgggtcgccaaggct
ggcggcaccatctcttccttcagggtgacccaacccagactgcaaaggtctccaggaccagggctgactgctcatgctttag
agtgtaggctgtttgtaggtgactgccacagccctccggagccttccctgagtggcagcttagaagggtccgagtgggagtg
tatgatctccaagccagccactgaccctgcatcccccacctgctccccctgctcagcctgcttggtgcggtccaacacatctc
cgggcaagctgaggcctgccctgagttgatgaatagtcataaggaataaggggcgggcccoggtttgttgttggatgcagc
cagttgacagaaatgagggagatgggcagggtgagaatgccaactctcagtccgcacgcctctgagcatcctccgctcctgc
cttcctagccacagagcctcaacccctcagtccaccccacgggcagccaccagtctaccectacccacctagccacccag
acccatgcctcgtcccgcggcacaccagctcctcagcgtgtgcagacccccacgagcctacccatgctttacgtcggtgaccc
catgagacacctcgccacggtaggtgtaacgtgcctggtatagggtctgcttagaggcctgatgccatccacctaggggct
tggcagagtctgccatggttggggttccagagagacgttctcttgactgcctgatggcagaggggtaggctggagagtggaca
ggttctgcttctgttcatccttggggcagctctcgaggatcagcagctccgggctgggcaggaagtgggatgtgggatggga
ggcttggctggcgtctggtcagggtggtagagctgctgccccagcccctgggttggatacttctgagatgactgttgaggct
ggtggctctggccatgctcagggtccccaagatagtctgccctaggagcgctgcaaagaggtcatctttgtttgggctttgg
cgtgaagctgccccaccctgccaagagcatcctcacctgggagtttgttcacttgacagcgcagatggggcgtttctcatag
ccatgggctctcctccgtgtgggtgtgaactccaaggcagagacaggcagcggctggacccaaggctccctgttgctcctc
tcaagcaggtacagccagcctggcagagagcagaaggacagaaggatggaaggagccacagcctgtgcttggcctgagccca
agggacttgggctcatttccagacttgccaggtccctggggtcaggcagacaccaggctgctaattgagcagcctttattga
ccagttaaaatggggagatatcacatgagatcacctgagtaagtgacccactgcatgatcgtcattggggccagccctc
ttgatgaagcagaattaacatcagaatacaaagggcagcttagaagcagaattaacatcagaatacaaccagcagcaggaca
acccacaacacctgggtacagctgccccacaaggctatttcccttttaggagagcagagagagtaaggaattgtacaggaat
cctgggatggcagaggtgtgtgtgtgggtgtaggggtgtgctggtaagggtgtgcatgtggcgtgggggtgtgcatgtggcg
tgtatgcatcctcttatgatcagggaaaagactgagtgtgggttgaatcacggttttgcacaggtgcccttcctgaggccag
taggaggcagagtcactatccaggaccacacagagacctgcccccaagacagccgctgactctggtcctggtgccgctgccc
taggtctcagaacccgtggtggctaccatgtcatgatatttctcatttgtgtgtgctgtggagcagtgtgctgtggtgtgt
gtgtgtgtgtagtacaggtggtgtagtgtgtgtgcatgtggtatgtatgcatgtgatgtgtatatatgtgtgtgcatatggt
gtgtgtgtgcgcgcgcgcatgtggtatgtgcatggtgtggtgtgtggtgtgtattcacatatgtgtgtgtttgtacccacaa
accatgtgtggtgtgtgtgtgtttatgtgtatgcaaacgaaggctagaggtgaacctgggtatcactcctcaggtgctgtc
cctgtactctgagtctctcacttgcacctggggtatgctgtgtgctgagtaggctagactggtctatctgtctgtctctgcc
tcccaacactagaattacaagcacacactgccatgtctggtctgttacatgggtcctttggatcaaatgcaggtccttattt
ttttgtggcatgcacactaccaacagagccacctccctgggcccgttgtttcttcttaaaacgcaggctctgtggctttc
tctccccttcattgcttcatcacagcaccatgcgcttcctctgcattctgaccagcgtagcagtgtagcttgggatttgctg
gggctccaaggctgggctgagccatcattctacctgcgtgggtgacttagtttcctcatttctttgtgagaggatcgtgtag
gagagcatagcctttttgcccagagaatgttaaatccaatgtggatggagccttcgcccgtgtgtcactccccacccatctgc
ctttgttgtccttacaacttgcagcagtcccttgggagctcacaggcaagacctgtccttggagaccggactgatttcagg
atgccaccttatccctggatgggtttctcataagtgtatcccatcttggtttgggggctcagtatacaagttcaggctttat
ctctggtgacccactagctatggttttgggatgagacatgtgaggccatgggctgagacagtttccttctctgtaagcaggt
agtagcaactaactctcatgcctgctcaggccgcagatatgagctatgaggtaccatggcctctggccatgactgtgccagc
ctttatagtcagtggaggtacagagaagctggcctagagaactgggcacatgttcttcctcctgtgagcctgcctcccac
cttcccttctctctctgaggactagagactttgaccgagtgatgacctacagctgagtgcagccctgtatgtaaggcgaggt
tggctcggtcctcctgcacacggtgagcccatttacagagctggaaagagctgaggccactggagctgggcctgatagatgg
gatgagatgagcggggagaggctgcaactgccactatctcctgatgccccaaactcttagcttcttcatcagcttccagttc
tcctgcatgtacacgtctctctctctctctctctctctctctcacacacacacacacacacacacagagagagagaga
gagagagagagagagcagctcccaggatatagtaaggcaagtgtgctctggttcttcagtgtcttctgtgtgaagtggggct
cagctttctttctgcagaaccagcatcatggttgcaggactggtgaacctggttatcctccaatcccttaacccccagacca
acacacacacacacacacacacacacacacacacacatgctcttataggcaccacacatacatatgaacacaaacacaccat
acatgcacacacaaacacacacatatgaacacacacatatgaacacaaacacaccacacatgcacacacaaacacacacata

FIG. 4 (Continued)

tgaacacaaacacaccacacatacacacacaaacacacacatatgaacacaaacacaccacacatgcacacaaacacacaca
tatgaacacaaacacaccacacacgcacacacaaacacatagcacagcacatatcaatatacagtggtgcatgaatacctca
tactcttgtgtaaggcagcatagacgtgcatgcacagcccagggctggagttcaccctgtctggagcaggcttccctgtgct
cctgcagaaagcatggcttctggaccggaggagcccgagggggcagccccaggtgagagaaggtagccgagtaacaggaaag
agctgtaggacagacgagtggagctggtgcagtgctggtaactgaccacacgggggcagggccgagactgggagaagggatt
tggtccaggtggggccaccagcacctagggaagtcagagtagaggaaattctggagattctgcactggacttgctgactgg
ctagatgtcggggaaggagtgtgttagagtggcctcaaaggctttcgactgtgatggggaattgctgcaggggctgagaagt
gagattgggcatttctgtgcagtgtttgggggggggggggcttcagcagttgagcagatgaggtagagagggtggccgggac
aggacatctgtggaggtggtcagatgtgagaccaagaccaggctagaggacaaggccacaattaccttagaaggcctgtagt
gatgattagaaacactgtagggttcttctgtgtgggaggtagacaaagagcctgagcatgtgggtgggagtggccaggtgga
cttgcaggtgtgggaggcaggtgggcagggtggtgtgatggacagatgcatgggtgggagtggccaagcagacatgcagttg
tgggaggcaggtgggcagggtggtgtgatggacagatgcatgggtgggagtggccaagcagacatgcaggtgtgggaggtag
gtgggcagggtggtgtgatggacagatacatgggtgggagaggacaggtggacattcaggtgtgggaggcaggagggcaggg
tggtgtaaagtggacatgagtgttatttaagtcggggaagggggctgtgttaagaggagtgggagacaattttgggaaagag
agccacactgaggagcagcctggaagccagaagagggcttcatggtgacccgggacaaaggaccccattacaaggttagaaa
agggaccagaatcagctgcattgagggagctggtgaccccggggagggtagaactaagtaggatcaggtctgaggccaaggc
ataccccaccagagtcggatccaagtaggtcatcctggacccatgtcccttctcagtcccctcgctgtgttggaacgcatctg
ctttccatgctccgtcccgctcccctgaaagccagctgatggggtgtcagcccatggagccaatctgagctcctaggaaaca
tcacctcagctggtgggaagtcttctccactggccccaaacccaaaccctggaactatcctcgatccccggcacaacacctca
tctatgccgtctgtgtgtccaagggcctcagagctggccacccagtgctcagacgtgcacggatccactgtcagatgtcctc
caccaccaagcaaggggactgtgcacggctagcctataaccctctctgctgaacccagaagttatgctctctcacctcttct
gctgtgttcatcacccatgcacttgctctggccagggtcctttccctgccaccccacacagaaccttgccgaatcccacaag
acctacagattaaaaccatggcagctcttgcctttcccagagccccaccctccaggacacggcttctgcctctttggtg
gtcagtattttctcccttacgtcccggaggccctaagcttgaatgctggttagctggatggcttgttactgtactacgaggg
gagagctcagaagcctctaccaagagatgtcaggagcctaactgagccagtcgatgccctggatatgtgggcagcctttgtc
ctcacctttcacagcccatcccccagcttatattgggatgccttctccatgggggggggtcccaagacaacgtcacagcct
cgctatgggtcgctgcaggtgacagggcgacacacatgggcccacatcacgcttagtgaacatctcatgtgtcactatctaa
tttctcagcttagctgctcattctttgtttctccctgacctaagatttaggaagagcccgggaggtccccactgactgtccc
atgaatggggacagtcccagtggggactgtcccatgaatgggacagatgggcagaaaggcagtagggggcgggggggaatgca
cgaacaccaatgctggatttgagactacaagaatgtgccagggagaggtgctggcagagctgtgtcccctcttctgttctct
cagacagacaactcgcctttgctgttggggtacactcggtgatttaaaaattcctgtgaatcactgcagcttgtaggcagtg
ccaaagagatgggggagctgcctagagaacccctggaaggctctgctctgtgatacccctggttcaggctatgttggtggagg
ggtggcctgggtgggtcttgcagacacatgcctggcagcccagtagagcttctgggggcacgtttcccgggtttgaggtgtg
gaaagttccacatggccctggcatgggacccgggcaaggccctgcctcggcgggcaaaaggagggtgcaatgcacatacctct
agggaggcagccgtccccccatgcacaagtcctgtcttgttgacatttccattcgtttaatcataggctcggggagactgtg
ggaaacaccatcaggatggaggtctccagctagcacagaggcgggagagatggctgtctccacagagccaggggctgtcag
tcactaaccccaggcaagcggaacccaggctctgacctgcctgcaggggaagacccggtttcagacgctttcttcccttta
gaagaatccacagtgttggctggtgttttggaagcaggaggaccctaactccccatccctcagtgctgggctcagagcagaa
tgagtgacatttgtcaccaggggccctggggtgagccattcctgcagaacaccaagattccctggaaacagatgtggtcac
aaggtcatgtcactcatacctgtgctggatgggtgaatgcctcttgaccctacccagaattacttcctagtaagggagcgg
tgaaggccatggggcagcaaatcacgtgcccagaggctgggccttgaatcgaggaagtgatgttgggataaaggaatggagg
ctgcgcagtggaacctgagaagccacagcacactatgctctgtaagctagctcctgtctccagttcctaccccagttgcttc
tgtgaggaagctagggtgggccacaactaacctgaaatccataggaagggggtgtgcagaggccagggcaaattctagaaag
aagggaggaaagaaaatggaggaagggagaaaggcaaagaagggagaaagggaggaagaagagggaagggggagagagtgaga
gaaggagagggagggaagaaagagagggaggaagggaagggagaggagaggtgagggagggagagaggaagggaaggagaga
gggaagaagaaaagggagaggggtagagggagagaaggagggaggagagggaggagggagggaaaggagaaaggggaagaag
ggagagaaggagagagggaggaaggagagaagacagaaaggaagaagaggaagtgatggagaaaatgcaggaaaagatggag
aaagtgtggggaagggaggaagtagaagcctaggcaaaatccctctcctactgaggtcactggatttgggtagggctgtgct

FIG. 4 (Continued)

ccatactctccagttgtcggtggtctatgagaccatgttcccagccgggcatggtgggcacgcttgtaatcccagcactt
gggaggcagaggcaggtggatttctgagttcgaggtcaacctggtctacagagtgagttccaggacagccagggctacacct
cgaaaccctgtctcgaaaaacaaagcaaaaaaacaacaaacaaacaaacaagagcccatgttccctctgtacactttgggga
ccacggtgggaactctgaccttaaggctgagttcccctgctgtgtgctggggatcctggtatcattcctgagagcctggct
gaggattagaattggtgggaccaggaagactgtcagagctgctgtgggctcagcatgaggccagcacacaggaagttctcct
tctgaaagggcatgctcaatacagggtatggagatggtgggtgcccctgccggccaggcagatgagcctctggctggtggc
tgtgaatcagggactggtgggtcactgtggcgagatctggaggcctgtgtgtggcttctcagaagcacaacagtgacagagt
caagtgcctgtgcctctctgagagggcagcgccgggtcaggacccagcacacttgaggccctgtgtgctacggtgacctgtt
ctcatttctttgtgtgtactgactccgagtccctcatcagcatcacaccgaatcacctcgatgtaaactgaggcagaggagt
cacggaaagggtttctgtgtgaagcagggttaggggagacggagataacacagataaactggaagggaagcccagagcgct
ggggcggcttcaggaggtaggatggctccgcaggctgatctcctgccgaggagatgcaggtcagcctattctcctggaactc
cgcatttaaatgtgacaaccgacaggcaggctttctgtcactgtttttatttgagaaataaacttctcggggggaattgggt
gtaatatgccctttgttgctaagcactggatgcagccagtccacctctgaggtccgtcttggtgttctgtgctatagcaaag
gctgccgtgggtactgaagtcagagaggagtcggtgtggaaggcacctgctcccaacctttaagaggtcgttcatttctgt
ctacatatataagaacagatcgatgagattgtttgtaggttagaaacagttaagatgtgagatgggagtcttcggggtaaaa
tcatagtatccaatgtgtgcatgtgagggcaggagcctgatagcaggacggtaagagcctccttgtctggttaggacaagag
agtggtggagaaaggagaggatagaggggggaggccctgccctcaatcaggcatcaaagagcttgtctaactatggttgggta
tccacttcaatgccacgtgttggtacaaccagtacacgtccaagagtgagaccccggctgctgttccccatgtccctgctt
tatgacgctgctcagctgcctctggagctcagcctttggagacagccttgctccttgtgggcagacaggctctgtcccttcc
tcactgggccttgtgttagtgggctggtgctgatgatggatcagttgcaaaagtgtcagagctcctggattctggcgtcctgg
tggctgaagcagggttgttccttctgaaagaacagccataggtttttcttgctcccagacctcgcccccacaaccatgcgaca
agctatgtgtggatttcattctcactatgcagaagataaaaatggaggccagggatgtggaataataccccattcctctcc
tgctcctactacctacctacctgccaaggtatagtgctcaccctgggctcatctgtcaacctagctcagccaagagagagtg
ctagaggagtgaaccagcgtcatctacgtctcccgatgctcaagggagataagaaactcagctgccttgtagcaggagcttg
gggacctaagggaccgttgtgagtgttctatgctgatgaccctctgctagtagagcgaggtcaccagcctgctgtcacccc
aggccctgaagaggccaagggagacaaggtgtgaatactgaagtctgagcctaaggaaagagagtagaagcaccagtggctg
tttccagcagaggtgcggggtaagccccagcagcactatctgcaaggaccaggaagagaccccggggactaagggaataaga
gatcctggccttctctgtagaggtggggctcactgagacccccatctgtctgagcccaaaataggtcttaccctcaattgcc
ctggggtttttctggatgatcccagaccctgtggtcacagtcagtgagcgacacagacctggcaatggggcgtgttctcaa
accctcatcccatcggaactattgtccccaattctgatgttggcctttcccatgaaggctggtccaccagtggcctggac
actgtaggaagggacaccctttggctccatgacgccctcattcctcagggctcttcaggtcacgcccagacactccacttg
caagtataggcacatgtgtgccgcgcaggccgggcatgccctaattagcccactatcttggagttctcattgaaagcaaaa
caaaccaaaaaagtttgggtttgcccaggttcttccctgaggccaagtgggtctcgtctgggcttccggggggcctctgggt
ctggggggacccctgggcttctgtgtagacctgcttaggcctctctgacgaggcttctcatttcaacagcatgacgggaggca
aaagtggggggccaggttgagcctcactgcctggcaatgaggaaatggtttccttcccatgagcctcaggaggagggaaccc
tgtgtagaaggaacgtctcttacactctccagtcactggggtctttaccatctttgggagacacggtagacactaagaccag
tgagggagtggaagatgaccttgggactgtaagaaacgagcaggcacaggagatccagcattcactagacaagggaacagac
tctactgggcagcctagtgcccctatagaagtctgcagaggcctgcctctctgagggccccgggcttgccacaccagccagg
ttttgcacccagtgctgagggcctgccttcccgaagcgcctggtccctcctgcataagctcccacagatgctatcgctgtt
cctttggttcaatgactaagtccttggcacccacctccaatcattgaagaatgcagacaagttaaaatatgaactcgctg
ccgtgggcctgcaccctgcttctgagacagggctccctgcccatcaaggatgatggggatcgggcacggaggggctgctgct
gccttctgcagatgtcatgacttcttccaaagccctttgctgggaagagagtgaacttggttgcaggaaggaggtggcgctg
cagcttcatcctggatctgaaacaatgtaaccaggttctgggatccctggaagcaggaaccaggaggtagagccatagtgca
tctctgctcattcctagacagccgcaccagagagagtgaccttcctgactatcacatagatgtgtgaagctgtcttcagact
tatcacattgttgtacattcactcattcattcactcatttgttaactctttcattcatccatccatccattcattcattcat
tcacttactcattcattcactcattcattcctctgccactttgtcctgacagaaaacgcttgagcaaccattccaaatcgg
gatcatgtggtccagatcagcaccactcagggaacacagtgggtgggatcctgtgtctatagagccatctgtctgtgggatt
gcctgagtctgttaaatcctttgtatcttcaggatccctgtgtctgtggggacccgtctctgtaggttctgcatcttcaaat

FIG. 4 (Continued)

tctaatgagtaggaatccagaaacatttggaaaaaatgcatttatactgaacatgtacagacatgattccttcatcctta
agcagtgtgttctaatggctacacggcatctgcagtgggttaggttttgtgagccagctcgggggatgtgtgcaggctctgta
taaatactacgccactgtctataaagggctttatttaagggtgtctgtggggttcctgggcctgatctctcatgaacgctga
gggtcacgggtagaatgggaaccacgtatggaattctgaaggtcagtagctggtttcacatggtgaaaagagggtcagagct
gtggctcagtagaggagtgtttgcctggtgtgtgtgaattgtgggttcgatccccagttctggaaagcaaaccaagaaagaa
actggtgaatgtaatcaataacttactcctgccactgtaggtcatagcggtgtgcagagagtccattggggtacttttcttc
ccacactcaaaccctttgtagccattggtccaaccttcagttctgtgtggttcctcacagactcacggctcaattgaggcat
aggagctgccttccagaggagagcattatgactggtcaaggccaacagcatgcaggcgctctagctgctgtagccagggcta
gcccctctgagctcagcagagactgtggcaagaccaaggtagaggcttccactgggcggttgggctgttgtcagaggccggt
gggagaatggggggtgcttgaatgggggctgtgctgggccaacggagttctgacttgatgttgctcaaattcctacctcag
cagaagtgggaccatgaattcctacctggagtctgttggcagaccttggagtggggtggggtctcctcagcctagaaaccc
acagagtgggaggtttacggcctgcctctttctgaaggggcagctgtcgtatcccttgttccctttgaatggccttggtgc
tgggagaggtaaaggttgggtgctttcctgttttagacagggttattaaggtataattcacagagcatacaatcttctcact
taaaatgtacagtttggtaggggttgtaactcgcatggcagagtgcttcttgcctagagtgtatgaggccatgggttcaatt
cccaacactgcacacagtgggtacctggtgcctgcctgtaatcccagcactcgagaggcatcggcaggaggatcaggaaag
agttcaaggtcagcttcctatataatgagctccaggctagcctggctgacatgagaccatgtctcagaaactaaaaataata
aagcaagcaagtaactaatgaaatgtactgctcagaagcttttgtctgaacagttgtatgtaagcattgcttctagaacatt
ccacccccaccagagagaaatcccgagtccctccactctcgatgtaaagcctagcagccttgtttgtgcctcctctctgtct
ggcttctgcctctctgtctttgccggttctgagtgtttacctagttgaagtcacactgtgtgtctgctcaaaacaaggttct
gaatttcatccacactgttgctatgttatcacaccccctgtggccagtggcaattctaacttgtttgtccacttccctgggt
agaggtagggagacagggcaggtgtcctgtgacacaacaatttgggaaggcataggaaggactatgggggaggattcatggg
ttggactatgtcctacaaacccagcccctctgtagagggatagttttatcctatggaaactttggtccccttgacaaggctt
ccacccaagtaaagtagggccttgcatattggtgggaaggcgagtccgagatgccccagtgtcccagagctggggccgccaa
ggaaatctctgctggattctcagaggctcagggtacagaggtcacagtagtggcaagagccagcactcggggttcgagagat
ggctcagtggctaagagcatttacttcctttacagaggacacaagttcggttcctagcactcacacggcagctcacaaccac
ccataactccagttctgggggtctgatgccctctccgtaattgatctggggatcacactctgtgtccgcagccaggcttga
ccacccatacttagtaagccaaatgccacactaggaagtgggacaaagagagccactcaagtttggcttggggtccaaagt
gagagtgaaacttaagctgaggaccaagaagttgctcatctaacactgggtcaaggtgtggggcagcccactggtgacccat
cactgcagtttagtttcagtgggggcaaggcattagaactctgtgaagtctcttttctgagagacaatcttcctttggggc
ctttcccttctccaagtaggagattcttggagggaaactccacttctttggggtccgttgtttaaactcccatactcaga
cacaagtttagattaccttcatttctaccaatcctcttacacctttctggcctgcttctgcacaggacacaagtgtgctgca
catacacgcatccaggcaaatactcatacatgtaaatttaaaaaaatcttaaaacaaaacaaaacaaacaaccagggctgga
gagatggcttagaggttaagagcactagatgctctcttccagaggtcctgagttcaattcccagcaacccacatggtggctca
caaccatctataatgtgatctggtgccctcttctggcctgtaggcatacatgcaggcagaacactgtatacataataaatta
ataaatcttttagaacaaacaagcaaataaaccaacaaactagactgttacttgcctttgcacgctcagcttttctact
gtctcctgagctgctctccctcctgctgggcggtccttagtaggacccttccttctgtatcagcttccttgactctgaccta
accccaaaaactcctgtcaagggttcacagtggaccactgaggccttgtcttctctggccacctcctgcaaccatcctccat
cctggactgaggcacaggagggctgagcacaaggtccccagcagagagagacccgtggcatggggcagtgtccagtccagg
ccttgggtcttagcctcccttgttgtctgcaaacacttcttgttctgaggcttagaggaggcaggctggtggcaggagatat
atgtgcagaggttccaaggcctctctgaagagggcaatggggtaaagggggcactttgctctgagatcacacttccgcgtg
atctagtctcccgtagattgctggtcaattggacctgctcattcctgcctcacaccttgggcccctcttctgtgatgtggg
gacaaggacagtgcccacctcaggcctgcgggaatccatctgagcttgagggaaggttcgtcagcacagacaggatcgatta
agcatctacacttagggacccattctgcacagccattgggtagtcttccccaaatcctgcttgccatctctggacgtggact
gggtagtcctcccattgataatttgttgaaacacccaaggaaggaaggtgagacttccttaaagctcctagggaaggctgac
ttgtcctggggtcccaaggacagagaaagagggttcccagagctcaggttccttgaatatgtgatttaggggaaggactggg
ctgcctgggctagcctgagaaccagcagggatgctgggaggagctaccaaccctggaggcctggggaaggctttgtaatgga
gataaagtcagtttaaataaattcctctggaggctgtcacttagatctctggtggctgagcagccttggcggagtccatcac
ttagagggctgtatctaagaatcctgccttccagggcacccatgctctaaatcctgctgtacccccagccccaccttgcagc

FIG. 4 (Continued)

cagcatccaggctctcaggtctatgtgagcactccagcctctgggctgacctgggagcatggtggtacccacaggggtctcc
ggctgggaactttcccaaccaaacagctcccttccaggtaggtgtgcaaagccccaatccaccttgctggcagctgggtgga
tcccaagaagccctggcaccggggaggcggacggagaggggcaggcaggagaggtgaatgtgcgtttatcccaacacaagta
gtggcctgttggggtggggtgggggccccaggaaatatttgggatgacttggagcccgctggccctttaaggctcctgtaac
aagacacctccccgacgggacagaagcggtagctggggcttccaccttagcccttgtttctcccctcccacctccccttcc
ttgccagGCCCAGTTCAATTTGCTCAGCAGTGCCATGGACCAGATGGGCAGCCGTGCGGCCCCGGCGAGCCCCTACACCCCG
GAGCACGCCGCCAGCGCGCCCACCCACTCGCCCTACGCGCAGCCCAGCTCCACCTTCGACACCATGTCTCCGGCGCCTGTCA
TCCCTTCCAATACCGACTACCCCGGCCCCCACCACTTCGAGGTCACCTTCCAGCAGTCGAGCACTGCCAAGTCGGCCACCTG
GACAgtgagtagccgtgttgccagtggatgcgtgaagggagggcagcggggttgagtgccacggtcctggtactgaggactg
aatgagcacacaggctgtccacatggggttcccacctggccagagccaggaggagcatcgagcaggaggcgggccctgggc
tgggcagtgtgggtgtggccaccccttggacttgtggccagagtcagccagcctcccactgagtccggaaaggtcagagtgt
tgttgccagtgaggtccatggggcaggaagagtggccgggtttctatactcagtgccttgaaattggtctggtcctgaact
tctgctgaaagtgttgggagcccacaggggcccacccgtttgctagttgtgggtttgtgttttgccctcatatctctctgtg
cattggcttgggactggctctccaggtgctggggctctggtcctttccctggtgcctccaggaacaacctggcatgtggct
gggattagcagatgttgacaaagtcccacctgtacacttgctgagagttgggcagacagctaagtactttgacttgcccaag
gtggagtctgtgcccatttcacagtcagggaagctgaggtatgaaaagggaaagcagtttgctcaagttatgcagaaagtga
gtagatgctggactggggacacatggccgtgagtgttcttacccactgagcacccaggctctctgtgggagatggggctgca
ggaagagcagactgggacttcagaacgctggtctgggcacacaggacattgggtaggaagggcagccctagagccatccagg
tctccatacccagctaagtctgagtagagggaaccctgagcctgggacagtaggaggtgcactgagggatgttaagtcatcc
accactctctccagggagcagctggagatgcagccatccacgcagtgcaagctctatctcactctcctccagcggctcttt
aaaaactaactcccacagtgtggctctcacattctctttggagactgaagagctggacagagccagaccttgtaggtggcca
cgggtgatcagctgtgcctgactggctctggtttcaggctttgacctcctagagtttctttacctactgttctggtgggct
ccccagtcactagaccatcaccaattgaatgctcagcccagctgctggagctctgaggggcttcagtgggccgagagggtct
gggtacctgtggtgctccatcccgagtcactgtgggccagtgtgctccactctccgtgaccacaaattattggaaggcactg
aggtcaggaggtctgaatgagacaggaatggtagagtacacagctgttactcctgtcctgggacagtggaggaaaccatcta
acatggcctcctgaagttggtctttgtgtagaactacctgctaaaggcctcctcttctgcactgtctgtagttttggggtt
gaaggggacctaggctcttcctccacccaagctgagtgacctagggtcaggtcaggaagcccaggagacacatgggtaccta
cctcagtcacagcgggctctctacgctgctcttctacttccaatgcattccctagctccatcttagagtgaggcggggtcct
gtctgtcataaagatctggtgatgctgtatgtgggattgcctccctttctcttccttgccagagagtgttgatgaggtcgct
ctttgccgtgcctatgggctcaggtgcctctgatggtcagggctggtctttgacaggggtgacagtgcccactctactgaat
tcttcctcccatttgggtcctgtgcagtcccctctgaggcactggacatcaagcgtcccatgatggcctgtgttcctgctgc
tctgctctaactgtccccaggggttagtctgctcagactggccagacataccaaagatcagggaaggcttggcctcccaacc
caacttccacccaggaccagggcagcagagctgagctgtcaggcaggaggatgctactgccagcccctcccggccctgtca
cacaggggcagaggtgggaccaacattgataatgagatttttggcacctcggcgatctgggagcagacacccaagggttttt
ctcgatgctgagagaagggactggcagcagctgctctcagctctggggtccaactgtgtgggtgctgcccagacttgccac
cgaggcccctgccacgccaccggctggtaactgatagataattcatatttttctcaagtactattccatattgactgctgcc
cccattcctctcagattggcaaaaacatgctcactggcctctaagtgaccacagctgttaatggggcctttggtcttgccat
tgctgaagccactgtgggactctctgaccccaaaggatctacttacttgtcctgaccaacttccctagcctgaaatctgc
tggtgcaataagaggtctgggaccttagagtgtgaccctgcatgtatgaacacatacgtgtatatatacatgcacaaggtcc
catatgcccggacacctaggtacacaggtgtgtgttatgcatacatgtatatacctatgagcacacatgggtgtaaatatat
atgtgctcaggggcctatatatatggatacacagatgcactcacatatacctgtaaacatgccggcatgtgtgtacatatgc
acacacatacacatgccaacagatgagcatgtgaacatgcatgctaatctccctggttgctgcctggggacagctggtctc
aggagtccctcagtggaggaggaagtgggacaaggtcctttacatatccaaacagcaagatgggttccctgctgctgtctag
cgccagctcagcccttcaccctggctttgccttgctgagagagacggctcttttcagtattggagacattgagagacagag
ttctgtggttaggcaagaggacccgtgtggatggatggtaaccctggcctggtatgatgtctgtagaacaccaagggcaggc
tgtgacaccgccagcctactacagaggcagctgcagaggagcccaagagtgagggcgcgctcatgaatggcttgactgcctg
agagcattacagatagacagacagacagacagcctggacatagtcttaagtgaccttcaggtgaagctgccttcaacctgtg
tgtgtgtgtgtgtgtgtgtgtgtgtgtgtatgtctgtctgtctgtctttatgtctgtctatgcttatctgtcctgagaga

FIG. 4 (Continued)

gagagcccctacctacccacccacccacccacccacccagccaggcagcagcccctggagggaagccaaagcctctgtgag
ggattcttagggaggacagggctgagtcaacactaatggatttggagcaaactttccagcccctcggaggtttgcaaagcac
aagaatagaggaggtgtcccgacatgattgtggtatcaattgcgttatcctaaaagtttatggaatgcataaatggaattaa
taccttttactggcacggggagcaattatgtatatttaaagcccagagaagagttctaacaatgtttattgtggagatgaaa
cgtgaattattaggggaaacaagagcacttatggagaaatcgcagcaattgctcatattgtgtctagctttgccggagagaa
tgggctgccagtaggctggctccggcttggtctgagcagggtacctgcacccgagatgtatgtctgctctctccatccacta
gtggtctaaaggactttggtccccaggaggcacagaatctagcctggagactctgaactcctgaatccaactgcagctcgac
actggcaggctggtccctgtgtctaagggtgctccctccccagctgagtggtcacatcacatacctcagggttctagcaggg
gacaggagacagggcaccttggaggacaggactctatcctgtgatgctgagatgcagggcagggctcagtccagcagggaa
atgtaccatgaatcaacaataggaaatgaaggaggggtgttccataggtctgactggcctcctcatcttggaggttggtcac
ttctagaacgttctaatcagaaaccatttatgaatctacccagggaggatggtgggcagatagtgtgtctctggccagcac
agtgctaaggaacaagccaggcccccttttgaggcaagcaggcgggcctctgggcatcagagcctccttgctcctgctca
cagagctcctaggatcccagaaccactcctagggacttggagcagtgggcagggcagagagaaagagagttcctcaaactc
ttgggatatgctgttgggttcaccattttgtttctgccctttgctgatgggtgacctgcccttgacccggcctccgagatcc
tctttctgtaaagtgggaaaggaggtatacatgcctactgcaggccgagggatggcacctggggtcccgagatgcccattcgg
gtcgggtctctatcccctctcctgtaaagttctccccagtgtggcatgagcagatgtgagacagtctgaggaagggtcagct
ctaggccttccagagtcacaccagttctcctgaggggaggaccggggagtgaaccaggaacacactcccagtacacacagcc
agccctgaaaaatggacagttctttgtaatgtgtgaattagcactcaatcctccattgacagcacccccccccaaacccca
gggatagaggccagtgtgggagtgtccatggtaggttaaagctggtcaggagttggctaacactgccaggtgagatccagg
tgagttgaatgttgcttacctgggccctccaggctggtggtaggctctagggaaaccacctgaaatgtattagactccatcc
tgtgccctgaaggctcaggccctgtcacctcctcttaggaaaggtcacagccacatccaggacctcttgctcttatatgag
ttagaatattctaggctttgagagctgtaagtcagggtcctgcaaccaccacttatcagtgcaagaagccaaggtgggctaa
gactggcgctctgagatcggataacccggttctaggtccggctgtgcggtacacctgaaggtagagatgctctttggaaaaa
ttgttggtgtggtaggtaaggcagaaaccattcagtgaccccaaatccccacgcctgtgtctgcctctcacctctgtctgtgat
aggtcagctctcatggtgctgaacctggggagggtgagatgggctgtgccgcgctctgcacctgggcctggttccagggagg
ctctcactagctttgctcagtacaagatcagagatttagaccccagagtgtccctgtcctatagttccaataaagatgttta
aagttcaatgacaacttatattttaaggagctattgcctacagcactgaagactggctctttcaaacatgcacacgcatata
tgcacatcacacactcaggtacatgcacacacacattacacacacactcatgcacacacatacacacactcatggcacac
acacactcatgcacacacatacacacatacacacacacactcaggtacatgcacacacacattcacacacacacactcatgc
acacacacacatacacacacacacacactcaggtatatacacacacattcacacacactcatgcacacacatacacacacac
atggcacacacacactcatgcacacacatacacacacacacacacacacacacacacacacacacgcgcactcacgcacgca
cgcaccttgcctccctggctcctggctatcactagcccctgagactgtatggaaagtcacaggtccttagagaaggagctgg
ctaagatgagtgtttagaagggtcacagctggagcggaatgtgtgactgccctgagatacccttgcaatctcaagctgatga
ggttgatcccgactgtggaagctacagctggggatggggtagggacttcaccactgacagccaacaggggatccatactgtg
cacagagcaggctggctaccagcctcgctgtgggttcctgtactggacggtcctgtgacctgcaccccagccctaatcacag
gtgggagaggctgatggctggtggccagaggagaggctactcaggactgcctgaaggagtggccaaggcacagctctcctgc
tggctgggtcaggaagaagggcagcaggggcccctttgaactcacagggaaggtgagcctatggttctttggatctggtcac
agactgttctcagactacactctttcttcctgaagtccccagatgggtcctgggtcctggaaaaagattagatgtccaagt
tagggctggagtgacggaggtgacagggcctcctaggaatatctctgaaaccccgacagtggcctttctggagctggagcat
catacagcaaaggaggtcagccgcacccagccaaccagccacctggagcctccatcccccccatgacttgatgtcaggggag
acacttcccagtaagaccagggcaggccaggttcccccacccccacccgcccctgcctggcagcttcctcaccccccagga
acacaaccccagcccagagctgcctgtctttcctgcctttggtgttctacttggtcacctgactgtcctcttaaccagccta
tctggatcctgatctctggtctctgacctggtaagtctgatggaaatgaaagacccaaagatggaggtgtcgggtcttgagaa
gacaaaacccaaactggaactcacttctaagacttctatgacccccctcatccccaaaggtggttctcaaccttcctttaacac
agttcctcatgctgtggtggcccccaaccataaaattacctttattgctatttttgtaactataatttttgcatggggtaaggt
gaggtggggaaggaagtaagagacaagatggagaaaggatgtgagtctcccagtcctctctggctctgctctctctgggcac
catctccaagtacctcctcactcctagctgtccaggagctgaccaagccctgtcctttgggatttgtacagacacttcatta
tgtagccatgattagtctcctgacattcgggacctgattgaccttcatcctctgtgctccgtcccaaaggctggggctgagg

FIG. 4 (Continued)

ggtcacacatactaactggatctttcatcaggggtgctcaggaaagcagccccagccctcagccccagccccagcccc
caggccccagccctcagccccagccccatccccagccctcagccttcagcctccaggccccagtccccagccctcagcc
cccagccccagccccagccctcagccctcagccccagtccccagccccagcccttagccccagccctcatccagtca
ttagcatgtaaaagagcaactgttgcttggcagtcctctagatttatgagcattttaccagaaacccgaggtctacagcca
atgcaatgcaacctctgattactgctctaccccagctcagctggcaactttagaaacaaattctagttcctaaaatgtc
caggtgaagggtcagagtaggcaccttacagagaaagcagcacagaccgggcccatgttattcctttggtctctatgtaaag
ccatcagctgcagagctatgtagagcagcctcccaaattcccaacccactaccttctccctctctgagatgagactaccaggc
cctcacacatcagctcctccgcctggggcagaaactactggaaggttctctgctcctgccaaggataaatgggctccaaacc
ccatgacctgggaccctctgacttcccagtcttagtgcaaaaaaaaaaaaaaaagaaagaaagaaagaaagaaagaaagaaag
aaagaaagaaggagggggagggggctggagagatggctcagcagttaagagcattgactgctcttccgcaggtcccgagttc
aaatcccagcaaccacatggtggctcacaaccatctgtaatgagatctgagaccctcttctggggtgtctgaagacagctac
agtgtacttacatataataaataaataactctttaaaaagagagagagaaagaaagagagagagagagagagagagagaga
gagaaagaaagaaagaaagaaagaaagaaagaaagaaagaaagaaagaaagaaagaaagcactctgtctcccaggccaccaaggt
gcccatatggctcttgcttgcctgtttgagatcttgctcaagggtcgggggtggggagcaggttactcagctcctgagggt
gccccagctagctcctggccaacctctctgtaggggaacagactatggccttccactcacagagcaatcagtcagacttcac
atctgcctcccggagtgtcctttatcttctttcagaccgctgttctttaggaacaactacagccctcttcctgcacacttgg
caggggcaggcactggggcctccaatgatgtgtttatagaacatggagcctccttgccctcagcctgcatcctggcttgatg
gtgccagtccggtgacggttacccgagcatcattccctccctaaggttctatcggggctccctaagctgtgcaagagctcac
ccctgctctcaggtgctccctgaatgaccgaataattgaacaatgtaaattgtgcgagtcaaggccaagatgtacccacaaa
ggggctgccccaggacctcttcttggatgataggatccataggttgctcctctcgcagtggcatttctccaagagaaacgaa
aacatggtggggagtcatattcaggggctgtggacctgggttcctccagatttgagagatcagactgagtctaccagacctg
tgccctgctctgtggatctgccctaggaagagtaaaagcctgtgatcccagagatgattctcaaagggtctacggcctcag
agatcagaaactctcacacacacgtatacacacacacacacacacacacacacacacacacacacacacacacaaagtgg
gctacaaaaaaaagtatttttaaaaagccccccacccacagcctttcgttctgaatctgtcctaacagattcaccccaagctggt
taacggtatttgcggtttgcaagatactacatgtcccgggaaaatgacagacaagttattatcaccttcccactgtcctcct
gccccaaacctgcctgtgccggggcacccagctgccgggagcgggtgcgaggaaattaacagccctgtgccgcgcccgcccccg
cccgccctctcacccacccacccctgcacccggtcctgccaggctaggggcttccagccaggcccggcccatcttggactgtggc
ggggggggggggtggggggtggcgggggggggtggcgaggggggggcgcggggggggggagggaggggagagaaggaggaggagg
ggtcaggatagcagccgtggcaggagggacgtctgctccgctccgatgttgggcaaagtatttcctgcaagccccgcggaac
acacgcatccgcgcaggcaagtctggacggcgctgtgtcaacagcccgaagataaataagatttttatcagctcggaatctgtt
gaaacacatccatctagcggttctagggaaggagaggcaggaggagggcagcagggaggaagcatccccacatgacattctg
gaaacagagtctgaccctgtgtaggaaggggagcgctggcaacttcctagtctccgggagactcgatatcctggagtgttgt
ttttaccacctgatcttcggaggtgtgggaaagctttggtatctctcgctgaaattccccacctctggctaaaatggactac
cacaaacttaacctgtggccggggtggggctggtaggtgtgtgcgcccaaagccccacgatcattggattcaagacggcatt
caagggtgcagaagtgaaggagccatgtatcttcatgggcttggatttttccttccaccctgacggggtgggagacgtgtccc
acccagagatgactctctcaactctgattctttctctgagaggagacagcctttccgcagctgctgagttggtaccagggaca
gctccaggcgctttaagctcctccccagggtggggcattcagtggctcatccttaccagccggctactctgcaactatcct
tagctttccctagacctcctagggtcccactccaggccatggaaaacagtgccaccttctggggaggagggtcaggcctcag
ctacctctgacccacaccttggtagtgttagtgcatggtttggggttgtaaacaattatcctaggtcctcagaggacagggat
ggaaaggacaattgccttcagggtcacagcagggctccagggatgggcactgtggtcaggcgaggtttgaagcctcattgct
caggagtgggtgggtgaggggagctctgatgcccctccctgtggctgagctgtgccctgagcctggctccatcctgataaga
acacggaggtgaagctgatgcaccctttctccctccaggcatgtttgggcttcccaggaatgtggccttaggcacccattaca
cctgacttgctcccagcccatcttggctcctgccttggtgggtctatgaccccctcttaggtcattgttcatgagctagagc
actggaggggaaaggttaactctgtaggagactccaggtccatgagccccagcagctgtgccaacccccacaaattaccttacct
ggtaatgagcaacccatgctagaataaggggcctctgaccttgctggctctctacccacacagctggcatctggggggttgagtg
gtaagtcagtggtagacaaacctggcaggtggtccaatttaggggaatccagcctgaattcctgagccagaacagggagcca
agggccagccttcaaaggctaatctccttttccgcccctggtgactttggtctcagtgtctccccaacccactgtgggcaa
ggcctgtttcatggggggtgttggccacctccacccctcagtctatttctttaggtagctaggcctcacaaacaatgggcac

FIG. 4 (Continued)

tcgggagatgtttggtaatgcttgggactgtcacctttaccaggaagttgcctgattggcctcaggttgagtctctctgagc
tcaggatgagctgggttcccttcaccgttaggcctttgcaattgtctgagcctggggcttgctgggaaaccttcatttgtgg
ataagcaagagcccagggcacttcactgtcactgtatatgaatttacttaatgtcgggaggggcacctcgcactgtgaactt
catgccaccccgtgtccttcctagggagcccacagtaattacagagctagtgtgctttttaccaagtgcaggctgtagacccc
caacacctgcaggctgctgctgctgctgaaggacaggtgtgtgtgtgtagctgtttattggcctttccccagggaaccagct
actcctgctactctgtccccagcctgcacagatggagaccaggctgcagtgtactaacttgaggagaggccgttgcaaaaaa
ccaaagcccagatttggatgtgcagaggtcaggtgtaccctgtccaagtctcagagtccccatgtatcctggggatgaggc
tgtggctccttcctccagaatgttaggatgaggatcccacacaccagcagacagtggtcacccccctcccgaaagtcacac
caacctgctggtgtggccattagctctccctcagctgctccccctcttaggctctctcagctttcaaaacagtcctgaag
ccttctgtggggtccctatagtgagtatctcttgcttttaaacaggagggaagggactatgtcatgggcgcctctccctgcc
ctcccttcattgcatttgcctatggtatatgctatttctgcatactccattgtggagaaccataagctatatagggttaggg
tggtcagaatcccccactgtcccttgcaaaggaaagatttggtgtgtgagcacccacctgcccattcctgttttgttaacagc
ttaccatctctggcctcagcttcattaactgtcacaagggagcatggtgtatataattcatgtgtggtggagactttagagt
gaagtggagcttcataaaatcccttgggagccaggcggtggtggcacaccccttaatacccagcacttgggaggcagaggc
aggcagatttctgagtttgaggccagcctggtctacaaagtgagttccaggacagccagggctacatagagaaaccctgtct
cgaaaaccaaaaaccaaaccaaaccaaaacaaaacaaaacaaacaaacaaaaaaaaaaaaaacccttgggaagagctagagaga
tggctcagaggtcagaggtcctgagttcaattcccggcaacccacatggtgtctcataaccatctataatgagatctggtgc
cctctcttctggcctgcaggagtacattcagacagaacactatatacataatagatagatagatagatagatagatagatag
atagatagatagatctttttaaaacaaaatcacttgggaaggaagacaagaggagtgagtcaccaggggtttcaggagccata
gtgagagtcagctagcaggtgaataaatgggtatcttgcttttccagcctagatcaggccgctggctgcataggtaggattt
gcagcattgagcccgtttgacaagctcagaattgcatcctctgccttgcatagaatagtctcactctgattctgaaactgac
ttggtcttggcagggccagtacaatccttagaagagtgacctgggacacggagggggcgggggaggcatgatgacgtcccat
tgtccctgagagacatcctggcatgacctcaggtccagtcagtttccaggatggggaaagcgggtcttgccccccacaacag
cttggctgcctggacttggtgactttacttggtggcacagtgctggtgactggtcaacagcatgcaaggtcttgctggttca
gagagttctccattggaggataaaggcaaaggcagaaggggcaagccacccacctactgagtgattcttctatgcaaggtag
aaggatgcaattctgagctcgtcaaacccacctcaatgctgcaaatcctaccctgcagccagtggcctgatccaggctggga
aagcaaaactaggactgattcccactgacctctgacccacacccccaacactgtcttaccctttgtcatccttatgcaacgg
tccaccgctcgcagcctttgagatgcaggtgagacacatagccaggcaggtgatgagcaggcaccaggcacgcccatctcta
caatctgaagcatgcctgaagcatctggaagcaggcctcatcggagcgcttgggaaaggggtcttgtggaagcatccggaac
tgagctgccatctcaacctggcccctttctcctccagTACTCCCACTCTTGAAGAAGTTGTACTGTCAGATTGCTAAGA
CATGCCCATCCAGATCAAAGTGTCCACACCACCACCCCCGGCACGGCCATCCGGGCCATGCCTGTCTACAAGAAGGCAGA
GCATGTGACCGACATTGTTAAGCGCTGCCCCAACCACGAGCTTGGAAGGGACTTCAATGAAGgtgagcccccctcccctc
ccagctgtgggacactgaccagaggcatagctgagagatgtaggccagtgagcacagcggtaagctgctctcaactctcccc
tcacaggaacccacacctagccctctttccatttcctcagctctgactacagtccaagaggctgatggtccagcaagggtg
tagtctgagggaccagctgaccttggagaatcttgtgaagcatccctgcagtgtccctggtgaagcctgtgacaccccagg
gtcagattatctggggacagcttctgtcccgctcaaggccacctaaatgagggttgcacagctctgagccttgcctgggact
ctcacggggacaagccctgtggcctcagttctgccacacgcctggtacaggggtatgggatggaagatgggccctctctaa
agctgtgtcccctcctggcagGACAGTCTGCCCCGGCTAGCCACCTCATCCGTGTAGAAGGCAACAACCTCGCCCAGTACGT
GGATGACCCTGTCACCGGAAGGCAGAGTGTGGTTGTGCCGTATGAACCCCCACAGgtaggcggggtccaggctgggatacaa
agccaaccttacagggtggggttccctgggcctctgctctgacctcagcctgcctctcaggcctttcctgacagttcattt
cactgtgggcagcgagcttgggcctgtgctcaagccaactttagctctctgtctctctgtctgtctctcgtctgtctgtctc
tgtctctgtctgtctctcgtctgtctgtctgtctgtctgtctgtctgtctctgtctctctctgtctctgtctctctctcgcc
tcagctatatagcgaggtatagttatatgacctccaacctttcaaccctgccctccctggagggtctaatcttcaatcttct
tgcttgtttctctcaagtacagtcttctagacatggaagaaagagttcccagacatctcaggctccatttgcagggacaaaa
gcaagccagcaagcatggggtggtgggtagagggtgggcaattccatgtgtgggggggtagtgatcatgaaaggcctcctag
accaggctggggaatcacagaggacgcctacaggagattggagccgtggaacacaggctcaggagagtagggaagacagag
atgatcggtcagccttaagagggcctgtgtgcagagcctcgggagagtggtgccagctggatggagggtacagtggaggtga
ccagacatgctgcacactgaggtgcagggtggatacggaggttcaggctggaggcgaagggctcagaccacaggtgaggct

FIG. 4 (Continued)

ctaagggagggaaccaggctggaggtggtggttgccaaaagtagacaagtgaaggaagactggaggaggcagctgtccactt
tgacaccagaagagtgtgtggtcaccttctagatctgatatgagccccagttggggccaaaggcaaggtgaagggacttcag
tactgatgtgggaggtatcagggcggagactcaggaggactggggttaggtctcatctctgacccatcctctaccaagccct
ggggtcctgtgaggcagctttgaatgtcagtgggacagggccccatatacacacagacacacacagacagacatacacatag
acacagattcacacacacagacatacacagagacacacagagacatacacacctacacacacacagacacacacacacagac
aaacacacacacacacagacacaaactgagaaacacatggacaaacacagagacccccacccacccacacacacacacagaa
acaggcagagacacacagaacacagaaacacacacacacacatacacacagacacacacacacacacagacacacagacaca
cagacacacacaccccacaagcatcctcccctctcatcagaaaagcctcacccagctcaggcatgagacacaacgtaggttt
ctcttgccctctagtggttggcaggtgtaagttctgtgaaggactggggtttatggcgtttgtaccctaacctttgaaactc
ctttctggggatggagtccctttcattcctctgcccagatgagtccacagtactcatcacacacttgacacaaaggctcaca
cacacccactcacatacagccctgacatttgacctctgcctgtgttaaggaagatgactgcagcaagcacaccacaaactct
gtacctcccctaagagctgaaaccaagactgagctctcagcccagagccagcacagggctgtgacggcacagatggatcggt
gggagggcgggcaatctcacgtgagtgtagatggctgaatggatgggtgagtgagtggatgggtgggtaggtaggtgggtga
tagtcaggcacccactggggtgggcaggagagcaggtgagcaggagtgtaagtgggtgtatgggtaggcaagtgagcaggtg
tgtggatgtatgtgtcaatggatgagaggttgacggcaagtgagtggggtaggtggatacgtgggtgtgtagacaggcgtg
tgagcagatggatggatgtgtagacaggcgtgtgagcggatggatggtttggtggatggtaggtggataagtggcgagatgg
atggataagtgcaaagatggggtggtttgggtagatagatgggtagatgacagtgaaccatactgcagcgtccctatgcctcc
tcagaaccagggccagaggtggcagctacaagtcctttttcttagaaggtgggccctgcatgctgactgatactaagcccttc
ccctgtctcccctgtggacagGTGGGAACAGAATTTACCACCATCCTGTACAACTTCATGTGTAACAGCAGCTGTGTGGGG
GCATGAATCGGAGGCCCATCCTTGTCATCATCACCCTGGAGACCCGGGAgtgagtctgccgtggaaggatggtagaggtggg
gccgtgggggggcatgtcatggacacagggagggcttgctctcctcggtgggcattcagcttcaaggccagtcacgagggt
ctgcgggagttgggcagggtcaagagtggtctcttgagctcacagccacgctgtgccgacccaacagTGGACAGGTCCTGG
CCGCCGGTCTTTCGAGGTCGCATCTGTGCCTGTCCTGGCCGTGACCGCAAAGCTGATGAAGACCATTACCGGGAGCAACAG
GCTCTGAATGAAAGTACCACCAAAAATGGAGCTGCCAGCAAACGTGgtgagtggggctctgggtcagggtatgggcggaggg
tggagttggatgcacctgagtgtggggagtacctgctccaaaggtgccaagcatagcttcatccaaagatggatctgggtct
gaatggctgaggctgggaagcctctccaggcgggacagggcgaatgtggcccaagacatctcacttgtctatgctctgaggc
taggagcatgtgggaccctggtccagctccttccagcctaggtttgccctgtgtgcacaccacacccatggcaggtgttcac
ctgggcatctcagtctttgctctctggctcatttatctttcccgacctgccttctagCATTCAAGCAGAGCCCCCCTGCCAT
CCCTGCCCTGGGTACCAACGTGAAGAAGAGACGCCACGGGGACGAGGACATGTTCTACATGCACgtgagtgggctgggaggg
caggtctgtgtgttcccatcacccaagatcccaggctggggaagtacagatgtcaccagagatgggcaagggtggcatgctg
acacctgaggatttgaaactgtggccctgaaggaggtggggttcaaaggaggctctgtttagagtcagaccctgaactcactg
agtgtgaacatgccagccaagtcagctgtgcatcaaggagacctaagggcaccctttataatggagacccccagggtggagt
ttcagtaggaacccatgatcctatagggttcagcctgtgtttaaatccatggtcctatagggttcagcctgtgtttaaatcc
atggtcctatagggtatagcctatgtttaaatccatggtcctatagggtacagcctgtgtttaaatccatggtcctataagg
tatagcctatgtttaaatccatggacctatggggtatagcctatgtttaaatccatggtcctatagggtatagcttgtgttt
aaatccatggacctatagggtatagcttgtgtttaaatccatggtcctatagggtatagcttgtgtttaaatccatggtcct
atagggtatagcctgtgtttaaatccatggtcctatagggtacagcctgtgtttaaatccatggtcctataaggtatagcct
atgtttaaatccatggacctatggggtatagcctatgtttaaatccatggtcctatagggtatagcttgtgtttaactccat
ggacctatagggtatagcttgtgtttaaatccatggtcctatagggtatagcctgtgtttaaatccatggttgtatagggta
tagcctgtgtttaaatcaatagttctatagggtatcagcctacatggctcgatgtgactgtggtaccaatcccagtggtaag
atcatggtgcactccgaaagagtgctatttccttgcctgtgagtcctcctttaagacttagagctgttataacttagagcct
cttagcagggaagaataaacatggtctctgaaccccgagggacccacttctaaacctgcccctgggaagaggaaagccagag
tatcctgagcgttggggtacggggaaactccaagagcagatcaacactttgccatagcctggagtcctcctgaggctacggc
catccccgtcccaccagggggtttggggccagtggaatctcccaggtacctgggccgagactctgtttttctgtgcccagGTG
CGAGGCCGGGAGAACTTTGAGATCTTGATGAAAGTCAAGGAGAGCCTAGAACTGATGGAGCTTGTGCCCCAGCCTTTGGTTG
ACTCCTATCGACAGCAGCAGCAGCAGCAGCTCCTACAGAGGCCgtgagtgaacccaccatctgtatggggaagtagggata
ttctgacccagcagggagagggccaggagcacaggaggtatggtaccctggactggactggactgtaagatcagcacagctc
agctggcacctttctcctccaggaagccttctgggacttagcctgccctgagatcctgggtccctgtgttcagcacaccctg

FIG. 4 (Continued)

cctcccacacaagggccttggaaatgtggatggggaagggactggaagggctgtatttgctgaagctggtgaggtgttagct
ttcttcctaactctctgagaggcagggtctacatctacctgcatcccagggtgtccacagaggtaccacgtgggggaggagt
tgcttttacctcttgcgaatgcgcactgttgctttccaagcagGAGTCACCTGCAGCCTCCATCCTATGGCCCCGTGCTCTC
CCCAATGAACAAGGTACACGGTGGTGTCAACAAACTGCCCTCCGTCAACCAGCTGGTGGGCCAGCCTCCCCCGCACAGCTCA
GCAGCTGGGCCCAACCTGGGGCCCATGGgtgagtccctggagcattggaggcctcatgtgggtcatagagacccaagggagg
gcctgggtggatttacccgagatcacaaacaggatggcgggggacctttgatggccacctcttcctgcagctccagcctgcag
gagggcaatggctatggaggcgttcattccaatcccaggagttctatgcctgggaggttgcaaaggtggtagagttaagaac
tcatgcctgccacaggatcttgaagaagatccctagcctcagtttcccccatcagtaaaatggcaacaccaaatccccctcttc
tcaggggttacaggacatgagacctcattgagaggcagctgtagggaacccttacaatgctgtaccacactgccaggctaga
ccacagcctgggacataccccactatgtgtggggcttgctctcaggttccctgaccactcttttgcccagGCTCCGGGATGC
TCAACAGCCACGGCCACAGCATGCCGGCCAATGGTGAGATGAATGGAGGCCACAGCTCCCAGACCATGGTTTCGGGATCCCA
CTGCACCCCGCCACCCCCCTATCATGCAGACCCCAGCCTCGTCAGgtgtgtgggtcgcggctggatctgggtttgtggttca
ccctccaccccctcaccccatgcctcccactaactgtgcggttcctgctggagggagcagccttgcatgtggctctgtctgac
cctgttttaattgcttggctggcctgagggaagacaggcctatcagggctcgtcagcagatgctgagaaaggcactagatgg
ttaggcactgagggtgggggtggggtttggaggggtttgggggcatcctcttggagacaggggatgaggaatgagatgag
cagctgtgggaggtcagaccaggagaggtgggtaatgattggactgtaaaaatataaaagtaacatacacacacacgtatat
atgtgtatgtgtatgtgtatgtgtatgtgtatgtgtatgtgtatgtgtatatacacacatacacatatacacacatgtacat
atatacatatatatgtgtacatatatatatacacacatatatgtacatatatatgtaacaaaaattaaaataaaataaataa
taaaataaagaaataaaaaagaaaacctgccctgagggagggaccagcagttttgcccactgtaacaggcagttccctccac
gtcagggccactcctgtgagacccgagtgcacagccagttgatgctactttctcaaactctctctgcagTTTTTTGACAGGG
TTGGGGTGTCCAAACTGCATCGAGTGCTTCACTTCCCAAGGGTTGCAGAGCATCTACCACCTGCAGAACCTTACCATCGAGg
taaatgtcccaggtctttccaaagggacggaggacctgtctggaggcacagtgcactgactagggtgactagtggggaaact
cccagagactcccaccagcaatcagattctgttctgaagtcagcaggattcggtaatgtgaaggagactgggtagacaatca
catgtcccggtcccgggcagttaccctggagagctttctctcttgttagagcctcctggtggcccagccaggctaccctttgat
ttcttaggcagggttgtttccaggacccaatgtgtgagaagtgtagaagctaagggggggaacagacctagaaagaatgaatg
ggtctccacatccagcctacacgtgagacacagaacattctgggttgaaagtgggatagaaatcttctggaaggccctgcat
cctgttacagcctagccacacagactgccttgatgtatccatgagacatgggtccagtgtgcaacagctcagcccctcctgc
cccagggcccagtgtgcaacagctcagcccctcctgccccagggcccagtgtgcatcagctcagcccctcctgccccagggc
ccagggtgcaacagctcagcccctcctgccccagggcccagggtgcaacagctcagcccctcctgccccagggcccagagtg
caacagctcagcccctcctgccatgcctcccaaaactgtttttctagactctcacccaggctaagaggccatatttgtcacct
acccaggaactcaggctggacacaaatatttataagaggttgtggggctagagtctaacacctgcatttatgggaccactga
ccactacctttcccatccttgagtcatacattaacccttgtctcaccagagcttgaagctaaaggatgtgcctggagttagc
tgccaattaatggcttccaagggacacctgtggccaagagatgcatgggtggtctcctaggtctccattgctgttctcgctg
tgtccaggcctcaggctgatgagcaggccctcgtcactgtcccctctgtcacctacacatgtcatctagctgtcctagacaa
ttatgtgactagacattctgtgcaggtgaccctgatgctgtccctaccctgtcaccccacacagtcaaggtctgataagtcag
ctgccccctcagacagaggcttcctagcaggtaggacacccttgcaggtgtgagggacacacaactctgtagcttccctctt
gtaacccaaaggtgcccatcgctcttgcagGACCTTGGGGCTCTGAAGGTCCCTGACCAGTACCGTATGACCATCTGGAGGG
GCCTACAGGACCTGAAGCAGAGCCATGACTGCGGCCAGCAACTGCTACGCTCCAGCAGCAACGCGGCCACCATCTCCATCGG
CGGCTCTGGCGAGCTGCAGCGGCAGCGGGTCATGGAAGCCGTGCATTTCCGTGTGCGCCACACCATCACGATCCCCAACCGT
GGAGGCGCAGGTGCGGTGACAGGTCCCGACGAGTGGGCGGACTTTGGCTTTGACCTGCCTGACTGCAAGTCCCGTAAGCAGC
CCATCAAAGAGGAGTTCACAGAGACAGAGAGCCACTGAGGAACGTACCTTCTTCTCCTGTCCTTCCTCTGTGAGAAACTGCT
CTTGGAAGTGGGACCTGTTGGCTGTGCCCACAGAAACCAGCAAGGACCTTCTGCCGGATGCCATTCCTGAAGGGAAGTCGCT
CATGAACTAACTCCCTCTTGG

FIG. 4 (Continued)

SEQ ID NO: 4

>gi|107830767|ref|NM_000546.4| Homo sapiens tumor protein p53 (TP53), transcript variant 1, mRNA gattggggttttcccctcccatgtgctcaagactggcgctaaaagttttgagcttctcaaaagtctagagccaccgtccagg
gagcaggtagctgctgggctccggggacactttgcgttcgggctgggagcgtgctttccacgacggtgacacgcttccctgg
attggcagccagactgccttccgggtcactgccatggaggagccgcagtcagatcctagcgtcgagccccctctgagtcagg
aaacattttcagacctatggaaactacttcctgaaaacaacgttctgtcccccttgccgtcccaagcaatggatgatttgat
gctgtccccggacgatattgaacaatggttcactgaagacccaggtccagatgaagctcccagaatgccagaggctgctccc
cccgtggcccctgcaccagcagctcctacaccggcggcccctgcaccagccccctcctggcccctgtcatcttctgtccctt
cccagaaaacctaccagggcagctacggtttccgtctgggcttcttgcattctgggacagccaagtctgtgacttgcacgta
ctcccctgccctcaacaagatgttttgccaactggccaagacctgccctgtgcagctgtgggttgattccacacccccgccc
ggcacccgcgtccgcgccatggccatctacaagcagtcacagcacatgacggaggttgtgaggcgctgcccccaccatgagc
gctgctcagatagcgatggtctggcccctcctcagcatcttatccgagtggaaggaaatttgcgtgtggagtatttggatga
cagaaacacttttcgacatagtgtggtggtgccctatgagccgcctgaggttggctctgactgtaccaccatccactacaac
tacatgtgtaacagttcctgcatgggcggcatgaaccggaggcccatcctcaccatcatcacactggaagactccagtggta
atctactgggacggaacagctttgaggtgcgtgtttgtgcctgtcctgggagagaccggcgcacagaggaagagaatctccg
caagaaaggggagcctcaccacgagctgcccccagggagcactaagcgagcactgcccaacaacaccagctcctctccccag
ccaaagaagaaaccactggatggagaatatttcacccttcagatccgtgggcgtgagcgcttcgagatgttccgagagctga
atgaggccttggaactcaaggatgcccaggctgggaaggagccaggggggagcagggctcactccagccacctgaagtccaa
aaagggtcagtctacctcccgccataaaaaactcatgttcaagacagaagggcctgactcagactgacattctccacttctt
gttccccactgacagcctcccacccccatctctccctcccctgccattttgggttttgggtctttgaacccttgcttgcaat
aggtgtgcgtcagaagcacccaggacttccatttgctttgtcccggggctccactgaacaagttggcctgcactggtgtttt
gttgtggggaggaggatggggagtaggacataccagcttagattttaaggtttttactgtgagggatgtttgggagatgtaa
gaaatgttcttgcagttaagggttagtttacaatcagccacattctaggtaggggcccacttcaccgtactaaccagggaag
ctgtccctcactgttgaattttctctaacttcaaggcccatatctgtgaaatgctggcatttgcacctacctcacagagtgc
attgtgagggttaatgaaataatgtacatctggccttgaaaccaccttttattacatggggtctagaacttgacccccttga
gggtgcttgttccctctccctgttggtcggtgggttggtagtttctacagttgggcagctggttaggtagagggagttgtca
agtctctgctggcccagccaaaccctgtctgacaacctcttggtgaaccttagtacctaaaaggaaatctcaccccatccca
caccctggaggatttcatctcttgtatatgatgatctggatccaccaagacttgttttatgctcagggtcaatttctttttt
cttttttttttttttttttctttttctttgagactgggtctcgctttgttgcccaggctggagtggagtggcgtgatcttgg
cttactgcagcctttgcctccccggctcgagcagtcctgcctcagcctccggagtagctgggaccacaggttcatgccacca
tggccagccaactttttgcatgttttgtagagatggggtctcacagtgttgcccaggctggtctcaaactcctgggctcaggc
gatccacctgtctcagcctcccagagtgctgggattacaattgtgagccaccacgtccagctggaagggtcaacatcttta
cattctgcaagcacatctgcattttcaccccacccttcccctccttctccctttttatatcccatttttatatcgatctctt
attttacaataaaactttgctgccacctgtgtgtctgaggggtg

SEQ ID NO: 5

>hg18_knownGene_uc002gij.2 range=chr17:7512445-7531588 5'pad=0 3'pad=0 strand=-
repeatMasking=none
GATTGGGGTTTTCCCCTCCCATGTGCTCAAGACTGGCGCTAAAAGTTTTGAGCTTCTCAAAAGTCTAGAGCCACCGTCCAGG
GAGCAGGTAGCTGCTGGGCTCCGGGGACACTTTGCGTTCGGGCTGGGAGCGTGCTTTCCACGACGGTGACACGCTTCCCTGG
ATTGGgtaagctcctgactgaacttgatgagtcctctctgagtcacgggctctcggctccgtgtattttcagctcgggaaaa
tcgctggggctgggggtggggcagtggggacttagcgagtttgggggtgagtgggatggaagcttggctagagggatcatca
taggagttgcattgttgggagacctgggtgtagatgatggggatgttaggaccatccgaactcaaagttgaacgcctaggca
gaggagtggagctttggggaaccttgagccggcctaaagcgtacttctttgcacatccacccggtgctgggcgtagggaatc
cctgaaataaaagatgcacaaagcattgaggtctgagacttttggatctcgaaacattgagaactcatagctgtatatttta
gagcccatggcatcctagtgaaaactggggctccattccgaaatgatcatttggggtgatccggggagcccaagctgctaa

FIG. 4 (Continued)

ggtcccacaacttcgggacctttgtccttcctggagcgatcttccaggcagccccggctcgctagatggagaaatcca
attgaaggctgtcagtcgtggaagtgagaagtgctaaaccaggggtttgcccgccaggccgaggaggaccgtcgcaatctga
gaggccggcagccctgttattgtttggctccacatttacatttctgcctcttgcagcagcatttccggtttcttttttgccg
gagcagctcactattcacccgatgagagggggaggagagagagagagaaaatgtcctttaggccggttcctcttacttggcagag
ggaggctgctattctccgcctgcatttctttttctggattacttagttatggcctttgcaaaggcaggggtatttgtttga
tgcaaacctcaatccctcccttctttgaatggtgtgccccacccgcgggtcgcctgcaacctaggcggacgctaccatgg
cgtgagacagggagggaaagaagtgtgcagaaggcaagcccggaggtattttcaagaatgagtatatctcatcttcccggag
gaaaaaaaaaaaagaatgggtacgtctgagaatcaaattttgaaagagtgcaatgatgggtcgtttgataatttgtcggaaaa
acaatctacctgttatctagctttgggctaggccattccagttccagacgcaggctgaacgtcgtgaagcggaagggggcggg
cccgcaggcgtccgtgtggtcctccgtgcagccctccggcccgagccggttcttcctggtaggaggcggaactcgaattcat
ttctcccgctgccccatctcttagctcgcggttgtttcattccgcagtttcttcccatgcacctgccgcgtaccggccactt
tgtgccgtacttacgtcatcttttcctaaatcgaggtggcatttacacacagcgccagtgcacacagcaagtgcacaggaa
gatgagttttggcccctaaccgctccgtgatgcctaccaagtcacagaccctttcatcgtcccagaaacgtttcatcacgt
ctcttcccagtcgattcccgaccccacctttatttgatctccataaccattttgcctgttggagaacttcatatagaatgg
aatcaggctgggcgctgtggctcacgcctgcactttgggaggccgaggcgggcggattacttgaggataggagttccagacc
agcgtggccaacgtggtgaatccccgtctctactaaaaaatacaaaaattagctgggcgtggtgggtgcctgtaatcccagc
tattcgggaggtgaggcaggagaatcgcttgaacccgggaggcagaggttgcagtgagccaagatcgtgccactacactcc
agcctgggcgacaagaacgaaactccgtctcaaaaaaaaagggggaatcatacattatgtgctcattttgtcggcttctg
tccttcaatgtactgtctgacattcgttcatgttgtatatatcagtatttgctcctttttcatttagtatagtccatcgatt
gtatatccgtcctttgatggccttttgagttgtttcccatttgcggttatgaaataaagctgctataaacattcttgtaca
atttttttgtgatcatatgtttcgtgtttcttggagaaatacttaggaggggaattgcgagtttggaagtaaaaagtagc
tgtattttgaactttttcagaagctctgagtttccagagcggttgtaccatttacactcccaactagcaaggtatgggagt
tattatggttgtgccacagccttccggacattaggtattgtcagtctttctaatgtggtatatccctgtggttgtaatttac
agttctctattgactaaggatgttcagcatttttcatgtgcctattggccattcgtattttgttgtaaagtagctcttcg
agtcttttacctgttatttggtttttgtttgttttattgttcagttgtgggactgctttatacattctggatacaagtc
ctttatcagatccatgtgtcgtgaatgtttctctgatctgttgcttgcctatttgtttgctttacagagtttacagtatc
ttaagaggagtggatttatctttttatgttcagtatttgccttgtcctgtttaggacatcttttttttttttttttaacccc
agggtcatgaagatattatcttacatttctttttaggacctttatggttgtaagttttacagtaaggtccttgagccattaa
ttaattcttaaaattaattgtttatggtgtgaggtgtaggagtcagtctctggtatctttcctgtatggaaatccagttatt
ctgtctccacttgttgaaataggcttcctttctctactgaatgcttttaattttaattatttacagttggagtataggggct
accatttagtgctattttcttttttttctttgttaatttttgagacagggactcacactgttgcccaggctagagtacaatg
gcacaatcaaggcttactgcagcctcgaacccctgggctcaagcagtcctctagcagcctcacgagtagctgggattactcc
accacacccagctaactatttttatttttttgtattgacaggatctcactatgttgcccaggctggtctcaaactgctggcct
caagctttcatcccatctcggcctcccaaagtgctgggattacaggtgtgagccaccatgcctgacctcttagtgctatttt
ctatttatctcctctgttctctgctctctttaaacgttggaggaagaaacagtacccatcttacacaaactcttcagaaaac
agaggaacagactgggcgcggtggctcatacctgtaatctcagcactttggtacgctgaggcaggggatcatttgaggtcgg
gagttcgagaccagcctggccaacacggcgaaaccccatctctactaaaaatacaaaaagtagctaggcgtggtgacacata
cctgtaatgccagttactcaggaggctgaggcacaagaatcccttgaacctgggaagcggaggttgcagtgagccgagattg
cgccactgcactccagcctgggcaacagagtgagaccctgtctcagaaaaaaaaagaaagaaagaaaaaatagaggaatatt
tcccaacttgttttcgaagccagcataatcctggtaccaaaaccaaacaaggacattataagaaaagaaaatatagaccaat
attcctgttagcatagacatgcaacagctaaccaattttagcaaaccaaactggtaatatagaaaaaaggataaataggcc
agtcgcggtggctcacgcctgtaatcccagcactttgggaggctgaggcaggcagatcacttgaggtcaggagtttgagacc
agcctgaccaacatggtgaaaccccgtttctaataaaaatacaaaaatcaggctgggcacggtggctcacgcctgtaatccc
agcactttgggaggccgaggtgggcagatcacgaggtcaggagttcaagaccagcctgaccaatgtggtgaaacgccatctc
tactaaaaatacaaaaatcagccgggtgtggtggcacctgcctgtaatcccagctactcaggaggctgaggcagaattgcttg
aacccgggaggcagaggttgcagtgagccaagatcgtgccactgcactccagcctgggcgacagagcaagacttcatctcaa
aaaaaaaaaaaaattagctgggcatggtggtgggcacctgaaatcccagctactcgggagtctgaggcaggagaatcgcttg
aacccaggaggcagaagttgcactgagctgggatcacaccattgcactccagcctgggcaacagagtgagactccatctcaa
aaaaagaaaaagaaaaaggataaatacattctaacccaaataatgtttatctcatgattgtagctgattcaacattcaaaaat
tggcctggtgcagtagctcaggcctgtaatcccaacatttaggaggctgaggcaggaagatctcttgagcccaggatttca
agaccagcctgggcaacatagtcagactggtctttactgggggaaaaaaatcagtctgtgtaattcaccacattaacaaag
ggaaacataaaaaccctatgatcatttcaacagatgtagcaaaagcagttaatgatattcaacacatatgcatgattacaaa
ccaaccaacctcctagcaaactagggaaaggaaacttaacctagtttgataacagggcgtcccagtcggagttccactagc
agcatacataatggtagaaaactcagtgctgccgggcgcggtggctcacgcctgtaatgccagcactttgggaggcctaggc
gggcggatcacgaggtcaggagatcgagactgtcctgactagcatgctgaaaccccgtctctactaaaaatacaaaaacaaa

FIG. 4 (Continued)

aaattagccgggcatggtggcgggcgcctatagtcccagctactcgggaggctgaggcgagagaatggcgtgaacccgggag
gcggagcttgcagagcctagatcgtgccactgcactccagcctgggtgacagagtgagacttcgtctcaaaaaaaaaaaaa
aaaaaaaagaaaagaaaactcaacgcttttcctctaagatcaggaactagaaaaggatttgactctcacaacgttgatacc
atactggaggtttaaccaggcaagaaaaagaaataatgagggccgggtgcggtggctcaggcctgtaatcccagcactttg
ggaagccgagacgggtggatcacgaggtcaggagatcgagaccatcctggctaacacggtgaaaccctgtctctactaaata
tacaaaaaattagccgggcgtagtggcgggcgcctgtagtcccagctactcgggaggctgaggcaggagaatggcgtgaact
caggggcggagcttgcagtgagctgagatcgagccactgcactccagcctgggcgacagagcaagactgtgtctcaaaaaa
aaaaaaagaaaaagaaataatgattagtggcccgatgtctcacgcctataatcccagcactttgggaggccgaggtgggcag
atcacctgaggtctggagttggagaccagcctgacaaagatggtgaaacctcgtctctattaaaatattaaaaaaatagcca
ggcgttggccgggtacagtggctcatgcctgtaatcccagcactttgggaggccgaggtgggtggatcacctgaggtcagga
gttcaacaccagcctggccaacatggtgaaaccccatctctactaaaaatacaaaaattagccgggcgtagtggcgggcgcc
tgtaatcccagctacttgggaggcttaggcaggagaatcgcttgaacctgggaggcggaggttgtagtgagccgagattgca
ccattgcactccagcctgggtgacaaaagcaaaaactccgtctcaaaaaaaaaagaattagccagggtagtggtgaacgcc
tgtagtcccagctactcaggaggcagaggcaggagaatcacttgaacccaggaggcagaggttgcagtgagccgagattgtc
ccattgcactccagcctaggcgacaagagcaaaattccatgtcaaaaaaaaaaaaaaaaaggaaagaaaaaaaataacgat
tagaaaggaagaaataaaacacattcacagccagtatgattctatacatacatgtcctaatggggccaggcgtggtggctca
tgcctgtaatcctagcactttaggaggctgaggcaggtggcttccctgggaccagcctggccaacatggtgaaaccccaac
tctaataaaaatacaaaaaatcagccaggcgtggtgacgggcacctctaatcccagctactcaggaggctgaggcaggagaa
ttgcttggacctgggaggcagaggttgcagtgagccgagatcgcgctattgcactccagcctgggcaacaagagtgaaactc
cggcagggtgtggtggcttacgcctgtaatcccagcacttcgggaggctgaggcaggccgatcacctgaggtcaggagtttg
agaccaacctaacatggtgaaaccccgtctctactaaaaatacaagaattagctgggtgtagtggtgggcgcctgtaatccc
agctacttgggaggctgagacagaagaattgcttgaacccaggaggtggaggttgcagtgagctgagatcatgccattgcac
accacgccgggcaacagagcgagattccgtctcaaaaaaaaaaaaaaagagtgaaactctatctcaaaaaaaaaaaaaaagtc
ctaatggaaaatccataaaaagctaccaaaactaataaataaatatagcagggttgcaggttacagggcaatatagttatcc
ctctatctgtaggggcttggttctgggactcctcacacaccaaacccacagatgtctaagtcccatatataagacggtatag
tatttggatttaacctacacatatcctcccatatagtttaaattatctctagattacttacattacccccatacaatgaaaa
tgctaatgtacatgcaagtatgtatgtaagtacttgtactatattgtttagggaatcactggacatataggccttcaagact
gataccagcagccactgttaagattctggtcaggcctgcccctgttggggtctcagttgatctcattgccttcccacccag
ccaagggcacctgcatttctcttggctccctggccatttggaaggctagttcagcctggcacatttgtatcctggcccact
gatgctggtacccctgggaaggtcctgctctgaaaaacacggagatttagttgctactgaagatttgagagataaagacag
ggagacctgtctgtagacctgtgtccctccaagtgggattgagactttgggcccccatttcaggacagcacctcctggcct
gttgactgaatagatccctgaaggaggtgtacttgcattaatggagtggggtgggagcagtaccacagatccgcactaaca
atcacacagttctctctagaataataatatagaacaagtgaaatagaacaattgcagaaaagagctaacctttgttgagctct
tactgtgtgcccagcactttcctcaactctacatttcccataatacacagagtactaggtaggccaggcttggtggctcacg
cctgtaatcccagcactttaggaggccaagggggtggatcacctgaggtcgggagttcaagaccagcctgaccaacatggt
gaaaccccgtctctactagaagtacaaaattagccaggtgtggtggcacatgcttgtagtcctagctactcagcaggctgag
gcaggagaatcatttgaatccgggaggaggttgcagtaagcggagatagtgccactgtactccagcctgggcaataagagct
gagactccgtctcaaaataaaataaaataaaataaaataaaataaaataaaataaaaaaagaaaagagcctgccattaaagg
agctgtttggtaggggatgttttgtcagtgcaaacaacagaaaagtgggctgggcacagtggttcatgcctgtaatcccagc
actttgggaggccaaggcgggcggatcacctgaagttgggagttcaagaccagcctgaccaatatggagaaaccccgtctct
actaaaaatacaaaattagccgggcgcagtggcgcatgcctgtaatcccagctactcgggaggctgaggcaggagaatcgct
tgaacctgggaggcagaggttgcggtgagccgagatcgcaccattgcactccagcctggacgagagcaaaactctgtctcaa
aaaaaaaaaaaaacagaaaagtgtaacaaacacttacagtaggcatgtttcttagcaaatctgatgacaaatttggcataa
gaaagagagcatccctgaaaaaaaaaaaagaaaagaaagagagcatcctgcctgggcaacatagtgaaaccctgcctcta
caaaaaaactcaaaaattggccgggtgcagtggctcacacctgtaatcccagcactttgggagtcggaggcgggaggatcac
ctgaggtcaggagttcgaaaccagcctggccaacatggcaaaaccccatctctactaaaaatacaaaaaattaatcaggcgc
attggtgggcgcctgtaatcccagctactcaggaagttgaggcaagaggatcgcttgaatctgggaggtggaggttacagtg
agtcgagatcacaccactgcactctagcctgggtgacagggcgagactccgtctccaaaaaaaaaaagaaaagaaaaagac
taaaaaattagccaggcaggcctctgtggtcccagctacttgggaggctgaggcaggagaatcactgagcccaggagtccga
ggctgtagtgagccatgattgcaccactgtaccctagcttgggcaacaaagcaagaccctgcctcaaaagaaaaaagaaaga
aagaaagaacatggcgggccaggcacagtggctcacacctgtaatcccagcgctttgagaggccgaggcaggtggatcacaa
ggtcaggagttccacaccagcctggccaacatggtgaaaccctgtctctactaaaaatacaaaaaatcagccaggcatggtg
gcagggcctgtaatcccagctactcgggaggctgaggcaggagaattgcttgaaaccagaaggcagaggttgcagtgagcc
tagactgcaccactgcactccagcctgggcgaaaagagccaaactccatctcaaaaaacaaacaaaaaaacaaaacaaaaga
aaacatggcaaagcctttgaaagcttgtctgggagaaggtgcgatgatagttgcataacttcgtgcaagatgctggtccaca

FIG. 4 (Continued)

caggggctgcccttgctctttctcgctctcttaacctctcatataacaggcttgtgtgttattcacatttattgagcccaa
gcaggtgcaaggcattgtgatctaatactttggtcagcaagacaacaagatagatcactgccctgcccttaggaagtgtata
tgctattagaggaaacagataaaataaacaaggaaaagtatcagacaatgtaagtgctatgagaatgcaaatgaggtgatgt
gaattaaaataggatgacttaaagtctgcacgggaaggagcctacccccatgttcctggctagccaaggaaccaccagttga
ttagcagagaagggcagccagtctagctagagctttggggaagagggagtggttgttaagagatgagattaaagaagccga
gacgggccattcgtgaggggtttgtaatgcagggctgaggagtgtccgaagagaatgggcaggtgagcggtgagacagttgt
tcttccagaagctttgcagtgaaaggaatcaaagaaatggagccgtgtatcaggtggggaagggtgggggccaagggggtgt
ccttccccatacagagattgcaggctgagaatgactatatccttgttaacaggaggtgggagcagggcacggtagctcacac
ctgtaatcttggcactttaggaggctgaggcgggccgatcacctgaagtaaggagttcgagaccagcctggccaacatgcaa
agccctgtctctactaaaaatacaaaaattagctgggtgtggtggtactcgcctgtaatcccagctactcgggagactgagg
caggagaatggcttgaacccggaaggtagaggttgcagtgagctgagatcatgccactgtgctccagcctaggtgacagaga
gagactccatctcaaaaaaaaaaaaaaaaatacaggaagggagttgggaatagggtgcacatttaggaagtcttggggattta
gtggtgggaaggttggaagtccctctctgattgtcttttcctcaaagaagtgcatggctggtgaggggtggggcaggagtgc
ttgggttgtggtgaaacattggaagagagaatgtgaagcagccattcttttcctgctccacaggaagccgagctgtctcaga
cactggcatggtgttggggggaggggttccttctctgcaggcccaggtgacccagggttggaagtgtctcatgctggatccc
cactttcctcttgcagCAGCCAGACTGCCTTCGGGTCACTGCCATGGAGGAGCCGCAGTCAGATCCTAGCGTCGAGCCCC
CTCTGAGTCAGGAAACATTTTCAGACCTATGGAAACTgtgagtggatccattggaagggcaggcccaccacccccacccca
ccccagccccctagcagagacctgtgggaagcgaaaattccatgggactgactttctgctcttgtctttcagACTTCCTGAA
AACAACGTTCTGgtaaggacaagggttgggctggggacctggagggctggggacctggagggctgggggctgggggctga
ggacctggtcctctgactgctcttttcacccatctacagTCCCCCTTGCCGTCCCAAGCAATGGATGATTTGATGCTGTCC
CCGGACGATATTGAACAATGGTTCACTGAAGACCCAGGTCCAGATGAAGCTCCCAGAATGCCAGAGGCTGCTCCCCCCGTGGC
CCCTGCACCAGCAGCTCCTACACCGGCGGCCCCTGCACCAGCCCCCTCCTGGCCCCTGTCATCTTCTGTCCCTTCCCAGAAA
ACCTACCAGGGCAGCTACGGTTTCCGTCTGGGCTTCTTGCATTCTGGGACAGCCAAGTCTGTGACTTGCACGgtcagttgcc
ctgaggggctggcttccatgagacttcaatgcctggccgtatcccccctgcatttcttttgtttggaactttgggattcctct
tcaccctttggcttcctgtcagtgtttttttatagtttacccacttaatgtgtgatctctgactcctgtcccaaagttgaat
attccccccttgaatttgggcttttatccatcccatcacaccctcagcatctctcctggggatgcagaacttttctttttct
tcatccacgtgtattccttggcttttgaaaataagctcctgaccaggcttggtggctcacacctgcaatcccagcactctca
aagaggccaaggcaggcagatcacctgagcccaggagttcaagaccagcctgggtaacatgatgaaacctcgtctctacaaa
aaaatacaaaaaattagccaggcatggtggtgcacacctatagtcccagccacttaggaggctgaggtgggaagatcacttg
aggccaggagatggaggctgcagtgagctgtgatcacaccactgtgctccagcctgagtgacagagcaagaccctatctcaa
aaaaaaaaaaaaaaaagaaaagctcctgaggtgtagacgccaactctctctagctcgctagtgggttgcaggaggtgcttac
gcatgtttgtttctttgctgccgtcttccagttgctttatctgttcacttgtgccctgactttcaactctgtctccttcctc
ttcctacagTACTCCCCTGCCCTCAACAAGATGTTTTGCCAACTGGCCAAGACCTGCCCTGTGCAGCTGTGGGTTGATTCCA
CACCCCCGCCCGGCACCCGCGTCCGCGCCATGGCCATCTACAAGCAGTCACAGCACATGACGGAGGTTGTGAGGCGCTGCCC
CCACCATGAGCGCTGCTCAGATAGCGATGgtgagcagctggggctggagagacgacagggctggttgcccagggtccccagg
cctctgattcctcactgattgctcttagGTCTGGCCCCTCCTCAGCATCTTATCCGAGTGGAAGGAAATTTGCGTGTGGAGT
ATTTGGATGACAGAAACACTTTTCGACATAGTGTGGTGGTGCCCTATGAGCCGCCTGAGgtctggtttgcaactggggtctc
tgggaggaggggttaagggtggttgtcagtggccctccaggtgagcagtaggggggctttctcctgctgcttatttgacctc
cctataaccccatgagatgtgcaaagtaaatgggtttaactattgcacagttgaaaaaactgaagcttacagaggctaaggg
cctcccctgcttggctgggcgcagtggctcatgcctgtaatcccagcactttgggaggccaaggcaggcggatcacgaggtt
gggagatcgagaccatcctggctaacggtgaaaccccgtctctactgaaaatacaaaaaaaattagccgggcgtggtggct
gggcacctgtagtcccagctactcgggaggctgaggaaggagaatggcgtgaacctgggcggtggagcttgcagtgagctga
gatcacgccactgcactccagcctgggcgacagagcgagattccatctcaaaaaaaaaaaaaaaaaaaggcctcccctgcttgcc
acaggtctccccaaggcgcactggcctcatcttgggcctgtgttatctcctagGTTGGCTCTGACTGTACCACCATCCACTA
CAACTACATGTGTAACAGTTCCTGCATGGGCGGCATGAACCGGAGGCCCATCCTCACCATCATCACACTGGAAGACTCCAGg
tcaggagccacttgccaccctgcacactggcctgctgtgccccagcctctgcttgcctctgacccctgggcccacctcttac
cgatttcttccatactactacccatccacctctcatcacatccccggcggggaatctccttactgctcccactcagttttct
tttctctggctttgggacctcttaacctgtggcttctcctccacctacctggagctggagcttaggctccagaaaggacaag
ggtggttgggagtagatggagcctggtttttaaatgggacaggtaggacctgatttccttactgcctcttgcttctctttt
cctatcctgagtagTGGTAATCTACTGGGACGGAACAGCTTTGAGGTGCGTGTTTGTGCCTGTCCTGGGAGAGACCGGCGCA
CAGAGGAAGAGAATCTCCGCAAGAAAGGGGAGCCTCACCACGAGCTGCCCCCAGGGAGCACTAAGCGAGgtaagcaagcagg
acaagaagcggtggaggagaccaagggtgcagttatgcctcagattcacttttatcacctttccttgcctctttcctagCAC
TGCCCAACAACACCAGCTCCTCTCCCCAGCCAAAGAAGAAACCACTGGATGGAGAATATTTCACCCTTCAGgtactaagtct
tgggacctcttatcaagtggaaagtttccagtctaacactcaaaatgccgtttttcttcttgactgttttacctgcaattggg
gcatttgccatcaggggggcagtgatgcctcaaagacaatggctcctggttgtagctaactaacttcagaacaccaacttata

FIG. 4 (Continued)

ccataatatatatttttaaaggaccagaccagctttcaaaacagaaaattgttaaagagagcatgaaaatggttctatgacttt
gcctgatacagatgctacttgacttacgatggtgttacttcctgataaactcgtcgtaagttgaaaatattgtaagttgaaa
atggatttaatacacctaatctaaggaacatcatagcttagcctagcctgctttttttttttttttttttggagacagagtc
tcactctgtcacccaggctggagtgcagtggcgggatctcggctcactgcaacctccgcctcctgggttcaagcgattctcc
tgcctcagcccactgagtagctgggattacaggcacctgccccgacgcccagctaatttttgttatttatttatttttttt
tttagtagagatgaggtttcaccatgttggccaggctagtctcgaactcctgaccttgtgatctgcctgccttggcctccca
aagtgctgggattacaggcgtgagccaccgcacccggcctgcctagcctactttttattttattttttaatggagacagcatct
tgctctgttgcccaggctggattacagtgatgtgatcatagctcattataccctcctgggctcaagcaatcccccctaactct
gcctccccagtagctaggacccacaggcatacaccaccatacccagctaatttttaaaatttttttgtagatagatagagtctc
actatgttgcccaggctggtctctagcctactttttttgagacaaggtcttgctctgtcacccaggctggatagagtgcagta
gtgcagtcacagctcactgcagcctccacctcccaggctccatccatcctcccagctcagcctcccaagttgcttcaactac
aggcctgcaccaccatgcctggctaatttttatttatttatttttatttttatttttattttttttgagactcagtctca
ctctgtcgcccaggctggagtgcagtggcatgatctcggctcactgcaacctctgcctcctgggttcaagtgattctcctgc
ctcagcctcccgaatagctaggactacaagcgcctgctaccacgcccagctaatttttgtatttttagtagagacagggttt
caccatgttggccaggctggtctcgaacttctgaccatgtgatccgcccgcctcggcctcccaaagtgctgggattacaggt
gtgagccaccacgcccggctaatttttatttatttatttaaagacagagtctcactctgtcactcaggctagagtgcagtgg
caccatctcagctcactgcagccttgacctcctgggctccggtgatttcacctcccaagtagctaggactacaggcacat
gccacgacacccagctaatttttatttttctgtgaagtcaaggtcttgctacgttgcccatgctggtatcaaacccctgggc
tcaatcaatccttccacctcagcctcccaagtattggggttacaggcatgagctacccacactcagccctagcctacttgaa
acgtgttcagagcatttaagttaccctacagttgggcaaagtcatctaacacaaagccctttttatagtaataaaatgttgt
atatctcatgtgatttattgaatattgttactgaaagtgagaaacagcatggttgcatgaaaggaggcacagtcgagccagg
cacagcctgggcgcagagcgagactcaaaaaaagaaaaggccaggcgcactggctcacgcctgtaatcccagcatttggga
ggctgaggcgggtggatcacctgaggtcaggagttcaagaccagcctagccaacatggtgaaaccccgtctctactaaata
caaaaattaaccgggcgtgatggcaggtgcctgtaatcccagctacttgggaggctgaggcaggagaatcgcttgaaccagg
aggcggaggttgcagggagccaagatggcgccactgcactccagcctgggcgatagagtgagactccgtctcagaaaaaaaa
gaaaagaaacgaggcacagtcgcatgcacatgtagtcccagttacttgagaggctaaggcaggaggatctcttgagcccaag
agtttgagtccagcctgaacaacatagcaagacatcatctctaaatttaaaaaagggccgggcacagtggctcacacctgt
aatcccagcactttgggaggtggaggtgggtagatcacctgacgtcaggagttggaaaccagcctggctaacatggtgaagc
cccatctctactaaaaacacaaaaattagccaggtgtggtagcacacgcctgtagtcccagctactcgggaggctgaggcac
aagaatcacttgaacccagaggcggagattgcaatcagccaagattgcaccattgcactcccgcctgggcaacagagtgag
accccatctcaaataaataaataaatatttttaaaagtcagctgtataggtacttgaagtgcagtttctactaaatgcatg
ttgcttttgtacgtcataaagtcaaacaattgtaacttgaaccatcttttaactcaggtactgtgtatatacttacttctc
ccctcctctgttgctgcagATCCGTGGCGTGAGCGCTTCGAGATGTTCCGAGAGCTGAATGAGGCCTTGGAACTCAAGGA
TGCCCAGGCTGGGAAGGAGCCAGGGGGGAGCAGGGCTCACTCCAGgtgagtgacctcagcccctttcctggccctactccct
gccttcctaggttggaaagccataggattccattctcatcctgccttcatggtcaaaggcagctgaccccatctcattgggt
cccagccctgcacagacatttttttagtcttcctcggttgaatcctataaccacattcttgcctcagtgtatccacagaac
atccaaacccagggacgagtgtggatactttctttgccattctccgcaactcccagcccagagctggagggtctcaaggaggg
gcctaataattgtgtaatactgaatacagccagagtttcaggtcatatactcagccctgccatgcaccggcaggtcctaggt
gacccccgtcaaactcagtttccttatatataaaatggggtaaggggggccgggcgcagtggctcacgaatcccacactctgg
gaggccaaggcgagtggatcacctgaggtcgggagtttgagcccagcctgaccaacatggagaaaccccatctctactaaaa
atacaaaagtagccgggcgtggtgatgcatgcctgtaatcccagctacctactcgggaggctgaggcaggagaatcgcttga
acccgggaggcagaggttgcggtgagctgagatctcaccattacactccagcctgggcaacaagagtgaaactccgtctcaa
aaaagataaataaagtaaaatggggtaagggaagattacgagactaatacacactaatactctgaggtgctcagtaaacata
tttgcatggggtgtggccaccatcttgatttgaattcccgtttgtcccagccttaggcccttcaaagcattggtcagggaaaa
ggggcacagaccctctcactcatgtgatgtcatctctcctccctgcttctgtctcctacagCCACCTGAAGTCCAAAAAGGG
TCAGTCTACCTCCCGCCATAAAAAACTCATGTTCAAGACAGAAGGGCCTGACTCAGACTGACATTCTCCACTTCTTGTTCCC
CACTGACAGCCTCCCACCCCCATCTCTCCCTCCCCTGCCATTTTGGGTTTTGGGTCTTTGAACCCTTGCTTGCAATAGGTGT
GCGTCAGAAGCACCCAGGACTTCCATTTGCTTTGTCCCGGGGCTCCACTGAACAAGTTGGCCTGCACTGGTGTTTTGTTGTG
GGGAGGAGGATGGGGAGTAGGACATACCAGCTTAGATTTTAAGGTTTTTACTGTGAGGGATGTTTGGGAGATGTAAGAAATG
TTCTTGCAGTTAAGGGTTAGTTTACAATCAGCCACATTCTAGGTAGGGGCCCACTTCACCGTACTAACCAGGGAAGCTGTCC
CTCACTGTTGAATTTTCTCTAACTTCAAGGCCCATATCTGTGAAATGCTGGCATTTGCACCTACCTCACAGAGTGCATTGTG
AGGGTTAATGAAATAATGTACATCTGGCCTTGAAACCACCTTTTATTACATGGGGTCTAGAACTTGACCCCCTTGAGGGTGC
TTGTTCCCTCTCCCTGTTGGTCGGTGGGTTGGTAGTTTCTACAGTTGGGCAGCTGGTTAGGTAGAGGGAGTTGTCAAGTCTC
TGCTGGCCCAGCCAAACCCTGTCTGACAACCTCTTGGTGAACCTTAGTACCTAAAAGGAAATCTCACCCCATCCCACACCCT
GGAGGATTTCATCTCTTGTATATGATGATCTGGATCCACCAAGACTTGTTTTATGCTCAGGGTCAATTTCTTTTTTCTTTTT

FIG. 4 (Continued)

TTTTTTTTTTTTTCTTTTTCTTTGACACTGGGTCTCCCTTTCTTGCCCAGGCTGGAGTGCAGTGGCGTGATCTTGGCTTACT
GCAGCCTTTGCCTCCCGGGCTCGAGCAGTCCTGCCTCAGCCTCCGGAGTAGCTGGGACCACAGGTTCATGCCACCATGGCCA
GCCAACTTTTGCATGTTTTGTAGAGATGGGGTCTCACAGTGTTGCCCAGGCTGGTCTCAAACTCCTGGGCTCAGGCGATCCA
CCTGTCTCAGCCTCCCAGAGTGCTGGGATTACAATTGTGAGCCACCACGTCCAGCTGGAAGGGTCAACATCTTTTACATTCT
GCAAGCACATCTGCATTTTCACCCCACCCTTCCCCTCCTTCTCCCTTTTTATATCCCATTTTTATATCGATCTCTTATTTTA
CAATAAAACTTTGCTGCCACCTGTGTGTCTGAGGGGTG

SEQ ID NO: 6

>gi|110224474|ref|NM_000314| Homo sapiens phosphatase and tensin homolog (PTEN), mRNA.

cctcccctcgcccggcgcggtcccgtccgcctctcgctcgcctcccgcctcccctcggtcttccgaggcgcccgggctcccg
gcgcggcggcggaggggcgggcaggccggcgggcggtgatgtggcgggactctttatgcgctgcggcaggatacgcgctcg
gcgctgggacgcgactgcgctcagttctctcctctcggaagctgcagccatgatggaagtttgagagttgagccgctgtgag
gcgaggccgggctcaggcgagggagatgagagacggcggcggccgcggcccggagcccctctcagcgcctgtgagcagccgc
gggggcagcgccctcggggagccggccggcctgcggcggcggcagcggcggcgtttctcgcctcctcttcgtcttttctaac
cgtgcagcctcttcctcggcttctcctgaaagggaaggtggaagccgtgggctcgggcgggagccggctgaggcgcggcggc
ggcggcggcacctcccgctcctggagcggggggagaagcggcggcggcggcggccgcggcggctgcagctccagggagggg
gtctgagtcgcctgtcaccatttccagggctgggaacgccggagagttggtctctccccttctactgcctccaacacggcgg
cggcggcggcggcacatccagggacccgggccggttttaaacctcccgtccgccgccgccgcaccccccgtggcccgggctc
cggaggccgcccggcggaggcagccgttcggaggattattcgtcttctccccattccgctgccgcccgctgccaggcctctggc
tgctgaggagaagcaggcccagtcgctgcaaccatccagcagccgccgcagcagccattacccggctgcggtccagagccaa
gcggcggcagagcgaggggcatcagctaccgccaagtccagagccatttccatcctgcagaagaagccccgccaccagcagc
ttctgccatctctctcctcctttttcttcagccacaggctcccagacatgacagccatcatcaaagagatcgttagcagaaa
caaaaggagatatcaagaggatggattcgacttagacttgacctatatttatccaaacattattgctatgggatttcctgca
gaaagacttgaaggcgtatacaggaacaatattgatgatgtagtaaggtttttggattcaaagcataaaaaccattacaaga
tatacaatctttgtgctgaaagacattatgacaccgccaaatttaattgcagagttgcacaatatcctttgaagaccataa
cccacacagctagaacttatcaaaccctttgtgaagatcttgaccaatggctaagtgaagatgacaatcatgttgcagca
attcactgtaaagctggaaagggacgaactggtgtaatgatatgtgcatatttattacatcggggcaaatttttaaggcac
aagaggccctagatttctatggggaagtaaggaccagagacaaaaagggagtaactattcccagtcagaggcgctatgtgta
ttattatagctacctgttaaagaatcatctggattatagaccagtggcactgttgtttcacaagatgatgtttgaaactatt
ccaatgttcagtggcggaacttgcaatcctcagtttgtggtctgccagctaaaggtgaagatatattcctccaattcaggac
ccacacgacgggaagacaagttcatgtactttgagttccctcagccgttacctgtgtgtggtgatatcaaagtagagttctt
ccacaaacagaacaagatgctaaaaaaggacaaaatgtttcactttgggtaaatacattcttcataccaggaccagaggaa
acctcagaaaaagtagaaaatggaagtctatgtgatcaagaaatcgatagcatttgcagtatagagcgtgcagataatgaca
aggaatatctagtacttactttaacaaaaaatgatcttgacaaagcaaataaagacaaagccaaccgatacttttctccaaa
tttaaggtgaagctgtacttcacaaaaacagtagaggagccgtcaaatccagaggctagcagttcaacttctgtaacacca
gatgttagtgacaatgaacctgatcattatagatattctgacaccactgactctgatccagagaatgaacctttgatgaag
atcagcatacacaaattacaaaagtctgaattttttttatcaagagggataaaacaccatgaaaataaacttgaataaact
gaaaatggaccttttttttttaatggcaataggacattgtgtcagattaccagttataggaacaattctcttttcctgacc
aatcttgttttaccctatacatccacagggttttgacacttgttgtccagttgaaaaaaggttgtgtagctgtgtcatgtat
ataccttttgtgtcaaaaggacatttaaaattcaattaggattaataaagatggcactttcccgttttattccagttttat
aaaaagtggagacagactgatgtgtatacgtaggaattttttccttttgtgttctgtcaccaactgaagtggctaaagagct
ttgtgatatactggttcacatcctacccctttgcacttgtggcaacagataagtttgcagttggctaagagaggtttccgaa
gggttttgctacattctaatgcatgtattcgggttaggggaatggagggaatgctcagaaaggaaataattttatgctggac
tctggaccatataccatctccagctatttacacacacctttctttagcatgctacagttattaatctggacattcgaggaat
tggccgctgtcactgcttgttgtttgcgcattttttttaaagcatattggtgctagaaaaggcagctaaaggaagtgaatc
tgtattggggtacaggaatgaaccttctgcaacatcttaagatccacaaatgaagggatataaaaataatgtcataggtaag
aaacacagcaacaatgacttaaccatataaatgtggaggctatcaacaaagaatgggcttgaaacattataaaaattgacaa
tgatttattaaatatgttttctcaattgtaacgacttctccatctcctgtgtaatcaaggccagtgctaaaattcagatgct
gttagtacctacatcagtcaacaacttacacttattttactagttttcaatcataatacctgctgtggatgcttcatgtgct
gcctgcaagcttcttttttctcattaaatataaaatatttgtaatgctgcacagaaattttcaatttgagattctacagta
agcgtttttttctttgaagatttatgatgcacttattcaatagctgtcagccgttccacccttttgaccttacacattcta

FIG. 4 (Continued)

ttacaatgaatttttgcagttttgcacatttttttaaatgtcattaactgttagggaattttacttgaatactgaatacatata
atgtttatattaaaaaggacatttgtgttaaaaaggaaattagagttgcagtaaactttcaatgctgcacacaaaaaaaga
catttgattttcagtagaaattgtcctacatgtgctttattgatttgctattgaaagaatagggtttttttttttttttt
ttttttttttttaaatgtgcagtgttgaatcatttcttcatagtgctcccccgagttgggactagggcttcaatttcacttc
ttaaaaaaaatcatcatatatttgatatgcccagactgcatacgattttaagcggagtacaactactattgtaaagctaatg
tgaagatattattaaaaaggtttttttttccagaaatttggtgtcttcaaattatacctttcacctgacatttgaatatcca
gccatttttgtttcttaatggtataaaattccatttttcaataacttattggtgctgaaattgttcactagctgtggtctgacc
tagttaatttacaaatacagattgaataggacctactagagcagcatttatagagtttgatggcaaatagattaggcagaac
ttcatctaaaatatttcttagtaaataatgttgacacgttttccatacctttgtcagtttcattcaacaatttttaaattttta
acaaagctcttaggatttacacatttatatttaaacattgatatatagagtattgattgattgctcataagttaaattggta
aagttagagacaactattctaacacctcaccattgaaatttatatgccacctttgtctttcataaaagctgaaaattgttacc
taaaatgaaaatcaacttcatgtttgaagatagttataaatattgttctttgttacaatttcgggcaccgcatattaaaac
gtaactttattgttccaatatgtaacatggagggccaggtcataaataatgacattataatgggcttttgcactgttattat
ttttcctttggaatgtgaaggtctgaatgagggttttgatttgaatgtttcaatgttttgagaagccttgcttacatttt
atggtgtagtcattggaaatggaaaaatggcattatatatatttatatatataaatatatattatacatactctccttacttt
atttcagttaccatccccatagaatttgacaagaattgctatgactgaaaggttttcgagtcctaattaaaactttatttat
ggcagtattcataattagcctgaaatgcattctgtaggtaatctctgagtttctggaatattttcttagactttttggatgt
gcagcagcttacatgtctgaagttacttgaaggcatcactttaagaaagcttacagttgggcactgtacatccaagtcc
tttgtagctcctcttgaacatgtttgccatactttttaaaagggtagttgaataaatagcatcaccattctttgctgtggcac
aggttataaacttaagtggagtttaccggcagcatcaaatgtttcagctttaaaaaataaaagtagggtacaagtttaatgt
ttagttctagaaatttttgtgcaaatatgttcataacgatggctgtggttgccacaaagtgcctcgtttacctttaaatactgt
taatgtgtcatgcatgcagatggaaggggtggaactgtgcactaaagtgggggctttaactgtagtatttggcagagttgcc
ttctacctgccagttcaaaagttcaacctgttttcatatagaatatatatactaaaaatttcagtctgttaaacagcctta
ctctgattcagcctcttcagatactcttgtgctgtgcagcagtggctctgtgtgtaaatgctatgcactgaggatacacaaa
aataccaatatgatgtgtacaggataatgcctcatcccaatcagatgtccatttgttattgtgtttgttaacaacccttat
ctcttagtgttataaactccacttaaaactgattaaagtctcattcttgtcaaaaaaaaaaaaaaaaaaaaaaaaaaaa

SEQ ID NO: 7

>hg18_knownGene_uc001kfb.1 range=chr10:89613175-89718512 5'pad=0 3'pad=0
strand=+ repeatMasking=none cctcccctcgcccggcgcggtcccgtccgcctctcgctcgcctcccgcctcccctcggtcttccgaggcgcccgggctcccg
gcggcggcggaggggggggggcaggccggcgggcggtgatgtggcgggactctttatgcgctgcggcaggatacgcgctcg
gcgctgggacgcgactgcgctcagttctctcctctcggaagctgcagccatgatggaagtttgagagttgagccgctgtgag
gcgaggccgggctcaggcgagggagatgagagacggcggcggccgcggcccggagcccctctcagcgcctgtgagcagccgc
ggggcagcgccctcggggagccggccggcctgcggcggcggcagcggcggcgtttctcgcctcctcttcgtcttttctaac
cgtgcagcctcttcctcggcttctcctgaaagggaaggtggaagccgtgggctcgggcgggagccggctgaggcgcggcggc
ggcggcggcacctcccgctcctggagcgggggggagaagcggcggcggcggcggccgcggcggctgcagctccagggagggg
gtctgagtcgcctgtcaccatttccagggctgggaacgccggagagttggtctctccccttctactgcctccaacacggcgg
cggcggcggctggcacatccagggaccgggccggttttaaacctcccgtgcgccgccgccgcaccccccgtggcccgggct
ccggaggccgccggcggaggcagccgttcggaggattattcgtcttctccccattccgctgccgccgctgccaggcctctgg
ctgctgaggagaagcaggcccagtcgctgcaaccatccagcagccgccgcagcagccattacccggctgcggtccagagcca
agcggcggcagagcgagggcatcagctaccgccaagtccagagccatttccatcctgcagaagaagccccgccaccagcag
cttctgccatctctctccctcctttttcttcagccacaggctcccagacatgacagccatcatcaaagagatcgttagcagaa
acaaaaggagatatcaagaggatggattcgacttagacttgacctgtatccatttctgcggctgctcctctttacctttctg
tcactctcttagaacgtgggagtagacggatgcgaaaatgtccgtagtttgggtgactataacatttaaccctggtcaggtt
gctaggtcatatatttttgtgtttcctttctgtgtattcaacctagggtgtgtttggctagacggaactcttgcctggttgca
agtgtcaagccaccgattgctttcttaggctatctatatggtctcttcctgagggctattgtccgttaatacagaatacagt
acactgttagtggattagcgagctcggtaatccggtctcctaaatgaacaaaaagtagacgcttttgaggttgagcatat
ttcgattaaatcttggcttaggccctagatcaagggtttagatcagaataaaatgaaattagtgttgcacgtacgcatatt

FIG. 4 (Continued)

gaatcagaatcttgcagtgattgttttagtttcctgagttgcattgatagattcttttaaaatatgactgatttgcataact
ttagaagcagaatcattttcagtatatatggtgcacattgagggcaaaaagtagttttgttaatgtttaaacttaagttacc
tacaactttgaactgtatgtagaagttttgtagtttgaagtcaatagtgccataatataccttataaggcgttcttactaga
tctttgttatatttaccttttctctccctatggggtgatgtaggatagtgcttgaaatttgcacttcagtagcatttaatg
ttcagtgctcttgtcataaacatagaatggatattgagtagtttctgatcccagatggtaatgtgtaggttcaagggtattg
tgtgtagcaagtgaagattgcagaaataaaacttcagttcatgcttgaaatttaagtattgttgtgatgccagaattgctgc
tcaccgttttaggtttcaggtcctctgacacctttggtatcgttaattttactgatttgtgtagaatgtcagttgtattt
taccagctaatatctagaaatgctggcaagaggggtttactccagctttagattgtaggtatgttagcttttttcatacagt
gtatttaaatttactgagtcagcttgctgaataagacagaagcccaagaattttaacagtgtgtagctttagttgtctaaaag
ttaggccttcgggctttcaaaagttagtggtcatcgaaaagcattaatctttgcagtttcaggtacaacacattggttttgat
tagggatggggatggggccctctttttgcagaatggggaaagtattgacaggaattgagagctattggtaggccagtgtata
aggtatgtgaaaacagaattaagttattggtctgaagtgactgaagcatttaggctctatcaaggcctaaaatttggtaata
tgagtttggtaatgcgaattgtggcagtggacaatatttagttaaaattatgtaattgcataagtactagcacagtatttttt
aataaaagttatttcttagcaaatgtcagttgcatttgtctaaaggtagagtgacactacagtgtctatatgtcctgctaa
aaattgtggggaatatttttttttaagacagcgtttatatcgggagaggtttttattccgttggattatgttagctgcatata
aatgtgcacagttaattttgcccaagttttttgttttgaaatgaatgtaaaaccttactgaagaagtagcttcccaaaatttag
ttttctgttaagcccaaaatattattttaaaagagtatttgcaaatttttgaagttgacattaattgagaatgttactaaggc
taaactggacccgcttgcccagaagataattatggaaaaattctttttgtgacttccaaagcagtctactattagcatgaatt
actgacagtcatcccaaatatataggaacaaaaaattaaatgtttatgtaactttgaaaaaaaagcctttgaagaaaataatt
gaatgctgtctgggagacagatttctttcagcacttaaagtacataacacactactttttacttttcccacttgattttaaat
tatcagggttattaagaccttaaaattatttttaccaggtttttacatgtgagctgtgacatgactggcatttttctttgattt
cagcgtatgttggtctctacacatgaaatttgtgtgacttaaaactttctctaaaactgtactttttagttatgatatgcata
gaaagcagtatcaaatattgcgtcaaatgactaataacacttaatttctagagttgtggtttttattgagccaaaagttgata
tgaaaaaagtcagtaaggaaagtcagtgaagtgcttgctttttttgataattgcactcccaataatttttgatattccaacgt
acttggtttgcttgttttcacgttaatgtttttctgtttattggagtgggaaggcattaaaattgtcattgaagactttgtct
ttgacatgttgtagtatttatttcagtaactaacctgtgaaaagttaaattcctttatgaaagtagtgattggagtattttt
atctgataaagaaagattaataatgaagccatttctccgaggaaaattgaggacaataattcagtttttaaaatattatcgca
aaattaaattattctaaaaatttgttagtagggttatatgcttaatattagtctgaaatatagtgctgaatttgagactata
gaaaaattaagtgtatttagggtatgtggaaacgttaggcttcgttgtatttttattgttttggtagatttgcctctttttca
aataaatgttcacagggaatactttttaacttgtagagagtacagtgactattgaagttacctaaattacctcaaggtaagtg
attactgaaattaatcatgagggtttttaaaaagtattctattcacaacatttatttttacattgttttgtatctgctaagtta
tatttcctgaaaaacatgactggaccacctaattgctgtatgataacttacaaacttcatttttcatagtgcttattcaagt
gtaaagcacaactgaaaggagtaatgtacagtttatatgaggaaaaaggaatttttatttgctgccagtgtaaaagtttgcaca
gcagtatagtcatcaatgcagatttacatttgcttataatatactaagtaaatactaaatgattaaagataataaaatatggt
gaggtataaccaccttcattttaaacttagtttttagaagatagtaaagaaagattcctttattaccttttttagaatttttatt
tttaataacatgggaaaggcaactggtgatattttaatttttgtatggaacagtgcatctgctttctcatagccacataaaa
tacataaacttcttagtgttatgaaatggcttacttttttggaagtgaagaagtcttcaattcttatttttctaatgttatttt
gaatttgcctccatttgctgtttgttcatttggtgatagcgcaacacttaaaaaaatatttttaagccgcttctgaagtaat
cacttcagtgactttttaatggaggagtatttgttatgggaaattcacttcacaaagttttaacattaattcacttgaagtaa
acgtgctattttttaaatttttcatctcaatctttttaagtaagacgaaagcttaggaaatcactttttattattgatattgtgtg
tgacttcagagtttgtaaagagaattgtagaagtgttgcatgcatatgacaattttctgcttaattgaaatgtgaggcctct
gccatactacaaggatttagcttccagaaaatgtaatattaacatagcttaagaaatgtattttttttttttctgtagaaacc
gttgggttaaacaaacagttcagaagttttattacatggaacccattagttcttaatcttgttaccttttttcttcatttttt
ctgttaaacttgattttcacagtcagcattgaagaattcatcttgtggcctgaattcattaagaaaagatgttaggatttgt
tctgaagatagtgacttaggaaatttgtgagactggggtcagtcagttctgtttttacaattgcttttctatttggtagctttg
aaattaatttagttgcttatcagagagaataatgttgaggttagactaacctttaaattggtaaggctttgctgagcaaactg
ataactgtaagtcttttatagggtgcattactgccacatatacgttcttccataggtggttaaaagtatattggtctgtgtt
tggtgattctctttgtacatattgagtatatgcattcactaatgtaaaataatttgccaagaaaggtgaaattagtatattg

FIG. 4 (Continued)

tacttgactattcacctttcccttagtttttgaatttttttcattggttgcagaggaagtattagcaatttaattctttta
aaataatttgcactggaataaataagtatcggcaaatataagaagagtaacataatttaagggtgaattaattttatttggg
aagttttagttctgtatagttaaggcagattcttcatttgcaacagttgacattgggacatgtgtgaacatcttcaaggtat
taggacatcttcaaggcattacttttggcagtgttgagaatttttttttttttttttttttttgagatggaatctcgct
ctatcgcccagtctggggtgcagtggcaggatctcggctcactggaacctctgcctcccaggttcaggcgattctcctgcct
gaacctcccaagcagctgggattataggtgcatgccaccacgcccagatagtttttgtactttttagtagagatggggtttta
ccaccttggccaggctggtctcaaactccagacctcaagtgatccgcctgcctcggcctcccaaaatgctgggattacaggc
gtgagccactgcgcctggccagtgttgagaatattgagagatggatattgtagctgtacctgccatcaaaagaattttcttg
acctccacatagtgtgaaaaagaagactgtttacacattatatttaagtaattatacacataattattatcagtactcacc
acttcaaatatgaacagtgaatctaaccagtgtttgatttctctgtgtgtgtatgtgtatacaaagttagcaaacctttat
cttaatatttattaaaaacgaattttgtttctttaaagaaaagactaccttagagaatattgttctatagtttttaaata
tggtcagatctattttaaattatgttaaaatttgagtattacgtttatctatactttaagcatatatacattgtttcatt
ttagatttagggaggcagtgtgggctctggagccagactgcttgttttgtaatcctggatcttccatttagtagctggatg
actttgagtaggttatttagattttctcaatctatttatctgtaaaatggggatgataatggaacctacgcatacgttta
tcttgaatagtaagtgagataataataagtaatttcatttagcatagtacctgccacattgtaaatacttaaatggtagcta
ctgctctgaaaaactgtaatttcaggttatgtatgtagggaaattatttgtatttttcatttatggtgtatgattgtaactga
atttcctcagtttgggccatgttaggattttgtttcaagttataagtgtttttaaaaataagggtattcctttaggaagtct
gggtatgacatgtctgtgattttgctggttcatcacaaatgggaaataaatctctgctaactcaaactgttgaccaaagtaa
aattaattatgccaatcaaaaactatttgctttaaaatataaaggcaaaaacttcctattagcataatgaagtagaatttt
taaactttgttataatcttaaatttctttagtgttgaagataggtcaacttaactatcatacattttattcacataaagt
aaactctgcctcaaatgtaataaacttaatatgagttatgtaaactttggtcaatagaggtatatttttagcatttccttt
tgaaaatttcagcctttgagggagtcttgcaactgaatgtcaagttacatttattacaataaaatggacacttaatataat
ctgtaatgcattaacataatatgggaactttaaagtattcagtctctgtattattgagtcctatttccacatttggccagg
atttctcaatatgatttaggcccaagacgtgggaagaaagaagtaaagaactaaaggatttttttcttcatttttttaattga
atatggggaaagatggaataagcttatctgtccagtaaaggccattatgtgtacatagggattattattttccccccttg
ggctgtactgatttccccagatgtaccacagcactcttagtagtgaagcacttgacttctagtgagtggatttttttgtgtgtg
tgttttatattgcagagtgaatacactctgtctgatactatgtgactttctgattatgtgatttttatgcattttatgtgtt
ttgtaaactagctgtatttttggtccatgtctaggttgtagaattgaattgtgcattttggcatctgagcacagctgagttt
tctaaatcaatctctctccttgcacctagtttttgctttagatcactacctaagacttactgttgatttaatattagagcac
ttaagcatagctttgactttttatttccttgattttgtagattttcaggctgaagtacaataaggttctctgttctttact
agtaattgcaaagattgtattctgtgaatttttatttgtttaatactttttgatctttttgaagaggatgtaattatttaaggta
ttatgaaatgcattgtgatttgaattagatactctttggagatggagttttgctgttgttgcccaggctggagtgcaatggt
gtgatctcggctcaccacagcctccgcctcctgggttcaagcaattctcttgcccagcctcccaagtagctggaattacag
gcatgcgccaccacgcccggctaatttttatatttttttttttcagtagagatggggggtttctccatgttggtcaggctggcc
tcgaactcttgacctcaggtaatctgcctgtctcagcctgctaaagtgctgagattacaggcatgagccactgcgcccggcc
tcagatactcttttaattagatgcgtttaaaaatttaacccaccattgctggcatgaatagatgtatttttagagtgattca
taaatatcgtatacatgtttaaagttacaaactttttgcttatttcaaaatgcaggattcttttccatttaaaattccctct
ctttgtgagacttctttttgagtattctggttactctaaactgattggagatgaaattagatagaattgaaaactgtacttt
taaaatgaaattttggggatgtcattaagcttgatttttttaggttttttttttagtgtgtattataaattatttacactga
ttgtcagcgataaaatggaatgcctgggatttttttaaaatttactttattcatttttataaggtaaaaacagtgttttgcta
ggcttaatttgaccatgttgtaaaatttattgtatacctgaaagaatcatttatgaaagatactgaattagctaatatata
ctctgtcttatgtagtttttgattaacaatacactttttaaatcattagctcatttgattttgcaaagaagaacaggtaacc
taagaggcagacagaacaggcattactttttattttctttctttttttattttattttatttatttatttatttttgca
gcttaggaattgtagctccagtggaatcagtatcttgttaatggctagtgaaagactgagtctgaagaaggatgcaggactt
ttttggcacttggtgcagtattttcccattatgttacatgagtggttcttaaacttcagtgtgttagaacaacctgaaggg
cttattaagctatggattgcttactccaccctcagagtttctgattcagtaggtctggattgggacctgagaattttttattt
cttagaagttttcaagtgatgctgatgctggtgctctggggatcacactttgaggaccaccaatgaacattatctcccacca
agcaaaccctaacatgttatactccttttaggttattagaatttatacatgcattatttcatttgacctgtaaactctaagt

FIG. 4 (Continued)

aactttgcatggaaaatgttatcctgattttatagacgagatagtgagtttagaaaggcagtatggtggaatggagcataga
tttggagttggctagacctaaagtccagattaaatctctgctcaaggctgggcgtggtggctcatgcctgtaatcccagtgc
tttgggaggccaggcgttggcagattgcttgagtctggaagttcgagaccagtctgggcaacataggcagaccctgtctctac
aaaaaaaaatacaaaaattagtcgggtgttatagtgcgcattggtagtcccagctactgaggaggctgaggtgggatcacct
gagactgggactttgaggctgcattgagctgtgattgggacactgtactcctgcctgggtgacagagtgagaccctctctca
aaaataaataaataaatacatccccgctcagccacttatcagttacgtagatacactgcctaaccttagtgaaccctgtttc
gacaactccaaaatgggagtaaaaatcctaaacttgtacagtggtttttagttttgttaaaagtacaggtgaggtttttt
cagagtattggttgccatctgagagtgatcccctttcacctcctctaggactttagcattttctggagacattttggtggt
cacagctggggtggtagagtgtgctattggctagggcttgaagccagtgatgctgcttaacatcctatatggcacaagacc
cctccccatcaacaaagaattatctagcccaaaatgctgtgtaaaatgtctggtatataataagtataatatttgatgaaaa
tcagtacctttgccccaggtgtgatatttaagaaggtcaacttactaaatcagtgatggagttagtcctaacatctgggtg
ttctgactgctgctaggccagtattctttatatgataataagaactttgtccacagaagatatccctaataacaaaaaggt
ttatttgaagaggactcatgtgttctttggctgattgtgaaagtgttgctttgaacttctgttagaaaaggttgaagctgtt
ttccgtaagtgtttttaatactgtacgtagtattcagaaggatgtttaatttttttttttaatttgctagtagtttttaaag
taatccttttccttaattatgtagttgttgaactgttgggagttacttttctcttactatttgttatttaatgtattct
ttgaccttatgctttttatttctaaagctgctttattatagtcagatatgatgaagttaaatgtacaatgtaaaattgcaa
atttccaacgagctatacaaacttaaatatttctaagtaaagaaaatagggctgactctaaggttctttgatccatgtgttg
cattctttttctaggccctaaatttgctatgccagcctgttgaattaaagtgctttatttatctaaattagaaacttgtatta
aagtgaagtttagaaaaaagaaacaaaatcggaatggagtttaggttagcccagagatgggaagatgccaagaaggtag
ctttagtggattctgaatttttggtttgtttgtttttagggcaggcaaatgtaattacaaaagggttctaggaatagat
tgctgtgatttttttctgtttgcatgatttacagtttgctttgcctctcactttgaatgcagaataaaatgtcaaggcc
ttatttttttttaaattcttaagaaatttaagatttgactgttaattcctttgaaatatgggatatttgagataccaatt
atttaagacaaataggactcattgttacaattcagttgaataaggcttatgatgtttatttcagtatatgaatgaaactat
gtgcttattgtacttaagaaaatttctttttattaaaaacatgactaaagagaatttaaaaatcacccactgtcctacttct
ctaaaacttaatgtttcatattagcttccagtttgttcatatgcatatactttaaaacctagttcatggtgaacttaaga
gggtgttctttttaaaaacaatttccattgcactttgtcgttgccttaattaaatggtgaaatcatcagaaatatttattt
tcctatacttatacatttattaagcttgtttccatttttttatttgtgatttttaagtggatttaagataacctaaacat
tagagaggattttcatggttttgattcatgaaatcataatgttatacaaacctaactgaagtgttagagccttgaagatttt
tccccgaattacatatagtaactctacttgtatttaatactgaaagcatatttacttatttaagtgagacaaagtaaaat
ttagctgaatactttagatctatcatttcctttcctgttgtaagaacattacattgtgttgaaattaaagtggatatagaa
ggtaattagaataaactgccacatcatttttatagtaaagtggtaataacactattgctttctgtttttttaatcagaagga
gtatgggcttataatgatgttactgttccctgaagcatatttgaatgatacggtttatatttgcacagttgcccaggtaat
cattgtgatattaattgatcaatttgctatttatttgcgttttaaatcagtactagtatttgtgcttaaaaatttgcatat
gttttatcagatttaatttttaagtgtcagatactaaaacaaataaccttaactttattaaattataatttttttatcatgag
gtggtattcatttattcatatagttagaacaaaaaatatttaaaatattgaggtagaaacaaattagtctcttttaattaa
aagccagattacttgttagagtaacatttcccaaatgaggtaaaattgctgcgactgttaaacttaaggaaatttgatct
aggtgtggtatatacctttcttgtggggtgctaatgaaaacagggatggcaaaaatatttttgtttgtgagtgtatgcatttat
gctttttgacaacctaagaaacactcttacatctgagtatctttcatggactagctgtaggaaatctatataaaatagctta
gtatactgaaagtatgacatagttttacatatctagattgtggttgtgattatatataatactataaaatatgctaacgtgc
tgcttaataatactatttggattttttttaatactgaaaggtcacacagattgtgattatttgtgtagtgtccaagaactaa
ggcctaccatctgttactcaaatgtatgaaaaagttaagataatttagtgatataagtggttttgacaccactgtttttgga
ataatctaattatgattttttataaagactaatatcaaatttaaacgtttgcaaaaatgaaacctaatagttatactgttat
ttatatttttctattacaatacagatactggctgagaactaaagattgtgtaataaacgcctggccttcagtcatttggttt
ttttttccctcgattgtttggatagttaactggacatcatgttttaacttgagaaattaagttatacaagattttgatatt
ttaaactagttttcctaactggttgagatatataagaatttagtattacaggactcaatcagggaactgatttaataagaat
ttcttaaaaatttgtttaaatattttcaagttcttttcttcatcttctacaacttaattcttgtctgtatgcaaatgagct
tccccatttaaaatttgctgttgcattttaggccactatagaagttgtttctttaatttcactcacaagaatttggtctt
acaaaattgtgtaaatctttaaaattgtgtatttggcttaatattatagaatctgattgatttaatctaccttgtttcattt

FIG. 4 (Continued)

agtatgttgacatttcttgagaaatttgttatgccaaatgattaacataataatatttttaagtttagatatgattttgaat
ttacattttcaaatgcaactttgtgtctgtggcctttttttttttttttttttacgagaaacatcttgccaattttcagat
taatctgtgaggaaagtagattggtttactagactcagtttgtagactttggtgagaactgaattggaggctatgaaaaaaa
tacctttttgggcctttctgaatagacatatatacataaattatatctcttacattaagtgaggcacatatgtaggtgagatt
tttacctgaatattaaaagtttaaaagtcgttacctattctgtttacttaatagtatttaaagggtgtgagaggtgttatgt
gtttctgtcccttgtttttattcctatccctcccatctaactgttggtactcttatcttcccaggtattaaacttgtatgtt
ttaaaagcttatttacttgttgaaatggttaacttaattagtttttttcttgaagtttcagcctaaatattttctgtttttt
tatatgtcctttaaatatgaaaattctacagctaatcataattagtaattgtacttttttcccctattacaataactggtttc
ataataaaatggtatcccttcaataacaagcatttatagtagtttattaaaactaagggtgttatctattcaaaccaagcaa
tgcagacttactgttgactctgttaatatatttttaaaattgcatattactaaaatttaaaatatgattttgactagtatttt
ggtgtatgttattttagatatttttgattatgcactacttaagaatgaattgtcaagtatgattataaagttgatataatagt
taaccttcagtgggaataggaatcatttaatattgttagatatttgtattattagaacaatctcctatgattcttactaata
tagtaatgaatgacagacaatatgttggctttcatatttaaaaattcacatgcatttctagtttatgtttttcttcgactaa
aattctgcagcacttaggcaaagctatttttaccagttggaaaaaaagtaagtcatttccaaccaattttcctggcttgtag
tatagaataaagagacttgatttttattacattaaagccaaatataaaatgatgcaatctagcacacacttgtttggaacttt
tctcttttaaatattcagattaagaggacgttgaaaggtaaattttttttttttttttgagacggagtctagctctgtcaccc
aggctggagtgcactggcacgatttcggcttactgcaagctctgcctcccaggttcatgccattctcctgcctcagcctccc
gagtagctgggactacaggcgcctaccacggtggcgcccggctaatttttttgtatttttagtagagacggggtttcaccgtg
ttagccaggatggtctcgatctcctgacctcgtgatctgcctgcctcggcctcccaaagtgctgggattacaggtaaatttt
gattgttattagcaactataaaagtttttgcagttggcttattggaaaaagaaaacctccttgccggagacggagacgcattt
gtattagaactttgtttttctgagtaccttacctatagtaggtttcaaatattggtgaactagttgatggttaggtctgcata
attactgcgtatggaaattctggaaccctatttttttcaaaatgcagctaatgttgagagaatatgcactaaatattactaga
tctttgtttttcaagatgctgatatcccttaacatcttctgcactttacctgtttgaatatcttttttgctgtaaaaattag
tggccttatgtctttctgcataattatagagtagccaaaacctgttttaggttaatcacctctggcaaaataaatgataaaa
gcatagcttttgtaagcagaatgatattacagaagttaacttataaatctaagtgtattaaagacacttaggaaatttatga
taatgctgggtcagcattacagttttaactttttacagtttttcatatgctttttttgtgattttgctgtagaaaattaaca
gttggcatttggcttagttcaagtataatgctgttgacaagtatatctgacacgtcattgaactaataatatttttgaaagc
tgataggtaagttatatctatttttgtttcattcgtcattagtgatcggtcttagatgtttttagcgagagcaaaactgtaga
ggaatgtgtgtctgtgtgtgtatatgtgtgtgtgtgtgtgtgtattttaacagcaggagagttctgaaacaggaaaccagtc
ttatcatattcatccagagacctaggaagaaggtaattgtttggtatactcgttaaaaccagttggttgggcaacttaaatt
tttagaggatcacagatgtaggcttgagcagttgtagatagatgatttctttttttttctttctttttttctttttttttga
gatagagtctctctctgtcatccaggctggagtgcggtggcgcgatcttggcttactgcaacctctgcctcccaggttcagg
cgtttctcctgtctcagcctcctgagtagctgggattacaggcgcatgctgccatgcccggctaatttttttgtattttagta
gagacggggtttcaccgtgttcccaggctggtctcgaactcctgagctcaggcaatctacccacctcggcctcccaaagtg
ctgggattacaggcgtgagccaccgtgtctggcgatagattatttcataattaacacctgctatgaagaaaaattgattaaa
atagttgagaagtctagtacactctcagctaatatactaaattatactatggatttttagagtattgttaacattatcagtga
cttgatatcttcctgaggttctaatttgcttaactttaaataattggggttcagatcaccttgattgttcccttaaagatta
aattttgtaaaactgtgtgtaatttttcctgtatctggtttggatagctttaaaaatggttcttaagtttaatgagttcaact
gggaaaaaagttagttctatttttagatgttgtgtcactggaaattatgtttcccgttttgttatatgcacattattacaaag
ttgtaatcaatgtttttcatactgttctctggtctgtttttttcacaaataacttttttatttgtcgccaggtacttattttt
aaagctatagaggtaatatttcatcaggtgagggtaactaccatggtttgtttgctatactgtgttagggttattttcgttt
tttttttcttttataaactatagttgtgaatatgtttatgtagtttactttttggtttattagaatatattgctagagtggga
ttacaggattaaagagtgtacagtatttttagtttttttttttttttttttacaagttgcagatttgttgccaaatgaacgagttt
gtagtattgctaacaaggagaagaattactagcaagtcttgatgttacttttgaagagtgtgatgattgcatttaggaagat
atctaaacttctgtttcaaagcaaaaagtatgtgcaaatttcttactcatgacaaattcatataatataaaaacatgaaagt
tgtgaggtcaggttgtttggagaagtagaaaacttcagtagagtttatagataggcagtcttcctttctggtttggcactga
cagcagattaactagaaagtgttagaaggaacctaaaatttatactaaagtcaatttaagttaattaatataccagaattcc
ttctttttacaatttatttataaaaacacccatattgagttgccttgtaatgagacatttaaactaaatttaaataacagaatt

FIG. 4 (Continued)

catgcaccatctaataacaacccccttatttacaattatagagtcctttgcaattttatagatattttcatgtatcccatttg
gtccttgaaacaattaatgaagaagttacagcaagtggtattatcattattttacagaagaacaaaacaaaaatatatgtgg
cccagagattgagtgatttacctgaggttataggctttagattgcatagctggaagtagaaccttgttcttctatattaaat
gacaatattcattaagtacttagcacaggatttggtacctagtaaatatttaaatgttcctgtgttattcctgactattcct
tctttattcttaaaacgccatttttgagcactcttaatatttatagttcaaactttgtacctatgtaccttttctctttta
gaaaataagatttcaggctgcattaatttgatctgtacaggaatgattatatgttttacatattgggacaaattgctctttt
tttatatacctttaagctctagggtacatgtgcacaacatacagatttgttacatatgtatacatgtgccatgttagtgtgct
gcacccattaactcatcacttacattaggtatatctcctaatgctatccctccccccttcccataccccatgacaggccctg
gtgtgtgatgttccccaccctgtgtccaagtgttctcattgttcagttcccacctatgagtgagaacacgcggtgtttggtt
ttctgtccttgcgatagtttgctcagaatgatggtttctagcttcatccatgtccctacaaaggacatgaagctcatccttt
tttatggctgcatagtattccatggtgtctatgtgtcacattttcttaatccagtctatcattgatggacatttgggttggt
tccaagtctttgctattgtgaatagtgctgcagtaaacatacatgtgcatgtgtctttatagcagcatgatttatactcctt
tgggtatatacccagtaatgggattgctgggtcaaatggtatttctagttctagatcactgaggaattgccacactgacttg
aactagtttacagtcccaccaacagtgtaaaagtgttcctgtttctccacatcctctccagcacctgttgtttcctgacttt
ttaatgatcactattctaactggtgtgagatggtatctcattgtggttttgatttgcatttctctgatggccagtgatgatg
agcatttttttcatgtgtctgttcgctgcataaatgtattcttttgagtagtgtctgttcatatccttcgcccacttttgat
ggggttgtttgattttttcttggaagtttgtttaagttctttgtagattctggatattagccctttgtcagatgggtagatt
gtaaaagttttctcccattctctaggttgcctgttcactctcatggtagtttcttttgctgtgcagaagctctttaggacaa
attgttcttaaataatgaacagttggcacttttttcaactggaaaattcaaggaactgctctttctgctttctgctcaatatg
aatcttcaatttagaaatgagagtccatcattaacaattcaacatagcttattaataggaaaaaaaaacctagtaacaaatg
taaaatctttgattaaatgagaaagtcatagaagttcatcagatttgtatttaaagcatgatttcattagaaaagttgataa
taaggatttaactgtgacataattggaaaatacttgtttaaacttaaatttttgaaaagaaatgtaaatgtgatgtaactta
tgaatcagtggttgagtttcttttttgctcacaagaaccctaactgtgtgttacttgaaagcactgatggaaatcagggaaa
aagctccagaagttcctacgaaataaaattaaatgataaagtcctggtatctgctaacttgccttccattcctgttatcttt
tcttcttagtctgacttcattaattcttttcaccctggctactggttagctcagtgttttatgagccaggcagcttcagact
ttgcttttgatgctctttgttcattacctctaaagctgtattatcactttcattttatcattaatgtttcatgtatatgtta
tagtttcatattgttactgcaactttttacttagctataatttaaaaaatatctgtgatctgtggaaataattattctatggc
agaaaagtagttattgcattttactttataagttgtttaaggataagcatacctatatattaagcactacaaagaaactttt
acaatggctttattttagcaaaccatcatagttaaaataagatttagtgtacatgtcaggaacacagtcttatgaaataag
gtttagggagctattttttagttactatatcctacttgaaaattgtagttaaatttctagcatatacccctattaatttagatg
caagtacagatttgagataaggtagatacattatttggatgtcaactcggaagttgttcaagaaaagatattttgttattta
gatgtaacttggaacatatttctagtgtttcaagtcatgattgtatgcctagaacaggcaataaaaatttacttagctggta
aaacagccacattatttcaaatatagtttagttatattatggattaaattgattttgtggacagactttagaacttaattg
ctattaattacatttttttctttgggacggtatttgttctttggtgagaaaggattcttgtaacacctaaatcaagactgtcc
aaacatggcatatgcagtttaccagtcaaaacaaactaatcacttaagatctgtgtattttgttttatttgaattatacctc
aattaaaacaaatttagcatgtttacacaaaggtgggggaaactgtctaatatatctgagatctgttggagctggggtgac
catccaacttaggcaagatagctagtaccatgtatgcatttctttttaccttttcttattgtatatacagtaatcactgatatt
atgagaaaaagaactttttaataattcaggagatattttatcgctagtatatattgagtgcttattatgtgccttatatact
ttggactcatttaatcctcaacacaacaaccctatgtagttcatactagaattattcccatttaaagatggggaaagtgatg
tttagagaggctaagtgacttgcccatggccaagtattagaactgggatttgaacacaggtagcctgattcctaaataaat
gaccactaacattaaaaagacataaacatagaggtgtttgttgcaatgttagtcataatacctaaaaattgtgaactagtta
aatgtccaatagtagtaaaatggttcattaaccatggtacacccatcaatataatgttatattgtcatttaaaattgtattc
ccaagtttcgtatcaggaaaatataataaatttttgaaaaatgtaatgggatatattgtatttataatacagtaatcactat
gtaaccaacatttttatttccatcaaaaattagttataaagaaatagaaatctaagaagtttaatagatattaccattgaac
actagatttgtattagtatctttatatttatctctctcatttcctatattggccatgtttactttaaaatagtaaaagtc
ataagctctatttttaaaaataaatgttagtttattaacccaagaataatagctaactataaattcatatttgataaaataaa
aagatgacattcatcataagggatacatacctgtgctagcatatggcatttttaaaatcacatgagtaatttgtaatcatca
tagaaatattagaaaatacaaataagcaaacacatactgaaaatttagtgttcccaaatctaaaacagagacactgttttt

FIG. 4 (Continued)

tctttgggattgtatttagatatgttcttaagttataatcaagtaaatacttaaaggcaaattgatacattaaggattt
caaagagtaaaactttttgttaagctttgatgttctttagaaagtttagattattccacaagtcactgtcgttgaaagaaaa
gtagttacagtggggtcttatgggataaggcattaccatttgttcagttgagagacagctatcactatgttttaagcattgt
tcatatattagctcatttaatcctcatagcaacccttatatgataggtacctttattagccccattctgcttaggaagcaaca
gaaagagtatgtatttgcctaaggttgcacaataagttaagctggggttccaattctagcaagttggttctagagtgtatg
ttatttaaccattatgccgtagtgcctgcaagtagatctctagatgtcagaaatactcatcttcctctggttacctggttgtt
ataaatctttatgcttaatacttatgtcattatatgtaaatttcgtattaaacactcaacttattcagaagaatatcaggta
agtgtaggttaaggctgttttctatcagaaatcattatatgtatatatattcctcagttcttatgttgtttagttttttctaa
aatgtcaaattttataatatatggagaagtataaatgtatattagaaagattttgttttatttgtgtaatttgtggcataaga
aatatttgcctcaagatttggtgcttgtttaggtagttgctggcattactttttggaaatgtcagtaaattttcatactgtct
tggaatttttttcaatttttacattttattagtaaatgtaattacaggttagtaaatcacttatttgaacctgtttcctttga
aagttttatattttttatttggaaatagaaaaaccttaatttcctctcgttgggcagtatggtgtcaaaagctgggctttgg
agcttcgtatataatctgggttcaaattataacttactagttactaacttgggcaaattacccagtctttttgactctcaat
ttctttgtctatgaaatgtaatactatttaggattgttaggcttaaatgagaatatatttggcatactgtctggtacatgat
acttaacaggtactagttgtctacatctttctaacttaggatggatgccgatgtcttgggtaacatctcaaactttatcagt
aaggaaggtgagaatctgaagaaaatgaaaccttaaaaagattgaattcctggactccatttaaaggagtaaatagctcacg
aacaagacttgctgctctgcaaagtcttccatgttgatcctggtctttgactccttatctgtctgattaaattgaattcgct
gccgtggcatccttaaagctggaccttactttgtcagtcctgccttctccatgttgctttgtgtgtaagcttcactggactg
tttgctttttgctgattatttatgtatttccatatgtctactttagcctttgcttggaatgttctaactgctcttgtttct
tcctctgtttactggtttctgacttaactcttaaggattatctaatatattacctacttggtgaaggtttatctgtgtcccc
acagaattaatccttccctctttaactcttaagctatcttatttttttatctaatcgggtctttggcacaattataggtctgt
gtgtctgtcttccctaatagaataggaaagccttgaggacagtagtctttgcttacttagccttatattctcagtgcccctt
gtgcaaaacgttcaatatatgtttgaatgattatgtgaatgaaggaggggccagctgaatttactttaatgattatgtaac
acccatttatgtatagttatagacttgtctgaaatgagttaaatcctttgcaacgtttgctgctatgctttgaatgtctctt
acaaaactcatgttgaaatttaattgccattgtaatggtattaagagatggaacctttaagaggtgattagataatggtatc
tctatccttatgaatggattaatgctgtttgaatggtagtggatgagttatcttgggagtttggcctcctccgtctcacatg
cttccttaccttctgccatgtggtaactcaacacaaagatccttgccagatgctgatgccatgctcttggacttcccagtct
ccagaacgtgagccaaatacatttctgttcattctaaactacctgttttgtggtattctagtaaagcaacataaaatttac
taagaaaactggtaccaagagtgtgattgttgccataacaaatacctgaaaatgttcaaatggcttgggttctggctagaga
aggatggaagagtttggatgaacaggctagaaaaagcctgtattgctgagaatagagcattaaggacaattctgatgaggat
tcagaagaagagagctgtagggaaaatctggaacttcttagagagttgtcatcagttggtagaactataagtggtaaaggtc
tttctgatgatatctcagaaatgaagaacaagatactggacactggagtaaaggccatccttgttaaatagttgcaaagaac
ttggcgaaattatgttcatatcctaagactttatggaatgcagaatttaagagtgatgaactaggatatgctgcagaagaaa
taactcagcagcagagcatttaggttactggatggctactttttaaccacttaaactaagctgggggaagggaatgacttgaa
gacagaatttataattaaaagagaggcagaatggaaatacttggaaaatttgcagcctggccatagtaaagaatgcaaaagg
tatgtttaggagagcaaaccaagggtgtggtccaggaaccatttgctgaagagattaatattcctagaggagacccaagggc
tatttatcaagacagtggaaaaagacccagaggcatttttggagatctttgaggctgcctgccccatcacaggcccagagct
ctaggagggcagaatggtttgtggctcaggtggtccttcacaagcttgctgcccagggctacctcagctccccatatttcaa
cccagtgggccttggctgtcctaggtctggttcagaggggcccaggtgtggcttaggctactgctgagtactcaaatggtaa
accttggcagcgtctatatggtgctaattctgcaggctcacaggatgaaagagctgtgggagacatggctaccaccaccagg
atttcaaaggatgatggggatagtctgggagagacttgccacaggcttggagcctctgaagggtggaaatgtgggttggagt
cactacagagagtccctactagggcattgcataatggagccatggcagcaggccccaccaccaaagcttcagaactgtagagc
tacaagtatacagtgccagcctgggagaacttcaggcttgagaccctaacctgtgaaagctgcatgggctaagtacagcaaa
gccatggaggtggggcttcccagggtctattgggatgaaacgaatgtatttttgtaggtgagaaggacatgagttttgaggcc
caggggcagaatgctatggtttggttgtttccttcaaaactcatgttgaaacttcattgccatgtggcattattatgaggtg
gaacctttcagaagtggttacattataagggctttgccttcattaatggattaatgccattattgcaggtgtgggttagtta
tctctggagtttggccccctttttctctatcatgtgctcatgccctctttttgccatgtgatgccttctaccatgttatgatg
catccagaagactctcaccacatgcagcccctttgatcttagacttctcagcttctagaactgtgagtgaaataaacttcttt

FIG. 4 (Continued)

tctttataaattaccccgtctgtggtattgtatagcagcagaaatagacatcagcctgaagttcccccaggctggcattaa
atactaattattaattagtatttatagtgcaaggataaattcaagtttagccctggttagaatgaccacatttcaagggagg
ggctttgtacttctgtgcatatctgtaaggataaaaatcttaatactattctcactgaaattaatggtttaggttaggtaag
gttgttagtgctaataattatttctttaataaaatattcttagttgcgttgttcaaaaaacatagatgatttgaatttata
tttttggccaaaatatatttataattttgagtaggaattccagagtattggtagctataaccactttgggttccctgccat
tgcttctggtgcctcatttttctgacgtcttccatttcttacatttgtcttctaaggtggagttaagattactcagttaa
gattatttcactttaggcctctgctgtcttctgcttttttttttaaaatgaatggatataatatcccaatacatttgataa
ttgaacaacagctacattttaagtgaggctactttcttctaattttttaaatttatttttctcagtttttaaaaaaaatgt
cagattggctaagagttggggcagctttcttatgtgagagtagtagatgacagcaaatatttgtgatgttaaaatgataatc
ctaatagtttttctttagaatctttataataaaaacccttgaggctgagggtgaatttgtatgttcctaaagtgacaaaaa
atgttcttggggcatagtaatttaaatcttagatgcttttattagtataatttttggtagaaatttggcattaaaaaatgc
atacagagctttttctacatacagggcaagacagcattttgtcatggcaattagtaaatagataattataaaacatctaatt
ttaagcaatttgttacagaaacgatacaggtacattgtggcaaaatagaagatacaaaacaagcaaatatgagaaaaata
tacatgccaccacctatatatgactttagtactttataatctttgtctatatatgtctatatggatatatacgtattctt
tttatccaaatggtattacattgtacattctgtttgaaacctgcctttttagtcatttacatctactttccatctcagt
aactttcatcttgtgtaatgcccggatcacattaaaatgtttccaattagctcaaaaatgtcctttatggctggtttggct
aaaacagtatccaggccagcattgcacctatgaaattggctgttaggaatcttgtatctttaaaaatcaagggcagcaaccc
atcctcccgcttcccccacctcccaccaccccccccaccttttttttttcttaaagatactggcttgttgaagagagaatggg
tcatgtcctacaaactgtctgaatttgtccagtttgctgtctcatagtgtcatttagcttgttttatcctatgtatttcctg
caaattaaaatttgtatctgaatccttggtggatttgagttgaagatccttaaccatcatagatgatgctgtgtcctttata
ttgcatgtcagaagttacatgatctttacttgattcatgatgaggagatggccactgaaattggacagtgacagtcttttct
gcccattgttcaattatattcgtctctttacattagaaagtatttgggtagtagtatttggtgctgtaagaaagttcatt
ttctcatcaacccactcacctattggtttaacacccatttgttgatctttgagtatatcagtaatttcatcagggtttgcaaaa
taagactttaaattctattgtttttacattattaattgatgtttttttgataaggtagaacttgtgaaatgggactatttgttt
gtctttaaatacagtctctataggaaagacaaaataaatacttaaatctcactctttaccatttttcaaagtgaagaactat
tccgttaacccacctcaaaagatgatcaaataaaaagggtattttagttgtttcaactttttttttttttttgagatggggtc
ttactctgttgcccaggctggtgtgctgtggtgcaatcatggtacaccgaagcctcagtctccctgggctcagatgattctc
ccacctcagcctgggactaaaggtgtacaccaccatggccagccaatttttttgtatttttttgtagagatggggtttgcca
tattgcccagcctagcctcaaactcctgggctgaaggaatccacccatctcagcctcccaaagtgctaggattacagacgtg
accaacaatatccggccttaactttttcttttgagtgtctttatagactcaaggactttatttaattcagggtgttagta
ccatttaaatgttttctttgatgctcagattatcacagctagtcatttggacctttatacccacctcctatgtccatttgata
taggccattaatctctataagccttcctccttctcttggaatgaaaaggtatcctaggctcacctgtaccttccctactcca
gacctggcattaagtctttttccaaggagtttggtacctttttagtttattatgatattagagatgaaaatctgtgttctagg
aatgtttattactgctagagtgatgttgcttttaggccatttcagagaaaagacctagaaaacagattttttacaaacatgaa
ttcatactgatatttttagtttttttacatgatttcttgatttttacaatattatctgctttcttaacttaaaattatgaacct
taaagtcattagcataacttctttgcttatttctacaacataaagaaaatagtcctggtgcggtggctcacactgtaatccc
agcactttgggagattgaggcaggtggattgcttgagctcaggagttcaagaccaacctgggcaacatgatgaaaccttgtc
tttacaaaaaattagctgggcatggtggcatgtgcttgtattcccagctactcaggaggctgaggtgggaggatcacctgag
cccaggaggtcaaggctctagtgagccatgatcatgccaccacactccagcctgggtgacaaagtgagaccctgtttcaggg
ggaaaaaaaagataaaatagtttgaggaggctggatgtagtggctcatgcatgtcatcctggcactttgggaggtcaaggtg
ggaggatggcttgagcccaggagtttgagaccagcctgtgccacatcatgagacctggtctctatttaaaaaaaaaaaaaaa
agaaaatagtttgaggatatcaataatgatattactagaatcagtaaaactaccaaaagaagtttaaagtttcttcctagtg
tttttttgttcttagaatacttcctacccaagaagtgcagtaaaagtgcagtgtcccaaatagcccttgtaacaaaaccttct
ctttctcctgggtgccaatttgacatttaatcagtttttgtttctagcagtgttcaatttattagattataagtcttttttt
ctttatattattctaagatcaaaaatatataaagatatacacaggagtcctgctgctacctgttcttgctatgcttttcccc
ttttcttcccttttctctgtgaagcagccatttttattagtttcttgtttatcactcatgcatgcatatgtttattgaggatg
ttgacattcaagcaaatatatgggttaacattctttttgtcatccctatacgaaagatatacccagtatactctattgggtg
ggtttttttccttaaaatattcagtagatctctccagttagcacatagttatcttatagatagaacatatacatataacctt

FIG. 4 (Continued)

ttcttaaactatgctattaaaataatagctttcagtaacttgataattcttttttggattgaaaatactactgaaatcaactc
aatcatgtgaaagctgcagaaagaaaaagacctagaaaaagggcattggattaggtcaactttgaattttatttggaagata
aatgagtccagaagtgagtgggcagagattattggagttggtcttgaaatgaggcgttaggcagattgactgggctggtgtg
aaaggtctgtcagaaaatcatgagattagattgaggtacctcaaaaaatgagagctggtatgatgagtgggtaagaatcata
aaagcgtagagtgttgatgatttttatagtttataaatggttcttgtgtgtagagtttttgttttttatgctagctatagtctg
taacataattcactataatgggcatgctaaatatccatgacagttgacccttgaacaacacagagggtagggcgcctaccc
ctgtgcagttgaaaattcacatgtaacttttgactccccaaaacttaatatttagcctatacttgactagaagtcttactga
tgacataatgttcgttaatacatattttatatatgtgtcagatagcatatttgtataataaagtaagctgcaggaaaaatat
taaaatcataaagaagagaaaatatacttactattcattaagtggaagtggatcctcataaaggtcttcatcctcactgcct
tcactttgagtaggccgaggagtaggagagagaggaaaggtcagacttgctgtctcatgggtggcagaggtagaagaaggtc
cacatacaagtggtccgacacagctcaaaccggttttgttcattggccaactgtagtttgattgaaagtaataataaatgaa
gtttctgcctcagttcagtattatcaagtcatagatagcaagggctggaagaaaccttagtagtaatctctttgagtctaat
tatcatgtagaataggaaattgcggtctagaaaggttaagtgacttgtccaaattacacaactagttagagacatagccagc
tcttaaatctgacttccagatttttcactgtgtcttctttttttctgtaacgtgttgccttttttagccatgaaaaattagaag
ttgaactcttgtcttttcaggcaggtgtcaattttggggttttgttttgatttttggtttttgacataaagtactttagttc
tgtgatgtataaaccgtgagtttctgtttttctcatatacctgaatactgtccatgtggaagttacctttatctttaccag
tattaacccataaatggttatacataaatacattgaccacctttattactccagctatagtggggaaactttctttttcat
aactagctaatgttttaaaaagtattcttttagtttgattgctgcatatttcagatatttctttccttaactaaagtactca
gatatttatccaaacattattgctatgggatttcctgcagaaagacttgaaggcgtatacaggaacaatattgatgatgtag
taaggtaagaatgctttgatttttctatttcaaatattgatgtttatattcatgttgtgtttcatttagaaaagatttctaa
gccacagaaaaagatactttgtgatgtaaactattattgtagtgctctataatcatttttttggcttaccgtacctaatggac
ttcaggggggatacagttcatttgataagaactgaccttatacattacataatcaggtacttatgtgatatcatttcctggac
tccataaaatgctggtcaccaggtttaatacctggattccattacagtgtgatttttgtcttatttcatagttggggattag
gcttaaaatcctagagtggatttattcagttaaatttattcacactaagatgtagatgactaatactgtatattttttatgta
gaccaaatttttaaggtaccactgtgcatatgtataccaactacctgaagaagtatttggttggtacaagagatatagaaagg
aatcgctggggtgtaccaaggctaatcagttttataatttttgcataattttctaactgcgattatcatttagtttagaacaat
ttatttctcaaggcccatgtaaatattatttttaaaatatacagtcttaagaattcatggcatattttatgaaaggaggaat
tcatgtctgatgtgcaaatagtcttaacatattttctaatttcagagcaaaaatatatatgtatgaataaattaactgtaa
ttgtcagtaggaaccttaagaattcgtgggtattttatgaaaggaattcatgtctgatgtgcaaatagtcttaacatattt
gctaatttcagagcaaaaatatatgtgtattaataaatcaactgtaaattgtcagtaagaaccttaatggcttttaaaagtta
aaatttcaggtcaagcattgtggtgtgctcctgtagtcccagctacttgggaggctgaggtgggaggatcacttggcttgaa
cccccaggtagagggtagaggccagtctgggtaacacagcgagaacccatctcttaaaaaaaaaagtttaagttgtggattat
ttcctttacactctttcattagtatctttcctggagactttcaatttaaatacttggtgcttatgacaattagatgttaaaa
tggatgggaaagtactttgtaacttataaagcattatgcagatgtagactcctttttataatagttgtgtaagtatataagac
aacctacattcttcatgagctagccataagttttagcaacttgctttgaaccacggtagatttacaatttttctgtagtattg
agttgtgttcatttagaatttttgtaatatttatattgaaaatcaaattttttgtacctacaaaaactacaaaaaatcccccta
gtttttatagtttctattaaaattatagctggtacatagggatgccagaaggactgtttaagaagctgaaaatagagaaatg
aatttatcttctcatagttaggcagggcacagtagaaggatgcttaacattgcaagctgatgggaacagcaggttgatatag
cttgtgataacacttctaaagaaaaagcaatgagccatagaaaaaagaaaaagatacattttgaattaaggaagatggtgaa
tctgggaagtgagcagtacagtcaccagacgtgtatcctctccctatggtacagaagtgtttattgggtctcttttatggcctg
catgatatatcccacaagatgacctacttcacattatttttaattctgtattcaactaagcactaattcaacccagccagatt
agtactcatacccaaaaaagagtgaatactctgaatagagggcaggtttttctgattatggtgagaatatctttgtggtaaatt
aatctggtgtgctagtttttacgttggtctcttctcagtgtcgttagtcactgaggctgattgatcatctttttaggttactg
ataaagttcctgtacagctgattttcagaccttagattgcaataacttcaccaagaaaatacttcattgggaagcattttgg
tccttccatttgattcataactcttacctttatgcctctgaaggaaaagatttatacattcagcttgtaattagtaatcaag
actgaggtttagtctatctagcttcacaatctatctagtttgttttgtctagccatatgatttcttcaaatatgccatttct
taaaaaaaaatgttttatgtatcccgattaatatttagccagtggttcttttagccgatggatcttgtcacctcttatgata
ctattaatagcatgtcaacatgaagaattatctgctgaatataatagctatgctgtccttgtttccttttgtctcattcttt

FIG. 4 (Continued)

tttgattggggataattggccaataaagctttgatagcctctattgcccaggcccctcctcttcttttatgagagaaagga
tgaacagtgaccagaaataaaggtattgtttttttctatcaactaaaatggaaataaataattcctaagtaatttgcctgtt
aggattaaagtctccaagagaatggctgtgcctagtacctaagtgattaatttccttgattggttcacattatattgaggat
attagtaatcagtagtgattcctttttggttcaaagatgatagtgtcacagtgaaaaatgtttttaaaatttttgtatact
taatttttctgttaacgaaagtattttcagttggattttgtttgccctctctattagaatgcccaaagaatatttaaaatt
ttcctttctcttatactgcatatttttcctgtgatttttccccaaacggaaatactctgcagagattagactttgttatt
gttgtactacatcattgctttgactaaaataaactcagattgcaaatacctttcaagcttacattgctcagtattttttttt
tttttttttgagacggagtctcactcttgtcgcccaggctggagtgcagtggtgccatctcagctcactgcaacctctgc
ctcctgggttcaagcgattctcctgcctcagcctgcggagcagctgggattatagatgcccgccccacgcccagctgattt
ttgtatttgtagtagagatggggttttaccttgttggccagtctggtctcaaactcctgacctcgggtgatccatctgtctc
ggcctctggaattacaggtgtgagccgccacgcctggctaaattgatcagtattatttaactttgagggatatgatttgtta
tggaatgcgaagttttatacttgaggtactcagagtcctttgagacaaatatttaacttctcctttgaggttacccgccta
cgatttgggaattaatgtaaaaaataagccaaaagaaagtgagggaaaagtgaacccagctgtaatttttttactcttttta
ttgttgttgttattgttgctgtttttttactatcttgattgcaacagtttggcttatatatatagcatttggaattgacagta
agaaagccacatctcatagaagctaactattcccaaattgttttttctttcttttcctcttactactgctgttttcctcctt
tcttgctgctaagctcttgtcctgacatgctggtaatatgaaacagtgttttattcagataattgattattctgtaatatgt
atgttaatctttttttattacacttaagtaatagggtacatatgcacaacttacagattcgttacatatgtatacatgtgcc
gtgttggtttgctgcacccattaactcgtcatttacattaggtatttctcctaatgttatccctctcccaacccccaccc
aggacaggccccggtgtgtgatgttccccgccctgtgtccaagtgttctcgttgttcagttgccacctgtgagtgagaacat
gcggtgtttggttttctgtccttgcgatagtttgctcagaatgatggtttccagcttcatctatgtccctacaaaggacgtg
aagctcatcctttttttatggctgcatactactccgtggtgtatatgtgccacattttcttaatccagtcagtcattgatgga
catttgggttggttctaattctttgctattgtgaatagtgctgcagtaaacatacgtatgcatgtgtctttatagtagcatg
atttataatcctttggatatatacccagtaatggaattgctgggtcaaatggtatttctagttctagatccctgaggaattg
ccacactgtcttccacaatggttgaactagtttacagtcccaccaacagtgtaaaaatgttcctgtttcctccacatcctctc
cagcacctgttgtttcctgactttttaatgatcgccattctaactggtgtgagatggtatctcattgtggttttgatttgca
tttctctgatggccagtgatgatgagcatttttttcatgtgtctgttggctgcataaatgtctatcaaatgtcttctttttggaa
agtgtctgttcatatcctttgcccactttttgatggggttgtttgatttttttcctgtaaatttgtttaagttctttgtaga
ttctggatattagcccatttgtcagatgggtagattgcagaaattttctttcccattctataggttgcctgtccactctgatggt
agttttcttttgctgtgcagaagctctttagtttaattagatcccatttgactatttttggcttttgttgccattgcttttggt
gttttagtcatgaagtccttgcccatgcctatgtcctgaatggtattgcctaggttttgcttctagggttttttatggttttag
gtctacatttaagtctttaacatttaagtctttaatccatcttgaattaatttttgtataaggtgtaaggaaatgatccaat
ttcagctttctacatatgactagccagttttcccagcaccatttattaactagggaacccttcccccatttcctgttttttgt
caggtttgtcaaagatcagatggttgtagatgtgtcatgttatttctgagggctctgttctgttccattggtctatatctct
gttttggtaccagtaccatgctgttttggttactgtagccttgtagtatagtttgaagtcaggtagtgtgatgcctccagct
ttttctttctgcttaggattgtcttggcagtgcgggctctttttttggctccatatgaactttaaagtagtttttttccaatt
ctgtgaagaaatttattggtagcttgatggggatggcattgtttctataaattaccttgggcagtgtggccatttttcacgat
attgattcttcctacccatgagcatggaatgttcttccatttgtttgtgtcatctttttatttcgttgagcagtggtttgtag
ttcttgaacaggtccttcacatcccttgtaagttggattcctaggtattttattctctttgtagcagttgtgagtgggagtt
cactcatgatttggctctctgtctgtctgttattggtgtataagaatgcttgtgatttttgcacattgatttgtatcctga
gactttgctgaagttgcttatcagctgaaggagatttttgggctgagacagtggggctttctaaatatacaatcatgtcatct
gcaaacagggacaatttgacttcctctttttcctaattgaatacccttttatttctttctcttgcctgattgccctggccagaa
cttccaacactgtgttgaataggagtggtgagagagggcgtccctgtcttgtgccagtttttcaaagggaatgcttccagttt
ttgcccattcagtatgatactggctgtgggtttgtcataaatagctcttattatttttgagatacgttccatcaatacctaat
ttattgagagtttttagcatgaagggctgttgaatttttgtcaaaggcctttttctgcatctattgagataatcatgtggtttt
ttgtctttggttctctttatgtgatggattatgtttattgatttgcgtatgttgaaccagccttgcatcacagggatgaagc
caacttgatcttggtggataagctttttgatgtgctgctggattcggtttgccaatatttttattgaggatttttgcattgat
gttcatcaggggtgttggtctaaaattctcttttttttgttgtgtctctgccaggctttggtatcgggatggtgctggcctcc
taaaatgagttagggaggattccctctttttctatgaattggaatagtttcagaaggaatggtaccagctcgtcttttttacc

FIG. 4 (Continued)

tctggtagaattcggctgtgaatctgtctggtcctggactttttcggttggtaggctattaattattgcctcaatttcaga
gcctgttactggtctattcagggattcaacttcttcctggtttagtcttgggagggtgtatatgtccaggaatttatccatt
tctttctagattttctagtttatttgcatagaggtgtttatagtattctctgatggtagtttgtatttctgtgggatcagtgg
tgatatccccttatcatttttattgcatctatttgattcttctctcttttcttccttattagtcttgctagcagtctatc
aatttttgtttttttaaaaaaaccagctcctggattcattgatttttttttgaagggtttttttgtgtcctatctccttcaatt
ctgctctgatcttagttatttcttgccttctgctagcttttgaatttgtttgctcttgcatctctagtttgttttaattgtga
tattagggtgttgatttttagatctttcctgctttctcttgtgggcatttagtgctataaatttccctgtatacactgcttta
aatgtgtcccagagattctggtacgttgtgtctttgttctcattggtttcaaagaacatctttatttctgccttcattttgt
tatttacccagtagtcattcaggagcaggttgatcagtttccatgtagttgtgcagttttgagtgagtttcttaatcctgag
ttctaatttgattttactgtggtctgagagacagtttgttgtgatttttatttctttacatttgctgaggagtgagtgcttt
acttccaactatgtggtcaattttggaataagtgtgatgtggtgctgataagaatgtatattctgttgatttgggatggaga
gttctgtagatgtctattaggtctgcttggtgcagagctgagttcaaatcctggatatccttgttaaccttctgtctcgttg
atctgtctcatattgacagtggggtgttaaaatctcccgatattaactgtgtgggagtctaagtctctttgtaggtcactca
ggacttgctttatgaatctaggtgctcctgtattgggtgtatatatatttaggatagttagctcttcttgttgaattgatcc
ctttaccattatgtaatgcccttctttgtctctttgatctttgttggtttacagtttgttttattagagactaggattgca
acccctgctttttcttgctttccatttgcttggtagatcttcctccatcccttttatttgagcctgtgtgtgtgtctgcatg
tgagatacatctcctgaatacagcacactgatgggtcttgactctttatccaatttgccagtctttgtctttttaattgggc
atttacccatttacatttaaggttaatattgttatgtgtgaatttgatcctgtcattgtgatgttagctggttattttgcc
cattagttgatgtagtttcttcctagcatcaatggtctttacaatttggcatgtttttgcagtggctgataccagttgttcc
tttccatgtttagtgcttccttcaggagctcttgtaaggcaggcctggtagtgacaaaatctctcagcatttgcttgtctgt
aaaggtttttatttctccttcccttatgaagcttagtttggctggatatgaaattctgggttgaaaattcttttctttaaga
atgtagactattggcccccactctcttctggcttgtagagtttcagcggagagatctgctgttagtctgatgggcttccctt
tgtgggtaacccgacctttctctctggctgcccttttacatttttttcctgcatttccaccttggtgaatctaacaattatgtg
tcttggggttgctcttctctaggagtatctttgtggtggtctctgtattccctgaatttgaatgttggcgtgccttgctatg
ttggggaagttctcctggataatatcctgaagagtgttttccagcttggttccattctccccgtcactgtcaagtacaccaa
tcaaacgtagatttggtcttttcaccatagtcccatatttcttggaggctttgttcatttctttttactgtttttttctctcaa
cttctcttcttgcttcatttcattcatttgatctgcaattactgatacccttttcttccacttgatcgaatcggctgctgaag
cttgtgcatgcgtcatgtagttctcgagccatgattttcagctccatcaggtcatttatggtcttctgtacactgtttattc
tagttagccatttgtctaatctttttttcaagatttttagcttccttgcgatgggtttgaacatccttcctttagctggagaa
gtttgttactactgaccttctgaagcctacttctgtcaactcgtcaaagtcattcttcatccagctttgttccattgctggt
gaggagctgtgatcctttggaggagaagaggcactctgggttttagaattttcagcttttctgctctgttttctccccatct
ttgtggttttatctacctttggtctttgattatggtgacctacagatggggtttttggtgtggatgtccttttttgttaatgtt
gatgctattcctttctgtttgttagtttttccttctaacagtcaggtccctcagctgtaggtctgttggagtttgctggaggt
ccactccagacactgtctggatatcaccagtggaggctgcagaacagcaaatattgcagaacagcaaatattgctgccggag
ccttcctctggaagcttcgtcttgggggcaccggctgtatgaggtgtcagtcggcccctactgggaggtgtctcccagtta
ggctacaaggggggtcagggacccacttgaggaggcagtctgtccgttctcagagctcaaacactgtgctggtagaactactg
ctctcttcagagctgtcagagagggatgtttaagtctgaggaagtttctgctgcctttttgttcagctatgccctgcctccag
aggtggagtctacagaggcaggcaggcctccttgagctgtggtgggctccacccagttggagcttcccaaccactttaccta
ctcaagcctcagcaatgatggacgcccctcccccagccaggctgctgccttgaagttcaatttggaactgctacgctagcag
tgagcaaggctctgtgggcgtaggacctgctgagccaggcacgggatataatctcctgttgtgccatttgctaagaccgttg
gaaaagcgcagtatttgggtggcagtgtcccaatttcccggtatagtgtgtcacagcttcccttggcttggaaagggacat
ccccgacccccttgtgcttcctgggtgaggcaatgccccgccctgcttcagctcaccctccgtgggctgcaccccactttcca
accagtcccagtgagaagaaccaggtacctcagttggaaatgcagaaatcacctgtcttccgcgtggatcatgctgggagct
gcagacaggagctgttcctatttgaccatcttggaatgccaccttttttttttttttttttttttttaaggcagtttcttgct
ctgtcacccaggctggggtgcagaggcatgatcacggctcactgcaacctctgcctttctgggctcaagtgatcctcccacct
cagcctcccaagttgctgggaccacagccacgcatcaccaggcctggctaatttttgtgtttttttgtagagatagggtttcg
ctgtgtttcccaggctggtctcaaactcctgcgctcaagcgatccgcctgcctcagcctcccaaagtgctgggattacaggc
atgagccactgcacccggccaatatgtatgttaatctcatccctcaagctgatactgaagtttttcaatttatgttatttgg

FIG. 4 (Continued)

tgtaaatctaggcagtctttaacaaaattggtgcttcatgtgtttaagaggcataacttaagaattgtttgtttcttataa
tcaggagaatggaggtttaatagaggtgaactgtctttctcactgcagaacctttaatatgccactatgcattgtaaatctc
ccaagagtgagattctagtatgatgcttttcttttccttttctgttctttcctttccctctacctccttttttctttcttt
gttggtggcatgagtcctatattataaggaaatgcttttagagtacagtcttctgatatatagtgatttttgaaaaagattt
atttattgtcttgttcactgtgagcttttttccccatgtataagcagctgtgtaatagattcaagagcacccccctcgcccct
ttttttttgagacagagtctcgctcggtcactcaggctggagtacggtggtgctgtgatcatggttcacctcgacttctggg
ctccagcgatcctcccacctcatcctctcaagtagctgggaccacaggcgtgtgtcaccgtacatggctaatttttctattt
ttagtagaggcagagtttcgccatgttttccaggctggtctcgaactcctgaactcaagcagtccacctgtctcagcctccc
aaagtgctgggattacaggcgtgagcctccactcccagtctcaaatattcttttgaaatatttgaaatatgttgatctctca
gtctttcaaccttagttgtatgttgatttttcaataaaaaggaagtatttgttgccctaacatcagtattggctattcagttt
aaaaaaggagttaaagagatgttatttataggcaggcttcaaaagaggaaagaatgatcagtttcattctctgtttctagca
tattctgactccttctctcatattacctcgttttttccccacatttttttctttaataaagtgaaattcacataacagctaacca
ttttaaccacggaaagtgtacattccgtggcatttattaccttcacagtgttacctctacctttatcaagtttcaaaacatt
ttatcaccccaaaagaaagccctgttcttattgggtgcctcttgcttttttttttttttttttttttaaatcttgagacggg
gtcttggtttgtttcccaggttgtagtgcaatggggcgatctcatctcattgcaacctctgcctcccgagttcaagcaattc
tcctgcctcagcctcccgtagctgggactacaggcacgcgccacatgcctggctaatttttgtatttttagtagaaacgtgg
tttcaccatgttggccaggctagccttgaactcctgaccttaggtaatctgcctgccttggcctcccaaagtgctgggatta
taggcgtgagccaccgttctggccacctcctacttctttcattagtcttaattccttagtggatttgacagtgtttatatta
tctacaccaatgcatttttttgtatgttaataataggagatatttattgggcatttatttacatacttatttgcatgtgtaa
ctgttgtatagccagtttatgtatataatcttactaaatctctacagtaaatctatccccatttcatagatggtttaaaaga
agttaacttccccaagcattactttagtaagtagtgagactgaaggttgagttctggtctgtcagattccgaagttgtttc
cttaggaaccatattatcttgtgtacaactcttgggctaatcttgttaatattctttatttgacctcacactgttgattcat
accatgtttcaaattgaaatacattacctatatttaaaaattgagacctcacataaaaagctatatttctagctgcttttga
aatttcgaaggatcttccaacacttggctgacattcctgcgtgacaaaatcagctggagctgtgtaatgtccgacctgtct
ctgtcaatgaacagattattcattgtcatttctcatctgtttttgagattgtaactttgattctgtataactcatagaatta
gtagttagacctatatatgttagttattacattatttgtatatgtacagactgctttagacaatattgtagtgttatatgtt
aattttatcaattaaaatgtgctataggatcattgtagagatcttgtctctaattaacaggattcataaagagaaaacaaag
gagagaaacatccagattgaaaagacctacatagtgccaagcacaataaagaaaccctatactaggcaaattattatgaa
tttgttttaggacaccagaaataaagataatatctaaaaactttttagaatcgcctaggagggattaggaatatgaatagca
tctaacttgttggcagtagaattgaaggtagaaggtggtaaaacatcaccttgaaagttctgcattcagcctagaattctgt
atccagttaaaccatcaatcaagtgtgaaagtaggggggaaaaactcaaggactaaaaaaatgtgctcatgaagaacatttt
tttggacattacccagaagatgtggttcaacaaaacaagggaataaaccaagaaaggaaataaaagagcttcagtaaacaga
gaatcccactcagaagcaacaaagaagaaagtcccaggatgccagctgtgacacaagctgaaaagttaccagttttgcttgg
agcaggagattagaacttccgggaaaataatcaaattgatagatggatgttgaaatatttggagaaaaatgtaatggattct
tgcaaaactgagcaaattagaaaaaggaaacaattattagcattggtggtttgagttaacccaaaattgtgatgttgctatt
ttaggggaattaagataagtgaaacacgtatggaatactgctagttttgtaagtctccttaccatggcaggacatctgtag
ttaataaatctgtaagaagcagtattaagaataatatttaaaatacctaattaaataggaggaaaaagaatccgagtagtt
gagggtgattgcatctggggagaagcaggaataaaggtttgaagataaatagggccagagatgagtaatttgttactgtga
taatatatttatatatatgtgtatgtgtgtgcgtgtgtatatatatatatgagatatatctcatatatatgagatatatat
gatatatatatgatatatatgatatatatatataaaacatacagttcagtagcattaacatctagcattcagtacatttaca
ttgttgtgcaattgtcacaactgtccatctctagaactttttcattatcccacactgacataccacacccattaaataataa
ctcctcattgctcctcctgttagtaccaaccattgttctactttcatctctatgtatttgactattctaggtacctcgtata
agcggaatcacgtgatatctttttgtaactggcttatttcactaactatcttcgaggttcatccatgttgtagcagttgtta
gcatttccttcctttaaaaggccgaataatattccattgttatgtatataccatattttgtttatccatttattcatcaat
agacacttttggctgttgtgaataatgctgctatgaatatgggtatgtaatacctgtttgagtatctgctttcatttctttt
ggatatgtacccaaaagtgagattgctggattgaatggtaattctatatttaaatttttgagaaaccaccatactgtttgat
atactggctgcccaatttttacattaccaccagcaatacactagggttccgaatttgccacatcctcaccatcgtgttgtttt
gtttatgtttttttttaataatagccatcctaatgggtgtgaagtctcattgtggtttaatttgcattttcctaatgatca

FIG. 4 (Continued)

gcgatattgaacatttgcacatgcttatttggtcatttgtatatcagctttggagcaatgatgtctcttgaagccttttgcc
catttatgaattgagtagtttgggattttaaattgtgttttagaagttctttgtatactctggctgggcacggtggctcgt
gcctttgggaggccgaggcaggtggatcacgaggttaggagttcaagaccagactggctggtatagtgaaaccccatctcta
ctaaaaatacaaaaattagctggtgtggtcgggcgtgatggtgcacacctgtagtcccagctgttggggaggctgaggcagg
agacttgcttgaacccggaaggtggggggttgcagtgagctgagattgtgccactgcactcagcctgggtgacagagcgag
actctgtctcaaaaaaaaagaaaaagaagttctttgtattctctgaatattaatcccttattggatatgttatttgcaaata
ttttctcccataaagaatgggttactttttcactctgttgattgtttcctttgctgtgcaggagctatttagcttgaaaaaa
tccaacttgtctgttttctttgttgcctgtacctttggtgtcacattcaagaaataattgccaaattcataccatgaaact
ttccccatgttttctcctgaaggttttatagttttagctctcacatttaggtgtttgatccatttttgagttaaatttttgt
atataatgttatgtaagagtccagcttcacactttggatgtgaatatctagttttcccagcattatttgttgaaaagagtg
tctttttccccattgaatagtcttggcactcttgttgaaaattatttgacaatagatgcaagggtttattttttgggctctct
cgactattctgttagactatatgtttgttttttatgtcaggaccaccctaatttttagtactgtagctttatagtaaaattt
gaaaccaggaagtatatgtcttgtgtatttatttacttatttttgaaatagcatctggctctgttgcccaggctggagtgc
agtggcacaatcttagctcactgcaacctccacatctgaggttcaagcaatcctcccacctcagcctcctgagtagctggga
ttgtagacacataccaccatgctcagctagttttttgtatttcttgtagagacagggtttttgccatattgcccaggtgggtct
cgaactcctgagcccaagcagtctgccctcctcagtgtcccaaagtgttgcgattacaggtatgagccacccgtgcatggccc
caacttcttatatttcaagatggttttggcccttcagggcccttgtgagttttaggatggatttttttttttaacttttcag
tttaggggtgcatgtgcaggtttattacataggtaaatttgtgtcaaggtgttctgtttgtatagattatttcatcacccagg
tattaagcctagtacccattagttatttttcctgagctcgcctcctcccacctggattttttttttttatttctaccagaaac
attgttgggatttttggtagggattgtattagtctgtagattgcattgaatagtactgacatcttaacaatattaagtctttta
aagccatgaacaccagatgtctttccatttatttacgtattcttctttttcttttcagcaatgttttgtaattttcagtgtac
aagtatttttacctccttggttaagttaattcctaagtattttattcattctgatgatcttataaatctgttttcttaatttc
ctttcctaattgttcattcttagggtatagaaacacaactgattcttcgcacattaaatttgtgccctgcttcttcgcgggt
ttgtttattcttttttttgtgtttgaaatccttgaggttttctgcatataagattatatcatctgcaaatgagataattttac
ttgttcctttccaatttgagatgatttttattcatttttcttaatgctctctcatacattcaatactatgttgaatggaagtg
gtgaaagcaggcatcctgtcttgtttctgaccttataggaaaagctttcaattctttgccattgactatcatgttagctatg
ggatttttttttttcccccagatagagtctcgctgtgtcgcccaggctggagtgcagtggtgcgatctcggttcactgcacc
ctcctcctcccgccaggttcaagtgattctcctgcttcagcctcccaagtagctgggattacaggtgtccaccactatgccc
agctaatttttcgtattttttagtagaaacatggtttcaccatgttggccaagctggtctcgaactcttggcctcaagtgatttc
acctgcctcggcctcccatagtgctgggattatagtcagccaccatgcctggccactgtgggattttttatatatggccttca
ttatgttgtggtaatttcttttttattcttagtttattgagtgttttttatcataaaatcttgttgaatttttttcaaatatttt
ttctgtgctagttgagatgaccatgtgatttgttttcttctttctattaacatgatatattgtttttcatatattgagccat
ttttgcatcccaggaataaatttttacttggtcttcgtgtataatccatttaataagctgtggaattcagtttgttggttctg
tgttgaggactttatatcaatgttcctaagggctactggtctatagttttcttttgtagtttctttgactttgctatcaggg
caatgctggcctcattgaatgtgttaggaagtgtttcctcatccatttttggcaaaactttgggaaaaaacgatgttctttta
aatgtttgatagaattcacagataaaaaaatcacatctagggctttgtctggaatttttttattgttattattgattcagt
cttgttactagttataggtctattcagattttcttttgtgtgtgtgattcagtattagtacattttgtacttctcgttatt
tctccatttaatctatattatctaatttgttggcatacaattgttcatagtactgtctttctcttttttttaaacttctgtgc
agttgatactaatgtccctacttttatttcagattttagtaatttgaatcttctttatcttaatacaggtaaagctgggtca
atttgttaaaattttttcaaagaaccagttttggtttcattgattttctctgttattttctattatttatatcctctcta
agctttgttatttccttcatcctgctagctttgggtttattagtttgttcttttttctagttccttaagatttgaagttggat
tattgatttgagatcgtttttcaattaaatgtgtacaactacaaatttccctcttaggactgcttttgctgttctgtaatttt
tggcatgttgtgtttttttgtttaatttatttctaagtattttctaagttcccttgtgatttcttctgcgtttaaccgtgt
atttttttaatttccacagttggtgaattttctactttttcttcagttattgattttattgattttcagtggcatcctgttgt
gatagaagatactttatttggttccctgtttttttttttaaaacagagtgttgctctgtcacccaggctggagtgcagtggtg
cgatcttggctcactgcaacatccacctcctgggttcgagcaattctcctggtctcagcctcccagtaggtaggattacag
gcacatgccaccatgcccagctaatttttgtatttttagtagagacagggtttcgccatgttggccaggatgatctcgaact
cctgacttcaagtgatccacccgccttggcctcccgaagtgctaggattataggcgttagccaccttgtctggcccagatcc

FIG. 4 (Continued)

tctatttttcttgcctatattctgactgggtgtttttgtccattattgagagtagggtatcgaagtgtccagctgttatttca
gaactgtctgtttaccttcaattctgtcaatttttgcttcatataattgggtggtctcttattaggcatgtaaatgttttt
gattattatatcttcttgctatattgacacttattgatgtgtaatatctttttttgtctcaaccttgttttgatttagtttgt
ctaatattaatgtagctacctgcactctcatttggttattacttgtatagaatgtcttttttacatcccttatttgtgtcttt
ggatctgaaatgagtctcttgtagacagcatatacaatctcttgtagattgtgtttttcttatacattctgtcaaactctgc
ctttgattgaagagttttatcatttacaattaaagtaattattgataaggatttaactgctgccatttttgctgtttatttt
ctatatgccttacagctttttttgtccctcatttcctgccttactggcacttgtgtttagttgatatttttgtggtgaagtgtt
ttaatttccttgttatttcctttttgtttatattctgctatttttctgtgtgtgtgtgtgtgtggttgccattggggtcacat
ttaatgccctaaagttataacactgcaatttcaatttataccaatttactttcaatagcatacaaaaaattcagctcataaga
ttcagtccctgctcccttccagttattgatgtcataaaattacattttttatgtattgtgtgtctaaaagcgtagactaataa
ttgtttttaatgcagtagtgtcttaatttgtggaaaacaaaaagtggagttgtaaaccaatgttacaataatgctagcttt
ggtaattgctcatgtatttatcatttctcagatctttatttcttaatacagcttcaagttactgtctagtctcctttttattt
cagcctgaaagactcacttcagcgtttcttgcaggacaggtctggtgataatgaactctctcagatttgttaatctggaaa
tgtcttaatgtcttcatttttaaggacattttgctggatatagtattctcagttgacaggtatttgtgtttatttgtttgt
ttcctttcaggatttaaatatatcatcccactgccttctgtccttcaagagttctgatgagaaatctgctgatattgagga
tccctttgtatgttacaagttgcttctctcattccatgttcaggattctcttttttcatagtttgattataatctatctcag
ttttcctacttggatctctgagtttttcctacttggagttaattgagcttcttgaatatttatattcatgtctcatcaaat
ttgggaagtttttgattaatatttcttcacataatctttttgcccctttctctctttttattctgggattcccagagtgt
gtatgtgttggtccacttgatgatggtgttccacaggtgtcttaggctcttgtcttcaattttccttcagtttttttttct
gttcctcagacacgtggtatttttcagctgttctgccttccaagtttactgattcttctgcctgcccaaattggctttgaat
tcctctagtaaatttttatttcagtttttgtactttcagctccagcatttatttttgatttttttatgtttttctctttat
tgatatttcaatttgtttttgacattatccatatcttccttagctttttgagcacctttcaacatttgtttaaagtct
atgtctagtaagtgtctgccatctgatcttctcaggcacagtttctgttaatttatttttttccttttggcctatacttaat
gttttgcttggggtagtttttttttttggtatgctttgtgattttgttgttgttgtcaaaaactggaatttgaatcttaaa
gagtggtaactttggaaattagatttttctcttttctctaagatgtgctattttgtttggttttttttatttgttgtagagta
ttctatgctgggtgtaatcttaagatcttctcggcctgtgtttttccctgggcatgtgtagtgactttctaaattgccta
tgtatgcagttctttttgcagtagtatcctccttaaatgtttggctcctaaaaggcaaaataaataaataaataaataaaaat
taaaaattaaaaataaatcaaaggggtgaaatagctctggatctttaaatccctggagcaattttttcagccaatggcagtt
aaataatgatagtctgcctctgtgtcacatttgatcagaagcagcaattagcaatcagaacacagattcctgatatttgga
gggcaaggtctttgttgccaaccttgactcttacaaactgtgtgcagggtgctctgggaacatgtgcatggttgcctgcttt
gagagtgggtgatgggtagccgcgacggcacaaagagctgaaattgactcaaactaactgatttaccattcaagtctttcct
tagaaactgaaaacctgaatagactccagagttccagaatcacagattctgcttacagtcgtctaggtggggagatgggttc
ctggtacttctgattctgccatctttctttgactaatttttttttttttgttcttgagatggagtcttactctgttgcccgcc
caggctggagtacagtagcatgacctcggctcactgcaacctctgcctcccgggttcaggcaattctcctgcctcagcttcc
caagtagctggaattacaggcgtgcaccaccatgcctggctaatttttgtatttttagtagagacagggtttcaccatgtt
ggccaggctagtctcgaactcctgacctcaggtgatcaacccgcctcagcctcccaaagtgctaggattacaggtgtgagcc
actgcacccagctcttagacaaattttttattccaaactttttttattttatcatttgaaaggtatatgtttattattttgt
caaaaataattttaaaacgtattcttgaagcttatttagatctgtttcataggaactgtgaagaaagtaaagaatttaaaaa
atgaagacagatttctcaccctgcttatgggtgcttctcgtgctagcctttgcaagtgtcgggaagtgtaacctgcagga
ggcatcagggctttgggcctgcatggtctgagtgctgccctgtgagtttcagaaggcgcagcaacctgtatacctgaaagcc
atctctgctggggcaggtacctagtgtccccacctacctgggtcgtagtcaggccctgggcaagcctgctatgcttttcctt
ccctaatccctcaggggtgggatagagagcacagtggcctcccagggaggtagaagctgctccagactaacaatcagagctg
ccagttcttaatccccaagacccgccagacttcacaaagacataccgaggtctgtgctgtcagtgccccactactacactccc
ttaagtagccccacattcttgtgcttgtttcttttttctgctctctttccttgcccaggtaagaggtctgcccataagggat
atttgcagcatgtgaagcttttttaaaaagttaggcttattgaagtataatttacacacaaagtacaaaaaaaaaaaagactg
tgttctcaaatctgtgagtcattaatgggtttagatgtttatatattgaaattattggaagtaaggtatgtttatattagaa
agatttgtagtctagattatccaagttttgggagtattacctctctgctttttgtttatctactttttttagtctctactttcc
aagtatctataggcaaattttcccatttccctttggaaagtgctgtttttcttgctttttttccgcctttccattgtgtcaga

FIG. 4 (Continued)

cttataaggcaatcagccaactgtgggcatgaaatccttgggaggaagagaaggaagtgggagggcagccatggtgaatg
tttccctaagttatagtcaagttctttgagagaacataacctcatccccttttttaaactgttgtaatactttcttttaaata
gattgtttattctcctgcaagtctcacagttgttcacagtggtaggtaagaaatcataaagttcaaatattaaagggagctc
acaaaagagcatggtttcaccagccctcactaaaaacaaaattatgggaaaatgctgtaaaagaaaccagaattcttggttg
caaatgatagaaagtgactctgatttacctaatcagaaaggaatttttaaaaaagtattaggtaggtcatagtttgacaaca
agacttggaagataggtggaagctaagggaagcaagacatggccccaaggtttcaacaggagcaatctgcttaggactttgc
tgcttggacacttggtgtaatagctgctgccactatgcctcgaaactggtgactctgctcattaactcacctcctctggtga
tctctaggaataatctctgactctcctgtaccttgtcctcactaggattgggtatccacggcaaaaagatctattaatagtt
ggtatcaggcctgtacatgtgttaagagaaagatgaggaaagaagtatctgcttctaatctcttgaaattatctccaaattg
aaatggtatttttggttgcctaacagcctgaagatgacaaatatcccctacaaatttctcctatttttacccctcttcctaacta
tatctgtaatttaaagtttcacatattcttttgaaaattgttttcattgtttacccacttttaagaaaagcaaatgggaac
atactacccactgttttggcccttttcaaaaatttatatctgaggaatcttccatattgttgtggacatctacctacctgatt
ctttttattaactacctttttatttcatttttatgatcatgctatcattaataggcccctatgatgaatatataagttgtttcca
gttttttttttgtcattgagaacagttcacatatgtatcttgttgtcttttccaagtatatctttaaggcaaattcttagca
gtggagttgctaggtccattgcgtctatggtttaaactagtgccttcaaaaatggtatttttatatactcactgtttaagagt
gctttcttccttctatccccactaactttggcaaactgaatagtttcaaactttaacttttttatagcttgttggcaaaaaatg
gtatcttgttatttgatcgtgtttttttaattgtgaggtttagcgactttttgatgtattggtcttatgtactttctggtgt
gtgtgtatgtatatactgacccctattttcaacttattttttcttttagtttgttttgtattttccttaatgattttcaggaaac
caatttttattctttcttcagacagttgtctaatgttctgcttctcttgccatttgaatttttgtgactacaaaattcagatga
aacaataatagcataaagaacttggtgggttatctttttgtttttgcattattgattgtttattaagaaatattctttaaaagt
caccttgcttaaattagcaagtaggaaatgctttcaataaagagaactgtcatgtacccactactccttacttactgaatca
tctttcttttggatagagaagataaaagtgaaaagggaatttaagagttcctgccttttttccttgtctttagcattatatagc
tgtttaatgtgtgggagtctaatttctttttttctttcttgagacaaagtctcactctgttgcccaggctggagtgcagtggc
acagtcttggctcactgcaacctctgcctcccaggttcaagcaattctcctgccttagcctcctgagtagctgggactacag
gcatgtgccaccatgcccggctaatttttgtatttttagtagatatggggacttcaccatgttggccaggctggtcttgaact
cctgacctctagtgatctgcctgctttggcctcccaaagtgctgggattacaggcatgagccactgcacctggcctaatttt
tttattgttcttttttggtgtgaacattctcccctcctccaagcctttttgttttttactattttcatgttcctttatatgtgct
gctgttttgtttcatctgtaattatctctcatcccctttttttggctattataatatatatatgtacgttttgaatctgagct
ttgaaggtaaattcactgcagctgtgttggttgatttttagataatttgtgtatttcctcctttgtctttttttaaactggagt
catttgtagttgtttatacagaatttttagtttttaaaaccacaagtctttcattataggttgagttatgaattcatagcctg
ttatttaaatgaagcttttgaaatctgttttttactgatctgtatcatatctaactacgccagtattttccttccttgtctgacg
tgaactctaaaattatgtgaacactttctccctgttttcctggcatttccactcaaacttgttcctcattcttagttagaaat
atatccagaattgtagtttctttctaatctaatgacagaagcaaattaatcaagcatggcaagaatttattggaaaactgca
tgtagttgaaaatatgtttagtatatattttgacagctgtgaagtctctaatttttttactgtaccttttctctgttccaatttt
tatgctctattctaaggatgtacccatttctactacctgactagggagcatgtgtattgtatcccagcagattttttttttc
atagatagatatcctttagatatctgttatccagtgtaggtagccactagccacatgtagctatcattatgtttaaatgtaa
ataaaataaaataaatttactgagttgtttttgctagctacatttcttgtgctcagtagctacatgtggcttgtgattactg
tatttaagacagcacagatacagaacatttttcattattgcaaaagttctgttagacagtgctgttctatacagtgtcattctg
cctctcattctaaaagttctaattcctgaagttgatgtactctttctgttgctgtcctctagcttaatcaaaataaatttg
agtctttttaaaggtaggttgcattttacatactgatatttctaaatcagaggctattttatattactttttttttatattactt
ttaaaaattagctttattggagtataatttacatgcaataaaatctacccatttttaaatgtacggttcattgactttttgaga
aatacacacacacacacacacacacacacaccttcttgtaaacacacaccttctgtaaacacaacaaccaagatttagaac
actcgctttatgaaaagtttccctcatgcccatttgtagtcagtccccaaacctggtttcaggcaatctctgatctgctttc
tatatgctttgcctatactaggattacatataaatacagtcatatagcatgtattcctttttgtgtctggctttcttttctttt
agtataatattttttgaaatttatccctgttgttactagtatcaataatttgttctttttttattgctgactaatattacattg
tatggatatgacatttctttattagtgtggtgggcatttgagttgttttcagtttgggtctgttatgaacaaagctgctgta
agcattcatgtgcaagactttttgtggacatatatttttgtttctgtttattcaatacctttgagtagaattgttgggtcaca
tgatgtagatcagttgaacagagtagattccagaaaagttcacatacacatttcttgacaaaggtgctgagattattcatgg

FIG. 4 (Continued)

gaaaaggatcaatcttttaaacaaataatactggaacaatagagaaaacaaagtgaaccttgacttttatgtcttatcatata
caaaaattaatttgaagtggattgttgacctaaatgtaaaagtaaaatttaaaaatataaaacttctagatgaaaacatagg
agaaaatctctgtgacttttggtttaaagatttcttagacagtacatataaattaactatataaggaaaaaatggacaaat
ttgactttatcaacattaaaaatttctgctcattgaaagactcaaaatgaaaaggcaagcagttttggagaaaatatttgca
atacatatatctgaaaaaggacttgaatgtataatatatacataaagatgctcttacaacttcataatgagaaaataacccc
ataaagagaagggcaggccgggtgcagtggctcatgcctataatgccagcactttggaggctgaggtgggtgaattgcttg
agcccaggagtttgagaccagcctgggcaacatggtgaaacccagtctctacaaaataaaaaaatacaagaaattagctggg
catgatggcatgcacctgtagtcctagctgtttgggaggctgaggtgggaggatagcttgagcctgggaggcggaggctgca
gtgagctgtgatcgcaccgctgcacgcttgcctgagcaacacagtgagatcctgtctcaaaacaaacaaacaaaaaaaaaa
caaaaaatggaaacagaaattttacaaaagaagatatatagatggccagtaggcatatgaaaagatgttaaaatcagtcat
cagggaaatgaaaatttaaacgtaatgagatagctcatatttactggaatggctcaaaaagggcttacaggaattggcaaag
acatagattaactggaactcttatgcatgttggttagagcacaaaatgatatgatttcttgggagaaatatttggcagtttt
taagattatttttgatagccttctgaatttcttagtgagttataggtcagttctgccactgtttctttctttttctttcttc
tttctttccttccttccctttccttcccttccttgcctgtcttgcctgccttccttgccttgcctgccttgccttcctttctt
cctttctttcccttttcttttctttcttttcttttttttttaaaggagtctcgttttgttgcccaggctggagtgcagtggca
cgatcttggctcactgcaacctccacctcccgggttcaagcaattctcctgcctcagcttccccaatagctgggattacag
gcgcgttccaccatacttggctaattttttttaatttttggcagaggcagggtttcactgtgttggccaggctagtctcgaacca
cctgacctcaagtgatctgcccgccttggcctcccagagtactgggattacaggtgtgagccactgcgcctggcctggcact
gtttatttcttttccctccagttttatacctatttagagagattagattttcttgagtactaggaatcactattttgagca
gaattattcaaaactgttattatttttttctttaacttgaggcaatgtaggagaaagcagtactgtgcaggtgaaagttacaa
acaagaacatttaaacaagatagttactttccatgtattggatacgtaacagaattaattctaataaccatcctgaagatg
gtcaggaggcattagttaagaattgaaatgtttggagcttgcctgtgttgatgggattaaggcagggatgatttatgtgtaa
atttatgcgttagtaacagcagtaaccgctgtagttacactagggttctaagagcaaatgttgattaaacatgaatgtagca
ggagtgataaggtttggctctgtgtccccacccaaatctcatgtggagttgtgatcctcagtgttggaggaggggcttggta
ggaggtgattggatcatgggagtggtttgtaatggttttagcactatcaccctagagctgtctcgcgaaagagttctcctga
gatctgcttgtatataagtgtgtagcacctcccctctttgctctctctcttcctcctactcctgccgcgggacgtgcttgc
tttcccttggccttctgccatgattgtaagtttcctgaggcctctgattaaacctttcttcttctaaaagattacccagtct
caggtagttctttatagcagtgtgagaatggactaatacaagggggaaatatatatggttaccaaatagcgaattagccatgg
gaaaaagtagcaaataaataattattttacttttttcagatgctaatttttcttttcgtttattttaggattggtgggagctg
tccaatgtccttaggctgttttccaaatgagataccaaaagctagttctccatcgggttttctcaggctgctagaagcattca
ttattatggttgtcattacttcgagttctgttgccgctatgcccacagtagtatttgttacataacaggtgcttgataaata
tttgctaaatgaatttttggaaaatacaatctgccacacctttcttctacagtttacaatcttctgttgagatcatccgata
gatttttttttcttagatattgtactttgaggcctcaaattgctgtcttttgtattttctatgtctgcagagactttccatc
tttcactcattgtattcattgtttttttaacatctttgtacatatttatagtaactgttttaaagtcactgtctgttaattca
aacatctggttcatcttggagtctgattctattgcctgctcttttttctttgtaataggtcatgtttttctgctttgcctgt
ctagtaaattttaatcgtatgttgaaatgtagggagtttggattgttacttcctttaagggtgctgagtttcatttttgtcag
gcatttaaattgatagttgatttagtattgtcaggtttggttctctttgttaaagcaggcatttttcagatttgtcttttgt
cctagggcatggtttttaacttcaaggttgccctttccaatgtctcagctaagtatctggggtgttccatgaggtctcttcc
actttgcctaggccagaactccagcttctcccagtattatatttcgttacctctggcgtcatctccgttatgctttcagatc
ctgcgcatagacagcccagcccccagccaaggacctgagatgaaatccatacaaaattcttagtccttgctccacaaactc
caacagccttagcagtctaatctcttcctgtttacctcagtgaaatctgtgttccacttgagttccatttccttctgtatca
gagaagagccaccatgctgaaagcaaggggcactatgtttctttgttcttaaggatggtagcctatctgcaacaactgtagt
gtgatataaaaatatataatttatgttgctgacagttacaaatactgcttgcagtactttgtaacataatttttcagattca
agttcatatactcttttttttccacatcaccacacacatatttttcagacttcctcctcatccttcttcttgccagtagttgta
ttataattcctgccagtagttacattataatttttggttatatcaatattgagttttttatgggattataactagataaatgcc
attcatagttaagtgatagagtatattgtgactttttttcctgcatgttttatttttttctggacttcacagttgtctctcttt
tttttaaaaaaattagttttcaatgttcttagctttaattcataaactcaccccctaattgtataaatctctcaacatgttta
agcacatttggcattatatcaattttatctttttccaggtgccttctaatctgtcccagtctggactaattgttcttcctggc

FIG. 4 (Continued)

ttgctgtatggctgtctactcaagatgtcccttcaccatcattctagggattcccttttcctctcttgtgggttagattctt
cagttcttggagactgtcatcttctttcatggtttcccactcttgttttggcggagcacatctttagtaacttcctgacaaa
gtgtatggtttgagatttcgctgattttaaaatgcccttattatatagtcacacttgatttatagtctgtcttggtatagaa
ttctaggctgagaagagttttccctcaaaatcagaaggttttgcccaattgtttttttagctgctagtattgctgttaaaaag
gataatgtcatttgattctagattcttttatgaaacctgtttcttctctggcagcttttaggatcttctgttttctttggta
ttcagaaatttcatgagatatgtgtgcttctatttttggtcttatttttcatctgttttgccaggtactcatgcaactttccag
tttgaaaactcacatccttcactttgagtatttttcttgagttatgtcttcggtttcttctcagtgttctctgtttctgga
actcctaaaatatatttaacatcctgaactcttagtttttgtttagtcttctgattttcatttgtcttttttattctgtatat
tctgttaattcctcggcttcatggtcttctagcccttcttttgcctatcttatggggttgaggattaaacagtttatatacc
tgaggtgcttaggatatgtctgtcatatagtaagtgcttgtgttagctgtaattgttgtttactttcataactgtcttgagg
gaaaggtctttggtcttgattctttgacttcttggctgtacatgaccttggacgagttatgtaatctctttgagacctacct
ccctcttctgtatagtgttaataagctctagctctcagatgtttgtgagggtcgaatggagtatatatgtgaaaatgtttaa
taccttttgtacagaattaatagttagtacgtggatctttcaaatatcaaaagttttcagtttgatgggaaaatgatgtctga
atttcagggttatttttaagagtacttgattatgactgtcttgtaaatctctatgagctaggtatacttgcactaaatgct
aatgcttttaaagaagttatgtcttaatattcagtctcattatgttaggttgaagatagaagattatgaaaatattctctg
aaaagctctggtttttacttcagattgtataaatctgtgtaatgtaataattatttaagaatgacatgattactactctaaac
ccatagaaggggtatttgttggattatttattttcacttaaatggtatttgagattaggaaaaagaaaatctgtcttttggt
ttttcttgatagtattaatgtaatttcaaatgttagctcatttttgttaatggtggctttttgttttgttttgttttgttttaa
ggtttttggattcaaagcataaaaaccattacaagatatacaatctgtaagtatgttttctttatttgtatgcttgcaaatat
cttctaaaacaactattaagtgaaagttatctgcttgttagagtgaggtagagttaaagatacatttttaacagaattgtatt
cctaaaccgattaagtcaagaagtccaagagcattgttagatcatttagaaagtgtagtgatgaggtaaaacattgttggca
cagattcatgttacttgatctgctttaaatgacttggcatctagcccatatttgagcccataaccgtgtggtaatttgaagt
gtaattcaccgtagagcttctgttaaagcactaatagcatcttccatggaggtatacttcagagtgaatataatttttgtttta
tcctgtgtctctagagctattgactgaaaaagctgttagggcattctctaactgtacatcacctaagttatttaaaattgct
gaattaggtggcttgtcttgtctaggacagagttttaaggactgcccacctgattgatagagctagttgaccttatctttaa
cttttgtttttttcttttgactttgggagtagagatgtgaaaaggtaaaaaggaaggaaggaagagaaaacttaactcttttt
gcccatgaagactgtttttccttctcaaaatattgactatttttctgatttgtaaaaatcggcacataaaacgtgttatttttt
tacttgactttttatctttcccatgtgatatctataaattatagataggaaaaatttatctgtaatttagtgatctttctagt
gtgataaaacgtcagaagtactgagagtggagtggacattgatattgttactctcagtaagttttcactgatttttctcaga
gtcatgaaggaacaaacgttttgttaagtccttatcacttattagataacacaaaacatgttgggggggtgtgtacagaggtg
agtaagatgtagctcccattctcaagtcgcttacattctaatgtaaaaggtagacaaagcattacagaagaagtaactctgc
tatagaaggttgcaatgaagagaacattggaaacactaatttttacccttataaagaaggtttcataaaggaaggcaagtttga
gctggggtgaaaaggaccagtaagggttgactttcaagccaaggagaggaggggaagtgatgttacaggccaaaggaatggc
attgtaagaagcttgttggcataaaagtgtttagaatatggcagcgaattcattatcatcagattgtggtgtctgtatgttg
ggggtgggagagaattgtggtggcaataggcaacaagataaaagaaagtaaaaggtgttatggaaacttaatgggtccagct
tacaaatgatctatgcatttaggggtctttctcttttcctgataaacctctcctacaaagagccttgttgcggatacccatag
tgtttctttggaggaaaataaaaactacaaagctttgtatttttttgcacaactggattcagaatataagtaataaaaaagga
caagaactttcaaaagctagaagccattaaactgagtcacttcagggttagactatcagaactggggatttagaaagtctca
gaatggaaatcgaaggacaccaaagacaaattcggcctttttcaaaatttttattctagtttaacatattcaaagaaagggaa
ggaaattcttttcattcctgtgtgtagtgacttcctgctttaagaacttaggacttcagctgtactatcagtattgtaggcc
acttaacattattatggttaaagttggcattggagagagcctaggaacctaactgcctgttttgtttttatatttccaaccat
tggattcccaagttaatgaagtctgtttattagttgagggtagctcttaatgcatatatttttaatgcccctccccacatgg
aatcataagctttcagaactggagagtacctgaaagagatcatttagtccaaccttctcatttttacagatggggaatctgag
gcctagagaagttaagtgagttgaacaaggtcacacaggtacatatggtagccgaccatccactgtttatgccaatattccc
tttacgttttgctttttttgcttgttcgttttaacctctccaaatttttactgacttcagaagtttctagaactaagttatagc
atgttttgagttctaatgtcactttccgatcttctttaccttttttctacctctgtttgtatttctggttctggttaagtga
gtctggtaagcagcaggtgttctatttttatttcttttattttttaggatagtattacatgtgatatatatgtctttgcaaaca
tacataatttgaagatcttaaaatatttgcactaggcatacccacatttaatagtatgttaaatctttttatagcaattatga

FIG. 4 (Continued)

tatacatgggtgaagaagagttcctaatatggcctttctgattaactgtatctgtttatatctgtgttttcttcaggcattc
ataacattaagcaaattcaggtgtactgttacttaattgaattaatcagtttgttttgtacaagtatatttttatttttgttc
cttgttgtataatctggtaggaatggggaaggggagatagtgaataaagagatgtatacttcttgcctttgaggaatttaag
ttttcactgtataccaattttttaaaggtatttactatatttcagtgcatattttatttgacatactttatcattttgtggt
aaacctttagctttactaattttcatctattaagttttctttttgtaagatggtgatagcttcatcaaagagagtaaagaaga
gacctgcctacctagctgattctatggcaaatctcacttctctggaagcttttcctgttaatcttattccttcagtttctgc
ctcttgtttcataaaaactcattctttaaatgcttattcatttctcttgtctcatataaaccaatatgaggtactggtatct
tttgagttttagttataaggaagcataaatggttaaatttaaatggctaaaccccatttgccatttgtgtatctttaatttt
agtttgttgagagacttatcactaccaaaccacaaagaatttaaaagaaactgtcagtaggtataggtggaaggagggcatt
tatcagagatttaatttaagaagaaagtcttcatccttatcctaccaacccccattccctgagcatatttatcattactag
tcccagcatatttgctcccatatttcctatgcttacctgtgaagattttcataactttttccttgctttttactgtcactgt
tggttctgtgatttatgacagatactgctcttgtaggaatgctggctttgactgaaatttgttactgcttttgtatttaaaa
ctttttttttattataagtagaattatggaacagtagtagaaaaagtttgacttttgtaatcagagatactgagcttgagtt
ctggctctttcatttgtatactgttatttggggcaagtttttttaatgctcttaagtcttagctttctcatatataaaatgga
gataataacagttatcacgtgattgtgaggatgaaacaaaaaaaagtggaaactctttgtaaggtgtgttcatctggttgac
acttagtagtcattacttcccactttccgtccatatagtcctcttaacagtaatatttgagaggcatttttattaaagcagtc
ttaaggagtgttcgtcaaacccacatgttctgggatcctgagaaagtaggggaagtttagagaactgaagctgcacaaaacta
atgtttattttctgttgtgttgtcctgagaccagcttcttagattgtgtttcctagtcctacatctctgattccttataaaa
tattccattatgaattcttcactattgacaatttctccccttttatcttaaaagtaccaaagaaagtgtaaaatgtgactgt
cttgtcagtccctctttttcctgttttcatgtcagtgggtatgaaattactagcaaggatgcatatatgtgcatatgtcatt
actaaatgcattttctttctagaaaaactcaatatactaaattgtactaaaaaggaaaagcttgttttgttttgagtggtag
tatgaaagttgttttatttaggtctgaccagttagaaacccaatggattgtagtttatttataattagttaaaccttcatgt
gaatttggttttgaattacctttaaggtagagaagaaactatatagatgtttttcagggttctaaatgtacaatacaggtt
cacaatcacttatttgaaactcttggggccaagtatgtttccatttttcagaaattttagttttcaaaaggtagcacagataa
atatactttacataaacaccccagtggggtgtgggtcagtacctgaaatgaaatgttttactcttcgctctaagtgtatta
aatattatgtacaatcttattacttcagatcaggatttgctgtagttgagtttgccataaaacttaagagaaaatttttagat
gtttgaactttgggatattgaaattgcaggttaaggagctatggacctttatttgttttaaaatgctaagagtttatttt
aagtaatttttaaaaatttgttttgcatagtagttggagttaccagggtactgctaaccacactgatatgtaagatctctt
tctgagcctttcattgtttgtaaacatggcctgttaatcattagaaagccagtacatactaacatatcactgctattaagac
aaatattagcatactctagtaatgacaagtcagcattttactactctgtattgattttacttattctttcattactctcata
ctgtaattaaaacttgcaatctgagagactgttgaaaaaggtgatcgttggcttttcaacagggagtaaggtctggtttaaa
aaaaaattagtaagcatttggccaagtagattaacaacattcagtttttctttactgtccttatgcttttactatttttaac
atatatctttttgaagaatagtttgagaattatgtatgcttaactatgagatacagatactattgaaactagtcagttgttt
ataggtacttgtaaaattaaaaatatattccaatagcatgcagatttttcatagaggaaatttgaaagcatggaagcacctg
aatttacagtactctgtattagtggcatcacaagtttttaagcaaatgtattagctctaattgcatacacttaatctttaa
gctttggttttattattataatatggggggtgataacagtatctacttaatagaattcttgttattacatgaaataattaatg
ttaaacacagcataatatgtgtcacattataaagattcaggcaatgtttgttagtattagtactttttttttcttcctaagtg
caaaagataactttatatcactttaaactttcttttagttgtgctgaaagacattatgacacgccaaatttaattgcag
aggtaggtatgaatgtactgtactatgttgtataacttaaacccgatagactgtatcttactgtcataacaataatgagtca
tccagattatcgagtgagatacatatttaagaattatctttaaaaatttcaaaaatttttaatttactgttgtgttttagga
aaaagtattgcataaagctattaatattgtcaggaagactaaagtgcagcatagactaagaattaggaaaattcctagacta
aaaatagtataaggagagggtttacctactatttgaggcagttggtctaatagtaagcaatcacagggagaaagcagaacta
cttaactcttctgtgttgaggaatgacataaaaggtaggaaggatataacaaatgttgataagaggagtctgatggatgag
aggagggaactgctttaaatgagtttctacttcagacataagttaattctcagagcccacaaaaactttcactttatttgt
gaaatacaactcagttctcatggcttaacactttaaaccatgagaaaactgaagagttgagaagcttggcagatgctgctgt
gatagtcaaaaagaaagtgggtgccatgagctactattgatgtatttgccattgatccctcctgaaaatctagaatggactt
tcagacaaatggtttgaaaattctaaatcactaatgattgagatttagtataggtttactaagaacgggttttttttgtttt
tgtttttggtggatttaggctgttgcttactaagcaaagcaggctttagttgaggtttatcttgctttaaacagatatttaa

FIG. 4 (Continued)

cagattttcctggaggtttttgtgtaccactgggaaaatgaagttaggcagatgactaagtgaaagctgtcctgctgactcc
ttataatgatagtcattgtctaccagaagatctctcctgtcacaccaaaggataattgattatatcctgtaccatattatga
gtcacctgattggagatataagacatacttctcacatatttagatgacacaggttagtacattgaatatcagccagggtttt
taaggatcttaatagagtggaactaaggtagaaactattaagagcaattaatagtgatatatctatagtcctgtttctaaac
aagtttttttaaaaacctcaactctgactatagtgaacagagaagtcttggactcttacaattcatgtgagaagacctgaaa
ctttgataacaattatatacatttgtgagtaatttctttggtgtatgccttcacatatctctggtatgtgacctatgctgc
agtccattgagcatagattcccagaatgtattctcctgcagaaaatggaggaaaataatacttggcttccctaatgattaca
tgtgtatacaacactaacatttgcaagaccacctttaaataacacacttagcattttttattttatgaaatgtaatatgtagt
tctttgcatagtttatcctattagtaatctattctgtctttggaatatgttttgtgatgatgaaataaatactataaatagt
attattcctttttgcattgagagtcctgacgaaatgtccatgtgacagttcatttttgggtttagctctacctctaatatgtga
cctatgctaccagtccgtatagcgtaaattcccagaatatatcctcctgaataaaatggggaaaataatacctggcttcct
taatgattatatttaagacttatcaagagactattttctatttaacaattagaaagttaagcaatacattatttttctctgg
aatccagtgtttctttttaaatacctgttaagtttgtatgcaacatttctaaagttacctacttgttaattaaaaattcaaga
gtttttttttcttattctgaggttatctttttaccacagttgcacaatatcctttttgaagaccataacccaccacagctaga
acttatcaaaccctttttgtgaagatcttgaccaatggctaagtgaagatgacaatcatgttgcagcaattcactgtaaagct
ggaaagggacgaactggtgtaatgatatgtgcatatttattacatcggggcaaatttttaaaggcacaagaggccctagatt
tctatggggaagtaaggaccagagacaaaaaggtaagttattttttgatgtttttcctttcctcttcctggatctgagaatt
tattggaaaacagatttttgggtttcttttttttccttcagtttttattgaggtgtaattgacaagtaaaaattatatataaata
caatgtataaatatgatgttttgatgtatgtgtatatacattgtgaaatgattactacagtcaaactacttaacatattcatc
acctcacataacttattattctcccccaggtgaaagcatttaagatctacaagctacaattttcaattatacaatgttatt
attaactatagtcactatgctgtccagtagagcttcagatcttgttcatcttgtgttcctccctccccaccctcagtccctg
gaaaacaggttttaaagatagttgctaatcctttatttcttctaaatttttaaatcagttgctgcctcaatttctatatgaga
aatgactgattgatttcatttttctgttcacgctaccattttcatatcatactagcacatgttacccattaactgtattgca
gatttggtctcacaaaattcttctaaaataacattttttaaaaagcatattaatcaaaaataagctttatatttctgaagctt
gtttgagcatagaatgcctttggataaaataccattacctagtaaagtgtgaactttttataatccataaaaattattctttt
ataagaatattcataaatgtagttagattaatagaagattctcgattctttgatcagaaaactaaggactatattgaaaaat
cagtgacaaatttaattcttatagtacatctgaaagaaaaaagaaaactcttgggagaactttttacagtgatttaatttttgc
tgttgatatatttctttgggtggtaagtatggcaaaacatgttaaaatttaatgcaaagagattttgtacatttttccatct
ctaagaaggacaaagcctaagcccctccagatagatagaaaaactcatttagagagttctccttcatgttaatctaatttct
tcttaattcagctgtaaaacagaaatagaatgatcgtattaatcatttaaagctgtgtaattgcatagattccttgttcctt
taccccctcttatatcttgtttcctatcctttgtgactttttttgcattatatataaggatgccgaaatactgtttattgtt
gatagtttacaaaattgaatcttacattagtgcataattttggtgaatgttgaagattatggtagattgccttacatttctg
catattgtttgcaccttggaatgatagcactggcatgaattatagagctgaggatctaaagattttttactttgatttatccc
attatcatctgcagggaaacaattgctttttactgattaaaaatgcaggctgggcacagcggctcacgcctgtaatcccagta
ctttgggaggccgaggcgggcggatcacaaggtcaagagatcgagaccatcctggccaaccaacatggtgaaacctcatctc
tactaaaaatacaaaaattagctgggtgtggtggcgcgtgcctgtaatcccagctactcaggatgctgaggcaggagaatcg
cttgaacccgggaggtggaggttgcagtgagccgagactgtgccactgcactccagcctggtgatagagggagactccatct
caaaaaaaaaaaaaaatgcagtagcaaaagcgatggtagaaatttaaaacagagttgatgagcagcatatatttggtagtg
gaaaaaaaggtaaaaaatttttttgtaataaaatagaaaaatttgtaatgtggaggcgcagaacactagatttaagccaggg
ggtcttaaattgtgttacattcctttttaaagtctgatggaaggtataaatgttctcccctcaaaaaatgtgcatagtgtaca
taaaatttgcagtttttttattacattgaaatatattcttttagacagaatgtaaaagaaccttcatgaaaactatgtcactt
ttttatgcaaaaaccagtggctactacatgagagcaatgaataaatctaagtggtacaaattaaccaaaattaagctttagt
tctgttcaatactaaattttaatgaaaagactgctatttaacttttaaaataacaagttgaaactatgctctttgactttga
ctttgcaactttttatatgatctttgatatccaatcagtgttgactttggtaaaaagtgctgaaaatgctattttacaaaaga
aagaagagtaaatggaatctgtagattctattgcctgatgaaagtagacgtgtcaagaaataagaattctccaaggctcttc
agataaattcatgtttcatcatttttctttgccttcaagttactgagatcatttttggcaagatctgtatcattaatgctgtg
ttaggaaagaaaagattatgactcccacatttttactttcaaggttgaagagttaaactgtttaaaaagagtgtatgttatcct
gtaaacagcagtatcaggctgtagaatttgtctttctgaaagcagggaacttatatatagcaaagaacttcatagtgctccca

FIG. 4 (Continued)

tttcttgacaaacctctcgagaagctcttgattgaaagtcttggctttcatgaatctggcagctttcacaatagtggattt
ttcatgacaaatcatcttacacagggaattattcaagggttggcacttgaaacagtagaatactttcacaacaagagataag
atttctttcaggattgatgacagtcttgcaccctagcgcatactgatgaagagagcagtgggtgaccatgacatggagagct
tctgtctttaccagtgccccaatatcagatgtgttgtctggcagtaaggtgtactgtctgcctacagaatactgaggtttct
tcaggagaagtttttggtaaagaaactttaccatttgaaagtgttaatgttttctgaagcttccaaaaagattccaaaat
gggaatgtttccttgattgtgtcaccatgcttgcatttgatgaaaacttgtagccggctatactgagaaatcatatctgaag
aaaggtggtacttccaatctttttgtgacctactttattattgtttttttaatgtcagggtttttttggaatggagaaaag
tatttgatagaggtattgcaacagtcttattcttcttcatgctacaagtatatttgactctttctaagatacttgccttcac
tgttcaactgtgtgactttttgtttgtttagcattacaatcaatatcctagtaggatgatttaatcaatgatttttaattgg
aacaaatagtttttgtaatggtctaggcttttccaacttaactgtgctctcacatgtggtctcttttttctccctctttcctc
cttcttatacactctcacccacacacatatgcatacatacctgtctgatgtatctgcttcttcagaatagttggctgtgct
ctgctgatgatgagaacttgccatttaagaaggacttgggatagtccatgtcatcatgttcagggataaaagtaaaaccca
gggcatttaaactttattgtattttattttctgtttccagtccaaattaaatccaagagaaggctccataatcaaaagtaa
ggacatattttaaatttgccaatgggaagatattctagtcattacagtctggtaatactatcaattctgtttctcttcagag
gtgaggggagactatttgatgaaatcgtaagtcctgtagggtgttgtgaaatagggcagaatgaaagatagcaagaatagt
gttatgaaaataaaatgcaaagtttataatatcatgtggtaaaatgtaatagtatttacttcatcagtagaactgctctagt
agctgtatattctccatccttgcataggttggaatatccccaagtgaaagagattgatgggctaatagttaatagaaaat
ggagatctgtacatacagtgttaagaatgtagatattaaattgttatatttagctgttacataatattaagactcagagtt
aagtaatttcactgaaattgattgctttttgtgtcttggagtcaaaataaataactgaaatctactatacttggctcatgct
taattaatatacttagaccatatttcggatgaattattcacagaatctaaaggagtatcctcgtgttcttaccttctttatc
cctgtgtttatttaaaaaggcaaaaaaaatggagcagatgctgttggttgaccatattttactgaacagtagcatttgtgtt
taggttgaaacagcattagaaaactagatacggattaaagtcagtggtaggttttttttttttttcttccaggaatgtttc
ttatagatgatcaaacaggcacaggaaggggaagtgttgtgatcaatattatccagttaatattagcattcagaggaaaatt
tgagtccctctgatacactgttaaatttctttctatactatcaagtccacaaatcctggaactgcaaaagaatttttgagactg
ttcaaaataattaatctctgtataggctcaggctttcctgcaaggttatgaaatgctgataaaattggtcttattttgaaag
gctcctcagcttatacctttccttacaaatgcttccttacaaatgctaaagcatttaatgactcctgacttaaagggaattt
ggacagattgaggttgttggtcttggaaatataatactgcaggcttctgtaaaatacttgaaatgtaattgttttaaaactt
tcaaagataccacttgtttgcctgttggttagaatactggtgaaataatttttaatctttttatgaataactaatttcatcat
aagaaaacttagctaagcatggtaaagctgttgttatacaactgtggaattcttcctgaggagtaactatcttataataaat
gtagttgattatctaaagtagtttttattcttggaatatctcataataggtttattctctcttgtcagtatttccttgtaga
ttgagcctgtggatttgcatttttgtaattgtgaatcaccattataggagatacatgcattttatctactttcagtttgta
tggggttaactttattagaattatctttaatgttattttgcttatatccttaattttaattatagacaaacattaagaagct
ggagaaaattatgttctagtgacatttatatagaagaagaatctttttttcccccttttctttttgaagggagatgaggcagt
catattttggtaaagaatttgtagactttgcagaggtctcttcaaaataatctggctcagagtcttgacatatcctcagcag
acatggtgcaaattagatggcagagtggtgggtacaagttgaccataaaataacgcattaggttagtaatgcccaaataata
ctttgggttttcagtgttgcagagaagtcagacaactgatagttattataaagaaaaatgttctgagagtgaggtaaccgct
taagggaaggaagcctccttctgtcttattcactaatttacaagaagataattgtgttacacttccttaggagtcattcatt
tgtatatttgacacttttgctttatgaacatgtgaagattattcaaaagtaagctgttggtgatttttttcttccaagaaag
catgccacagggcaacttctagggttggttctcatctagtcctgtgctccacactatctgcatctgcacttaagtttcaata
ttagataactcacatgtttaaactatgaagaaagagttaaaacatcctgagaatgctagtaagtatgtattttgaaaggac
ttccaaaatttgagtttaaagaggtaaactcctttacatgacaaagttacttagaaacactactgctgtttccctctccct
tgccttctccctgtcccatgcataccccagctgtgttccagaatgatggcacataaagtaaacattcatatttatttccct
ttttttgtttttttttttttttttttttttgcttgtttgttttgtttttttgtttgagacagtctcactcaatcacccagg
ctggagtgcagtggcaacatctcagctcactgcaacctctacctcctgagttcaagcgattctcctgcctcagcctcccgag
cagctgggattacaggcgcctgcccccacgcctggctaatttttgtatttttagtagagatggggtttcgccatgttggcca
gactggtcttgaactcttgacctcaagtgatccgcccacctcggcctcccaaagtgctgagattacaggcatgagtcactgt
gcctggcctcttatttttttctttggttaaacttttagggaaaaagtttgagctgctttttaatttttctttttttgttttttaaata
aattattaaagtttctctatgttaggaactcttgtgtacatgagttcattgagcttattcttaataaagacaaatcttctag

FIG. 4 (Continued)

aaataatagttgtatctttaaatgatctcaaggaaaatgtttggtttctctggggaatgaattttcatgacctaatcttaaa
tcaggttattttttctagcctgtttactaaatttctacatgttataacctaatgaaattttcttacttcctctttatttaaa
acaaactataattactgtctttttaaaaatcttccaatgtggcgttcttattttttcttaacatttgaattttcctgggccaa
accatgttactatgatacacattatttaaggctgttatataatacagtaaaattgtagaactttcatacctgaaggatctt
agcaattatttaattcaaacccattctaacatagatgataaaacagatttgcagggttgggcacggtggctcatacctatat
tcccagcactttgggagactcaagcgggaagattgcttgagcccaggagttcaagaccagcttgggcaacatagtgagaggc
tgtctctacaaaaaaatatttaaaaaatagccgggcatggtgtcacgtgcctgtagttccagctgcttgggaggctgaggtg
ggaggattgccagagcctgggaggttgaggctgcagtgagccatgatcacaccacagcactctagcctagagcctccctgtg
tggcaggctctacacttcagataggcaacagatcgagaccttgtttcacaaaacgaacagatctgcaaagatcaacctgtcc
taagtcatataatctctttgtgtaataataaaaacccatcttctaaccttaaactggtattttttttctacgaaactatgt
tctgcagtccaaattattttttcttttattattttgaatcctaaagtagaaatagaaacttagaaaaataaaaagcaactcctt
tatgacatatgaggacttttttcagttttaaataagaaaaacccaactcaaagtagcttaaataaaaggagacatttttttgac
ttacataacctaaaagctctggcctggatctaggtgctcaacagatctcaagagtatctctcttattctctctccctccctt
accctcctcctctttttctctcttctgtatatatgttattttcaaacaggctctcacaagtagtggcaagatatagttcctaa
tagcttcaggtttgcattctacctactttagcaactatgatgagaagagagctacaatttgagcaaaaatttgtagggtgag
ttctgatttccctggattgaggcacatgcctattattcctgaaccaaatattctgtccagggaatggaattctctggggcat
gtatctaaagctgaagtgtagagcctgcccacacagggataataatagttttccaaagaaaaatcaaggaggggaaagaatgt
tggaaagagaaaaaaatatcagttgtctgcttcacatttgttctcaataattagtttcatagaagtgaaatactgtgtaaca
ccctaaactttagagattcttcgtagacaggaaaaataagaactcaatgaagttgtgacttcattcaaatcacgtagtttat
atacatgctattagtaaaacccaggacagctgagtacaagttttaccctttatattcacattgaggtccagatcctggtttctg
aatgagataattacgtgcagtcggactgttttctgatcctaaaaatagagacaataatatctatcttgtaaagttatggtag
tgttaaagatatataaaatgttggcaagtaccttaatatacaataactactgctatatgttgtcattgtaataataatcata
tttcttcctttgttgaattgctttcctgtagtaatcttattgtgatcatcctgaaacatagatttccgagcttcaagcaaac
actattatgttgaaaaatctacattatttctaagtttagcagtgccagtggaaagtttattgaaatagaaaattactttttt
aactgaggagtgtagattgtgaattcgtgattcatcttcttaggagatgatcggaatattgataaatattgatgcatagaat
atgaacaaaacattacatatcttgtgctgtgatattaaagtagtattctgttctggtagtagtatggcagtattttaggtct
gaaagatgtacataatctgtactttgaagtctgttttttaagagattaatcacaagagatttacataaaacaactaaggtta
aaaataaatggtggattagagatacatcaggcaaatttcaatttcaaaagcagatgacagaatctcagtatcagggtagcat
ttaaagcaaaaagcattaaactggatcaaaaatgtcattttacatcaacacagggtacactccaggtaaagacttaacagtt
atgaacgaatgtgctaaacatcaaaatgtattaagtaaaagctgaaagaaatgaagaataattggtagaaaagcaatgatag
gaatccttaatgtacttcaaaggcacgaagtaagaaggtacagtcatgtaccacataatgatgtttgagtcaacacctgac
ctggtatacgacaatggtcctataaaattataatggagctaaaaagcttctatcacctagtgatgttgaagccgttgcaatg
caatgtatcactcacatgtttgtggtaatgctggtgtaagcaaacttactgtactgtcagttgtataaaagcatagcacagt
tatgttcagcacataatactttataatgataaacgaatatgttactagtttacgtgtttacagtactattatttagcatgt
gctttctgcttattaaaaaatgttaactataaaataatctttaggcagatcctacaggaggtattccagataaaggcattatt
gtcataggagatggcagctccatggatgttattgccccttaagaccttccagtgggacaagatgtataggtggaagacagtg
atattgatgatcctgaccttgtagaggccaaggctaaagtatgtatttattagttttttaacaagagtttaaaaagtaaaaa
aaaaaataaatttaaaaatagaaaaaatcttaataaggatacaaagaaaaaatgttttttgtgtagctgtgtaatatgttttt
gttttaagttaaatgttacaaaagagtcagagttaaattttttttatatttataaagtgaaaaagttataaaatgctaaggtt
aatttactgaagaaagaaaaaatttttaaacagatttagagtagcatgtttataaaatctacagtagtttacagtaatatcc
taggccttcacattaactcaccactcacccactgactcacccagagcagcttccaatcctgtaagctccattcgtggtaagt
gccctatacaggtgtacaatttttatatcctttataccattttttactgaacctttttctgtcttttagatacacaaataacat
tgtgttacagttgcctatgatattgaatacagtaacttactgtacaagtttgtagcataggagctgtatcatatagcctggg
tgtgtagtgaactataccatctaggcttgtgtaagtatattttatgacacagtgatgaaatcatccagatacagtttctctt
aagcaacacataactgtatatatatatatataggtggctttaataataaaataatgaaatatatttcttttttttctgtcatt
gacaaaacaattacagtcttactaattagatcaactgcaaaacaaaatctcactcaaaaataaaaatatgtaagtcccatt
ccttgattacaattcattagaactggagattttttaaaaatgtttaaatttatatggaaatataaaatcatgttttaaataat
ttttgattcaatgaggaaatgtaaatttagaactaaagattaataactagagatttataaaggcaaaaatgttaatgaatta

FIG. 4 (Continued)

ggaaacagtaaaccatttgaactaatctaaatactgattgcatgaaaatgccaataaaatcaatacatatttttaaaagcca
gtcaaggataaaagaaaagagggaaactaaaagtgagacattaagtatgagaaaggagataaaactaaagtgtggaggtgat
gttaaaaattatattcaggtctgtgctaatcattttggaaatttcagtgagaagtgggcaattttcagtgaatatatcattg
taaatgctttgaggagagacaaaatctgaatagaccctgcaataatgaaaatgtctaggagccctcaagaaatacctggttt
aaattgcatttcaggtggctggttatcacaccttgaagtatcaagtaattatgttatctaaattggaccaggtgttagaaaa
atatgtgagacttcacaggtggctgcttatgtagcccttatacctaatctgataaaggtagcatatatttaaaaagagaga
aaaccagaaggtacaatttagggaaaattaaatacttctatttggccaaagtaagagtacattcaagggaattgtgagaggt
aagagtggaaacagaggttggagctgtatttttatgctgtgattgaattacagtgtgtgataaatattgctcttatttgggt
agattaccatttaacattttgaattaattggtaattggattaatcttaacttttaaaaaactaatctgagagtggtataaag
gatagattacagaatggataaagggtgataaatcagttggctatggcaaaattgcaggaagaaactgaaataggccacagaa
aactgaaactgacattttgagtagtatttcagaatcaagatctggattttggcaactgaatagatgcgtaggaatcaaagat
gagtatactaaatgaacttaatctatgatttgtctgtcattttattgtgtaccattagtgtgtatgcatgtatgtatgtgcc
aggtagttaataggctgactgtgtctcttagctccactctgctgcctgggcctttgccatagtgctggagttccctcacttc
tctttctgtaaccctattatattactgctgtctctcagctgtgtttcattcctcaagcagaaagaagatgggaggatcata
tagtagttgactagaagctgtggagtttgagtgctgggattatatctagttccattacttatgaagattatatctagttcca
ttacttcacctcatctataaaatggtttaccaatagtacctaccttacatggttttatgagtattaaattatgtatttctaa
agacatttagaacaatacaaagaatatagtgtgggctcaataagtgacgatggtgttagttattagaaggccatcgagtgct
ggagaaaataattgaatatcattgatggaaataaaggaagttttccacgttaaaaagcttcggtttttggaaatgtgtgttt
tcagtatttctgagattaccaggtagaaattccagccagatgttggaattctgcactggcagttgggaataaagtcatgtta
aaggagataagtttggagttattgtgtaaaattggtaaagcactggaatagattggtttgacagaggggaaactcttttttg
agataggcctatatttagggacaagagaagagacaaccaataagggttgaaagaaaccttgagagagtaagtcctatgacag
aagcagggaagtttcagaatgattgcagaaagatcagccaggctcttcctgttctccatcgtggtgcaggatcaaggtgaaa
aggataaccccatgcaggaatttgcatctgcaggctccgcttcaacatctgtttaggagaaagtggagacagactgacctg
agtaactaaggtcttggaacagcttacaggtcagaaccaggtgttttccaaagctagatatactgttagcgcctttggcaac
agaagaaatgaaaagactgttgtctgctgcacagttcgagggccaaggcagacgaaatcctggagaatgatctaaaggtgc
aggagtgtgagttaagaaaaaataacttctcagatactggaaacttggtttttgggacccaggaacacattgatctgggtat
cagatatgacccaagcattgatgtctacagcctggacttctatgtggtgctggaaaagccaggtttcatcattgcaggtaag
aagtgcgggacaggcttcattggtgccaaatagaatcagcaaagaggaggccatgcgctggttccagcagaagtatgatggg
atcatccttcctggcaaataaatttctcatttctacccaaaagggtaataaaaagttttcagtgaaatgttaaaaaaaaaat
aaaaaaaagatcagccagcagccaggatgggattgtgaaaacagcaggaaattagttgttgacaaagcattaatgaccatta
agaaatcagcctcggctgggcatggtggctcatccctgtaatcgtaacactttgggaggccaaggcagatttcttgagtcca
ggagttgagaccagcctaggcaacatggcaaaaccctcgttcctccttaataaataaataaatgaataaataaacaagcaag
caagcagggcttggtgttaggcgcctgtactcctagctactcgggaggctgaggggttgaacctgggaggcaaaggttgca
gtgagccaagattgcactactgcactccagcctgggtgacagagtgagaccatggcacccccctcccttcaaaaagaaatc
agcctcataatcaatttctctggattaaggagtaagagcgtctcaagatttgctgtttatagagagggaggctaatagtttg
agagagatacagaatctagggagagtgtgggtttttggtctttcagttgtttgccagccttggataaagaatgaagattact
tgagcatattatttagagacaagtggagagaataaaggcacatgccagataggagataattaataaagcacttgtccaaaat
agaaacttgtttgaacaggaagagacgtcaagtataaggagatttaagatgggagaagggaatttttgagtgtttgtattgga
tgacctcagggttcccagtaaagcaggagctgaattcatcgaaggtgatgtgttggtcaggatcaagagagaggttgggaga
acaaagtgctaaaatcgttgtggtcaagagtttaaaagtgtataccagaagagttattgagtgataggggtttgaaatagg
caaagctgtaggaaagggggctggaaggaatattaggaggaacactaaatatacttctgaggtctacctcctggtctgtgaa
cataaaggagctgaaagagtaatggctgaagttctttagtttagctaaagtttttttagctaaagctagaattgttgaaagtt
gtatttgaggaaaaaaagttaaggatacagttgaccgttcgataatgtagcccactgttgaccagaagccctacccacaaca
taaacaggcaataacacatatttttgtatgtgtattatatagtatattcttaacaataaagtaaactagagaaaagaacatgt
atcaagaaaatcataaggaagagaaaacacatttacagtactgtactgtatttattggtaccatacatttatgttgctgttt
acaagatgaagcatctgtctgaaatggccagcagctacagctgtacctatctactgtacatatcaagcaagtcactttattc
ttataatgtctatgacttctttctttgaaagcgcttccatcatcactgttggcacttcatatgggtctcatggtgttaaggt
ttacggcattgcactagacacaatgaaaactacacaagagggccgggcacggtggctcacgcctgtaatcccagcactttgg

FIG. 4 (Continued)

gaggccgaggcgggcggatcatgaggtcaggagattgagaccatcctggctaacacagtgaaaccctgtctctattaaaaat
aaaaaaattagccaggcatggtggcacgtgcctgtaatcccagctaatcgggaggctgaggcaggagaatcgcttttccca
gaaggcgtaggttgcagtgagccgagatcgtgccactgcactccagcctggatgatagagggagactctgtcgcaaaaaaaa
agaaaagaaaaagaaaagaaaagaaaacacacaagagccgtgagagagatagcttttgattgcaatacacaatttactgga
gagatgagctgatcatacagagatgattagtgtcacacagtgttttaaacagattcttgcaaccctggagttcactgcagta
gcaacagaagttagctatgagattttaacagtagtatagtatgtactacagttaatattaggtagctatgatttaatgctgc
atctttgcatttgtttacatttatcttgactacaagtggtattatgtctggtcttaaggtttgtgtgcatatgttttgatga
attttaacttttataataggtttgtgtatattttatggcagtaaatgataaaacagactaatctacatatattttatgtag
tcatgacataaacctaactttttcttaacttttgatatttctagtctatgtgtttcatctgcaggtttttcaaattgttg
aaatctctgaaaaatttattgaaaaaaaatccatatatgtaagtggacccacacatttcaaacctgtgttcaagggtcagc
tgtgtaaataattttcctcaaaattaaagtggaaaggagagttactactagtagaaagtagaactgtacccttgggcaggg
gtgtgtgtgtgtagttaaagatcaatttaacttaaaaggtcttggttagagaataaaaactggcccttattagctttcattt
acatgaaaatgaaaattttaggccaggcacagtggctcaggcctgtaatcccttaactttgggagaccaagggagtgga
tcacttgaggtcaggagttcaagacagcctggccaacatgctgactcaccettccctactgaaatacaaaagttagccagg
cgcagtggccatccctacagtgctagctactcgggaggctgaggcaggagaattgcttgaacccgggaggcaaggttgcggt
gagctgagatcgcaccactgcactccagactgggtgacagagcgagactccatctcaaaaaaaaaaaaaaaaaaaaaagatt
tgaaaacagagtatttttttaatctgcaagagctttacagcctttattcatatgtataagctttaaagatgactaaaattt
tagtgtggactttccactcattggaaatcctatattgcaggtgttaattcaattttagtgagtgtgcatcatggctcagaga
gataggactagaatgaggaggtcacattggagactctgaaacagatacatgtgagcctcccaactttttaatatttgttaat
ctagaagtgttgaatttgggtgctgacaaggcagcaggtagataagaattgcaaagttaagaaaatagactgtaatattga
tggtaaactaattgattaaattttaaaatgtactttccatgtttttctttgaattgtcagtaatttgtttcaactggtat
tcatacatagattattcacccaatgttgacaactagtagatttatatatttttatgttgcctatcctttttgggtaagga
ttaacagaatgtataatcacctacattataggtacactactaatcacttgctacttgaacaaacctaaagctttgaaatctt
tttatttattgcacacaaacttatgccaaaaatggagataaagagaaaatgtcatccactaaacccccaacaaataatgttga
caatgtggtctactcgtagactcgcattgacttaatttttttaaatcttattgcatatttgactagataataaatgcatat
ggttaaaaattcacatggttcaaaaaagtacacctcccactcatcttccatgtgatatttcctttctgcttagcaattctg
tatttatcttgctaaacatgaatgacagttgtttgctgaaattacattaaatgtgacgtaataaaatcattgtaagtttaca
tttttaactttaataatttttaatgttttaatgaagagtatgaagagtagtagtactgctcttcaaagtactactacttta
cctttacctttttactgttttgttaagaaaattaggccgggcgcagtggctcacgcctgtaatcccagcactttgggaggccga
gacgggcggatcacgaggtcaggagatcgagaccatcctggctaacacggtgaaaccccgtctctactaaaaatacaaaaat
tagccgggcatggtggtgcgcgcctgtagtcccagctacacgggaggctgaggcaggagaatggcgtgaacccgggaggcag
agcttgcagtgagccgagatcgcaccactgcactccagcctgggcgacagagcgaaactccgtctcaaaaaaaaaaaaaaa
aaaagaaaaagaaaattatatagaaataaaattccagctattccaaaactgcaccttgaatacaggtacagaattgctaaa
acgtgtaccatttgtagttttagcatgcttttgtgtaactgcatctggtgtttgatcctcatgagagccctgttaaggaa
gggtacatattattgtcctcattttccttcgaaaacacatcagagtttgtatttgactgtcagcattcaaatacaagtctt
ttatttataaaatttggtctttatactgtggctaaaaatcttaaatcacttgtcatgatttgaaatggtttataccgattt
ttttgacatttatacacacatacacatattttttaaattgtctataataaaatcatgctcatctttgaaaaaatattaggag
tactacagtggatacctacatacttgctattcagcatacctggtttttgtttgtttttgagacagtcttctctgtggtcc
aggttggagtgcagtggcacgatctcagctcattgcaacctccgtctcccaggctcaagtgattgtcctgcctcagcctccc
aagtagctgggactgcaggtacacatcaccacgcccagctaattttttgtatttttggtagagacggggtttcaccatgttg
gccaggctggtctccaactcctgacctcaagtgatcagcccacctcggcctcccagagtgctgggattacaggttgtgagcc
actgcacctggcctgtttttaaattcacataaatatgtttttatatttttcattagggagaagaaggttgtgtctacaatttt
taagacattggggagatttagatgccagtagtaacttaaaagagaaataattgcaaattctttttcctcttgagtatacttt
catttaaggtacagtgttctgtaagttacttttaccgttaaacttcttaatgttgcttattgtttgtcttacattttaggt
tggattttcttaagtcacatgtctaataaaaaaaacccttaaatacctcatttattcgtcttcgttagtgaatgcattgtt
gtacatattagatttttctctttagataactcagcttccctattaagtgccacatgtattacaaaatttttatttatgtttt
attgtttaataaactcttgagaactagatacatttaatcatttgtaatacttacattttctaaaacacttcattttccct
ggtttcttcaacaaagagatgcatgtagtacaaggatagctttacctgtgttagaagattgtttcacacatttacatcaact

FIG. 4 (Continued)

gcatagtcctgtttttgttgggccctaatgccagcatcactttttgctactgctgtttctgccttaaggcaatatgcctct
gtctagtttgctgattctgatactctttcccctggaaagtaggtaatcaagtttgtgaggagctgtgtgtttaaggagtcca
taaatccttgtggggagccctaggtgtatagagcatagctgtagggcagaggcctttgacacttattctggatatgcagtgg
cctttgcctatggggttcatgggtcagagcgctgttgtgacctttgaataaatgggttgttatgataattgttttaaggggag
gagagttattctgatatcctttgtattgatattgctcttatttattattgagctggatttaagtattaatcatttaaggtca
aatttctaatgtatatatgttcttaaatggctacgacccagttacccatagcaatttagtgaaataactataatggaacattt
tttttcaatttggcttctctttttttctgtccaccagggagtaactattcccagtcagaggcgctatgtgtattattatag
ctacctgttaaagaatcatctggattatagaccagtggcactgttgtttcacaagatgatgtttgaaactattccaatgttc
agtggcggaacttgcagtaagtgcttgaaattctcatccttccatgtattggaacagtttttcttaaccatatctagaagttt
acataaaaatttagaaagaaatttaccacatttgaaatttatgcaggagactatatttctgaagcatttgaacaaattaatt
agctttgttgttcaactcattgggctaaagaagccaaaagcaatgggttttaatgtagtcgaagccaaattatatttatgaa
agaaatattctgtgttataaccaccaaatacagcccaattctgactagatgatggaagaacctgtcccatcagaggtccagc
atgaggtccagcagaggtccaccagaggagttcagcaatttgctgctcttagggcagggatcaattccttaatatcttagga
agactaggtattgacagtaatggtgacaaagcaatgaaaaggaaaggaagaagtgataagacgtggcagcaagctgaagtat
gatgagtaaagaataggaatcaaagtatgtggagtgttagagaaaacctggatttagatccagattctagtcctatctctgt
cattaatctattgcgtaaccctgagcatatcatctacctctctttgagtttgcttgtcaataaaatgaagagactttgaaat
ctgagacttcctggataagtactaaatacagattatgtcactgatgtctgcctctatttatttctccctttaccctaatct
ctataagtctacctcagtcatcctgatcctattctacttctctgatgttgttgtcagataggtgtgatcatcctcatcagat
cttttctgtattcttagagacagataactttatcaaagaccacagatttattagtatagcatgttaaagtctttctaaagagt
ctcattgatgctctttttcatctcagtacaatttttaaaactgctgaatgcaaggtactgagctgttggaagtgactgacaga
tgaatgtaacagattcatagagaaggaaaaaggaagaaaaactcatgctcttcctatagtattgatatcagtgtaagagcca
agagaaaggtataaagtatcatgcagatattaagggaaagaaaacattcactttagtaatctttcctcatttctagtttcc
tcttatgtactatgatttaatactgtagtaaagttttaataaaatatgagctatatgtaattaagtgggaggttgtggggct
aggcacgaggctcacacgtgtaaccccagcactttgggaggctgaggcaggcggatcgcttgatctcaggagttcgagacca
gcctggacaacaaggtgaaaccccatctctactaaaaacacaaaaattagctgggcatagtggcacacacctgtagtcccag
cttcttgggaggctgaggcaggagaatcgcttgaatccaggaggcagaggttgcagttagccgagatcatgccactgcactg
cagcctggacatcggagcaagactttgtcttagaaataaataaataaatataaaataaaataaatgggaagttgtgtatata
aattataaatgctacattcagaaaagctttttgaaggttgtcagacagtttcttaaaggaagttcaccagttctttattgaac
attgaagaaaacatacagtttagactggcattaaaactgaaagaagtggccagacgcagtggtagacgcagtggttcacgcc
tgtaatcccagcactttgggaggtcaaggtggatggatcacctgaggtcaggagtttgagatcaggctggccgacatggtga
aaccctgtctctactaaaaatacaaaaattagccaggcatggtgatgcgtgcctgtagtcccagctacttgggaggctgagg
caggagaattgcttgaagccgaaggtggaggttgcagtgagccgagattgcgtcattgcactccagccagggcggtaagagt
gaggctccgtcttaaaaaaaaataagtaaataaattaaaactactgaaagaagtattacaggcaatgggaaatagcttga
gtggaagtgcagcagaaggaaaaagctggacaagaatgtagtgtcagagaataggtatggaacgtgtgagtgactgttagag
gatcttgaatggggataacagacttgatttcataaatactgagatgtcatgataatacttgaggactaaacatgttttaag
gacagttgtatgcaaagttgtaatcgcaagaggaaaaaatagtggaaaagaaaccagtaataaaacttgccttaatgcaggt
atgctaagacaatcaaatgggatttcattaatttttttatttgccatttatagccaaagatttttgtaaaagttttgagcccag
tcaggtgaaatagtctcagaaagaaagaaaagtgaatctgagacttggagacattaatgttgatatttttggttttaaacgtg
ttttaaatccggtaaaagtgagcttctcacatgacaatattcagtgggtacttgggagtatgggttcgaatctaggtaggag
atatatcgatatttttgggcatcatcaggaaagggagagtagttaagcctttcatataaataatggtgtggcgtttgggcatg
ggaagtcttggaggaaaggaagaaaaggagagggtgaggactgagataagaatggcaacttgggtttaggaagaagaagagg
aatcaatgtagagaacagatagtgctgaaaaatacagcatcttctgtagggattggcagcttttttcttgattttgtcttaa
tatttctaagagatggaaaaagctactatattctagacatttaacagggttaaaaatgttactaaaagatgatcaatgtggt
tttcattcaagactataacaatatgtatatatccaaggaaatttaattctgacttaaaaaaattgttttgcttgtatagatt
tagggacacaagtgtaatttttgttacatgcatagagtgtatagtttcaagtcagggctttaggttgtccatcatctgaata
atatacattgtacccattaagtaatttctcatcttctactcaccgtttcaagtctccactatttatcattccattctttaca
ttctgattttcatttactaggtgtattagtctgtttttgcattgctttaaagaaatacctgagactgagtattaaacaggtt
taacctgtttctttatgaattcttctttaattggctcatggttctgcacgctgtacagaaagcatagcagcatctgcttct

FIG. 4 (Continued)

ggggaggcctcaggaagcctccaatcatggctgaaggcaaaggggagcatggtgagaatgggagccagaaagagaaggagt
ggtggggagaaggtgccacccactttaaatgccagctcacttaccaccaagaggatggcccaagccattcatgtgggatct
gccccatgattcaagcttcttccaccaggcccccacctctagcactggggattacaattcaacctgagatttgggagggaaa
gatatccaaactatatcactaggtctggatcttgttatttatttttggaacatagtcatatatatccaaggatatatattg
tagaagtccacagaaccatactaatattggacttctgcttagttaggtcttatctatctgaaacatgatattcatattgcag
agaagattattttctttagtgattgaggaaatctttactacttatacattttaatataatactataatatttgaagatgca
cattttagatgtagtttaattgaaacctggaaatactattaatttgctttttaaagtcctaaaatcaggattatcagattct
gaattaatggagtttaaatcaaaaagattacaaggcagtttttcagttttattctggttaattttatcacagctttggaatc
ctactttgtttatttgcttcttgaagttagatttcccagtgaaatttcagtatcacataaagtcttatgaaatggctcattg
cactttgaactttgagtcaaggaagtgaaatttattgatagattgttggtgtaatatttatcctgtttgtggtagcttttt
gaataataagtgtcttagaagaccatgttggagtagcctgcatgctttatcaaacatattaattatgtgatggctgatact
gctttagatattacatagaaatagtagtaggtgtttactaaactggaaatttcatttaacttggtttagctttgccttgttc
tcagtcacattgataaaaatgtaagacttttgtttatctttagaataatgacacctttggtgctgagaatttttgtttt
atatatatatatatatacgtaatataaatacaaaatatatttaaatatgtataatatttctcatacactttatgtaactt
tgtgttcctgtttctctattatcttggcatgttttcttcaaatggcacttcttaacctcctaaggttaataaatttctttgt
aatggactttgtttttctaattcctcagcgtatgacaaatgaattatactttgtcaaattatttaggtaactttcagttttt
gaagtcctgggatcctaacattcatcagtctttaatttctgtcattaaggtcattagctataaatgaatttatgagtagatt
taaaaaataaaacatacaatccttcccttaacacactttcccacccatttggttcaactgctagtgtaaaagcatgatgaatt
ttgagaagttatattttaccagttactttattttttaccagttatttaaaacagacatgagccaaagccagaatacttgtta
atgaaaatgaggtgtttggaggaaaggaaggttgtgctgcagtttttacttgaaatctgttacatttctttacagaaattt
caaatctcttgtttcctgttatgatggtggcattatatacctttaaaatgtgagctataggaaaatgaatgatggttaattt
tttaataaatatttagacttgtgtttttgaaatttttttataacattgttataggttttatcctctttctcttgtgaacatgt
agtgatttgtattttgtgatcttgccgcatgctagagacttaagaatactatagcaaatatctgtcttctttacatttaaa
aatttttcgtgactactccctgttgatatctgtcttaaaagttactttgatgtagttcacaaatgtaccagataattattt
catcgtttttaatgcttaaagtttttatttgtattaggatttttagtatgatttttaatgttaaagttttgaagttactctgc
cactagaagtctaatttgggacttactattcatgaaataggaattgactttttatataagtaataggaccttattttgaagg
ttcaaactggagaaaatcttacattgtttatatttttatttcatttatttcagttgatttgcttgagatcaagattgcagat
acagaatccatatttcgtgtatattgctgatattaatcattaaaatcgtttttgacagtttgacagttaaaggcatttcctg
tgaaataatactggtatgtatttaaccatgcagatcctcagtttgtggtctgccagctaaaggtgaagatatattcctccaa
ttcaggacccacacgacgggaagacaagttcatgtactttgagttccctcagccgttacctgtgtgtggtgatatcaaagta
gagttcttccacaaacagaacaagatgctaaaaaaggtttgtactttactttcattgggagaaatatccaaaataaggacag
attaaaagctatattttattttatgacatgtaaggaactataatttgtttttctattagatctgcaggtgttttgcttactct
ggcattggtgagacattataagggtaaataatcctgtttgaaggaaaaggccttatggcattgtaacatgagaggaattttt
cttaacaaggatggttaactgagaagaaattagcatgggaccaatatttttaaaaatttggtctataggtagaaatgagatc
tgttctgtggtcttatgtagtgacacaaaccacttttttctccatttggcttatgtttctttttctttccttttttttttt
ttccttttttgttagagacagggtcttgttctattgcccaggctgagtagctaagactacaagcatgtgccaccacacccagc
taatttttttttattttttattttttgtagggacagggtctcactatgttgcccaggctggtctcaaactcctgggcacaagcag
tcctcacgctttggcatcccaaagagttggaattacaggtgtgcgccatcatgcctggccttaacgtttcttaagacttgat
tatttttctatttagcttctgtggatttactgattaattttttaactaggagagaaatcagtatgaagaggaagtaataaaga
atgaaaacatggtatttaaatgtgcaggtttagaaagttaatgaagttttgaatttgattgatctgtatttagagaaggcaac
gtcttattatttttaaaaccaactatccgccctgtgcggtggctcacgcctgtaattccagcactttgggaggctgaggtggg
cagatcagctgaggtcaggagttcgagaccagcctggccaacatggttaaaccccatctctactaaaaatacaaaaaaatta
gccgggtgtggtggcaggcgcctgttttcccagctactcaggaggcttgaggcaggataattgctgaacccgagaggcggag
gttgcagtaagccaagaatgcaccattgtactccagcctgggcaacaagagtgaaactccatctcaaaaaaaaagaaaaaa
aaacaacaactatcttcatttaaaatattaaatgtgaatatttaaagtgagactaaggtgcaacattttttagatagtaatga
agaaaaggactaactttgtagtgttgctgccttgttaaacatactagatagcatattgccaatctttaaacattctcaatga
taggatttatttactttttctgatttttagctttttctttttgaaagaaaataagaggaagtttcatttactgcaaaattttaa
atgctgctttgatgtatcagtagagatataattttcctttatccagaatccaagtagctggaaaaaaaatcaaaatatgct

FIG. 4 (Continued)

gaacttttttttttttagccagaaacccatttcctatcgtctgtacaaataaaagttaaatatatctcaataacttagaaa
attatttttgataatccaggaagtattagcaactgttttaaaattaagataactagtaagttttatttagctttcaaaaat
aggcatctacatcatcatctctgcataccttttaggaatttcctaattcttatttcccttcatctgtactttaacacatgcaa
aattgaaggttagattaaatatttatgatttatttgtttatccttgactacataaatttccattttattgattttccctgcc
ttatttaagaatatgctatgattaaaacacaaaaaatttttagtataacccatatatatatagaattcaccttttgttattt
aaatattattggcttattttcttctaagtaaatacaattactggctaaataattgaaataagcaaaaaaaaaatttttaaa
gaccttgtatacaagattactttgccaggtactgttaaaagatgcaatgacatttaagacgtaacatccttaaggatcttat
tttctggggataaaaaactttaagataaattagaataaaagatttaaatggcattttaaggtaccaggtaccagataagat
gtcacaaggctgtatatcattaattgccaaatgatttatacaggccagatttctttgttggtcaatagaggtttaaagtgat
gaacttctgttgtgttttttttattaagaaggtattatcttattagtaagaagtgattttttttaagaacaagcattttataa
catcaaaagaaatcagtagtactctttcctacccccctcatatttattctgaaagtattcaagcattatattgtcatgtaaga
aactggagcttctcatgtttgtattgctgtagaagtaaacatgtatttgccatgcgtcatcagggaagttgcactcacgtc
caagaactttgttaaagtaaatcttggaataggtagctcatttgaaatgtagaaaaaattaaatccatatctgaattttgt
ttatatgtatgtacacgtaaactaaaaacgtatttaaagctagtattagatgagaaaagaggtttttttacttaaaatttta
aggcaaaagtagtttatcttagatcttgtgagattgtatttttggtttaaaatttgagaatttgagtgaagaaaaatcatgt
gaatgaaaatgcaacagataactcagattgccttataatagtctttgtgtttacctttattcagaatatcaaatgatagttt
attttgttgacttttttgcaaatgtttaacctaggtgacagatttttcttttttaaaaaaataaaacatcattaattaaatatg
tcatttcatttcttttttcttttctttttttttttttttaggacaaaatgtttcactttgggtaaatacattcttcataccca
ggaccagaggaaacctcagaaaaagtagaaaatggaagtctatgtgatcaagaaatcgatagcatttgcagtatagagcgtg
cagataatgacaaggaatatctagtacttactttaacaaaaaatgatcttgacaaagcaaataaagacaaagccaaccgata
ctttttctccaaattttaaggtcagttaaattaaacattttgtggggttgttgacttgtatgtatgtgatgtgtgtttaatt
ctaggagtacagctgatgaagaacttgcttgacaagtttttaacttatgtattatttcgaagcagtgtttacgtagcagtaa
catgaaagtttctaataaaatacccaatgtacacagcgtcaaaaaagctgcatttttcctttttcctaattcttcgttgtttg
ctgaaatctggggcaaaggtgcgggagggggctaaatgactgggatatgaagtaggaatgggagaggaaagaaatagatggg
aactcagtcatttgggaatgattcatatggaatgtttttactgcttccactcctgtctgccttccaatttattctcaatccc
tcagagtgatcttaaaaatagacttgattgtgtcactttctgtttacactttataaggaccttgtgttttttttttttaccctg
acctacaaggcccagcataatttagcacagggctacctcctacatcagcactagtcacctctctcctgtttcttgagatt
cagtcatactggtctttcttcagttcttcaaaatgctaagcttctgcctcttctagtctttccagttattttccttctccct
gtaccttttcatctcagccttttccccctgaccttccatagctatcttcatatttccagccttagcttcaatctcatattctc
tgaagtcctttgattgtcctccgttattcttttttttaaaaatcctatttccttatattgtatcttagaattatttggtttg
tttcattttttgcctatgtgtgatatatgtatttctacataggtatatatatctacttatagacaagaattcttcagattaaa
aaaatctgatttgtaaacattcccaagtggttgtttaccatttttttttcttccccctttcctatttcttattctacctgatttt
cccctgttcattcacccactcgtttctttctcttttttactctctcttaattttttcattcaattttttataacatgtaataa
atctaactgtagcgtctgagtattaagaatattgctagtaatacttcacctgtaatcccagcactttgggaggctaaggcag
gcggatcacttgaggcccaggagtttaagaccagcctggccaatatggcgaaaccctatctgcactacaaatacaaaaattag
ctgggcatggtgtcgcacacctgtaatcccagctacttgggaggctgaggcacaagaattgcttgagcctgtgagatggagg
ttgcagtgagccgagatcacaccagtgcacgtgcacttcagcctgggcaacagagcaagactctgtcttaaaaaaaaaaaaa
aaaaaaaatatatacacacacacacacacacacacacacacacacactattactacccaatatacatacatatatgtatg
tatgtatgtatgtatattggtagtaatagtaatacttgggccctgcacgttttaagtgaaaatagatctaatattaaatgt
ctttagcccttaaattttttttttaagtgttcagaagtttcccttaaaaaaattttttaatatataataattgtacatatttat
gggatacagagtgatatttttcatgtatgcagtgtgtgatgatcaaatcaggataattagcatatggatcacctcaaacattt
gtcatttctttgtgttaggaacattcaaaattctgtcttctagctatttgaaaatatacagtaaattattgttgactagtta
cagttctatagaacactataatttattcctcctgtgtgtaatttttttatctttttaacccaacatctccctatcctcccctccc
actccctttcccggcctctaataacccacactcttatgagctcaactttttttagcttccatatatgagtgagaacatacggta
tttatctttctgtacctgacttattttacttaacatcatgtcctcgggctagacattctcttttagaatccacaggtttcct
ttcttttctctaaatctgcatttttgctcagccattaactttttaaaatgtcttttttccctttagtttttattgtttttcctattttt
aatattgcaagatgtttttatatttgtgattacaaataaaaactccattattagtaaacaaatacaatgtcatatagtagtaa
gtgctataaaaaatagacaggatagaaagtaatcttggtttgtatgtttttttgtttttttagcaaagatgattagagaaggcc

FIG. 4 (Continued)

caacccaagcagataacatttaagcagaggcctaaatcatatcagtgagttatacaaatatctgggaaaagagttaagagtac
agatgcaaaagcccttagacaagagaatgagcttggtatatctgaagagtggataagtcatttgactgaaacagagtggac
aagaaaaccagtccaagtgtaaagacactagtgtgtgttcagcataggaaggatgtaatctgaattttgtgtttaatattcc
ctgtgttcatgctttcaaaatacagatgagtgaggaaagtagggagaaggggtaataaaggaagctgagagatcagttaaga
ggtacttgaatagtttagtaaagatgagagaagatgtttgcttcttgttgcccctcactgcttagaatagtggcagtgaagg
gtaacaagaagctgtcagattaacttaaagagtttactgatgcagtggatgttggttgtaagagaagaattgataatgactc
ttggataatagggggagggaggggctgtcaatataatataatgaagaagggatttgaagtcatttctgatttaaatctcacat
ccactacctactttaatagatatgtagcctttaacaagttccctaacctttctgggccttagctacctccccttggaaatg
gaaatacctaacatgtaaggttgttttgacagttattttcactaggcatgtaaaggcacttgactctctgttatagaccact
gtattatgttaatgtccctctccttcctccctttaggtaaagttttagggctaataaatcccaaatatcaatgttgatcag
tagtttgtgtttgtgtagtgttgtttatatcaaaaactacattgaagccgggcacagtggttcacgcctaaaatcgcaacac
tttgggaggccaaggtgggcctcccaccttgaactaaggagtttgagaccagcctgggcaacatggtgaaatcccatctcta
caaaaaatataaaagctagctgggtgtggtggcatgcacctgtagtcctagctacttgggaggctgaggttgatcctgggag
tttgagcctgcagtgagctgtgaagatgccactgcactctagtctgggtgacagagcaagaccctgtctcaaaaacacacac
acacacacacacacacaaagaaatacattgattttcacataggtagtaagagaaacattctttttgaactcagctgttt
gtgaattgaattttgtaattcaaatgctatattatgtaaactattgatgactttcaatctgcatttattttgtataattatt
tagttaatatttgccacttatattccttaaaaaataaaattgaggttgggcgtggtggctcacacttgtaatcccagcactt
tgggaggctgaggcaggcagattgcctgagctcaggagtttgagatcagcctgggcaacatcatgaaccccatttctactaa
aatacaaaaaattatctgggcatggtggtgtacacctgtagccctagctgtttgggaggctaaggcacgagaattgcttgaa
cccgggaggcagaggttgcagtgagccaagatcatgccactgcactccagcttggcaacagagcaagactcttgtctccaga
aataaaaataaataaattgtattaacatcctgatagtttatctgtttagtacctagcaagaaagaaaatgttgaacatctta
agaagagggtcatttaaaaggcctcttaaagatcatgtttgttacagtgcttaaaattaatatgttcatctgcaaaatgga
ataaaaatctgttaaaatatatttcactaaatagtttaagatgagtcatatttgtgggtttttcatttttaaatttttcttttc
tctaggtgaagctgtacttcacaaaaacagtagaggagccgtcaaatccagaggctagcagttcaacttctgtaacaccaga
tgttagtgacaatgaacctgatcattatagatattctgacaccactgactctgatccagagaatgaacctttgatgaagat
cagcatacacaaattacaaaagtctgaatttttttttatcaagagggataaaacacccatgaaaataaacttgaataaactga
aaatggaccttttttttttttaatggcaataggacattgtgtcagattaccagttataggaacaattctcttttcctgaccaa
tcttgttttaccctatacatccacagggttttgacacttgttgtccagttgaaaaaaggttgtgtagctgtgtcatgtatat
accttttgtgtcaaaaggacatttaaaattcaattaggattaataaagatggcactttcccgttttattccagttttataa
aaagtggagacagactgatgtgtatacgtaggaatttttttcctttttgtgttctgtcaccaactgaagtggctaaagagcttt
gtgatatactggttcacatcctacccctttgcacttgtggcaacagataagtttgcagttggctaagagaggtttccgaagg
gttttgctacattctaatgcatgtattcgggttaggggaatggagggaatgctcagaaaggaaataatttttatgctggactc
tggaccatataccatctccagctatttacacacaccttcttttagcatgctacagttattaatctggacattcgaggaattg
gccgctgtcactgcttgttgtttgcgcattttttttaaagcatattggtgctagaaaaggcagctaaaggaagtgaatctg
tattggggtacaggaatgaaccttctgcaacatcttaagatccacaaatgaagggatataaaaataatgtcataggtaagaa
acacagcaacaatgacttaaccatataaatgtggaggctatcaacaaagaatgggcttgaaacattataaaaattgacaatg
atttattaaatatgttttctcaattgtaacgacttctccatctcctgtgtaatcaaggccagtgctaaaattcagatgctgt
tagtacctacatcagtcaacaacttacacttattttactagtttcaatcataatacctgctgtggatgcttcatgtgctgc
ctgcaagctttcttttttctcattaaatataaaatattttgtaatgctgcacagaaattttcaatttgagattctacagtaag
cgtttttttttctttgaagatttatgatgcacttattcaatagctgtcagccgttccaccctttgaccttacacattctatt
acaatgaattttgcagttttgcacatttttttaaatgtcattaactgttagggaattttacttgaatactgaatacatataat
gtttatattaaaaggacatttgtgttaaaaaggaaattagagttgcagtaaactttcaatgctgcacacaaaaaaaagaca
tttgatttttcagtagaaattgtcctacatgtgctttattgatttgctattgaaagaatagggtttttttttttttttttt
ttttttttttaaatgtgcagtgttgaatcatttcttcatagtgctcccccgagttgggactagggcttcaatttcacttctt
aaaaaaaatcatcatatatttgatatgcccagactgcatacgatttttaagcggagtacaactactattgtaaagctaatgtg
aagatattattaaaaaggtttttttttccagaaatttggtgtcttcaaattatacctttcaccttgacatttgaatatccagc
cattttgtttcttaatggtataaaattccattttcaataacttattggtgctgaaattgttcactagctgtggtctgaccta
gttaatttacaaatacagattgaataggacctactagagcagcatttatagagtttgatggcaaatagattaggcagaactt

FIG. 4 (Continued)

catctaaaatatttcttagtaaataatgttgacacgttttccatacccttgtcagtttcattcaacaatttttaaatttttaac
aaagctcttaggatttacacatttatatttaaacattgatatatagagtattgattgattgctcataagttaaattggtaaa
gttagagacaactattctaacacctcaccattgaaatttatatgccaccttgtctttcataaaagctgaaattgttaccta
aaatgaaaatcaacttcatgttttgaagatagttataaatattgttctttgttacaatttcgggcaccgcatattaaaacgt
aactttattgttccaatatgtaacatggagggccaggtcataaataatgacattatcatgggcttttgcactgttattattt
ttcctttggaatgtgaaggtctgaatgagggttttgattttgaatgtttcaatgttttgagaagccttgcttacattttat
ggtgtagtcattggaaatggaaaaatggcattatatatattatatatataaatatatattatacatactctccttactttat
ttcagttaccatccccatagaatttgacaagaattgctatgactgaaaggttttcgagtcctaattaaaactttatttatgg
cagtattcataattagcctgaaatgcattctgtaggtaatctctgagtttctggaatattttcttagacttttttggatgtgc
agcagcttacatgtctgaagttacttgaaggcatcactttttaagaaagcttacagttgggccctgtaccatcccaagtcctt
tgtagctcctcttgaacatgtttgccatactttttaaaagggtagttgaataaatagcatcaccattctttgctgtggcacag
gttataaacttaagtggagtttacggcagcatcaaatgtttcagcttttaaaaaataaaagtagggtacaagttttaatgttt
agttctagaaattttgtgcaatatgttcataacgatggctgtggttgccacaaagtgcctcgtttacctttaaatactgtta
atgtgtcatgcatgcagatggaaggggtggaactgtgcactaaagtggggcttttaactgtagtatttggcagagttgcctt
ctacctgccagttcaaaagttcaacctgttttcatatagaatatatatactaaaaaatttcagtctgttaaacagccttact
ctgattcagcctcttcagatactcttgtgctgtgcagcagtggctctgtgtgtaaatgctatgcactgaggatacacaaaaa
taccaatatgatgtgtacaggataatgcctcatcccaatcagatgtccattttgttattgtgtttgttaacaaccctttatct
cttagtgttataaactccacttaaaactgattaaagtctcattcttgtca

FIG. 5

Natural antisense sequence (p73as): SEQ ID NO: 8

>gi|16445433|ref|NM_017818.2| Homo sapiens WD repeat domain 8 (WDR8), mRNA

GTTGCAGCCTGCTGCGCGCCCAGGGGTCCCGCGGGTTTTCGGGCGCAGGGTGGCGCCCGCGGCAGGCGGCGGCCATG
AACTTCTCCGAGGTATTCAAGCTCTCCAGCTTACTCTGCAAGTTCTCCCCGGACGGCAAGTACCTGGCTTCCTGTGT
CCAGTACCGGTTAGTGGTCCGGGATGTGAACACCCTTCAGATCCTTCAGCTGTACACGTGCCTAGACCAGATCCAGC
ACATCGAGTGGTCGGCAGACTCGCTCTTCATCCTGTGCGCCATGTACAAGCGAGGGCTGGTGCAGGTCTGGTCTTTA
GAGCAGCCCGAATGGCACTGCAAAATAGACGAGGGCTCAGCCGGGCTGGTGGCCTCGTGCTGGAGCCCGGACGGGCG
CCACATTCTCAACACCACGGAATTCCATCTGCGGATAACCGTCTGGTCCTTGTGCACAAAATCCGTGTCTTACATCA
AATACCCGAAAGCTTGTCTGCAGGGAATCACCTTCACCAGGGACGGCCGCTACATGGCGCTGGCAGAACGGCGCGAC
TGCAAAGATTACGTGAGCATCTTCGTCTGCAGTGATTGGCAGCTCCTGCGGCATTTTGATACGGACACCCAGGATCT
CACAGGGATTGAGTGGGCCCCAAACGGCTGTGTGCTGGCAGTGTGGGACACCTGCTTGGAGTACAAGATTCTGCTGT
ACTCATTGGATGGCCGGTTGTTGTCCACGTACAGCGCTTACGAGTGGTCCCTGGGCATCAAGTCTGTGGCCTGGAGC
CCCAGCAGTCAGTTCCTGGCAGTTGGGAGCTATGATGGAAAGGTGCGCATCCTTAATCACGTGACTTGGAAAATGAT
CACGGAGTTTGGGCATCCTGCAGCCATTAATGATCCCAAGATAGTGGTGTATAAGGAGGCCGAGAAGAGCCCACAGC
TGGGACTGGGCTGCCTCTCCTTCCCGCCGCCCCGGGCCGGGGCCGGCCCTCTCCCGAGCTCAGAGAGTAAATATGAG
ATCGCCTCTGTCCCAGTCTCCTTACAGACACTGAAACCTGTTACCGACAGAGCAAACCCGAAAATGGGCATAGGAAT
GCTGGCATTTAGTCCTGACAGCTACTTCCTGGCGACAAGGAACGACAACATTCCCAATGCCGTCTGGGTCTGGGACA
TTCAGAAGCTGAGGCTGTTCGCGGTGCTCGAGCAGCTGTCCCCAGTGCGCGCGTTTCAGTGGGACCCGCAGCAGCCG
CGGCTGGCCATCTGCACGGGAGGCAGCAGGCTCTACCTGTGGTCCCCAGCGGGCTGCATGTCGGTGCAGGTGCCTGG
GGAAGGCGACTTTGCAGTGCTCTCTCTGTGCTGGCATTTAAGCGGAGACTCGATGGCCCTCCTCAGCAAGGATCACT
TCTGCCTCTGCTTCCTGGAGACAGAGGCAGTGGTCGGCACAGCCTGCAGACAGCTGGGCGGCCACACGTAGCAGCGG
TGCACTAACGTGTGCAGAAACAGGGCTACTCTGTGTTTCCAGTGTGGGAAAAAACACAGCTTCACCAGGAGGTTCTC
CACTGTGGTGGTCTGGATTCAGTGATTGATTCTATTTTTCTATAGCAAAGCATTTTTGTAAATATGTATGGTATAAA
ACTGTAGTTTTATTATTTAAAATAAATACTTGCTGATTTAAAAAAAAAAAAAAAAAA

FIG. 5 (Continued)

p73Natural antisense sequence (Hs.668503): SEQ ID NO: 9 gcaagaggGCTGCCAAGGCTACTAATCAGACATGCTGGGTCCACAGGGCTGTCCCCAAACTGGAAAGAAGTCCTAGAAAATA
GATGATTCTTCCTAAAACGTAAATTGGATCATGCCTCTCCCCCAACAGTCTCATGGCTATGGAAGGGAATCCTGTCCCCCAA
GGGGTTCTCCCTCCTGTCTCCTCCAAGAACCAGGCAGTGTGGGGTGGGCAGCAGGACCCAGGGTCTCgGAGCTGGGGCCTC
CCCAGCCTCACTTGGGGCCTCCAAGGCTAAGTTCTGTGACCTCCAGGGCCCAAGAGTGAGTTCCTCTGGCTGCTCCAGAAAG
TGAAGAGAGAAGAGCCAACCCCGGCTCGGGCCACGAGCCCCGAGGCaCTGACCACAGCCAGAGCAGGCCTGCTGGAAGCTCC
GTCCCTGCTGCAGATCCCTGCGCCACATGATATCAGCAATTGCTGCAATTTCGCCCTAAGTACTCTTGTTTCCCCTAATAAT
CCACGTTTCATCTCCACAATAAACAT p73Natural antisense sequence (Hs.674463): SEQ ID NO: 10

CACTACAGGGAACGGCCCAGGAACCCATCCACCCGTCCCCAGCTCTCATCACTCTGACCTCTGGCTTTTTGTTTCCTGGGGC
ATTTCACAGCAAATTCCACCTATGAGACCGTCTCATCCGTAATACACCAGTACATGCTTCCAGCAGCTTGGTGACATGAAAG
GACCTCCGTGGCTGGCCTTACTCCCTGTGGATGCCACAGCTGCAGGATCCTGGGGCCCCAACAGAAGCCGGTGAAGGAAGAG
TTCCTGCTCCAGCAGAACAAAACTGCCCTTTGCCCAGAAATCCTGCAAACTGAGGCTGGACGACTTGAAATACTCATCAGCG
AGATTACCACGAAGCCCAGGTGCGAGGGACCCTCACGCCTGTTGCTGCGTGGGCCGCCCAGACATCGCCAGAGACCAAACCG
CAGAAGATGCTCGGAGCCCAACATCTACAAACCTGCCCCGCCACGGaCCCCAGGCTCAGAAACTGGTTTTTAGTCAGCTCCA
ATGATTAGCTTTTTTTTTTTTctcTTTGgTTcCCATAGAAATGCCTCTTCAAAGCATTATGGGACAACACACCCACCCAGTT
TCTGTACCGgTGGAGCTTCTgGGGGAAGTTTCAGgACTAGGAAcacacagggcGGCTCAGGACACAtTCACCCCAAAGTATG
ACTGTGGAGACCAGAATACGCCACCCTAAATATGACTATAGGAGACCAGAATACGTACCCCAAAATATGcCTGTGGAGACC
AGAATAGCCACCCAAATATcc Natural P73 antisense sequence (Mouse) (WD repeat domain 8): SEQ ID NO: 11

>mm9_knownGene_uc008wbj.1 range=chr4:153516481-153542372 5'pad=0 3'pad=0
strand=+ repeatMasking=none GTACTTCCGGCCGCTGCCTGGGCGGTTGCGGGAGGTACTTCGGAGCCGGGCTGGCCCGGGCTGGCCGTGGCCATGAACTTC
TCGGAGTCATTCAAGCTCTCGGGCCTGCTCTGCAGGTTCTCCCCGGACGGCAAGTACCTGgtgagctgcggcgcgctgggcg
gaacctaagtgtgggcgcgcgacttgtgcacggggccggggcgggccgaagggggggcgggaagggggcccgagccgggcggc
cgcgggggactcaggctggacttagggggcggggtgggaggtgggagagggaggcaggcagaggggtttcagcccagatgagg
gagaaccagatgattagagagaacgaacctgaagccgaagagggatccaggccagccaggctggggggatcctggcaggtgac
cagggtggagaaagaggacgtggagcagagtggggatggagttggggttgctattctggcaggtggtcagggttaggaagga
ggtcttggagcaggtggccagggctgggtgggtgccaggctcccggctccagtttcccttcatcaaagttggataagatgac
tctgctttcacacatttgagggcacaggggatggcagctcattgctatttgtatgttttctgtgagcgagctggttaaacg
gggccctcctttgtgaaactcgtcataagcaaatggtttaaataactagctttcattgccagggttggatgttagctgtcta
ttctttgggtggcagaatagtgttcagatgggtgtttcaaggtacgccaacatgaccattgtgcatttgtagaaggctgacg
ttaggaagccatcagggaaaactcaagtcttattttaaaaactgtggttccgtgccagtcgggtagcttggctagtaacgg
tacctgccaccaaacctgatgacctgagtcccagctctaggacccactttaatggaaggagagaactgtctcctgcatgttgt
cctctggcctccacataagccgtaactagtgcctgacccttctcacatacaaatgcaatcctaattttaacaagttttctt
tgattaatctatcattctcttttaactgactgataccattgattgattgattgactgattgacagggtttctctgtagctc
tgaccaggttggccttgaactcaaagatctgccccttgtctcctgagtgctgggattaacggagcatgccaccatgcctggc
tgtcttgattctcagttcacaccctgctgtgtttgtccaggctttgagacatcctttaccctccttatacacatcatcct
aacaatgtaggaagtgtcagggtaggacctgcttagcagggaaaggtactgccatgcaagcccgaggacttgagctcggct
cgggaacccacgtaaaggtgggaggagaccatcagcctcgcacacattgatacatttaccttttccaagtgcctccagag
actaaggttgctttacggttctgaaagtctcagtgaacagcaaagaagttgcatttgggttagctgatatttgtgcttgccg
ctcatcaaaatatcgtggagctcttaataattgtttctttcaagtttgtcctaaatcctgagcagagcgagtccatgtttc
cagtgttggtgtcttaagtgattcctaaggaatccattgtaacaggttactgctcaccaaactctaatgtgagaacacaagc
cctttgataggtcctccttctgatctgcacttgccctcttgctctctttccacagaagacaaatgtggcttcattaaaaaaa

FIG. 5 (Continued)

aaagagtctgtgtgtgtgtgtgtgtgtgtgtgagtgagagagagagagagacagagacagagacagagagacagagatagaa
acagagagatgctacaacacacgtgtagagggcagaggacaaccccccagtgttattccttaccttccaccttgtttgagaca
aggtctcttgctcttcactgcataaagcaggctagctggcccacatgtacctgcctcagcctcccctctgcctcccctctgc
ctcctcatagaaactaggatttttaaacagtttttaggattaacacagttttatgtggcttctgtgcatccaaacctgtttct
gaggcaagtgcaagtttttggctttagacaatggcataatatgcaaagctggcctcagactcagaaagtagttgagcacct
ccctagtacagtgattacaagtgtgcacccatcactcccaagtagtaaaaaaatacacacacacacacacacacacacaca
cacaggctttttgagacagtttctctgtgtagccccagctgtcctggaactcactcagtagagggaggctggcctcaaactc
agggatctgcccacctctgacttctgagtgctgggattaaaggagtgcaccaccccatctttaaatttacttgtacagatg
gctcagcgggtaagagcactgactgctcacccaaaggtcctgagttcaaatccccgcaaccacttggtggctcacaaccacc
cgtaatgagatctgatgccctcttctggtgcatctgaagacagctacagtgtacttactatataataataaataaatcttta
aaaaaatttacttgtacaaatttgtgggttagagtatgataatttggttaatatatactgtgtggaacttttaaactttga
atgctccacctttatcttttctaactcatttgcaatgagacccatcagttttggtccacatgaagctaagtgtgtcgaa
caggaggggaggagctggccattgaggcaaggctccctgctgtagaagagatgctatcccgtgctgtctgcctcactttta
gGCTTCCTGTGTCCAGTACCGATTAGTGATCCGGGATGTGACGACCCTTCAGATCCTTCAGTTGTACACATGCCTGGACCAG
ATCCAGCACATAGAGTGGTCTGCAGACTCCCTCTTCATCCTGTGTGCCATGTACAGGCGGGGCTTGTGCAGgtttgtacca
ccatgtattagtagagtgtatagatgggtgctacatgtctgtgggccttgaacaggcatgtgccacttacatatatgatgtg
tgtaggcaggcacatgccacatatacataagactcacataagtgtgtctcatgtgtaactaactggtctggcgctgtttctg
tagcagagttagaattaggaaacgtttccaggagtgtgactaggaaggagtccaggtgtttgcaccctctttcaggtttag
ggggaaatgcaatgagactcaaggttgcctttcttttcttatgtgtaatttatttattttatgtgcattggtgttttatctgt
atgcatttctgtgtgatggtgtcaggtctcagagttaccgatagctgtgagctgcagtacgggggctgggaattgaacgggg
tcatcaggaagagcagtcagtgctctcggctgctgaggcatctctccagccccccagatatgctttctttaaaatgtaatgc
tctctaatagtttaatccaaacactttttgatgtggaaaaacaaacaaacaccacccaaaacagtaaattgttctcagtctttg
agcatgatttttctttttttttttttttttaaagatttatttattggttatatgtaagtacactgtagctgtcttcagacact
ccagaagagggcgtcagatctcgttacagatggttgtgagccaccatgtggttgctgggatttgaactcggaccttcagaa
gaacagttgggtgctcttacccactgagccatctcaccagccccgagcatgatttttctgagcgggaggtatttgcaatggc
agtggaacaacttggacagggttctaggaagttctagaaggttctagaaggccgtgttccagtattcactaagcctaactaa
tgaggtcacagggatgggcacatgagcagacccttcaaaggtgcactgcagtgaagtcaccaggaagtgtggcttgtagcca
ctgggccatctgaggtagcatggtgtatatcctctccctcagagaggcctcctgcgtggtacagctatttgcactcctctgt
gtttcttttatgaatcaagGTCTGGTCACTCGAGCAGCCAGAATGGCACTGCAAGATCGACGAGGGCTCTGCGGGGCTGGTC
GCTTCCTGCTGGAGTCCAGATGGCCCCCACATCCTGAACACAACCGAATTTCATgtaagctggccaaacgtagcccactctg
ttcttcgcctaaaatagcctgggaatgtgaaagtctggttctggagcagtattcaggccagagttcataaacagtataattt
ttaaactctatttaaagaaaaataggacattaaaggagttggcaagatggctcagtgggtatggctcttgctacccaagcc
ttgcccacatggtggagggtaagaacgacagatgccccaaagttagagtaacaagggaaaatgtatgtcttctgtaatgggct
gttacaggctgcagtgctcatgctgacatcttaaagggacaggtgctcatgttgacatcttaaagggacaggtgctcatgtt
gacatcttaaagggacaggtgctcatgttgacatcttaaagggacatttggcctgggctttggctgcatatttgagtgttt
tctagacccactttggccagcaatcttcatgcttatggagttctgcagacccagagtccagcttccagatctcatagacttggg
ctcagtccctccgttaatggcccaaaggaaaggttacccactgcagaatttataaactgttttttaatgtactttttttattc
agcagctgtgttacactcactgaaatggaaaggaacatttggacagagagtagactgtacagactgcctctgtacactgtta
acctactgctaggtcatagccactgtgcctgtgacattaaagtgaatggcaacatcctgtgtggaggaatatgtcacagcaa
ggggaccctgaaaaatatacccctcctttttgttgtattgagatgggatctcactgtgtagccttgactggcctggaacgca
ctatgtagactaggcttgcctcaaactcagagagctgcctgcctctgcttcttgactactgggagtaaagtagccaccagtc
ctatcttattccaagcctttagatttagcttctaaaagtcccacagacttcatttacccaccagctatgctcagtagtcagg
aggtgaccctgtgcgcatgacagattcgtagagtggacacataactgagagtcatatgttcccgctcacaacagttagatcg
ctgtgtactcttctgggggcaggaagtccacgtgagggtgctgcaagatggagagaggcccagctcccatgagacaaggga
agacgattgaattgtgtggctggtgtctgtctggtccgtggaagacactcccctgcacacgcacacttcccagagcacctcc
aggccttgagaggctgccagcctccagagggcacctttgactgcattgcacaaaagccatttcaccttttggagagtct
tggggtccccgatgcatatgacactgtgcggtttacagcagctcacaggttacattgcctgtacaagggccctcctagccgg
catagctgctgctcttgttccttgtgaggaaaggctctctggggcacactcacctgccgtctgctgctgggcatgagttgtg
aggcaccagtggctttggcctttcttatgcacctcttctagtgtctggatccttccaggctagtgcaggtgggtgtgtgcgc

FIG. 5 (Continued)

agcttccaggctagtgcaggtgggtgtgtgcgcagcttccaggctagtgcaggtgggtatgcgcagcttcccgagggtttgc
atcaggatttgaagtggcgagacgttgcagcatcgtggggcttttgaaaatctcagttactctccactttatattttgaggc
aatgtctcttacttgaacccagagctccccagttctgcagttcagctagcttcctgtccctggggtcatagacaggtcaccg
cacaccctggggtgtgcaggagtgctggggttccagactcacttgagcagtaaggcttccccggagatttccccagccccac
actgtgtgtgtgggctcagttgtcacctggcgaatggagacatttgctctcatggctgctctgtgtgggtgcactgaagtaa
actgcacatgagtgtgcggtgtgggtccatgtttatgtattccagctttaagactctttgtgaagatgggaagcatcctaac
ccttctctcccctttccctggcagCTGCGAATCACGGTCTGGTCCCTGTGCACCAAATCTGTATCTTACATCAAGTATCCCA
AGGCCTGCCAGCAGGgtgagtctgtctttacacagtccttgtaactgttctgagagtgtgcacttagagcagatagaggagc
tacagcagcacctctcccccagcctccatcactgtgcacccctcccccagcctccatcactgtgcacccctcccccagcct
ccatcactgtgcacccctcccccagcttccatcactgtgcacccctcccccagcctctatcactgtgcacctctccccca
gcctccatcactgtgcacccctcccccagcctccatcactgtgtacccctcccccagcctccatcactgtgcacccctccc
ccagcctccatcactgtgcacacctcccccagcctccatcactgtgcacacctcccccagcctccatcactgtgcacccct
tcccccagcctctatcactgtgtacccctctcccagcctccatcactgtgcacccccctcccccagcctccatcactgtgta
cccccccagcctccatcactgtgcacccccctcccccaagcctccatcactgtgcaccccctcccccaaagcctccatcact
gtgcacccccctcccccaaagcctccatcactgtgcacccccctcccccagtctccatcactgtgtaccctcccccaaagcct
ccatcactgtgcacccccctcccccaaagcctccatcactgtgtaccccctcccccaaagcctccatcactgtgccatcctctg
tgctccttcctgtgtgtctgtgagattccctccatgccatttctttgacaacaggatgctgtaaaaagtagacaggcattgt
cctgggaggagaacctttaccttcattcacacagggcactcagcttgcctttggtgcctagctgtcagcttcacttcactaa
ctttttttagtcaagatttattttaggatgtgtgtgtgtgtgtgtatgtgtgtgtgtgtgtataagagagagagagaggtg
tatctgtgtgtgtatgtgcatgcatatgtgtgtctgtgtgcatgtatgtgtgtgagagagagggagagggagaggaagagat
gtgtatctgtgtgtgtctatgtgtctgtatgcatgtgtgtgtgtgtataggtgtaggtataggtgtgtatgtctgtctgcgt
gcatgtgtgtgtgtatgtgtgtgtgtgtgtgtgcgtgtggtgtatgggtaatgtgaatgcaagttgaagttacaggtgatag
tgagctgcttgttctgggttctgggatcagtttcaggaaagcagcacttttaaaaaagatttatttatattatacataa
gtacactgtagctgttttcagacatgccagaagagggcgtcagatctcattacaggtggttgggagccaccatctggttgct
gggatttgaactcaggacctcagtgccctacctgctgagccctcgccagcccacagcacaagtctttatccagtgagccat
ctccagctcagctcactagctcttctgtcgggatggcatgctgtctgtcacctctgagcatctcagaacagggaaaggagga
aggctgggccgagtgcatggggtgacgggtggtcatgccacccacctgccccaaacccagaaactaacagtagagggcacac
agtagggggcacacagaggggcacgaagtaggggcacacataggcatgctcttgtttgtttgttgccacaaggacaatatgtc
taatgttgcagatcacattagactgatggcatcgtaagtctgtttgtgggttttgtgtcttaagtgctactggatctaaagaa
cagtctggccctgggtgcaggtggtcctcaagtctgttatctgaagtgttcttgtcattcttgaggccttgaccgcaggcct
tttacagtaatgcagggctggaaaaaagttacttaatgtttttaagtaagattgtcccgaatatttctttacaactttagtta
tttgaaatgacaagttcaaaaggtgactcagcatctttcagaggactctaggtcactgcccagcacccaggtcaggaggctc
acaactgcctgtagcttcagctccgacggaatggactcttccgtcctcggcgcgcaccctgcaggctgtgtgtataccta
tacacagatgtacacacatccatacactaattaaaataaaagcgaaacgaaatgcagtgacacagctgactcagtgtata
aagtgctttgtggagcatgagaacgggagttcaaatctccagacctacaataaaggccaggtacagaggcagaagtctgtgat
cccagcacccccacatcaagatgggaggtggaaactaagaattccagaagcttgcaggccagctagactggcatgtgcagtt
gcaaacaaaagatctgtctcaaacaaggtggatgagcaatatagacgcccaggttgtcctcttagccctcatacatacata
tgcatggcacatgtgcctaaattcacacacatggaccaccaccacccacacacacacaactgcaagctgggtttgacccatca
ggtatgcctgtagttccctttgtgaaacatggccctctgctgtgtttcacaaagtgacatttgtgactctttaagaatcagg
tccttgggtttgattctgtataatcacccgcctcacctgcaagagggataagggctctgcttgtcagagtcctacgtgacaa
tgtcttgctcatgggaagatgagaaggacacatttccggggcggggcggggagagctcgctccccccttgtcccttttaaaa
agtccctgatgtgctccagtcctttcccacacttggttccatctggttccagtttaccatctctctccacagGACTAACTTT
CACCAGGGATGGCCGCTACCTGGCCTTAGCAGAGAGCCGGGACTGCAGGGACTATGTCAGCATCTTTGTGTGCAGTGACTGG
CAGCTCCTCCGGgtaaggccatccctctgctgctggctgggaaaaggggtagaactagcgttcctggtgatcccagaggctgt
tgcagcccctggggtagacagaatgatggggttcccatggccagaggacaggggccctgtgtgtgactccaagcagtgcaca
ctacgtgtgatctagactccctggtgcatgcacacttggtgcacagtagaagttagcatgttgacatgaactttgaaccctc
tttctccataagggaattcctccctgggaggaatgcagtttttgttggcctgggtaaaatgtctcaggagccgtgacactgag
caaatgctctctgtgcccacaagcttcagtgtcagagtgttagagagacatctgaaggggcgccctgggaagcagggtgcgg
gtgggcaggggtccatgggatgagggcatgcggccttgcccagcatggttggcacactgtgtgcactcaccagaacaacac

FIG. 5 (Continued)

acagatactttgtctgttgctgcatataaaatgatacatgaaccaaaagcattagttagaaaataaatgcactacttgtcta
aggacatgttttccaactgtcatgttttttttctcatctggaagCACTTTGACACAGACACCCAGGATCTCACAGGGATCGA
GTGGGCCCCGAATGGCTGTGTACTGGCCGCGTGGGACACCTGCTTGGAGgtatagcacatgaccagcagcacagtccctttc
aggaatgttcacctgcaggtacctgtgtgctcagtgcatcgagctgctgggtgctggcgtgccgcacgcagggcctgtgact
gtgtcaatgtctcatctgcagTACAAGGTTCTGCTGTACTCCTTGGACGGCCGCCTGCTGTCAGCATACTGTGCCTATGAAT
GGTCCCTGGGCATCAAGTCTGTGGCTTGGAGCCCCAGCAGTCAGTTCCTGGCCATTGGGAGCTACGATGGAAAGgtaggaag
tggctcagggctcaggccaactcgacgagctgtaggacacctgcagccgtgagctacctgcatgtcattctcacggttcct
tccccagGTGCGCCTCCTAAATCACGTGACCTGGAAGATGATAACTGAGTTTGGGCATCCTGCAACCATTAACAACCCCAAG
ACAgtaagtctgcatacgcttccacccgagcaccgtggtctcccgggtgcagggagccgccctgaccctccttagttgctg
tgatgttgtcttccctgttctgcccctcatgccctccttggtgaagggcatttggagtccaggctcgtccgtggactgatcc
tgtcctagccggatgctcatcatgctctgccctcggcagatccctgggagagtgagctgaggaatcctgagcgtgggccatc
ctgccagagcagggcacaccgcaggcagagaggccgggagagctggtctgtatggactgcagctagggcggcccaggcccag
gcccaggggtgcagagttgaaggcaggttctgaagctcagaggtgctgagtccgctgtcttctgtcagtgctgaagctcagt
agtgctgagtcctctgtcttctgtcagtgctgaagctcagtagtgctgagtcctctgtcttctgtcagtgctgaagctcagt
agtgctgagtcctctgtcttctgtcagtgctgaagctcaggagtgctgagtcctctgtcttctgtcagtgctgaagctcagt
agtgctgagtcctctgtcttctgtcagtgctgaagctcagtagtgctgagtcctctgtcttctgtcagtgctgaagctcagg
agtgctgagtcctctgtcttctgtcagtgctgaagctcaggagtgctgagtcctctgtcttctgtcagtgctgaagctcagt
agtgctgagtcctctgtcttctgtcagtggtctggaccaaggacaggtttctgcttcccttggacaaggagggccagggcca
tggccggggctcagttagctgccccaaagcctatgtctgcagaaccctgtaggaaggagaagctaggtggaggctgggctt
tagtcagggtgctcctcctgtaacagtggttgaaccttagagatgacagagtacaggctggccgtgcaggctgccaaggttt
gcctgtggttcaagcgcctgtctccccacgtgtgcactggtggtttctctgcctgggactgcggagtaccccactaacccta
agcgtgtgagtgaactttgtgtcacccgggtcagaggacccggggacacgatcaacctagttaaagtagaacgggttcatttt
ggctcctaatttctgaggtttcagtccatggtcccttcaccatttactttgggtagcacattgtggtggggacaaatggcag
agcagagctgaccttcagctgctctggccaagaagcagagaggaaggacaggtgaggtcccaatgtggccttcaaagtcatg
ctcccagtggcccgggcctgtaaggtccatgctagcaccaagtctgtcaggcctggccgtttgctactccacaggctcgctg
ccaccactgtcctctcctggcctactttctcctgtgcacacacaggccactgccgaatcgctgtgacatagctcaccatgt
aaacatagccatgtgctcagagccctctctaaaggacagcctggccagcagtactgcggtggcagctgcaaagggtcagact
tggccgccgcctcttcccagcgacctccgtgtggggcacatagataggttgggccaccttccactggctctcgtcacagact
gctagcagccacatcattgtttttcagGTTGTGTATAAGGAAGCTGAGAAGAGCCCACTGCTGGGGTTGGGCCACCTGTCCT
TCCCGCCGCCCCGAGCAATGGCTGGTGCCCTCTCTACCTCAGAGAGCAAATgtaagcagcagagggctgtgtcctccatggg
agaaagcttgtttttctctcttaaatgagaatcctctgtccacgtgaatctcagaggctgcttgttttgggtgtggaagat
gttaagatggggtctcaatcctgcagtgtagagacggcaggtgttctcctgtgaagcctgcctttcctccctgctctgcag
tccctgaaggagtgaggggacatcagctgtgcagcacccgcttggagggggggaggcagccaggctgtaggttgctcatgct
ggcttgtgcttacttatttctgttgggtgatagttctttgattcccagctggaaaggggtagccacctgtgccccgagacg
ctggaaatgggtggacagaactgccaggtgtccaagtagtggggactagctcagaaagcagggcttcagagcagggctgtat
cctgcactggaactgttgtccccagggaacctgtgaacgtgcctctcacccacagctgtcctcttaatccctcctgtgcttct
ctgcagtgtgtttccttccctctctttgccctctccccttaaccagtgcccttagcccgtccccgtcgtgttgcagATGAG
ATCGCCTCGGGACCAGTTTCCTTGCAGACTCTGAAGCCAGTAGCTGACAGAGCGAACCCGAGGATGGGTGTAGGGATGCTGG
CTTTCAGCTCTGACAGCTACTTCCTGGCATCAAGAAATGgtcagtgccacactcatttcgtaggcagggtcagctgctcgcg
gcccttttgaggcggagagtagagatgaaccgagaagcaaaggggcagctgtgtgctcctctccctggttcctgcagaaatgg
gcgttcagcacagcagctcctttctgcacagcagctccttgcccatggcctggccgcctggctgctccctcctgcactcctc
actgtgcaagaacagggcttacctctagtttgtttgcatttttttgggggggtgcctctgtgttttaatagtttatctcc
tttatatactttgtatcttgaccacagcctccctccttcctcgcctcccagtcccacccatacaaatccttccccattgccc
tgtcccctcctcctcagaggaggcgccctcccccacccccacctggggcaggactaagcacacttctcccactgaggccc
aactcggcagtccaggtaggggaaagggatccaggggcaggggctggacctaggcctccacactgtaggaaatgtacagttg
gtcttcttgtgggctccctaacaagtgaagtgggggctgtcttgtttgcatttgtacatctacagatgtaaaaaccacag
gaagaagaggtgtggctttggcaggccatgtctttgttctgggtgctggtccctgagaacagccagagggctggcagtgcca
gcactgacatgtgtcccgtctctgcttccttgcagACAATGTCCCCAATGCTGTCTGGATCTGGGACATTCAAAAGCTGAAG
CTGTTTGTGGTACTAGAGCATATGTCTCCAGTGCGCTCATTTCAGTGGGACCCACAGCAGCCGAGGCTGGCCATCTGCACAG

FIG. 5 (Continued)

GAGGAAGCAAGGTGTACCTGTGTGTCCCCAGCAGCTGCCTGTCGGTGCAGCTGCCTGGGGAAGgtaagcgtaagccagcaca
tgctggcctcagacaggctgacctgcttaaacctattgccacgtgtcatgcatgggaaagatgcccttctgcatcctgtagg
accttgcccagattgtgtgcctcacaggaactggctgtccttaaggtttactggctttgtcttcagccctggggtgaccaga
ctcctcactcacccgcaggccccggtctctaaccctctggctgcctgtctctctaggtgactttccagtgctcggactgtgc
tggcacttaagtggggattccttggccctccttagtaaggaccacttctgtctctgcttcctggagaccaaggagagggttg
gcacagcctacgaacagcgggacggcatgcctaggacctgagtggaaacccaggcagtagactgctgattccaacgtgagct
aacggctgcacaggttctccagatgggatgggctattctgcccagtttctgtaaatatgtataaagttatgtaaagtaggt
atttgctaatccattgaacagtggtggttgtttcttcaaggccttagctcacagacccaaggtcttgggaggataaagaat
cctgaagtaaggactcaagcctgcctcatggccttgcagactctgaagccagtagcgaacccgaggatgggtgtagggatgc
tggctttcagctctaacagctacttcctggcatcaagaaatggtcagtgccacactcattcgtaggcagggtcagcattccc
tgaggggtttctgtcagtgggctttggaacaaggtggactaatgtcagactggccagccctcctgcagctggatgtactca
gaagtgccccgcacctgtgcctgtccccgtgtgagctgtaaatcccacaacagttgggcaggtctctggccttacaagtgaa
ttctgcagagaggcctgggtcactgcctggtagagtggaagagctcagcccacccaaacctctctatctctagtaagtgcct
tgaaagcagacagaccagtatgtctgtactggtgaccagggttcccacaggactgcacacttgtgtatctgagtttctgta
aagaggaccatgctcacaagggtcctcagtcagccagacttcagtcctcaagacagtctttggcactcctgattctgtgaca
ataacttcaaaaaggagcaactccatttggtttaaatgtctttactagaacaaaagcacaggctgaaaacaggtgcatctga
ggtcacctttcctcttggataggccatggcattcggtcacatccatgccggttaactaaagcgagaggtatagagtgacag
gccagcatctacagtgcactggcaaggctagaacgacagcagcaagctgtgtgtggctggcgtgtcaaagctcagcagtgct
cagtgagctctaggatgctcgtctgtttatagcatgcacttttaaaacccaactattcagtccctttaaacagagacagga
tgatagaaacccaccaccatgacttcggaaggggctagcttatgttatgagagtaaccttttgggcctaggaaaactgctg
tattaacacaacctggattaatttataaagtgtgattctaagtcagacacattcacagaaaggcaggttcaccaggagctgc
caggcagactgtctttcttagtgactggctgctggctgctactgtatttagcttttttaaaaaacgggctgaatttaaaat
acagcacttgagagttaatatatagggagagttaaatatgtgcagaagccgctcactgtactcagctgtatgcaacagtcta
cacagcacaagtgggtggacattgtgctcggcatgctggagggagaacgtggcgttacagaaggaacacagtggtatgggg
cagctgaatctgcctttgtaagattgtgttgccaagatgtccaatatccaactaaatatacataatccacttgactattcta
atcggatacatgccctccttccctccagccagtgggtggcatgaggtggacagggagtccccaccaccttggtttccggga
cgcagctgtctagaagcctatcttgcccctggtcatggagtagcccagcttggcttcattgttgatgaaggacatgagcccc
acgtaggtctcgatgaggaggggggcgctccagcaccagcacggtattcgcctgccctggcagtgggctctccttctgggcct
tcttgacagcttggatcaggagagccttgaagctttccaactttgaagagaataaacatggagccttaacctcatgccaaga
cagcagtactgggaaacgaggattctgagttcaaatcctcccaaataccacatagtgatgacatcaccaatgacaggttggg
ccctatgagctgtgtcatcaggtggttcatcatgtacaaacatcatgaagggacctgccttaagtccaacctagagagtacc
agtctatctctaaagatgcagtcaggagattcggcagcctgagacaaggtactgccagtgccaacaggtggaaaatctttt
tacagacgcacatgctctggagtgcacctcactaagcaggtgatgctgtaattgcacacgctgcctgcactggtgtgctgtg
cactgactgacaggtagcatcacagatggaggaattcatgaggactatgatgtcaccaagtgacagggctttctcagccta
ctctaactgtgcagaatgctcagcgctccctcagcacctctcctgggaacttccagagtacctgtgtcacacagcagcacctg
ccaagccccgccagtactgtgggctttcccatgctcgctcacccacccagtccagactgagcatcctgcaatgggatggtg
actctgttcttaaacagcacccacctagcttcctactgtggaactgcacctccagggttcacactgacagtggccttggcctg
cttacatggcacagagacgctgtcttctcgtccatgccagccattgggtgttctatgaaggtggcataggcatgtttgtag
accaggggttccatctgttgatgaaggaagggcggctctgcttgtcccactgaatgcgaacccaaagccttctctcctgat
gggggaggggggagaaagccttgcttaccacaggaatacaacattgcattcagtatcagggatggctggggaacctgtgacct
agtgtaacaatggcctccactaacagcttcacacacttccaaagcgtaacaagttaatgagcctcctttgcagcctatgaaa
ccggcacacagtccaacctggcctaattatggccgtgtttgttcttaatgttactgaatgatgcttaagttagtagccatta
gcttcctggagtccctagtcaaataattcttttatagcaagccaaccagtctctgaaggctgttaggtgttttgcgatgtat
cgaattttttagtaatactgagcacatgccctgtgtctccctcctgctggagttaaaactcccagactccctacatagcttat
gacagtgggctctgattccatgtatcttaacggtatttaaatgaatggttttagtggggacagagtggccgactgtgccag
catccctttcaaggaggtactgagcaaccccggaaatcaccagcctctacttaaaggtcctttccactggttcttcaagatga
gacctttacctcacaagagagtgggtcaataccacttacaggatccgctggggccctgccgtgtagtgcgctggtgcaccta
cttgttgagcgacttcggaggaaactggaattctccacaggagatggtgtctacgcgctgagcgcgcaccctgaccacctgc
tggcactgaaggctgatgaagtcatatttgcagatgagcagcgactggtcggtgaccagcaccagcgctccttctcgttgt

FIG. 5 (Continued)

tccagtggtccaccctggagaggagagggggccgcccatcaccaagagccccgcctgccccgccgcccccgcccagtgtcc
ccgcagtccctcgcgccggcttactcggtcagcagccacaccccctggatctcgccgtcctccacgggccgtaccacgggcg
cggatctcctcgaccgcctgctcgatggtgccgggccggaacacgaagtactccttgacgcgggcgcggcgtgtagggtcgt
ggacgttcagcggccacaacgtctggcgcagcggtgtgcccgccccaggccggcccgcacccgcgtcctcgccggccgccag
caccgccgtggggctcgtgcccgccgagtccaccgtgtcccgcagctgcagcatcgcgccgccaccggcagcctccaccgac
ggccgccgccccggcgtccgcccggccgcgccccgccctccctcgttcgccttgtgattggttgagtcctgcagagccccgcc
ttccggacccgcctccagctccgtcgactgcgtctcgcgattggctttccctaagctgtcttctgcaattgggtctaaagt
gctgccgttcatgattacggcggccctcctgggccggaagctgccgccacgcgggagccacttcctgtttacaggaaggg
cgagttaaaaaaaaaaaaatgccggtcgggggttcctggctgagaacggggaaagggacgccatggactcgcgcggaaggg
ggcacttggggctcgtgcgtagggcgttgccccgacagtgtgtcctcgcttggtccgtgccctcaccttcgggcttacg
gtgcacttcgggcggaggtgtgcggcgcacttaggaggtgtgcatgcctggggagtgtgaaagtgtgggcatgggtgtgtgc
gcgtctgaggattgtgaaaggcgtgggaatgggtgtgtgcgcgtctgaggattgtggacactgtgtcggggcacctcagatag
aggcttctcaggagtgtgctgcactccttgggcgtggtcaccttgggagtgtgggtttatagggtgtgtgcacactggagat
aggagtgtgtgcaggtcagaggtggctgtcagagggttctttatattgggcatgatacgcacaagtaagctaccatgtcacc
gaagagtgctgctggggcgggggtgggggagttggaaggaaacgccgtaggatgctcttgggccctgcagcttctccctg
ggacagaagccatgcgagatgtccctgagttcctgctcccacggggtgccagcagtgtgcctgggttgatggagctaatgg
accgctatgatagtgtggcccaaaagtctttttctaacagtcaccaagacataggttagactcatcagtgaatgacagcccaa
gatacagctcaggcctgtagtctgtctcctgaccgttgtgagggctccttagcctgctggacctttacagtgtggcttcgt
cagagaatccagtccaatgaggtctccgggacactggtgggagcagccacgatgacgtgaattcccacagaggttcctgaga
ccgctgtggatgtgaagagtgtgctgaaagctgacagagaaaggggagatgaatagataagtgcatataaggcaataagcca
gggatggagaggtggctcagcagttaagaacactggctgctcttgggcgtggtggcgcacgcctttaatcccagcactcggga
ggcagaggcaggcagatttctgagttccaggccagcctggtctacatagtgagttccaggacagccagggctacacagagaa
accctgtctcgaaaaaaaaccaaaaaaaaaaaaaaaaaaaaatcaaggaggcttctacctttagggctggtaagatggctcagt
tggtaagagcacccgactgctcttccgaaggtccaaagttcaaatcccagcaacccacatggtggctcacaaccacccgtaat
gagatctgatgccctcttctggtgcatctgaagacagctacagtgtacttacatataataaataaataaataaatctttaaa
aaaaaaaacaaaaaacactggctgctcttccaaaggactggggttcaatccccagcacccacatggcagctcacgactctta
actccaggatccaatacccttacacagacttatatgcagacaaaacaccaatgcacataagaataatgtttaataacaccaa
taagcaaatgtcaagtttgtggcatgcatgaatcctaggtgtgagagagaaacatcatctatttctggctcagcctttctta
tacaacacaggactaccttgccctaaggtggcacccacatgaaatgggcagagccccccccccccatattactcaccaattaag
aaaatgttacagccgggcgtggtggcacacgcctataatcccagcactcaggaggcagaggcaggtggatttctgatactgg
cacttagagcctctcattcaaaggatcacggctaagcaggtgctctgtatctgtccggagcagaggggacgagcagcaggtg
tccgctctgaaacctggcttctacagaagtgtaaatcctttactaccgtgaggagtctccagtatccacactgtgaataaac
accattatatcttacgtgaggctgccaggacagacccacagactggcttgctggaagtaaccgaagcatgtagtgaggttgct
gagaccagagcggccagaaccacagtgtgtgtgcatgtgcgcttgcatgtgcatgtatgtgtgtccttctgatacctgaggc
acatgtcttcctttgcctttccagcctccctgttgtcagccatgctggatgtccctcagcctgtggctgcctctcccgtt
ggctgactttccatagtcatcgtcgctttctcatttgtaaggattcctgacgttggcacaggcctgccctaacggccccctt
ttgacctgatcatgttcacagactattttccaaagatggtgagagtcatggagactggttgggacttgcgtgtatcattaac
aggtacataattcaactggtgtgtgtgtgggggggggagggtgtttcgggcaggtgcaagcgatgaagcatttagatgacc
tccacgtgtgcacacaggtcacggcgggggcaaggagcaagacatgatgactgtgactagggagtaaggtattgggggccca
gagcttgggttggtcctgaggtccactagccgttgccagggatttttcaagaggctgttcccaaagtggtcagcagatggcgc
aactacccacacatggcctccctgggagatcacagtttggcaggtatgggatgttttcaagtcctagatgaagctgttatct
ttctgtagaagactcagaagctcagctataacaagcagattcttgccttaatttcctgatgctgtgacttagcattttggga
actcagcgggccctcctttttgaagtgctgagaatggatcccaggcctcccacatgctctgccacttgagatgcttcctcta
agactgagccccacctttgatacctgtgagaatcctgagcacgctggggtgggttctcagagctgcatggggctcctccaga
gctggtaccacacacacacacacacacacacacacggaggattgttgtgtgtgtggtccttccagagccagctgcactttgggt
cgtgcacagggtgtgcaccgctggaagtttgcctcaggaggcaatcctcgcactgccccaagctctgcgattgttgtgcttc
ccatgttaacctcggtcactgagtcaaagaatccacaacagatgcagaggtaactttgaaagagaaccgggttcccagactg
gagaggtggctcagcaggcaaaggtctttgctgccaccctgatgaccagagttcaattcctgggtcccacacagtggaagga
gagaagaaactcatgtagattgtcctttgacctccacacactctgagacatacgtatatacacacatgagttaaatgcacac

FIG. 5 (Continued)

acagacgggactagagaaagagcacagctcctaccacccagcccatcttggcagttgtctccctgatgtcccctctcacat
ctccctctctgttctcctacagggacccattctgataatccagaatgatctgatctgagaccccctctctcagtaacttcac
caaagaccccgtttccaaatcaggcccacgggggggatgtgggcatgaggacatgggctttcctagggaagctatgcaattc
agatgtgccatctccccagatgtgaacagataccatccctgcttgcagtgatgggtaaatatcccatacacttgccatccca
ggccttcctccctgacccccctgtggtaaagggtagatatacagtgatgggtggaggcctgggatgggccaggccaggccta
tgctgggaaacccacatggtggctggacggcagtctgctgtgtagcgttatatcggcttgatactggctagagtcattgggga
aacctcagttgagaaaatagcccccaccagacaggcctgtgggcaaacttatgtaacatttctttctttctttctttctttt
atttatttatttatttatttatttttggtttttcgagacagtgtttctctgtatagccctggctgtcctggaactcactctgt
agaccaggctggcctcgaactcagaaatccgcctgcctctgcctcctgagtgctgggattataggcgtgtgccaccacgccc
ggctgtaacatttcttaattggtgagtaatatggggggggggggctctgcccatttcatgtggtgccaccttagggcaagg
tagtcctgtgttgtataagaaaggctgagccagccttgggaggtaatgcagtggtgagcagaatctctctacggcctctgct
tcagttcctgccttcaaattcctgcctcgagttcctggcctgacttccctcagtgatggactctgacctgagagttgtaaga
agaaataaatctttcctcttctaatcactttcgatcatggtgtttcatcacagcagtgaaaacagaaactaagacagtagct
agatacccattgaagctggacaggctggatgctcagttactgagcaggagccagcctccagggacatagttaggtttcatgt
catgctcaaggtcaggatagagtgagtggtataggccaggcagctggccgccaacagggccaagcctaagccctgggcaaaa
tcctatgccctgaccccgtagtgagccttagcccatgtgagtcagcgtacttaggggccttccatttggcttctctctcac
agcagggttggagctttagaaatggatgtgggaatgggcgaacccacaggcttgtaaatggatcgtttgtcgtttagatgggg
cattgcatgtgtgctttgctctccagagactatccccatctgtctcttgagttttgccaaattctgctcaccccctaatgatg
ccatctgccccaaacaggtgactgtggtcacccacactgcacctgaggacctgatgatactttaggtgtctgtttctctttttgc
ttttgagagagagagtcttaacatgttgcacaggtcagcctccaaactccgatccttctgcctcagcctccttggtggagt
actgggatcaaagacaggcgtggctcttgggctgtgagccaacctttggtatcacttaggctagcctctcacctgttagaag
ctgacatgaaactcagacaaaacactagattgtcctcttgggatggtggccttcggctcagcagctgatgtccctgtggct
gctggggtactttgggtttctgtctggagggctatctcttccagctctgagatgcgtcaggctggagagcaggcagccagca
tggttctgggaaggagggagcggtttgctttggaaattagcgctgtggttcgagctctcctcttccccacattattttccc
tccagccaaagacgattctaatttatttccagtagagaatgagacaaggacagcgaaaagtatcgtctgctcggggaacaacg
gtgaaggccttaatcccatgccactgggagagacaggcagagctctgtgaattcaaggctaaactggtctctacagtgagctt
gagcacagccaaggctagtggaggtgtgggggggagtgcttttaggaaaatgagagcagttgttctccaagtgtgaaaaaaa
tggaactgcagcctcgcctcttgtctccttgggatgaactgccaagcaaagtccaacccagagtgtcatcagggttgtgact
cagtgacatttagcacactgctggtggaagccacggcggcagggtggacggaggaagggaaaatcctaggagatcctagga
ggtgggtgctgtagccacgggttctggcctggtgtgaatacccactcaattcgtgaaaactcaggactaaataaataaatata
tgtgtgggccaggcatggtggcacatgcctttaatctttagcattcaggagtcagaggcaggtggatctttttagttcaaggc
cagaatggtctacagaaagagttccaaggcagccagagctatatagagaaaccctgtctcaaaaaacaaaaacaaaaaaaaca
acgaaatgtttgtgtgtggtgtattaatgttttgctttaataaatatatttgtgtttcacatgatgctcaatgtccacagag
gctcagaagaggacatttggatccctaggaattagagttacagagcattgagtgactggccatgtgggtgctgggaatcaaac
ccaggtcctctaggagagcagtcagtgctcttaaccactgatttatctttccagACTCAAGGGCAAATTCGATCTTTACCCT
GTGAATGGGATGATCAGACCCTAAACTGGAATGTGACACGTGACCTATTTTCAATAAAGGATAGAACTGATGGCCCACCCTC
CTCCTGAAGCCAGCACTGTGGTTCGTCAATATGCCCAAGCCCACAAGAGGGCGCCATGCCAACAGTCCAGTTCCTGCAGATA
TCCTGAGGTTCTTGACAGCACATTTAAGGCAGTTGCAGCTAAATTCCAAAGTAACTAAAAGGAACTGGATAGATTAACCTCT
AAATTAATTTGGAACAATGACCAAGAATTGCCATTATAAGACCAACAAGATTCCTCGGCAGGTAAAAGTGACTGTTGACAAG
CCTAATGACCTGGGTTTGACCCCCGTGGCACACATCATAGAGGAAAAGGACCAGTTCCATCAAGTTGTCCTCTGATCCCTAC
ACGTGCACAGCGGCACATGTGATACCCAATAAATGAATGAGTCTAATAAAAAAATTTAAAAGTATCTGCAGGGAAAACCAAG
TAACGGATTTCTCAGACCTATGGATACAGCTATGTAAAGCCAATACCCAGAGTTATATCAGGAAGGTCTCAGTGGCCAGCTC
TTGCTCTGTCTTGTTCCAGCAAGGAAGGACAACTGACACAACAATTCTAGATGCAGTCATTGGAAACACCCAGAAGCGGGTG
CTGCATGTGTTGAGCTAGGAGAGAATATGATATCAGTAGTATCCTGGTGACCAGCTAGCCATTCGTCCTCTCCCTGAATGGC
AGACAGGGATGGACTCCGAGTGAGAAAATACACACAACAGATTGAACAACAGAGCAAGCAGCCACCTTCCTGAGCCAAGTGC
CTTATGCATTTTCACAGGCATGTTTACATGAGGACATTATCATGCAAGTACTTGATGAACCCGGAGTGCGCTCTCCCCCTCG
ACTCGCCCCTGCACTTATTTCTGAGTGATGGGGAGACAAGCCGAGTGCACACCTCGTGGAATTGAGCCGCCCTGTTGACCAT
GTTGTGACTGTCACTCCAGCCCGTGAGACAATTTGAAATAATCATGTCCAACCAGCTGTCGTAATTTGTTAGCTGTAAAGTT
GCAATATGCTTGCTGTGAGTTACAGAACTGTATTAAATACATTGTCATTTGATTCCTAGTTT

FIG. 5 (Continued)

Natural Antisense sequence Human Hs.668503 aligned to mouse chr4:SEQ ID NO:12 atggagagagcagacatacatctcaggtgcaggtaccctgctcagaccaagccggagccagcctactggcagcccattctct
ccggcaaagctagacacaATATgAGCAATTGCTGCgATTTCtCCaTAAGTgCTCTTGTTTCCCCTAATAATtCACGTTTCAT
CTCCACAATAAACATtgttagaactcttctctgggctttaaatatacataattgctcccgtgccagtcaaaggtattaatt
ccatttatgcattccataaactttttaggataac p53 Natural Antisense sequence (NM_018081.2):SEQ ID NO: 13

>gi|221136853|ref|NM_018081.2| Homo sapiens WD repeat containing, antisense to TP53 (WRAP53), transcript variant 1, mRNA GTCCCGGCTCCGCGGGTTCCGTGGGTCGCCCGCGAAATCTGATCCGGATGCGGCGGCCCAATCGGAAGGTGGACCGAAATC
CCGCGACAGCAAGAGGCCCGTAGCGACCCGCGGTGCTAAGGAACACAGTGCTTTCAAAAGAATTGGCGTCCGCTGTTCGCCT
CTCCTCCCGGGAGTCTTCTGCCTACTCCCAGAAGAGGAGGGAAGCACAGGTGGGTTTCTTTAGCTCTGCGTCGGATCCCTGA
GAACTTCGAAGCCATCCTGGCTGAGGCTAATCTCCGCTGTGCTTCCTCTGCAGTATGAAGACTTTGGAGACTCAACCGTTAG
CTCCGGACTGCTGTCCTTCAGACCAGGACCCAGCTCCAGCCCATCCTTCTCCCCACGCTTCCCCGATGAATAAAAATGCGGA
CTCTGAACTGATGCCACCGCCTCCCGAAAGGGGGGATCCGCCCGGTTGTCCCCAGATCCTGTGGCTGGCTCAGCTGTGTCC
CAGGAGCTACGGGAGGGGGACCCAGTTTCTCTCTCCACTCCCCTGGAAACAGAGTTTGGTTCCCCTAGTGAGTTGAGTCCTC
GAATCGAGGAGCAAGAACTTTCTGAAAATACAAGCCTTCCTGCAGAAGAAGCAAACGGGAGCCTTTCTGAAGAAGAAGCGAA
CGGGCCAGAGTTGGGGTCTGGAAAAGCCATGGAAGATACCTCTGGGGAACCCGCTGCAGAGGACGAGGGAGACACCGCTTGG
AACTACAGCTTCTCCCAGCTGCCTCGATTTCTCAGTGGTTCCTGGTCAGAGTTCAGCACCCAACCTGAGAACTTCTTGAAAG
GCTGTAAGTGGGCTCCTGACGGTTCCTGCATCTTGACCAATAGTGCTGATAACATCTTGCGAATTTATAACCTGCCCCCAGA
GCTGTACCATGAGGGGGAGCAGGTGGAATATGCAGAAATGGTCCCTGTCCTTCGAATGGTGGAAGGTGATACCATCTATGAT
TACTGCTGGTATTCTCTGATGTCCTCAGCCCAGCCAGACACCTCCTACGTGGCCAGCAGCAGCCGGGAGAACCCGATTCATA
TCTGGGACGCATTCACTGGAGAGCTCCGGGCTTCCTTTCGCGCCTACAACCACCTGGATGAGCTGACGGCAGCCCATTCGCT
CTGCTTCTCCCCGGATGGCTCCCAGCTCTTCTGTGGCTTCAACCGGACTGTGCGTGTTTTTTCCACGGCCCGGCCTGGCCGA
GACTGCGAGGTCCGAGCCACATTTGCAAAAAAGCAGGGCCAGAGCGGCATCATCTCCTGCATAGCCTTCAGCCCAGCCCAGC
CCCTCTATGCCTGTGGCTCCTACGGCCGCTCCCTGGGTCTGTATGCCTGGGATGATGGCTCCCCTCTCGCCTTGCTGGGAGG
GCACCAAGGGGGCATCACCCACCTCTGCTTTCATCCCGATGGCAACCGCTTCTTCTCAGGAGCCCGCAAGGATGCTGAGCTC
CTGTGCTGGGATCTCCGGCAGTCTGGTTACCCACTGTGGTCCCTGGGTCGAGAGGTGACCACCAATCAGCGCATCTACTTCG
ATCTGGACCCGACCGGGCAGTTCCTAGTGAGTGGCAGCACGAGCGGGGCTGTCTCTGTGTGGGACACGGACGGGCCTGGCAA
TGATGGGAAGCCGGAGCCCGTGTTGAGTTTTCTGCCCCAGAAGGACTGCACCAATGGCGTGAGCCTGCACCCTAGCCTGCCT
CTCCTGGCCACTGCCTCCGGTCAGCGTGTGTTTCCTGAGCCCACAGAGAGTGGGGACGAAGGAGAGGAGCTGGGCCTTCCCT
TGCTCTCCAGGCGCCAGGTCCACCTTGAATGTCGGCTTCAGCTCTGGTGGTGTGGGGGGCGCCAGACTCCAGCATCCCTGA
TGATCACCAGGGCGAGAAAGGGCAGGGAGGAACGGAGGGAGGTGTGGGTGAGCTGATATAAAAAGGTTTTTATGATAAAAAA
AAAAAAAAAAAAA PTEN Natural Antisense sequence (Hs.624903):SEQ ID NO:14 taaacgggnaaagatgccttnCTTTTTAAnCCTAATTGAATTTTAAATGTCCTTTTGACACAAAAAGGTATATACATGACAC
AGCTACACAACCTTTTTTCAACTGGACAACAAGTGTCAAAACCCTGTGGATGTATAGGGTAAAACAAGATTGGTCAGGAAAA
GAGAATTGTTCCTATAACTGGTAATCTGACACAATGTCCTATTGCCATTAAAAAAAAAAGGTCCATTTTCAGTTTATTCAAG
TTTATTTTCATGGTGTTTTATCCCTCTTGATAAAAAAAAAATTCAGACTTTTGTAATTTGTGTATGCTGATCTTCATCAAAAG
GTTCATTCTCTGGATCAGAGTCAGTGGTGTCAGAATATCTATAATGATCAGGTTCATTGTCACTAACATCTGtTGTTACAGA
AGTTtAACtTGCTAGCCTCcGGATTTGACGGCTCCTCTACTGccTTTGaGAAGTACAGtTTCACCTtaaatttttggagaaaa
cgttcacgttgactttgtctttattttcttacggcaagacaatttttgttataagtaagttcctatacttcccttgcattt
attttacaccctcctatatctgtcaatctttatctatttttttgtttaacaataaacccactaatttccctactttttcttc
caacgttatccacctatcacctggatcataaataatgtttttcttccccataagttcaaaactttttcccctcttttttc
cacccctcttttgattcttcgcaataaacctttatttgtttctccccac

FIG. 5 (Continued)

PTEN Natural Antisense sequence (Hs. 607931): SEQ ID NO: 15

AAGAAAATGGCATATTTGAAGAAATCATATGGCTAGACAAAACAAACTAGATAGATTGTGAAGCTAGATAGACTAAACCTCAG
TCTTGATTACTAATTACAAGCTGAATGTATAAATCTTTTCCTTCAGAGGCATAAAGGTAAGAGTTATGAATCAAATGGAAGG
ACCAAAATGCTTCCCAATGAAGTATTTTCTTGGTGAAGTTATTGCAATCTAAGGTCTGAAAATCAGCTGTACAGGAACTTTA
TCAGTAACCTAAAAGATGATCAATCAGCCTCAGTGACTAACGACACTGAGAAGAGACCAACGTAAAAACTAGCACACCAGAT
TAATTTACCACAAAGATATTCTCACCATAATCAGAAAACCTGCCCTCTATTCAGAGTATTCACTCTTTTTTGGTATGAGTAC
TAATCTGGCTGGGTcGAATTAGTGCTTAGTTGAATACAGAATTAAAATAATGTGAAG

FIG. 6

| Sequence ID | Sequence |
|---|---|
| SEQ ID NO:16 | G*C*C*T*C*C*T*T*A*T*A*C*A*C*C*A*C*T*A*T*C |
| SEQ ID NO:17 | G*T*G*C*T*G*G*A*T*C*T*G*G*T*C*T*A*G*G*C |
| SEQ ID NO:18 | A*C*C*A*C*T*G*C*C*T*C*T*G*T*C*T*C*C*A |
| SEQ ID NO:19 | rCrUrGrCrUrCrUrGrGrCrUrGrUrGrGrUrCrArGrUrGrCrCrUrCrGrG |
| SEQ ID NO:20 | rArUrUrCrCrCrUrUrCrCrArUrArGrGrCrArUrGrArGrArCrUrGrUrU |
| SEQ ID NO:21 | rCrCrArArGrCrUrGrCrUrGrGrArArGrCrArUrGrUrArCrUrGrGrUrG |
| SEQ ID NO:22 | rArGrArCrGrGrUrCrUrCrArUrArGrGrUrGrGrArArUrUrUrGrCrUrG |

FIG. 7

| Sequence ID | Sequence |
|---|---|
| SEQ ID NO:23 | G*A*T*G*T*A*T*G*T*C*T*G*C*T*C*T*C*T*C*C*A |
| SEQ ID NO:24 | G*G*C*T*T*G*G*T*C*T*G*A*C*C*A*G*G*G*T*A |
| SEQ ID NO:25 | C*C*T*G*C*A*C*C*G*G*A*G*A*T*G*T*A*T*G*T*C |
| SEQ ID NO:26 | C*C*G*G*A*G*A*T*G*T*A*T*G*T*C*T*G*C*T*C*T |
| SEQ ID NO:27 | G*C*C*C*A*C*C*A*C*C*T*C*A*T*T*A*T*T*C*C*C |
| SEQ ID NO:28 | C*C*A*G*T*C*C*C*A*A*G*T*C*C*A*G*C*A*G*A |
| SEQ ID NO:29 | G*C*C*T*C*C*G*T*G*A*A*C*T*C*C*T*C*C*T*T |
| SEQ ID NO:30 | G*T*T*C*C*G*C*C*C*A*C*C*A*C*C*T*C*A*T*T |

FIG. 8

| Sequence ID | Sequence |
|---|---|
| SEQ ID NO:31 | GGAGCAAGAACUUUCUGAAtt |
| SEQ ID NO:32 | CCAAUCAGCGCAUCUACUUtt |
| SEQ ID NO:33 | CCACCAAUCAGCGCAUCUAtt |

FIG. 9

| Sequence ID | Sequence |
|---|---|
| SEQ ID NO:34 | rUrUrCrArUrArArCrUrCrUrUrArCrCrUrUrUrArUrGrCrCrUrCrUrG |
| SEQ ID NO:35 | rArUrUrCrUrGrArCrArCrCrArCrUrGrArCrUrCrUrGrArUrCrCrArG |
| SEQ ID NO:36 | rArUrUrArCrCrArGrUrUrArUrArGrGrArArCrArArUrUrCrUrCrUrU |

FIG. 10

| Sequence ID | Sequence |
|---|---|
| SEQ ID NO:37 | rGrArGrGrCrArCrUrGrArCrCrArCrArGrCrCrArGrArGrCAG |
| SEQ ID NO:38 | rCrArGrUrCrUrCrArUrGrCrCrUrArUrGrGrArArGrGrGrAAT |
| SEQ ID NO:39 | rCrCrArGrUrArCrArUrGrCrUrUrCrCrArGrCrArGrCrUrUGG |
| SEQ ID NO:40 | rGrCrArArArUrUrCrCrArCrCrUrArUrGrArGrArCrCrGrUCT |

FIG. 11

| Sequence ID | Sequence |
|---|---|
| SEQ ID NO:41 | ACCTCTGGAGCTCTCTGGAAC |
| SEQ ID NO:42 | TATGATGGAAAGGTGCGCATCCTTA |

FIG. 12

| Sequence ID | Sequence |
|---|---|
| SEQ ID NO:43 | CTTCCCTGGATTGGCAGCCAGACTG |
| SEQ ID NO:44 | ATATGCAGAAATGGTCCCTGTCCTT |

FIG. 13

| Sequence ID | Sequence |
|---|---|
| SEQ ID NO:45 | rGrArGrGrCrArUrArArArGrGrUrArArGrArGrUrUrArUrGAA |
| SEQ ID NO:46 | rGrGrArUrCrArGrArGrUrCrArGrUrGrGrUrGrUrCrArGrAAT |
| SEQ ID NO:47 | rGrArGrArArUrUrGrUrUrCrCrUrArUrArArCrUrGrGrUrAAT |

TREATMENT OF TUMOR SUPPRESSOR GENE RELATED DISEASES BY INHIBITION OF NATURAL ANTISENSE TRANSCRIPT TO THE GENE

CROSS REFERENCE

This application is a divisional of U.S. application Ser. No. 14/533,371, filed Nov. 5, 2014, which is a continuation of U.S. application Ser. No. 13/133,039, filed Jun. 15, 2011, which is a National Phase Application of PCT/US2009/066654, filed Dec. 3, 2009, which claims benefit of U.S. Provisional Application Nos. 61/119,973, filed Dec. 4, 2008, U.S. Provisional Application No. 61/154,594, filed Feb. 23, 2009, U.S. Provisional Application No. 61/157,249, filed Mar. 4, 2009, and U.S. Provisional Application No. 61/166,381, filed Apr. 3, 2009, which applications are all incorporated herein by reference in their entirety.

FIELD OF THE INVENTION

Embodiments of the invention comprise oligonucleotides modulating expression and/or function of Tumor Suppressor genes and associated molecules.

BACKGROUND

DNA-RNA and RNA-RNA hybridization are important to many aspects of nucleic acid function including DNA replication, transcription, and translation. Hybridization is also central to a variety of technologies that either detect a particular nucleic acid or alter its expression. Antisense nucleotides, for example, disrupt gene expression by hybridizing to target RNA, thereby interfering with RNA splicing, transcription, translation, and replication. Antisense DNA has the added feature that. DNA-RNA hybrids serve as a substrate for digestion by ribonuclease H, an activity that is present in most cell types. Antisense molecules can be delivered into cells, as is the case for oligodeoxynucleotides (ODNs), or they can be expressed from endogenous genes as RNA molecules. The FDA recently approved an antisense drug, VITRAVENE™ (for treatment of cytomegalovirus retinitis), reflecting that antisense has therapeutic utility.

SUMMARY

This Summary is provided to present a summary of the invention to briefly indicate the nature and substance of the invention. It is submitted with the understanding that it will not be used to interpret or limit the scope or meaning of the claims.

In one embodiment, the invention provides methods for inhibiting the action of a natural antisense transcript by using antisense oligonucleotide(s) targeted to any region of the natural antisense transcript resulting in up-regulation of the corresponding sense gene. It is also contemplated herein that inhibition of the natural antisense transcript can be achieved by siRNA, ribozymes and small molecules, which are considered to be within the scope of the present invention.

One embodiment provides a method of modulating function and/or expression of an Tumor Suppressor gene polynucleotide in patient cells or tissues in vivo or in vitro comprising contacting said cells or tissues with an antisense oligonucleotide 5 to 30 nucleotides in length wherein said oligonucleotide has at least 50% sequence identity to a reverse complement of a polynucleotide comprising 5 to 30 consecutive nucleotides within nucleotides 1 to 1675 of SEQ ID NO:8 or nucleotides 1 to 518 of SEQ ID NO: 9 or nucleotides 1 to 759 of SEQ ID NO: 10 or nucleotides 1 to 25892 of SEQ ID NO: 11 or nucleotides 1 to 279 of SEQ ID NO: 12, or nucleotides 1 to 1982 of SEQ ID NO: 13, or nucleotides 1 to 789 of SEQ ID NO: 14, or nucleotides 1 to 467 of SEQ ID NO: 15 (FIG. 5) thereby modulating function and/or expression of the Tumor Suppressor gene polynucleotide in patient cells or tissues in vivo or in vitro.

In another preferred embodiment, an oligonucleotide targets a natural antisense sequence of Tumor Suppressor gene polynucleotides, for example, nucleotides set forth in SEQ ID NOS: 8, 9, 10, 11, 12, 13, 14 or 15, and any variants, alleles, homo logs, mutants, derivatives, fragments and complementary sequences thereto. Examples of antisense oligonucleotides are set forth as SEQ ID NOS: 16 to 36 (FIGS. 6 to 9).

Another embodiment provides a method of modulating function and/or expression of an Tumor Suppressor gene polynucleotide in patient cells or tissues in vivo or in vitro comprising contacting said cells or tissues with an antisense oligonucleotide 5 to 30 nucleotides in length wherein said oligonucleotide has at least 50% sequence identity to a reverse complement of the an antisense of the Tumor Suppressor gene polynucleotide; thereby modulating function and/or expression of the Tumor Suppressor gene polynucleotide in patient cells or tissues in vivo or in vitro.

Another embodiment provides a method of modulating function and/or expression of an Tumor Suppressor gene polynucleotide in patient cells or tissues in vivo or in vitro comprising contacting said cells or tissues with an antisense oligonucleotide 5 to 30 nucleotides in length wherein said oligonucleotide has at least 50% sequence identity to an antisense oligonucleotide to an Tumor Suppressor gene antisense polynucleotide; thereby modulating function and/or expression of the Tumor Suppressor gene polynucleotide in patient cells or tissues in vivo or in vitro.

In a preferred embodiment, a composition comprises one or more antisense oligonucleotides which bind to sense and/or antisense Tumor Suppressor gene polynucleotides.

In another preferred embodiment, the oligonucleotides comprise one or more modified or substituted nucleotides.

In another preferred embodiment, the oligonucleotides comprise one or more modified bonds.

In yet another embodiment, the modified nucleotides comprise modified bases comprising phosphorothioate, methylphosphonate, peptide nucleic acids, 2'-O-methyl, fluoro- or carbon, methylene or other locked nucleic acid (LNA) molecules. Preferably, the modified nucleotides are locked nucleic acid molecules, including α-L-LNA.

In another preferred embodiment, the oligonucleotides are administered to a patient subcutaneously, intramuscularly, intravenously or intraperitoneally.

In another preferred embodiment, the oligonucleotides are administered in a pharmaceutical composition. A treatment regimen comprises administering the antisense compounds at least once to patient; however, this treatment can be modified to include multiple doses over a period of time. The treatment can be combined with one or more other types of therapies.

In another preferred embodiment, the oligonucleotides are encapsulated in a liposome or attached to a carrier molecule (e.g. cholesterol, TAT peptide).

One embodiment provides a method of modulating a function of and/or the expression of a Tumor Suppressor gene polynucleotide in patient cells or tissues in vivo or in vitro comprising contacting said cells or tissues with at least one antisense oligonucleotide 5 to 30 nucleotides in length wherein said at least one oligonucleotide has at least 50% sequence identity to a reverse complement of a natural antisense of a Tumor Suppressor gene polynucleotide, thereby modulating a function of and/or the expression of the Tumor Suppressor gene polynucleotide in patient cells or tissues in vivo or in vitro.

One embodiment provides a method of modulating a function of and/or expression of a Tumor Suppressor gene polynucleotide in patient cells or tissues in vivo or in vitro comprising contacting said cells or tissues with an antisense oligonucleotide 5 to 30 nucleotides in length wherein said oligonucleotide has at least 50% sequence identity to an antisense oligonucleotide to the Tumor Suppressor gene polynucleotide; thereby modulating a function of and/or the expression of the Tumor Suppressor gene polynucleotide in patient cells or tissues in vivo or in vitro.

Another embodiment provides a method of modulating a function of and/or the expression of a Tumor Suppressor gene polynucleotide in patient cells or tissues in vivo or in vitro comprising contacting said cells or tissues with at least one antisense oligonucleotide that targets a region of the natural antisense of a Tumor Suppressor gene polynucleotide; thereby modulating a function of and/or the expression of the Tumor Suppressor gene polynucleotide in patient cells or tissues in vivo or in vitro.

In an embodiment, a function of and/or the expression of the Tumor Suppressor gene polynucleotide is increased in vivo or in vitro with respect to a control.

In another embodiment, the at least one antisense oligonucleotide targets a natural antisense sequence of a Tumor Suppressor gene polynucleotide.

In an embodiment, the at least one antisense oligonucleotide targets a nucleic acid sequence comprising coding and/or non-coding nucleic acid sequences of a Tumor Suppressor gene polynucleotide.

In an embodiment, the at least one antisense oligonucleotide targets overlapping and/or non-overlapping sequences of a Tumor Suppressor gene polynucleotide.

In a particular embodiment, the at least one antisense oligonucleotide comprises one or more modifications selected from: at least one modified sugar moiety, at least one modified internucleoside linkage, at least one modified nucleotide, and combinations thereof.

In a related embodiment, the one or more modifications comprise at least one modified sugar moiety selected from: a 2'-O-methoxyethyl modified sugar moiety, a 2'-methoxy modified sugar moiety, a 2'-O-alkyl modified sugar moiety, a bicyclic sugar moiety, and combinations thereof.

In another embodiment, the one or more modifications comprise at least one modified internucleoside linkage selected from: a phosphorothioate, 2'-O-methoxyethyl (MOE), 2'-fluoro, alkylphosphonate, phosphorodithioate, alkylphosphonothioate, phosphoramidate, carbamate, carbonate, phosphate triester, acetamidate, a carboxymethyl ester, and combinations thereof.

In an embodiment, the one or more modifications comprise at least one modified nucleotide selected from: a peptide nucleic acid (PNA), a locked nucleic acid (LNA), an arabino-nucleic acid (FANA), an analogue, a derivative, and combinations thereof.

In another embodiment, the at least one oligonucleotide comprises at least one of the oligonucleotide sequences set forth as SEQ ID NOS: 16 to 36.

The invention also provides a method of modulating a function of and/or the expression of a Tumor Suppressor gene in mammalian cells or tissues in vivo or in vitro comprising contacting said cells or tissues with at least one short interfering RNA (siRNA) oligonucleotide 5 to 30 nucleotides in length, said at least one siRNA specific for an antisense polynucleotide of a Tumor Suppressor gene polynucleotide wherein said oligonucleotide has at least 50% sequence identity to a complementary sequence of at least about five consecutive nucleic acids of the antisense and/or sense nucleic acid molecule of a Tumor Suppressor gene polynucleotide; and, modulating a function of and/or the expression of the Tumor Suppressor gene in mammalian cells or tissues in vivo or in vitro.

In an embodiment, the oligonucleotide has at least 80% sequence identity to a complementary sequence of at least about five consecutive nucleic acids of the antisense and/or sense nucleic acid molecule of the Tumor Suppressor gene polynucleotide.

Another embodiment provides a method of modulating a function of and/or the expression of a Tumor Suppressor gene in mammalian cells or tissues in vivo or in vitro comprising contacting said cells or tissues with at least one antisense oligonucleotide of about 5 to 30 nucleotides in length specific for noncoding and/or coding sequences of a sense and/or natural antisense strand of a Tumor Suppressor gene polynucleotide wherein said at least one antisense oligonucleotide has at least 50% sequence identity to at least one nucleic acid sequence set forth as SEQ ID NOS: 1, 2, 3, 4, 5, 6, 7, 7, 9, 10, 11, 12, 13, 14 and 15; and, modulating the function and/or expression of the Tumor Suppressor gene in mammalian cells or tissues in vivo or in vitro.

One embodiment provides a synthetic, modified oligonucleotide comprising at least one modification, wherein the at least one modification is selected from: at least one modified sugar moiety; at least one modified internucleotide linkage; at least one modified nucleotide; and combinations thereof; and further wherein said oligonucleotide is an antisense compound which hybridizes to and modulates expression and/or function of a Tumor Suppressor gene polynucleotide in vivo or in vitro as compared to a normal control.

In an embodiment, the at least one modification comprises an internucleotide linkage selected from the group consisting of: phosphorothioate, alkylphosphonate, phosphorodithioate, alkylphosphonothioate, phosphoramidate, carbamate, carbonate, phosphate triester, acetamidate, carboxymethyl ester, and combinations thereof.

In another embodiment, the oligonucleotide comprises at least one phosphorothioate internucleotide linkage.

In a related embodiment, oligonucleotide comprises a backbone of phosphorothioate internucleotide linkages.

In an embodiment, the oligonucleotide comprises at least one modified nucleotide, said modified nucleotide selected from: a peptide nucleic acid, a locked nucleic acid (LNA), analogue, derivative, and a combination thereof.

In another embodiment, the oligonucleotide comprises a plurality of modifications, wherein said modifications comprise internucleotide linkages selected from: phosphorothioate, alkylphosphonate, phosphorodithioate, alkylphosphonothioate, phosphoramidate, carbamate, carbonate, phosphate triester, acetamidate, carboxymethyl ester, and a combination thereof.

In an embodiment, the oligonucleotide comprises a plurality of modifications, wherein said modifications comprise modified nucleotides selected from: peptide nucleic acids, locked nucleic acids (LNA), analogues, derivatives, and a combination thereof.

In another embodiment, the oligonucleotide comprises at least one modified sugar moiety selected from: a 2'-O- methoxyethyl modified sugar moiety, a 2'-methoxy modified sugar moiety, a 2'-O-alkyl modified sugar moiety, a bicyclic sugar moiety, and a combination thereof.

In another embodiment, the oligonucleotide comprises a plurality of modifications, wherein said modifications comprise modified sugar moieties selected from: a 2'-O-methoxyethyl modified sugar moiety, a 2'-methoxy modified sugar moiety, a 2'-O-alkyl modified sugar moiety, a bicyclic sugar moiety, and a combination thereof.

In another embodiment, the oligonucleotide is of at least about 5 to 30 nucleotides in length and hybridizes to an antisense and/or sense strand of a Tumor Suppressor gene polynucleotide wherein said oligonucleotide has at least about 20% sequence identity to a complementary sequence of at least about five consecutive nucleic acids of the antisense and/or sense coding and/or noncoding nucleic acid sequences of the Tumor Suppressor gene polynucleotide.

In another embodiment, the oligonucleotide has at least about 80% sequence identity to a complementary sequence of at least about five consecutive nucleic acids of the antisense and/or sense coding and/or noncoding nucleic acid sequence of the Tumor Suppressor gene polynucleotide.

In another embodiment, said oligonucleotide hybridizes to and modulates expression and/or function of at least one Tumor Suppressor gene polynucleotide in vivo or in vitro, as compared to a normal control.

In an embodiment, the oligonucleotide comprises one of the sequences set forth as SEQ ID NOS: 16 to 36.

The invention further provides a composition comprising one or more oligonucleotides specific for one or more Tumor Suppressor gene polynucleotides, said polynucleotides comprising antisense sequences, complementary sequences, alleles, homologs, isoforms, variants, derivatives, mutants, fragments, or combinations thereof.

In a certain embodiment, wherein the oligonucleotides have at least about 40% sequence identity as compared to any one of the nucleotide sequences set forth as SEQ ID NOS: 16 to 36.

In an embodiment, the one or more oligonucleotides comprise any of the nucleotide sequences set forth as SEQ ID NOS: 16 to 36.

In another embodiment, the oligonucleotides set forth as SEQ ID NOS: 16 to 36 comprise one or more modifications or nucleotide substitutions.

In another embodiment, the one or more modifications are selected from: phosphorothioate, methylphosphonate, peptide nucleic acid, locked nucleic acid (LNA) molecules, and combinations thereof.

An embodiment of the invention provides a method of preventing or treating a disease associated with at least one Tumor Suppressor gene polynucleotide and/or at least one encoded product thereof, comprising administering to a patient a therapeutically effective dose of at least one antisense oligonucleotide that binds to a natural antisense sequence of said at least one Tumor Suppressor gene polynucleotide and modulates expression of said at least one Tumor Suppressor gene polynucleotide; thereby preventing or treating the disease associated with the at least one Tumor Suppressor gene polynucleotide and/or at least one encoded product thereof.

In a certain embodiment, a disease associated with the at least one Tumor Suppressor gene polynucleotide is selected from: a disease associated with decreased or increased apoptosis, tissue/cell aging, a cancer (including those mentioned in Table 1), an autoimmune disease, an immunodeficiency disease including AIDS, senescence, a neurodegenerative disease or disorder (e.g. Alzheimer's disease, ataxia telangiectasia, Parkinson's disease, amyotrophic lateral sclerosis, Huntington's disease etc.), a hyperplastic disease (e.g., cheloid), rheumatoid arthritis, coronary heart disease ischemic cell death, a lymphoproliferative disorder, atherosclerosis, osteoporosis, a myelodysplastic syndrome, a toxin-induced disease, a viral infection, wound-healing, Cowden disease (CD), Lhermitte-Duclos disease (LDD), Bannayan-Zonana syndrome (BZS, also known as Bannayan-Riley-Ruvalcaba syndrome, Ruvalcaba-Myhre-Smith syndrome and Riley-Smith syndrome), transplantation, an apotosis-related disease or disorder, a metabolic disease or condition (e.g., diabetes), a kidney diseases or disorder, myocardial infarction/heart failure, ischemia, sepsis, an inflammatory disease where particular haematopoeitic inflammatory cells are in excess, a proliferative disease, or a disease or disorder wherein there is a therapeutic paradigm for treatment of inflammatory disease through increasing apoptosis.

An embodiment provides a method of identifying and selecting at least one oligonucleotide for in vivo administration comprising: selecting a target polynucleotide associated with a disease state; identifying at least one oligonucleotide comprising at least five consecutive nucleotides which are complementary to, or in an antisense orientation to the selected target polynucleotide; measuring the thermal melting point of an hybrid of an antisense oligonucleotide and the target polynucleotide under stringent hybridization conditions; and selecting at least one oligonucleotide for in vivo administration based on the information obtained.

Other aspects are described infra.

BRIEF DESCRIPTION OF THE DRAWINGS

FIG. 4 shows:

Figure 1A:
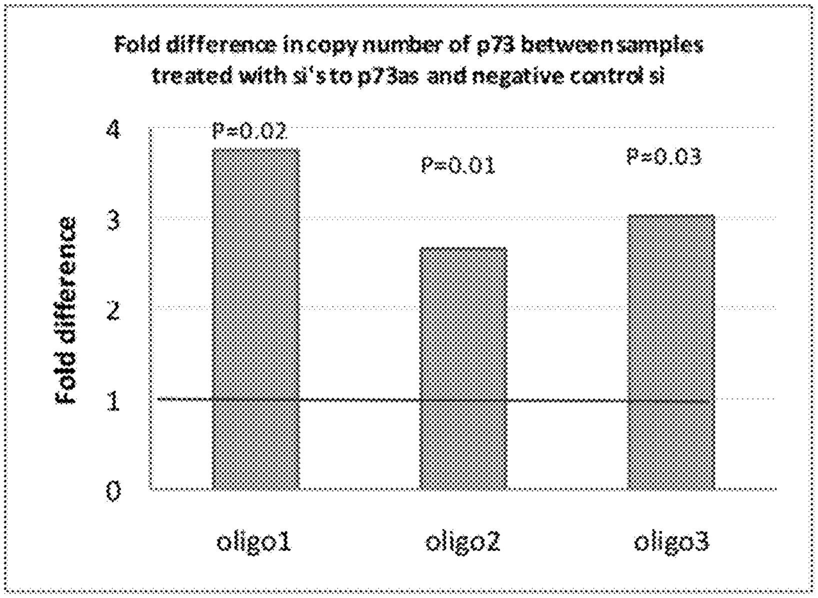
FIG. 1A and FIG. 1B: is a graph of real time PCR results showing the fold change in TP73 mRNA after treatment of HepG2 cells with phosphorothioate oligonucleotides introduced using Lipofectamine 2000, as compared to control. Real time PCR results show that the levels of the p73 mRNA in HepG2 cells are significantly increased 48 h after treatment with the oligos designed to p73as (FIG. 1A). In the same samples the levels of p73as RNA were significantly reduced after treatment with oligos to p73as (FIG. 1B). Bars denoted as oligo 1, oligo 2 and oligo 3 correspond to samples treated with SEQ ID NOS 16, 17 and 18 respectively.

SEQ ID NO: 1: Homo sapiens Tumor Suppressor gene (TP73) transcript variant 1, mRNA. (NCBI Accession No.: NM_005427.2)

SEQ ID NO: 2 shows the genomic sequence of p73 (exons are shown in capital letters, introns in small).

SEQ ID NO: 3 shows the mouse genomic sequence of p73 (exons are shown in capital letters, introns in small). SEQ ID NO: 2: Homo sapiens tumor protein p53 (TP53), transcript variant 1, mRNA. (NCBI Accession No.: NM_000546.4)

SEQ ID NO: 4: shows the genomic sequence of p53 (exons are shown in capital letters, introns in small).

SEQ ID NO: 5 shows the genomic sequence of p53 Isoform D (NCBI Accession No: NM_001126115).

SEQ ID NO: 6: Homo sapiens phosphatase and tensin homolog (PTEN), mRNA. (NCBI Accession No.: NM_000314).

SEQ ID NO: 7: shows the genomic sequence of PTEN (exons are shown in capital letters, introns in small).

FIG. 5 shows:

SEQ ID NO: 8: Natural antisense sequence p73as (NCBI Accession No.: NM_017818.2)

SEQ ID NO: 9: p73 Natural antisense sequence Hs.668503

SEQ ID NO: 10: p73 Natural antisense sequence Hs.674463

SEQ ID NO: 11: p73 Mouse Natural antisense sequence

SEQ ID NO: 12: p73 Mouse natural antisense sequence: Hs.668503 (Matching bases in cDNA and genomic sequences are indicated by capital letters)

SEQ ID NO: 13: p53 Natural Antisense sequence (NCBI Accession No.: NM_018081.2)

SEQ ID NO: 14: PTEN Natural Antisense sequence (Hs.624903)

SEQ ID NO: 15: PTEN Natural Antisense sequence (Hs. 607931)

FIG. 6 shows the antisense oligonucleotides, SEQ ID NOs: 16 to 22. 'r' indicates RNA and * indicates phosphorothioate bond.

FIG. 7 shows the antisense oligonucleotides, SEQ ID NOs: 23 to 30. * indicates phosphorothioate bond.

FIG. 8 shows the p53 antisense oligonucleotides to natural antisense sequence NM O 18081, SEQ ID NOs: 31 to 33.

FIG. 9 shows the PTEN antisense oligonucleotides to natural antisense sequence Hs.624903 and Hs. 607931, SEQ ID NOs: 34 to 36. 'r' indicates RNA.

FIG. 10 shows the sense oligonucleotides, SEQ ID NOs: 37 to 40. 'r' indicates RNA.

The sense oligonucleotide SEQ ID NO: 37 is the reverse complement of the antisense oligonucleotide SEQ ID NO: 19, the sense oligonucleotide SEQ ID NO: 38 is the reverse complement of the antisense oligonucleotide SEQ ID NO: 20, the sense oligonucleotide SEQ ID NO: 39 is the reverse complement of the antisense oligonucleotide SEQ ID NO: 21; and the sense oligonucleotide SEQ ID NO: 40 is the reverse complement of the antisense oligonucleotide SEQ ID NO: 22.

FIG. 11 shows SEQ ID NOs: 41 and 42 of the assays designed by Applied Biosystems Taqman gene Expression Assay SEQ ID No.: 41 is the p73 target sequence, exon 2 (Hs00232088_ml)

SEQ ID No.: 42 is the p73as target sequence, exon 7 (Hs00215135_ml and Hs00892470_gl)

FIG. 12 shows SEQ ID NOs: 43 and 44 of the assays designed by Applied Biosystems Taqman gene Expression Assay.

SEQ ID No.: 43 is the p53 target sequence (Hs00153340_ml)

SEQ ID No.: 44 is the p53as (WDR79) target sequence (Hs00216360_ml)

FIG. 13 shows the sense oligonucleotides, SEQ ID NOs: 45 to 47. 'r' indicates RNA.

The sense oligonucleotide SEQ ID NO: 45 is the reverse complement of the antisense oligonucleotide SEQ ID NO: 34, the sense oligonucleotide SEQ ID NO: 46 is the reverse complement of the antisense oligonucleotide SEQ ID NO: 35; and the sense oligonucleotide SEQ ID NO: 47 is the reverse complement of the antisense oligonucleotide SEQ ID NO: 36.

DETAILED DESCRIPTION

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the ordering of acts or events, as some acts may occur in different orders and/or concurrently with other acts or events. Furthermore, not all illustrated acts or events are required to implement a methodology in accordance with the present invention.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In preferred embodiments, the genes or nucleic acid sequences are human.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "mRNA" means the presently known mRNA transcript(s) of a targeted gene, and any further transcripts which may be elucidated.

By "antisense oligonucleotides" or "antisense compound" is meant an RNA or DNA molecule that binds to another RNA or DNA (target RNA, DNA). For example, if it is an RNA oligonucleotide it binds to another RNA target by means of RNA-RNA interactions and alters the activity of the target RNA (Eguchi, et al., (1991) *Ann. Rev. Biochem.* 60, 631-652). An antisense oligonucleotide can upregulate or downregulate expression and/or function of a particular polynucleotide. The definition is meant to include any foreign RNA or DNA molecule which is useful from a therapeutic, diagnostic, or other viewpoint. Such molecules include, for example, antisense RNA or DNA molecules, interference RNA (RNAi), micro RNA, decoy RNA molecules, siRNA, enzymatic RNA, therapeutic editing RNA and agonist and antagonist RNA, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

In the context of this invention, the term "oligonucleotide" refers to an oligomer or polymer of ribonucleic acid (RNA) or deoxyribonucleic acid (DNA) or mimetics thereof. The term "oligonucleotide", also includes linear or circular oligomers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. Oligonucleotides are capable of specifically binding to a target polynucleotide by way of a regular pattern of monomer-to-monomer interactions, such as Watson-Crick type of base pairing, Hoögsteen or reverse Hoögsteen types of base pairing, or the like.

The oligonucleotide may be "chimeric", that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide in the case of an oligonucleotides compound. These oligonucleotides typically comprise at least one region wherein the oligonucleotide is modified in order to exhibit one or more desired properties. The desired properties of the oligonucleotide include, but are not limited, for example, to increased resistance to nuclease degradation, increased cellular uptake, and/or increased binding affinity for the target nucleic acid. Different regions of the oligonucleotide may therefore have different properties. The chimeric oligonucleotides of the present invention can be formed as mixed structures of two or more oligonucleotides, modified oligonucleotides, oligonucleosides and/or oligonucleotide analogs as described above.

The oligonucleotide can be composed of regions that can be linked in "register", that is, when the monomers are linked consecutively, as in native DNA, or linked via spacers. The spacers are intended to constitute a covalent "bridge" between the regions and have in preferred cases a length not exceeding about 100 carbon atoms. The spacers may carry different functionalities, for example, having positive or negative charge, carry special nucleic acid binding properties (intercalators, groove binders, toxins, fluorophors etc.), being lipophilic, inducing special secondary structures like, for example, alanine containing peptides that induce alpha-helices.

As used herein "Tumor Suppressor gene" and "Tumor Suppressor gene" are inclusive of all family members, mutants, alleles, fragments, species, coding and noncoding sequences, sense and antisense polynucleotide strands, etc.

As used herein, the words Tumor Protein 73, p73, TP73 are used interchangeably in the present application.

As used herein, the words TRP53, Tumor suppressor p53, p53, P53 Antigen NY-CO-13, Cellular tumor antigen p53, FLJ92943, LFSI, and Phosphoprotein p53 are used interchangeably in the present application.

As used herein, the words PTEN, 10q23del, BZS, MGC11227, MHAM, MMAC1, Mutated in multiple advanced cancers 1, Phosphatase and tensin homolog, Phosphatidylinositol-3,4,5-trisphosphate 3-phosphatase and dual-specificity protein phosphatase PTEN, PTEN1, TEP1 are used interchangeably in the present application.

As used herein, the term "oligonucleotide specific for" or "oligonucleotide which targets" refers to an oligonucleotide having a sequence (i) capable of forming a stable complex with a portion of the targeted gene, or (ii) capable of forming a stable duplex with a portion of a mRNA transcript of the targeted gene. Stability of the complexes and duplexes can be determined by theoretical calculations and/or in vitro assays. Exemplary assays for determining stability of hybridization complexes and duplexes are described in the Examples below.

As used herein, the term "target nucleic acid" encompasses DNA, RNA (comprising premRNA and mRNA) transcribed from such DNA, and also cDNA derived from such RNA, coding, noncoding sequences, sense or antisense polynucleotides. The specific hybridization of an oligomeric compound with its target nucleic acid interferes with the normal function of the nucleic acid. This modulation of function of a target nucleic acid by compounds, which specifically hybridize to it, is generally referred to as "antisense". The functions of DNA to be interfered include, for example, replication and transcription. The functions of RNA to be interfered, include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of an encoded product or oligonucleotides.

RNA interference "RNAi" is mediated by double stranded RNA (dsRNA) molecules that have sequence-specific homology to their "target" nucleic acid sequences (Caplen, N.J., et al. (2001) *Proc. Natl. Acad. Sci.* USA 98:9742-9747). In certain embodiments of the present invention, the mediators are 5-25 nucleotide "small interfering" RNA duplexes (siRNAs). The siRNAs are derived from the processing of dsRNA by an RNase enzyme known as Dicer (Bernstein, E., et al. (2001) *Nature* 409:363-366). siRNA duplex products are recruited into a multi-protein siRNA complex termed RISC (RNA Induced Silencing Complex). Without wishing to be bound by any particular theory, a RISC is then believed to be guided to a target nucleic acid (suitably mRNA), where the siRNA duplex interacts in a sequence-specific way to mediate cleavage in a catalytic fashion (Bernstein, E., et al. (2001) *Nature* 409:363-366; Boutla, A., et al. (2001) *Curr. Biol.* 11:1776-1780). Small interfering RNAs that can be used in accordance with the present invention can be synthesized and used according to procedures that are well known in the art and that will be familiar to the ordinarily skilled artisan. Small interfering RNAs for use in the methods of the present invention suitably comprise between about 1 to about 50 nucleotides (nt). In examples of non limiting embodiments, siRNAs can comprise about 5 to about 40 nt, about 5 to about 30 nt, about 10 to about 30 nt, about 15 to about 25 nt, or about 20-25 nucleotides.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

By "enzymatic RNA" is meant an RNA molecule with enzymatic activity (Cech, (1988) *J. American. Med. Assoc.* 260, 3030-3035). Enzymatic nucleic acids (ribozymes) act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through base pairing, and once bound to the correct site, acts enzymatically to cut the target RNA.

By "decoy RNA" is meant an RNA molecule that mimics the natural binding domain for a ligand. The decoy RNA therefore competes with natural binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA (Sullenger, et al. (1990) *Cell,* 63, 601-608). This is meant to be a specific example. Those in the art will recognize that this is but one example, and other embodiments can be readily generated using techniques generally known in the art.

As used herein, the term "monomers" typically indicates monomers linked by phosphodiester bonds or analogs thereof to form oligonueleotides ranging in size from a few monomeric units, e.g., from about 3-4, to about several hundreds of monomeric units. Analogs of phosphodiester linkages include: phosphorothioate, phosphorodithioate, methylphosphornates, phosphoroselenoate, phosphoramidate, and the like, as more fully described below.

The term "nucleotide" covers naturally occurring nucleotides as well as nonnaturally occurring nucleotides. It should be clear to the person skilled in the art that various nucleotides which previously have been considered "non-naturally occurring" have subsequently been found in nature. Thus, "nucleotides" includes not only the known purine and pyrimidine heterocycles-containing molecules, but also heterocyclic analogues and tautomers thereof. Illustrative examples of other types of nucleotides are molecules containing adenine, guanine, thymine, cytosine, uracil, purine, xanthine, diaminopurine, 8-oxo-N6-methyladenine, 7-deazaxanthine, 7-deazaguanine, N4,N4-ethanocytosin, N6,N6-ethano-2,6-diaminopurine, 5-methylcytosine, 5-(C3-C6)-alkynylcytosine, 5-fluorouracil, 5-bromouracil, pseudoisocytosine, 2-hydroxy-5-methyl-4-triazolopyridin, isocytosine, isoguanin, inosine and the "non-naturally occurring" nucleotides described in Benner, et al., U.S. Pat. No. 5,432,272. The term "nucleotide" is intended to cover every and all of these examples as well as analogues and tautomers thereof. Especially interesting nucleotides are those containing adenine, guanine, thymine, cytosine, and uracil, which are considered as the naturally occurring nucleotides in relation to therapeutic and diagnostic application in humans. Nucleotides include the natural 2'-deoxy and 2'-hydroxyl sugars, e.g., as described in Kornberg and Baker, DNA Replication, 2nd Ed. (Freeman, San Francisco, 1992) as well as their analogs.

"Analogs" in reference to nucleotides includes synthetic nucleotides having modified base moieties and/or modified sugar moieties (see e.g., described generally by Scheit, Nucleotide Analogs, John Wiley, New York, 1980; Freier & Altmann, (1997) *Nucl. Acid. Res.,* 25(22), 4429-4443, Toulmé, J. J., (2001) *Nature* Biotechnology 19:17-18; Manoharan M., (1999) *Biochemica et Biophysica Acta* 1489: 117-139; Freier S. M., (1997) *Nucleic Acid Research,* 25:4429-4443, Uhlman, E., (2000) *Drug Discovery & Development,* 3: 203-213, Herdewin P., (2000) *Antisense & Nucleic Acid Drug Dev.,* 10:297-310); 2'-O, 3'-C-linked [3.2.0] bicycloarabinonucleosides (see e.g. N. K Christiensen., et al, (1998) *J. Am. Chem. Soc.,* 120: 5458-5463; Prakash T P, Bhat B. (2007) *Curr Top Med Chem.* 7(7):641-

9; Cho E J, et al. (2009) *Annual Review of Analytical Chemistry,* 2, 241-264). Such analogs include synthetic nucleotides designed to enhance binding properties, e.g., duplex or triplex stability, specificity, or the like.

As used herein, "hybridization" means the pairing of substantially complementary strands of oligomeric compounds. One mechanism of pairing involves hydrogen bonding, which may be Watson-Crick, Hoögsteen or reversed Hoögsteen hydrogen bonding, between complementary nucleoside or nucleotide bases (nucleotides) of the strands of oligomeric compounds. For example, adenine and thymine are complementary nucleotides which pair through the formation of hydrogen bonds. Hybridization can occur under varying circumstances.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated. In general, stringent hybridization conditions comprise low concentrations (<0.15M) of salts with inorganic cations such as Na++ or K++ (i.e., low ionic strength), temperature higher than 20° C.-25° C. below the Tm of the oligomeric compound:target sequence complex, and the presence of denaturants such as formamide, dimethylformamide, dimethyl sulfoxide, or the detergent sodium dodecyl sulfate (SDS). For example, the hybridization rate decreases 1.1% for each 1% formamide. An example of a high stringency hybridization condition is 0.1× sodium chloride-sodium citrate buffer (SSC)/0.1% (w/v) SDS at 60° C. for 30 minutes.

"Complementary," as used herein, refers to the capacity for precise pairing between two nucleotides on one or two oligomeric strands. For example, if a nucleobase at a certain position of an antisense compound is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleotides which can hydrogen bond with each other. Thus, "specifically hybridizable" and "complementary" are terms which are used to indicate a sufficient degree of precise pairing or complementarity over a sufficient number of nucleotides such that stable and specific binding occurs between the oligomeric compound and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The oligomeric compounds of the present invention comprise at least about 70%, or at least about 75%, or at least about 80%, or at least about 85%, or at least about 90%, or at least about 95%, or at least about 99% sequence complementarity to a target region within the target nucleic acid sequence to which they are targeted. For example, an antisense compound in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. As such, an antisense compound which is 18 nucleotides in length having 4 (four) noncomplementary nucleotides which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., (1990) *J. Mol. Biol.,* 215, 403-410; Zhang and Madden, (1997) *Genome Res.,* 7, 649-656). Percent homology, sequence identity or complementarity, can be determined by, for example, the Gap program (Wisconsin Sequence Analysis Package, Version 8 for Unix, genetics Computer Group, University Research Park, Madison Wis.), using default settings, which uses the algorithm of Smith and Waterman (*Adv. Appl. Math*., (1981) 2, 482-489).

As used herein, the term "Thermal Melting Point (Tm)" refers to the temperature, under defined ionic strength, pH, and nucleic acid concentration, at which 50% of the oligonucleotides complementary to the target sequence hybridize to the target sequence at equilibrium. Typically, stringent conditions will be those in which the salt concentration is at least about 0.01 to 1.0 M Na ion concentration (or other salts) at pH 7.0 to 8.3 and the temperature is at least about 30° C. for short oligonucleotides (e.g., 10 to 50 nucleotide). Stringent conditions may also be achieved with the addition of destabilizing agents such as formamide.

As used herein, "modulation" means either an increase (stimulation) or a decrease (inhibition) in the expression of a gene.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs,) or single base mutations in which the polynucleotide sequence varies by one base. The presence of SNPs may be indicative of, for example, a certain population with a propensity for a disease state, that is susceptibility versus resistance.

Derivative polynucleotides include nucleic acids subjected to chemical modification, for example, replacement of hydrogen by an alkyl, acyl, or amino group. Derivatives, e.g., derivative oligonucleotides, may comprise non-naturally-occurring portions, such as altered sugar moieties or inter-sugar linkages. Exemplary among these are phosphorothioate and other sulfur containing species which are known in the art. Derivative nucleic acids may also contain labels, including radionucleotides, enzymes, fluorescent agents, chemiluminescent agents, chromogenic agents, substrates, cofactors, inhibitors, magnetic particles, and the like.

A "derivative" polypeptide or peptide is one that is modified, for example, by glycosylation, pegylation, phosphorylation, sulfation, reduction/alkylation, acylation, chemical coupling, or mild formalin treatment. A derivative may also be modified to contain a detectable label, either directly or indirectly, including, but not limited to, a radioisotope, fluorescent, and enzyme label.

As used herein, the term "animal" or "patient" is meant to include, for example, humans, sheep, elks, deer, mule deer, minks, mammals, monkeys, horses, cattle, pigs, goats, dogs, cats, rats, mice, birds, chicken, reptiles, fish, insects and arachnids.

"Mammal" covers warm blooded mammals that are typically under medical care (e.g., humans and domesticated animals). Examples include feline, canine, equine, bovine, and human, as well as just human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

As used herein, the term "cancer" refers to any malignant tumor, particularly arising in the lung, kidney, or thyroid. The cancer manifests itself as a "tumor" or tissue comprising malignant cells of the cancer. Examples of tumors include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. As noted above, the invention specifically permits differential diagnosis of lung, kidney, and thyroid tumors.

Polynucleotide and Oligonucleotide Compositions and Molecules

Targets: In one embodiment, the targets comprise nucleic acid sequences of Tumor Suppressor gene, including without limitation sense and/or antisense noncoding and/or coding sequences associated with Tumor Suppressor gene.

Tumor Suppressors are genes whose products act to control cell division. They differ from oncogenes in that tumor suppressors produce products that inhibit the division of cells if conditions for growth are not met. The conditions that would trigger the 'brakes' of the cell include DNA damage, a lack of growth factors or defects in the division apparatus. When the tumor suppressor gene is mutated to cause a loss or reduction in its function, the cell can progress to cancer, usually in combination with other genetic changes. This is in contrast to the oncogenes which have gained functions (or lost the ability to be controlled) in their mutant form. Examples of tumor suppressor genes include p53 (TP53): a transcription factor that regulates cell division; Rb: alters the activity of transcription factors and therefore controls cell division; APC: controls the availability of the transcription factor; BRCA: involved in DNA repair.

p53 tumor suppressor exerts anti-proliferative effects, including growth arrest, apoptosis, and cell senescence, in response to various types of stress (Levine A. J., (1997) *Cell* 88:323-31; Oren M., (1999) *J. Biol. Chem.* 274: 36031-034). p53 can be thought of as the central node of a regulatory circuit that monitors signaling pathways from diverse sources, including DNA damage responses (e.g., ATM/ATR activation), abnormal oncogenic events (e.g., Myc or Ras activation) and everyday cellular processes (e.g., growth factor stimulation). While p53 mutations have been in more than half of all the human tumors (Hollstein et al., (1999) *Mutat Res.* 431:199-209), defects in other components of p53 pathway, such as ARF tumor suppressor, are observed in tumor cells that retain wildtype p53 (Sherr, C. J., (2001) *Nat Rev Mol Cell Biol* 2:731-737; Sharpless N. E., et al., (2004) *J Clin Invest* 113:160-8). Activation of the p53 pathway appears to be a common, if not universal, feature of human cancer.

Regulation of these polynucleotides would be of great benefit in the treatment of cancer and other disorders in which abnormal cell proliferation plays a role. For example, p53 is a short-lived protein whose activity is maintained in low levels in normal cells. The molecular function of p53 that is required for tumor suppression involves ability of p53 to act as a transcriptional factor in regulating endogenous gene expression. Thus the regulation of p53 itself is important for its effect on tumorigenesis and the maintenance of normal cell growth. An antisense compound is specifically hybridizable when binding of the compound to the target DNA or RNA to cause a loss of utility, and there is a sufficient degree of complementarily to avoid non-specific binding of the antisense compound to non-target sequences under conditions in which specific binding is desired, i.e., under physiological conditions in the case of in vivo assays or therapeutic treatment, and in the case of in vitro assays, under conditions in which assays are performed.

Table 1 shows a list of some tumor suppressor genes

| Tumor Suppressor | Function | Cancer |
|---|---|---|
| APC | Controls the function of specific transcription factors | Familial adenomatous and non-inherited colorectal carcinomas |
| BRCA1,2 | DNA damage and repair | Inherited Breast cancers; ovarian cancers |
| CDKN2A | Gene locus that encodes p16 and p14 ARF | Brain Tumors |
| DCC | Function is still unknown | Colorectal carcinomas |
| DPC4 (SMAD4) | Mediates signaling from growth factor receptors | Colorectal tumors, pancreatic neoplasia |
| MADR2/ JV18 (SMAD2) | Mediates signaling from growth factor receptors | Colorectal cancer |
| MEN1 | Codes for the menin protein that interacts with transcription factors and prevents transcription of certain genes. | Multiple endocrine neoplasia type 1 |
| MTS1 | Inhibitor of cyclin-dependent kinases | Melanomas |
| NF1 | RAS GTPase activating protein | Neurofibromatosis type 1 |
| NF2 | RAS GTPase activating protein | Neurofibromatosis type 2 |
| p53 | Encodes a transcription factor for p21 that arrests the cell cycle in G1 phase | Bladder, breast, colorectal, esophageal, liver, lung, prostate and ovarian carcinomas; brain tumors, sarcomas. Lymphomas and leukemias |
| PTEN | Lipid phosphatase that regulates cell survival | Cowden syndrome; increases risk of breast and thyroid cancer; Lhermitte-Duclos disease (LDD), Bannayan-Zonana syndrome (BZS); Source: US20020058638] |
| Rb | Alters activity of certain transcription factors that play a role in the control of cell division | Retinoblastoma, sarcomas; bladder, breast, esophageal, prostate and lung carcinomas |
| VHL | May target proteins for degradation | Renal cell carcinomas |
| WRN | Involved in DNA repair | Werner syndrome |
| WT1 | Transcriptional repressor | Wilm's tumors (pediatric kidney cancer) |
| TSC1 | Forms complex with TSC2 protein, inhibits signaling to downstream effectors of mTOR | Seizures, mental retardation, facial angiofibromas |
| TSC2 | See TSC1 above | Benign growths (hamartomas) in many tissues, astrocytomas, rhabdomyosarcomas |
| LKB1, a nuclear localized kinase, also called STK11 (Serine threonine kinase 11) | Phosphorylates and activates AMP-activated kinase (AMPK), AMPK involved in stress responses, lipid and glucose metabolism | Hyperpigmentation, multiple hamartomatous polyps, colorectal breast and ovarian cancers |
| MSH1, 2 | DNA mismatch repair | Colon Cancer |
| CDH1 | Cell-Cell adhesion protein | Gastric cancer, lobular breast cancer |
| PTCH | Transmembrane receptor for sonic hedgehog (shh) | Basal cell skin carcinoma |

It is understood that this list is non-limiting, and that the invention encompasses the use of other tumor suppressors not specifically listed herein. One of skill in the art working in the field of tumor suppressors can identify additional tumor suppressors described in, e.g., the published literature.

It should be appreciated that in the above Table 1, an indicated gene means the gene and all currently known variants thereof, including the different mRNA transcripts that the gene and its variants can give rise to, any further gene variants which may be elucidated, and antisense sequences. The list also includes the non-coding RNA molecules or the portions of polynucleotides. In general, however, such variants will have significant sequence identity to a sequence of any polynucleotide in Table 1 above, e.g., a variant will have at least about 70 percent sequence identity to a sequence of the Table 1 above, typically at least about 75, 80, 85, 90, 95, 97, 98 or 99 percent sequence identity to a sequence of the above Table 1. Sequence identity of variant can be determined by any number of standard techniques such as BLAST program (ncbi.nclm-.nih.gov/blast/).

In another embodiment, the oligonucleotides are specific for one or more molecules that inhibit abnormal cell growth or tumors. This includes factors which inhibit molecular activities such as for example: transform cells, factors involved in pre-tumor stages, malignancy, pre-metastasis, metastasis and the like. Other examples include without limitation: developmental gene products (e.g., adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors); oncogene products (e.g., ABL1, BCL1, BCL2, BCL6, CBFA2, CBL, CSF1R, ERBA, ERBB, ERB2, ETS1, ETV6, FGR, FOS, FYN, HCR, HRAS, JUN, KRAS, LCK, LYN, MDM2, MLL, MYB, MYC, MYCL1, MYCN, NRAS, PIM1, PML, RET, SRC, TAL1, TCL3, AND YES); tumor suppressor gene products (e.g., APC, BRCA1, BRCA2, MADH4, MCC, NF1, NF2, RBI, TP53, and WT1) and enzymes (e.g., ACC synthases and oxidases, ACP desaturases and hydroxylases, ADP-glucose pyrophosphorylases, ATPases, alcohol dehydrogenases, amylases, amyloglucosidases, catalases, cellulases, chalcone synthases, chitinases, cyclooxygenases, decarboxylases, dextrinases, DNA and RNA polymerases, galactosidases, glucanases, glucose oxidases, granule-bound starch synthases, GTPases, helicases, hemicellulases, integrases, inulinases, invertases, isomerases, kinases, lactases, lipases, lipoxygenases, lysozymes, nopaline synthesis, octopine synthases, pectinestrases, peroxidases, phosphatases, phospholipases, phosphorylases, phytases, plant growth regulator synthesases, polygalacturonases, proteinases and peptidases, pullanases, recombinases, reverse transcriptases, RUBISCOs, topoisomerases and xylanases.

Exemplary Tumor Suppressor gene-mediated diseases and disorders which can be treated with cell/tissues regenerated from stem cells obtained using the antisense compounds comprise diseases associated with decreased or increased apoptosis, tissue/cell aging, cancer (including those mentioned in Table 1), autoimmune diseases, immunodeficiency diseases including AIDS, senescence, neurodegenerative disease or disorders (e.g. Alzheimer's disease, ataxia telangiectasia, Parkinson's disease, amyotrophic lateral sclerosis (ALS), Huntington's disease etc.), hyperplastic diseases (e.g., cheloid) rheumatoid arthritis, coronary heart disease ischemic cell death, lymphoproliferative disorders, atherosclerosis, osteoporosis, myelodysplastic syndromes, toxin-induced diseases, and viral infections, wound-healing, Cowden disease (CD), Lhermitte-Duclos disease (LDD), Bannayan-Zonana syndrome (BZS, also known as Bannayan-Riley-Ruvalcaba syndrome, Ruvalcaba-Myhre-Smith syndrome and Riley-Smith syndrome), transplantation, apoptotic related diseases and disorders, metabolic disease or condition (e.g., diabetes) modulating apoptosis in acute diseases, kidney diseases and disorders, myocardial infarction/heart failure ischemia, sepsis, inflammatory diseases where particular haematopoeitic inflammatory cells are in excess, and proliferative diseases, or where there is a therapeutic paradigm for treatment of inflammatory disease through increasing apoptosis.

In a preferred embodiment, the oligonucleotides are specific for polynucleotides of Tumor Suppressor gene, which includes, without limitation noncoding regions. The Tumor Suppressor gene targets comprise variants of Tumor Suppressor gene; mutants of Tumor Suppressor gene, including SNPs; noncoding sequences of Tumor Suppressor gene; alleles, fragments and the like. Preferably the oligonucleotide is an antisense RNA molecule.

In accordance with embodiments of the invention, the target nucleic acid molecule is not limited to Tumor Suppressor gene polynucleotides alone but extends to any of the isoforms, receptors, homologs, non-coding regions and the like of Tumor Suppressor gene.

In another preferred embodiment, an oligonucleotide targets a natural antisense sequence (natural antisense to the coding and non-coding regions) of Tumor Suppressor gene targets, including, without limitation, variants, alleles, homologs, mutants, derivatives, fragments and complementary sequences thereto. Preferably the oligonucleotide is an antisense RNA or DNA molecule.

In another preferred embodiment, the oligomeric compounds of the present invention also include variants in which a different base is present at one or more of the nucleotide positions in the compound. For example, if the first nucleotide is an adenine, variants may be produced which contain thymidine, guanosine, cytidine or other natural or unnatural nucleotides at this position. This may be done at any of the positions of the antisense compound. These compounds are then tested using the methods described herein to determine their ability to inhibit expression of a target nucleic acid.

In some embodiments, homology, sequence identity or complementarity, between the antisense compound and target is from about 50% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired. Such conditions include, i.e., physiological conditions in the case of in vivo assays or therapeutic treatment, and conditions in which assays are performed in the case of in vitro assays.

An antisense compound, whether DNA, RNA, chimeric, substituted etc, is specifically hybridizable when binding of the compound to the target DNA or RNA molecule interferes with the normal function of the target DNA or RNA to cause a loss of utility, and there is a sufficient degree of complementarily to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

In another preferred embodiment, targeting of Tumor Suppressor gene including without limitation, antisense sequences which are identified and expanded, using for example, PCR, hybridization etc., one or more of the sequences set forth as SEQ ID NO.: 8, 9, 10, 11, 12, 13, 14 and 15, and the like, modulate the expression or function of Tumor Suppressor gene. In one embodiment, expression or function is up-regulated as compared to a control. In another preferred embodiment, expression or function is down-regulated as compared to a control.

In another preferred embodiment, oligonucleotides comprise nucleic acid sequences set forth as SEQ ID NOS: 16 to 36 including antisense sequences which are identified and expanded, using for example, PCR, hybridization etc. These oligonucleotides can comprise one or more modified nucleotides, shorter or longer fragments, modified bonds and the like. Examples of modified bonds or internucleotide linkages comprise phosphorothioate, phosphorodithioate or the like. In another preferred embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In embodiments of the present invention oligomeric antisense compounds, particularly oligonucleotides, bind to target nucleic acid molecules and modulate the expression and/or function of molecules encoded by a target gene. The functions of DNA to be interfered comprise, for example, replication and transcription. The functions of RNA to be interfered comprise all vital functions such as, for example, translocation of the RNA to the site of protein translation, translation of protein from the RNA, splicing of the RNA to yield one or more mRNA species, and catalytic activity which may be engaged in or facilitated by the RNA. The functions may be up-regulated or inhibited depending on the functions desired.

The antisense compounds, include, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

Targeting an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes Tumor Suppressor gene.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

In a preferred embodiment, the antisense oligonucleotides bind to the natural antisense sequences of Tumor Suppressor gene and modulate the expression and/or function of Tumor Suppressor gene (SEQ ID NO: 1, 4 and 6). Examples of antisense sequences include SEQ ID NOS: 8 to 36.

In another preferred embodiment, the antisense oligonucleotides bind to one or more segments of Tumor Suppressor gene polynucleotides and modulate the expression and/or function of Tumor Suppressor gene. The segments comprise at least five consecutive nucleotides of the Tumor Suppressor gene sense or antisense polynucleotides.

In another preferred embodiment, the antisense oligonucleotides are specific for natural antisense sequences of Tumor Suppressor gene wherein binding of the oligonucleotides to the natural antisense sequences of Tumor Suppressor gene modulate expression and/or function of Tumor Suppressor gene.

In another preferred embodiment, oligonucleotide compounds comprise sequences set forth as SEQ ID NOS: 16 to 36, antisense sequences which are identified and expanded, using for example, PCR, hybridization etc These oligonucleotides can comprise one or more modified nucleotides, shorter or longer fragments, modified bonds and the like. Examples of modified bonds or internucleotide linkages comprise phosphorothioate, phosphorodithioate or the like. In another preferred embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes has a translation initiation codon having the RNA sequence 5'-GUG, 5'-UUG or 5'-CUG; and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding Tumor Suppressor gene, regardless of the sequence(s) of such codons. A translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions that may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a targeted region is the intragenic region encompassing the translation initiation or termination codon of the open reading frame (ORF) of a gene.

Another target region includes the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene). Still another target region includes the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. Another target region for this invention is the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. In one embodiment, targeting splice sites, i.e., intron-exon junctions or exon-intron junctions, is particularly useful in situations where aberrant splicing is implicated in disease, or where an overproduction of a particular splice product is implicated in disease. An aberrant fusion junction due to rearrangement or deletion is another embodiment of a target site. mRNA transcripts produced via the process of splicing of two (or more) mRNAs from different gene sources are known as "fusion transcripts". Introns can be effectively targeted using antisense compounds targeted to, for example, DNA or pre-mRNA.

In another preferred embodiment, the antisense oligonucleotides bind to coding and/or non-coding regions of a target polynucleotide and modulate the expression and/or function of the target molecule.

In another preferred embodiment, the antisense oligonucleotides bind to natural antisense polynucleotides and modulate the expression and/or function of the target molecule.

In another preferred embodiment, the antisense oligonucleotides bind to sense polynucleotides and modulate the expression and/or function of the target molecule.

Alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Variants can be produced through the use of alternative signals to start or stop transcription. Pre-mRNAs and mRNAs can possess more than one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also embodiments of target nucleic acids.

The locations on the target nucleic acid to which the antisense compounds hybridize are defined as at least a 5-nucleotide long portion of a target region to which an active antisense compound is targeted.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure.

Target segments 5-100 nucleotides in length comprising a stretch of at least five (5) consecutive nucleotides selected from within the illustrative preferred target segments are considered to be suitable for targeting as well.

Target segments can include DNA or RNA sequences that comprise at least the 5 consecutive nucleotides from the 5'-terminus of one of the illustrative preferred target segments (the remaining nucleotides being a consecutive stretch of the same DNA or RNA beginning immediately upstream of the 5'-terminus of the target segment and continuing until the DNA or RNA contains about 5 to about 100 nucleotides). Similarly preferred target segments are represented by DNA or RNA sequences that comprise at least the 5 consecutive nucleotides from the 3'-terminus of one of the illustrative preferred target segments (the remaining nucleotides being a consecutive stretch of the same DNA or RNA beginning immediately downstream of the 3'-terminus of the target segment and continuing until the DNA or RNA contains about 5 to about 100 nucleotides). One having skill in the art armed with the target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

In embodiments of the invention the oligonucleotides bind to an antisense strand of a particular target. The oligonucleotides are at least 5 nucleotides in length and can be synthesized so each oligonucleotide targets overlapping sequences such that oligonucleotides are synthesized to cover the entire length of the target polynucleotide. The targets also include coding as well as non coding regions.

In one embodiment, it is preferred to target specific nucleic acids by antisense oligonucleotides. Targeting an antisense compound to a particular nucleic acid, is a multistep process. The process usually begins with the identification of a nucleic acid sequence whose function is to be modulated. This may be, for example, a cellular gene (or mRNA transcribed from the gene) whose expression is associated with a particular disorder or disease state, or a non coding polynucleotide such as for example, non coding RNA (ncRNA).

RNAs can be classified into (1) messenger RNAs (mRNAs), which are translated into proteins, and (2) non-protein-coding RNAs (ncRNAs). ncRNAs comprise microRNAs, antisense transcripts and other Transcriptional Units (TU) containing a high density of stop codons and lacking any extensive "Open Reading Frame". Many ncRNAs appear to start from initiation sites in 3' untranslated regions (3'UTRs) of protein-coding loci. ncRNAs are often rare and at least half of the ncRNAs that have been sequenced by the FANTOM consortium seem not to be polyadenylated. Most researchers have for obvious reasons focused on polyadenylated mRNAs that are processed and exported to the cytoplasm. Recently, it was shown that the set of non-polyadenylated nuclear RNAs may be very large, and that many such transcripts arise from so-called intergenic regions (Cheng, J. et al. (2005) *Science* 308 (5725), 1149-1154; Kapranov, P. et al. (2005). *Genome Res* 15 (7), 987-997). The mechanism by which ncRNAs may regulate gene expression is by base pairing with target transcripts. The RNAs that function by base pairing can be grouped into (1) cis encoded RNAs that are encoded at the same genetic location, but on the opposite strand to the RNAs they act upon and therefore display perfect complementarity to their target, and (2) trans-encoded RNAs that are encoded at a chromosomal location distinct from the RNAs they act upon and generally do not exhibit perfect base-pairing potential with their targets.

Without wishing to be bound by theory, perturbation of an antisense polynucleotide by the antisense oligonucleotides described herein can alter the expression of the corresponding sense messenger RNAs. However, this regulation can either be discordant (antisense knockdown results in messenger RNA elevation) or concordant (antisense knockdown results in concomitant messenger RNA reduction). In these cases, antisense oligonucleotides can be targeted to overlapping or non-overlapping parts of the antisense transcript resulting in its knockdown or sequestration. Coding as well as non-coding antisense can be targeted in an identical manner and that either category is capable of regulating the corresponding sense transcripts—either in a concordant or disconcordant manner. The strategies that are employed in identifying new oligonucleotides for use against a target can be based on the knockdown of antisense RNA transcripts by antisense oligonucleotides or any other means of modulating the desired target.

Strategy 1: In the case of discordant regulation, knocking down the antisense transcript elevates the expression of the conventional (sense) gene. Should that latter gene encode for a known or putative drug target, then knockdown of its antisense counterpart could conceivably mimic the action of a receptor agonist or an enzyme stimulant.

Strategy 2: In the case of concordant regulation, one could concomitantly knock down both antisense and sense transcripts and thereby achieve synergistic reduction of the conventional (sense) gene expression. If, for example, an antisense oligonucleotide is used to achieve knockdown, then this strategy can be used to apply one antisense oligonucleotide targeted to the sense transcript and another antisense oligonucleotide to the corresponding antisense transcript, or a single energetically symmetric antisense oligonucleotide that simultaneously targets overlapping sense and antisense transcripts.

According to the present invention, antisense compounds include antisense oligonucleotides, ribozymes, external guide sequence (EGS) oligonucleotides, siRNA compounds, single- or double-stranded RNA interference (RNAi) compounds such as siRNA compounds, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, doublestranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines, however, in some embodiments, the gene expression or function is up regulated. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

In another preferred embodiment, the desired oligonucleotides or antisense compounds, comprise at least one of: antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof.

dsRNA can also activate gene expression, a mechanism that has been termed "small RNA-induced gene activation" or RNAa. dsRNAs targeting gene promoters induce potent transcriptional activation of associated genes. RNAa was demonstrated in human cells using synthetic dsRNAs, termed "small activating RNAs" (saRNAs). It is currently not known whether RNAa is conserved in other organisms.

Small double-stranded RNA (dsRNA), such as small interfering RNA (siRNA) and microRNA (miRNA), have been found to be the trigger of an evolutionary conserved mechanism known as RNA interference (RNAi). RNAi invariably leads to gene silencing via remodeling chromatin to thereby suppress transcription, degrading complementary mRNA, or blocking protein translation. However, in instances described in detail in the examples section which follows, oligonucleotides are shown to increase the expression and/or function of the Tumor Suppressor gene polynucleotides and encoded products thereof. dsRNAs may also act as small activating RNAs (saRNA). Without wishing to be bound by theory, by targeting sequences in gene promoters, saRNAs would induce target gene expression in a phenomenon referred to as dsRNA-induced transcriptional activation (RNAa).

In a further embodiment, the "preferred target segments" identified herein may be employed in a screen for additional compounds that modulate the expression of Tumor Suppressor gene polynucleotides. "Modulators" are those compounds that decrease or increase the expression of a nucleic acid molecule encoding Tumor Suppressor gene and which comprise at least a 5-nucleotide portion that is complementary to a preferred target segment. The screening method comprises the steps of contacting a preferred target segment of a nucleic acid molecule encoding sense or natural antisense polynucleotides of Tumor Suppressor gene with one or more candidate modulators, and selecting for one or more candidate modulators which decrease or increase the expression of a nucleic acid molecule encoding Tumor Suppressor gene polynucleotides, e.g. SEQ ID NOS: 16 to 36. Once it is shown that the candidate modulator or modulators are capable of modulating (e.g. either decreasing or increasing) the expression of a nucleic acid molecule encoding Tumor Suppressor gene polynucleotides, the modulator may then be employed in further investigative studies of the function of Tumor Suppressor gene polynucleotides, or for use as a research, diagnostic, or therapeutic agent in accordance with the present invention.

Targeting the natural antisense sequence preferably modulates the function of the target gene, for example, for example, the p73 gene (NCBI accession number NM_005427.2), p53 gene (NCBI Accession No.: NM_000546.4) and PTEN gene (NCBI Accession No.: NM_000314). In a preferred embodiment, the target is an antisense polynucleotide of the Tumor Suppressor gene gene. In a preferred embodiment, an antisense oligonucleotide targets sense and/or natural antisense sequences of Tumor Suppressor gene polynucleotides (p73: NCBI accession number NM_005427.2; p53: NCBI Accession No.: NM_000546.4; PTEN: NCBI Accession No.: NM_000314), variants, alleles, isoforms, homologs, mutants, derivatives, fragments and complementary sequences thereto. Preferably the oligonucleotide is an antisense molecule and the targets include coding and noncoding regions of antisense and/or sense Tumor Suppressor gene polynucleotides.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications (Fire et al., (1998) *Nature,* 391, 806-811; Timmons and Fire, (1998) *Nature,* 395, 854; Timmons et al., (2001) *gene,* 263, 103-112; Tabara et al., (1998) *Science,* 282, 430-431; Montgomery et al., (1998) *Proc. Natl. Acad. Sci. USA,* 95, 15502-15507; Tuschl et al., (1999) *genes Dev.,* 13, 3191-3197; Elbashir et al., (2001) *Nature,* 411, 494-498; Elbashir et al., (2001) *genes Dev.* 15, 188-200). For example, such double-stranded moieties have been shown to inhibit the target by the classical hybridization of antisense strand of the duplex to the target, thereby triggering enzymatic degradation of the target (Tijsterman et al., (2002) *Science,* 295, 694-697).

In a preferred embodiment, an antisense oligonucleotide targets Tumor Suppressor gene polynucleotides (p73: NCBI accession number NM_005427.2; p53: NCBI Accession No.: NM_000546.4; PTEN: NCBI Accession No.: NM_000314), variants, alleles, isoforms, homologs, mutants, derivatives, fragments and complementary sequences thereto. Preferably the oligonucleotide is an antisense molecule.

In accordance with embodiments of the invention, the target nucleic acid molecule is not limited to Tumor Suppressor gene alone but extends to any of the isoforms, receptors, homologs and the like of Tumor Suppressor gene molecules.

In another preferred embodiment, an oligonucleotide targets a natural antisense sequence of Tumor Suppressor gene polynucleotides, for example, polynucleotides set forth as SEQ ID NOS: 8, 9, 10, 11, 12, 13, 14 and 15, and any variants, alleles, homologs, mutants, derivatives, fragments and complementary sequences thereto. Examples of antisense oligonucleotides are set forth as SEQ ID NOS: 16 to 36.

In one embodiment, the oligonucleotides are complementary to or bind to nucleic acid sequences of Tumor Suppressor gene antisense, including without limitation noncoding sense and/or antisense sequences associated with Tumor Suppressor gene polynucleotides and modulate expression and/or function of Tumor Suppressor gene molecules.

In another preferred embodiment, the oligonucleotides are complementary to or bind to nucleic acid sequences of Tumor Suppressor gene natural antisense, set forth as SEQ ID NOS: 8, 9, 10, 11, 12, 13, 14 and 15 and modulate expression and/or function of Tumor Suppressor gene molecules.

In a preferred embodiment, oligonucleotides comprise sequences of at least 5 consecutive nucleotides of SEQ ID NOS: 16 to 36 and modulate expression and/or function of Tumor Suppressor gene molecules.

The polynucleotide targets comprise Tumor Suppressor gene, including family members thereof, variants of Tumor Suppressor gene; mutants of Tumor Suppressor gene, including SNPs; noncoding sequences of Tumor Suppressor gene; alleles of Tumor Suppressor gene; species variants, fragments and the like. Preferably the oligonucleotide is an antisense molecule.

In another preferred embodiment, the oligonucleotide targeting Tumor Suppressor gene polynucleotides, comprise: antisense RNA, interference RNA (RNAi), short interfering RNA (siRNA); micro interfering RNA (miRNA); a small, temporal RNA (stRNA); or a short, hairpin RNA (shRNA); small RNA-induced gene activation (RNAa); or, small activating RNA (saRNA).

In another preferred embodiment, targeting of Tumor Suppressor gene polynucleotides, e.g. SEQ ID NOS: 8, 9, 10, 11, 12, 13, 14 and 15, modulates the expression or function of these targets. In one embodiment, expression or function is up-regulated as compared to a control. In another preferred embodiment, expression or function is down-regulated as compared to a control.

In another preferred embodiment, antisense compounds comprise sequences set forth as SEQ ID NOS: 16 to 36. These oligonucleotides can comprise one or more modified nucleotides, shorter or longer fragments, modified bonds and the like.

In another preferred embodiment, SEQ ID NOS: 16 to 36 comprise one or more LNA nucleotides.

The modulation of a desired target nucleic acid can be carried out in several ways known in the art. For example, antisense oligonucleotides, siRNA etc. Enzymatic nucleic acid molecules (e.g., ribozymes) are nucleic acid molecules capable of catalyzing one or more of a variety of reactions, including the ability to repeatedly cleave other separate nucleic acid molecules in a nucleotide base sequence-specific manner. Such enzymatic nucleic acid molecules can be used, for example, to target virtually any RNA transcript (Zaug et al., 324, *Nature* 429 1986; Cech, 260 *JAMA* 3030, 1988; and Jefferies et al., 17 *Nucleic Acids Research* 1371, 1989).

Because of their sequence-specificity, trans-cleaving enzymatic nucleic acid molecules show promise as therapeutic agents for human disease (Usman & McSwiggen, (1995) *Ann. Rep. Med. Chem.* 30, 285-294; Christoffersen and Marr, (1995) *J. Med. Chem.* 38, 2023-2037). Enzymatic nucleic acid molecules can be designed to cleave specific RNA targets within the background of cellular RNA. Such a cleavage event renders the mRNA non-functional and abrogates protein expression from that RNA. In this manner, synthesis of a protein associated with a disease state can be selectively inhibited.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, (1979) *Proc. R. Soc. London, B* 205, 435) have been used to evolve new nucleic acid catalysts capable of catalyzing a variety of reactions, such as cleavage and ligation of phosphodiester linkages and amide linkages, (Joyce, (1989) *gene,* 82, 83-87; Beaudry et al., (1992) *Science* 257, 635-641; Joyce, (1992) *Scientific American* 267, 90-97; Breaker et al., (1994) *TIBTECH* 12, 268; Bartel et al., (1993) *Science* 261:1411-1418; Szostak, (1993) *TIBS* 17, 89-93; Kumar et al., (1995) *FASEB J.,* 9, 1183; Breaker, (1996) *Curr. Op. Biotech.,* 7, 442).

The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 min-1 in the presence of saturating (10 mM) concentrations of Mg2+ cofactor. An artificial "RNA ligase" ribozyme has been shown to catalyze the corresponding self-modification reaction with a rate of about 100 min-1. In addition, it is known that certain modified hammerhead ribozymes that have substrate binding arms made of DNA catalyze RNA cleavage with multiple turn-over rates that approach 100 min-1. Finally, replacement of a specific residue within the catalytic core of the hammerhead with certain nucleotide analogues gives modified ribozymes that show as much as a 10-fold improvement in catalytic rate. These findings demonstrate that ribozymes can promote chemical transformations with catalytic rates that are significantly greater than those displayed in vitro by most natural self-cleaving ribozymes. It is then possible that the structures of certain selfcleaving ribozymes may be optimized to give maximal catalytic activity, or that entirely new RNA motifs can be made that display significantly faster rates for RNA phosphodiester cleavage.

Intermolecular cleavage of an RNA substrate by an RNA catalyst that fits the "hammerhead" model was first shown in 1987 (Uhlenbeck, O. C. (1987) *Nature,* 328: 596-600). The RNA catalyst was recovered and reacted with multiple RNA molecules, demonstrating that it was truly catalytic.

Catalytic RNAs designed based on the "hammerhead" motif have been used to cleave specific target sequences by making appropriate base changes in the catalytic RNA to maintain necessary base pairing with the target sequences (Haseloff and Gerlach, (1988) *Nature,* 334, 585; Walbot and Bruening, (1988) *Nature,* 334, 196; Uhlenbeck, O. C. (1987) *Nature,* 328: 596-600; Koizumi, M., et al. (1988) *FEBS Lett.,* 228: 228-230). This has allowed use of the catalytic RNA to cleave specific target sequences and indicates that catalytic RNAs designed according to the "hammerhead" model may possibly cleave specific substrate RNAs in vivo. (see Haseloff and Gerlach, (1988) *Nature,* 334, 585; Walbot and Bruening, (1988) *Nature,* 334, 196; Uhlenbeck, O. C. (1987) *Nature,* 328: 596-600).

RNA interference (RNAi) has become a powerful tool for modulating gene expression in mammals and mammalian cells. This approach requires the delivery of small interfering RNA (siRNA) either as RNA itself or as DNA, using an expression plasmid or virus and the coding sequence for small hairpin RNAs that are processed to siRNAs. This system enables efficient transport of the pre-siRNAs to the cytoplasm where they are active and permit the use of regulated and tissue specific promoters for gene expression.

In a preferred embodiment, an oligonucleotide or antisense compound comprises an oligomer or polymer of ribonucleic acid (RNA) and/or deoxyribonucleic acid (DNA), or a mimetic, chimera, analog or homolog thereof. This term includes oligonucleotides composed of naturally occurring nucleotides, sugars and covalent internucleoside (backbone) linkages as well as oligonucleotides having non-naturally occurring portions which function similarly. Such modified or substituted oligonucleotides are often desired over native forms because of desirable properties such as, for example, enhanced cellular uptake, enhanced affinity for a target nucleic acid and increased stability in the presence of nucleases.

According to the present invention, the oligonucleotides or "antisense compounds" include antisense oligonucleotides (e.g. RNA, DNA, mimetic, chimera, analog or homolog thereof), ribozymes, external guide sequence (EGS) oligonucleotides, siRNA compounds, single- or double-stranded RNA interference (RNAi) compounds such as siRNA compounds, saRNA, aRNA, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, double-stranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines (Hammond, et al., (1991) *Nat. Rev. genet.,* 2, 110-119; Matzke, et al., (2001) *Curr. Opin. genet. Dev.,* 11, 221-227; Sharp, (2001) *genes Dev.,* 15, 485-490). When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

The antisense compounds in accordance with this invention can comprise an antisense portion from about 5 to about 80 nucleotides (i.e. from about 5 to about 80 linked nucleosides) in length. This refers to the length of the antisense strand or portion of the antisense compound. In other words, a single-stranded antisense compound of the invention comprises from 5 to about 80 nucleotides, and a double-stranded antisense compound of the invention (such as a dsRNA, for example) comprises a sense and an antisense strand or portion of 5 to about 80 nucleotides in length. One of ordinary skill in the art will appreciate that this comprehends antisense portions of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides in length, or any range therewithin.

In one embodiment, the antisense compounds of the invention have antisense portions of 10 to 50 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the oligonucleotides are 15 nucleotides in length.

In one embodiment, the antisense or oligonucleotide compounds of the invention have antisense portions of 12 or 13 to 30 nucleotides in length. One having ordinary skill in the art will appreciate that this embodies antisense compounds having antisense portions of 12, 13, 14, 15, 16, 17, 18, 19, 20, 21, 22, 23, 24, 25, 26, 27, 28, 29 or 30 nucleotides in length, or any range therewithin.

In another preferred embodiment, the oligomeric compounds of the present invention also include variants in which a different base is present at one or more of the nucleotide positions in the compound. For example, if the first nucleotide is an adenosine, variants may be produced which contain thymidine, guanosine or cytidine at this position. This may be done at any of the positions of the antisense or dsRNA compounds. These compounds are then tested using the methods described herein to determine their ability to inhibit expression of a target nucleic acid.

In some embodiments, homology, sequence identity or complementarity, between the antisense compound and target is from about 40% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

In another preferred embodiment, the antisense oligonucleotides, such as for example, nucleic acid molecules set forth in SEQ ID NOS: 16 to 36 comprise one or more substitutions or modifications. In one embodiment, the nucleotides are substituted with locked nucleic acids (LNA).

In another preferred embodiment, the oligonucleotides target one or more regions of the nucleic acid molecules sense and/or antisense of coding and/or non-coding sequences associated with Tumor Suppressor gene and the sequences set forth as SEQ ID NOS: 1, 2, 3, 4, 5, 6, 7, 8, 9, 10, 11, 12, 13, 14 and 15. The oligonucleotides are also targeted to overlapping regions of SEQ ID NOS: 1, 2, 3, 4, 5, 6, 7, 8, 9, 10, 11, 12, 13, 14 and 15.

Certain preferred oligonucleotides of this invention are chimeric oligonucleotides. "Chimeric oligonucleotides" or "chimeras," in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense modulation of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art. In one preferred embodiment, a chimeric oligonucleotide comprises at least one region modified to increase target binding affinity, and, usually, a region that acts as a substrate for RNAse H. Affinity of an oligonucleotide for its target (in this case, a nucleic acid encoding ras) is routinely determined by measuring the Tm of an oligonucleotide/target pair, which is the temperature at which the oligonucleotide and target dissociate; dissociation is detected spectrophotometrically. The higher the Tm, the greater is the affinity of the oligonucleotide for the target.

Chimeric antisense compounds of the invention may be formed as composite structures of two or more oligonucleotides, modified oligonucleotides, oligonucleosides and/or oligonucleotides mimetics as described above. Such; compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In another preferred embodiment, the region of the oligonucleotide which is modified comprises at least one nucleotide modified at the 2' position of the sugar, most preferably a 2'-Oalkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target. The effect of such increased affinity is to greatly enhance RNAi oligonucleotide inhibition of gene expression. RNAse H is a cellular endonuclease that cleaves the RNA strand of RNA:DNA duplexes; activation of this enzyme therefore results in cleavage of the RNA target, and thus can greatly enhance the efficiency of RNAi inhibition. Cleavage of the RNA target can be routinely demonstrated by gel electrophoresis. In another preferred embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance. Some desirable modifications can be found in De Mesmaeker, el al. (1995) *Acc. Chem. Res.,* 28:366-374.

Specific examples of some preferred oligonucleotides envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly CH2-NH—O—CH2, CH, —N(CH3)-O—CH2 [known as a methylene (methylimino) or MMI backbone], CH2-O—N(CH3)-CH2, CH2-N(CH3)-N(CH3)—CH2 and O—N(CH3)-CH2-CH2 backbones, wherein the native phosphodiester backbone is represented as O—P—O—CH). The amide backbones disclosed by De Mesmaeker et al. (1995) *Acc. Chem. Res.* 28:366-374 are also preferred. Also preferred are oligonucicotides having morpholino backbone structures (Summerton and Weller, U.S. Pat. No. 5,034,506). In other preferred embodiments, such as the peptide nucleic acid (PNA) backbone, the phosphodiester backbone of the oligonucleotide is replaced with a polyamide backbone, the nucleotides being bound directly or indirectly to the aza nitrogen atoms of the polyamide backbone (Nielsen, et al. (1991) *Science* 254, 1497). Oligonucleotides may also comprise one or more substituted sugar moieties. Preferred oligonucleotides comprise one of the following at the 2' position: OH, SH, SCH3, F, OCN, OCH3 OCH3, OCH3 O(CH2)n CH3, O(CH2)n NH2 or O(CH2)n CH3 where n is from 1 to about 10; C1 to C10 lower alkyl, alkoxyalkoxy, substituted lower alkyl, alkaryl or aralkyl; Cl; Br; CN; CF3; OCF3; O—, S—, or N-alkyl; O—, S—, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a rTumor Suppressor generter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH2 CH2 OCH3, also known as 2'-O-(2-methoxyethyl)] (Martin et al., (1995) *Helv. Chim. Acta,* 78, 486). Other preferred modifications include 2'-methoxy (2'-O—CH3), 2'-propoxy (2'-OCH2 CH2CH3) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleotides include adenine (A), guanine (G), thymine (T), cytosine (C) and uracil (U). Modified nucleotides include nucleotides found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleotides, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. (Kornberg, A., DNA Replication, W. H. Freeman & Co., San Francisco, 1980, pp75-77; Gebeyehu, G., (1987) et al. *Nucl. Acids Res.* 15:4513). A "universal" base known in the art, e.g., inosine, may be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger, et al., (1989) *Proc. Natl. Acad. Sci. USA* 86, 6553), cholic acid (Manoharan, et al. (1994) *Bioorg. Med. Chem. Let.* 4, 1053), a thioether, e.g., hexyl-S-tritylthiol (Manoharan, et al. (1992) *Ann. N.Y. Acad. Sci.* 660, 306; Manoharan, et al. (1993) *Bioorg. Med. Chem. Let.* 3, 2765), a thiocholesterol (Oberhauser, et al., (1992) *Nucl. Acids Res.* 20, 533), an aliphatic chain, e.g., dodecandiol or undecyl residues (Saison-Behmoaras, et al. EMBO J. 1991, 10, 111; Kabanov, et al. (1990) *FEBS Lett.* 259, 327; Svinarchuk, et al. (1993) *Biochimie* 75, 49), a phospholipid, e.g., di-hexadecyl-rac-glycerol or triethylammonium 1,2-di-O-hexadecyl-rac-glycero-3-H-phosphonate (Manoharan, et al. (1995) *Tetrahedron Lett.* 36, 3651; Shea et al. (1990) *Nucl. Acids Res.* 18, 3777), a polyamine or a polyethylene glycol chain (Manoharan, et al. (1995) *Nucleosides & Nucleotides,* 14, 969), or adamantane acetic acid (Manoharan, et al. (1995) *Tetrahedron Lett.* 36, 3651). Oligonucleotides comprising lipophilic moieties, and methods for preparing such oligonucleotides are known in the art, for example, U.S. Pat. Nos. 5,138,045, 5,218,105 and 5,459,255.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

In another embodiment, the nucleic acid molecule of the present invention is conjugated with another moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of one of ordinary skill in the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

In accordance with the invention, use of modifications such as the use of LNA monomers to enhance the potency, specificity and duration of action and broaden the routes of administration of oligonucleotides comprised of current chemistries such as MOE, ANA, FANA, PS etc (Uhlman, et al. (2000) *Current Opinions in Drug Discovery & Development* Vol. 3 No 2). This can be achieved by substituting some of the monomers in the current oligonucleotides by LNA monomers. The LNA modified oligonucleotide may have a size similar to the parent compound or may be larger or preferably smaller. It is preferred that such LNA-modified oligonucleotides contain less than about 70%, more preferably less than about 60%, most preferably less than about 50% LNA monomers and that their sizes are between about 5 and 25 nucleotides, more preferably between about 12 and 20 nucleotides.

Preferred modified oligonucleotide backbones comprise, but not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus containing linkages comprise, but are not limited to, U.S. Pat. Nos. 3,687,808; 4,469,863; 4,476,301; 5,023,243; 5, 177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative United States patents that teach the preparation of the above oligonucleosides comprise, but are not limited to, U.S. Pat. Nos. 5,034,506; 5,166,315; 5,185,444; 5,214,134; 5,216,141; 5,235,033; 5,264, 562; 5, 264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen, et al. (1991) *Science* 254, 1497-1500.

In another preferred embodiment of the invention the oligonucleotides with phosphorothioate backbones and oligonucleosides with heteroatom backbones, and in particular —CH2-NH—O—CH2-, —CH2-N(CH3)-O—CH2- known as a methylene (methylimino) or MMI backbone, —CH2-O—N(CH3)-CH2-, —CH2N(CH3)-N(CH3) CH2- and —O—N(CH3)-CH2-CH2- wherein the native phosphodiester backbone is represented as —O—P—O—CH2- of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O-, S- or N-alkynyl; or O alkyl-O-alkyl, wherein the alkyl, alkenyl and alkynyl may be substituted or unsubstituted C to CO alkyl or C2 to CO alkenyl and alkynyl. Particularly preferred are O(CH2)n OmCH3, O(CH2)n, OCH3, O(CH2)nNH2, O(CH2)nCH3, O(CH2)nONH2, and O(CH2nON(CH2) nCH3)2 where n and m can be from 1 to about 10. Other preferred oligonucleotides comprise one of the following at the 2' position: C to CO, (lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a rTumor Suppressor generter group, an intercalator, a group for improving the pharmacokinetic properties of an oligonucleotide, or a group for improving the pharmacodynamic properties of an oligonucleotide, and other substituents having similar properties. A preferred modification comprises 2'-methoxyethoxy (2'-O—CH2CH2OCH3, also known as 2'-O-(2-methoxyethyl) or 2'-MOE) (Martin et al., (1995) *Helv. Chim. Acta,* 78, 486-504) i.e., an alkoxyalkoxy group. A further preferred modification comprises 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2-O—CH2-N(CH2)2.

Other preferred modifications comprise 2'-methoxy (2'-OCH3), 2'-aminopropoxy (2'-OCH2CH2CH2NH2) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures comprise, but are not limited to, U.S. Pat. Nos. 4,981,957; 5,118,800; 5,319,080; 5,359,044; 5,393,878; 5,446,137; 5,466,786; 5,514, 785; 5,519,134; 5,567,811; 5,576,427; 5,591,722; 5,597,909; 5,610,300; 5,627,053; 5,639,873; 5,646, 265; 5,658,873; 5,670,633; and 5,700,920, each of which is herein incorporated by reference.

Oligonucleotides may also comprise nucleobase (often referred to in the art simply as "base") modifications or substitutions. As used herein, "unmodified" or "natural" nucleotides comprise the purine bases adenine (A) and guanine (G), and the pyrimidine bases thymine (T), cytosine (C) and uracil (U). Modified nucleotides comprise other synthetic and natural nucleotides such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleotides comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch, et al., 'Angewandle Chemie, International Edition', 1991, 30, page 613, and those disclosed by Sanghvi, Y. S., Chapter 15, 'Antisense Research and Applications', pages 289-302, Crooke, S. T. and Lebleu, B. ea., CRC Press, 1993. Certain of these nucleotides are particularly useful for increasing the binding affinity of the oligomeric compounds of the invention. These comprise 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-Omethoxyethyl sugar modifications.

Representative United States patents that teach the preparation of the above noted modified nucleotides as well as other modified nucleotides comprise, but are not limited to, U.S. Pat. No. 3,687,808, as well as U.S. Pat. Nos. 4,845,205; 5,130,302; 5,134,066; 5,175, 273; 5, 367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

Another modification of the oligonucleotides of the invention involves chemically linking to the oligonucleotide one or more moieties or conjugates, which enhance the activity, cellular distribution, or cellular uptake of the oligonucleotide.

Such moieties comprise but are not limited to, lipid moieties such as a cholesterol moiety (Letsinger, et al., (1989) *Proc. Natl. Acad. Sci. USA,* 86, 6553-6556), cholic acid (Manoharan, et al., (1994) *Bioorg. Med. Chem. Let.,* 4, 1053-1060), a thioether, e.g., hexyl-S-tritylthiol (Manoharan, et al., (1992) *Ann. N. Y. Acad. Sci.,* 660, 306-309; Manoharan, et al., (1993) *Bioorg. Med. Chem. Let.,* 3, 2765-2770), a thiocholesterol (Oberhauser, et al., (1992) *Nucl. Acids Res.,* 20, 533-538), an aliphatic chain, e.g., dodecandiol or undecyl residues (Kabanov, et al., (1990) *FEBS Lett.,* 259, 327-330; Svinarchuk, et al., (1993) *Biochimie* 75, 49-54), a phospholipid, e.g., di-hexadecyl-rac-glycerol or triethylammonium 1,2-di-O-hexadecyl-rac-glycero-3-H-phosphonate (Manoharan, el al., (1995) *Tetrahedron Lett,* 36, 3651-3654; Shea et al., (1990) *Nucl. Acids Res.,* 18, 3777-3783), a polyamine or a polyethylene glycol chain (Mancharan, et al., (1995) Nucleosides & Nucleotides, 14, 969-973), or adamantane acetic acid (Manoharan, et al., (1995) *Tetrahedron Lett.,* 36, 3651-3654), a palmityl moiety (Mishra et al., (1995) *Biochim. Biophys. Acta,* 1264, 229-237), or an octadecylamine or hexylamino-carbonyl-t oxycholesterol moiety (Crooke, et al., (1996) *J. Pharmacol. Exp. Ther.,* 277, 923-937).

Representative United States patents that teach the preparation of such oligonucleotides conjugates comprise, but are not limited to, U.S. Pat. Nos. 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, each of which is herein incorporated by reference.

Drug discovery: The compounds of the present invention can also be applied in the areas of drug discovery and target validation. The present invention comprehends the use of the compounds and preferred target segments identified herein in drug discovery efforts to elucidate relationships that exist between Tumor Suppressor gene polynucleotides and a disease state, phenotype, or condition. These methods include detecting or modulating Tumor Suppressor gene polynucleotides comprising contacting a sample, tissue, cell, or organism with the compounds of the present invention, measuring the nucleic acid or protein level of Tumor Suppressor gene polynucleotides and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

Assessing Up-regulation or Inhibition of Gene Expression:

Transfer of an exogenous nucleic acid into a host cell or organism can be assessed by directly detecting the presence of the nucleic acid in the cell or organism. Such detection can be achieved by several methods well known in the art. For example, the presence of the exogenous nucleic acid can be detected by Southern blot or by a polymerase chain reaction (PCR) technique using primers that specifically amplify nucleotide sequences associated with the nucleic acid. Expression of the exogenous nucleic acids can also be measured using conventional methods including gene expression analysis. For instance, mRNA produced from an exogenous nucleic acid can be detected and quantified using a Northern blot and reverse transcription PCR (RT-PCR).

Expression of RNA from the exogenous nucleic acid can also be detected by measuring an enzymatic activity or a reporter protein activity. For example, antisense modulatory activity can be measured indirectly as a decrease or increase in target nucleic acid expression as an indication that the exogenous nucleic acid is producing the effector RNA. Based on sequence conservation, primers can be designed and used to amplify coding regions of the target genes. Initially, the most highly expressed coding region from each gene can be used to build a model control gene, although any coding or non coding region can be used. Each control gene is assembled by inserting each coding region between a reporter coding region and its poly(A) signal. These plasmids would produce an mRNA with a rTumor Suppressor generter gene in the upstream portion of the gene and a potential RNAi target in the 3' non-coding region. The effectiveness of individual antisense oligonucleotides would be assayed by modulation of the rTumor Suppressor generter gene. RTumor Suppressor generter genes useful in the methods of the present invention include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Methods to determine modulation of a rTumor Suppressor generter gene are well known in the art, and include, but are not limited to, fluorometric methods (e.g. fluorescence spectroscopy, Fluorescence Activated Cell Sorting (FACS), fluorescence microscopy), antibiotic resistance determination.

Kits, Research Reagents, Diagnostics, and Therapeutics

The compounds of the present invention can be utilized for diagnostics, therapeutics, and prophylaxis, and as research reagents and components of kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics and in various biological systems, the compounds of the present invention, either alone or in combination with other compounds or therapeutics, are useful as tools in differential and/or combinatorial analyses to elucidate expression patterns of a portion or the entire complement of genes expressed within cells and tissues.

As used herein the term "biological system" or "system" is defined as any organism, cell, cell culture or tissue that expresses, or is made competent to express products of the Tumor Suppressor gene genes. These include, but are not limited to, humans, transgenic animals, cells, cell cultures, tissues, xenografts, transplants and combinations thereof.

As one non limiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis known in the art include DNA arrays or microarrays (Brazma and Vilo, (2000) *FEBS Lett.,* 480, 17-24; Celis, et al., (2000) *FEBS Lett.,* 480, 2-16), SAGE (serial analysis of gene expression) (Madden, et al., (2000) Drug Discov. Today, 5, 415-425), READS (restriction enzyme amplification of digested cDNAs) (Prashar and Weissman, (1999) *Methods Enzymol.,* 303, 258-72), TOGA (total gene expression analysis) (Sutcliffe, et al., (2000) *Proc. Natl. Acad. Sci. U.S.A.,* 97, 1976-81), protein arrays and proteomics (Celis, et al., (2000) *FEBS Lett.,* 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., (2000) Anal. Biochem. 286, 91-98; Larson, et al., (2000) *Cytometry* 41, 203-208), subtractive cloning, differential display (DD) (Jurecic and Belmont, (2000) *Curr. Opin. Microbiol.* 3, 316-21), comparative genomic hybridization (Carulli, et al., (1998) *J. Cell Biochem. Suppl.,* 31, 286-96), FISH (fluorescent in situ hybridization) techniques (Going and Gusterson, (1999) *Eur. J. Cancer,* 35, 1895-904) and mass spectrometry methods (To, Comb. (2000) *Chem. High Throughput Screen,* 3, 235-41).

The compounds of the invention are useful for research and diagnostics, because these compounds hybridize to nucleic acids encoding Tumor Suppressor gene. For example, oligonucleotides that hybridize with such efficiency and under such conditions as disclosed herein as to be effective Tumor Suppressor gene modulators are effective primers or probes under conditions favoring gene amplification or detection, respectively. These primers and probes are useful in methods requiring the specific detection of nucleic acid molecules encoding Tumor Suppressor gene and in the amplification of said nucleic acid molecules for detection or for use in further studies of Tumor Suppressor gene. Hybridization of the antisense oligonucleotides, particularly the primers and probes, of the invention with a nucleic acid encoding Tumor Suppressor gene can be detected by means known in the art. Such means may include conjugation of an enzyme to the oligonucleotide, radiolabeling of the oligonucleotide, or any other suitable detection means. Kits using such detection means for detecting the level of Tumor Suppressor gene in a sample may also be prepared.

The specificity and sensitivity of antisense are also harnessed by those of skill in the art for therapeutic uses. Antisense compounds have been employed as therapeutic moieties in the treatment of disease states in animals, including humans. Antisense oligonucleotide drugs have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of Tumor Suppressor gene polynucleotides is treated by administering antisense compounds in accordance with this invention. For example, in one non-limiting embodiment, the methods comprise the step of administering to the animal in need of treatment, a therapeutically effective amount of Tumor Suppressor gene modulator. The Tumor Suppressor gene modulators of the present invention effectively modulate the activity of the Tumor Suppressor gene or modulate the expression of the Tumor Suppressor gene protein. In one embodiment, the activity or expression of Tumor Suppressor gene in an animal is inhibited by about 10% as compared to a control. Preferably, the activity or expression of Tumor Suppressor gene in an animal is inhibited by about 30%. More preferably, the activity or expression of Tumor Suppressor gene in an animal is inhibited by 50% or more. Thus, the oligomeric compounds modulate expression of Tumor Suppressor gene mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

In one embodiment, the activity or expression of Tumor Suppressor gene and/or in an animal is increased by about 10% as compared to a control. Preferably, the activity or expression of Tumor Suppressor gene in an animal is increased by about 30%. More preferably, the activity or expression of Tumor Suppressor gene in an animal is increased by 50% or more. Thus, the oligomeric compounds modulate expression of Tumor Suppressor gene mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

For example, the reduction of the expression of Tumor Suppressor gene may be measured in serum, blood, adipose tissue, liver or any other body fluid, tissue or organ of the animal. Preferably, the cells contained within said fluids, tissues or organs being analyzed contain a nucleic acid molecule encoding Tumor Suppressor gene peptides and/or the Tumor Suppressor gene protein itself.

The compounds of the invention can be utilized in pharmaceutical compositions by adding an effective amount of a compound to a suitable pharmaceutically acceptable diluent or carrier. Use of the compounds and methods of the invention may also be useful prophylactically.

Conjugates

Another modification of the oligonucleotides of the invention involves chemically linking to the oligonucleotide one or more moieties or conjugates that enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, rTumor Suppressor generter molecules, polyamines, polyamides, polyethylene glycols, polyethers, groups that enhance the pharmacodynamic properties of oligomers, and groups that enhance the pharmacokinetic properties of oligomers. Typicalconjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-Hphosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

Representative United States patents that teach the preparation of such oligonucleotides conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,165; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Although, the antisense oligonucleotides do not need to be administered in the context of a vector in order to modulate a target expression and/or function, embodiments of the invention relates to expression vector constructs for the expression of antisense oligonucleotides, comprising promoters, hybrid promoter gene sequences and possess a strong constitutive promoter activity, or a promoter activity which can be induced in the desired case.

In an embodiment, invention practice involves administering at least one of the foregoing antisense oligonucleotides with a suitable nucleic acid delivery system. In one embodiment, that system includes a non-viral vector operably linked to the polynucleotide. Examples of such nonviral vectors include the oligonucleotide alone (e.g. any one or more of SEQ ID NOS: 16 to 36) or in combination with a suitable protein, polysaccharide or lipid formulation.

Additionally suitable nucleic acid delivery systems include viral vector, typically sequence from at least one of an adenovirus, adenovirus-associated virus (AAV), helper-dependent adenovirus, retrovirus, or hemagglutinatin virus of Japan-liposome (HVJ) complex. Preferably, the viral vector comprises a strong eukaryotic promoter operably linked to the polynucleotide e.g., a cytomegalovirus (CMV) promoter.

Additionally preferred vectors include viral vectors, fusion proteins and chemical conjugates. Retroviral vectors include Moloney murine leukemia viruses and HIV-based viruses. One preferred HIV-based viral vector comprises at least two vectors wherein the gag and pol genes are from an HIV genome and the env gene is from another virus. DNA viral vectors are preferred. These vectors include pox vectors such as orthopox or avipox vectors, herpesvirus vectors such as a herpes simplex I virus (HSV) vector [Geller, A. I. et al., (1995) *J. Neurochem,* 64: 487; Lim, F., et al., in DNA Cloning: Mammalian Systems, D. Glover, Ed. (Oxford Univ. Press, Oxford England) (1995); Geller, A. I. et al., (1993) *Proc Natl. Acad. Sci.*: U.S.A.:90 7603; Geller, A. I., et al., (1990) *Proc Natl. Acad. Sci USA:* 87:1149], Adenovirus Vectors (LeGal LaSalle, et al., Science, 259:988 (1993); Davidson, et al., (1993) *Nat. genet.* 3: 219; Yang, et al., (1995) *J. Virol.* 69: 2004) and Adeno-associated Virus Vectors (Kaplitt, M. G., et al., (1994) *Nat. genet.* 8:148).

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein by reference.

The present invention also includes pharmaceutical compositions and formulations that include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage, form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogeneous systems of one liquid dispersed in another in the form of droplets usually exceeding 0.1 μm in diameter. Emulsions may contain additional components in addition to the dispersed phases, and the active drug that may be present as a solution in either the aqueous phase, oily phase or itself as a separate phase. Microemulsions are included as an embodiment of the present invention. Emulsions and their uses are well known in the art and are further described in U.S. Pat. No. 6,287,860.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids. When incorporated into liposomes, these specialized lipids result in liposomes with enhanced circulation lifetimes relative to liposomeslacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein by reference.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating nonsurfactants. Penetration enhancers and their uses are further described in U.S. Pat. No. 6,287,860, which is incorporated herein by reference.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoyl-phosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein by reference. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein by reference.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents that function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bischloroethyl-nitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclo-phosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. For example, the first target may be a particular antisense sequence of Tumor Suppressor gene, and the second target may be a region from another nucleotide sequence. Alternatively, compositions of the invention may contain two or more antisense compounds targeted to different regions of the same Tumor Suppressor gene nucleic acid target. Numerous examples of antisense compounds are illustrated herein and others may be selected from among suitable compounds known in the art. Two or more combined compounds may be used together or sequentially.

Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on EC50s found to be effective in in vitro and in vivo animal models. In general, dosage is from 0.01 μg to 100 g per kg of body weight, and may be given once or more daily, weekly, monthly or yearly, or even once every 4 to 30 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1: Design of Antisense Oligonucleotides Specific for a Nucleic Acid Molecule Antisense to and/or Sense Strand of Tumor Suppressor Gene Polynucleotide As indicated above the term "oligonucleotide specific for" or "oligonucleotide targets" refers to an oligonucleotide having a sequence (i) capable of forming a stable complex with a portion of the targeted gene, or (ii) capable of forming a stable duplex with a portion of an mRNA transcript of the targeted gene.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarily to corresponding nucleic acid sequences in other species. One skilled in the art will realize that there is considerable latitude in selecting appropriate regions of genes for use in the present invention.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays The hybridization properties of the oligonucleotides described herein can be determined by one or more in vitro assays as known in the art. For example, the properties of the oligonucleotides described herein can be obtained by determination of binding strength between the target natural antisense and a potential drug molecules using melting curve assay.

The binding strength between the target natural antisense and a potential drug molecule (Molecule) can be estimated using any of the established methods of measuring the strength of intermolecular interactions, for example, a melting curve assay.

Melting curve assay determines the temperature at which a rapid transition from double-stranded to single-stranded conformation occurs for the natural antisense/Molecule complex. This temperature is widely accepted as a reliable measure of the interaction strength between the two molecules.

A melting curve assay can be performed using a cDNA copy of the actual natural antisense RNA molecule or a synthetic DNA or RNA nucleotide corresponding to the binding site of the Molecule. Multiple kits containing all necessary reagents to perform this assay are available (e.g. Applied Biosystems Inc. MeltDoctor kit). These kits include a suitable buffer solution containing one of the double strand DNA (dsDNA) binding dyes (such as ABI HRM dyes, SYBR Green, SYTO, etc.). The properties of the dsDNA dyes are such that they emit almost no fluorescence in free form, but are highly fluorescent when bound to dsDNA.

To perform the assay the cDNA or a corresponding oligonucleotide are mixed with Molecule in concentrations defined by the particular manufacturer's protocols. The mixture is heated to 95° C. to dissociate all pre-formed dsDNA complexes, then slowly cooled to room temperature or other lower temperature defined by the kit manufacturer to allow the DNA molecules to anneal. The newly formed complexes are then slowly heated to 95° C. with simultaneous continuous collection of data on the amount of fluorescence that is produced by the reaction. The fluorescence intensity is inversely proportional to the amounts of dsDNA present in the reaction. The data can be collected using a real time PCR instrument compatible with the kit (e.g.ABI's STumor Suppressor genene Plus Real Time PCR System or LightTyper instrument, Roche Diagnostics, Lewes, UK).

Melting peaks are constructed by plotting the negative derivative of fluorescence with respect to temperature (-d (Fluorescence)/dT) on the y-axis) against temperature (x-axis) using appropriate software (for example LightTyper (Roche) or SDS Dissociation Curve, ABI). The data is analyzed to identify the temperature of the rapid transition from dsDNA complex to single strand molecules. This temperature is called Tm and is directly proportional to the strength of interaction between the two molecules. Typically, Tin will exceed 40° C.

Example 2: Modulation of Tumor Suppressor Gene Oligonucleotide Gene Expression Treatment of HEPG2 Cells with Antisense Oligonucleotides HepG2 cells from ATCC (cat #HB-8065) were grown in growth media (MEM/EBSS (Hyclone cat #SH30024, or Mediatech cat #MT-10-010-CV)+10% FBS (Mediatech cat #MT35-011-CV)+ penicillin/streptomycin (Mediatech cat #MT30-002-CI)) at 37° C. and 5% $CO_2$. One day before the experiment the cells were replated at the density of 1.5×$10^5$/ml into 6 well plates and incubated at 37° C. and 5% $CO_2$. On the day of the experiment the media in the 6 well plates was changed to fresh growth media. All antisense oligonucleotides were diluted to the concentration of 20 µM. Two µl of this solution was incubated with 400 µl of Opti-MEM media (Gibco cat #31985-070) and 4 µl of Lipofectamine 2000 (Invitrogen cat #11668019) at room temperature for 20 min and applied to each well of the 6 well plates with HepG2 cells. Similar mixture including 2 µl of water instead of the oligonucleotide solution was used for the mock-transfected controls. After 3-18 h of incubation at 37° C. and 5% $CO_2$ the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) or High Capacity cDNA Reverse Transcription Kit (cat #4368813) as described in the manufacturer's protocol. The cDNA from this reverse transcription reaction was used to monitor gene expression by real time PCR using ABI Taqman gene Expression Mix (cat #4369510) and primers/probes designed by ABI. The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems Inc. or Mx4000 thermal cycler (Stratagene).

Fold change in gene expression after treatment with antisense oligonucleotides was calculated based on the difference in 18S-normalized dCt values between treated and mock-transfected samples.

p73 Expression Assays used (ABI cat #s), all probes with MGB

```
p73:
Hs00232088_ml (target sequence
ACCTCTGGAGCTCTCTGGAAC, exon 2 SEQ ID No.: 41)

p73as:
Hs00215135_ml (target sequence
TATGATGGAAAGGTGCGCATCCTTA, exon 7 SEQ ID No.: 42)
and

Hs00892470_gl
```

Figure 1B:
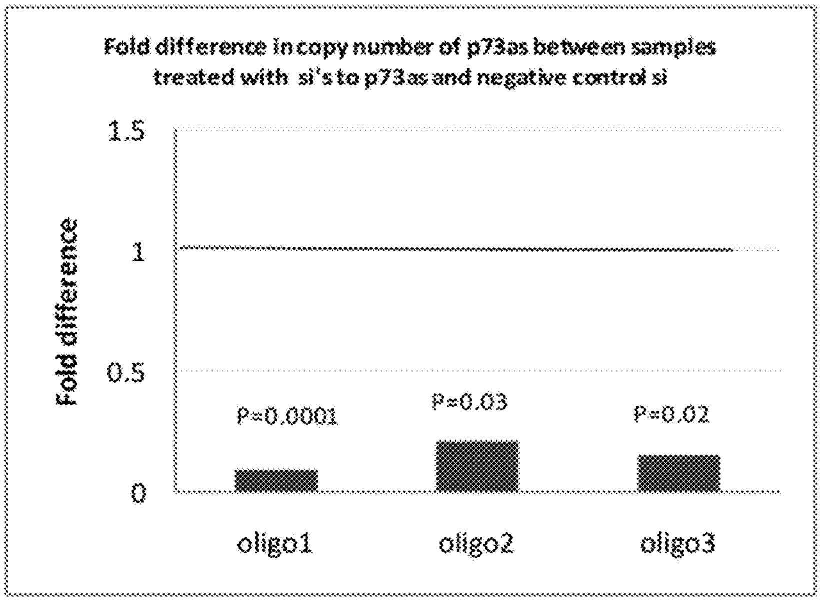

Results:

Real time PCR results show that the levels of the Tumor Suppressor gene mRNA in HepG2 cells are significantly increased 48 h after treatment with two of the siRNAs designed to Tumor Suppressor gene (Tumor Suppressor gene_1, P=0.02, and Tumor Suppressor gene_2, P=0.04, FIG. 1A). In the same samples the levels of Tumor Suppressor gene RNA were possibly decreased after treatment with siRNAs to Tumor Suppressor gene (FIG. 1B).

Figure 1C:
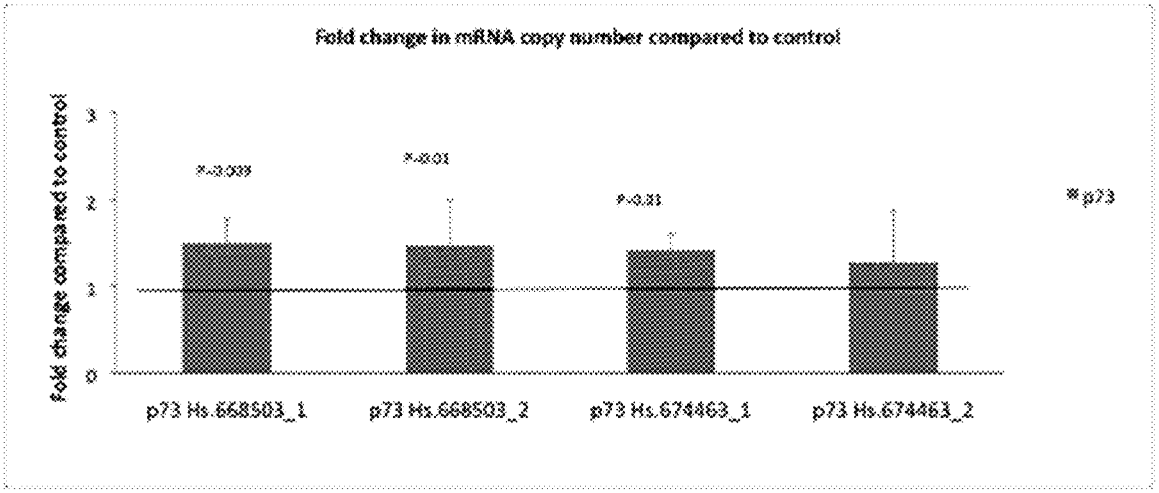
FIG. 1C: is a graph of real time PCR results showing the fold change+standard deviation in TP73 mRNA after treatment of HepG2 cells with siRNA oligonucleotides introduced using Lipofectamine 2000, as compared to control. Real time PCR results show that the levels of the p73 mRNA in HepG2 cells are significantly increased 48 h after treatment with two of the oligos designed to p73 antisense Hs.668503 and one of the oligos designed to p73 antisense Hs.674463. Bars denoted as p73 Hs.668503_1, p73 Hs.668503_2, p73 Hs.674463 1 and p73 Hs.674463_2 correspond to samples treated with SEQ ID NOS 19, 20, 21 and 22 respectively.

In FIG. 1C, the Real time PCR results show that the levels of the Tumor Suppressor gene mRNA in HepG2 cells are significantly increased 48 h after treatment with two of the oligos designed to Tumor Suppressor gene antisense Hs.668503 and one of the oligos designed to Tumor Suppressor gene antisense Hs.674463.

Figure 3:
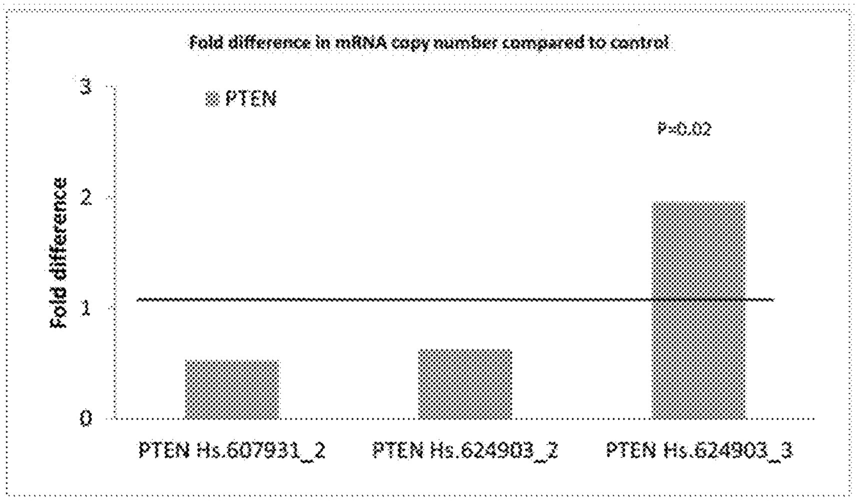
FIG. 3 is a graph of real time PCR results showing the fold change in PTEN mRNA after treatment of HepG2 cells with phosphorothioate oligonucleotides introduced using Lipofectamine 2000, as compared to control. Real time PCR results show that the levels of PTEN mRNA in HepG2 cells are significantly increased 48 h after treatment with one of the oligos designed to PTEN antisense Hs.624903. Bars denoted as PTEN Hs.607931_2, PTEN Hs.624903 2, PTEN Hs.624903_3 correspond to samples treated with SEQ ID NOS 34, 35 and 36 respectively.

Real time PCR results show that the levels of PTEN mRNA in HepG2 cells are significantly increased 48 h after treatment with one of the oligonucleotides designed to PTEN antisense hs.624903 (FIG. 3). (Detection probes: Applied Biosystems Taqman Gene Expression Assay: Hs02621230_sl)

Treatment of TM4 Cells with Antisense Oligonucleotides

TM4 cells from ATCC (cat #CRL-1715) were grown in growth media (MEM/EBSS (Hyclone cat #SH30024, or Mediatech cat #MT-10-010-CV)+10% FBS (Mediatech cat #MT35-011-CV)+ penicillin/streptomycin (Mediatech cat #MT30-002-CI)) at 37° C. and 5% $CO_2$. One day before the experiment the cells were replated at the density of 1.5×$10^5$/ml into 6 well plates and incubated at 37° C. and 5% $CO_2$. On the day of the experiment the media in the 6 well plates was changed to fresh growth media. All antisense oligonucleotides were diluted to the concentration of 20 µM. Two µl of this solution was incubated with 400 µl of Opti-MEM media (Gibco cat #31985-070) and 4 µl of Lipofectamine 2000 (Invitrogen cat #11668019) at room temperature for 20 min and applied to each well of the 6 well plates with TM4 cells. Similar mixture including 2 µl of water instead of the oligonucleotide solution was used for the mock-transfected controls. After 3-18 h of incubation at 37° C. and 5% $CO_2$ the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) or High Capacity cDNA Reverse Transcription Kit (cat #4368813) as described in the manufacturer's protocol. The cDNA from this reverse transcription reaction was used to monitor gene expression by real time PCR using ABI Taqman gene Expression Mix (cat #4369510) and primers/probes designed by ABI (Applied Biosystems Taqman gene Expression Assay: Mm00660220_ml by Applied Biosystems Inc., Foster City Calif.). The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems).

Fold change in gene expression after treatment with antisense oligonucleotides was calculated based on the difference in 18S-normalized dCt values between treated and mock-transfected samples.

Figure 1D:
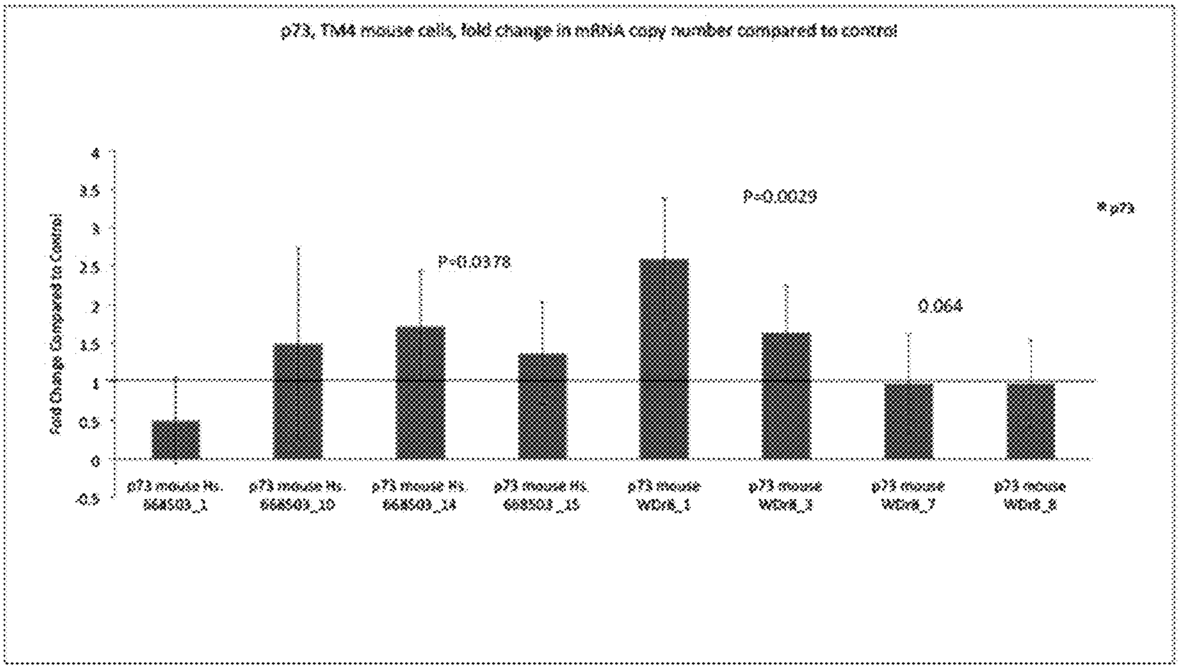
FIG. 1D: is a graph of real time PCR results showing the fold change+standard deviation in TP73 mRNA after treatment of TM4 cells with phosphothioate oligonucleotides introduced using Lipofectamine 2000, as compared to control. Real time PCR results show that the levels of the p73 mRNA in mouse TM4 cells are significantly increased 48 h after treatment with one of the oligos designed to mouse p73 antisense Hs.668503 and one of the oligos designed to mouse p73 antisense WDR8. Bars denoted as p73 mouse Hs.668503 1, p73 mouse Hs.668503 10, p73 mouse Hs.668503 14, p73 mouse Hs.668503 15, p73 mouse WDr8_1, p73 mouse WDr8_7, p73 mouse WDr8_8 and p73 mouse WDr8_3 correspond to samples treated with SEQ ID NOS 20 to 30 respectively.

Results:

Real time PCR results show that the levels of the Tumor Suppressor gene mRNA in mouse TM4 cells are significantly increased 48 h after treatment with one of the oligos designed to Tumor Suppressor gene antisense Hs.668503 and one of the oligos designed to Tumor Suppressor gene antisense WDR8 (FIG. 1D).

Treatment of HUVEC Cells with Antisense Oligonucleotides

HUVEC cells from ATCC (Promo Cell cat #C-12253) were grown in Epithelial Growth Media (Promo Cell cat #C-22010) at 37° C. and 5% $CO_2$. One day before the experiment the cells were replated using Promo Cell Detach Kit (cat #C-41200) at the density of 1.5×10^5/ml into 6 well plates and incubated at 37° C. and 5% $CO_2$. On the day of the experiment the media in the 6 well plates was changed to fresh Epithelial Growth Media. All antisense oligonucleotides were diluted to the concentration of 20 μM. Two μl of this solution was incubated with 400 μl of Opti-MEM media (Gibco cat #31985-070) and 4 μl of Lipofectamine 2000 (Invitrogen cat #11668019) at room temperature for 20 min and applied to each well of the 6 well plates with HUVEC cells. Similar mixture including 2 μl of water instead of the oligonucleotide solution was used for the mock-transfected controls. After 3-18 h of incubation at 37° C. and 5% $CO_2$ the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) as described in the manufacturer's protocol. The cDNA from this reverse transcription reaction was used to monitor gene expression by real time PCR using ABI Taqman gene Expression Mix (cat #4369510) and primers/probes designed by ABI (Applied Biosystems Taqman Gene Expression Assays: Hs00153340_ml and Hs00216360_ml by Applied Biosystems Inc., Foster City Calif.). The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems Inc.) or Mx4000 thermal cycler (Stratagene).

Fold change in gene expression after treatment with antisense oligonucleotides was calculated based on the difference in 18S-normalized dCt values between treated and mock-transfected samples.

P53 Expression Assays used (ABI cat #s), all probes with FAM/MGB: 18S: 4319413E

```
P53:
Hs00153340_ml (target sequence
CTTCCCTGGATTGGCAGCCAGACTG, SEQ ID No.: 43)

P53as:
Hs00216360_ml (target sequence
ATATGCAGAAATGGTCCCTGTCCTT, SEQ ID No.: 44)
```

Figure 2:
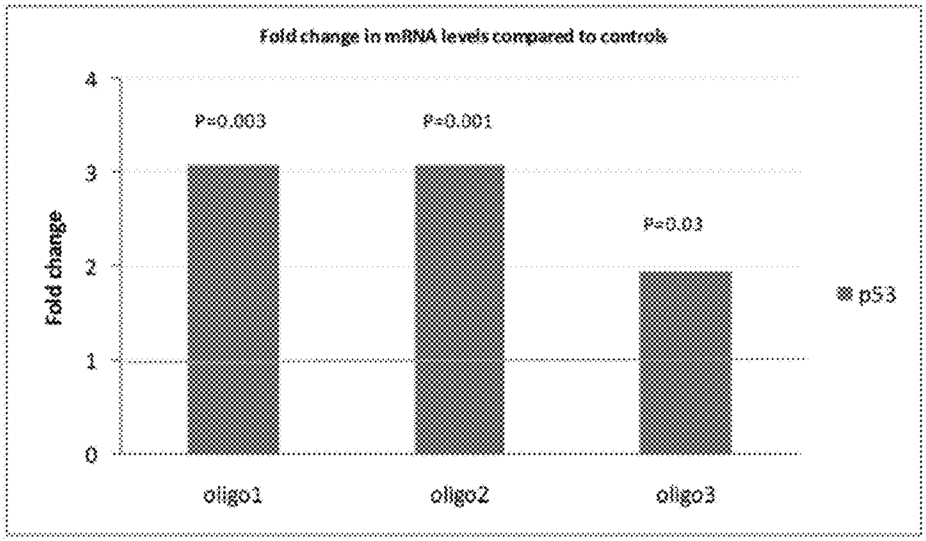
FIG. 2 is a graph of real time PCR results showing the fold change in p53 mRNA after treatment of HUVEC cells with phosphothioate oligonucleotides introduced using Lipofectamine 2000, as compared to control. Real time PCR results show that the levels of p53 mRNA in HUVEC cells are significantly increased 48 h after treatment with all of the siRNAs designed to p53as (oligo1, P=0.003, oligo2 P=0.001, and oligo2 P=0.03). Bars denoted as oligo1, oligo2 and oligo3 correspond to samples treated with SEQ ID NOs: 31, 32 and 33 respectively.

Results:

Real time PCR results show that the levels of p53 mRNA in HUVEC cells are significantly increased 48 h after treatment with all of the siRNAs designed to p53as (FIG. 2).

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the disclosure will allow the reader to quickly ascertain the nature of the technical disclosure. It is submitted with the understanding that it will not be used to interpret or limit the scope or meaning of the following claims.

What is claimed is:

1. A single-stranded synthetic, modified oligonucleotide of 15 to 27 nucleotides in length comprising at least one modification, wherein the at least one modification is selected from: at least one modified sugar moiety; at least one modified internucleotide linkage; at least one modified nucleotide; and combinations thereof; and further wherein said oligonucleotide is an antisense compound which is 100% complementary to and specifically hybridizes to a target region of a human natural antisense polynucleotide selected from the group consisting of SEQ ID NOs: 14 or 15, and wherein the oligonucleotide upregulates expression and/or function of a human PTEN gene polynucleotide having SEQ ID NO: 6 in vivo or in vitro as compared to a normal control oligonucleotide, wherein the target region on SEQ ID NO: 14 is selected from nucleotides 1-75, 137-159, 161-191, 196-301, 317-337 and 399-789 on said SEQ ID NO: 14.

2. The oligonucleotide of claim 1, wherein the at least one modification comprises an internucleotide linkage selected from the group consisting of: phosphorothioate, alkylphosphonate, phosphorodithioate, alkylphosphonothioate, phosphoramidate, carbamate, carbonate, phosphate triester, acetamidate, carboxymethyl ester, and combinations thereof.

3. The oligonucleotide of claim 1, wherein said oligonucleotide comprises at least one phosphorothioate internucleotide linkage.

4. The oligonucleotide of claim 1, wherein said oligonucleotide comprises a backbone of phosphorothioate internucleotide linkages.

5. The oligonucleotide of claim 1, wherein the oligonucleotide comprises at least one modified nucleotide, said modified nucleotide selected from: a peptide nucleic acid, a locked nucleic acid (LNA), and a combination thereof.

6. The oligonucleotide of claim 1, wherein the oligonucleotide comprises a plurality of modifications, wherein said modifications comprise internucleotide linkages selected from: phosphorothioate, alkylphosphonate, phosphorodithioate, alkylphosphonothioate, phosphoramidate, carbamate, carbonate, phosphate triester, acetamidate, carboxymethyl ester, and a combination thereof.

7. The oligonucleotide of claim 1, wherein the oligonucleotide comprises a plurality of modifications, wherein said modifications comprise modified nucleotides selected from: peptide nucleic acids, locked nucleic acids (LNA), and a combination thereof.

8. The oligonucleotide of claim 1, wherein the oligonucleotide comprises at least one modified sugar moiety selected from: a 2'-O-methoxyethyl modified sugar moiety, a 2'-methoxy modified sugar moiety, a 2'-O-alkyl modified sugar moiety, a bicyclic sugar moiety, and a combination thereof.

9. The oligonucleotide of claim 1, wherein the oligonucleotide comprises a plurality of modifications, wherein said modifications comprise modified sugar moieties selected from: a 2'-O-methoxyethyl modified sugar moiety, a 2'-methoxy modified sugar moiety, a 2'-O-alkyl modified sugar moiety, a bicyclic sugar moiety, and a combination thereof.

10. The oligonucleotide of claim 1, wherein the oligonucleotide comprises SEQ ID NO: 36.

11. A pharmaceutical composition comprising one or more modified oligonucleotides according to claim 1 and a pharmaceutically acceptable excipient.

12. The pharmaceutical composition of claim 11, wherein the modified oligonucleotides have at least 90% sequence identity as compared to the nucleotide sequence set forth as SEQ ID NO: 36.

13. The pharmaceutical composition of claim 11, wherein the modified oligonucleotide comprises SEQ ID NO: 36 and has one or more modifications.

14. The pharmaceutical composition of claim 13, wherein the one or more modifications are selected from: phosphorothioate, methylphosphonate, peptide nucleic acid, locked nucleic acid (LNA) molecules, and combinations thereof.

* * * * *

```
SEQUENCE LISTING

<160> NUMBER OF SEQ ID NOS: 47

<210> SEQ ID NO 1
<211> LENGTH: 2845
<212> TYPE: DNA
<213> ORGANISM: homo sapiens

<400> SEQUENCE: 1

aggggacgca gcgaaaccgg ggcccgcgcc aggccagccg ggacggacgc cgatgcccgg      60

ggctgcgacg gctgcagagc gagctgccct cggaggccgg cgtggggaag atggcccagt     120

ccaccgccac ctcccctgat gggggcacca cgtttgagca cctctggagc tctctggaac     180

cagacagcac ctacttcgac cttccccagt caagccgggg gaataatgag gtggtgggcg     240

gaacggattc cagcatggac gtcttccacc tggagggcat gactacatct gtcatggccc     300

agttcaatct gctgagcagc accatggacc agatgagcag ccgcgcggcc tcggccagcc     360
```

-continued

```
cctacacccc agagcacgcc gccagcgtgc ccacccactc gccctacgca caacccagct    420
ccaccttcga caccatgtcg ccggcgcctg tcatcccctc caacaccgac taccccggac    480
cccaccactt tgaggtcact ttccagcagt ccagcacggc caagtcagcc acctggacgt    540
actccccgct cttgaagaaa ctctactgcc agatcgccaa gacatgcccc atccagatca    600
aggtgtccac cccgccaccc ccaggcaccg ccatccgggc catgcctgtt tacaagaaag    660
cggagcacgt gaccgacgtc gtgaaacgct gccccaacca cgagctcggg agggacttca    720
acgaaggaca gtctgctcca gccagccacc tcatccgcgt ggaaggcaat aatctctcgc    780
agtatgtgga tgaccctgtc accggcaggc agagcgtcgt ggtgccctat gagccaccac    840
aggtggggac ggaattcacc accatcctgt acaacttcat gtgtaacagc agctgtgtag    900
ggggcatgaa ccggcggccc atcctcatca tcatcaccct ggagatgcgg gatgggcagg    960
tgctgggccg ccggtccttt gagggccgca tctgcgcctg tcctggccgc gaccgaaaag   1020
ctgatgagga ccactaccgg gagcagcagg ccctgaacga gagctccgcc aagaacgggg   1080
ccgccagcaa gcgtgccttc aagcagagcc cccctgccgt ccccgccctt ggtgccggtg   1140
tgaagaagcg gcggcatgga gacgaggaca cgtactacct tcaggtgcga ggccgggaga   1200
actttgagat cctgatgaag ctgaaagaga gcctggagct gatggagttg gtgccgcagc   1260
cactggtgga ctcctatcgg cagcagcagc agctcctaca gaggccgagt cacctacagc   1320
ccccgtccta cgggccggtc ctctcgccca tgaacaaggt gcacgggggc atgaacaagc   1380
tgccctccgt caaccagctg gtgggccagc ctcccccgca cagttcggca gctacaccca   1440
acctggggcc cgtgggcccc gggatgctca acaaccatgg ccacgcagtg ccagccaacg   1500
gcgagatgag cagcagccac agcgcccagt ccatggtctc ggggtcccac tgcactccgc   1560
caccccccta ccacgccgac cccagcctcg tcagtttttt aacaggattg gggtgtccaa   1620
actgcatcga gtatttcacc tcccaagggt tacagagcat ttaccacctg cagaacctga   1680
ccattgagga cctgggggcc ctgaagatcc ccgagcagta ccgcatgacc atctggcggg   1740
gcctgcagga cctgaagcag ggccacgact acagcaccgc gcagcagctg ctccgctcta   1800
gcaacgcggc caccatctcc atcggcggct caggggaact gcagcgccag cgggtcatgg   1860
aggccgtgca cttccgcgtg cgccacacca tcaccatccc caaccgcggc ggcccaggcg   1920
gcggccctga cgagtgggcg gacttcggct tcgacctgcc cgactgcaag gcccgcaagc   1980
agcccatcaa ggaggagttc acggaggccg agatccactg agggcctcgc ctggctgcag   2040
cctgcgccac cgcccagaga cccaagctgc ctcccctctc cttcctgtgt gtccaaaact   2100
gcctcaggag gcaggacctt cgggctgtgc ccggggaaag gcaaggtccg gcccatcccc   2160
aggcacctca caggccccag gaaaggccca gccaccgaag ccgcctgtgg acagcctgag   2220
tcacctgcag aaccttctgg agctgcccta gtgctgggct tgtggggcgg gggctggccc   2280
actctcagcc ctgccactgc cccggcgtgc tccatggcag gcgtgggtgg ggaccgcagc   2340
gtcggctccg acttccaggc ttcatcctag agactgtcat ctcccaacca ggcgaggtcc   2400
ttccaaagga aaggatcctc tttgctgatg gactgccaaa aagtattttg cgacatcttt   2460
tggttctgga tagtagtgag cagccaagtg actgtgtctg aaacaccagt gtattttcag   2520
ggaatgtccc taactgcgtc ttgcccgcgc cgggggctgg ggactctctc tgctggactt   2580
gggactggcc tctgccccca gcacgctgta ttctgcagga ccgcctcctt cctgccccta   2640
acaacaacca cagtgttgct gaaattggag aaaactgggg agggcgcaac ccccccagg    2700
```

cgcggggaag catgtggtac cgcctcagcc agtgcccctc agcctggcca cagtcgcctc 2760
tcctcgggga cccctcagca gaaagggaca gcctgtcctt agaggactgg aaattgtcaa 2820
tatttgataa aatgataccc ttttc 2845

<210> SEQ ID NO 2
<211> LENGTH: 81339
<212> TYPE: DNA
<213> ORGANISM: homo sapiens

<400> SEQUENCE: 2
aggggacgca gcgaaaccgg ggcccgcgcc aggccagccg ggacggacgc cgatgcccgg 60
ggctgcgacg gctgcaggta ggaggcccag ggccgggggg cggttcggct ccgcgggcgg 120
gggctggagc gcagcgctgg gcaggcacct gggctcgcag ctccgaagct gggaggtgag 180
gggagagcga tcggggacga gctgggacaa ggcgacacag gggctccctc ggagttggat 240
cggcccctgg gacttggcgc tcgcgagagg ctggagcggc cagagtctag cctgcgagga 300
gacgcgggtc ctgccctcag cgccggccgc ctttggcgcc aaagacagcc ccgcaggggt 360
tccgggaggg ccctcctcct gctgtcccct ctccaccccg ggctccgagg gccgttggga 420
gggtaacccc gggaagaggc cggggtgcgg ggcgcgggtg caggtggaaa tcgccagcaa 480
gctcctcccc gcccgcgcgc tccctccgac ctgcagggct gtgccaatcc cgaggcctca 540
gcttccctga ggagccaggg ccaggccccc ctctggacag ggagaaggat ctgggcgggg 600
gccttgaccc atggagttgg ttactaagcg gtttcgatgg tttcccgagg gacagctccc 660
tgtggctctg agtttgtctg tcgagggctc ctggcctgtc tccggagcgg tcccaggtag 720
agaaagcccg tgaagaaatg gcccgggccg gcctggaggg agacacctca cgccccctta 780
gctcctgggc cgcctcctcc tgcagcccct gcctttcccg gggcttggac ttggggagcg 840
atgattacct ttgctcagct tgtattttgg cctggacgct aggagataag cccatgtagt 900
atgcacacgt ctgctacata aacaggggac agatagacga tcttcaacca gcaagggtgc 960
agggaaaagc aatgcacccc aaacttctga ccagaggtca tttgcttcca aagatgctgc 1020
catctgttta ttcactgtct ggacatttgg aaatggctca ggctcattaa cacaatgctt 1080
tggtttttgt tgttttgttt tttgttgctg tcattgctgt ttatttgttc agccttagct 1140
ctgggggagg agtaaacaaa gcgcgtggcc tctggcactt actgagcgct gagccacccc 1200
tctttggatt tattcgggga aagattaaaa agcatttcat taagaacagg acacggtgtt 1260
tgaaatgttg ccatatatga atgtatgcat tacgtatgta gtttttaaaa taagataaaa 1320
agttggctgg gcacggtagc tcacgcctgt catccctcac agcctttggg aggccaaggt 1380
gggtggatca cctgaggtca ggagttcgag accagcctgg ccatcatggt gaaacccagt 1440
ctctacttga aatacaaaaa ttagctgggc atggtggcag gcacctgtac tcccagctac 1500
tcgggaggct gaggcacaag aattgcttga acctgggatg gagaggttgc agcgagctga 1560
tatcatgcca ctgcactcca gcctgggcaa cagagcaaga ctctgtctca aaaaataaga 1620
tgaaataaga taaaagttgg tgtcagaggc tgcagtgtgg cagctgccta ttgtcaatca 1680
gaggtagcct ggggtgaacg gaaggcggac ctgagcgggg cttgtctatg cgcggcggcc 1740
accagagaat ggctcgggat gtgagccctg ccttgcagtc cttctcgtga aagctacagc 1800
gaacagtagc tgtctccaaa tcccgaaggc cagtcgcatg gagaagctgg tctggcacag 1860
tggttaatgg ggtagtatgg aagtcagaat gctggggttc aaatctcctc ttccccattt 1920
actccagcaa gtcacttaac cacttggagc ctcaggttac ccatctgcag agtcgggtaa 1980
tagtagttcc tgcctcagag gcttggagaa cagtcagtga ggtgccgtcc gaagggcttg 2040
ggagagtgcc tggcacccac tcagtgtcct cacacatgat ggcttcgggt cccaggtgct 2100
gttccagagc tgggagagcc aggagccctg ggagagagacc cggctcctta gtatctggta 2160
ggtatctcca gggcaggagg gatggcagtg aggcaggcat ctgcccaagg cgtgggtgga 2220
agctgatggc atctgtcaga agtatgcact ggggcaagga tgcctggttt agtatttatt 2280
tatagggcat gccccaccca ggtccaagaa tggattgata acactgagca cgtgtgaaag 2340
gcacggctaa agtggagaga agagaagagg ctgagggccg agagaggagc cgcacaccca 2400
ctccagaacc cggacgaggc cctgcccttg cccagcggcg gtattaaccc tgagattccg 2460
agcacaccaa agtgacatcg cgtacacggt gaaccctgtg tttgcaaaaa gtcagaaaaa 2520
gtcttcaaaa catcctttaa ggccaggcgc cgtggcccac gcctgtaatc tcagcccttt 2580
gggaggccga ggtgggtgga tcacttgaga tcaggagttc aagaccagcc tgggcaaaat 2640
ggtgaaatct tgtccccacc aaaaatacaa aaattagccg ggggtggtgt ctggtgcctg 2700
tagtctcagc tactcaggag gctgaggcag gagaatcgct tgaacttggg aggcagaggt 2760
tgcagtgagc cgagatcacc ccactgcact ccagcccggg caacagagcg agactctgtc 2820
tcaaaaaaac acgcaaaaaa tacttttggt gtgtgtttca tgtaacgagc tgccattttg 2880
cggcttgcct ttgttttcca gtgtggggag ggctaaggca accttttaag atatctgtat 2940
gttatttcct cgtgattttg ctttaaaagc aaaaaagaaa aaagctgaga tgagttacta 3000
aatgacaata acgcctactt ttcttttgaa ttcccgtgtt atttgtatct gaatgtggtg 3060
aaagttttct aaatgtaatg ttttatcacc agtaagtagg ctgagtgatc acttactcct 3120
accagtattt aatacttcca tgttctgccc agattccttt aacaaataca caaaacacac 3180
ttgtagctgg caacatccac tcgtgtataa tgaaaacaca caatggcttt cttagaagtt 3240
tgccttctta agtgggttac acaggatgcc tcgaaaatcc ttctctgtgg gtcgtgcaga 3300
aggtatttta ttctaaaaat tccctctact cagccgggcg cagtggctca cgcctgtaat 3360
cccagcattt tgggaggctg aggcgggtgg atcacgaggt caggagatca agaccatcct 3420
ggctaacacg gtgaaacccc gtctctacta aaaatacaaa aaattagtcg ggcgtggtgc 3480
gggcacctgt agtcccagct acccaggagg ctgaggcagg agaatggcgt gaacccggaa 3540
ggcggagctt gcagtgagct gagatcacgc actacactcc agcctgggcg acagagcgag 3600
actacgtctc aaaaaaaaaa aaaaaaaatc cctctgctca ttggcatttg agtgtaagac 3660
agcttatacc aaagtgggct cagacagaca tatgcacatg tttacagact ttctgcctgc 3720
cccctggcag tccactctgt gctcagtatt tctttgcagg ctaaacactc gctcatccaa 3780
agtgctttct tttcctggac aagttgcaca tcacagaccc aaagaagaaa aagataatcc 3840
agcccaactc ttgtttttta atgtttcctg taataactca catttagccc atggtggctg 3900
tgagctggta cttggctaaa aagtttacat ttttttccct gtaatcccca caatagcccg 3960
ttgaagtaga tactataatt atgcccattt acagatgagg aaactgaggc ttcaactggc 4020
tattctactt gcacagggtc acacagctgc aaagtacggg agtggggact ccagctatga 4080
ccacgaagct gggactgggg ctgccaaacc atcctttgcc tgggtctgcc gttggctcag 4140
acacggcccc cagacaccta ggaccgtgga acattcaggc cggaagggcc cttccagaac 4200
atctaagcca ggggtagaga gtccagggtg ctgtgagcct ggatggggaa aaatggcacc 4260
ttgtattaac ctcaaagcaa atttcagcat ttcctctagt tttgaatgta ggcagcaaac 4320

-continued

```
tacagtcata gcagtacctg tgacctcacc agtgggaacc actgatattt tcatggtgtc   4380
cggtaatagc tgcagcatct taaaaagtgg tttgtgcttg tcgctccgtt gcaattatgg   4440
cggtgattag atctgctctc aggcttacga cttaatgtat gaacaaagaa gcgcacatat   4500
gatcacctcc cagttttgct ttttaaatat tagggtcact ttgtaagttt tctcaggctg   4560
ctgttacaaa tgaccacaaa ttaagtggct ggaaacaata gagagtgttg tctcacggtt   4620
gtggaggcag gaatctgaag ccaggtgtgg gcagggtcgg gttccctcgg aggctctgag   4680
agggggctcg cctcctgtct ccctcctagg atctgggggc tgccggccat cctgtggttc   4740
ccaggcatgc agatgcacca cccagtctct gccaccatct tgccatggcc ttctcctctg   4800
tgtccctgtg tgtctctcct tttttgtccc ttagatggac acctgtcctt ggatttcggg   4860
cccacctgga aaatccagaa tgatcttatc ttgagaccct tacctaagtg gcatctgcaa   4920
agaccctgat tccaaataac atcccattct gaggctcgtt cccagaggct gcatccaacc   4980
cactagagtg gctatgtttc agtaactcgt gatcctgtgt attttgcttc atgtatttaa   5040
aacattctcc cggacaaggc gtctgagatt ccccaggctg ccagaggggc catggcgcaa   5100
acggggaaga aacctggtct aagccacgcc cctcttttca ggacgaggat cttggaaccc   5160
ggacactgaa ggtcggggtt gggcacagcc ggggatgggc agccccccctc tcccccagca   5220
cctcccgcct ggcgcctcct ccacagcccc tgcatcctgg aaaacagact gttccacaca   5280
ctccagcagc tcctctacct ggggactgct tgggccgcat agcccccagt tagggacaga   5340
aaccagaggt attgaacaag aagccccacc gggagaggcg agacccgggc cccagccctg   5400
gacctggccg tgggtgctac agaaggtcgg gggacatcgg tctgcgcgga agggtctgga   5460
gaggcacctc tcagggagtt ggacagagag gagacgccgt cccagtggtg gcctccagtg   5520
aggcctggag agaccaggtg gcaggaaggg ccctgctggg gccagagcaa gggcacggaa   5580
ggcaggtctc atggagcagg gaccgtggag gggacatggg ggacacatta gggatggaca   5640
gtggccggaa gattccgtgg gccttggaga ttaaatcggg ttccccaaag agcaagctgt   5700
ggagagggga agggaaagtt gcctccctct tccctacggg gttcttgtca ataaacgatt   5760
gacaaaagac agactcacaa gagacaacag ttttaaggct gtgcccccgc ccggaagtgc   5820
cataaaaaca ggagactcag cagtaaccag atgggagcgg tgcagatgtc cgtcctctgt   5880
gacagaaagg aaagggggcc tgggcttctg gggagcggta gagacaaatg aggagagggt   5940
gagggaggaa acgtctgggc ataaaggctg cctcgtggtg cagctatcag tctcatggtg   6000
agaaaatgcg tcttggcgcg cggctctctt cctggcacac agaccattac taatgaaaat   6060
gtcctttata gatgtcaatt ttctttagaa aagagagttt tttactttat tttagggagc   6120
tgaagagctt tttttctgtt ggctggttct cagttgcttt tagctcaaag taatcaacat   6180
gtcaacatgg catattttgg ggtgacgtat tctggtctcc tacagtcata ttttggggtg   6240
acgtattctg gtctcctaca gtcatatttt ggggtgacgt attctagtct cctacagtca   6300
tatttagggg tggcgtattc tggtctccta cagtcatatt ttggggtggc gtattctggt   6360
ctcctacagt catattttgg ggtggcgtat tctggtctcc tacagtcata ttttggggtg   6420
acgtattctg gtctcctata gtcatattta ggggtggcgt attctggtct cctacagtca   6480
tactttgggg tgatgtgtcc tgagccccat tgtttcctag tctgaaactt ccccaagaag   6540
ctccacggta cagaaactgg gtgggtgtgt tgtcccataa tgctttgaag aggcatttct   6600
atggaaacaa aagaaaaaaa aaaaaagcta atcattggag ctgactaaaa accagtttct   6660
gagcctgggg gccgtggcgg ggcaggtttg tagatgttgg gctccgagca tcttctgcgg   6720
```

-continued

```
tttggtctct ggcgatgtct gggcggccca cgcagcaaca ggcgtgaggg tccctcgcac   6780
ctgggcttcg tggtaatctc gctgatgagt atttcaagtc gtccagcctc agtttgcagg   6840
atttctgggc aaagggcagt tttgttcttc gtgattccaa taagaacggt gggagaaaat   6900
tgaaagtgtt agtttgggag ttgcagccag atactggagg aaactagaaa catcaggaac   6960
ccgtccagtt tgtagacatc aatagataac aaaaccccaa agacgttaaa caggacaaga   7020
atctaatatg gggcgcacaa tatggctttc tactgaaata tatgttcttt ctacatcacc   7080
cctctttcta ctaaaaataa tctcagtaag attattatta ttattattat ttttgagaca   7140
gagttccact ccgtcgctca aggctagagt gtagtggcat catctcgact cactgcaaac   7200
tctgcctccc gggttcaagt gattctcctg cctcagcctc ctggagttac aggcatgcac   7260
caccactaat ttttgtatta ttattacttt tttttagtag agacagggtt ttgccatgtt   7320
ggccaggctg gtcttgaact cctgacctca caggatccac ccacttcggc ctcccaaagt   7380
gctaggatta cagacgtgag ccactgtgcc cagcctagtc agattaactt gtttgtaaag   7440
taagtctagc ctcattaaaa ttggcctgat tatttgcaca agtgcagcaa gaatagtaag   7500
tggccagcta ggctttcttt aggtcagctt tgctggaact tttaataaat ctcaggttag   7560
gctttcaaaa gcctcttgag gctaagaagt caagccaagg acttgatatc agacttcacc   7620
tgcaatacct atagatttgg gtggattcct ctttctcaag gttcccaacg tattcttgag   7680
aattactgcc aaaaaatcac agtctttcct caacccgtga ggctgcagaa gccctttaat   7740
ccaggtacaa gggcaatttt gttttcctcc aacgggtttc attggctcca taaagtcaac   7800
cttagttcct taaagctact cacatctgat tttatgcaca tcactctcaa atatgatatt   7860
ccggtcaaac acttggtgag ctaaccaaca tttccagttg tttcctatta caaggcagca   7920
gattcatctt gaacttaagc aaataactct atggccgtaa aaataaaaat gctaatagtt   7980
tctaaattct ggagagatca ggtagggaga aaagtcatca tttcaatttt gcttataaaa   8040
gtgtaatgta ccagaatgct gtaagttata aatagtttct tcatttacat tctggaaatt   8100
cttgccatcc agtggtgtga tcttaatgta tcagaaacct gtactggtca aagtcttccc   8160
catgaaatct tctcgaagac acaacatttt agaattatag ttgcttgcaa aagctttcgg   8220
gaaagcatca gagccaaaca gttaactgtg tatgacagaa aggcttaaaa tggccttggc   8280
taaagatgtg atgacatcat tacaatgtaa ctgatgagga agtttggtta ttcctgtggt   8340
gtatactttc acataataac tagaattaca actaatatag aatgtatcag atttctaaga   8400
atttcatata atttctggaa ctcttatatg aatatatatc catgcaaata taactcaccc   8460
agagaaggtt aatcatcact tcatatttta cagtgcttcc atgcaaattt agttgatcaa   8520
ataagcccaa tttatttaat atctttttat tttatctaaa acaattttcc ctttaacatt   8580
ggcaaaataa tctatgtttt tataaggaga gaaaataaat ccttttgaga tattccaggg   8640
gccaatctag gaaatcccaa acgttaattc agggtcaaaa agacttaatt tagagtgtgt   8700
gattttggaa agttgtcaaa atgtcaaaag gttgaaagca cttgattaaa tagaatccca   8760
gatcattatg aaataatact taattctcat ttaatcaaag taacaatgaa atattcaaag   8820
agaaatgcag aaagttagat agtttaaaat actcttagat ctggccaggc atggtgggtc   8880
atgcctgtaa ttccagcact ttgagaggct gacatgagcg gatcactaga gcccaggagt   8940
tcgagaccag cctgggcaac atggcaaaac cccgtctcta ccaaaaatac aaaaattagc   9000
caggcatggt ggcacatgcc tgtaatctca gctactcggg aagctgagat aggaggatcc   9060
```

-continued

```
cttgaaccca gggagattca tgccacagtg agctgagatc gcaccactgt actccagcct   9120
gagcaacaaa ctgtatatac acacacatgt attttgtgta tatatatata tatataatat   9180
gtattacata tatacataca ctatatataa tatgtattat atatatacat acactatata   9240
taatatatgt attatatata tacacgctat atatataata tatgtattat atatatacac   9300
acaatatata ttttttattt tattttttat tttttatttt ttttaattag ctgggtgtgg   9360
tggtgcccac ctgtctccca gctactcggg aggctgaggt ggcaggatcc cttgaagccc   9420
aggagttgag gctgcgatga actatgatgg tgccactgca ctctagcctg ggtgacagag   9480
tgagaccctg tctcaaaaaa aaaaagaact agttcacacc catgtttcct cctgctgccc   9540
caaattgcca ctctcctgga gcagcccctg aaggtggaga ccaggcacct gctggagcag   9600
gaactcttcc ttcaccggct tctgttgggg ccccaggatc ctgcagctgt ggcatccaca   9660
gggagtaagg ccagccacgg aggtcctttc atgtcaccaa gctgcagggg aggaaaagtg   9720
acatcagaca gatcaacagg agaaaaccca ttttaatgat atgtccacga atgggagtcc   9780
cacacggaga tgaaactggg ggaaggggcc agatggcgga ggcgtctgcg tcatcctcag   9840
ctgcaggaag atacaggact gtggggctgc tgcaggctga accagctata gcaggggagt   9900
tgactggtga atgaaggtgg tttcgtcacg cggacatgcg tctctcaggc gatcagagtt   9960
acctggagcc gctctcctcc cggcatagag acctttacga atggaaatgt ctttcatttc  10020
tctcccagac aggcagctgg gcagagccac tcctgtgtct gcagttactc gaaataatgg  10080
atatacccaa ggcatgtttg gggtggcaca ttctgccccc tcaagccatg ttttggggtg  10140
gggtggcgtg tcctgagccc caacccaggt gtcagggcta tggaggggac attgcaaggg  10200
ggcctagagg ggcctctatg ggccttggag atggaatcag ctccccacca ggccccagga  10260
cagacctggc tggggagcgc agggaggggt ccccagtgtg aggacagcat ggggctgcct  10320
cttccagcag ctccgagcgc tctcagagaa aaacgaaatt ctcttttata agagaaactt  10380
gtctctggtc ccatgtgttg ccctttgggc actggcatga gtaatctgag ggcggcgctt  10440
tcctcactgc agtggcatca tacagatgag ggctttgctg atcattatct ggaaacagtg  10500
atcactgtcc cattcacaga tggggaggct gaagcctggg agatcaattc atgccaccaa  10560
gatcagctgc aggccgggcc acccatgcct gaggggagaa ggggcctctc ttcttcacga  10620
ggctggtggc tgcggcacct acaaagacag gttaacaaga ggaccctctg cctatcacga  10680
gcctggtggc tgccgtacca gtaatgaaag acaagttaac aagagggccg tgcaggctta  10740
tttacgagaa gttccatgtg acacaggagc cttgagaatg gaacacccat cgaaccgggg  10800
aactctgcat attttcctcc tgggtttgtg gggtgtggac agcacggagc gtgatgaaag  10860
gatacaggcg gctgggcgtg gtggctcacg cctgtaatcc cagcactttg ggaggctgag  10920
tcgggcggat cactaggtca ggagatcgag actatactgg ctcacacggt gaaaccccat  10980
ctctactaaa aaatacaaaa aattagccag gcgtggtggc gggcgcctgt agtcccagct  11040
actcgggagg ctgaggcagg agaatggcgt gaaccaggaa ggtggagctt gcagtgagcc  11100
aagatcgtgc aacaatgcga gactccatct caaaaaaaaa aaaaaagaaa gaaagaaagg  11160
atacagacat cctgaaccgg gggctggggc caggtctgaa ggctctgatc ttcctttctt  11220
ctgggtctag ggcacatgag ggtctgtgac ctaattcaga ggaaggccag agaactcttt  11280
tatggcctgc ctcagggtga cagggagcag gagagagcat acctgctttc cctggcttct  11340
cagatgccac cgtgccaggt tttggggtag tggtatgtct tgagcccaat cagtaccctg  11400
ggggtcgtgg ccggcccccc tccctccatg ccacaggctc tctggagagg ccactgctgt  11460
```

atccccactg tgagctcgat ctgagctgcc tatgggacca cacctgagaa cccccaaggg 11520
tggcactggc agacttgagg tgcccaagtg aggctggtgc agcccctctg ccctgccagt 11580
ctgggcacgg gcccctgggc atcgcgactc ctaccttcct accagcccag atgcagggcc 11640
tgagccggca gggcttccac ccagcccagg gtgtgtcccc ctaccagagg cgctgcattg 11700
gataggaagg acccacctgt ttccctgccc agtaccagct ggcaggcccc ccgtggctca 11760
gggtgcctgt gaggaggggt gggggctcta attgctcacc tgctgctctg aggtgtcagg 11820
cagggttggg ggtggcacct ggggaaggct gggctgaggg ggcaggctgc ccctcctgca 11880
ggagaggtgc agtatttcac tgggtccttt ggaaagggca gggaagctcc tgctcgcccg 11940
tactgcacca tttcctgtga tcttagcaat gacttcctgg ctccattttc tccaccagtc 12000
cgaatacatg agccagaccc gcagctttct cttccacagc ctcctggcct ccgggtccac 12060
ctgggtggtg cccacccgcc agactggggc ctggtggttg taggggacgg ggagcagcct 12120
tgcttcagtg tgggtcattc ctgactgtga gatggttggg gggcaggggt tgtagagtct 12180
gtgggaggcc tcggctgggc ctcagagagg ggtatctctt ctgcagaaaa cccagccacc 12240
cttaccagat gcggtcaggc tacaaaggga agatgtgctc cctctttaga ggcaggtgat 12300
tcctgtgaat ccgatgaccg agataaggtg cacgattcag tgggcaaggc aactcaccat 12360
cctctcttta tggtcctcgc aatttgcacc atgcacaatg cagggtgaag tcagccccca 12420
aattacagag gaaagactct gcggtctttg tcagttaaac aggagatgca aactccaagc 12480
tagttaatga gctgtgatcg gccacgctca cgattcagtg caggtctctc cttcctgcta 12540
tcacagtctt tgccggctgc atcatgacta ccaaccagtc ccctcataat tacaagagtc 12600
tcctgtcatg ttttcttctg gagcgaggca tgctccaact tgcttctggg ttcttaattt 12660
ttgatcaggg acggctcctt gactaattat ttggcagtaa tgagggagga cagatcgagt 12720
tgtgaaagtc ccccccaagc ttttagaagg aagctgcaaa ttaaaaaatg aggtattggt 12780
aaacaggatg ctaattggat taatatgaaa atgatgaatt ctgataaaaa tagcaaaata 12840
caccgttgta agattgaggc cagtataact ccaagaattc attgtctaat gttcagctgg 12900
tcagtctggt ctttgaaagt attagaataa cagaaagagt ctactcttga cgatgaagta 12960
tacggttagt aatttatgca aaacagaact ttaaaaccgg aaggacttga tatgagtggg 13020
gtgcatggaa atcattcgta ttttgaagtt tcataactct gacccctagg tcctttggtt 13080
tgtctctctt ttcttttttt ttttttttta gacaatttct ctctctgtca cccaggctgg 13140
agtgcagtgg catgatcttg gctcactgaa acctccacct cccaggttca agcgattctc 13200
ctgcctcagc ctcctgagtg gctgggatta caggcatgaa ccaccgtgcc cggccttttt 13260
ttttttttt ttttttaaga gacagaatca ccaggcaagg tggctcacac ctgtaatccc 13320
agcactttgg gaggccaagg caggtggatc accaggtcag gagtttgaga ccaacctggc 13380
caacatacag tgaaacccca tctctactaa aaatacaaaa attagctggg tatagtaatt 13440
ccagctactt gggaggctga ggcaggagaa tcgcttttga agccaggagg cggagtttgt 13500
ggtgagctga gatcgcacca ttgtactcca gcctgggcaa caagagcaaa actctgtctc 13560
aaaaaaaaaa aaaaaaaaaa aaaaaaagag agagagagag agagaatctc actctgcagc 13620
ctaggctggt gtgcagtggt gcagtcacag ctgaccacag cctccaactg ctgggctcag 13680
gccatcctct tgcctgtgtc ctgagtagct gtgaccatag acacacacca ccacatccag 13740
ttaatttagt tttgttgttt cttgctttta gagacagggt cttgctatgt atcccacact 13800

-continued

```
aatgaatgta aaatcttaaa atggtgcctg gtgcagagta agctgtgtgt tggtggggtg  13860
taattatggg tcatattgac agtttcactt ctgcggcatg ccctcaggaa ctcactgatg  13920
cacacagagg gacctgctgg caaatactga agagctgtgg ggagaaagga aggggtctga  13980
cagtgaaggt gggtgcgtgg gcggggggct tttaatggtc cctctgctgg ctccctcccc  14040
accacctcct gcccacctcc ctggccttgg ctgcaggcta gggtgccctt tgacctcaaa  14100
gaggcctgtc ctgtgtgtct cactgagcag gaacaaaccg tcccagaagc ccttcagctc  14160
ggaagtgagt aagcattggc ggtggggatg gtgctctgag cagacgcgac tcagtgccat  14220
gcgggcgtct ctcccagggc ggctttcaga ctgaccccca aacagagggc tcagaaaaga  14280
tgtttttcaa tgagggacat ttatggttgg caaaaaaaag tggctcccca aaggtcttca  14340
cgtcccaatc cccagaaccc gtgtctatgt tatttcccat ggcaaagggg accgtgattc  14400
agctattttg agatggggag gccatctggc aggatccagg tgggtccagt gtcatcaggg  14460
ggccccacaa gaggggtgag agagggagct gatgatggag gcagaggttg gagggatgca  14520
tttcagagat ggaggaaagt gtcacatgcc aaggaatatg cctgcggaag caggagagga  14580
cggggaggta gggattgtcc cagggcctcc agaaccaaga gaagacaggg gagtagggat  14640
tctcccaggg ccccccaaag acaggaagag ggggaaatgt attctcccgg ggtctccaga  14700
agcagccagc cctgcccgca gtttggcttt agctccctgg tacccatctc ggactctgac  14760
ctacagaact gtaagagagt aaatttatct cattctgtgc tgctcattgt gtggtcattg  14820
gttacggcag ccacagaaaa cagacagtgc gcacatccgc atggtcccct ctccagctct  14880
tgcctgatag gcataaacga gggcagctgg gcgcggtggc tcacgcttgc aatcccagca  14940
ctttgggagg ccgaggcggg tggatcatga ggtcagaaga ttgaaactat cctggcccac  15000
atggtgaaac cccgtttcta ctaaaaatac aaaaaattag ccaggcgtgg tggcacgtgc  15060
ctgtagtccc agctattcag gaggctgagg catgagaatc gcttgaacct gggaggcaaa  15120
ggttgcagtg agccaagatg gagccactgc actccagcct gggcgacaga gagagattct  15180
gtctcaaaaa aaaaaaaaaa gaaagaaaaa aagtaaaaaa gaaaaaaagg aaataaacaa  15240
gggcttgccc tgtagttcac atctggacca cccagcttaa aatagggcag gggagttcag  15300
gaatagcttt gcaacccttg tgttacggtg cacaggtgtg caaaaattct ccttgaactc  15360
ccccttcagt gtccccccag ggctcatggc cactgtcact ctgtgctagt tgctcttcag  15420
accagggaac agacttggcc atggctatgg ccagggtcca gctgctattg ctcctcctgt  15480
cacccaccca ccttttgtct ccaacaagga tgttgagagg agccaggcac cagcctccct  15540
gggttcaggt ctttcctctc ccctcacttt cctatgaact aggggtgggg gaggaggagt  15600
gcctgccagg aggtcactgc agccaaggaa cccaaattgg tgtgcttgag aatgacccat  15660
ggatacactt tccaaagagt cacccggctg cgatgagggg ccatctcccc tcctggagcc  15720
aacagccatg agtagctgtc acacacatcc gtgcagcacc tagacacaca tccgtgctgt  15780
ccactccgtg ctgctgcaat tgtgggggag gaaggtggca cagtggcagc gacacacact  15840
tccctctcca aaattggggc ggggctcctc aaaatcctct gaccagcatt aaagattcag  15900
aatttgatat tatggctgca tataatgttg aattatctga acttgctgca cgtgtgtgtg  15960
tgtgtgtgtg tgtgtgtgtg tgtattgttg gtaggaccaa aacggttaat tatcagcaat  16020
ttcatggttt gacctaatat tttaaaagag aggttcttac ctgctggaag catgtactgg  16080
tgtattacgg atgagacggt ctcataggtg gaatttgctg tgaaatgccc caggaaacaa  16140
aaagccagag gtcagagtga tgagagctgg ggacgggtgg atgggttcct gggccgttcc  16200
```

```
ctgtagtgct gagtgtgctt ggaagtgtcc acaatgagga gtagaaacga gtacaaagct  16260
gggtggagac agccctgtcc tggctgccct gagctcggcc ctgtcagtcg ccttgaggag  16320
ggttgggggg agcagggatg cagggtggcg cgtgcatgcc aggtggcagg cggcaggtgc  16380
tggctccagg cccgtctcca gccccagggc tccaggccat gctccgcccc cagctgccct  16440
gcagctccag gccggccacg ctgccgccta gtttcgcaac tccaatgtca tcacctaggt  16500
gacagggacg ctgctgccac cgcccgcctg cgggagccag gagccagccg agggccactt  16560
ccacctggcc ccaccgaccc tccggggccc aggcttagcc aaggtaggct tgggcttggc  16620
tcgccctcct ctcggcctga gtcgggggga gtctccttgc caccgtgggt gcagtggctc  16680
cgggggccca ccctggggtg cagagagccc ctctacggcc tcccaggagg cggcttggaa  16740
atgcagtact gttcaggcca gggtggggag gccttgccca cagttctcct gatgggacaa  16800
gccacagctc tggggagcca tctgccccaa gtggcacatc agggctcctc gtgtgaccct  16860
aggatcgggg gcagaagtgg ctctggtacc gccacctcca ccccttggac ccaccaggag  16920
ctctttccac ttcctgccaa ggaggcgcag agtgactgcc ccagcctggc acgtccgggg  16980
gcttcccggc tgggggccgc catcctcagc ctcacacagc tgatccagaa cctcccagtt  17040
ctccccagcc ccctcactct tttgtggccc cggagcctct cccggcaaca gcaagccatg  17100
ccccggcctc cccggcactc acgcagctac tcccaagcct gaccatgacg tggacggcag  17160
gaaggggctg ggcatgtcct gttccttctg cctgggtcct gcttccaggg ctggactccc  17220
aggctgggga atcctcaggg acccatcaaa ctgggggaca ggggaggggc ttgtggggat  17280
ttgctgtgag gagggcagag tgtgtacgtg gcagtgcctg cggacacatg tgtgcgcata  17340
tgtgaatagg tgtgtccatg tgcatgtatg tgcaagtgtg ttgctagagg tgagagggtg  17400
ggtagggaaa ctgagtgacc agctcctccc tgaagccttg gggaatgtcc cgaggggcca  17460
gggcctctgg atcctgttcc cttggctctt tgcaaagtct ccagcctggc ctcctggatg  17520
ggcatgtggc tcgggggcg agaccatggg ctcttcctgg cttgctgtgt cgctctgggt  17580
gcgttttaca ccactctgag gatctctctg ctcatcccta aggcagggat gatgatgggg  17640
ccaggggacc acatgggcac aggtaaggca gggatgatga tggggccggg ggaccacatg  17700
ggcacaggct tctggaatgt gggtgtcgtc tccctggggt cccgcagtct gaactcaaga  17760
ctcaagagcc ccatgtccag gtggggatgt acaggagccc cttagaagtg gggaagaagg  17820
ccaggcgtgg tggctcacat ctgtaatccc agcactctgg gaggctgagg cgggtggatc  17880
aacagaggtc aggagttcga gagcaacctg gccaacatgg tgaaccctgt ctctactaaa  17940
aatacaaaaa ttagctgggc gtggtggcgc acacagctgt aatcccagct actggggagg  18000
ctgagtcaga agaatcattt gaacctggaa ggcggaggtt gcagtgagct gagatcgtac  18060
cactgcactc cagcctgggt gacagagcga gactctatct caaaaaaaat aaaataaaat  18120
aaaaaagata ggaaaagaaa aagaaaaagt gaggagaaat gaggaggaag tcgagcaatt  18180
taaccccaaa tggtgcttct ccagcagtca ctctgttcct gtcctgacct gacctgctgg  18240
gccccgcccg ctcaaaccaa atcatggatt ctgtcatcgc ttcttcacgg agcacctact  18300
gtgtgccagg cgggtgctgg ggctgcagcg cagagagcag tcagggcttg gtggtctggc  18360
ccgcaaagag tcagcatgtg aatgtctctc catgcgatgg gtgctgggag ggaggagccc  18420
tggcaggtct ggggaagacc agcgtctctt aaatgggggt gcgcgggccc tgaggagtga  18480
ggcttcctga cagccgtccc tcgtgggtgc catgctggtc agagtggggt ctggctgcac  18540
```

-continued

```
agcctccctc agggctgggc tggaagcaca ggtcggctgg cacctgtcca ggtttcaggg  18600
ttccagggct ccagctggaa ctgcctcagg gatggcaggg gtgggcctgt ccctggagag  18660
gcgtggggtg tgggagctgg gagcgtgacg ggaagcagcc ccctcagacc tggagtagca  18720
tggagcctag gatccattgt gaccttggtg gtcctgtacc ctgtccagct ccagttgctg  18780
ttcctgcctc tccctgacct actggctgcc caggctgccc cttggccgag ctccaccatg  18840
gccagtgccc ctccattcgc ttgtgagtcc cacaagatca cagccctgcc cagggcctag  18900
gcagctcttg ggctgaccca gccatcgtcg ggagccccct tcgtgacggg ggcaaaggct  18960
ggatcgttgt ctgccctgca ggagccgggg cctccagagg acgggctgcc tggcgggaag  19020
gtggagctca ccggagccca gcctaagcca gctgtggtgc ttctgagatg tgcggccctg  19080
ggcaggctgc tcgccctctc ggggcctctg ggaacacctg gggacttccc gctgggttcc  19140
tctgaggatt gaatgagctt gaaaatatgg aggatttggc acagggaatg ctgggcagca  19200
atatcagaaa ggcaaccctg agagccagcg gacagccact ctgaggaaca gcagtggctg  19260
cctctggaag gagtgagggg tgggtggacc cccgtgatcg ctgcacgggg gaggtcacgg  19320
ggctgagcgg ccaccactgt gcaggggagg tcacagggct gagcggctga ctccagaaca  19380
ggaagggaac acgccaggag ggaggattgc tcactgagtc agggcgggac tcagagggac  19440
gcatgacaag ttcagggagt tgacagctgt ctggaagggc acgtctgctc agaccgcagg  19500
gtagggagtg gtcagcaggg agacatgtcc actggtgcag cgggcgtgtc ccagacccct  19560
tagagaaaag cccagagcca ggggtgaggg gtatgtgtag ggtggggaca tctcagagtg  19620
gagcatcccc accaagggtg tccagaggag ggtggccagg tggggacagc agcttgagaa  19680
gggtcattct ctcttggttg gaggagtgga agtgcttctc tggggaaaga aagaagattc  19740
tggaggacag cacaggcact tccaacatgg gcgctggccg cacaaaggct agtgacaccc  19800
ggtgtgatcc cttggggtag aaagggggtg tgagaggagg atcggagggg gcagaggaca  19860
gggatgtgtc tgtgcagaac gaggctgtgg cagctccagc gaaggcggct gcggccccat  19920
cagtcacctg ccctgctgag ggcagcgctg tactcatcac ctgtgaacac aggtatcgac  19980
tcagacaccc actctggcca taagctccgc tctgtcccag ccctggaccc ctcacccccct  20040
atccttggca gtcggtcctc tgggtcttct tcctgtgccc actgtgctgg tctgaacctc  20100
ccttagtgac agatctgctc ctaccacccc cgccagggtc gcccttcctc taacaggtgg  20160
gctcctggca ggaaacatca ccaagctcag cgccccagtt ccctgacagg gccccacttc  20220
cctcctgccg ccaacctcgt ccccccaagg gccatgtccc tgcccacccc ttccacccct  20280
ttcttagagg aagctcagcc catcaggccg ctcatgcttc tgaccccacc tccaaaccct  20340
cctgacccgc ttacccccag gagcaccgcc cactccaagg cgcaagcaag ctggggctgg  20400
ggtgcagact tctcttccac cacccaccct cctcataccc agcctctgag ggcctcacag  20460
acatacatga tttgcctcca gtgggccagg gttatctgtt taccgcgttg catgccccccg  20520
ggcatggagc tggcaccggc tgccgctgca actgggcact acccgtttcg aggacgcctc  20580
attccctgag agactgagga taggctggtg ctctgcaaaa gggtgcggag accactgtaa  20640
aagtggggtg agacacgcgt gctgaccatg aaatggagag gcactcgaag gagccaggga  20700
cccggcagcc agcagacccc acctttccgc ccccgtgtgt gcagttctgt cgctcagcct  20760
ggtgcctttg ggacccgggc ctcattggtt cttcctccac tgccaccacc tgatactaaa  20820
taaccgtcgg tcaatggcaa ctcgatacgg tttatggggc atccacggtg tgcccagata  20880
gaggagtgct ttcgcttttg atatgcgtag agttacttca ttccacctag cgcttctagg  20940
```

```
aggcactaca attatctcca ttttacagac aaggaaacag aggctcagaa tgggcaagac  21000
atctatctga ggtcacacag ctagagcgcg gcagaggtgg gctgcgtggg cagagcagga  21060
gagggaactg gagtgtgtgc ccggcagtgc tgggcttcag ggcacgaagc ggtggggcag  21120
gaatcatgtg tcttggtatg acccaaacac atatatgaca gcaagaaggc ctgggcaggc  21180
agcagaggac aaggcgggcc tcttggatgt ctggatgtgg attgggcctc aatgtaccgg  21240
tgaagataga tggacaggca ggggatttcc agagaggggc ttcccaggca gggtgcgggg  21300
tgtggctgtg cggtgggaac acggactggg gaggggattg cagccgggcc cgtgcctccc  21360
ttgctcagct ccaggtcagg ccagggtaga gccaggctgc tgggttcgac ctccaccctg  21420
accagctgtg tgcccatgga gggctggtct tccctctctg tgcatgtctc ctggttggta  21480
acaggtgtgt ggcctcactg ggccgtcgtg gggtggctgg aatccccggg aattagccat  21540
gctttggtgt ttctacattt cacttggctg agtgtgaact gacccaggaa gctggttggg  21600
ggcaccccca cccacggggg gtcgggcatt ttggtttggt catggcctca aagcttctgg  21660
ggtgaggctc agggattccc ccagactgtc ctgggcatct gcctcccctc ccctcccgct  21720
tcccgtgggc cacggcccag gagagagagg gcagcttgct caggcacctc cagctgtccg  21780
catatttcac acggtgcacg ctaccccacc gtgggaggct gtgtttgtct ttcatcccca  21840
tgctgggctt ccccaaacta ggggagtggg gcagcaggcg tgccatctgt ggcggtgagg  21900
ggggctctca gccgcatcct cctcaccagg ccctgcggac aggccttcgt ccctgcccct  21960
gacctgctga cgaagccgtc ctggcaaccc tgtctgaagg acctggcccc atcgtaccca  22020
cagagggagg ccacatggtc cttagcctct gtcgggaggg gcaggcaatg ctggcagagg  22080
gccttgcccc tgagagggag gccctcctgg ccctcactcc gggggacccc tgtccttggc  22140
cccagcctgc caagcgagag cggcccctct tcttgcggtg gctggagggg agagtgaggc  22200
cccttggcac agagggcccc aggaggctgg gctctgatga cgccctgcag gaattccgct  22260
gggctgctgc ctgggagagc cgctgtctca cacagggcca gcctgcctgg cttcattctg  22320
gtgcgctgac cgcccgaccc ctctgcccag gcgggggctc ttctgggttc tgggtcctgg  22380
gacctgcctg agtccctggg aaaagggcac aaggggattg agacggtctc ctcccacaat  22440
ggcccaggtg tctcctccca caatggccca ggtgtctcct cccacaatgg cccaggtgtc  22500
tcctcccaca atggcccagg tgtctcctcc cacaatggcc caggtgtctc ctcccacaat  22560
ggcccaggtg tctcctccca caatggccca ggtgtctcct cccacaatgg cccaggtgtc  22620
tcctcccaca atggcccagg tgtctcctcc cacaatggcc caggtgtctc ctcccacaat  22680
ggcccaggtg tctcctccca caatggccca ggtgtctcct cccacaatgg cccaggtgtc  22740
tcctcccaca atggcccagg tgtctcctcc cacaatggcc ccaggtttct ttgccacttc  22800
agattggaat cgttgatctg ctgaaataac aggtaaaatc attggtggtt tgggaaccac  22860
cggaatcaga agtgcattga gatgtttgct ttaggggtgg cccggggcgg gtggagttcc  22920
tgggggcttt tccctcctcc ctgaatggag gaggacaccc tgcacccctc ctgtgatccc  22980
ccttaagagc cagtgtccgg gatggctggg ccagacgggg cagaggggcc tgtgtctcct  23040
gcccaggctg agtgcggacg gctcggtctc agagctccac cgaggggtgg gtaggtaaca  23100
gcagccctgc ggccagggcc cctgcaggtg ggagtgggtg tccccatggg gagtgcctct  23160
tccagagtgg gctcagtcgg ggtggagtgt cctggcttat caaaggtggt tgtggagccc  23220
tgtctgcccc aggcctgggc agaggtggaa ggggttgggg aactgacgag gccttacctg  23280
```

-continued

```
tgggcccatg gccaaggaaa tgtctggtct cccacctcct gtcaggtggt gaggggagag  23340
gatggggcgt cagccggaga cggggttcct agaggaggct gggtcctggc ctggcctgga  23400
gagataggga tgagatggga gggcaggaag ggggtggtag acaaaggctg aacacagaga  23460
gcacatagcc aggcatgtgg ggactgggga caggggacaa ggagggcacc catggggaca  23520
agagataggg agaggacaga gggacaggag acggggaggg acagaggatg ggggacaagg  23580
aggggacagg aggacgggga cagggagggg acacagaaac aggagctagg acggggacag  23640
aggatgggag aaggagaggt caaagggaca gggaacaggg aggggaccca tggggatagg  23700
gcagggatct atggggacaa gggacaggga ggggacagag aaacaggaga tggggagggg  23760
acagagggat gcagacaggg aggggataga agatgggggg ctaggggaca aagggaaagg  23820
ggacagggaa ggaacctatg gggacaggg agacaggggg acagggagag gacagaggaa  23880
caggggacag ggaggggatg cttggggaca gggagggaat gcttgggaca gggcaggggg  23940
acagggggct gtggctttcg tgggaagcta tggaagacga ggccagaggg gttgggcagg  24000
gtgagatgag agaggctgag agcccctcac cggctgcgga ctcctcccca cagggcagag  24060
gggagcattc gggtgcggcc aggccatcag aggacctggg cttggctgga gtcccagctc  24120
ctcagccctc agtagctttg ggccagccac tgggcctcct ggcctccact tgctcatctc  24180
tgaactgggg cagggttggc gtgtgagcct gaggccctgc aaagtgcctg gccagcctca  24240
gctcggagcc atggcacagc accccctctc cgccacggcc ccgacagctg ggcgtgcgtt  24300
ctgctgtggg cagctgccct gagcaacgta gggtgctaag cagcatccct gtcttgcaca  24360
ctagattcca cagcaccctc tgaccccgtg gaaaatgtcc ccacatggga atatcctctg  24420
ggggtggaac tgcccctggt gagaacccct aggctgagac ctcagaaggc cctgagtcaa  24480
accgagaagt catcagagag ccttgttttc agctccaggg agcttgggca ggctggtttt  24540
ctgggccaca cagtcccctc cccagcccac ctgtgctccg tgggtcccgg ggaagctgtg  24600
ggggcctaat tgctggtgtg agttcctttc ctgttctgag tcacacgtgt gtgggggctc  24660
tccctgtggt gcagctggta cagcggcccc tggagttgag gatccaagca ggctgaggtc  24720
tgggtttgcc ggagggccct cggtggctgg tctttgtcct gctcccactg ctgtgggcac  24780
tgtaggactt ggaacgctgg tcacctttcc agcctggcaa agggagggga cttgtctgag  24840
gcctcatgga agttggggca gggtcgaggt gccctgcttc ctgggtgtgc cagcagccta  24900
cagcctggct acagcgtaac caggaacacc cagcacaact gtcctttgca actctgtgcc  24960
ctgacttgat ggtgccaggg ctggggggt gccggccagc agctccccaa tgaccacccc  25020
caaatgctgt ggccacacaa agccttccac tgcaagacct gtggtaatac acactggacg  25080
cccctgttac aactgagaac tcatttattt catttccttc cttccctttt tttttttttt  25140
ttttttagag ttgtggtcta gctctgttgc ccagactgga gtgcagtggt gcaatcatgg  25200
ctcactgcag cctcgagccc ctgggctcaa gtgattctcc cacctcagca ccctgcgtgg  25260
tttggactgc aggcacatgc catcacgccc tcatgcccag ctaatatttt tttaagtttt  25320
tggagagctg aggtctccct gtgttgccca ggctggtctc aagcccttgg gctcaagtaa  25380
tcctccctcc ttggcctcct aaagtgttgg gattacagtt atgaaccact gcacccagcc  25440
catccctcct agactaaatc ttcttagaaa aacctacact tccaataatg tatttgcatt  25500
ttatgatgtt gataaaactt cctaaagatg tcttatgaaa ttggtctcct ttccccattg  25560
atacacatga tttttaaaac tattggcaac gtttcaaaag caatttctgt tttgtcccag  25620
aaccgtgatc cccttgtgaa cgaattttca aattaaaagg caaatggttg ggaaaattgg  25680
```

-continued

```
atttaattga aaggccattt tattagaatt gacttatttt tctcgccact gggatccttg  25740
cctgaaaggc ggctgtgggc agagggcaca tactccccct gccccagcgc agcgtccctg  25800
cacccccaac agagcttcct gttcctcatg cccagtactc ccagatgcct gcggagccag  25860
tcatcagctc aggtgtgtga ggccggttgg gggagcccct gcctggcgcc tgtgcctgtg  25920
agcagtgttc ctgtggggcc ctgggaccaa tgctaccagc gttggcgttt tcccaggaag  25980
ttgggaatca ggcatctcgt ggcttccggt tcaagttcct ccgtgtgctt taagtctggg  26040
caggtttccg ggtcctggtt ttggctaatg aggaacccga ttcccatggg ggaggccggt  26100
ggctgcagca gggccccgag cagtggcaag gctggccctc atgacagtgt cctcctcagg  26160
gggcctgtcc caggctcttc atgactcccc tggaggcttg ttaaaggggc agattcctgg  26220
gccctgcccc agccccactg tggggagggg tgtcctggaa gatgcatctg cccagggctt  26280
ccggctggtc cacacgcctg cacctggagg cccactgccc acatctcagg caaacaggcc  26340
tggggatgtt tggggaccca actcctggcg tggaggaagc ccctttccca ccccacatgc  26400
tcctggtggt ggcctgtcct gtgagcctgg agggccggac gggtgggatc ggggacccac  26460
gaccacgctc gctggcctct gtcctgtgcc caggcaggga tgagaggcca agctggtgtc  26520
ctgcagtgca cagtgggtgc cggtcagggg atgtggaagc tgggtctccg gcaggcagag  26580
gcgcgctgac aagaagggtc gctgttcctc attcagggtt cagtgggaag agagggtgtc  26640
gcttcagggg gagttcacag gatgccgact tgaaaataca gccaacgccc atgtcccagg  26700
cataagatca caaatcatgt tttgccgacc agttcctgtg agccctgagc cctgcgcgga  26760
gggatgcccc gtgcacacct gttcacggaa cccctggacc tccagtaggg gtgcggcggg  26820
atgccgtcgg ctcccacgct gtctgtctcc ctgtccctct ctctttccct ctgtttctct  26880
gtctgtctct gtctgtctct gtctccctgt ctctctccat ctctctctgt ctctctccct  26940
gtctctctgt ctctgtctct ctccatctct ctgtctctct ttgtccttgt ctctccctgt  27000
ctctgtctct ctcactctct gtctctcttt gtccttgtct ctctgttttg tctctctttg  27060
tccctgtctc tctgtctctg tctctctctc tctttgtcct tgtatctctc tgtctctctt  27120
tgtccctgtc tctctctgcc tttgtctctc tccgtctctc tttgtccctg tctctctctg  27180
cctttgtctc tctccgtctc tctttgtcct tgtctctctg ttttgtctct ctttgtccct  27240
gtctctctgt ctctgtctct gtctctcttt gtccttgtat ctctctgtct ctctttgtcc  27300
ctgtctctct ctgcctttgt ctctctccgt ctctctgtct ctcttcctgt ctctctctat  27360
ctctttccct gtctctttct gtctctcttt gtctctctct ttgtccctgt ctctctgtct  27420
ctcttcctgt ctttctcttt ctttgtcctt gtctctctct ctctgtctct ctcttcctgt  27480
ctctatccct gtctctatgt ctctgtctct ctttgtcctt gtttctctct gtctctctgt  27540
ctctgtctct ctctgtcttt gtcccacctt agccttggga ggggacagct cacaggctga  27600
cagatgaggt catgtgtcct gagcatgagg ttttcaggtc tcacccacgc tgtagcatgt  27660
cagagcttcg ttccttttca tggccgcgta atgttccatt gcttgctggc accacatctc  27720
ctgtgcccgg ccctctgctg atgggcgtct gggctatgtg caccgttcag ctaccaggaa  27780
tggtgctgct gtgaagggag ctgggatttt gtcatccacc tgctgtggat ggcaagtcca  27840
tttccatctc tggactcagg tggcccatct acaaaatgaa ggggatgcga cccagaggcc  27900
tctggcggca aaaccttccc aggcttgtcc tcttggatct aagggaattt ctttcctccg  27960
agtccagccc ctccagtgct cctgcccttc aggaaacatg cctgggaccc ctcacttgtg  28020
```

-continued cccacccagc cttggcccac atacctgcac caagaggcta ccctactcat actgctcagc 28080
ccaaagggac ccaccgtggg gtatgggcaa gggcgggttc tgctctcccc cggggccctg 28140
tgccagcctc agctggacct gcggttctgc ttcctgtcac actctcccat tttaaattaa 28200
cggaatggtg cggtccccat gcacaccctc agctccactg gggttttagc ccagcccagg 28260
atcggaggcc tgcaagggca cacccacctg gccacgtgat ggtgaagtgg ggtggggcag 28320
ggcaaccaaa ttaacttcta attctaagag cccctggagc attcatcacc agcacttaca 28380
gccgtgtgac ctcacacaag tcacttaacc cctctgagcc ttggggctcc tgaaaagtgg 28440
atggagcggt cacgcccacc tgggagaggt ggcttgggcc agcaccctct aagctgcttg 28500
tcccaggcca tcatggctca cggaccgccc ctcagcctgg cctgtgccac ttctccaggg 28560
cccggcacgt ggcagccaca ggcttctatc agctcccgcc tgcctgggga aggacaaaaa 28620
cgacaggttc caggccatgg cctgcacccc cgctggccgt gggcaggtcc aggcctgcct 28680
gcctgagcat tgcagggcgg tggccaagcc tgtcccatag cacctcaccg aggacctggg 28740
aggctggccc aggggagagg tcacctcagc cggggctggg ggctgtgggc agggtgggct 28800
cgggtttccc tgtcccctcc cccagctgtg ctctgcctgg acactgccac ctcctcatgg 28860
gtgtccaggg ccactgggag ctgggcccag gggttctcag gggagcaatg gtggagacaa 28920
agaccagcgg acgggcgctg gggtcagagc tctccaatcc ctgggtgtct ccttctcaag 28980
gcgtgaccac ccaggcagtg gccggctgca ggacagggca gcttcaagtt cccagccttg 29040
ccaggcttcc ctgtggccct ggggtgcagg aaggagcccc agctcagaag gcgagggggc 29100
gtctgtgtcc tgcagcagtg ggcacagcta ggctctagcc gggggcttgg ctgcagcctc 29160
cagcgcagcc ctcacacacg ctgttcccaa gatggggtga ccgggaccgg agccacctcc 29220
aggtcccggg catcagggag accccaaacc tggctgcatc cccccaggcca aacccagaca 29280
caggggatcg taacagacca caggcctcac acacttgttc cggcccaagc atcccccagg 29340
ccaaacctag acacagtgga tcataacaga ccacaggcct cacacgcttg tcccggccca 29400
agcatctcaa agagtctgct ctcctgaagg ccctcaaggc agccccagga gcgggtgttg 29460
ctgtcacccc ctcttccaag gcgacggctc tgagaagctc ctgcctgccc agggcacccc 29520
cacggatggg tctgatccag gcccgccacc tccaaggcag agctgcccac ctggccttcg 29580
gtttccagcc gcggggaaca gggtggacga aatgacagtg gagagggcac agggagggca 29640
aggcgggggc acctgctcca gggatgcccc aggcaggccc acttgcctgc cgccccccacc 29700
gaggctgtca caggaggaca gagcacgagt tcccagggtg ctcaggtgtc attccttcct 29760
tcctgcagag cgagctgccc tcggaggccg gcgtggggaa gatggcccag tccaccgcca 29820
cctcccctga tgggggcacc acgtttgagc acctctggag ctctctgtga gtgcgcttgg 29880
ctggccagag ctgggggccc ccctgggagg cactctgggc tagcctcagc caccttcgct 29940
gggctaactg ggccagagca ggaggggtgg ccccgggagg actctgggct agccccagcc 30000
accctcactg agactttggg ctaaacttgg caaccctcac tgggattctg ggctagcctc 30060
gaccacccctt gctgcactaa ctggaccaga gcaggagagg tggctccaca ctagtcttgg 30120
gctagcctta gccaccctca tcagcttggg gacagggcgg gtcggagggg cagggaagag 30180
ggactgctgc cctaggcctt ccctggggat gcaggaccaa aattcagact cttttctctg 30240
gccagctctg gagagggccc atggccagca gaggcccaga ataacagagc ccatgactgg 30300
ctctgcctct ctggcactca cagcagccct ggaatggcag gtggaggaca gagatgggat 30360
gagagggaat gggaagggca ggagacgtag gcctcaccag gagtctcagg ctagccttga 30420
gctctgggcc tgggaggtat tggggtgaca cccaaactgg ggactgacgc ttctattttc 30480
ctctccctgc cccagggaac cagacagcac ctacttcgac cttccccagt caagccgggg 30540
gaataatgag gtggtgggcg gaacggattc cagcatggac gtcttccacc tggagggcat 30600
gactacatct gtcatggtga gtggggggc tgccctctgc aagaggactg gagtggggac 30660
aacaaatgtg gcctgtcctg tcttgggagc ctggcagaac caggagatag cctcttggtt 30720
gtacagcttc ccctgtgggt ttctgaggac acttcaaatt gcaaaggaga aaatgtatca 30780
gctcatgtaa ctgtcaatcc agagatagga atggattcag gcatggctgg atccaggtgt 30840
aggaagggct tcaggcatgg ctagatccag gtgtaggaag ggcttcaggc acagctagat 30900
ccagatgtag gaagggcttt ggacatgggt gggtccaggt gtaggaaggg cttctactgg 30960
tggatccagg tatagaaagg gctttgggca tggctgtgtc caggtgcttc acagctgcct 31020
cgctcagtct cttggtctgc tttcccctgc agtgactttg tttttaggcc gcatctcctc 31080
tcatggtgaa gagtaccagg ctccaccagc atgccctatc cctgtggaga ggagatccct 31140
cttttcccat agtccagcag tcctgcctcc cgttgatctg aatgtggtca tgggcccatc 31200
tctgagccac atctgtgcct ctgattggcc tggcctccac catcagtgga acagggtgac 31260
aatggaatgg agtggggtgg gcctccccac acagggaccc ccaaaggaag atggaggtgc 31320
tgtttccagg agaagaggac tggatagggg gcaggcaggg ccagtgaggc ctccggcacc 31380
ccatcttggc aggctccccc attcctggga gtctcaagcc ctgccccatt ggctgctcct 31440
ctgggggaaa aggccaggct gtgggagctg gtgggggcca cgctcctgcc tacctctctg 31500
gctgcccata gccaggcctc gactgtgccg ggaggtggat ggcaggtggg caccacacgt 31560
gaggagagag caaagatccc gacctgggag gcccagcgag gccagccgtc cccgctggac 31620
tcgtcagctg ctcggccccg cccacaggct ggctgccccg ccccgcctcc gccgcccagg 31680
gattcgtagg tggggaattt gtttgcgctg cggaaaacca gcccgaactg tggggatacg 31740
cggaacagcg cgtctggggc agggtcgggc ctccctcact tatgctcagc ccgaaaggga 31800
gggaggcgat gctgggcctc tgggggcctg agagcacccg gcctggccct cctcctccct 31860
caagtcccca ttccaggagc tggagcccct tccttgcccc tgcgcacgac tgactgtctg 31920
aggcatgggg gtgggcggcc cagccaccct gagcactgga gggagtgggg gctgtggggc 31980
tccagtcaga acgaacagag tgaagcgggg tgggggagtg tagaggtgga ggggccgtgt 32040
tgcctgttcc gtctccattg cggatgctgg gctggcccag agccatgtgg ggccagagaa 32100
ggcacctcct tgggcagcca cagtcccggg gggtcaattc ctccgaggag cccctcagcc 32160
tgtatctgag ggttcgaccg cctgcccctg ccctcccacc cctgctcagg agaccgtccc 32220
agtggaaaca ctcgacagtg tctgcgcgtg ttctagtccc gtgttatggg tgaggaaacc 32280
gaggcagatg ctgggaaagg gtgggctggg gatggggccg ggtagtgcaa gaaagtgaga 32340
ctgcaacctc tcccctctct cgctttggaa cagttctgcc ggctgctctc tggggacaag 32400
ggtcctgacc ccaccccctc caggtcccct tctggacatc cgtgtcctcc aatctgggga 32460
ggggcaggaa ctggccgctg gaccccaggg agggagggag gaagacccat aagattgtcc 32520
cctgagatcc agaagccacc tcccaacccc aagttgctca gccactcccc ctgcagaggg 32580
cagaaggccc ctaagatggc acagacccac cctgtgtcgg gaggaggacc tggactcagg 32640
gaggcagaag gagcagttct acattcctga gtgggtggag cgtgcttgtc ctccccagcc 32700
ccggagggtt ccctgagctc catatcgggg tctggtccga gcccccgcct gctggaacgt 32760
gccactcccc agccacaggg tgacagtggg agcctcgaac ctccgcaaac agcaaggtgg 32820
ctggatctgt ctggcagcga cacgcctcct cccaaagcca tgtatgaaat tcctaggtgc 32880
acagctcgac tcacggagat gggggattcc ctggaatgaa ggcaggccca ggcctgcgtg 32940
gggagagcca agcctcattc tgaccccagg gcccagcccc ctcacaacag tggctgctgg 33000
gccaagagca tgctgtcccc taccccctgac tcccatggga gcgccaggta caaagacaga 33060
gactccgaag ggcgccaacg ggtgggctcg ggcagcctgg cacagggccc agggcttagc 33120
tgccttgaga atggcccctg gcccgctaac tccaggggtc ccagagtggg gctggagctg 33180
aactgggggg cattgtttta aagttcagcc caggagctca gggaagctgc tgtgctgggg 33240
ctggggacct ggacccggtt cagtgcggat gcgggcatgg ggggctctga gtgccccctg 33300
gaaaactgcc acctgcagct caggggccca gttctagccc caccacgagg ctggtgacct 33360
tggacaagaa acaccacaca ggcccggcct cgggtcagac aggcggttct agtgccggat 33420
gtttccgggg ctaccgatag tcctgagttc gtggctcagg tggggggcct gcttgtggaa 33480
gtggctgcac acgcacctgc ccccacctgc ccctggcggc tccctctggc cacctgtccc 33540
tgggtgttgg tggcatctgg ctgctcccat actcaggggc gggtctggga ctcatccagc 33600
aaaggggcct cagctcgggc aggcacagtg cttgagcgca ggacactggt cctctgcagt 33660
ggggcgtgcc ttccgcatct gggggacgtg ggtctccccg aaccacgagc aggcagattg 33720
gttcccgttg gacacagggt gtctgaggga tgccttagcc acctgcttag cagccgtggg 33780
agacaggcgg agcaggtggt ttcaagctcc cacaattctc tgagcctcca tgtccttgct 33840
ggtgaagctg gggtgacagg gggtaggagc ccagagcaga gagccctttg ggaggtggca 33900
tagactctgg gatgccaggt gctgggtgct ggctctgccc aaccccgtgg gcctcggaca 33960
accctcctgc cacactggcc cctgcagagg aggctgagtt taggcagttc aggagagtgg 34020
ggtgtgggca agagcagttg aaccctcagt gggctctaga ggagtcccag gccacagact 34080
tattggggag actgtgagct ctgtgtggcc atagcaggaa acagaccccg tggtcactgt 34140
ggccatctga ctgaggtggc ccagaaagtc cagcaggccg aggtgggtgt ggctgggggc 34200
tccgaggcca ggtttgctga gctcaggacc taccccttcc cttctgagct gggcaacttt 34260
taaagaatta catagccctc tgggcctcag tttcctgtct ataaatggcg ctactgagag 34320
gctccaagtc acccacgatg tgaggatgtc cagtggtgcc gggcccatcg ggagtatgtg 34380
acaaacgcta ggtgtgaggg tgagggcagg gaggaggccc tgtgtttaag aaagctgctc 34440
ctcggacacc agaacagcag agccaggagg gcctaggata ggatctggga ccagggcctg 34500
ctgcctttgc ctggcacagt tcctgcctga gctgtcccgt gccttaggct ctggctgtcc 34560
ctgaagaccc tacatggctc acagggacct cactctaaaa tagggccccg ttctgcaaga 34620
ggagagcagg gggaagcctg tggcccgggc ctccccatgg gctggggagg gtgggccgag 34680
gagccacagc taaaactggc ccagcccctg ccctctcagg accctggctg gttccctgaa 34740
tgaggaaggc ttgacgggct tctggatgcc acctgggtgg ggtctgccct ggccaccccc 34800
acaccgtctg ggaagagctg cagaggataa agctccctcg taggctcgca ggctgcgagg 34860
aggcagtgtg ggtgtgatgg tggggcgggg gtcctatcct cacccggacc cacccgagga 34920
gtctctgcag tgctgggcct gggcttggaa gcgaatccct gcccctctga gcgctagcgt 34980
cccctcggac aaaaccagcg cagggcaatg agacctgcgg cccttgctgg ctctcaggat 35040
gctccacaag gagggaggac acaggagggg agaaaaggag agagaggcaa gtgtctcctc 35100
cctcccctcc cctccactct gctccgctcc cgtcctctcc cctcccctct ctgtccctag 35160

-continued agcctcctcc agggctggcc cctcccctgt gccccttcct gcctctcctg gcgcctttct 35220
ctgacaacag gtgttgtggg caggtgggcc acagagcggg gtctacagct ggtggggcag 35280
aaggcaggct gatctaccct gggagccccg ggaacccagt ggcaggacag acacccgggg 35340
tcagaacctt cggacacttg gggcttgag accctagagg tcaccccaga taggccttgg 35400
tgacttcagg gagaggtatt ctccccaggc ccaggagaag gaagggcgca ggtcccgtgc 35460
atgtgtggcc cccaggaaag ggcaggcgga cagagggaga aggacacccc tcccttccag 35520
ggaggatctg tagctggagg aagggtgggg tcatgcgtgg gagcagggag ggggctcagc 35580
tcaccacggt cagctctgag actccagccc acccgttacc ccctcccaga gagcccccac 35640
tcagcctttc ctttggtggg ctttcgtgac aaagcacttt ggggctgcac agaagtgaac 35700
cccacccagc acccaggtct cagagccttg cagcttctgc ggcctcttcc atgcggtggg 35760
atgaagccag ctgcccagca gggaccctgt gccatgagtt tggccttgaa ctgacacatc 35820
actggcacca ggaaacgaag tccccctgtc tgttctggca cataacccct cccactaact 35880
ggttcctgaa gagtgccgtg gcctgcggca gcgtcgttcc cccctgtcct gcggcccagg 35940
gtcctgcgga aagtcaggcg gaatccccgg tgagtcagaa gcagaatgaa agcagaatgg 36000
aggacccagc agggagggaa cctggaggag gcgctaaggg ccacgccaag gggtgtggc 36060 cccagatccc ctgtccctgt cctctgcaag gctgggcctt gggaacgttt gcagaaagct 36120
gggtgccgct ctggggcaga ggccagtggt tttgggtgct tttgagttgg aaacgtgtag 36180
ctcagccgca ctgggatccc cgcagcctgg cccagatgct aagggtggag agatgcgggg 36240
tctcaggcac ggtgccctgg gcatgggtgg ggctcgtgct gaaggcagcc tggctgtctt 36300
ccttcctcac gtccttccac ttggcgctct ccttttggct atttataaaa ccatcaggcc 36360
ggccctgtgc atgggactcg cctgagtctc cttttcaatg catcattccc tttggcagga 36420
gaggacaccg cctacagagg ctgaggatgt gccctgtggg ggtcgggagc ggaacccagg 36480
ccccgcctcg gccctgctct gagggtctgt ccatccctgg ggagcccgcc cccaacccaa 36540
gaggggtccc aggctcagaa gcagaaggca ccctcatccc cagggcatcc ccgatcccag 36600
caggagtctc ctagtgctcg ccctgggctc tcctgcaagg aggctgctgc tttccccaga 36660
acatccagtc tgggccccag ccgacccccct gcagggggct tcccagagac gcccttcctg 36720
aacctgatct accagacaaa actgtctttt tctcagtcgt ctcctcctga gtgctgctgc 36780
ccttcctgtt gggggctgag atcctctgcc acaggaagag acgggcgtcc aggactcacc 36840
tgctgcctcc cggccctagg gccctgagct gggctctcca ggccccagcc ccttggggca 36900
caacacctgg aatcgtcctt tcgtcctcag cccggcctgc tggtggggca gggcgggtcc 36960
ccagggctcc tcaggcagct gcagtccaaa cctcccctgc cctcacccag ctctgcccgc 37020
tctcccgggg gtgggggtgg ggagcgatga ggcccctgcc ggctctcggt ggggacgaca 37080
gggaggaagg aagctgggga gatggagaca agagaaagca ggcaggtggt ttgggatttg 37140
gcaggaaaag gttggaagga aaggggaaag ggtctccgca tggatttctc agctccccat 37200
ggatttctca gccctcgtga gagccacggc gccctgggga ctggaagtgt gggtccgcag 37260
gccccagtcc ccaggtttgt ctgagcatag atgccctgcc tgcttccagg gggactcggg 37320
cccctctgcc agggtcaact ttgtacccaa gacggctgaa atacaatgga aattcagacg 37380
gcccaacagg gagtggcagt cacctcaaag gccccactag acgggtgcgg ggcaccactg 37440
cagagcccct ccctggctgt gccaaggccg tccacgcctg cagggggccc cactgccggg 37500

-continued ctgttctttg gcaacagtgg cttgtccctg tttcctgggg gcttggccag tgccagggtg 37560
ggctccaaac gcacggctct gggctcttgg actcacccct gctttgggca ggcagtggaa 37620
ggcaggcccc acaagagctg ctcactcccg tcacctgtct ccctcggggg tctagggtcg 37680
aacctcctgt gagcccctcc tctccatgca gcccttggac tggtcctggc ggaccaccga 37740
gttccccgcg caggggggcag gtgcgcccca cctgggtgcc aagggaggcg acaccatctc 37800 tccccccttgg ggtggcccag ccttgcctac catgatctcc agggccgggg ctcagccctc 37860
atgcctggga acagaggctg ctttacgggg tgagggcctg gggcccccccg agccttcccc 37920 aggcaggcag catctcggaa ggagccctgg tgggtttaat tatggagccg gcgctgaccg 37980
gcgtccccgc cctccccacg cagcctcctt ggtgcggtcc aacacatcac cgggcaagct 38040
gaggcctgcc ccggacttgg atgaatactc atgaggaata aaggggtggg ccgcgggttt 38100
tgttgttgga ttcagccagt tgacagaact aagggagatg ggaaaagcga aaatgccaac 38160
aaacggcccg catgttcccc agcatcctcg gctcctgcct cactagctgc ggagcctctc 38220
ccgctcggtc cacgctgccg ggcggccacg accgtgaccc ttcccctcgg gccgcccaga 38280
tccatgcctc gtcccacggg acaccagttc cctggcgtgt gcagaccccc cggcgcctac 38340
catgctgtac gtcggtgacc ccgcacggca cctcgccacg gtaggtgtga cgcgccattc 38400
ataggatctc ttcggggact ttgcgggggga ttttgctgca gtgtagggtt cagaggggca 38460
tccttctgcc tgccttcctg gcctggagtc tgctgccagt tggggtgagc agaggtagga 38520
agggaggcgt tgaggggcta gaggcaggtc ccaggcatgg aggcaagcag attcgggctc 38580
caacagcctg tgcccacctg ctgggcaggg acccgcagcc agggagagga ggccgggtcc 38640
atgccgatgg ggctgctggt gtttctgcct cgtgctcggg ggtctctgat gctccttggc 38700
tttggggctg gcggcttggt ccaggctcag agtttccgag ctgccctgcc ctgccccagc 38760
tgccaggagc tcagtgcacc ctagaagtca tctttgctcc tgggcttggg tgtgaagctg 38820
cccccgccct catcagggaa tttgctcatt tgacagcagt ggcagacggt gcttcttgtc 38880
agccccacgg gctcttctcg gtgtgggtct gagctccagg gccaggacct gtggcaaact 38940
gggcttgagg cctcttgcgc cacccgcccc ctgcagtggg ctgctggctt ggaagagggg 39000
agggaagggt ctgcagcttg tggttggccc ctgcagcctg agccctgggg acctggcctc 39060
acttccagac ttgccaggtc cctgggggcc aggcaggcac cagctgctaa ttgagaaggt 39120
ggaaggctcg gcacagctgc tccacgtggg gccgttcctc ctcccaggga agcagacagc 39180
tgggaccatg ggtacctgtg ccacacggga aactcagcca tgggcagggg gcagcgggca 39240
gataggcaga gtccaagtgc cccgaagctc tgctggcact gggatgtaga ggcccaaaga 39300
tctggggacg gaggcctttg gagccgtggg ctccccaggc agtgtgacca gggtgtgtgt 39360
gacagcgatg tgtgtgagcg tgcacatcaa tgtgcatgtg gcgggtgggt attggtgtgc 39420
gtgcatgtgt gtgtctaagc gtggatgtgc atgcaatacg caggcgagga tatgtgcaga 39480
tgtgtgtgtg tatgttatgg gtgtgtgtac aggctggtgt gtgtgtatgt acacgtgttt 39540
gcctgtgtgt tgtggtgtgt gtacgtgtga gcagattggt actgcaggtg tgattgtgtg 39600
atttgggtgg gtaggtgctc acgtgtgtcc gtatgtgtgt tgcgatggat acatggatgt 39660
ctgtgcctgt agctgtgtgt tcccaggcaa ggctttgaga agagaggcag tgtgtgtgtg 39720
tggcccagag ggtgggtgag ggtgtgggtg acccagcccc acagcctgcc cagatgctgg 39780
gtccatgcac tcgagtctgg cggcaccatg gcctctccac acgcctgcgt gatcttttta 39840
tctgaaaccc agtgctggga ctgtagccca gagcgtggaa cggctacatc aggcatgggg 39900

```
tgtccctctc tcccttgtct ggctgtcacc cacttgtgca ttgatacatg tatccaccaa  39960
cacgttgcta ttagaaacgc acagcaggcc tggggctcct ggggggctgc cttgtacccc  40020
cagactctcc caggaggtgt gtgagctggg aggggctatc tcccggctgc tggaccgcct  40080
ggaacccgag gtggatccag aagcctcggg tggagaggcc agtgtcgctg cctggccagc  40140
cgagaagcct ggggacctgg gggactctag tacaatcttt tcccttgaat ggagcagatg  40200
tcaccatgtg actcaccctc tcgggggact ccaccaaggt tgagtatgtg gttgcgcaga  40260
cgccattccc gggaggggtg gggaggtgga gccctgctgc cctggcctgc agaccctcac  40320
tgcctgcagg agctgctggt gtccactcgg ctgctgctgc ccggtgccct gggcgtcagc  40380
aatggccagc tgtgccatca ctgtttcttt ttacaccaag gattactgtg gttcgttcgt  40440
tcatttgtcc attcattcat cccatcagca agtgttaact gggcacgttt tgtgtgttag  40500
gctgagtgcc aggagcaggt ggaggcagtg cccagagcca gccatgtctc cagcacctct  40560
tccctctcgg ggggaggtgg gctaggctgg gccatcctaa tgggcggagt ggtgactcag  40620
tttccctgtt tctgtgccag agagagtatt catgacctca tcttactgca ggaacgtatt  40680
ttgagagaga aagtggtatt tggcccaaag ggttttaaac ccaaagtgag cgaatagagt  40740
tgtattggag ttggtggctt tgtgaggccc tggttattcc tatcaaagca cagtagctgc  40800
tccggagccc gctgggccag cctggccctg ggaagaggcc cctgggttgc aggacactgt  40860
ctgagccccc agctgggccc gccaattgcc cccagcctgg cacagggttc caggtgtggg  40920
cttggggtct gtctctctgg catctgccag ctgagtcttt ggtcagtgac gccgctctct  40980
gagcctcagt ctcctctatg atgaggacgg tgttcaccgt agctgctcgg ctgcggggcc  41040
caatgggagc cactggttac ttgctgcaga tggggacgca ggggggcctg gcctggagag  41100
ctgccgcctc agcccctcct cccacaatcc cacccatgca gccttagccc ctcctcctgc  41160
aatcccagcc ctgcagcctc agctcctcct cccacaatcc cacccatgca gcctcagccc  41220
ctcctcccgc aatcccagcc ctgcagcctc agcccctcct cccgcaatcc cagccatgca  41280
gcctcagctc ctcctcccac aatcccaccc atgcagcctc cgcccctcct cccgcaatcc  41340
cagccctgca gcctcagccc cctcctcccg caatcccagc catgcagcct cagcccctcc  41400
tcccgcaatc ccagccctgc agcctcagcc cctcctcccg caatcccagc catgcagcct  41460
cagcccctcc tcccgcaatc ccagccatgc agcctcagcc cctcctcccg caatcccagc  41520
cctgcattct cagcccctcc tcccgcaatc ccagccatgc agcctcagcc cctcctcccg  41580
caatcccagc cctgcagcct cagccccctc ctcccgcaat cccacccatg cagcctcagc  41640
ccctcctccc gcaatcccag ccctgcagcc tcagccccct cctcccacaa tcccacccat  41700
gcagcctcag cccctcctcc cgcaatccca gccatgcagc ctcagccccc tcctcccgca  41760
atcccaccca tgcagcctcc gcccctcctc ccgcaatccc agccatgcag cctcagcccc  41820
tcctcccgca atcccagccc tgcagcctca gcccctcctc ccgcaatccc agccatgcag  41880
cctcagcccc tcctcccgca atcccagcca tgcagcctca gcccctcctc ccgcaatccc  41940
agccctgcag cctcagcccc tcctcccgca atcccagcca tgcagcctca gcccctcctc  42000
ccgcaatccc agccatgcag cctcagcccc tcctcccgca atcccagccc tgcagcctca  42060
gcccctcctc ccgcaatccc acccatgcag cctcagcccc tcctcccgca atcccaccca  42120
tgcagcctca gcccctcctc ctgcaatccc agccatgcag cctcagcccc tcctcccgca  42180
atcccagcca tgcagcctca gcccctcctc ctgcaatccc agccatgcag cctcagaccc  42240
```

-continued

```
ttcctcccac aatcccaccc atgcagcctc agcccctcct cctgcaatcc cagccatgca  42300
gcctcagccc ctcctcctgc aatcccaccc atgcatcttc agcccctcct cccgcaatcc  42360
cagccctgca gcctcagccc ctcctcctgc aatcccagcc atgcagcctc agcccctcct  42420
cccgcaatcc cagccatgct cttcacttgc ttcccacact gtccttccac atgggggact  42480
ggataatcct gtggtggctc tggccaaaca aggccacgtt ctgagtctgc ggctcccacg  42540
gactggggtt gatcaatgcc caaccccgag gtggacacag agacattacc cacttctgcc  42600
tgtagcaagg aaggagccga tggctggatg agtggggccc ctctagaaga ggctgagcgc  42660
tggagacgtc ggagctgggt gctgtctacc aacacccagg agtctccctg acttcccaaa  42720
tgtccagttc atggcccctt gccccccact tcctcctggg gccgctgttc ttcagcttta  42780
gggtctcagg aggttagcca gggtgatggg agacacccct agctctcctg cgccctctct  42840
atggaggggc tggagcctgt ctcgccgcag ggcctgggct gtgcaccctt gggcctggcc  42900
tgttcccacc ctgcccctcc gcatggtggg catccatgcg ttgcgggaac gtggccaccc  42960
ctgtgctgag gagcagcacg gacggatctg gagctttgga caccccccact cccgtgcgcc  43020
ccatggagcc agtgtccact ctgttcctgc agaaagtgaa acctctgggc aggatgggcc  43080
tccaggacag ggccctgggg cgggggaag ccaatcagtg cagcaagctg cagttactag  43140
gcacctactc tgtacgtggg gctacggaac caagggacgc agctggcaga cgttctggga  43200
gggcccccgg ctgcagtgct ggggatagac cacagggggg cagggccaag gccaggagcc  43260
gcctgcaggc tgggacgatc cagggaatgg ggcagccccg ccggtcaggt ggtaccacac  43320
cgtgggattc tgggcaagat ttgctgatgg gctggatatg agggaagggg tgggggagac  43380
cccaagtttt ctgccctgag attggtagaa ctgcagcaga gcaggggtga aaacgccgcg  43440
gtcggccgtg gctgtgttgg agatgcccgg cagccattgc atagctgaga aggagccgca  43500
tgcagggagg aggacgacga gcgagcagtt cccaaagccc catgagggag gggtttccag  43560
tggtcctggg gcctgaaaag tgtgaccacc tggtggctca gtcctgtgtg catcagagga  43620
ggtggtgggt ggtggtcagg cttagggtgg agtttgaagg tgaccttaga ggaagagcag  43680
gggaggattc cagaaagatg ctgaggttcc atttgcaccc ttgcaggagg ctctgctgct  43740
ccccaaggca ggaaaggccg gcagggtctg gatgtgaggt gggtaaggag ttggggccac  43800
actggcagga gcggccatgt ggacactcag ttgctggtgt gggcaggcag gctgtggaga  43860
cgacctctag ggagtcctgc acatgggcac ttacagtcag ggctctgggg gatctgcacg  43920
gaggcaggga gagacagcgg ctggagctga gcactgggca ctacgacatc cgagacacca  43980
agcagagggg gagatgcaga ggggcagcct gggaggccag gaggcacgag aggctggctg  44040
ggagaacaga aaagggactg gggcttggca acccagaggc tgctgagttc ccacggtttg  44100
gagagggcag ggcccaactg ggaatggctc atgggattgc tgagcatggc caagggagcc  44160
ctcagcatcc tctccaggcc ttgtgtcatg aaagaccccg agcagcggtg gggctcaagc  44220
catgtggggc caggggaggg accagttgtc ctaactggag atccagggat cagaggagcc  44280
accccactca cccgcctgct gtgcctagtg cacgcccgcc tccggccccc ctgccaccct  44340
cggccagctg ctatttctgt ctcctttgtt ctgtccccca ttggacctcc ccccagtcac  44400
cagcctaata ggacctcaac ttgctaaacc caaactaaac ttatcttccc ctgagagggg  44460
atggtgccgt gtctcagcca gcaggaaatc cactctcgcc tttgctcagg ccagagccct  44520
ggaggcactc tccatgcctg aggtcctgtg aatcctgcct gcaaatgtgc ctggggcccc  44580
tgcggggccc acctcgcacc cgcggcccac gtcgcacccg cggcccacct cgcacccact  44640
```

gctcagatac atctcacaat tgctgccttt gctgacgccc gccctgtgtt ctcaacaccg 44700
gagccagagg gagcgctttg cagccccggg cgtctctgct cagctccgac cacctctccc 44760
gctatccccc tgggctccgt ctctccctgc acaggccctc ggcccttcct ctggctgcag 44820
gctctctgcc ctgctggtcc ccagcctgga aacaccccca ggcccaccca atacctgggg 44880
cagatctttc ccttcctgca ggcccgcctt cacctttttcc cgagcccgtc cttgcctgga 44940
cgccagccct ggcccctgtg cctggctctg tgtttctgag accacttttg atcccaagcc 45000
cctgcacgct tgctggctgg tttgtttact gtcgtcagca tggagggccg gggtcgtgtc 45060
tcgtgccggc tgccatcttc ctgcacctgg gagggtgcta ggatgtcaag cctaggaaat 45120
gggtgtgaag aggagacctg cctttgcagg agctgaccaa ggccagtgca ctgggcggga 45180
ccatccgtca ctcctgagcc cactaactgg ggaggggaca ggcagagcgg ggctgggtga 45240
ttcctgagca agcatgctgc tgtctctctg gctctggggc ctctgccctc tgcctcgatg 45300
gccccccaca gccgtcctgg accgccttct ccacctttgg gctcctgctc caatgtccgc 45360
ttatcaccga gggccatcgg aggtggcacg ccccgtgact gcctccccct ccctgtaccc 45420
tgcactgcac gtgtcataat tcaagttctc ggctcagcca cccattctcg gctcagccac 45480
taatgtgtgc tggaaggtgt ccaggaagcc ctgctaagca tctgtcagtg tctccagcac 45540
agcaggaggc tgttacaggt ggcgcctgat tcacatctgc aggacaggtg gatggatggg 45600
cagacagatg ggcaggggca tgtgtgcaag gacacaggat gtcagggctg acacctgggt 45660
tgggctctgg ggtgctggca gcagggttcg gagaggggag agaagcgtgt gtgagctgtg 45720
ccttccccct cgtcttcccg ggcactcggc attctgggtg ggagggcctg gaccagcccg 45780
tttccaggtg gttaaataaa gtctgtgcat cctgttggcc acctgcctct cataggcagc 45840
agcacagggc ctgatgggga tacagcctgg ataccccact ggggcctccc gcagacactc 45900
agggtccagg ctgcccctcg ccacaacctg gaagggaggg gctggtgggc cagccctctg 45960
gaggaggcct ctcaggggag gtgggctttg agcgggatcc gggaggcagg gggcagaagc 46020
tgagggacgt ggagaagggt ctgggggagg aggcggcggc accgtgagtg gactccgggg 46080
cggttagcag gtggaaggca gtgagggttg aggagagggt ggggcgaggc ccttgcacca 46140
ggccacagtg ggcggctcaa atgtgggtcc gtggaggccc ggggggcacc aggctaccct 46200
ggagtcatct gaagtcacct gggcgtgtgg agggacatgc atctgcaagg cccccatgtg 46260
gcgctaagca cagagtgggt gctgcagacg ggctcagccg ctgcgggcag gtgcaggcag 46320
gatagcagcg gtggccctgg gcctcgcagt cctgcagaca cacgtctggg gactgctcct 46380
gggggcgcgt ttctccggtg tgaggtgtgg aaagttccac atggccctgg cacgggattg 46440
ggcaaggcct cgcctcagcc ccgggtgaga gcagagggtg ctgtgggtga gagcacaggg 46500
tgctgtgggt gagagcagag ggtgctgtgg atgagagcag agggtgctgt gtgcacattg 46560
tcgggagagg gaggcttccc cccagccgca tgtcgaatct tgttggcatt tccattcgtt 46620
taatcacggg ctccgggaga tgctgtggga agtaccggca ggacggaggt cttgccctgg 46680
tgggatgggc tctcttcctc cgaagcccag gctgcttgtc agtcactcac ccctgggtga 46740
ggttggggcc caagttcaga catgcccacg agagatcagg gagtttgagg agcggcatac 46800
tctcaaaaaa ccacaacagt ctggtctcaa tattctccag ggaacgagga cacggacctc 46860
cttgttctac aagagctggg gtcacagctc agagcccctg tccaggctgg agggagaagg 46920
ccaggaggcc agagggaggc cagctgagcc ctcaggagac tccaggcagg ccccgatgcc 46980

-continued

```
agactccagc cctcaaacat gctgccttct ggaaacgtct gtcacgggca caccatgcac  47040
catgccatgg ctgccagtgg tggatgaaga agagcatgtc tctgccccgt ctggagctcc  47100
cggttcctgt cctagttgaa cagaatgaat gagagtgcgg gataaatgcc gggcggggag  47160
cagggatgct cgggcggggg caggagctgg agaggtgaca ggagcgaggg aggcggaggt  47220
ggagctgggg aggggccagc ggggcgtcag gatttcagct gacatcccta ctacgctttt  47280
tcacgtgcct ccctctctga ctcggatcct aagtgattag gatcagagga atctctgttt  47340
ccaagagaag gggactgca tggccagacc gtgggctcgg gccccagtct cctgatctcc  47400
gccaagccca gggccccagg aagcggcccc atccttggga gctgtcctgg cctcagctcc  47460
caaggatggg gtccctcggg aagctgttat tgctgtctac ggggcaggag ctccgtcttt  47520
cgagcctctg cacttgtgga gacaaaggtt tccgaatgag catttgtgcc ccgccctccc  47580
caccacccct gccaggccca atgcagggac caggctgcat gtgccttccc cgcctcacat  47640
ctcctccgct ggaggagtca gccaaaaccg tggcctttgg agatgtggcc agagtcattg  47700
tgaattttgc tggcaggttt ctctgttgtc atttccacta aaaaatacgt tccgttctgg  47760
acagtaccac atctgtcccc tgtcatccga tggcacggtc gtgacctccc atgccttgct  47820
ttgcattgtg tcttaaatat cctaggctct gataaaaggc actgtggata ccgggaagcg  47880
agaggagtgg actagggggg aacagggaca caaacttgaa aaagatttat ttcccatcta  47940
cttgtaaaaa aatcactca aatgccccac gcctgtaatc ccagcacttt gggaggctga  48000
ggtgggcaga tcacctgagg tcaggagttc gagaccagcc tggccaacat ggtgaaaccc  48060
ccgtctctac taaaaataca aaaattagcg tctgtaatcc cagctactgg ggaggctgag  48120
gcaagataat cgcttgaacc caggaggtgg aagttgcagt gagccgagat cccaccactg  48180
cactccagcc tgggcgacac agtgagactt cgtctcaaaa aaaaaaaaag tcacttgaga  48240
cggtttacac attttaaaca gtcaacaggt gcaatgggaa tcttttaaca aaaccacaaa  48300
atccaactta atctgaaata gaacagaacc catgcggcgg gagggtgatg atggggccca  48360
gctcccctcc agctcctggc cggtgaggac aaagagtctt tcaaggggct gtccccgccc  48420
tccacattct gaggaaggca gcctggaccc tgggcactgt ctgggcttgg ggctgtggcc  48480
gacatggcgg gcagtggcac accgtggcca cttcccccag ttggatggcc cgcgtggatt  48540
tcagggtctg tttcatccaa ccaagagttt ctgagcgtcc tgtcggtact ggctatctgg  48600
acacctcggg gaacaggaga gaccccgacc cctgtgagca cctgccccccg agagcacctg  48660
ctcttcccca tccgtccctg tgcccagggc ttagcgactg tcctctgcgt agtgaatctg  48720
gattcccgtc cctgttcctc ggcggagcct gcccagccgt cgttcctcct ggctgggttt  48780
ttgtgccaag gcgtggaggt catgcctcgt gcatgggagc ttcctggaca ttggttccag  48840
gagggctccc gggcgagagt cacttccgat gaagtctcag gttaccatac ttctggaccc  48900
tcttgatccc cacaaccatc ctacgaagtc cacgttgatt tcttttttgg tttttttcga  48960
gacagagtct tgctctgtca cccaggctgg agtgctgtgg cgtgatctca gctcactgca  49020
acctctgcct cccgggttca agcaattctc cttgctcatc ctcccaagta gctgggatta  49080
caggtgccca ccaccacgcc cagctaattt tttttgtag ttttagtaga gacggggttt  49140
caccatattg gctaggccag tcttgaactc cggacctcag gtgatccgcc tgcctcgtcc  49200
tcccaaattg ctgggatgac aggcatgagc caccacgcct ggccagtaca tgttgatttc  49260
atccccactc tgcagatgag aaaacgaaga cctagggagg tggagcgatg ggccaggtta  49320
cacaggtgga gctgagactt ggccccagga ctcctgacct cagagccctg cttggccccc  49380
```

cagtccctg ggaggtctct cctgcccctc tcctggatgg gcagagaggc ctggtttcca 49440
ggatggtggc gtaggggcat cagtagaccc agaagaacct gctgttctgg gatgggcagc 49500
cctggccacc acttcctgcc caccttgtgg gaacccccag acctcagcca tcaccgtccc 49560
cagcttggcc gacggtagat gctggtgctt ggattggggt gtccagccag tgggatgggg 49620
cttcagggct gggctgagct ctggcctccc ccacactgct cctctctgct ctcagacagg 49680
caggccaggg ggcaggcggg accctccaca gccctcctgg agggggccca gctactgggt 49740
ggcctctcag tctctgaccc ctcattttgg agcaaggtca ctggcctgct gccaccccag 49800
gggcatgggt ggatcaaacc agtgaggtct gggaactgtg ttgatacctg tgactggccc 49860
aggcgagaga gcagccccat ttaccactgc ctgctgccca caccccagcc cccagccccc 49920
agcccccagc ccagagctaa tctccagcac aggtgcaccc agggaggtcc ccaacccatc 49980
cgcagggagg agagatgagg cctcctgggt gggtgcgtgg gggctgcagt atttcccctg 50040
gcagagcact cctgccccgc aacaaggccc tggggcccca gcagggcctg gtgcgtccgc 50100
ggcctggagg ctggcgggaa ggccacccgc tggctctctg gctcccgcgc actccttggg 50160
tcaggcccag gagccctgca cacacatgta ggcacttgtg gccgccgcgg gccgggcgtg 50220
tcctaattag cccactatct tgggagctct tgttgaaagc aaaacaaacc aaaaaagtcc 50280
tggttgtgcc cgggttcctc cccgtggctt ccgggggccc tctggttgtg ggagaccccg 50340
ggctcctgtg caggcctgtg ttaggttcag ggttccctgt ttcagcagct tgaccccgag 50400
caggagccag gccccaggga aagctccttg ccgccaggca ggaagcgaaa gggaagacca 50460
gagtcccccg agccaggtgg aggggcttgt ggaggatgcc tggggaggcc taagggggag 50520
gtcagagacc cagaaagccc cctacacttc ccagatgctg cgttcccagc tgcattcata 50580
actgcagctg caaagcctct gccacccact gggggtgtga caggggcggt gaccacaggc 50640
agggccagcg tgcagggaga gaggtcccct ggaagcagga ggagaggaca gcgtcccctg 50700
ggcagaggac aggcccagta accctgggga ggagggggct tcagaggccc ccaccccgtg 50760
tcactgagcc tgaggatgag aggggaccag agggagaggc cgacatcggg gccctgcctg 50820
aggaaggccc tgctaaggga gcctgcctgg ggccctgggc cacagaggac ggcaccgaga 50880
gggcttcagg cctgctgtcc ggacacttgt ccactaatta ggattcccgc gtggggccgc 50940
ctgccgcaag ggcctggctc actcccgctg ggctgtgcta ggcgcagaga tcctatcagc 51000
tcttctcctc ttgcctcaat gactaattcc ttggcacctt cctcagatca tacaagaatg 51060
tggacaagtt aaaatatgaa acacgttgtc gtgggtctgc atcctgcttc tcccaaacaa 51120
gggaggcatg ggctttttgc cccactggct gtcctgttct cagggatgga gcagggatgg 51180
gagtcgggca gggggaccct ggagcctgcc cttgcctgtc atcctgacct gagaagcctc 51240
agctgggcag ccccttgagcc ccgggatgtt cttgcccggg ggactcaaat gagtcaggaa 51300
tggggaagtc gtgcatccct gaggccatcc ccgggcccaa aacagggaag acctttccag 51360
gaaggccacc gctggtcacc tggaagagag agggcaccac ggagaggggga gggtgggcag 51420 gctggcaccc ggtacccggt gatgggaggg gccggctcat gtcccacact cactcctggg 51480
cagctggact gggggagccg tcctgcattc gcttgttcgt ttgttctgcc agctcgcttg 51540
ttcagcgagc ctttcaagca gccacgctgt aataggagca cggactgagg gtgtcggctc 51600
cgagccgtgt gtgtaattct gctttttcta gtagccgcat tcaaaaaggt ggaaaggagc 51660
tggcggaagt catttaatta tttcctgtat tcacccgtaa ctgtgatcgt ttcagcctgt 51720

-continued aatcagtagg aaatggtgag cgaggtgttt tccgttcttt ccgtggtcct gagcccttgg 51780
aatcggggtg cgctcacaca ctgggctcag gtccatccac atttcacaca cccccaccct 51840
gtgtggccag tggccaccgt atccagggtc ctcgtgggtt cacagtcgag taggggagac 51900
agaagccatg gggacatgc gagcctgccc ttccggagaa tggctagaaa gatgctcaaa 51960
ccgggtgacg aaagagaaca cctgaggcct gggcgctgct cctgcccgtg tggccagggc 52020
tgacccctcg gaacagtgac ctctgagccc ggacagggct ggtgaagggt cgtgtgcaga 52080
ccacaagtgc aggcttccag gaagggcctg ggcccgtggt cgtaagcagg tctcagacac 52140
ctcagaggcc tcttgggcct cggtgaggag tctgggagcc ggggactctg gggcggggcc 52200
tgggctgtgc gaccagagcc tggcactgcc ccttgtcacc cccaccatca cccaacctcc 52260
catgtgtgta gctgaggcag gggtccatcc tctgtgccag aagcctactg gcagctcgcc 52320
ggtgcccagg gtgacaccca accagacacc aggaggagca ggagtagcct ttctacatct 52380
ttctctgagg ggggcagtgg ctgcttcccc agaccccctc acaatagccc aggagccagg 52440
agaggcgagg gtcacccttc cctgggatgt tatattttgt ttcgtttttt gagacaaagt 52500
cttgccctgt ctcccaggct ggagggcagt ggcgtgatct tggctctctg ccgtctcaga 52560
ttcctgggct caagagatcc tcccgcctct gccccccaga atgctgggat tacgggcgtc 52620
cccccgtgat gtttttaagc tggcaccatg gcttatccac gtggcagcgt gtgggagctt 52680
ccttctgtct tatggccgag gaagaggcca ctgtacagac acactgtttc tttatccatt 52740
tgccattcag tgaaccctgg gctcctggga aggacctgtg gtgcaggaag ttagggaggt 52800
tgtggggagc gcgacagacc aggaaggagg ctgcagtggt gccggagagg tgggcagggc 52860
ccgtgctgca gggggtcccc gttccactgg tgggtgggct ccccaggttg acagctcaca 52920
gccagcttaa tggtgccaga tgatggcagc ttcagccgag gcctcgtgcc aagacccttg 52980
cagtggagcc agggcacggg tcgcccctga cggctcaggc ctgctggggc tgttggctgt 53040
cctgggctgg agcacacagg gagagggcct gcctggcctt tggtggccct gggaacagtg 53100
gtgatggctc tggtgagcag cagtcccctg cctcctgccc ctccggcatc ccgggctgag 53160
ctgcctccac gttggactgc actcagtgga ggactcagta gaggactcag agaggacgca 53220
aactctggac ttgcctggcg tccttctcca ttggatgctg gaggggccgg gggatgcggc 53280
cctcgtcagg gacctcagtg gatgtgtgtc ctaggacctg cagagccgag ggcctctggg 53340
tcactaaacc caaccacctc tgatggagaa ggctgaggtg caggaagggg ctgagcctgg 53400
gagtcccggc gaggcccctg caccctcctg tgcgggcagt gcacgttttg ttttttggat 53460
tggagggggc aggctggtgg gagggaagag tgtgctcaca gcacaccaca gcttctctaa 53520
agagggacac agggcagaat gaccgccccc cgcccccggc ccgcctccgc ctggctctgc 53580
cccttcctgc cctgcaatcc cagttcacgg tctgggggtc tcagcctgca ccttgctgac 53640
tgctggtgac ctttgtgccg tctgctgggg ccgctagatc actggggtca atcgtttccc 53700
cagccccata gctcagtttc ctcatctgta aaatggggac aatcatggtg cccaccgcag 53760
gcctggggag aggggtaata gggacaatca cggtgcccgc cgcaggcccg gggagggggg 53820
taatagggac aatcacggtg cccgccgcag gcccggggag gggggtaata gggacaatca 53880
cggtgcccgc cgcaggcccg gggagagggg taatagggac aatcacggtg cccgccgcag 53940
gcccggggag agggggtaa aggcatttgt ttgcgttgag cctcgggggt cacagggaaa 54000
gcgctgttta tacatgtgca gtcttcctcc agcacccgcc tctggatttg gaaggagggt 54060
cttcctcagc agcccaccaa gtgaggtctg ccctgccctg gatctgagac atcgaggcca 54120
gaccagcacc ccctccctca gctggggcct cccttaagct cctggcagag gctgatccat 54180
gctggggtcc cggggcgcca cagacggtgg cgcaggggac acacccacag gggttcctgt 54240
tccttggtgt gtggtcctgg cgggggagct gcgggtaggg gcctaacgag agaaccccgg 54300
gccagggggc agcaggggtg aggctttgcc ggcccctgag cgtggagcgg cctttccagt 54360
cggggtgagg ccgttcaccg agagatgagg ccgcccaact gggaaaattg ggctcagcca 54420
ttgaacagca gttccacctt atcccaccac ctagagggcc agacctagtg agagcccgga 54480
tctggtctcc agcacctcag gggcacccac gcacccaagc ccaggtgtgc gcaccctgca 54540
ctcagggccc acttgtgccc agcccacctc ccccactgcc tggctccctg gggctggatc 54600
tccccacttt gagctgtgag gtccagaccc cgatgccgcc cggagggtac agtgaagccc 54660
gtgtgggcat cagggcctgg gagcctcccc cacccgacgc ctcccctcca ggtgtgcaga 54720
gagtctattc cgcctcatca acggctgggt ggatccccag aaaccctggc accgggaggc 54780
tgatggaggg gagggcgagg tgaatatgtc agtttatccc aatgcaagta gtggcctgtt 54840
gggatggggg agagacccgg ggaaatattt gggatgactg gagccgctgg ccctttaagg 54900
ctcctgtaac aggacacctc ctagacggga caggacgact gactgtgtgt gtttcccccct 54960
ccctcctccc ctttcccgcg ccaggcccag ttcaatctgc tgagcagcac catggaccag 55020
atgagcagcc gcgcggcctc ggccagcccc tacaccccag agcacgccgc cagcgtgccc 55080
acccactcgc cctacgcaca acccagctcc accttcgaca ccatgtcgcc ggcgcctgtc 55140
atcccctcca acaccgacta ccccggaccc caccactttg aggtcacttt ccagcagtcc 55200
agcacggcca agtcagccac ctggacggtg agttccccta gtccctgagg gctgcgggct 55260
gcgggctgcg ggctggagag gaggtggctg cgttccccgc acctcaagag gtctgagctc 55320
gccccactgt ctgctcgggg ttcccacctg gcccgggcca ggaggagcat cgggcaggag 55380
gcgggtctca gggccgggca gtctgggtgt gcccacccct ctagacgtga gtggccagag 55440
ccagtcagcc tccaaagggc cacagagggg acggacttgg ccctgctggt gagatctctg 55500
ccaagactgg ccagcggctt ccccatgctc aggtgggatc tttggtttga aatcctgtcc 55560
tggacagagg cacgggctct gctgccaaga gttgtctgtc cgagacaggc ccacagccct 55620
agggtctgca gaacctgcct cctccaggca gcgagacgca tctgcgggtg ggtggatttg 55680
ggctttgctg gcactgtctc tggagtgtca tttccaggaa ttggcatgca ccaaggagat 55740
ggggtggaac caccgtgcca agggctcagg tcctcactgc ggtgcccctg gagacagact 55800
ggcccacggt ggggatcttg ctaattctga taacatcacc tgtgcacaag gccagtctcc 55860
tcgagccagg caccatgctc agggctttga gttgagctaa ctcttgcacc caccaacaac 55920
gcacagggct gactccatca ctgctcccct tttacagcca aggaggctga ggctcgggga 55980
gggaagtggt tcgcccagag ttctgctcat agtaagtggg ggcagccacc tctgcatctg 56040
tattcctaac cactgagctg ccctgcccag acagcttcag gggagggggt ctgtcaggag 56100
gggcaaggtg aaggctgcat gaccccagcc aggagtggag ggcacgcagg ggctgggcgg 56160
gaaaagcagc cccaagagcc ctccgggtct cccctcctgc accgaggagg gggcaagtga 56220
gccctgcctg ggcacccagg ccatggctgc aggaggggct ctatgggaca catgttggtc 56280
cggcccactg ggcagcgtcc cctcccccac gaggccccgc ctccccgggc acagctcagt 56340
gctggccccc tgaagtccat gcagggcggc cgcattccca ccccctgtcg ggagtgctga 56400
gcaaggggcc cctcaggttt ttccgcttta agaatcgggt cccactgccc tgctggccat 56460

-continued

```
agctgcggtt ttcccacgct cctggagggc cgaggggcag ggcggagcct aaggtagact  56520
gtcaggctct gcaggtagcc ggacagtcct gccgggctgg tctggggtct gggttccagg  56580
ccccgcccgc ccccacctgc ggttgtttct gattctcact ccagccacgg gctcccccag  56640
ctgctggctc cgggctaaga gaaggctcag cccggactcg ctgggcttga tgggaggggg  56700
ctctgtgggc tgttgggctg aggggcagag gacctggcac ctcctccggg gcctccccacc  56760
tccatctggc aggcaatgcc gaccccagtg ctaacacccc gttttctcca tttggaaatt  56820
actcctccac gcaccttact gcacgatgga gataaggatg ggaagaccgt gccagggctg  56880
tggccagcac ggtgcttagc tcgcagcagg aggcccatgc gttgtcttaa ttgtggtggt  56940
ggtgtgctgg cctgggcctc ccaaatgagt ggttccgtgg cagctgcacc tgcctgtggg  57000
gcaaggggga ccaggcctat ccttccaccc cacttggagg tctgaagcca ggtcagaaag  57060
ccccaaggca tcctcacctg cacacctcca gcagcaggag cctcaccact gcttctctcc  57120
cacactcagg cttgttgcct aagtccactc tctcccctct aaggacactg acctcctgcc  57180
ctggggttta tgatgctggt ggtttctgga gagtgtctcc ctggagtcct ggcaggcagc  57240
ttgtgggagc tctgcctccc ttcctcccat ggtctgagga tgctgatggg gtcttcacca  57300
tgcttggaat gcactgcatg tggtctgagc tgatcctcat ggaaggacag gagcaacccc  57360
ctctctggct ggcttccccc atctagggta tctgccaccc ccaccccctg ccaggtgtgt  57420
ggcatcaggt tcaagggact tcatggtttt gtctcaactg ccttgtcctg caggacgggg  57480
tggccttgcc ctgtgggatg ggctggtctg ctcagaccag gcatcccggg ctggtcagct  57540
gcaccagcgg gaggggaaag ctgtgcctgg tgcccagcag aggagcagtg acacctcctc  57600
gctccctccc tgctgggctc tgtggatgct ggggcggggg gagggtgggg gggcgcgaac  57660
tggggaggaa aatgctgtcg cctgcaccca gggctcctcc tccgaagccc tgtggatcca  57720
gggggtggga caaacattga taatgagatt tttggcacct cagctctctg gggccagaac  57780
cccctccacc agggcttctt tccttgccca gggaggggca ggcaagtggt cggctcacag  57840
tgcagaacgg ggccgccggg cagcccgctt gctcccagct ctggggtccc accatgcggg  57900
tgctgcccag ccctgctgcc tgtgcttgcg tccggcctct gcaccgtgac tcctggggct  57960
cccggcacgc cagccggctg gtaactgata gataattcat atttttctca agtacaagtc  58020
cacattggct gccgccctcc tttctccccg atcaggaaaa acaccctcac cagcccccaa  58080
gtgaccacag atcagacctc agatctcctt gggcactgag aggtctggag gctgcggttc  58140
acaggtctgt gcatatgtgt gcatacacac gcatgtgcac acacacagac acagcaccct  58200
cccacatgca tgcacacacg tggatacaca agtaccttat gcacacgcag acacatgtaa  58260
acacacaggc atgcgtgtac atgcacaggc ctccccccat cactgcccag ggttctagta  58320
gctcccaccc catggaaacc caggaggagg aggaggcgag tcgtgggtaa ccgagcagcc  58380
agaggaagga tttgtgttta gccacgagag tgtaaccagt gaccagtgac agggcaaggc  58440
cggcatttgg tgagagggac cctgcatggt gagaggggtg gagctggcgt ctgctggggt  58500
cccaatccca gagctgcccg tgagcacctt ctgcttcgcc cctctgccct ggcatcctca  58560
cctgcaaaga gaggtatggc ctgccagcca tggtggggac aaaggagctg gctcttggga  58620
cttcttaggt cagggcaggg tacctgggga gcgctccaca cacgtgagct ctgagtgcag  58680
tgctgatggt gacaccagtg cccttctccc agttcaacac cctctgtggg acagtgtggg  58740
ctcagagtgt gggcagagct ctctgcaggg catgcatgac ctggcctctg agccctgctg  58800
gccactcctg tcctgggagc cctgcaggtt ggcagtggtg tggacagctg gttccaggag  58860
```

```
gccctcgggg cagagaatga acaggagttc ctctagctgt cagaacagcc cgacgcgatg  58920
ggcatcggat gctgtgacac cccggctcag ccgttctgcc cccagctcag cctcatcagg  58980
gaaggtggct gtccttggtg tttgggaagt ttggggacgg ggctctgagg tcaggcaaga  59040
aggcagtgtg gggttggaag ccctggccca gcacagcatc tgtgggcacc tcagggcatg  59100
ctgagtgaca ccacccacag cccacgaggc aggctgccat ggcaggatgg tgaggacaca  59160
cacaggtgcg atggccagct gccccagcat tcctccagac agaaagatgg cccggacaca  59220
gccccctgag tgccctccag ctgctctcag actcagcgtg tgtgtgtgcg cgagcgtgtg  59280
tatgtgtgtg tgtgtgtgtg tgtgcgcgag catgtgcaca catgtttgtc ttaggggaga  59340
gctggctcca cgggtaggaa agccccccgt ccaggaggga catatggaag gacggccagg  59400
gaagcacaaa ggctctgcac gggattcctg gggagaatga ggctgagtca acactaatgg  59460
gtctggagca accttcccag cgcctcggag gcttgcaagc aggagaataa tagcggaggt  59520
gtcccaacac gatcatggta tcaattgcat tatcctaaaa gtttatggaa tgcatgagtg  59580
gaattaatac cttttactgg caccagaagc aattatatgt gcgtaaagct gagggaagag  59640
ttctaacaat gtttattgtg gagatgaaac gtggattatt aggggaaaca agagtactta  59700
gggcgaaatt gcagcaattg ctgatatcat gtggcgcagg gatctgcagc agggacggag  59760
cttccagcag gcctgctctg gctgtggtca gcgcctcggg gctcgtggcc cgagccgggg  59820
ttggctcttc tctcttcact ttctggagca gccagaggaa ctcactcttg ggccctggag  59880
gtcacagaac ttagccttgg aggccccaag tgaggctggg gaggccccag ctctgagacc  59940
ctgggtcctg ctgccccacc ccacactgcc tggttcttgg aggagacagg agggagaacc  60000
ccttggggga caggattccc ttccataggc atgagactgt tgggggagag gcatgatcca  60060
atttacgttt taggaagaat catctatttt ctaggacttc tttccagttt ggggacagcc  60120
ctgtggaccc agcatgtctg attagtagcg ttggcagcag cattgcccct atgtgcaggg  60180
cctcccacac tccccatttt acagatgagg aaactgaggc tcccagaggg cacaccaggg  60240
tcacctgtca gcagagggca gagccggacc tggccccagc agccagaccc ctaaccttgc  60300
ccttgcagcc cgtgtggtgc cccaccccgg cccctacagg tccctggaca ggtccccacg  60360
agcagcccct gccccctgcc ccaccctctg ctcccagctc tgtggggcag gtccctgtga  60420
ccctcagggc ccccagggga accagtgata aggaggtgct gacacctcag agggacctgc  60480
ctgtccctag gggagaaagc cttggaccga atggggtgtg gggggagccc aggctgtacc  60540
ttggccccca tgagccttcc actgctgtct gccagtgaat caaactggga ctgggggtgg  60600
agagctgtcc ctgtctgctt tcactgcttg gttttgttga caaaggaaaa tccctcaaga  60660
acgctttatc actggagtgc tccgaggctg gcgagcctca tgggcgagaa gccaggcagc  60720
tgggcttggg gaccggcctc tcctggtgcc tccctgcccc ctctgccttc acccctccca  60780
ggcctggcct cactgccact aactcccgtt gacaggggga aagagaggcc cacaggggag  60840
ggccgtccca ggcttctcct ggacccagtg ctgacgccaa gatgcggtcg taggtgacct  60900
ggaccttggg ccgtgtggga ctcggggcaa ggtgggggc tcagctgggc agtgagttag  60960
ttttgcttcc cggtctggtg ggtttctgcc accccaggcc agtggtcact tctgggattt  61020
tctgagattc caaaagttga agccacggac cctggagacc cggaccctgg aggcccagcc  61080
cctgcctctg ggtagagaag gccctgagcg acctccagac cttctgtccc ttttccgagg  61140
agcctcagga agagggggac agacaattcc agggtgtccc ggctggaaag aaaagcatct  61200
```

-continued

```
tctctgcact ccaggcggac agcgtgaggc tcagagatta cgtggcggcc gaggctggtg  61260
tccacagcca ggggttacga tggggctgca gaggccgtga gcggaacagg gcattttagg  61320
gcagaaagac ccttttggag aaggtaacag cactccaggc ttcagtgagg cagaagtcag  61380
agcccatggg gaaaccgcac agggggatta cctaaagccc agagccaccc caagggttgc  61440
aaacccaccc ctcccccagc catgccactg gagcgaggca cccagctcct tgcacctggc  61500
gttggggaga caccactctc tgcaggggtc agagattcgg aggccaaaat tctccttccc  61560
ccaggcattt caatgaagat ttacaaagtt tagcaaaaac ctagattcta gccaactatt  61620
accttaaaag ctgaagaggg accaccccac catgtccaca gcttactccc ctccctccgc  61680
tgtctccggc cacctccagc tgctgccaat tccagccccc aaggctgtcc caggaagctg  61740
tggccagaga ctccgggact gtcctgtgag cagagggcac ccactgaccc tggggcaccc  61800
ttccaatccc cacagctgac aaagccgggc ctcaaaaggc tgggttaatc ctggcttctc  61860
ctcaaagcca ccagtcaggg tgggggtgag gatggtgggg gcaaggatgg tgggggcttc  61920
ctccccagga gttaaggggc cctctctgca gtgagcagag caggcctgtt gccagcctgc  61980
tgggcccctc gtgggacagc tccagggcct ggcccacagt cccgctagct aggtccttgc  62040
cagaggccgg aggagaggcc aggctactgg caacggcccc tccagctggc gctgtcaaaa  62100
agcaagttgc gggcagagga ccctgcgctt ggtcccggcc cagggcagag gctgagtgtg  62160
gtgctttgaa cactctgtgt cttcagagcg gaggggcagc tgctggtggg cattccgggg  62220
ccctctgcaa gccccagctt ttgtctctgc ggacccaggg cactgccctg ccaccccctc  62280
tgtccccaag gccccagatg gggtacctgg gtcctggaat aagagcagat ggagttcctc  62340
gccctgcctg ggcagctcat tccttcccgg gcttgggcag agtgacagtg atagtagcag  62400
ccacagggca cccgcacgcg gtctcagtga atcaggacag cggcgaccgg gtggggactg  62460
ggccctgagc tcctcacaca gcatctcggc agcaaagtgg aggctggagc tgtccaggct  62520
gggccaccca atcccagcca gacacaaggc agtctgtgtg agtctcagtc tctattgtcc  62580
atggagaccc atccccagca ggaccagggc aggtgaggcc cctggctgtt gttcccctta  62640
cccctaaggg gcttaagtcc agccacgggg taagaagccc atgtcccacc tgacacctct  62700
gtagtaccgt ctttctggaa cccggggtga cgcctctgca gtgcccagtc ttcctggaac  62760
ccaggggtga cgcctctgca gtgccgtctt cctggaaccc aggggtgctt aaggcgggtc  62820
tctgcctaga ccccgacccc aggccccagg acccaagtca agcccagcag tgacaaaggg  62880
ctgggagatg gagcttgggg gtcagacagc tatggtctgg gtgctggtcc accccagctt  62940
agcaggcagg tttgggtcac taaacggagt gacagtgcct gacctcccag ggccaaggtc  63000
aggtgagggc cccgcgcagg gcaggcacca gtgggcagtg gatgtggcca tgagggtgga  63060
cccaggtgcc ccattccctg gcaggtggac agcactcact gtctccccag gtctccacac  63120
caacagaggc agacaccttg ggcaaacgct gcctcgcagc ctcccccaac actaggcccc  63180
tcttatctcc tctgcctgtg gccctcgtct cctactggac ccctgggcct tcactatgca  63240
ctggagacaa agccaccaag tctatcctgg gctcagcaca tacctgcttc cctcccctac  63300
cccgatcata gcccaggatg gagatcccta gaggcagccg tgcatgggac gaggatcgag  63360
caggctccag ctcctgtggt ctgggtgcac tcagtgtctc ccagggagcc gcgcttccag  63420
gccgttgaga gtcccccgtg tggctcctgc tcacctgttt aggacatggc tcaaggtcgt  63480
ggtggggcag actgcccagc tcctcagggt tcccacttgc cctggcctg  ccctccccag  63540
tgagcagttt cttgtccaca gcctctgggg ctctagcagg cctccgtcag ggctgaggat  63600
```

-continued cgcttggcat ctgcagagga tgtttctgcc tctggttcat cctccataga gctcctggcc 63660
tgggagcccc ggctggccag catgggggtg ccagcagaca catctgtctc ctgcagcccc 63720
cccagccagg agctctttca cagcagcctc ttttcttggg cagcgctggg cctggcactg 63780
gctgtggcct cacaggcatt ctgaagctcg cttgggcctc tcatctgcct ggcccatggg 63840
ctgtggatgt cctggtgagt gagccgtcac tgcctcgacc atgggagccc cagcttaaca 63900
ccaaggtgtt ctgaaacagg ggcgattgcc acatgtgtcc tttccccctc cccaggctag 63960
tggcttccct ggggcaggga gggaccagcc ctgtgacatc ctgccaggcc tccctgacat 64020
ctgtcagagc ccagcctgtg ctcccagcag ctctctgagg gcgacagtga ctgtgcacca 64080
gtgaaggcca cagcctccca cgaagggggc tgtcaccaag gggccctgt ggctgccacc 64140
tgaggatacc cttcctctct cagaaggaga aagggaccca ggaggaccct aatccacagg 64200
ctgttgaccc tggctcaggc atgtgtttta gggggtccat ctgtgaaccc acgaatttaa 64260
tggaaagggt tctgtggctc agccccagga gcttttctag ggagaggaag ggtccagggc 64320
cttggcagag ggtgggctca aagaggcccg taaccccaga gaggagagag atgcacccct 64380
aaacacacag acgcacacac aagcaaggga actggataaa agtgagcaat aaaaaaaatc 64440
gtttaaaaaa taaaagcccc cactgcaggc cccatcttcc agaatctgtt gcaacagatt 64500
cacccacgct ggttaacggt atttgcggtt tgcaagatgc tacacgtccc aggaaaatga 64560
cagacaagtt attatcacct ctccgctgtc ctcctgccca aacctgcccg tgccgggcac 64620
ccagctgccg gggagcgagg agcgggcaca aggaaattag cagccccccg ctgcaccctc 64680
ccctcaccca cccccgcacc agccctgcca ggcccagggc tcccagccag gccgggccca 64740
tgttgtactg gggcggggga ggaggggaag gagaggaggg tcggagagga gccggcagcg 64800
tggggaggga tgggcacagt ggcgtttggg caaacccttt cctgcaagca ggacggtgca 64860
cgcaccctgg gcaggcaagt ccaggcggct ccgtgtcaac agccgaagat aaatacgatt 64920
ttatcagctc ggaatctgtt gaaacacatc catctagcgg ttctagggaa ggagaaggca 64980
ggaggggggc ggcggagggg aagtgtctcc acgtgacctt tcctatagaa taggctccac 65040
cggagtcctc ctcctcctgc ccgttttcca cagggccaag cccaggcctg aagcctagag 65100
gcctgctggg gagacaggag gaaggagctg ggggagcgct ggagccgtcc tgggctcagc 65160
caccctctag aaggacctgg atctctcagg gctcccttcc ctcctgtggc cacctgtgtc 65220
acccaccccc agatgctgcc agggcagggg acatcacaga catcctcccc gaggccaccc 65280
agctccggcc cggctgggca cctggggtcc agttagtgcc agggtgaggt ctgccaggca 65340
tgtatgcccc aaaggccatg tgagcactgc actggggaca cctgtgggga ggagagccag 65400
gcccaggacc ttggtggcct tactggccag aggggaggag aagtgctcac atcgcctgag 65460
gacaggggcc tccttgctct ccaccctgag gcctgggcct ccctccgcca ctggcccagg 65520
tcgaagacct gtccgttcta ggccgctcca cactccagtc cgagccccca cttcccgggg 65580
tgggtggtcc ggccgccgcc tgcaccgagt accagggaca gctcccggcg cgcccaagct 65640
cctccccggg gcggggcggg gcggggcatc cacagtgctc cccgcgcctg ggcccccagg 65700
acctcttgca gacgggagtc cctcagacag tgcagagacg ggagcacgca ctgggccctg 65760
cacccacttc gtagcgccct ggcctgggac gccccaccac gcagcttcca gagcaaggat 65820
cgccacttca ccctgcccgg agacccagag ggagtggggc gggctcagca gggcgctgct 65880
gagaggccgc tgcctaggtc tgcgaaatgg gagcactgct gaccctgagg cccaggcggg 65940

-continued

```
cgggagctca ggctccgcag aggactatgg ccgggggtgc tggggcaggg gcctagggga  66000
ggggctgcag gggccaggca ggagctgtga aacccctcac gctgttgaga ctccatgggg  66060
ctgtcaggga gcgacggctg ccggggcctc tgcccgcagg cttggttgca cccagagcct  66120
tactccatct gtgtccaact ggctgaggag cccaggcggc ctcccctccc cctgagtgtc  66180
tggggctcct tggtggatct aatgacccc atctcaggcc atgggctgtg gcactagggt  66240
ggaagaagcc tcgggggact cagccccgga aagggaactg tagggaagcg gggcctgtgt  66300
ggctccagcc ccccgcaacc aacacctcct cacctggtgc tgagaataac gagggcgcag  66360
tagccactaa cacctgcagg ccactgtgtt cccaggggac acgcagtgag tcagagatgc  66420
aggtggagag gcttgtgcag tggctagagg catcccagct gacgagcaca aagccaaaac  66480
tgccacccac agggccggac ctcagaggcc cttctccttt tgccgcccct gagactctga  66540
cctgagccac cccggccggg gtctgtttca agggggggtct gccgcgccct ccctgctctg  66600
tggtttccct agggagcggc taggatggat ggcatttgtt gagtaccacc tgtgtacctc  66660
catctgctac acgttactga ggagagacga gggggacaga gccaggtgcc tgaattccag  66720
ggggcctgtg tgctctgcac acaagaggtg ctccataaat gctcagcaat gggcagctcg  66780
ccctgcaggc tgccctggcc tcggagaagc ctggcgacac ggctgccggc cctgtgttcc  66840
tctcccctgc tcggggcact ggcagacaag agcctgccac cacctggccc ctcctccttc  66900
tgtccccaac cagcacagat ggagaccagg cgtggtgtgt agcttcaggc agggcctttg  66960
tccaagagac cagtgcctgg acacaggcca ctgcaagttt gggccaagag ccctccctgt  67020
ctgagtctcc tgagggtccg agtcccagag ggtctgtgct gcgagctgtt cccatgtgcc  67080
ctgggggcag ggctacctgc ttatccttcc aagtgatgct gtggggagca aagggggcat  67140
ttgtaatggt ggggacactg tacatcagtg gtcacctcca gggaagccag actgacccca  67200
caacaaggag actgctgtac ttcccgctgt gcccaagcct gcagctccga cagtccaggg  67260
caggcgcccg cacaggggtg ggctgctagc tctgcaaggc tgtttctgct tttcttttt  67320
tctctttgtg tgtgtgtgtg tgtgtgtgtg tgtgtgtgtg tgtgtgtgtg tgacggattc  67380
tcactttgtc acccaggctg gagtgcaatg gtgcgatctc ggctcactgc aacctccacc  67440
tcccgagttc aagcgattct cctgcctcct gcctcagctt cctgagtagc tgggactaca  67500
ggcgcccgcc accttgcctg gctaatattt gtatttttgg tagagacagg gtttcaccat  67560
attggccagg ctggtcgaac tcctgacctc agctgcctgc cttggcctcc caaagtgctg  67620
ggattacagg cgtgagccac cgccctcagc ccgtttcctg cttttctaaa cagcgcccag  67680
cctcccctgc agggctgtgc atgatggttc cttcctgtgt tttaaacagg actggggatg  67740
ggcggcttcc tgcctaaggc cctgtgccca aggtgggggt cgcaggcagg ggcagtggag  67800
ccactctggc tccaggggct ccaggtggac ggaggaccta ggaggggcca gctctttggt  67860
atccaattcc catcctgagg aggccactga aggacccccct tccacttgtc cctccagccc  67920
cctcacaccc atggcaggga cagaccagcg ttcctggctg ggtctcattc ggggagccca  67980
agtagctcac cagagagggg accgctccca ctgcacagga acaagggcac tcagggtgcc  68040
ggggacccag gccccaccca ccatggctcg cagcctccgt cagctccatc tcccctgtct  68100
ctttcctttt tccttcctgg cttttcgtgt gcctgcacct gccaaggacc tatgtggctc  68160
ctgagagccc ctcatgtccc ttgatggcca gagaggcagt actggtggcc agtgggggtc  68220
agggggtcag ggccccctaa cttccttggc aaagggaaga ctccacctgc agcttccctg  68280
gttctgccag tagctccctg tctctgacct cagtttcccc aactgttcca cggtggagtg  68340
```

```
cgatgggaca ttctccaggg cacttgcggc tgcagtgact tgtgattctg agtcatcggg  68400
ggctggtgag gggcacagag ggcatggggt ggcagcagaa gtcattctct gagcctgaga  68460
ctggggatca ttcctgatgg ccctttgggg agagagcatg aggactccca gcaggtgacc  68520
aggagccaga cgcttgggaa atcagccagc ttggaagtga gtggacgccc ctgcagcggc  68580
ctcagcgggg tcacttttag aactcatgag agccggcctg ggtcctcaga tgggcagccg  68640
ggccctgtga ggcaaagaag ctggaggcct ctgcaggggc tggctcagga agggtgtcat  68700
ccagtcctcc tgcagcaggg cccacgccag ctccagacag acctattagc tcctcgagtc  68760
ccaagctggg gatactgggg ctgtgagccc agaggggccc ccagagtggc caagaccaag  68820
ccacacagct cggctgctca gacttggtgg ccccagcagg agagggtgtc agagtcacca  68880
gggctgctga ggccatgaga ggccttcaca ccaacccaga gagctctcta tggaagcttg  68940
aatgcatagt gggcaaccag cccatcacac attaaccact tgctctgtgc aaatgccaga  69000
gaagcctagc tctggtctta aaaacagatt caatgctgca aacccacctc ttcaaaatgc  69060
cgcagtcagg gacatggctt ccacaggcct ggctcccagc cccgttccc gccctcactc  69120
tccagcagcc ccttcttgct ctcctggcct ttcttgtccc catccataaa cctaaagcct  69180
ctctgcctga ctgccaccgg cactcacacc cctgctgtca tggagcccaa atgacccgat  69240
ggctgtggag tgggtgccag ggcagctgtg cctggattca cgcctcaaag gacagacacc  69300
tggagggatt cagcagaggg gctgcttggg gcagtcttca tctgggggtt gtggaagggg  69360
cacccatggg gaggacgtgg ctcccaatgg ggggtggcct ggacaggggt gcagttggga  69420
ccactggtct cacccgctcc ctctccccca ctccagtact ccccgctctt gaagaaactc  69480
tactgccaga tcgccaagac atgccccatc cagatcaagg tgtccacccc gccaccccca  69540
ggcaccgcca tccgggccat gcctgtttac aagaaagcgg agcacgtgac cgacgtcgtg  69600
aaacgctgcc ccaaccacga gctcgggagg gacttcaacg aaggtgaggg cccccagctc  69660
ctctgcccac ggtggcactt tgcccagcat cccggacagc acagccgggg gctgcctaac  69720
tgggagagag tggggctgac agcatgggct tagccattcc cctgcggagg gctttcagtg  69780
cctccaccag cccccatttt cccagttctg agtgggacct ggggggcccc atgctcctgg  69840
gcaggggcaa gtggtctggg cagagtctga ggggcagcgg ccttctgggg ccccagagat  69900
cctatgagtc atagcccctc tctccagtgt gcctggcagg gcctacgggc taccccaagg  69960
attagcagga gaatcagggg gcagagccac tgggcaggca cccccagagc acaagggctg  70020
ccagctggcc tgagcctcac ctggaagccc acaggactgg gcctggtggt ctcagttctg  70080
ctgcgatgca cctggcacag ctgggcgcct ctctgcacct ggcacagggg tgggcacctc  70140
tctgcacctg gcacagggct gggcacctct cttcacctgg catggggctg ggcacctttc  70200
ttcacctggc atgggactgg gcacctctct gcatgtgaca cagaggtggg cacctggcat  70260
ggggccgggc acctctctgc acctggcatg gggctgggca cctctttgca cctggcacag  70320
ggtgggcacc tctgcaccta gcacaggagt gggcacctct ctgcacctgg catggggctg  70380
gacacctctc tgtgcctggc acagggctgg gcacctctgc atctggcatg gggctgggca  70440
tctctgcacc tgacaccggg gtgggcacct ctctgcacct ggcatgcagc tgggcacctc  70500
tctgcacctg gcactgggct gggcacctct gcacctaaca ggggtgggca cctttgcagg  70560
tggcacagag ctgggcacct ctctgtgcct ggcacggggc cagcacctct ctgcacctga  70620
catggggctg ggcacttctt tgaacctggc acggggctgg gtacctctct gcacctgaca  70680
```

-continued

```
tggggctggg caccctttga acccggcaca gggctgggca cctctctgca cctagcacag  70740
gggtgggcac ctctatgcac ctctctgaag tgtcgacccc tcccggcagg acagtctgct  70800
ccagccagcc acctcatccg cgtggaaggc aataatctct cgcagtatgt ggatgaccct  70860
gtcaccggca ggcagagcgt cgtggtgccc tatgagccac cacaggtagg ccaggagcca  70920
ggctgtgccc agggccctgc agtcagctgt acgggtcggg ggaggggtcc cctgaggcag  70980
cccctgtccc tcctcagttg gctgatctgc ctgcctgtcc tgtcggcatc tgtccagggc  71040
tccctgctct gtgataagtc tgtgtcggcg gctccttcct cacccacacc cgccccactg  71100
tgcacactgc tgctctgtcc ccacatccgc ctcgggcact ctcggggcct cagtgtgccc  71160
agctccatag tggggagtgg gtcttcagcc ttgccctctg ttggtgccca acactggttc  71220
cggcctgggg ctcccagaca cagggatttg ggagatgggg aggtccccgc ccatttagac  71280
cctggattgg ctggggcaga accaaaccag caacagcgcc tgaaggggtg gcaaattcta  71340
caaagggggt tgagggatgg tggaaagact cctaggccag gccaggggcc caggagaggt  71400
ggcctgcagg aggctgaggc tggtcagcag ggtggagagc cgggaggccc cgctgggcac  71460
cacgtgggtg gggggtgcag gggactgggg ggcatatagg ctggagggga ggggacacgg  71520
agaggctggg ggctttgact tttggcccaa aggcagcata agtttctggg acacaattct  71580
ggagctgatg tggggcccaa ctggtgtgaa aggctggggt agggggaaac agagggtttg  71640
aagttactgc gggatggtgg ggcaggggca gaacaggagg tgaggagtgg gtaccaggcc  71700
cccaggggaa ggcaggcaat ggcaggcctc tgccttccct gtacctggtt ctgagaccag  71760
gctccatgct gtacccagcc ccagcctccc ccaccaggtc cccatccctg taccagaccc  71820
ccaggacacc ccagactcct gtacccagtc tccaggtcct ccacaagcct ctaccctgta  71880
cccaggcccc cttcgacgtc cccatcccac catcctctaa gagcagcccc ttatgtcagc  71940
agaaccaggg cccgggaggg ctccctgaaa cccatgtccc accctcacct gcctaggcct  72000
gccaggaagg cagagctcta tcgcccccctg gtggctgccg tgtgacagca gttctgagaa  72060
aggccaagat tttcccaaac ccctaatagc ttttgtattt gtccccaggg tgacatgaaa  72120
actgcccaca ttgtggtctg gggacactca ttgatcaacg gttttggttc atggctgggc  72180
gcagtggctc acgcctgtaa tccaagcact ttgggaggcc aaggcgggtg gatcacttga  72240
ggttaggagt tcaagaccag cctggcccac agggcgaaac cctgtctgta ctaaaaacac  72300
aaaagttagc cgagcctcgt ggcgcatgcc tgtaattcca gctacttggg aggctgaggc  72360
aagagaatcg cttgaacccg ggaggcagaa gttgcagtga gccaagatcg cgccattgca  72420
ctccagcctg gggacagag agagactccg tctcaaaaaa aaaaaaaaga gttttggttc  72480
atgtctcagc tgtactgcaa aatccctggg aaacaggagt gtgctggggg tgggttcgct  72540
ggggacagct ctggttcctc tttctgccca ggtgagcccg cagcatgcaa cacacacgta  72600
gggccacaaa atctgtgcag gcacactcac acccagcatc tgggcttgac ctccagcctg  72660
tgtcagggga gaaggttggg gcaaacagac cacaggactc tgtgcttctc tgagagcaga  72720
gaccaggtct gagccctccc agaacccaga accagcccag tgcttggggt tcagtgatct  72780
tcatgaatgg gtggctggat ggggtgagtg ggtggatggg tggatggatg ggggtgggtg  72840
gggtggatga atggatggat gggtaggtag gtgggtggat ggatggatgg ataaatgggg  72900
tgggtgggtg agtggatgaa tggatggagt ggtgaatggg tgaatggatg ggtgggtgga  72960
cggatggatg aatagggtgg gcggatggat ggggtgggtg ggtgaatgga tggatgggtg  73020
ggtgggtgaa tggatggttg ggtagaggga tgttgaatgg atgggtgggt agagggatgg  73080
```

gtagatgggg tgggtggatg gatggatgga tagactgata ttgttgaatg gatgagtggg 73140
tggatggatg tttagatgga tggatagata ataaatgggg gagtggatgg atggatgggg 73200
tggggggtg gatggatgga tggataggat gatggatgga tggatggggt gggtgtgggg 73260
ggtggatatg tgggtgggtg agtggatgga tggagtgggt gggtgggtgg atggatggat 73320
ggattgactg atattgaatg gatgggtggg tgaatggatg gttggatgga tggacagata 73380
atggggggag tggatggatg gatggggtgg atgggtggat ggatggatgg gatgggtgga 73440
tggatggggt gggtgtgggg gtggatgtgt gggtggatgg atggagtggg tgggtgggtg 73500
ggtggatgga tggatttatt gatattgaat gggtgggtgg gtggatggat ggatggattt 73560
attgatattg aatggatggg tgggtggatg gatggttgga tggatggata gataataaat 73620
ggggggagtg gatggatgga tgaatggggt gggtgggtgg atggatggat ggataggatg 73680
gatggatgag gtgggtgtgg ggggtggatg tgtgggtggg tgggtggatg gatggatgga 73740
tggagtgggt ggatgggtgg atggatgaat ggatgggttg atattgaatg gatgggtggg 73800
tggatagatg ggtagataat aaatggggga gtggatggat ggatggatgg atggggtggg 73860
tgttgggggt ggacgtgtgg gtgggtggat gggtggatgg atggattgat attgaatgga 73920
tgggtgggtg gatggatggg gttggtggat gaatggatgg atggatattg aatggatggg 73980
taggtggatg gatgggtaga taataagtgg gggagtggat ggatggatgg atggggtgga 74040
tggatgcatg gatagacggg tgggtggatg gatggggtgg atggatggat ggattgattg 74100
atattgaatg gatgggtggg tggatggatg gttggatggg gtgggtggat ggatggggtt 74160
cgtggatgga tggggttggt ggatggatgc atggatggat attgaatgga tgggtaggtg 74220
gatggatggg tagataataa atgggggagt ggatggatgg atggatagat gggtgggtgg 74280
atggatgggg ttggtggatg gatggatgga tggatggatg aatagataaa tgggttcgat 74340
ggatggatgg atggacggat ggatggatgg atggggtggg ttggtggatg gatgaatgag 74400
tggacagata tacaaatggc aacaactata gagcagggca tccccctgcc tacgtggagc 74460
caggaccaga catggagctg gggctgcca ccttagtgga ttggggctgc gtgctgatgc 74520
tagcccctct ccctgctccc ccatgtgcag gtggggacgg aattcaccac catcctgtac 74580
aacttcatgt gtaacagcag ctgtgtaggg ggcatgaacc ggcggcccat cctcatcatc 74640
atcaccctgg agatgcggga gtgagtcccg ggcacacggg gtggaggtgg gacagggctg 74700
ggcaggcacg gccgggggag aaggggagct gtcatggaga cctgcaggcc aaggctagct 74760
tggggaagag actttggggt gtgctgctgg aggaaggaac cgccccctgg cctgcagggc 74820
ctgcctgggc acaagctggg cctccggagg gaggtgggag tccccggcga ggtctcaggg 74880
cagcctcaca gctttgagcc tctgactccc tctagcggga acactcgctg ccggcactgg 74940
gtgctctgtg gtgaccgagg gctctcaagg ccggtcctgc agggtccgag gtgggtgggg 75000
aaggtgggca ggttgagggt gggcagggtt gagctcacaa ttctggctgt gcccacccga 75060
cagtgggcag gtgctgggcc gccggtcctt tgagggccgc atctgcgcct gtcctggccg 75120
cgaccgaaaa gctgatgagg accactaccg ggagcagcag gccctgaacg agagctccgc 75180
caagaacggg gccgccagca agcgtggtga gcggccggcc aggggaactg gacgcgtgtg 75240
ggaggagaag gggacacatt ggcaggacac aatgtgagcc cgcgtcccag ggacagggcc 75300
agtccctgaa cggcccccca cgcccagact cctccctgac ggagcctgag agcagccccc 75360
atataagtcg cttgtcctgg gccaaggcca cctcagaggc ctgggtggca ccgcaggttt 75420
gcccgtccct gtgggttgct caccaccgga cccacctgga gaatcgattg gccccaaggg 75480
tggggcaggt ctccctcctc ccggaaggag gcctcaccct ctggtcctgc ctgctcaccc 75540
cgcctgccct gcctggcctt ccagccttca agcagagccc ccctgccgtc cccgcccttg 75600
gtgccggtgt gaagaagcgg cggcatggag acgaggacac gtactacctt caggtgagtg 75660
tgtgctcctg cacggcagcc gggagacctg cctcacctct gtcgtctgct gagcccaggc 75720
tgggccatgg ggagggactc tggagaccat ggtggagggg gcgggaggag cccagccctg 75780
tgtgagaggg tccagagggc agaacctgct tgcaagagcc agaccagcag gacccaactg 75840
cagggcattc ctgagagtcc cctcagtccc aaaaacccag cgtcatgcca tttacaatga 75900
agccatgtgt acatagcaca ggtagggtgg tgcggagtgc caccagggta gaagttcagc 75960
aagaatccag gaccctaacg ttggccagga cccgtggcca cggccagccc ccatgagtgt 76020
gcctctcaca tgtggcctcc aacaggtgaa ttaaatcggc acaggcttgg ctgggagtca 76080
tcttccatga tgtgaacttt ctgtttttg agctccagaa tgagccccag ttggggtcag 76140
tggctcatgc ctgtaatccc ggcattttgg gaggctgagg cgggtggatc acttgagccc 76200
aggagtttga gaccaaagtg ggcaacatgg tgagaaccca tctctacaaa aattagctgg 76260
gcgtggtggt ggcgtgcagc tgcagtccca gctactcaga agactgaggc aggaggatca 76320
cctgagggca ggaggatcgc ctgagcccag gagtccaagg ctgcagcgag ctatgatgat 76380
gccactgcac tctagcctag gcgacagagc aagacgctgt cgaaagaaag agagagagag 76440
agacagagag acagagagag acagacttgg tttctaaaaa cccagtatct gttggtaggg 76500
gaggaagagg gaggcttggg ggccacaagg agcaggcatg gttcttgggg acaggatacc 76560
tgcccactga gtcaggggct ctggttagac ctgcttcttg ggaagaggaa agaagatcag 76620
gggatcctga gcctctgggg tgctggggaa cccccagaaa ggacagatgc tttgccaagc 76680
ccaggtcctc ctgaggctgc ggccaccccc ctcccgtggg ggtctggggc acgtgggcag 76740
agatctgctc ctctgtgctc aggtgcgagg ccgggagaac tttgagatcc tgatgaagct 76800
gaaagagagc ctggagctga tggagttggt gccgcagcca ctggtggact cctatcggca 76860
gcagcagcag ctcctacaga ggccgtgagt cagccctagc ccaccatcag tgtggggaag 76920
gaggacatgg cttaaccccc caggagaagg ccaggaggac cagaaacccc tccagaaggc 76980
atcatctgcc agggacaggc agcagggtcc agagcagagc ccaccccaca tctcctcctc 77040
caggaagcct tctagcactt ggggctgccc tgggaccctg ggtcatggcc cttgctatgc 77100
ctctgccact gaggggcctt gtaaatgtct gctgagtgga aaggccagga ggggtggcca 77160
gagtgaccat gacccaccaa gaccagagtc cgattccagt ggcacaggtc atccccctgc 77220
ctcccggccc cgccatggcc agtgtccttc tcaggcgcag gcccagtggc cgtgcatggc 77280
catggttggg gacagggagg ctgggggagg atgaagccac tctctgacat cagaggctcc 77340
acccattcgc agcatggggg catcacgggc atgggtggtc ggtgggcacg aggctgcctt 77400
gcttcccacc catgcgagcc gttgcttctg agcaggagtc acctacagcc cccgtcctac 77460
gggccggtcc tctcgcccat gaacaaggtg cacgggggca tgaacaagct gccctccgtc 77520
aaccagctgg tgggccagcc tcccccgcac agttcggcag ctacacccaa cctggggccc 77580
gtgggtgagt cccttgggca gtgcgggccc acgggcaggg cggggaggcc cactgggggc 77640
gcctagctca ggacacacca cccagctcgg gacccagggc aggtgtctct gtggctggct 77700
ccttccagcg gttccaccct ctgggcagga ggcgcagcca cggatagccc tctctgccca 77760
ctcctggctg tgggaggtgg aggggggcgt ggttaagagc gtggaaccca catgcatgca 77820

-continued

```
ctgcctcttg gcaggcgagg gagcttgggg aaggctctta acattacaca gcctgtttcc  77880
ccatcagcaa atggccacag aagtaccagg ctcactcctt gtgaggaata aatggtgcaa  77940
gacctcatca ggggccccag cacaagccgg gggctccatt ggatagagtt tgggccccct  78000
tcccctggaa ggtcctcatg tgggcaggac caagcatgtt cccagtgccg tgagcaagca  78060
cccccaggtg tttcctgagg ccctgggatg tggccagcac tccagtgcca gctgcgattg  78120
cccttacaac ccagtgcccc gtacgcacgg tcacccccgt ccctactagg cggggcgagg  78180
agacagggcc ccaggtgttc agcccttgct caagcctcta gctggcaggg gtgatgccca  78240
gcgtcacatc gccaggcctt gggatggctc cctggtgtcc agaggtgtct ggagcctggg  78300
tggaggctgc acctggatgc ccagcctggc tgccctgatg gccccacctg cctctcaccc  78360
aggccccggg atgctcaaca accatggcca cgcagtgcca gccaacggcg agatgagcag  78420
cagccacagc gcccagtcca tggtctcggg gtcccactgc actccgccac cccccctacca  78480
cgccgacccc agcctcgtca ggtgcgtggg ctgccgaggg cctgagcatg tgctgtcacc  78540
ctgtctgttc acctctgtcc ttctggccat gtcagctgcc ctgccccacc ctgtgtgctc  78600
accactcgca accctggatc agacaggcgg gcgggggcag tcaggccagg agcatctgca  78660
gatgctgggg aaatggtcca cttagaggaa aagcacaaaa agccggggtc ctccactgac  78720
ctgtccccag ctgagcacgt cccctccctg agggatgccg tggccacctg tgggctggag  78780
ccacccttcg gagacagcgg cagtctccgc cccagccagg ccactctcag agatgggggc  78840
tcgcgcagcc ctgtgctcgg aagctaatgc tgcttccttt ctcaaattct ctctgcagtt  78900
ttttaacagg attggggtgt ccaaactgca tcgagtattt cacctcccaa gggttacaga  78960
gcatttacca cctgcagaac ctgaccattg aggtaacgcc cgggtggacc ccgctctgca  79020
gaggcagtag ctggaggggc ccctgtccgg agggcaaaga gccttctctt ccttgctctc  79080
gtggctggga aacttggaaa ccctttccca cgggcaagca gatgcgatga tttgactctt  79140
gagagcttag gcagatgcag ccaggcacgt ggctggtggc gcgggacaca ggcccaggcc  79200
tccggatgct gaactggtca tttgagcctt tttggactcc cagcagccag tgtgcctttg  79260
attttagggg atgggctgtt tccaaggcac aaagaacaga agaatgtaag gccccgaggg  79320
agtcagtcca gttcagtgcc atttacagag aggtcagcgc catttacaca gacaggaaag  79380
gggacctagg gaaggcaagc acctggcccg aggccacaca gctcttggca cccatggcag  79440
ctgactgcag gcaccatgat taaacagcca cggcttgtct ttgggttaga gactagtgga  79500
gtacaaagcc tgctggtagc ctaggacggt gtgaaccaca gggcaccgtc agtcaaggaa  79560
gagcaagccc tctggtggga acctgccccc cagccagtgc cgcggcccag gtccaaggcc  79620
cgtcccagac catccccagc ctggggctgc agacagagat gagggtcagt gcgagctagg  79680
gccagctgct cagcctaact gtccctcgtg cagagagtgg ccgcgtctgt gtccactaac  79740
cgccctcccc gcaacctgtc cccagtgacc cacgctgagc cagctccagg tcacgttaac  79800
ccttgcctcc cctgagtgat gtgtgtgctt ggtgtggtgc ccagagggtg ttgggagctc  79860
agggatgagc tgggggtcca ctccaggggg cagggacatg gagaccaagg agggccctgc  79920
cctgaggctg ggaggcagtt cctcccccag ggccaggtag atgctcaggg ggctccatgt  79980
ctaacactcc caggtcaggg cccaggcccc gcacaggcca ggagtgactc tggtgggctc  80040
tccccctccc ccgtctcctg cctactctgg ttgggggtgt aggggccagg gtgtggtgtg  80100
gccagacctc caggcccagg gcgacccccc ctgctctccc tgctccactg cccccctgccc  80160
```

```
ctaatgcgcc ggcctctcgc aggacctggg ggccctgaag atccccgagc agtaccgcat  80220
gaccatctgg cggggcctgc aggacctgaa gcagggccac gactacagca ccgcgcagca  80280
gctgctccgc tctagcaacg cggccaccat ctccatcggc ggctcagggg aactgcagcg  80340
ccagcgggtc atggaggccg tgcacttccg cgtgcgccac accatcacca tccccaaccg  80400
cggcggccca ggcggcggcc ctgacgagtg ggcggacttc ggcttcgacc tgcccgactg  80460
caaggcccgc aagcagccca tcaaggagga gttcacggag gccgagatcc actgagggcc  80520
tcgcctggct gcagcctgcg ccaccgccca gagacccaag ctgcctcccc tctccttcct  80580
gtgtgtccaa aactgcctca ggaggcagga ccttcgggct gtgcccgggg aaaggcaagg  80640
tccggcccat ccccaggcac ctcacaggcc ccaggaaagg cccagccacc gaagccgcct  80700
gtggacagcc tgagtcacct gcagaacctt ctggagctgc cctagtgctg ggcttgtggg  80760
gcgggggctg gcccactctc agccctgcca ctgccccggc gtgctccatg gcaggcgtgg  80820
gtggggaccg cagcgtcggc tccgacttcc aggcttcatc ctagagactg tcatctccca  80880
accaggcgag gtccttccaa aggaaaggat cctctttgct gatggactgc caaaaagtat  80940
tttgcgacat cttttggttc tggatagtag tgagcagcca agtgactgtg tctgaaacac  81000
cagtgtattt tcagggaatg tccctaactg cgtcttgccc gcgccggggg ctggggactc  81060
tctctgctgg acttgggact ggcctctgcc cccagcacgc tgtattctgc aggaccgcct  81120
ccttcctgcc cctaacaaca accacagtgt tgctgaaatt ggagaaaact ggggagggcg  81180
caaccccccc caggcgcggg gaagcatgtg gtaccgcctc agccagtgcc cctcagcctg  81240
gccacagtcg cctctcctcg gggacccctc agcagaaagg gacagcctgt ccttagagga  81300
ctggaaattg tcaatatttg ataaaatgat acccttttc                         81339
```

<210> SEQ ID NO 3
<211> LENGTH: 81365
<212> TYPE: DNA
<213> ORGANISM: Mus musculus

<400> SEQUENCE: 3

```
ggtcccgctt cgaccaagac tccggctacc agcttgcggg ccccgcggag gaggagaccc     60
cgctggggct agctgggcga cgcgcgccaa gcggcggcgg gaaggaggcg ggaggagcgg    120
ggcccagacc ccgactcggg cagagccagc tggggaggcg gggcgcgcgt gggagccagg    180
ggcccgggtg gccggccctc ctcccgccac ggctgagtgc ccgcgctgcc ttcccgccgg    240
tccgccaaga aaggcgctaa gcctgcggca gtcccctcgc cgccgcctcc ctgctccgca    300
cccttataac ccgccgtccc gcatccaggc gaggaggcaa cgctgcagcc cagccctcgc    360
cgacgccgac gcccggcccg gagcaggtag gcagctctgg gacccgagct agggccaggt    420
atttcgcacg aggctccgag gctggagttc gggtgtgcgg ctgcccgggt gctagccgag    480
tgaacggccc cagggactcc gcgtcagtgg caggaggggc cggccggagt gaggctagga    540
gtagaagcag ttggcacctc ggcaacccat ggacctgcct cctgcccaca ctgtccacta    600
caggtggcaa ggagtcgcca tacccggaga ttctggggct cgggtctggt aataggggaa    660
gttgggaggt gcgtgggtat cctacctcac aaggaatgca aatccccacc tctgtaaggc    720
agaaggcctt tcaggtcccg ctatggaagc agactaagag agaggaaagc caactagagc    780
ccaacctcta tgctggtccc aaggtgtggg gtcctggtgg gttactgctg ttctgtgatg    840
agtttactgt ggtgcctcac cagcctccct agtcttccag gtagagaacc cgggcagccc    900
acactctctc ctgctccact gggcagctgt caccttctca ctcttgagag atgagaacat    960
```

-continued

```
ctgtaggcac ctatccacat acacacccgt atgtgtgcgt gggcgggggc gggggggtgg   1020
tggtgtcagg aaaaaagctc tgacttctga gccccaagac acttggttcc ctgtatgtgc   1080
tgaggtctgt taattaatta agtgggcact tgggacctgg gtcgtaacaa tatttggggg   1140
aaggttgttg ttgtttttct tcatttaaaa gttaaattgt gtctgtgtga gtcgtgcacg   1200
ggtcagagga catctttagg agtcgattcc cattttccat tttatcagtc tcaaagattt   1260
actcaagtgg ccaggatagg cagcaagcac ctctacctgc tgagctccac tgcctcggat   1320
tggttttcgt ggtcgttgtt tgtgttgctg tttagctcta gaaaaaaaac tcaacagaga   1380
caaaatgtat cctgaatcct tggtgtgttg caaacgctgt cccggccccc cacccgcccc   1440
catcctttga tttattcaat aaaaatgtaa aacattactt tgtgaacaaa agataagtat   1500
ttaacatttt ctcatccatg actgtataga ttgtgtatgc agttttgaaa atcaggtaat   1560
cggtttcaaa ggtgttgcat acccactaac tagtcttgag ctactggcgg gcctatggga   1620
gcctgcctat caagcacagg taactaacga caggatgctg agcaatgttg tccttctagc   1680
gatggctctg tggaacaggc agggcttgcc cattctgatg gccaccctgt gtgacaacat   1740
tctggattag aagtcagatg ctgagttcaa atactctctg tgccctggga ccttgagcaa   1800
gttacttaaa tcctcagaac ctcagtttac ccatcttcga aatggagtca tagcactgct   1860
tttctcaaag agcttataga aacctggtca gtatgccttt gtaaacagaa tggaaactgc   1920
ctgaccctgg ctgaagaagg atatgagtga gatgcttgtg ttcatagagg tagagttatt   1980
tgtataagaa agaaactggc tcgggacctg tgagatggct ccttgtagaa gggtgcttgc   2040
tgccaagggt gatcatctga gttccatcca tggaatccac aagctggatt gtggatccac   2100
attgtcttct ggccatcaca tgtgcactgt ggcccacggg tgcacacata catacaaata   2160
gaaaagtaac caggatgcta tatccaaagt ccttggacaa gtgctgatac caagtgatct   2220
tttgagtcct agattttggc tctgggactg ggtggaccaa gaaagaactc agagaagaag   2280
gccagttcct aggttttgga gagatcatgg cagtaaggca ggaatttgcc tgcgacctgg   2340
gtggaggcta gcagcatctg tcaggagtat gtcctgtgat gaagatgctc ctgtttcatg   2400
tttatttata gagtatgccc aacccaggtc ctggaatggg cttctagtgc tgacacatgc   2460
gaaggagaat agctaaagtg gagatgaaga agggagacag ggatgagggc taaagggagc   2520
ttcatcaccc tgctgatatc cagggatgca ccaacccaag gctcctagca ctccaaagtt   2580
cttgtcattt ttgtcattgc atttttaaaa agtcccatgt acatctcagt gagaaactat   2640
ttctgtcacc aaattcaagg gtgatttacc tcccagaagc aagcacacac acacacacaa   2700
aaaaaattgc acttggtgaa tggtgttggg gcagggggcg gagagaaatc ctcaaaacac   2760
tcttctgtgt tccttctaag aaggaacttt gaggcagcct ttagttttcg cagaggatac   2820
ttttaaatgt tgctgacaac aactctactt atgagtaaca gtgtggcaga gactcctgga   2880
acccagatca ttcaatcttg tttcggtttg aatgtgcagc aaagagtgta acggatacat   2940
ttagtacagc tacagccacc ttacaaacag gcaaggtcct ctctatggga cccagcctgc   3000
agaacaaccc gtggtccatc tgcctttgta gactctgact ctctctgtct ctctctctgt   3060
ctctctctct gtctctctct ctctgtctct ctctctctgt ctctctctct gtctctctct   3120
ctgtctctgt ctctctctct ctctctctct ctctctctct ctctctctct ctccacttta   3180
tctttaaacc agtttgtttt ccctgaactt gttgctccac aggggaggat caaagagaag   3240
ggattgcttg gcaaaactat tgcttatgaa gtatctgcag gaattagcac ccagtgcaca   3300
```

-continued

```
tactggctgt gtgctggtat taggcttaat aatttaggat tttacctttg cttgtaattc   3360
tccaacatcc ccttgatgta ggttctgtaa ttatgcccat tttcagatga ggtcatggag   3420
gctttagcat gtgattcaag gggcctggag ttgtgccatc acagtgtggg atttgagatc   3480
tcagatctga caaacagtcc agggtatggg cttctgggtc gttctcgcca gtgtagctag   3540
tgctggatgt ataaatataa cctattaaac agagccacag gaccctagaa cccttgcaca   3600
gggcattctg ttgagaggac tgtttgaggc taggtgacta gaattaggcg tgatgtgaac   3660
tcatgtaggg agaaaagacg catcgtaatt tcatcagtac cgaagtgaaa tttctcatct   3720
tcagtcatga gtgtataaac aaacaagttt acagtccgtg gtactttata cagtccatgg   3780
tactttatac agtccgtggt gctcttctca ctcattgcag ttactgatct tttcactgga   3840
tgtcccagct tggcagaaag ctcaaatttt tgttctcatc gccaacctga aattctgagt   3900
tatgacagct gctgcttgac ttgaccttgt cctaacccag aggtatgatt gtcatagatt   3960
aatgtcactt gaacactgtg gccacttcat tagaaccatg ggtgggacca aacacctaca   4020
atggcagcac tggagaggct ggggtaaagg catcaagaat ccaagccccc acccccaggg   4080
tcagctctgt tgtgctgtcc ttattatgct gaaggtcaag agcacaaacc agtagtctaa   4140
tttgccacta tatattctga tggccagagg ctacatgtca gtgtgtgggc aagactagtt   4200
cccctcagat aggaatcccc tctatgttcc tccaagatct ggcaattctg gcagctcctt   4260
gccctgcagg tctgcctctg tcctatagtc tctgactctg tgcagcatgg ccttctcttt   4320
gctttctctg agtctaccct ctttgattgt agtcagatgt gtggctcgtc tgaggttctg   4380
gggagaattc cttgtattta attttatgta tttacaacac tcctccctgc ataaggttct   4440
acagtgtcag ggtcaggcag gttctgcttg ccccagctgt ctgtttaaac agaggctgct   4500
ggggtgcttc acaagacatc aacatggctt tcgggatagg agaggcatcc tgaagaagta   4560
gaaagagaag gggaggtgtt atcctaggac atctccactg aggctggagc gccggaccaa   4620
agaaacaacc ctgtctgtga aggaacaaga gctctgaaga caggtctagg caatggagga   4680
gacatgtgga catcagaggg ccagtggatg taacacttga tggcccttgc agatggagtc   4740
aggttcccca gagagtggcc tatgagggag gaaagcagtc ttcttccacc tgcccagact   4800
ctttgcttgg tgcgtgactt tgatggacat tgcccagatt gatgggagaa aaaaaaaatt   4860
ttttagaacc atgggtagga ccaaacacct acaatggcaa cactggagag gctggggtaa   4920
aggcatcaag aatccaagcc cccaccccca gggtcagctc tgttgtgctg tccaagcagg   4980
gtgcagggcc cactctccca aatgttgcag ccagtgaggg gcagggatag ctctcctgaa   5040
cttatgacct tgtggacagc tttccaacta ctggaagtgt ggagaggagg ggcatcatct   5100
ctacacccgt gccacctcat gacagacaag tggcagagtc agctattcca cactcatgct   5160
ctgagggtct gctcacccac actccacacc cacgagggtc atgtccactg tgctgcctgg   5220
gtgagggtgc agggcctgct ctccctagtg ctgctggtga gtgatggggc aagctctcca   5280
gagggcggca accagtgaag ggaggggcca gctctgccca gttcttggac atctgctctg   5340
acaagggata tcccatgttc tttaatggta atgtgagccg tggacatcaa cacccacctc   5400
tgcatagcca tgaacccagc tcaggctgcc acctcactat ggccccaggt ggctggccac   5460
tcacaacagg ctgctcctct ccatcctcca gtctccagat ccagctctct tcataatcct   5520
taagctgttc cacttctctc tctcccatct gaccaccaca tgctcgcaca ttgtggtggc   5580
tcccactgca ggctggccat gttgctgggg ggccctgggg tgacatcctt tggtccaagc   5640
tgcacggccg tgagcaggcc ctgcacctca cccaggcagc acagtggaca tgaccctggt   5700
```

-continued

```
gggtgtgggg tgtgggtgag ctgcatggca ttttggcaag tggttgtcca cagcctgcct   5760
gtgctgtgct ccagaggcag atctgtggat gctgtggcag gtttctgtct gcctttttcc   5820
ctcctcatgt gctgcactgc aggtggctat gtgtgtctat ggcctgctca tacagggtag   5880
agggcagatc tatggctatc tttccctgcc caaacattgt ggcatggtgg aacacagatc   5940
tctgtctatc ttcctcttcc cgtgccatgc tacctagatt tgatttgatt tgatttgatt   6000
tgatttgatt tgatttgatt tgatttgatt tgatttgatg agtcctagac ataaaacagc   6060
tttggtcacc aagccaggca tcgggccagg atgaacatag gactatcatc tgctctaccc   6120
ctgactgatg taagaatggc atcaccaata aggtgtctct ttgtccattg acaggggtta   6180
aagtttttta attggtaaat ttttactatg tagctctggc tagcctggaa ctctttatgt   6240
agaccaggct ggcctgaaac tttcagagct ctacctacta ttctctgcct cctgagtgct   6300
gggatcaaag gcgtgcattg cttggaatct cgaggggatg agggtgtggg gcttctgcag   6360
gagaaaggca ggtctcagga gcctgaggag gaatggaagg tcattagcag tctccttgct   6420
atgcagatat cttctgtcag ggaatgctct ctctctctct ctctctctct ctctctctct   6480
ctgacatttt ctatgtagta ctgatttcct gcacaagtag cggtttctca ttttgcttta   6540
ggcagttggg tggggttagg ctttgtatgt gttgctagtt ctccatcgat tttggcttct   6600
agtatcaggt aacgtcaaag tggcgggttc tggtttccta cagccccggt ctgaggtgac   6660
accatgaatc ccagcagttg tccacctaac actctccaaa gcaggctcac agtgcagacc   6720
ttggtgagtg tatttcttat cacagtccac taaagagggc tttatacaga ccaagggcaa   6780
aacagacatg aaccattgga agaggctgca aagcagtatg aactgcgagg gcagggcagg   6840
gcaggcacgg gtagggatgg agaggtctgc gggctgggcc ttccagttct tgcacagttg   6900
aggtcccagg aatgtgtgag tagccactgt cacccccttt gaaacctgcc cacagcagaa   6960
gcaccggagc ggggtttatg atgtgcagcc tcagcctgaa ggactttcgg gagaagggca   7020
ggatctacgc tccaaagcag aagcctgaga ggaaattaga accatggatt tgggcagtga   7080
cagccatgca cgggagctaa ctagctgatt caggatcctg cccattttgt agatgtttag   7140
tagtccagaa aggcagaaga tagtagatgc tagggacaaa cgtagttttc tatgaaaata   7200
tgatttttct ctatatcatt tcttcttaaa aaacatttag gtgggggctg gtgagatggc   7260
tcagtgggta agagcacccg actgctcttc tgaaggtcag gagttcaaat cccagcaacc   7320
acatggtggc tcacaaccat ccataacgag atctgactcc ctcttctgga gtgtctgagg   7380
gcacctacag tgtacttaca tataataaat aaataaatct aaaaaaaaaa aaaaaaaaaa   7440
aaaacattta ggtgtctatt tgttcatgtg tgtaggtgtg ccagggtgca tgtacaggtc   7500
agaggtcatg tccagtgtca tctttgcttc ctgcccacct tattgttttg agacagggtc   7560
tgtctcattg actctggact cagtgattgg gctggactaa ccagccaggg aactctggat   7620
ttcctctgac ttctgctccc cagagccacg cttgcaggca tttgttgcct acagtctgtt   7680
ttgttttaaa tttatattta ttcatttcat ttttatttgc attttgcctg catgtatgtc   7740
tgtgcaccac aagcttggca tgcctgtgga ggtcagaaga gggcatctga tcccttggaa   7800
ctggagttac agatatttgt gaaccagcat gtgggtgctg cggactaaac ccaggtcctc   7860
tgcaagagca gcaagtgctc ttaaccactg agacacccct ccagcccctt tgctgttgtt   7920
gtttaatgtg gattgtttat tggtattgct tttttttaaa tgtgggttct ggcatctgaa   7980
cacaggtctt cacactttcc tgactgagtt agttatcttg ctagtaaacc catttctacc   8040
```

-continued

```
aaaggtgatc acagtaaact gatttttatt ttcagaagca tgcctagtct tcctgaatgt   8100
gccctgcgta tttgcatagg tctggtgaaa ttactaagtg gctgtgctag tcaaataagg   8160
agcgtcagag cagatctcag aagcctgtgc tggcagcgga gccaggtcag ggtcccagca   8220
tcaaaatcca tctgcagagc ttctcccgct agagatgccc aaagaacttt aaggctggtg   8280
gtccctctgt cagttacagt ccttgtctgt gagaccatag agcccttgta agccagggac   8340
caaacaaagc attttatctg tctgtctgtc tgtctgtctg tctgtctgtg tgtatgtgca   8400
catgagcatg ccacagtgca tgtgtgatgg tcagaagaca atgttatctc cttccaccat   8460
atgaattcca tggatgacac tcaaataatc actattggta gtaagcatgc atatacacag   8520
agccatctta caggccctga ttcagtttct ttcttataca aataactcga cctctatgga   8580
aacaagcatc tcactcattt tccccttcag ccagggtcag gcagttccaa ttcagtttac   8640
aaaggttaat tgaccaggtt tctataacct atatatagct tctttaagtt tctagacatt   8700
tgtacccagt tcaaggggcc tgcctttgaa atgtgtgctg ggcagagtcc tttctcaaat   8760
ctccttgatc gaagctactg gcagaggccg tgagaacatg ggtagacagc ggctaactgc   8820
cagtggctgg agaaatggcc tgaatttgtg ggactcatca tccggtgggg ggtgtgtctt   8880
aaggcaactg gacgtgaaaa tctagatatt tctgtattag agaaaaaaac aatctgtttt   8940
aagaaaagtt tagaaggctc agtggttaag agcaccgact gctcttgcag aggacctgag   9000
ttcaattccc agtacctaca aggcagccca caaacactgt gactccaatt attctgacat   9060
ccatgggcac atggtactca cactacacgc tgacaacgca tttatacaca taaaataaaa   9120
tgaatctttt ttttaaaagt aactagaact actatagaga agtaggattt cttggggtat   9180
catataatta aataaatact cacacaagtg tgacaggatt gattttgtac tttattataa   9240
gggaaccatt ttttttttta atcgtccagg gttgcatctc agcctctgga gtaaggattc   9300
atggagagtt ttgtggggcc aatctgcaaa agttcagcag aaatcagaag ttaagaaagg   9360
tgatacagaa cttagcattg gaaagttctg gaactagagc tggaaagatg cctttgtgct   9420
gaagagcact cgctgttctt ccagagaacc agagttctgt tcccagtggc ccacaactgc   9480
ctgtatgtaa ctccagctcc aggagacctg acaccctctt ccagtctctg caggagcctg   9540
cacacacatg caatacacat acataaaaaa taataaaatt aagctttaaa acattttttt   9600
tatgaaagga agttatcagc caggcatccc cgcactcaca aaacagaggc agaggatctc   9660
ttgtgagttt gaagctgtag tggtagatac ataaaaagtt acaggtcagt cagggataca   9720
tagtgaaact ctgtctcaaa aaatatctac aatgaatcca attttagaca atttgtgctc   9780
agagatgtag ggcattcctg tgatcccagt acctaggatg ctaaagcaaa ggagaagctg   9840
agacggaaga gaaagatttg gagcttgagg ccagcctggg tcacacagtc caaatatata   9900
taaatatcca aatatataaa atagtttatg ccaacttgac acaggctaga gtcatttggg   9960
aagagggaac cttaattttt aaaaaaatga ctctactgaa tttacttgtg gtacattgtc  10020
ttgattgatg attgaatgtg aaagggtcta gctcactggg aggagggcca ctcatgggca  10080
ggtggttcca tggtgtaaga aagcagacca agaaaacaaa accacaggaa gcaagtcagt  10140
aagcagcttt cttcatggcc tctgacaatg gtcaacatga ccactgacac agtcctttgt  10200
ctctgttatg gttctttctc tccctccccc tccctctccc tcttaaagat ttatttattt  10260
tattaatatg agtacactgt cactgtcttc aggcacacca gaaaagggcg tcagatccca  10320
ttacagatgg ttgtaagcca ccgtgtggtt gctggaaatt gaacttagga ccctctggag  10380
ggtcagacag tgttctcaac tgctgagcca tctctccagc cccttatctc tttccaactt  10440
```

-continued

```
tctgtatcag ttgagttttt tttatccttc ctcttccccc acagtctgtc ttcctaccct  10500
tctttctccc ttccatccca gcctcccttc ctgtccttcc tcccctctcc cagtctacct  10560
tcttgtcctt tctctcccag ccccattcta agcccccctt ttttcctttc ctttcctttc  10620
ctttcctttc ctttcctttc ctttcctttc ctttcctttc ctttcctttc ctttcccttc  10680
ccttcccttc ccttccctcc cctcccctcc cctctcctct cctctctttt tctttcccct  10740
tcttccctcc ttctccctcc tcttttcttt tttctgaagc tgttttttaa ttaaccttca  10800
aactaaacac attctttccc ttgaacctca gactttcttt accacaaaat gtccctgcat  10860
cttctcatgt agagtgggtt ctcttatagc ttccacacac agacaaaaga attttaactc  10920
tctgtaattc caactcccag aagaaaacga aaggtgagta cggacggacg gggcaagtgt  10980
gggaacgccc acccgagtgc cacagagcgg ttttgctagc tgctcttgcc aagggctggg  11040
gtctggtctt gctatgcaca cagtggctca ccatcaccag taacttctgt cccagggaat  11100
ctgacattct cttctgatcc tccttggaca ccaggaacac acatggtaca catacatata  11160
tgtaggaaaa cccaatcata cacataagat aacaaaaaag taaatctaaa agcattttca  11220
aagatgtggg cagctatttt taaagcaggc atattatgat tcctcattgt catagaaatc  11280
tttgcttctt atacttttat tttttgagat tcatttaatt ttatagtttc taacaactgt  11340
gccttaatta tgaaaacacc aggagaaatt ttatgaaagc atcctgtttt aaaatgttta  11400
ttttaaaagt ttaggtttta ttattattat ttacgggtat gtgtgtatgt gtgtgcttgt  11460
ggggtgtgca tgtgaatgca ggtacttcca agccagagag ggtgtcacag tcctttggag  11520
ctggaggtac ctctccatcc ccagagtttc ctgtttttaa acaaggctag ctattaccca  11580
acaaccgtac ctcctgctaa atatttttca gcacgtttgt atcaggaaga gtcagaaagg  11640
caaagcctga gagaggtata cttagttctg ctcatttatt gttgagatga cctgcagaca  11700
ctgctgtgtg cctgttagtt cctgggttac tgcaaggtta gctgtcccag ggttcgaaca  11760
gacatggcca ggaaacacag gaagagcagc agttgtatgt ctgccttgtg tttggatggc  11820
ttggaagata tgtgtatgtt agttaatcca gtaaacgtaa gctagcagcc caggcaggct  11880
aggtggtcat gattcttctg ccttgtcttc tggagtgagc catgccttga tttggaactt  11940
taagaaactt ttccactctt gcttcatctc acagcaaaca gctctgccaa attcagtctc  12000
tggaggtgag gccaacttct gataatagag ttgtgaaaaa aatcctttca agtattttat  12060
tatcaggttt tagccagcca aatacttaag tgtttctgaa agtactaggg tctctctctc  12120
tctctctctc tctctctctc tctctctctc tctctctctc tctctctctc tctccttccc  12180
tccctccctc cctccctccc tccctccctc cctccctttc tccttctctc ttacttgtat  12240
tggaaattca acacccaaac cagcaagact tttatgacaa ccatgaatat aaaatagtca  12300
tgttcaaaca ggggcgggca gcctgcagcc cctgtgaccc ccaagttcac ttttagacag  12360
gtgggtaaag actacatggg ctctccagtc tccacttgct attctatgat ggatgtaggg  12420
aagttcctgt gggaaggtac cctaccagca ctgaccaggc atgaaggatg aaggaggacg  12480
gagagcccct aatagacctg ggcctcttgt ttatatagga tcttttgaga gctggggcca  12540
tggtgagcca ttgaactctg cctgactcag gccagcattg tgctataccc acagctgaga  12600
gagggagaag aatgtctacc aatcatagag cagagtggtc aggactcagg acaaactaaa  12660
gggaggatat catctagttt gactcataac aaaactgctc tatgcagatg tcagcctacc  12720
agaacccaga gccgctaacc tgggaagcca gtgggcagca gccttccagg ctggggttct  12780
```

-continued tgtcctgacc aagatgctat tcttcctgca aagacagagg ggaagaagcc agaaatgagc 12840
atgctcatac caatagagcc cagggctcag tagtaggaac gtgtctggtg tgcctggagg 12900
ctccgggctc catctcctgc tgcctagaaa gccagcaagg tctccgaatg agaactgtgt 12960
tccactgcat tccttctaaa tgagaactgc gttccactgg attccttcta ctgagcagag 13020
tctgaaaagg taaagacagt ttctgttctt attcccacca ggtccaggaa ggagtgtccc 13080
tcagtcaaac ctggtacctt tgctggcctc ctgctagggt tccaaatcct acagctgcta 13140
tgatcatccc agagaaggca ggcttcagcc actgaggtcc cttcccagtc actaaagtat 13200
aagggaaaaa agattacatc agataggta cagtaagttg tgcctatcca tatgcacggg 13260
tgccgtacag gggaaggtgg ctcttctgag tcccagagag aaaagtagct ctgggtggca 13320
cagaggctaa tgtagggatg tgaggggaag tgggcaagga atatgcagat atagcattgt 13380
gtgtgtgcat gtgtgtacat atgtgtgtgc atgtgtgtgt gtgtgtgagc aaggaatatg 13440
cagatataac attgtgtgtg cacatgcatg tgtgcatgtg tgtacatatg tgtgtgcatg 13500
tgtgtgtatg tgagcaagga atatgcagat ataacatgtg tgtgtacacg tgcatgtgtg 13560
catgtgtgta catatgtgtg tgcatgtgtg tatgtgtgtg tgtgtgtatg tgagcaagga 13620
atatgcagat ataacattgt gtgtgtgcac gtgcatgtgt gcctgtgtct acatatgtgt 13680
gtgcgtgtgt gtgcatgtga gcaaggaata tgcagatata acattgtgtg tgtgcttgtg 13740
gatgtggatg tgcatatttg tgtgtgtgtg tacatgtggg caaggaatat gcagacataa 13800
ctgtgtgtgt gcatgtgtgt gcatatgagt gtatgcatgt atgcatgtgt gtttacatac 13860
atgtatgtac atgtgcgtgt gagtgcatgt gtgtgttgtt cctcaggagg catccacttt 13920
ttttttttt ttttttttt tgagcatgag cctctccctg aatctctcca tcaggtctcc 13980
atttcccatc tctaccttca aagcactgtg ataacaagaa catactatca cgcctgtttt 14040
tgtttttaaa ggcgccaata tctccttaaa ttttagtgca tttattattt ttcacatgtg 14100
cgggtactca catgccacag catgcccatg gtggtcaaag tacagttttt cagagttggg 14160
tctctcctgc catgtggggt ctgggtttca aactcaacat tccaggcttg gctaccaatg 14220
cctgctgagc caactcaatg actcctcaca ccccaccttt gaaacacacc ttctggggat 14280
cacactcagg tcctcatgcc tacaagtgtg tactgaccca gccccagacg tgactttggt 14340
ttgatggttg cccagctggg accccttcc tgatgtatgt gtccttcaga gctgtaccat 14400
ctgctcctac acagggcagc ttctccatgt tcagtgcatc tgcagcctca gggtcacctg 14460
gactcactca gggtgcccaa caggttgttc tgcaatcatg tgtcccagtg tcctgcagac 14520
atgtgtcatg cagttatatg ttctgaatct caatatagac cttagaactg tggctgaaga 14580
aaggggatgt ggtgccagac tcagtttgcc caaagagcta gtgcaggatg gagctggctg 14640
gcactggcct agggcagact gaaaggtgca aggggccctt gggtggtgac acctggtgtt 14700
ttagaccgtt atgtgggttc ccaggaaaac cccctcttct gcaaaggaag cacttgtgtt 14760
ttcccagtat gctatgggta caaggatgac taacaatcat gacatttgca tggtgcttcc 14820
ttcaccgtag ctgcacacaa aggcccgtgc tttgctctct tggcagaggt aggctttgtt 14880
tcctcagttt acagataggg aggtggaggg ctgggaggtc attatagtca caagaggagt 14940
agagggctca gcacaaagta cgacaaagtc accgtaataa aattcaggcc tgggccatga 15000
tcctaactac tggggaggct gaagcaggag gatccaaagc ttaaagtgac cttcaagccg 15060
gtcctggttg acttagtgag accctgtttc aaaagggaaa gtcaaaagag tctggggtgc 15120
attttggcaa tacagtgtcc tgggtttgac ctcagagctg cggtgagagc aacgagaaag 15180

```
aacagattcg caacaggaaa gttcacaatg gatccagcac tagctttcaa tttttaagaa  15240
agattttaca ttttatgtct gttgtatggc catatgcttg tactctgtgg gggggggag  15300
aaagagagag atagggaggg agagagagag ggagagggag agagagaaag agagagagaa  15360
agagagagag agggagggag agagggaggg acggagagag ggagggaggg agagagggag  15420
ggagggtggg agagagagga agaaggagag aggagagaga gagagagaga ggaagaatga  15480
gagagagaaa gagagagagc tctcttaact gctgagccat ctctccagcc cctcaacaat  15540
agttttattg gacactaagg acttcagcga tgaagatcca aagacctgac taactttctc  15600
ccaagtttgt gtgtgtgtgt gtgtgtgtgt gtgtgtgtgc gcaaacatgt gtgcatgcat  15660
gctagaggga gcctgcccaa ctgaaccatt gttagaggac aagggttaga acaggaatga  15720
gtcaatccca tagtagggag ggtctgcatc cctgtgggat cctgtcccca agaacaggac  15780
acacaaggtc tcatgctatt cagggtcagg ctgagaattt gctcttcaag gtttcgtggt  15840
atgtattcct tgtatgtcat actgtgttgc gtaaggacat cttcctgcag gcatctatta  15900
tacagcaagt gtacatgctt cttccccctt ggtccattta tccctttaga caagtcactt  15960
ctgctttcct gtcacgtata catatgtgat ttttagatac atatgcaaaa acccaggaac  16020
aaaatatgag agaaaacatg tgatgctcgc tttgctgaga ctggcttaat tcacatacta  16080
caatcatgtc cgattgcctc cattttcatg aaaaggatgt aactttgtcc ttctttatgg  16140
ctggataaat gtatgaccat gtatagttgt catacttttc ttgtctgctc ctctgctctt  16200
gggactagtg ctacactgag cgctccttga tatactatgt tctacaatgt gcgttgactt  16260
tggggtaggt gtccgtgggt ggtatggtca catggtagat ctatttctaa agaccctcca  16320
tactgacttc catagtggtg ggaatggttt gccttgcctc tgttggtctg ggagggcgtc  16380
cttctgtcca cgtccccacc agcattggcc acttctgttt tcagccggtg gctgagatgg  16440
attctcagta tggttttgat ttgcatttct cagattgcac cttttaaatg catgtattag  16500
ctccttgtac ttcctctttt gagaattgtc tgctcaattc cgttttaagc accaggttgc  16560
ttgtgtgtgt gtttagtttt ttaaatattt gctttaggtt tacgtgtgtg tgtgtgagcc  16620
tgagtgtcca tctgtgcaac atgtgtttgc aggaacccaa acataccaga aggtgtcgaa  16680
tcccctggaa ctggagatac gggcaggtgt aagtcagctg acacaggttc tgggaattga  16740
actccgtctt atgcaacagc actaagtctt ttgactgctg aaccacctct gtcaccctgt  16800
gtttagtttt ttgagttctt tgtatattct attattttat ggcaaggaat gtttttgcct  16860
gtatgtatgt cttatgtaca ccatgtgtgt gcctggtgcc catgaaggcc agaaccagaa  16920
aagagagtgt taggtcctgg aacagttaca gatggttgtg agccgccgtg tgggtgctac  16980
aggttgaatc tagctccgct ggaagagcag ccaatgttaa cagctgaact gctgctctcc  17040
agtcgctttt tgtaaactcc agatgtcaat cctctgccag actgacagcc agcaatgact  17100
cccctaccct ccctgagctg ttcttcaccc aaatagttgt tttcatctct gtacaaagcc  17160
ttttgaattt ctcaaagcct catttatcaa cggtcttctg ccggaggaag aggctaggga  17220
cagaaagcac ggcctgccta ctgctctctg gagtgccatg gtgccacgtg ctgagctaga  17280
gtgttctgag ccccatcctg ggagttgtga gtcacctacc tgcctccact gcaggctctc  17340
ctacatccct cctgtgatct ttcctgagac accacaaacc acacctgaga cccccggggg  17400
agaaccttac agggatacca ggtacccagg aacatcatca cagcctccct accaaccaac  17460
tccagcatag atgccttggg catcttcttg tcaaccaggg tcaggtcctg gagtaggcag  17520
```

```
ggcgtgggaa ggagacccat gagagcgggc tttgtcagcc tgctcagggc tactgtatct  17580
acgaagggct gttccagtgt ccctgcccag tggcagctgc cagatccctt ccatggggac  17640
agcagggact ctaattgctc acctgctgct cagagtctct gccagccctg gaggtgtgtc  17700
tggggaagct gtgctaatta ggcacacggt ccatccttgt aggggcaata ggcatagtgt  17760
caacctttcg gtgcgtcctt cacagcaagt aaaggagctc cagtctccca ttctgatcta  17820
catcccggac cttagggatg acgtcctagc tgttgcctca ttgatgtcca ccttccagat  17880
ggacactgcc ctgctcaagc acagacctgg tgactctcag ctcagctgac ctatgggaag  17940
ccttggtcct tgtggggact gaggagagca tcccaggttg ggaagagagc atgtaggatc  18000
tttagggtgt ttccaccagc agcagagggg ggcctcatag tagagagggg gtctaacttt  18060
tgcagagacc acacagcggc ccttgctaaa tgctgtagcg ccgcaaaggg gagtcgagct  18120
ccacagtggg tacgtcctgg tatctgtgcc gcccagatca tgaacagtaa gcggcatatc  18180
ttatcattca tttaccaagc ctccattctc tggggtccct gggactcctt accacacagt  18240
acagactaga ttcagctcct gctcgctata gaaggaggct ctgctggtga tagtcatgta  18300
agttagagac agcaggtccc tgatctgcaa gacttggatt agacaatgtg gccccccctcc  18360
ttctcgccac cactgtcctc tgtctccccg tggtcaaccg ccatcaacaa gcctaattac  18420
aaaggcctcc tggcactttt tcttttggag taaggcatgc tccggcttgc ttctgggccc  18480
ttaatttttg atcagggaca cctcttcgac taattatttg tcagtaatga gggaggagag  18540
atgaggttgc gaaagcgtcc ctgagcttat agagagaagc tgcaaattaa aatacgaggc  18600
atccgtaaac agggcgctaa ttggattaat tcaaaagtga tagattggga taagaacaga  18660
gaggaagacc acaggcagat tgaggtcaga ataattccag gagcgttgcc cgggcttcct  18720
gtgatagatg tgagcctcaa agtccgagag ctacagaaag taaaatatgc tgctgtgtgt  18780
gcaaaacaca tctgagtcac tcaggcacac caaccaccca ggatgcatgg ccgtttctta  18840
agccctggca ctatctgacc cttgagtcat ttttggagag accagaactt tcatatgaca  18900
accgcctttc tttcctctgt tgtaataaag ccctctctat ttgttttaag gtttttaaat  18960
tatatgtacg tgtgtatgta agggtatgtg cacatgagtg ggagtgccca tgaaagccag  19020
aatctccttg tagctgcagt cccaggcagc tgcctggtat gggtgctggg agctaagctc  19080
ccaagtacat gggcctatgt gcatgttctt gaccgctgag ccatctctcc aggccctcat  19140
tctgatttct cttggtgctg tttagtgttt ttgcattctt tgaatcttga gccacactta  19200
tgcgtgggct atctaatgta attgaattta aaaaaaaaac cattatgtca gaaggtgata  19260
aaaattatga tgggaacatc ccacttctga acaggcagag gtgagctgaa cttttcaaga  19320
taaggggaag catctccctg tgtcccagtg agcactgtct gtccgtggct gcttctcctg  19380
gtatctcagc gaggcatcag gtttctgtag ggcatttgaa tcgcctcata gaccaaatgt  19440
gccctgacca cttcccctgg ccacagtgat gctttatagt ctggattaac tctgggctac  19500
tggcctcact cccagtcttg gctgacacct aggctgtggg agagctaata gcttattcat  19560
attatttaga taagtagcat agtatttgag ccgtgtacgt ttttaaaagc atcaagtctt  19620
tattcttagg gtgagcctta tcatataatc acaactgtgc accatttcag ttctcatggt  19680
tcttccatgg atcacactga acagtaagtc ctggctgcag aagagaatta tttttgcacc  19740
tgtctccaag tctattggtt caacataaac acaggcaata ctcgaaccat atgttatcat  19800
tccaccgagg ggctcctaga cacaccccca gtcagcttcc tgaatttcta aattcagaaa  19860
gggaatgtgg agctgggaag aaatagtatt tcacttaaga ctttacttac ccatcctgtc  19920
```

catttatcca tcccatctat ctacccatcc aacacattct cccatccatc tatccatcca 19980
tccatctatc catctcttca tcccatatgt ccataaagcc catcatatct acccatccat 20040
tgtttgttta accatctatc catccatcca tctatccatc tcttcatccc atatgtccat 20100
aaagcccatc atatctaccc atccattgtt tgttcatcca tctatccatc cacccatcca 20160
tctatctatc catccataca tccatccatt catccaccca tctatccttc catccatatg 20220
tccatccacc cacccaccca tccatcatcc agtctatcca tctacccgcc tgtatatcca 20280
ctcacccgcc cacccaccca cccacccaca aaaccactat aaaaacatcc atctctcatt 20340
cattactgag tacctgctgc atactaggtc ctgatctggg accagacaat tcaaacttta 20400
tacactcact cagtcttcac cattctgtga catcaacttg aagctgaggg tttaattctg 20460
cagagcgcag gcctcttgga ggtccccggg gcacaccaca gtataagaca cttcgtgtgg 20520
agcacagaag ccagtgtgcc aaggacaccc tttgctcctg ttgttcaggt gtgggtgggg 20580
atgggtctgg cagtgagaca agaggggcca tgttggatat gcgcctcaag ggaccatcat 20640
ctagcaagca gggtagcttc cagtgatgcc ctaggcacct gctctccgag gtcactccct 20700
ttaacttctg gaagacagga gaggacacag ccaaatgtac tgaaggcaga tttgcttagg 20760
atccaggcca ggcgtccatg gatctctgca aagagtgaaa gtagacactg caggggagct 20820
cggatggatg ctctgtcaag gcagacgaag tgggcactgt tccagtcatg aactgtatgt 20880
tatataaatc gacccctctg tttcctcatc ggggaacaga ggtagaaact cttctcacgg 20940
taccagtgta atggttgtgc tatggatagg tgtagacgct gaaattcatg cttagtgagc 21000
agcatcagct agggcatgag gtgtttgtca cattctctgt gtgactccta tgtgctctca 21060
gaactcactg agttgaggat gagagcgccg acggcccgga tggaagagtc agatgagaca 21120
aagaacaggt gctctggcaa tgtcaagcag gttgggaggg cagggagtct taactgggcc 21180
tccatctgcc aacctccctg gccttggctg tcagccaggg cagcctctga cctctgaagg 21240
gcgtgtcctc tgtttttctg agcaggagtt gggcccacaa aggcagccct tcagtctcgg 21300
acgtgagtaa atattgacgc tggggctttg ggggccctga ccgttgccac ttaagcatga 21360
tgtggatgtc tctattggaa gctcagagtg gctgaggact gagctagctg ggcaaacctg 21420
ctccctaagg caaccacgtt ctaaccagcc cccccactcc ctggagttct tcctcctgct 21480
tcagggctag gacgaccctg atcatcctgc acaattaatc aggcaggcaa cccagtgccg 21540
ccacaagcag tcattacgca ggtatttcta agatggaaga actggttgct tagaatagct 21600
aagaggaatg gaagccagtc cttccagcag cctctgtgga atgggggaga cccatggtct 21660
catatgttca gttgaaccaa tttagctgtc cccccccctg ccatcgccac ccccagtccc 21720
gtgtgagaag aggcacacgt ggtttgaagc caccaagcac cacctcagct ttgtattcat 21780
gagcactcgc gtgtgtgttc gttcacaagc tctctctgct gtccatggga atgcacagag 21840
gatatcttta aagtcagcac ctagacacca tcttgggccc ggtgtacagt gacagcagat 21900
cttcaacctt ggcctcattc gagagagatg tgcagaaaca cttgttgaat tccccacagg 21960
attccctgcc cggtgctgtc ctgtcacctt aacagttaag ctactgttgc ccaccgcaca 22020
gttgggcata tcttactttc caaacatttt tttttaattt gtattccctt tatccagtta 22080
gtcctctcga tcctttccct ccctctttac ccaagccttt ccaccctcag cattccccct 22140
ttttacttat gttctttata ctgacggtct accatctccc tgcctctaaa agccagctgt 22200
atgaggccac tgtccctgaa atgactaggt gtgaacaggg aagattccct catgagcatc 22260

-continued

```
agggggaaat cctatgatat aaaaatgtct gcagtgggcg ttggagagac caactagcca  22320
ttaagagtgc atactgttct ctaaagggac ctgagtttgg tacccacatt gggcagctca  22380
aaaaccactc tcagctccag ttccgaggga cccgacactc cagcctccaa gaggatttgc  22440
acccacatgc acatacagtc acaaatgtta ctttttaacc ttaaaaatgg ctgcagtggg  22500
atgagaagct gggaagttta ggcctggaga ttcattcata gaaaggaagc tggctctgct  22560
tccccagcca atctctgctg gatgtttgta aaccccaaat ttgatgctgt taacctttgc  22620
tctaccagcc aggctactcc agatggctct accggatgtt gtaagcatct gatttgatga  22680
cctcatgaat ttgagcaata gaaatgtctg ctggaaatgg tttaccttct agagacaggg  22740
tcttactata caaccttggc cgtccctgaa ctcactccat acctcggaac gcaggctggc  22800
ctcaaactca cagagatctg ccgcctctac ctcccaagtg ctggggttaa cggtgtgcac  22860
caccacacta ccagcaaggg ctatattttt tatgctcttg ctgtggactg ttctccttgt  22920
tacagagact ggggccagcc tgtaccaaga catagggttt tgaggagaca agggaacctc  22980
cccaccccca gagtctgctt ctgcagagcc taactggcac atgagagttt accaatataa  23040
tgtgtattac aacaggaata tagtagggtg ccctcaaaac ccgtacacta gtggttaaga  23100
atatgggata gaaattctga attcagcatt ctggctgttc attatcctgg gtccacagca  23160
actggagtct ggtgtggtat gaacaggcaa agtagatttc tgacatttaa gagaggagtt  23220
cttatctgcc gccagcctat ggagacctgt gttgttgaga tgacggtata caggacgtat  23280
tgtgaattgc aggggagggc aaaaaacagg gagagagatg agcccaaggt gttaaggggt  23340
ccattgtacc atccttggat ttagcttatg tgcttgagac catcaacagg gggagcagac  23400
attgtagggt tgccctctga gatttcaccc ccccagttca ctttcccagg tagtgggagc  23460
ctgcccccat gttggtcgcc aggagtagga tcaaacacaa tacccgtaag cctggtagcc  23520
agtccccaga cccagggctc cctgccaggc tccacccact ggcttggagc tggccacaca  23580
ggcctcccag cttccgtaac ttcaatgtca tcacctaggc aactggacgc tgccgccact  23640
gccctgccac tgcaagccac cacggggcct ccagcacctc tacccaagtc tatggaccca  23700
cccagggccc aggctcagcc aaggtaggca ggggctctgc ttgactctca gctctcaagt  23760
cagggttcgc ttgctgtccc ccttccccac agggcaacag cctcaaggtt ccatcaggat  23820
aaggaaaccc ctccccatca actcacctgg tagcccagaa gtaaggctcc atgtaagcag  23880
gcctgccaca cgggcaggct ggtggccgag acagtctgaa gagacaccat ctgtggctct  23940
ggtggcacaa ggcaacatgg tatggcactt tggaaagtca catgtactga gtagtctcca  24000
gggtctctct gtgcccctgt actgtgacag gtcaggatgg agacaaggga ttctgagatc  24060
tcccaaaagt ggttctggta tctccacagc cttcattcct ttaagccacc tgaatttctc  24120
tttattccat gtccaagaga caccaaacag ctacctggat cttccaaggc catggttagt  24180
gctataagat gttgccccta cccagtgcct cttcctaact ctccctccgc tacttagtct  24240
cagagtctct ttcatcctta gcctgtgctg ggcttcccgc ccctcacatg gctggtgctc  24300
aacatgtcta catgcaggcc taagtgttga gagatggggc ctcggtaggc cctgttcctg  24360
atgttgtcca cttgtgctgc tgtcctgtga acagggctgg atgtcctagg actggcaaac  24420
tatacagcgt catatcagga tgagatagag aaaatcctgt atagaaatta ttgcaatgag  24480
gccagagtga gtgagtgagt gtgtgtgtgt gtgtgtgtgt gtgtgtgcgc atacacgtga  24540
acacctcggt tgtgtggtgc attgtgagcc agtgtgcaca cgtgggtgga gaagcagagt  24600
atcaggagtg tatgggccat acactctttg tggttttacc accgtgttct cagcagcacc  24660
```

tagcggtggc cctggagccc aaatggctgg agtattgcct gaaagagaga tatctgcccc 24720
cagttttaaa gtcaagatct cattttgtag cccaaactag aattcactgt gaaccccagg 24780
ctggtcttgg atcctgatcc tcctgcctca gtctccccat ggttgaaatt acagacatgt 24840
tttaccatgg ctagttgtct tgggttttct ctaatttgat tggttacttc cactgctggc 24900
cctgttagca tacactgtat gcacaagacc atcatagcct gagacccata gcctgagacc 24960
ctcatagcct gaaacaccca tagcctgaga tcctcatagc ctgagacccc catagcctga 25020
gacacccata acctgagata cccatagcct gagaccctat gcctcgaggg tcttgtgcct 25080
acagtggatg ctgacaagac cagcaagaag acacagggcc ctgctatgtg tcacacaaag 25140
ccagtgctat ttccttgggt cccaaaatct gaactcctaa gggcccaaag cccaaatgag 25200
gatatatttg ctttttctta ttgttttaat tttatatgta tttattcatt gtgtctatat 25260
gtatgaaggc atgtgagcat atcctgagac tgaactcacg tctttgagct tggcagctgt 25320
acatttagtt gctgagccat ctcacctagc ccctggggtg tgaatggtga gttttgacct 25380
ctaactgctc actcctgggt ctgcccaact ttccctgacc tgcaaggcct tgagatcatc 25440
atactaaccg gttaattctg cctccaatgt ctattcactg agcaccaaac ttgtgctgtg 25500
cacttgctga gctacatggc taagcctgtc catcctcggc attacatctg aacacacata 25560
gggttttacc cctgcagcag atgccatgat acttgggggg ctaggggctg tccagaaacc 25620
ccgaggggca aggctctgta gctgttccca ttctgagatg actagtaaga gtctatcagg 25680
cagcacagag cctttcctca tggccccagg gctgagcaca agggattctg atgtgtttga 25740
catcgaattc taccaggtta aaggccacct ggaaccttct ccaaggtagc cccttggagg 25800
ggtaagtggg actggtagtg cctgcgagaa gccactttcc aaattcaaaa ccaaatggaa 25860
gctgggccat gaggccccac aggtggctaa attacagaca tagaactgtt gggcccttgg 25920
taaccttgtc cagcaatctc ctgaaagcct tgtgtagacc attcatgcaa ggaaggtgtg 25980
atagcctact tgagggacaa gaggctacag actccacaca caggaagaga tggagggccc 26040
tgaattgtgg cttgttgagg gttctgatgt tggtcagtcc agaggtctga gggtcaggat 26100
ggacactcta gactccgttt ctgtctgtgt cctcacttgt tctacctgtc cctaccacgg 26160
cactccggtc aagtcagctt gccaggcagg gatgcctaaa agctgctcat gaggcaaaaa 26220
gagtttcaca gaaactcact cctggagtct ggcgtgctct ctaaattttc cattcccgcg 26280
ttagtctagt ggatggatcc acatgctctc tttattataa gtgcctttta agattgaatt 26340
ctgacatagc taaagccttt cgccagtgtt ccaacagtcc tagaacgtct ttgagctaga 26400
cagtgacatt cagaatagcc tctggtatta cactatcaat aaaagccaag tcgttcccat 26460
atacaggaat ttacaatggt ttaggaagta gatcgggctg tggttttaga gtattgcatt 26520
atttatgaga tggttaagta gaacagaact ccctagttag aaccatgact tgggtgtgaa 26580
agcccttgcc ctaggagagt aaagacctca cacctggctt ctaagactat agctgagtca 26640
cacccataca cacgtattta caatggctta aggggaaggt agactattca atagactaaa 26700
ataggagcta tggcaagggc acgaagccct tgaccctggc ttttaagatt aagcaaatct 26760
tagatagagc cctttttgat cccagttgtt aacaatgaat tttatcccag gtggttcctg 26820
ttagaccttc tgtgtttaca ttcctctgtt ttatgtaaga atccagtaac ctctttgtac 26880
cttgctagtg tgtcacccaa cttccttatt gtcttttgca taaaaagtct gatgctcaat 26940
ttgacattac attcagattc cacacgacct ctcctgtgtg tgtctgtctg tcaattcatc 27000

-continued

```
ctacgctttg tccacccgcg actagagacc cgttccacac aaacaaaggg gcccagaggg  27060
tctatggcag ttggcgcctt cgaacaggga caccagagcg ggttagtctt tatttctttt  27120
tctttcgtgt cctggatcgg gcttgtctct gtgacttgca gtctctgcac cccacagctc  27180
tgtcagggag ttgggctgag tgtggaagag ctagggctgc gacaactcct gtgaagagga  27240
tgcttgccct gctgagacct gttctggcta cctgtacaca cagtctagac agacacccac  27300
cctgactaca gtctcctgtc tctcctgact tcagcatgag ctccactctg ccctcgatgt  27360
cgatggacct ggtcctcttt cctctccatc cttgctggcc caaaccagtc ttgccactca  27420
ctccccccac cctgcctggt ctcccttgga agctctcgcc acattgccag gaggggctg  27480
ctcccttgaa ttgcccctct atcaggcctg gtgtacctct gacccccgcc ctccaaattc  27540
accggtcccc ttattttcag ccacgataac ttggaggcat agggtaggag tccagactcc  27600
ctgggcttcc tggtccttct ccctagtacc cagccttgga catcagcaca ggatgatcat  27660
ccattctgcc tcctagtaac caggttaccc aggatcccct cttctataca ataggaatca  27720
atttggtttt tgagacaccc agtgctaggg acagtgctca gcaggcttga gaacactttc  27780
aaagagtggt gagaccacag ttgccgtgat ggggcagaga ccagatcaac gtatgtatga  27840
cacacgtatg tctgtctctg tccacagacg tagtttctca ccaggccttc ccctgacaag  27900
aggaccggac ttgttctctt ccactctgag ccctatacta aaggggctgt gactttgctg  27960
tggtttgtcc cctgctctat gcaggattgt cacctgcccg atgcttcacg ctcatcctat  28020
tacatcattc cacaggggtg ggtgtgacaa tccgcagtta tcacagagga cactctgtga  28080
gtgtcctctt tacagaggag gacactgaca ctcatgtggg catgtcacct gccctggttc  28140
gcacagctgg agaatggcag agggccatgt ggccagcaca ggaagagccc cagcttaagt  28200
gcctagcagg gctgaatttc aggttaggga atggtggagc tagaggccat atgtcccaca  28260
tggccccacc atggggtgaa gaaatggaag cagaaggcag gcctgagcag gtcagcagag  28320
agtagggtcg tctttggttg tctgaacatg ggcagggctt tggaaatgag ggtgtgggct  28380
tccccaggaa ggtaagagtg tgtactcgaa gtactatcat ctccagggag gggagagtag  28440
agtgcagggg tcaatagcta ggcactgtgt gccctgagtg agcaaataag atgcaagaca  28500
cacttactct ctgtatatcg aggggttcct gctgtcttgg gtagatgcat ggaggtcagc  28560
atgctacaat gttcacttcc tttggtcttg tctgagtttc cacgtggtgc caggtgactt  28620
agcatggatg ggaagtttgg tcaactactg tctctttcaa gaagcacagg gaatgttggg  28680
tggcctgagg gatgcaggct agtcttcctc cagccctgtt cccattccct ggcggatggc  28740
ctgagcccag gcgagagaag gttaatgctt cacatagcac accctgcccc acatggggca  28800
gctaaatttg tcttccttca ccagtacttg gctcccccag cttggggaga aggccaccgc  28860
tgccatctgg acatctaggg ccacacctgg ctagggaaca gaatgtcctg ctgaaggatg  28920
aggttgtctt gtgagagaag gggagggatc cagccagttt ccagatgggg caggaccaag  28980
atggttgcca cactggccct gaagaaggag gtacttctgc ctgcatcggg tgggacctca  29040
gcctctgtgt agcctccttt tctggaggta gcttgaggga aacaggcttc cggcaccaag  29100
gccccgatgt ggccaggttc ttgatactct gagttctgtg tctttgccac tgcccagaga  29160
taccgtcatt tcaggagaga cactccctgg ccatgttcct gagcctggca cgccctctgc  29220
ccacacaagg atctcatggt gctagagcct tcatgtccgc tggagggaaa ttcacacagt  29280
ggctgacatg ggtccagagg gcccctcctg tcatcaccac taatatacta gttacttctg  29340
atttcaattc ccctgtccac tggaacaaat tattagaagg gatgacagtg gagacaaacc  29400
```

```
acagtattga tcacgtcatg tagacatacc ataacagaga tttcccaggc cgggtaagtt  29460
tctctgggga tttccttgct gacccgaaaa aggcccttgc catagccagg ggacccagtg  29520
tcatcatgct gaagatcctg cctctcctgt gtctgggcta tatgtggaca gacttgcttt  29580
agtttccact agggaaggtg ggtattcagg ctcctagaag gtggggggta catccccatg  29640
gatggggtac cccttccaga gcaggttcgg gataattatg ggcatctggt atatcacagg  29700
tggcagtgag gctggggctg agcaggggtg agaggagatg gggaataaca aggaaggagg  29760
tccccatcct gtgtgattga agtgttctat gtggccaagt gacatctgtg tctcctcctc  29820
cagtcaggtg gcagggatgg ggaaggaagg ctcagactca gagctggtca agacagaggt  29880
tttcttgagg agccagccac ctctggcttt taagggagag gggggcttgg agagccaaac  29940
atttgaagtc acatgtatcc aaagccgtgg tgacagggca tgatggggga atgcttggga  30000
gaaggactcg gctgagttgg gagtatgtgg gggccaggca ggaggttcga aggttggtag  30060
ctcttgctgg gaagttgaga ctcgcggcca cgtgcagggt gaggtaatgg gagagtcgga  30120
gacttcctta ggggccagag gatagaggac atccccggca aacctgctct ggtgcaagcc  30180
ctagctgaat tacttgggca agccccttgg gtctcaaaca cagtttactc atctctgaac  30240
tagttggggg agcccatcta ggctgctgcg tgggcccaga agtcctgcca ggagtctggt  30300
tagcatccct gggctctctc tctccgtgga ggcccacggg gccttccacc acccagtttt  30360
gaggatggaa ttgttcccag cagatgtaaa tatccatggg ctcaagtcca gtcagagctg  30420
ccggagctcc gtggaggagc cgcgcccgcc gttggctcag tgaggagctg tgtcctccag  30480
tgaggaggcc tgtcattggc tcggtgttgg ctcagtggag gagccgtgcc gttggctcag  30540
tgagcatgtg ctatccgtgt gtgtggcttt ccgtttacag ccttattctc ctccgcatat  30600
cctggcacca caggtctggc tgctgtaccc ctgactctca tgcttgttgg gactccttgg  30660
gggggggggg cgggtagcag gtgctgaggt ctgagtttgg cacagaccat ctttgtcagc  30720
ttgctgtggt cctgtttcat gatgcaggca ctgccaggcc tggaggagat ccagctcagc  30780
aaaggaggag gctcatctga ggctttgacg gagctggagg caaggctagg gcagggccag  30840
agacagccca gatccctgcc atgcccacag cctgtgacct ggctgctgac agagcttctg  30900
acacggcggg ccaggcgggg ccagccctcc ttggttggtg cttctcccta aagtctccct  30960
ctgccgattc tgggccttct atgcctctcc tcacaccacg ggatgcgtgt tctctctagg  31020
aaaactcaag tcttcagtaa aaactacaat ctcagagcca gtgagatggc tcagtgggtg  31080
aaggtgcttg ctaccagttc tgaaaactcg agtttgatcc ctgggactta cagagtagga  31140
ggagaaaact gactcccgga agctgtcctc tgacctctga gttgagcatc tgcactcaca  31200
ggcatgcaca cacgcacaac gtgattattt tctatatctg tgcttcccaa cactgatttt  31260
tttttgtact ttccagagga caagtagttt ctcaaaactg gcctctttgc catcatgact  31320
tgatgtttta aatcactttc cgtgcttatg taatctgttc ctgcggtgtc tggggatcgc  31380
tcctctggtg gacacatctc ttagctagag gagtgtgtgg gacctataga aagggctcag  31440
taaagagctt gccatgcatc tatcaatcta tcatctatct acctatctat ctacatctat  31500
atatctatct atcatctatg tttgtatgta tctatcatct atctatctat aatctatcaa  31560
tctatcgtct atcagtctat catctatgta tctatcatcc atgtatctat ctatgtatct  31620
atcatctatg tatatatgta tgtacctatc atctatctac catctagcaa taatctatca  31680
atctatcatc tatctatcta ccatctatca gtctatctat ccattcattt atcttgcctc  31740
```

```
tgcccctgcc tctgactgtc atatgtctgt ctctctataa tctatctatc tatctatcta  31800
tctatctatc tatctatcta tctatctatc tatctatcca tccatccatc caactatcct  31860
atccctgccc ctgactctgg ctctgactct tcaattatct ctctgtctct ctgtgcccct  31920
ccctcccttc ctccctccct ctttcccttt ctgtctctct gaagagagag actataagtt  31980
tataatatag taaggttggg ttaccagctg caggaatttt gtagaaaatg gggggagggt  32040
gacagggctg ggtgatagtg gtggcttccg tgaggctgtg gtgctccatg agttcagagc  32100
tagatgctag taaggaccat ttaaggacgt gggcaaggag gcatgtccca gctgaaggac  32160
tagaagtaca gagccaaaca ctagcaggtg gcccatgtgc ctcccattaa gactgttagg  32220
actctagcaa ccagtgaggg gcaagatagg agggtgagca ggggcctgtg tccctggcaa  32280
gcaggtcaga atttgatctt cagcatgaga ggtttggttg gatgctcctt ccttgtgtgg  32340
gtgcaggagg acctggtagg caggaggtgt ggaaagcaga ggacttggca aggggtcttg  32400
gggcagagct gcaaactctg ccaagctcct ggaagtctgc tgcctgcagg tagccccttt  32460
cccacctccc gctctatttc caggcactgg gcacctgcca ttttttctt ccctctgctt  32520
gagctggcca tgtggacaca aggggtgaag agggacccaa atcctccctt gctttctcag  32580
taggctgtcc accttcagat atgccgtttc tggaattggg aaggcaagcc agcatgggtg  32640
tcaacaggtg gggtaaggtg tggcaggtag agttaccagc agagtactcc tggtacaatc  32700
tgtactgtga tacccagatc ccatccaatc caaggctctt gctgacaact tccaaggcta  32760
catctatgat gggaatcttc caggaacata cacttggagt cctcagccta acagggggtc  32820
tcaaagtgct cattcctatc ctgagaacat cagtgggtgt ggcaaaggaa tttgggagac  32880
catctcagac agtgtggtca cagcaggact gacattcatt ccaggtgctg cctgccacaa  32940
atgtctttcc cttttttttt ttttaattaa aaaaaaatgt gggccagtga aatggctcag  33000
tgggtaaggg tgattgctgc caagcctgat gacctgagtt caatccctga accccatgta  33060
ctggaaagaa agaatccact cctcacaatc aatcaatcaa tcaatcaatc aatcgaccaa  33120
tgtaattaag taaaaattta aggaatgccc tgaaattctc ctaacatata actagcattt  33180
tattctaaaa gtattattgt tgttgttttt gactgacctt gatctgatga gcttgcctca  33240
gccttgtcac agcagggact gcacgtgtgc accactgctg tcttccaaac aacattttga  33300
agcttgaagc tcagcgactt ccagcgtctt aaatccccag gagaaaccct ggccccatga  33360
gcccttgctc gctgccgtag cacctcaggc tggcaccccc aacctgcctt tgcctccctg  33420
ttcggatttc ctgttcagta catgttgctc ggacactagg tggttcagca cggtcttcac  33480
agtccgtcta cactgtgctg ttttgaatca gcagttcgtt cctggtcaca gtcaaatgtc  33540
acctaacatg tccgggtcat attgtatctg gcagttcctc ttctgatgtg ttcccagtct  33600
ctcaccctgt ctggctaaag tgaataatgt cactgcgaag gggcctggag tccattcact  33660
gtgtgacatg agccatgtcc tttccctttc tgagcttggc gtagtccttg taaaagggag  33720
aagaggacca agtggtccct ggggtaggac ttctaagcat gtcctcttgg gtctcagggt  33780
gtccaccagc ctggcccagc tgaccagccc actctgactg cgaagagata cctccctgac  33840
caatggctcc tcaccagaaa gtaccattcc cccggagctg gtgaaggcag ctctgtccac  33900
cttccatgct ggttggccaa tggcttgtca aaaccttcat gactgtgata aatgggaggt  33960
gggaaaaatt aatccttatt actggagaag agcataaatt atgttaattc ctgtgcttat  34020
tatagttgtg tgaccttggg caaggcatgt aaggcctctg agcctgtctt ctgagtaggg  34080
caggactgcg atatgtacag ggtacttgtc ctgtgtcatc ctcccttgct gactgagccc  34140
```

ccaccccact ctctacctgt gctcagctgg tccccttta ctggccctct cagcttgtgc 34200
cacttctctg aggacccatg gcctggcgcg tgccatctct agatgcgtgc cacaaaccac 34260
tatgagcagc ctcctgcctg gggtcagaca aaagcgacag atctgccctg ccagccctgg 34320
gcaagtctgg acctgtctgc ttggcagtgc agagctgggc caagctggtt tgcgggctta 34380
gaaggctgcc ccagggaggc tgctccttaa tgggcagcgg gcaggtgggc tggggtttcc 34440
ctgccccacc ctcccacaat ttactgtgcc tgagcgccct tacgctgccc cgcctccagg 34500
gtgactgtga gtgggcggag cctccgcgtg ggaggctgtg ctgaggaaat cgtggggaaa 34560
gcggttgtgg gtactagctg ggctagagt gaccctgctc ccctttatct cctttgagga 34620
gaccatccac aggtgacaac tccagggcag tcctaggact ttagccttag accttggagg 34680
gtgaggacca tagagggtct tgagtcccac ggtaacctgc ataactgtgc attacaggca 34740
tggttccagc agggggcgcc ctacacacgc tcttactaag aggaacggat gaagtttgag 34800
ctgtctcgaa gacctggcga caagtcacag ccttccccct ccaacataca caaaccaaga 34860
cctggcttga cctaaccctg gccgtcattg taggtttagg acacggtgac ggcagtcatg 34920
gcccattctc tcaaaaaact gacccaagac cacaaagact aaattccctt ctccaacagc 34980
atctacccaa tgtgagggca catgcccttc ttacccgttt tctggcagca gaatccggga 35040
atggcgtctc taaaaccaag cttgcctcag tctcacctcc tggaccagag aatgagctgc 35100
ttgggagtgg tgatggtagg gaggaagaga aggggagcta gacagggaaa agggaggcaa 35160
gggggggggg agaaagcaac gtgagtggaa ggacttagca cagctctggg gtctccttgc 35220
accatcatag gcagccccgc cgtccacttg gctcgcctgg tactgaggaa ggcaggattc 35280
cccaattctc agtgtcctcc ctcttcttcc agaatgagcg gcagcgttgg ggagatggcc 35340
cagacctctt cttcctcctc ctccaccttc gagcacctgt ggagttctct gtgagtatgg 35400
agaactccgc ctcactgggt ttggttggct tagctggctt ggaataaata ggttgggaga 35460
ggggtctgct gaggtagcag ctgccttggg ccatgtcctg tgtgcatgtg acccacagtc 35520
atggtctgtc ctctggccag ttctctagag ggctgtgggc acagagatca tgtgtatgaa 35580
gcattttcta atagtcctga agggcaagcc gagggctggc agggattgtg ggagctggaa 35640
aactccggaa gtccaaggac atatggctta tctcctggga tggacacaca cacatggggt 35700
agcctgatat cctgaaccag gggagcacag cggattctgg agcagatgct aacatccagt 35760
gtccttcccc tccaccccca cagagagcca gacagcacct actttgacct cccccagccc 35820
agccaaggga ctagcgaggc atcaggcagc gaggagtcca acatggatgt cttccacctg 35880
caaggcatgg tgagcggggc tgcgctaaag actggatgtt ggtgataaat gcgggttggc 35940
ttttctccgg tggaacgagg aagcagggct ttgggtagcc caccttgggt cggaagaaaa 36000
atatgcaatg agctcatggt actgtcgatt cctaggtaag aatggattca agcatgattg 36060
gacccagcgg taggaagagc ttcgggcatg gctggaccca ggtggttccc tgggaccact 36120
tcctctttca cttgcatctc tctttctctg gtttttcctg gggtaccttt gttctttgga 36180
agcctcggcc ctcagagatt gtccaacatt ttgaggcccc gtggagaggc caccccctctt 36240
tttcctttgc ccagaaacac tgcttcttca tgttggtctg agcatacttg tttgctatgt 36300
gcctctgagc tgtccctatc tttctgattg gcccatgttt ctatagctat ctctggactg 36360
gtcaggatga agggtactaa ggcaggctcc ttatattagg agaggaagat gtggccagtg 36420
gagacagtgg ttttattcct catcttgtgc gctctttcct gggaccaaga ggggtaccaa 36480
gcagccagcc tttggaattt gcctcctatt gggagctcct cttggcaaga agacacagta 36540
gctgtgggat tctgttcctg cctcactctc tggctaccac tgccgtgccc tggtggtgcc 36600
aggaactgga ggaaggtgac tgaagcatgc aaagggcaag tgaaggcctc tgttcccgag 36660
gaagtccctc gaggccttct gtcctcagca tcctccccta ctggaccacc aaagtgctag 36720
gatcccaaag gcgagagggt tgggaaagcg tcaggcgggg acttgttgga ggaaccctgc 36780
aagcacatta aggaagagca aagcccaagc cgagttggca catgtcggct gcagaggcac 36840
cagacagctg agcatgtctc cagtgtagcc ttcctcccac tagcacctga tgagccatat 36900
gctagaggcc cagggactct agaagccaag caaagtgtga ggctaacccc tacttggagg 36960
gagaagcctg gccactttag gcattagtga acaagggttg aagagacagg aggcactatg 37020
cccttactct cccctctctc tgtagaggtg gaaggttggt cagagcccac tgatctccca 37080
tggaactggg tgagactctc tatagtggca gccccagggg gtaagggtat catcctggtg 37140
atgcccactt ctctgagctc tgcctgtcca gccctgatct ctgccagctc aggagcctgt 37200
ttcagaatag cagttcacct gtaagtgtcc attttacagg caagggaact gaggcagatg 37260
ctgtggaagg agagcctggg gcttggggaa gagaatggtc ctgcatcatg gtgaggatag 37320
tcccccatcc tgcctgttac tccgtagaga catgattctg acacccatca tctaggatat 37380
atgtgttctc cagtatagag ggataggagg tggctactag gctccaggga gggagggcct 37440
tacacaaaga ctctaaagat gcctgcttta ggagttctgg aagctgcctc ccacagtcta 37500
agctacccag cttatgcctg agagggcaga gtgctcagag accccactgt gactgaagga 37560
agaagcaggg aacagccctg gggccccgga ggctagggat gtggtaccca ccccggcccc 37620
aaagatgccc aacgtaaacg tgttggcggg tgctcctggg tgctcacctg ctggggcatg 37680
ctgctcccag caggggtaac acgggcgggg ctcaacacct ccacaaacaa ggggccgctt 37740
tctcaggtag caacacgcct tgcagtaaag ccatggacga aattcctggg cgcacagctc 37800
agctcctaga agtgggaatt ccctggaaac aggacttcct ggcctccctt ctgcagggct 37860
cagctgaccc tcatgcacag ttctttcaag agacagctac tggtccaaca gcttcctgta 37920
tgctcagaac ttccagcagt cctgacagca aaaatcaaga ctcagagatg agtgacagat 37980
agggccatgt ggcagcaatg ctccagagct catctggact gcagggaact gggggtgggg 38040
tgaggtcttg caggtgctgc aggaagttgg gggtgggtgg ggggatgcag agagcactag 38100
acattgcatg ccatgaaatg aggtagatga agtttgatct cataaattac atggtcgatt 38160
acagcttatt aggatggcag aggaaagggg catccaggca ccacagggag catctttgag 38220
tccagggatg gaggcagcta tggaaatgac agtttggggt acagatgtgt gagagtggtt 38280
tggggaccta cagaatccat catcgtttca gggtgcagcc cggaggaagc aatggtctgg 38340
gtatagacta cagagtacag actggtctgt gaatgctgca gacagggtag cctgcccagg 38400
cccacattca gctccacagg tgctctgcta tgtccagtgt ctgaagtcca ggagctgagc 38460
ctgctgactc accctggggg ggggggctcc aaagtctgat gggcatcaga gggaggggtt 38520
gtggagcact ctcagaggga ggagttggtg agcactctca tagggaggag ggtgtgcatg 38580
ccatggattc acgtgttgtt tgcagcggct tctaaagtgc tgggaggttt taagagagtg 38640
cctgagtgtg tgtggtttag agttccaggg gctatgggag gcacagagag gaaagggccc 38700
taagagggct gggataccag ggccagctca gcgctgtgat gaggtggaag ctcccaaatg 38760
ctatccccat ccctgagaac tctagcccca tccctagctg ggtccaggac aagaaacact 38820
acccaggcat gttctcaggt caataggcag ttctggcatt tgaggttcta aggacttcca 38880
gcaactccac ctcctgtgtt ctcaggtacc ccctccaccc ccacagagcc ctactcagtg 38940
atgactggtg tccagttgtt cctgtgtgct ggacaatccc acccaaatac caggatagtc 39000
cagcaaaggt gtcatggctt aagccagcat ggcccttgag tagatgggat atgtattctc 39060
ttcaatggtt ccttctgtgt ctaagggacc tcaaacggga gattgctttc tgtcacatgg 39120
aatgtcctga gcaggtctac cagctgtggt gaaccctcag aactccatga tgctcttctc 39180
ccccaactta atggctgtca gaaaccggtg cagtcagtga gttcaagttc tcacatgctc 39240
ccgagtctcc acatccttgc ttgtgaagtt gaggtgatgg aaagggctag aatggagagg 39300
accctgggag atcggtgcag cctcctgggt accagcttgt ctgcctggcc ttgtgcagag 39360
gggtgggcca ggcctcgaca tctaaccatt cccgagtctc attggagtag agtgtgttgt 39420
aagattaaag caaatgggat gggcaggagc ggatgaaccc ctagtgggtc tgaggagaac 39480
cctaggcatg gtgagggacg cccttgtggc cttagcttcc tgtggccatg tagatggcat 39540
agcagagcct agacagttgt gataggtaaa gagggaactg aaggtctctg ggctcgatg 39600
tcctgggttt gtagcccatc ctggtcttcc tagttgggag gttctcagga tcctttagtc 39660
tcctggatct gagtggcccc atctctaaga tggggaagtg gacagatcag aagcccataa 39720
gtgctgtttc tcccacaggg agtgacagtt agctcaaggg cgaaggccta tgttttccac 39780
actgttggag actctgcaca gtttgccatg caggggcacc ggactctaga gctggctttg 39840
ccccttggcc attttggctt ctgcatatgg agctccttgc tcctgcaaat ggccttcagt 39900
tctagctgtc cttttagatt ccgggtgctt cacagaaact ccactttaaa aatggcctgg 39960
agactaggtg cggtggcacg tgcttaaatc acagcccctg ggtggccagt ggaggtggat 40020
ctaaagtttg aagccagcct gacctacaca gagaaaccct atctcaaaag tgaaatgatc 40080
cccctgccca gctagaagag aactcagaga tgcctctccc gggtgctgtg tagggtgagc 40140
tgaggggccc atgccaaagg ctagggctag tcacagggtg ctcagcaagg ttgagaatca 40200
atgggtgttg tcacatgtcg ggggacaggt cccagatcaa taaggcccta ccacagggtc 40260
ttgggagatt gagtggaggg caaagttcac attgtgagca ccgtgtgcca agaggcagtg 40320
gagggcttga ccctgagggc agaaatccca gttctcaccc tccatgccca gtgtttgagc 40380
agacctttct ctctgcttcc ctggttctcc atggaccaca agaaggtgga caccaagagc 40440
cagaggccgg tccagctctt caaatacaga aaaaggacag agtgctgatg gtcagcagag 40500
gaaaggggag agaggcaggt gccctgggcg cggctgcagg atcactgccc tttcccgcct 40560
cttcatgtcc tcctccaggc ctgcacctcc cctcagatgc ccctttcccg ctgtttctgg 40620
cgcctttctc tagcaacagc tgttaggaac agatgggccg cagagggttg gggaggtgct 40680
gcagctggct gggcagaagg tgctctgctg atctccctgt ggcctgcagg ggactgagcc 40740
agggagtaga tgccctgaga ccccaaggga cacccaagga aaccttgctg gctttgagaa 40800
agggatcgtc tctctcctgc ccaagagaag catgtgtatg ggccctgtgt atgaatcctt 40860
ggggcaggta ggtcaggaag gatagacctt ggcagggaga atttatatca agggaagggc 40920
agggcaaacg gagatggaga ctgagtttta tgtgatcctc ttggggaccc ccagctcccc 40980
caccacttcc agtggtttct gaccactctt ccttggcagg ctttggtagc aagagggtcg 41040
aaggtgtata gtactgaact tagctgagcc ccctccccag ttccagagtc tcactgagag 41100
cccattcctc tccccaactc cagggtccag aggaagaggg acaaagccac cagcagggac 41160
agtatgtggt gtgtttgctc ctgaatcaac acaccatact tgggcactgt agtcttgagc 41220

```
atgtgttgtg gagagaacgc caggggagcc tgcagaactt cacttccacc tcagctgtga  41280
gagctacagg agcagtcagc aaggcagagc ctccagtgtg ttacccccag agaagcaggt  41340
gctgaggacc ctggcactac ctaggggcac cggcagtgga ggcagacagg caaaccacct  41400
aggaggaagc aggagccagg ctggggctgt ggcagagagg agagctcagt ggtgggcgtc  41460
cctttccctg gccagaccgt tcctcagggc tcacagactc tcaggccagg tgcttcctct  41520
gggagtcagg tgtgagttct cacggacagt cccattctcc tttccggcct taatccttcc  41580
ctttattttc tccttggggt gtttgtgaag ccaacacgac aattgattga tgaggaccca  41640
gagtggctga gggacacaat tccttaaacc ccaatctaga aacttgaagg ccatctcttc  41700
agggctctct ggagcagcct ggccacacct acggggtggg agtctgtaaa ctcagccctt  41760
agtccccatg gagggaggct gcagttgacc cctggtctat ctattataaa tagatccctg  41820
agcagtgttt ctccaaagat tgctccccaa aattagacta gaaactgact ttattgttca  41880
tagctgactt atgagcagtg cacacctgtg cagccccagc catgaacatg cctctcagac  41940
cagcgtaggg atcagtatga agtagtccat ctttactgct tctgtgaatt ccagagcttt  42000
gaacaggggc tacagccact gccacagccc tctgaccaag cccagatact gcaagctctc  42060
tggagggaga aggaagctgg tttggaactt ggcgagaaag ggttaaacag aggactctgt  42120
cttcacacca tctctgcgtc ttcttgaaca tccttagact ctaaatgtgt gtgtgtgtgt  42180
gtgtgtgtgt gtgtgtgtgt gtgtgtgtgg cggagggggc tcaagctgtc cttctaggag  42240
gcctagagat tcagggccga tgaccctttt cacaggacac gcatctgttg tggaccacta  42300
tggtgacttc atgcgtgaac cagacctgaa actcaaatgc ccccagacaa ggggcagtgg  42360
tatccactgt atggtcccca ctaggcagat gctgatatag agcccctggc tctacaaact  42420
ctaccatgcc tgtggtgcct tctcgggtgg tccttcaaaa attctctttg gtggagtggc  42480
cctgtctctg cttcctggac ttagctagag ccaggacaaa aatgctgtct gtaaaactct  42540
gttatgggtt ctttggctcc aaccgccact ttgggccttt gacggtagtt ggccgtgttc  42600
tcgactctcc cctagcccaa gcatactggt gtgtctttcc tctactcagt ccttggggtg  42660
gtccctgtag gtccacgatt ccctggaagg aggcaggttc tctcccctgg gtcgccaagg  42720
ctggcggcac catctcttcc ttcagggtga cccaacccag actgcaaagg tctccaggac  42780
cagggctgac tgctcatgct ttagagtgta ggctgtttgt aggtgactgc cacagccctc  42840
cggagccttc cctgagtggc agcttagaag ggtccgagtg ggagtgtatg atctccaagc  42900
cagccactga ccctgcatcc ccacctgctc cccctgctca gcctgcttgg tgcggtccaa  42960
cacatctccg ggcaagctga ggcctgccct gagttgatga atagtcataa ggaataaagg  43020
ggcgggcccc ggtttgttgt tggatgcagc cagttgacag aaatgaggga gatgggcagg  43080
gtgagaatgc caactctcag tccgcacgcc tctgagcatc ctccgctcct gccttcctag  43140
ccacagagcc tcaacccctc agtccacccc accgggcagc caccagtcta cccctacccc  43200
acctagccac ccagacccat gcctcgtccc gcggcacacc agctcctcag cgtgtgcaga  43260
cccccacgag cctaccatgc tttacgtcgg tgaccccatg agacacctcg ccacggtagg  43320
tgtaacgtgc ctggtatagg gtctgcttag aggcctgatg ccatccacct agggggcttg  43380
gcagagtctg ccatggttgg ggttcagaga gacgttctct tgactgcctg atggcagagg  43440
ggtaggctgg agagtggaca ggttctgctt ctgttcatcc ttggggcagc tctcgaggat  43500
cagcagctcc gggctgggca ggaagtggga tgtgggatgg gaggcttggc tggcgtctgg  43560
tcagggtggt agagctgctg cccaagcccc tgggttggat acttctgaga tgactgttga  43620
```

ggctggtggc tctggccatg ctcagggtcc ccaagatagt ctgccctagg agcgctgcaa 43680
agaggtcatc tttgtttggg ctttggcgtg aagctgcccc accctgccaa gagcatcctc 43740
acctgggagt ttgttcactt gacagcgcag atggggcgtt tctcatagcc atgggctctc 43800
ctccgtgtgg gtgtgaactc caaggcagag acaggcagcg ggctggaccc aaggctccct 43860
gttgctcctc tcaagcaggt acagccagcc tggcagagag cagaaggaca gaaggatgga 43920
aggagccaca gcctgtgctt ggcctgagcc caagggactt gggctcattt ccagacttgc 43980
caggtccctg gggtcaggca gacaccaggc tgctaattga gcagccttta ttgaccagtt 44040
aaaatggggg agatatcaca tgagatcacc tgagtaagtg acccactgca tgatcgtcat 44100
tgggggccag cccttcttga tgaagcagaa ttaacatcag aatacaaagg gcagcttaga 44160
agcagaatta acatcagaat acaaccagca gcaggacaac ccacaacacc tgggtacagc 44220
tgccccacaa ggctatttcc cttttaggag agcagagaga gtaaggaatt gtacaggaat 44280
cctgggatgg cagaggtgtg tgtgtgggtg taggggtgtg ctggtaaggg tgtgcatgtg 44340
gcgtgggggt gtgcatgtgg cgtgtatgca tcctcttatg atcagggaaa agactgagtg 44400
tgggttgaat cacggttttg cacaggtgcc cttcctgagg ccagtaggag gcagagtcac 44460
tatccaggac cacacagaga cctgccccca agacagccgc tgactctggt cctggtgccg 44520
ctgccctagg tctcagaacc agtggtggct accatgtcat gatatttctc attttgtgtg 44580
tgctgtggag cagtgtgctg tggtgtgtgt gtgtgtgtag tacaggtggt gtagtgtgtg 44640
tgcatgtggt atgtatgcat gtgatgtgta tatatgtgtg tgcatatggt gtgtgtgtgc 44700
gcgcgcgcat gtggtatgtg catggtgtgg tgtgtggtgt gtattcacat atgtgtgtgt 44760
ttgtacccac aaaccatgtg tggtgtgtgt gtgtttatgt gtatgcaaac gaaggctaga 44820
ggtgaacctt gggtatcact cctcaggtgc tgtccctgta ctctgagtct ctcacttgca 44880
cctggggtat gctgtgtgct gagtaggcta gactggtcta tctgtctgtc tctgcctccc 44940
aacactagaa ttacaagcac acactgccat gtctggtctg ttacatgggt cctttggatc 45000
aaatgcaggt ccttattttt tttgtggcat gcacactacc aacagagcca cctccctggg 45060
ccccgttgtt tcttcttaaa acgcaggctc tgtggctttc tctccccttc attgcttcat 45120
cacagcacca tgcgcttcct ctgcattctg accagcgtag cagtgtagct tgggatttgc 45180
tggggctcca aggctgggct gagccatcat tctacctgcg tgggtgactt agtttcctca 45240
tttctttgtg agaggatcgt gtaggagagc atagcctttt gcccagagaa tgttaaatcc 45300
aatgtggatg gagccttcgc ccgtgtgtca ctcccccacc atctgccttt gttgtcctta 45360
caacttgcag cagtcccttg ggagctcaca ggcaagacct gtccttggag accggactga 45420
ttttcaggat gccaccttat ccctggatgg gtttctcata agtgtatccc atcttggttt 45480
gggggctcag tatacaagtt caggctttat ctctggtgac cactagctat ggttttggga 45540
tgagacatgt gaggccatgg gctgagacag tttccttctc tgtaagcagg gtagtagcaa 45600
ctaactctca tgcctgctca ggccgcagat atgagctatg aggtaccatg gcctctggcc 45660
atgactgtgc cagcctttta taagtcagtg gaggtacaga gaagctggcc tagagaactg 45720
ggcacatgtt cttcctcctg tgagcctgcc tcccaccttc ccttctctct ctgaggacta 45780
gagactttga ccgagtgatg acctacagct gagtgcagcc ctgtatgtaa ggcgaggttg 45840
gctcggtcct cctgcacacg gtgagcccat ttacagagct ggaaagagct gaggccactg 45900
gagctgggcc tgatagatgg gatgagatga gcggggagag gctgcaactg ccactatctc 45960
ctgatgcccc aaactcttag cttcttcatc agcttccagt tctcctgcat gtacacgtct 46020
ctctctctct ctctctctct ctctctcaca cacacacaca cacacacaca cagagagaga 46080
gagagagaga gagagagagc agctcccagg atatagtaag gcaagtgtgc tctggttctt 46140
cagtgtcttc tgtgtgaagt ggggctcagc tttctttctg cagaaccagc atcatggttg 46200
caggactggt gaacctggtt atcctccaat cccttaaccc ccagaccaac acacacacac 46260
acacacacac acacacacac acacatgctc ttataggcac cacacataca tatgaacaca 46320
aacacaccat acatgcacac acaaacacac acatatgaac acacacatat gaacacaaac 46380
acaccacaca tgcacacaca aacacacaca tatgaacaca aacacaccac acatacacac 46440
acaaacacac acatatgaac acaaacacac cacacatgca cacaaacaca cacatatgaa 46500
cacaaacaca ccacacacgc acacacaaac acatagcaca gcacatatca atatacagtg 46560
gtgcatgaat acctcatact cttgtgtaag gcagcataga cgtgcatgca cagcccaggg 46620
ctggagttca ccctgtctgg agcaggcttc cctgtgctcc tgcagaaagc atggcttctg 46680
gaccggagga gcccgagggg gcagccccag gtgagagaag gtagccgagt aacaggaaag 46740
agctgtagga cagacgagtg gagctggtgc agtgctggta actgaccaca cgggggcagg 46800
gccgagactg ggagaaggga tttggtccag gtgggggcca ccagcaccta gggaagtcag 46860
agtagaggaa attctggaga ttctgcactg gacttgctga ctggctagat gtcggggaag 46920
gagtgtgtta gagtggcctc aaaggctttc gactgtgatg gggaattgct gcaggggctg 46980
agaagtgaga ttgggcattt ctgtgcagtg tttggggggg ggggggcttc agcagttgag 47040
cagatgaggt agagagggtg gccgggacag gacatctgtg gaggtggtca gatgtgagac 47100
caagaccagg ctagaggaca aggccacaat taccttagaa ggcctgtagt gatgattaga 47160
aacactgtag ggttcttctg tgtgggaggt agacaaagag cctgagcatg tgggtgggag 47220
tggccaggtg gacttgcagg tgtgggaggc aggtgggcag ggtggtgtga tggacagatg 47280
catgggtggg agtggccaag cagacatgca gttgtgggag gcaggtgggc agggtggtgt 47340
gatggacaga tgcatgggtg ggagtggcca agcagacatg caggtgtggg aggtaggtgg 47400
gcagggtggt gtgatggaca gatacatggg tgggagagga caggtggaca ttcaggtgtg 47460
ggaggcagga gggcagggtg gtgtaaagtg gacatgagtg ttatttaagt cggggaaggg 47520
ggctgtgtta agaggagtgg gagacaattt tgggaaagag agccacactg aggagcagcc 47580
tggaagccag aagagggctt catggtgacc cgggacaaag gaccccatta caaggttaga 47640
aaagggacca gaatcagctg cattgaggga gctggtgacc ccggggaggg tagaactaag 47700
taggatcagg tctgaggcca aggcataccc accagagtcg gatccaagta ggtcatcctg 47760
gacccatgtc ccttctcagt cccctcgctg tgttggaacg catctgcttt ccatgctccg 47820
tcccgctccc ctgaaagcca gctgatgggg tgtcagccca tggagccaat ctgagctcct 47880
aggaaacatc acctcagctg gtgggaagtc ttctccactg gcccaaaccc aaaccctgga 47940
actatcctcg atccccggca caacacctca tctatgccgt ctgtgtgtcc aagggcctca 48000
gagctggcca cccagtgctc agacgtgcac ggatccactg tcagatgtcc tccaccacca 48060
agcaagggga ctgtgcacgg ctagcctata accctctctg ctgaacccag aagttatgct 48120
ctctcacctc ttctgctgtg ttcatcaccc atgcacttgc tctggccagg gtcctttccc 48180
tgccacccca cacagaacct tgccgaatcc cacaagacct acagattaaa aaccatggca 48240
gctcttgcct ttcccagagc cccacccttc caggacaccg gcttctgcct ctttggtggt 48300
cagtattttc tcccttacgt cccggaggcc ctaagcttga atgctggtta gctggatggc 48360
ttgttactgt actacgaggg gagagctcag aagcctctac caagagatgt caggagccta 48420
actgagccag tcgatgccct ggatatgtgg gcagcctttg tcctcacctt tcacagccca 48480
tcccccagct tatattggga tgccttctcc atgggggggg ggtcccaaga caacgtcaca 48540
gcctcgctat gggtcgctgc aggtgacagg gcgacacaca tgggcccaca tcacgcttag 48600
tgaacatctc atgtgtcact atctaatttc tcagcttagc tgctcattct ttgtttctcc 48660
ctgacctaag atttaggaag agcccgggag gtccccactg actgtcccat gaatggggac 48720
agtcccagtg ggactgtcc catgaatggg acagatgggc agaaaggcag tagggggcgg 48780
ggggaatgca cgaacaccaa tgctggattt gagactacaa gaatgtgcca gggagaggtg 48840
ctggcagagc tgtgtcccct cttctgttct ctcagacaga caactcgcct ttgctgttgg 48900
ggtacactcg gtgatttaaa aattcctgtg aatcactgca gcttgtaggc agtgccaaag 48960
agatggggga gctgcctaga gaacccctgg aaggctctgc tctgtgatac cctggttcag 49020
gctatgttgg tggaggggtg gcctgggtgg gtcttgcaga cacatgcctg gcagcccagt 49080
agagcttctg gggcacgtt tcccgggttt gaggtgtgga aagttccaca tggccctggc 49140
atgggaccgg gcaaggccct gcctcggcgg gcaaaaggag ggtgcaatgc acatacctct 49200
agggaggcag ccgtcccccc atgcacaagt cctgtcttgt tgacatttcc attcgtttaa 49260
tcataggctc ggggagactg tgggaaacac catcaggatg gaggtctcca gctagcacag 49320
aggcgggaga gatggctgtc tccacagagc caggggggctg tcagtcacta accccaggca 49380
agcggaaccc aggctctgac ctgcctgcag gggaagaccc cggtttcaga cgctttcttc 49440
cctttagaag aatccacagt gttggctggt gttttggaag caggaggacc ctaactcccc 49500
atccctcagt gctgggctca gagcagaatg agtgacattt gtcaccaggg ggccctgggg 49560
tgagccattc ctgcagaaca ccaagattcc ctggaaacag atgtggtcac aaggtcatgt 49620
cactcatacc tgtgctggat gggtgaatgc ctcttgaccc ctacccagaa ttacttccta 49680
gtaagggagc ggtgaaggcc atggggcagc aaatcacgtg cccagaggct gggccttgaa 49740
tcgaggaagt gatgttggga taaaggaatg gaggctgcgc agtggaacct gagaagccac 49800
agcacactat gctctgtaag ctagctcctg tctccagttc ctaccccagt tgcttctgtg 49860
aggaagctag ggtgggccac aactaacctg aaatccatag gaagggggtg tgcagaggcc 49920
agggcaaatt ctagaaagaa gggaggaaag aaaatggagg aagggagaaa ggcaaagaag 49980
ggagaaaggg aggaagaaga gggaagggga gagagtgaga gaaggagagg gagggaagaa 50040
agagagggag gaagggaagg gagaggagag gtgagggagg gagagaggaa gggaaggaga 50100
gagggaagaa gaaaagggag aggggtagag ggagagaagg agggagggag agggaggagg 50160
gagggaaagg agaaagggaa gaagggagag aaggagagag ggaggaagga gagaagacag 50220
aaaggaagaa gaggaagtga tggagaaaat gcaggaaaag atggagaaag tgtgggggaa 50280
gggaggaagt agaagcctag gcaaaatcct ctcctactga ggtcactgga tttgggtagg 50340
gctgtgctcc atactctcca gttgtccggt ggtctatgag accatgttcc cagccgggca 50400
tggtggcgca cgcttgtaat cccagcactt gggaggcaga ggcaggtgga tttctgagtt 50460
cgaggtcaac ctggtctaca gagtgagttc caggacagcc agggctacac ctcgaaaccc 50520
tgtctcgaaa aacaaagcaa aaaaacaaca aacaaacaaa caagagccca tgttccctct 50580
gtacactttg ggaccacgg tgggaactct gaccttaagg ctgagttccc cctgctgtgt 50640
gctggggatc ctggtatcat tcctgagagc ctggctgagg attagaattg gtgggaccag 50700

-continued

```
gaagactgtc agagctgctg tgggctcagc atgaggccag cacacaggaa gttctccttc  50760
tgaaagggca tgctcaatac agggtatgga gatggtgggt gccccctgcc ggccaggcag  50820
atgagcctct ggctggtggc tgtgaatcag ggactggtgg gtcactgtgg cgagatctgg  50880
aggcctgtgt gtggcttctc agaagcacaa cagtgacaga gtcaagtgcc tgtgcctctc  50940
tgagagggca gcgccgggtc aggacccagc acacttgagg ccctgtgtgc taccgtgacc  51000
tgttctcatt tctttgtgtg tactgactcc gagtccctca tcagcatcac accgaatcac  51060
ctcgatgtaa actgaggcag aggagtcacg gaaagggttt ctgtgtgaag cagggttagg  51120
ggagaccgga gataacacag ataaactgga agggaagccc agagcgctgg ggcggcttca  51180
ggaggtagga tggctccgca ggctgatctc ctgccgagga gatgcaggtc agcctattct  51240
cctggaactc cgcatttaaa tgtgacaacc gacaggcagg cttttctgtc actgttttta  51300
tttgagaaat aaacttctcg ggggaattgg gtgtaatatg ccctttgttg ctaagcactg  51360
gatgcagcca gtccacctct gaggtccgtc ttggtgttct gtgctatagc aaaggctgcc  51420
gtgggtactg aagtcagaga ggagtcggtg tggaaggcac ctgctcccaa cctttaagag  51480
gtcgttcatt ttctgtctac atatataaga acagatcgat gagattgttt gtaggttaga  51540
aacagttaag atgtgagatg ggagtcttcg gggtaaaatc atagtatcca atgtgtgcat  51600
gtgagggcag gagcctgata gcaggacggt aagagcctcc ttgtctggtt aggacaagag  51660
agtggtggag aaaggagagg atagaggggg aggccctgcc ctcaatcagg catcaaagag  51720
cttgtctaac tatggttggg tatccacttc aatgccacgt gttggtacaa ccagtacacg  51780
tccaagagtg agaccccggc tgctgttccc catgtcccct gctttatgac gctgctcagc  51840
tgcctctgga gctcagcctt tggagacagc cttgctcctt gtgggcagac aggctctgtc  51900
ccttcctcac tgggccttgt gttagtgggc tggtgctgat gatggatcag ttgcaaagtg  51960
tcagagctcc tggattctgg cgtcctggtg gctgaagcag ggttgttcct tctgaaagaa  52020
cagccatagg ttttcttgct cccagacctc gcccccacaa ccatgcgaca agctatgtgt  52080
ggatttcatt ctcactatgc agaagataaa aatggaggcc cagggatgtg gaataatacc  52140
ccattcctct cctgctccta ctacctacct acctgccaag gtatagtgct caccctgggc  52200
tcatctgtca acctagctca gccaagagag agtgctagag gagtgaacca gcgtcatcta  52260
cgtctcccga tgctcaaggg agataagaaa ctcagctgcc ttgtagcagg agcttgggga  52320
cctaagggac ccgttgtgag tgttctatgc tgatgaccct ctgctagtag agcgaggtca  52380
ccagcctgct gtcaccccag gccctgaaga ggccaaggga gacaaggtgt gaatactgaa  52440
gtctgagcct aaggaaagag agtagaagca ccagtggctg tttccagcag aggtgccggg  52500
taagccccca gcagcactat ctgcaaggac caggaagaga ccccgggact aagggaataa  52560
gagatcctgg ccttctctgt agaggtgggg ctcactgaga cccccatctg tctgagccca  52620
aaataggtct taccctcaat tgccctgggg ttttctggat gatcccagac cctgtggtca  52680
cagtccagtg agcgacacag acctggcaat ggggccgtgt tctcaaaccc tcatccccat  52740
cggaactatt gtcccccaat tctgatgttg gcctttccca tgaaggctgg tccaccagtg  52800
gcctggacac tgtaggaagg gacacccttt ggctccatga cgccctcatt cctcagggcc  52860
tcttcaggtc acgcccagac actccacttg caagtatagg cacatgtgtg ccgccgcagg  52920
ccgggcatgc cctaattagc ccactatctt ggagttctca ttgaaagcaa aacaaaccaa  52980
aaaagtttgg gtttgcccag gttcttccct gaggccaagt gggtctcgtc tgggcttccg  53040
gggggcctct gggtctgggg gacccctggg cttctgtgta gacctgctta ggcctctctg  53100
```

```
acgaggcttc tcatttcaac agcatgacgg gaggcaaaag tggggggcca ggttgagcct  53160
cactgcctgg caatgaggaa atggtttcct tcccatgagc ctcaggagga gggaaccctg  53220
tgtagaagga acgtctctta cactctccag tcactggggt ctttaccatc tttgggagac  53280
acggtagaca ctaagaccag tgagggagtg gaagatgacc ttgggactgt aagaaacgag  53340
caggcacagg agatccagca ttcactagac aagggaacag actctactgg gcagcctagt  53400
gcccctatag aagtctgcag aggcctgcct ctctgagggc cccgggcttg ccacaccagc  53460
caggttttgc accccagtgc tgagggcctg ccttcccgaa gcgcctggtc cctcctgcat  53520
aagctcccac agatgctatc gctgttcctt ttggttcaat gactaagtcc ttggcaccca  53580
cctccaatca ttgaagaatg cagacaagtt aaaatatgaa cctcgctgcc gtgggcctgc  53640
accctgcttc tgagacaggg ctccctgccc atcaaggatg atggggatcg ggcacggagg  53700
ggctgctgct gccttctgca gatgtcatga cttcttccaa agccctttgc tgggaagaga  53760
gtgaacttgg ttgcaggaag gaggtggcgc tgcagcttca tcctggatct gaaacaatgt  53820
aaccaggttc tgggatccct ggaagcagga accaggaggt agagccatag tgcatctctg  53880
ctcattccta gacagccgca ccagagagag tgaccttcct gactatcaca tagatgtgtg  53940
aagctgtctt cagacttatc acattgttgt acattcactc attcattcac tcatttgtta  54000
actctttcat tcatccatcc atccattcat tcattcattc acttactcat tcattcactc  54060
attcattcct ctgccacttt gtcctgacag aaaacgcctt gagcaaccat tccaaatcgg  54120
gatcatgtgg tccagatcag caccactcag ggaacacagt gggtgggatc ctgtgtctat  54180
agagccatct gtctgtggga ttgcctgagt ctgttaaatc ctttgtatct tcaggatccc  54240
tgtgtctgtg gggacccgtc tctgtaggtt ctgcatcttc aaattctaat gagtaggaat  54300
ccagaaacat ttggaaaaaa tgcatttata ctgaacatgt acagacatga ttcccttcat  54360
cccttaagca gtgtgttcta atggctacac ggcatctgca gtgggttagg ttttgtgagc  54420
cagctcgggg atgtgtgcag gctctgtata aatactacgc cactgtctat aaagggcttt  54480
atttaagggt gtctgtgggg ttcctgggcc tgatctctca tgaacgctga gggtcacggg  54540
tagaatggga accacgtatg gaattctgaa ggtcagtagc tggtttcaca tggtgaaaag  54600
agggtcagag ctgtggctca gtagaggagt gtttgcctgg tgtgtgtgaa ttgtgggttc  54660
gatccccagt tctggaaagc aaaccaagaa agaaactggt gaatgtaatc aataacttac  54720
tcctgccact gtaggtcata gcggtgtgca gagagtccat tggggtactt ttcttcccac  54780
actcaaaccc tttgtagcca ttggtccaac cttcagttct gtgtggttcc tcacagactc  54840
acggctcaat tgaggcatag gagctgcctt ccagaggaga gcattatgac tggtcaaggc  54900
caacagcatg caggcgctct agctgctgta gccagggcta gcccctctga gctcagcaga  54960
gactgtggca agaccaaggt agaggcttcc actgggcggt tgggctgttg tcagaggccc  55020
gtgggagaat gggggtgctt gaatgggggg ctgtgctggg ccaaccggag ttctgacttg  55080
atgttgctca aattcctacc tcagcagaag tgggaccatg aattcctacc tggagtctgt  55140
tggcagacct tggagtgggg tggggtctcc tcagcctaga aaccccacag agtgggaggt  55200
ttacggcctg cctctttctg aagggggcag ctgtcgtatc ccttgttccc tttgaatggc  55260
cttggtgctg ggagaggtaa aggttgggtg ctttcctgtt ttagacaggg ttattaaggt  55320
ataattcaca gagcatacaa tcttctcact taaaatgtac agtttggtag ggttgtaac  55380
tcgcatggca gagtgcttct tgcctagagt gtatgaggcc atgggttcaa ttcccaacac  55440
```

-continued

```
tgcacacagt gggtaccctg gtgcctgcct gtaatcccag cactcgagag gcatcggcag  55500
gaggatcagg aaagagttca aggtcagctt cctatataat gagctccagg ctagcctggc  55560
tgacatgaga ccatgtctca gaaactaaaa ataataaagc aagaaagtaa ataatgaaat  55620
gtactgctca gaagcttttg tctgaacagt tgtatgtaag cattgcttct agaacattcc  55680
acccccacca gagagaaatc ccgagtccct ccactctcga tgtaaagcct agcagccttg  55740
tttgtgcctc ctctctgtct ggcttctgcc tctctgtctt tgccggttct gagtgtttac  55800
ctagttgaag tcacactgtg tgtctgctca aaacaaggtt ctgaatttca tccacactgt  55860
tgctatgtta tcacacccct gtggccagtg gcaattctaa cttgtttgtc cacttccctg  55920
gggtagaggt agggagacag ggcaggtgtc ctgtgacaca acaatttggg aaggcatagg  55980
aaggactatg ggggaggatt catgggttgg actatgtcct acaaacccag cccctctgta  56040
gagggatagt tttatcctat ggaaactttg gtccccttga caaggcttcc acccaagtaa  56100
agtagggcct tgcatattgg tgggaaggcg agtccgagat gccccagtgt cccagagctg  56160
gggccgccaa ggaaatctct gctggattct cagaggctca gggtacagag gtcacagtag  56220
tggcaagagc cagcactcgg ggttcgagag atggctcagt ggctaagagc atttacttcc  56280
tttacagagg acacaagttc ggttcctagc actcacacgg cagctcacaa ccacccataa  56340
ctccagttct ggggggtctg atgccctctc cgtaattgat ctggggatca cactctgtgt  56400
ccgcagccag gcttgaccac ccatacttag taagccaaat gccacactag gaagtgggac  56460
aaagagagcc actcaagttt ggcttcgggg tccaaagtga gagtgaaact taagctgagg  56520
accaagaagt tgctcatcta acactgggtc aaggtgtggg gcagcccact ggtgacccat  56580
cactgcagtt tagtttcagt gggggcaagg cattagaact ctgtgaagtc tctttctgag  56640
agacaatctt cccttttggg gcctttccct tctccaagta ggagattctt ggagggaaac  56700
tcccatttct ttggggtccg ttgttttaaa ctcccatact cagacacaag tttagattac  56760
cttcatttct accaatcctc ttacaccttt ctggcctgct tctgcacagg acacaagtgt  56820
gctgcacata cacgcatcca ggcaaatact catacatgta aatttaaaaa aatcttaaaa  56880
caaaacaaaa caaacaacca gggctggaga gatggcttag aggttaagag cactagatgc  56940
tctcttccag aggtcctgag ttcaattccc agcaaccaca tggtggctca caaccatcta  57000
taatgtgatc tggtgccctc ttctggcctg taggcataca tgcaggcaga acactgtata  57060
cataataaat taataaatct ttttagaaca aacaagcaaa taaaccaaca aactagactg  57120
ttacttgccc tttgcacgct cagctttttc tactgtctcc tgagctgctc tccctcctgc  57180
tgggcggtcc ttagtaggac ccttccttct gtatcagctt ccttgactct gacctaaccc  57240
caaaaactcc tgtcaagggt tcacagtgga ccactgaggc cttgtcttct ctggccacct  57300
cctgcaacca tcctccatcc tggactgagg cacaggaggg gctgagcaca aggtccccag  57360
cagagagaga cccgtggcat ggggcagtgt ccagtccagg ccttgggtct tagcctccct  57420
tgttgtctgc aaacacttct tgttctgagg cttagaggag gcaggctggt ggcaggagat  57480
atatgtgcag aggttccaag gcctctctga agagggcaat ggggtaaaag gggcacttt  57540
gctctgagat cacacttccg cgtgatctag tctcccgtag attgctggtc aattggacct  57600
gctcattcct gcctcacacc tttgggcccc tcttctgtga tgtggggaca aggacagtgc  57660
ccacctcagg cctgcgggaa tccatctgag cttgagggaa ggttcgtcag cacagacagg  57720
atcgattaag catctacact tagggaccca ttctgcacag ccattgggta gtcttcccca  57780
aatcctgctt gccatctctg gacgtggact gggtagtcct cccattgata atttgttgaa  57840
```

acacccaagg aaggaaggtg agacttcctt aaagctccta gggaaggctg acttgtcctg 57900
gggtcccaag gacagagaaa gagggttccc agagctcagg ttccttgaat atgtgattta 57960
ggggaaggac tgggctgcct gggctagcct gagaaccagc agggatgctg ggaggagcta 58020
ccaaccctgg aggcctgggg aaggctttgt aatggagata aagtcagttt aaataaattc 58080
ctctggaggc tgtcacttag atctctggtg gctgagcagc cttggcggag tccatcactt 58140
agagggctgt atctaagaat cctgccttcc agggcaccca tgctctaaat cctgctgtac 58200
ccccacccca cccttgcagc cagcatccag gctctcaggt ctatgtgagc actccagcct 58260
ctgggctgac ctgggagcat ggtggtaccc acaggggtct ccggctggga actttcccaa 58320
ccaaacagct cccttccagg taggtgtgca aagccccaat ccaccttgct ggcagctggg 58380
tggatcccaa gaagccctgg cacccgggag gcggacggag aggggcaggc aggagaggtg 58440
aatgtgcgtt tatcccaaca caagtagtgg cctgttgggg tggggtgggg gccccaggaa 58500
atatttggga tgacttggag cccgctggcc ctttaaggct cctgtaacaa gacacctccc 58560
cgacgggaca gaagcggtag ctggggcttc caccttagcc cttgtttctc ccctcccacc 58620 tccccccttcc ttgccaggcc cagttcaatt tgctcagcag tgccatggac cagatgggca 58680
gccgtgcggc cccggcgagc ccctacaccc cggagcacgc cgccagcgcg cccacccact 58740
cgccctacgc gcagcccagc tccaccttcg acaccatgtc tccggcgcct gtcatccctt 58800
ccaataccga ctaccccggc ccccaccact tcgaggtcac cttccagcag tcgagcactg 58860
ccaagtcggc cacctggaca gtgagtagcc gtgttgccag tggatgcgtg aagggagggc 58920
agcggggttg agtgccacgg tcctggtact gaggactgaa tgagcacaca ggctgtccac 58980
atggggttcc cacctggcca gagccaggag gagcatcgag caggaggcgg gccctggggc 59040
tgggcagtgt gggtgtggcc acccccttgga cttgtggcca gagtcagcca gcctcccact 59100
gagtccggaa aggtcagagt gttgttgcca gtgaggtcca tggggcagga agagtggccg 59160
ggttttctat actcagtgcc ttgaaattgg tctggtcctg aacttctgct gaaagtgttg 59220
ggagcccaca ggggcccacc cgtttgctag ttgtgggttt gtgttttgcc ctcatatctc 59280
tctgtgcatt ggcttgggac tggctctcca ggtgctgggg gctctggtcc tttccctggt 59340
gcctccagga acaacctggc atgtggctgg gattagcaga tgttgacaaa gtcccacctg 59400
tacacttgct gagagttggg cagacagcta agtactttga cttgcccaag gtggagtctg 59460
tgcccatttc acagtcaggg aagctgaggt atgaaaaggg aaagcagttt gctcaagtta 59520
tgcagaaagt gagtagatgc tggactgggg acacatggcc gtgagtgttc ttacccactg 59580
agcacccagg ctctctgtgg gagatggggc tgcaggaaga gcagactggg acttcagaac 59640
gctggtctgg gcacacagga cattgggtag gaagggcagc cctagagcca tccaggtctc 59700
catacccagc taagtctgag tagagggaac cctgagcctg ggacagtagg aggtgcactg 59760
agggatgtta agtcatccac ccactctctc cagggagcag ctggagatgc agccatccac 59820
gcagtgcaag ctctatctca ctctcctcca gcggctcttt aaaaactaac tcccacagtg 59880
tggctctcac attctctttg gagactgaag agctggacag agccagacct tgtaggtggc 59940
caccggtgat cagctgtgcc tgactggctc tggtttcagg ctttgacctc ctagagtttc 60000
ttttacctac tgttctggtg ggctccccag tcactagacc atcaccaatt gaatgctcag 60060
cccagctgct ggagctctga ggggcttcag tgggccgaga gggtctgggt acctgtggtg 60120
ctccatcccg agtcactgtg ggccagtgtg ctccactctc cgtgaccaca aattattgga 60180

-continued

```
aggcactgag gtcaggaggt ctgaatgaga caggaatggt agagtacaca gctgttactc  60240
ctgtcctggg acagtggagg aaaccatcta acatggcctc ctgaagttgg tctttgtgta  60300
gaactacctg ctaaaggcct cctcttctgc actgtctgta gttttggggg ttgaagggga  60360
cctaggctct tcctccaccc aagctgagtg acctagggtc aggtcaggaa gcccaggaga  60420
cacatgggta cctacctcag tcacagcggg ctctctacgc tgctcttcta cttccaatgc  60480
attccctagc tccatcttag agtgaggcgg ggtcctgtct gtcataaaga tctggtgatg  60540
ctgtatgtgg gattgcctcc cttcctcttc cttgccagag agtgttgatg aggtcgctct  60600
ttgccgtgcc tatgggctca ggtgcctctg atggtcaggg ctggtctttg acaggggtga  60660
cagtgcccac tctactgaat tcttcctccc atttgggtcc tgtgcagtcc cctctgaggc  60720
actggacatc aagcgtccca tgatggcctg tgttcctgct gctctgctct aactgtcccc  60780
aggggttagt ctgctcagac tggccagaca taccaaagat cagggaaggc ttggcctccc  60840
aacccaactt ccacccagga ccagggcagc agagctgagc tgtcaggcag gaggatgcta  60900
ctgccagccc cctcccggcc ctgtcacaca ggggcagagg tgggaccaac attgataatg  60960
agatttttgg cacctcggcg atctgggagc agacacccaa gggtttttct cgatgctgag  61020
agaagggact ggcagcagct gctctcagct ctgggggtcc aactgtgtgg gtgctgccca  61080
gacttgccac cgaggcccct gccacgccac cggctggtaa ctgatagata attcatattt  61140
ttctcaagta ctattccata ttgactgctg cccccattcc tctcagattg gcaaaaacat  61200
gctcactggc ctctaagtga ccacagctgt taatggggcc tttggtcttg ccattgctga  61260
agccactgtg ggactctctg accccaaagg atctacttac ttgtcctgac caacttccct  61320
tagcctgaaa atctgctggt gcaataagag gtctgggacc ttagagtgtg accctgcatg  61380
tatgaacaca tacgtgtata tatacatgca caaggtccca tatgcccgga cacctaggta  61440
cacaggtgtg tgttatgcat acatgtatat acctatgagc acacatgggt gtaaatatat  61500
atgtgctcag gggcctatat atatggatac acagatgcac tcacatatac ctgtaaacat  61560
gccggcatgt gtgtacatat gcacacacat acacatgcca acagatgagc atgtgaacat  61620
gcatgctaat ctccctggtt gctgcctggg ggacagctgg tctcaggagt ccctcagtgg  61680
aggaggaagt gggacaaggt cctttacata tccaaacagc aagatgggtt ccctgctgct  61740
gtctagcgcc agctcagccc cttcaccctg gctttgcctt gctgagagag acggctcttt  61800
tcagtattgg agacattgag agacagagtt ctgtggttag gcaagaggac ccgtgtggat  61860
ggatggtaac cctggcctgg tatgatgtct gtagaacacc aagggcaggc tgtgacaccg  61920
ccagcctact acagaggcag ctgcagagga gcccaagagt gagggcgcgc tcatgaatgg  61980
cttgactgcc tgagagcatt acagatagac agacagacag acagcctgga catagtctta  62040
agtgaccttc aggtgaagct gccttcaacc tgtgtgtgtg tgtgtgtgtg tgtgtgtgtg  62100
tgtgtatgtc tgtctgtctg tctttatgtc tgtctatgct tatctgtcct gagagagaga  62160
gcccctacct acccacccac ccacccaccc acccagccag gcagcagccc ctggagggaa  62220
gcacaaagcc tctgtgaggg attcttaggg aggacagggc tgagtcaaca ctaatggatt  62280
tggagcaaac tttccagccc ctcggaggtt tgcaaagcac aagaatagag gaggtgtccc  62340
gacatgattg tggtatcaat tgcgttatcc taaaagttta tggaatgcat aaatggaatt  62400
aatacctttt actggcacgg ggagcaatta tgtatattta aagcccagag aagagttcta  62460
acaatgttta ttgtggagat gaaacgtgaa ttattagggg aaacaagagc acttatggag  62520
aaatcgcagc aattgctcat attgtgtcta gctttgccgg agagaatggg ctgccagtag  62580
```

```
gctggctccg gcttggtctg agcagggtac ctgcaccgga gatgtatgtc tgctctctcc  62640
atccactagt ggtctaaagg actttggtcc ccaggaggca cagaatctag cctggagact  62700
ctgaactcct gaatccaact gcagctcgac actggcaggc tggtccctgt gtctaagggt  62760
gctccctccc cagctgagtg gtcacatcac atacctcagg gttctagcag gggacaggag  62820
acagggcacc ttggaggaca ggactctatc ctgtgatgct gagatgcagg gcagggctca  62880
gtccagcagg ggaaatgtac catgaatcaa caataggaaa tgaaggaggg gtgttccata  62940
ggtctgactg gcctcctcat cttggaggtt ggtcacttct agaacgttct aatcagaaac  63000
catttatgaa tctacccagg gaggatggtg ggcagatagt gtgtctctcg gccagcacag  63060
tgctaaggaa caagccaggc ccccctttt gaggcaagca ggcgggcctc tgggcatcag  63120
agcctccttg ctcctgctca cagagctcct aggatcccag aaccactcct agggaacttg  63180
gagcagtggg cagggcagag agaaagagag ttcctcaaac tcttgggata tgctgttggg  63240
ttcaccattt tgtttctgcc ctttgctgat gggtgacctg cccttgaccg gccctccgag  63300
atcctcttct gtaaagtggg aaaggaggta tacatgccta ctgcaggccg agggatggca  63360
cctggggtcc cgagatgccc attcgggtcg ggtctctatc ccctctcctg taaagttctc  63420
cccagtgtgg catgagcaga tgtgagacag tctgaggaag ggtcagctct aggccttcca  63480
gagtcacacc agttctcctg aggggaggac cggggagtga accaggaaca cactcccagt  63540
acacacagcc agccctgaaa aatggacagt tctttgtaat gtgtgaatta gcactcaatc  63600
ctccattgac agcacccccc ccccaaacca caggggatag aggccagtgt gggagtgtcc  63660
atggtaggtt aaagctggtc aggagttggc taacactgcc aggtgagatc caggtgagtt  63720
gaatgttgct tacctgggcc ctccaggctg gtggtaggct ctagggaaac cacctgaaat  63780
gtattagact ccatcctgtg ccctgaaggc tcaggccctg tcacctcctc ttaggaaaag  63840
gtcacagcca catccaggac ctcttgctct tatatgagtt agaatattct aggctttgag  63900
agctgtaagt cagggtcctg caaccaccac ttatcagtgc aagaagccaa ggtgggctaa  63960
gactggcgct ctgagatcgg ataaccgggt tctaggtccg gctgtgcggt acacctgaag  64020
gtagagatgc tctttggaaa aattgttggt gtggtaggta aggcagaaac cattcagtga  64080
cccaaatccc acgcctgtgt ctgcctctca cctctgtctg tgataggtca gctctcatgg  64140
tgctgaacct ggggagggtg agatgggctg tgccgcgctc tgcacctggg cctggttcca  64200
gggaggctct cactagcttt gctcagtaca agatcagaga tttagacccc agagtgtccc  64260
tgtcctatag ttccaataaa gatgtttaaa gttcaatgac aacttatatt ttaaggagct  64320
attgcctaca gcactgaaga ctggctcttt caaacatgca cacgcatata tgcacataca  64380
cacactcagg tacatgcaca cacacattaa cacacacact catgcacaca catacacaca  64440
ctcatggcac acacacactc atgcacacac atacacacat acacacacac actcaggtac  64500
atgcacacac acattcacac acacacactc atgcacacac acacatacac acacacacac  64560
actcaggtat atacacacac attcacacac actcatgcac acacatacac acacacatgg  64620
cacacacaca ctcatgcaca cacatacaca cacacacaca cacacacaca cacacacaca  64680
cgcgcactca cgcacgcacg caccttgcct ccctggctcc tggctatcac tagcccctga  64740
gactgtatgg aaagtcacag gtccttagag aaggagctgg ctaagatgag tgtttagaag  64800
ggtcacagct ggagcggaat gtgtgactgc cctgagatac ccttgcaatc tcaagctgat  64860
gaggttgatc ccgactgtgg aagctacagc tggggatggg gtagggactt caccactgac  64920
```

-continued

```
agccaacagg ggatccatac tgtgcacaga gcaggctggc taccagcctc gctgtgggtt  64980
cctgtactgg acggtcctgt gacctgcacc ccagccctaa tcacaggtgg gagaggctga  65040
tggctggtgg ccagaggaga ggctactcag gactgcctga aggagtggcc aaggcacagc  65100
tctcctgctg gctgggtcag gaagaagggc agcaggggcc cctttgaact cacagggaag  65160
gtgagcctat ggttctttgg atctggtcac agactgttct cagactacac tcttttcttc  65220
ctgaagtccc cagatgggtc ctgggtcctg gaaaaagatt agatgtccaa gttagggctg  65280
gagtgacgga ggtgacaggg cctcctagga atatctctga aacccctgac agtggccttc  65340
tggagctgga gcatcataca gcaaaggagg tcagccgcac ccagccaacc agccacctgg  65400
agcctccatc ccccccatga cttgatgtca ggggagacac ttcccagtaa gaccagggca  65460
ggccaggttc ccccaccccc accccgcccc tgcctggcag cttcctcacc ccccaggaac  65520
acaaccccag cccagagctg cctgtctttc ctgcctttgg tgttctactt ggtcacctga  65580
ctgtcctctt aaccagccta tctggatcct gatctctggt ctctgacctg gtaagtctga  65640
tggaaatgaa agaccaaaga tggaggtgtc gggtcttgag aagacaaaac caaactggaa  65700
ctcacttcta agacttctat gaccccctca tccccaaagg tggttctcaa ccttccttta  65760
acacagttcc tcatgctgtg gtggccccca accataaaat tacctttatt gctattttgt  65820
aactataatt ttgcatgggg taaggtgagg tggggaagga agtaagagac aagatggaga  65880
aaggatgtga gtctcccagt cctctctggc tctgctctct ctgggcacca tctccaagta  65940
cctcctcact cctagctgtc caggagctga ccaagccctg tcctttggga tttgtacaga  66000
cacttcatta tgtagccatg attagtctcc tgacattcgg gacctgattg accttcatcc  66060
tctgtgctcc gtcccaaagg ctggggctga ggggtcacac atactaactg gatcttttca  66120
tcaggggtgc tcaggaaagc agcccccagc cctcagcccc cagcccccag cccccaggcc  66180
ccagccctca gcccccagcc cccatccccc agccctcagc cttcagcctc caggccccag  66240
tccccagccc tcagccccca gcccccagcc cccagccctc agccctcagc ccccagtccc  66300
cagcccccag cccttagccc ccagccctca tccagtcatt agcatgtaaa agagcaactg  66360
ttgcttggca gtcctctaga ttttatgagc attttaccag aaacccgagg tctacagcca  66420
atgcaatgca acctctgatt actgctctac ccccagctca gctggcaact tttagaaaca  66480
aaattctagt tcctaaaatg tccaggtgaa gggtcagagt aggcacctta cagagaaagc  66540
agcacagacc gggcccatgt tattcctttg gtctctatgt aaagccatca gctgcagagc  66600
tatgtagagc agcctcccaa attcccaacc actaccttct ccctctctga gatgagacta  66660
ccaggccctc acacatcagc tcctccgcct ggggcagaaa ctactggaag gttctctgct  66720
cctgccaagg ataaatgggc tccaaacccc atgacctggg accctctgac ttcccagtct  66780
tagtgcaaaa aaaaaaaaaa agaaagaaag aaagaaagaa agaaagaaag aaagaaagaa  66840
ggagggggga ggggctggag agatggctca gcagttaaga gcattgactg ctcttccgca  66900
ggtcccgagt tcaaatccca gcaaccacat ggtggctcac aaccatctgt aatgagatct  66960
gagaccctct tctggggtgt ctgaagacag ctacagtgta cttacatata ataaataaat  67020
aactctttaa aaaagagaga gagaaagaaa gagagagaga gagagagaga gagagagaga  67080
aagaaagaaa gaaagaaaga aagaaagaaa gaaagaaaga aagaaagaaa agcactctgt  67140
ctcccaggcc accaaggtgc ccatatggct cttgcttgcc tgtttgagat cttgctcaag  67200
ggtcgggggt ggggagcagg ttactcagct cctgaggggt gccccagcta gctcctggcc  67260
aacctctctg taggggaaca gactatggcc ttccactcac agagcaatca gtcagacttc  67320
```

```
acatctgcct cccggagtgt cctttatctt ctttcagacc gctgttcttt aggaacaact  67380
acagcctctt tcctgcacac ttggcagggg caggcactgg ggcctccaat gatgtgttta  67440
tagaacatgg agcctccttg ccctcagcct gcatcctggc ttgatggtgc cagtccggtg  67500
acggttaccc gagcatcatt ccctccctaa ggttctatcg gggctcccta agctgtgcaa  67560
gagctcaccc ctgctctcag gtgctccctg aatgaccgaa taattgaaca atgtaaattg  67620
tgcgagtcaa ggccaagatg tacccacaaa ggggctgccc caggacctct tcttggatga  67680
taggatccat aggttgctcc tctcgcagtg gcatttctcc aagagaaacg aaaacatggt  67740
ggggagtcat attcaggggc tgtggacctg ggttcctcca gatttgagag atcagactga  67800
gtctaccaga cctgtgccct gctctgtgga tctgccctag gaagagtaaa agcctgtgat  67860
cccagagatg attctcaaag gggtctacgg cctcagagat cagaaactct cacacacacg  67920
tatacacaca cacacacaca cacacacaca cacacacaca cacacacaca caaagtgggc  67980
tacaaaaaaa agtattttta aaaagccccc accacagcct ttcgttctga atctgtccta  68040
acagattcac ccaagctggt taacggtatt tgcggtttgc aagatactac atgtcccggg  68100
aaaatgacag acaagttatt atcaccttcc cactgtcctc ctgcccaaac ctgcctgtgc  68160
cgggcaccca gctgccggga gcgggtgcga ggaaattaac agccctgtgc cgcgcccgcc  68220
cccgcccgcc ctctcaccca ccaccctgca ccggtcctgc caggctaggg gcttccagcc  68280
aggcccggcc catcttggac tgtggcgggg gggggggggt ggggggtggc gggggggggtg  68340
gcgagggggg gcgcgggggg gggagggagg gagagaagga ggaggagggg tcaggatagc  68400
agccgtggca ggagggacgt ctgctccgct ccgatgttgg gcaaagtatt tcctgcaagc  68460
cccgcggaac acacgcatcc gcgcaggcaa gtctggacgg cgctgtgtca acagccgaag  68520
ataaataaga ttttatcagc tcggaatctg ttgaaacaca tccatctagc ggttctaggg  68580
aaggagaggc aggaggaggg cagcagggag gaagcatccc cacatgacat tctggaaaca  68640
gagtctgacc ctgtgtagga aggggagcgc tggcaacttc ctagtctccc ggagactcga  68700
tatcctggag tgttgttttt accacctgat cttcggaggt gtgggaaagc tttggtatct  68760
ctcgctgaaa ttccccacct ctggctaaaa tggactacca caaacttaac ctgtggccgg  68820
ggtggggctg gtaggtgtgt gcgcccaaag ccccacgatc attggattca agacggcatt  68880
caagggtgca gaagtgaagg agccatgtat cttcatgggc ttggattttc cttccaccct  68940
gaccgggtgg gagacgtgtc ccaccagaga tgactctctc aactctgatt ctttctctga  69000
gaggagacag cctttccgca gctgctgagt tggtaccagg gacagctcca ggcgctttaa  69060
gctcctcccc agggtggggc attcagtggc tcatccttac cagcccggct actctgcaac  69120
tatccttagc tttccctaga cctcctaggg tcccactcca ggccatggaa aacagtgcca  69180
ccttctgggg aggagggtca ggcctcagct acctctgacc acaccttggt agtgttagtg  69240
catggtttgg ggttgtaacc aattatccta ggtcctcaga ggacagggat ggaaaggaca  69300
attgccttca gggtcacagc agggctccag ggatgggcac tgtggtcagg cgaggtttga  69360
agcctcattg ctcaggagtg ggtgggtgag gggagctctg atgcccctcc ctgtggctga  69420
gctgtgccct gagcctggct ccatcctgat aagaacacgg aggtgaagct gatgcaccct  69480
ttctccctcc aggcatgttt gggcttccca ggaatgtggc cttaggcacc attacacctg  69540
acttgctccc agcccatctt ggctcctgcc ttggtgggtc tatgaccccc tcttaggtca  69600
ttgttcatga gctagagcac tggagggaaa ggttaactct gtaggagact ccaggtccat  69660
```

-continued

```
gagccccagc agctgtgcca acccacaaat taccttacct ggtaatgagc aaccatgcta  69720
gaataagggg cctctgacct tgctggctct ctaccacaca gctggcatct gggggttgag  69780
tggtaagtca gtggtagaca aacctggcag gtggtccaat ttaggggaat ccagcctgaa  69840
ttcctgagcc agaacaggga gccaagggcc agccttcaaa ggctaatctc ctttttccgc  69900
ccctggtgac tttggtctca gtgtctcccc aacccactgt gggcaaggcc tgtttcatgg  69960
gggtgttggc cacctccacc cctcagtcta ttttctttag gtagctaggc ctcacaaaca  70020
atgggcactc gggagatgtt tggtaatgct tgggactgtc acctttacca ggaagttgcc  70080
tgattggcct caggttgagt ctctctgagc tcaggatgag ctgggttccc ttcaccgtta  70140
ggcctttgca attgtctgag cctggggctt gctgggaaac cttcatttgt ggataagcaa  70200
gagcccaggg cacttcactg tcactgtata tgaatttact taatgtcggg aggggcacct  70260
cgcactgtga acttcatgcc accccgtgtc cttcctaggg agccacagta attacagagc  70320
tagtgtgctt tttaccaagt gcaggctgta gacccccaac acctgcaggc tgctgctgct  70380
gctgaaggac aggtgtgtgt gtgtagctgt ttattggcct ttccccaggg aaccagctac  70440
tcctgctact ctgtccccag cctgcacaga tggagaccag gctgcagtgt actaacttga  70500
ggagaggccg ttgcaaaaaa ccaaagccca gatttggatg tgcagaggtc aggtgtaccc  70560
tgtccaagtc tcagagtccc ccatgtatcc tggggatgag gctgtggctc cttcctccag  70620
aatgttagga tgaggatccc acacaccagc agacagtggt cacccccccct cccgaaagtc  70680
acaccaacct gctggtgtgg ccattagctc tccctcagct gctccccctc ttaggctctc  70740
tcagcttttc aaaacagtcc ctgaagcctt ctgtggggtc cctatagtga gtatctcttg  70800
ctttttaaac aggagggaag ggactatgtc atggcgcctc tccctgccct cccttcattg  70860
catttgccta tggtatatgc tatttctgca tactccattg tggagaacca taagctatat  70920
agggttaggg tggtcagaat cccccactgt cccttgcaaa ggaaagattt ggtgtgtgag  70980
caccacctgc ccattcctgt tttgttaaca gcttaccatc tctggcctca gcttcattaa  71040
ctgtcacaag ggagcatggt gtatataatt catgtgtggt ggagacttta gagtgaagtg  71100
gagcttcata aaaatccctt gggagccagg cggtggtggc acaccccttt aataccagca  71160
cttgggaggc agaggcaggc agatttctga gtttgaggcc agcctggtct acaaagtgag  71220
ttccaggaca gccagggcta catagagaaa ccctgtctcg aaaaccaaaa accaaaccaa  71280
accaaaacaa aacaaaacaa acaaacaaaa aaaaaaaacc cttgggaaga gctagagaga  71340
tggctcagag gtcaagaggt cctgagttca attcccggca accacatggt gtctcataac  71400
catctataat gagatctggt gccctctctt ctggcctgca ggagtacatt cagacagaac  71460
actatataca taatagatag atagatagat agatagatag atagatagat agatagatct  71520
tttaaaacaa aatcacttgg gaaggaagac aagaggagtg agtcaccagg ggtttcagga  71580
gccatagtga gagtcagcta gcaggtgaat aaatgggtat cttgcttttc cagcctagat  71640
caggccgctg gctgcatagg taggatttgc agcattgagc ccgtttgaca agctcagaat  71700
tgcatcctct gccttgcata gaatagtctc actctgattc tgaaactgac ttggtcttgg  71760
cagggccagt acaatcctta gaagagtgac ctgggacacg gagggggcgg gggaggcatg  71820
atgacgtccc attgtccctg agagacatcc tggcatgacc tcaggtccag tcagtttcca  71880
ggatggggaa agcgggtctt gccccccaca acagcttggc tgcctggact tggtgacttt  71940
acttggtggc acagtgctgg tgactggtca acagcatgca aggtcttgct ggttcagaga  72000
gttctccatt ggaggataaa ggcaaaggca gaaggggcaa gccacccacc tactgagtga  72060
```

-continued ttcttctatg caaggtagaa ggatgcaatt ctgagctcgt caaaccacct caatgctgca 72120
aatcctaccc ctgcagccag tggcctgatc caggctggga aagcaaaact aggactgatt 72180
cccactgacc tctgacccac acccccaaca ctgtcttacc ctttgtcatc cttatgcaac 72240
ggtccaccgc tcgcagcctt tgagatgcag gtgagacaca tagccaggca ggtgatgagc 72300
aggcaccagg cacgcccatc tctacaatct gaagcatgcc tgaagcatct ggaagcaggc 72360
ctcatcggag cgcttgggaa aggggtcttg tggaagcatc cggaactgag ctgccatctc 72420
aacctggccc ccttctctcc tccagtactc cccactcttg aagaagttgt actgtcagat 72480
tgctaagaca tgccccatcc agatcaaagt gtccacacca ccacccccgg gcacggccat 72540
ccgggccatg cctgtctaca agaaggcaga gcatgtgacc gacattgtta agcgctgccc 72600
caaccacgag cttggaaggg acttcaatga aggtgagccc cccctccccc tcccagctgt 72660
gggacactga ccagaggcat agctgagaga tgtaggccag tgagcacagc ggtaagctgc 72720
tctcaactct cccctcacag gaacccacac cctagccctc tttccatttc ctcagctctg 72780
actacagtcc aagaggctga tggtccagca agggtgtagt ctgagggacc agctgacctt 72840
ggagaatctt gtgaagcatc cctgcagtgt ccctggtgaa gcctgtgaca cccccagggt 72900
cagattatct ggggacagct tctgtcccgc tcaaggccac ctaaatgagg gttgcacagc 72960
tctgagcctt gcctgggact ctcacgggga caagccctgt ggcctcagtt ctgccacacg 73020
cctggtacag gggtatggga tggaagatgg gcccctctct aaagctgtgt cccctcctgg 73080
caggacagtc tgccccggct agccacctca tccgtgtaga aggcaacaac ctcgcccagt 73140
acgtggatga ccctgtcacc ggaaggcaga gtgtggttgt gccgtatgaa cccccacagg 73200
taggcggggt ccaggctggg atacaaagcc aaccttacag ggtggggttc cctgggcctc 73260
tgctctgacc tcagcctgcc tctcaggcct tttcctgaca gttcatttca ctgtgggcag 73320
cgagcttggg cctgtgctca agccaacttt agctctctgt ctctctgtct gtctctcgtc 73380
tgtctgtctc tgtctctgtc tgtctctcgt ctgtctgtct gtctgtctgt ctgtctgtct 73440
ctgtctctct ctgtctctgt ctctctctcg cctcagctat atagcgaggt atagttatat 73500
gacctccaac ctttcaaccc tgccctccct ggagggtcta atcttcaatc ttcttgcttg 73560
tttctctcaa gtacagtctt ctagacatgg aagaaagagt tcccagacat ctcaggctcc 73620
atttgcaggg acaaaagcaa gccagcaagc atggggtggt gggtagaggg tgggcaattc 73680
catgtgtggg ggggtagtga tcatgaaagg cctcctagac caggctgggg gaatcacaga 73740
ggacgcctac aggagattgg agccgtggaa cacaggctca ggagagtagg gaagacagag 73800
atgatcggtc agccttaaga gggcctgtgt gcagagcctc gggagagtgg tgccagctgg 73860
atggagggta cagtggaggt gaccagacat gctgcacact gaggtgcagg gtggatacgg 73920
aggttcaggc tggaggcgaa gggctcagac cacaggtgag ggctctaagg gagggaacca 73980
ggctggaggt ggtggttgcc aaaagtagac aagtgaagga agactggagg aggcagctgt 74040
ccactttgac accagaagag tgtgtggtca ccttctagat ctgatatgag ccccagttgg 74100
ggccaaaggc aaggtgaagg gacttcagta ctgatgtggg aggtatcagg gcggagactc 74160
aggaggactg gggttaggtc tcatctctga cccatcctct accaagccct ggggtcctgt 74220
gaggcagctt tgaatgtcag tgggacaggg ccccatatac acacagacac acacagacag 74280
acatacacat agacacagat tcacacacac agacatacac agagacacac agagacatac 74340
acacctacac acacacagac acacacacac agacaaacac acacacacac agacacaaac 74400

-continued

```
tgagaaacac atggacaaac acagagaccc cacccaccca caccacacac acagaaacag 74460
gcagagacac acagaacaca gaaacacaca cacacacata cacacagaca cacacacaca 74520
cacagacaca cagacacaca gacacacaca ccccacaagc atcctcccct ctcatcagaa 74580
aaagcctcac cagctcaggc atgagacaca acgtaggttt ctcttgccct ctagtggttg 74640
gcaggtgtaa gttctgtgaa ggactggggt ttatggcgtt tgtaccctaa cctttgaaac 74700
tcctttctgg ggatggagtc cctttcattc ctctgcccag atgagtccac agtactcatc 74760
acacacttga cacaaaggct cacacacacc cactcacata cagccctgac atttgacctc 74820
tgcctgtgtt aaggaagatg actgcagcaa gcacaccaca aactctgtac ctcccctaag 74880
agctgaaacc aagactgagc tctcagccca gagccagcac agggctgtga cggcacagat 74940
ggatcggtgg gagggcgggc aatctcacgt gagtgtagat ggctgaatgg atgggtgagt 75000
gagtggatgg gtgggtaggt aggtgggtga tagtcaggca ccactggggg tgggcaggag 75060
agcaggtgag caggagtgta agtgggtgta tgggtaggca agtgagcagg tgtgtggatg 75120
tatgtgtcaa tggatgagag gttgaccggc aagtgagtgg ggtaggtgga tacgtgggtg 75180
tgtagacagg cgtgtgagca gatggatgga tgtgtagaca ggcgtgtgag cggatggatg 75240
gtttggtgga tggtaggtgg ataagtggcg agatggatgg ataagtgcaa agatggggtg 75300
gttgggtaga tagatgggta gatgaccgtg aaccatactg cagcgtccct atgcctcctc 75360
agaaccaggg ccagaggtgg cagctacaag tccttttctt agaaggtggg ccctgcatgc 75420
tgactgatac taagcccttc ccctgtctcc cctgtggaca ggtgggaaca gaatttacca 75480
ccatcctgta caacttcatg tgtaacagca gctgtgtggg gggcatgaat cggaggccca 75540
tccttgtcat catcaccctg gagacccggg agtgagtctg ccgtggaagg atggtagagg 75600
tggggccgtg ggggggcatg tcatggacac agggagggct tgctctcctc ggtgggcatt 75660
cagcttcaag gccagtcacg aggggtctgc gggagttggg cagggtcaag agtggtctct 75720
tgagctcaca gccacgctgt gccgacccaa cagtggacag gtcctgggcc gccggtcttt 75780
cgagggtcgc atctgtgcct gtcctggccg tgaccgcaaa gctgatgaag accattaccg 75840
ggagcaacag gctctgaatg aaagtaccac caaaaatgga gctgccagca aacgtggtga 75900
gtggggctct gggtcagggt atgggcggag ggtggagttg gatgcacctg agtgtgggga 75960
gtacctgctc caaaggtgcc aagcatagct tcatccaaag atggatctgg gtctgaatgg 76020
ctgaggctgg gaagcctctc caggcgggac agggcgaatg tggcccaaga catctcactt 76080
gtctatgctc tgaggctagg agcatgtggg accctggtcc agctccttcc agcctaggtt 76140
tgccctgtgt gcacaccaca cccatggcag gtgttcacct gggcatctca gtctttgctc 76200
tctggctcat ttatctttcc cgacctgcct tctagcattc aagcagagcc cccctgccat 76260
ccctgccctg ggtaccaacg tgaagaagag acgccacggg gacgaggaca tgttctacat 76320
gcacgtgagt gggctgggag ggcaggtctg tgtgttccca tcacccaaga tcccaggctg 76380
gggaagtaca gatgtcacca gagatgggca agggtggcat gctgacacct gaggattgaa 76440
actgtggccc tgaaggaggt ggggttcaaa ggaggctctg tttagagtca gaccctgaac 76500
tcactgagtg tgaacatgcc agccaagtca gctgtgcatc aaggagacct aagggcaccc 76560
tttataatgg agacccccag ggtggagttt cagtaggaac ccatgatcct atagggttca 76620
gcctgtgttt aaatccatgg tcctataggg ttcagcctgt gtttaaatcc atggtcctat 76680
agggtatagc ctatgtttaa atccatggtc ctatagggta cagcctgtgt ttaaatccat 76740
ggtcctataa ggtatagcct atgtttaaat ccatggacct atggggtata gcctatgttt 76800
```

aaatccatgg tcctataggg tatagcttgt gtttaaatcc atggacctat agggtatagc 76860
ttgtgtttaa atccatggtc ctatagggta tagcttgtgt ttaaatccat ggtcctatag 76920
ggtatagcct gtgtttaaat ccatggtcct atagggtaca gcctgtgttt aaatccatgg 76980
tcctataagg tatagcctat gtttaaatcc atggacctat ggggtatagc ctatgtttaa 77040
atccatggtc ctatagggta tagcttgtgt ttaactccat ggacctatag ggtatagctt 77100
gtgtttaaat ccatggtcct atagggtata gcctgtgttt aaatccatgg ttgtataggg 77160
tatagcctgt gtttaaatca atagttctat agggtatcag cctacatggc tcgatgtgac 77220
tgtggtacca atcccagtgg taagatcatg gtgcactccg aaagagtgct atttccttgc 77280
ctgtgagtcc tcctttaaga cttagagctg ttataactta gagcctctta gcagggaaga 77340
ataaacatgg tctctgaacc ccgagggacc cacttctaaa cctgcccctg ggaagaggaa 77400
agccagagta tcctgagcgt tggggtacgg ggaaactcca agagcagatc aacactttgc 77460
catagcctgg agtcctcctg aggctacggc catccccgtc ccaccagggg tttggggcca 77520
gtggaatctc ccaggtacct gggccgagac tctgtttttc tgtgcccagg tgcgaggccg 77580
ggagaacttt gagatcttga tgaaagtcaa ggagagccta gaactgatgg agcttgtgcc 77640
ccagcctttg gttgactcct atcgacagca gcagcagcag cagctcctac agaggccgtg 77700
agtgaacccc accatctgta tggggaagta gggatattct gacccagcag ggagagggcc 77760
aggagcacag gaggtatggt accctggact ggactggact gtaagatcag cacagctcag 77820
ctggcacctt ctcctccagg aagccttctg ggacttagcc tgccctgaga tcctgggtcc 77880
ctgtgttcag cacacccctg cctcccacac aagggccttg gaaatgtgga tggggaaggg 77940
actggaaggg ctgtatttgc tgaagctggt gaggtgttag ctttcttcct aactctctga 78000
gaggcagggt ctacatctac ctgcatccca gggtgtccac agaggtacca cgtgggggag 78060
gagttgcttt tacctcttgc gaatgcgcac tgttgctttc caagcaggag tcacctgcag 78120
cctccatcct atgggcccgt gctctcccca atgaacaagg tacacggtgg tgtcaacaaa 78180
ctgccctccg tcaaccagct ggtgggccag cctcccccgc acagctcagc agctgggccc 78240
aacctggggc ccatgggtga gtccctggag cattggaggc ctcatgtggg tcatagagac 78300
ccaagggagg gcctgggtgg atttaccgag atcacaaaca ggatggcggg ggacctttga 78360
tggccacctc ttcctgcagc tccagcctgc aggagggcaa tggctatgga ggcgttcatt 78420
ccaatcccag gagttctatg cctgggaggt tgcaaaggtg gtagagttaa gaactcatgc 78480
ctgccacagg atcttgaaga agatccctag cctcagtttc cccatcagta aaatggcaac 78540
accaaatccc ctcttctcag gggttacagg acatgagacc tcattgagag gcagctgtag 78600
ggaaccctta caatgctgta ccacactgcc aggctagacc acagcctggg acataccccca 78660
ctatgtgtgg ggcttgctct caggttccct gaccactctt ttgcccaggc tccgggatgc 78720
tcaacagcca cggccacagc atgccggcca atggtgagat gaatggaggc cacagctccc 78780
agaccatggt ttcgggatcc cactgcaccc cgccaccccc ctatcatgca gaccccagcc 78840
tcgtcaggtg tgtgggtcgc ggctggatct gggtttgtgg ttcaccctcc acccctcacc 78900
ccatgcctcc cactaactgt gcggttcctg ctggagggag cagccttgca tgtggctctg 78960
tctgaccctg ttttaattgc ttggctggcc tgagggaaga caggcctatc agggctcgtc 79020
agcagatgct gagaaaggca ctagatggtt aggcactgag ggtgggggtg gggtttggag 79080
gggtttgggg ggcatcctct tggagacagg gggatgagga atgagatgag cagctgtggg 79140

-continued

```
aggtcagacc aggagaggtg ggtaatgatt ggactgtaaa aatataaaag taacatacac  79200
acacacgtat atatgtgtat gtgtatgtgt atgtgtatgt gtatgtgtat gtgtatgtgt  79260
atatacacac atacacatat acacacatgt acatatatac atatatatgt gtacatatat  79320
atatacacac atatatgtac atatatatgt aacaaaaatt aaaataaaat aaataataaa  79380
ataaagaaat aaaaaagaaa acctgccctg agggagggac cagcagtttt gcccactgta  79440
acaggcagtt ccctccacgt cagggccact cctgtgagac ccgagtgcac agccagttga  79500
tgctactttc tcaaactctc tctgcagttt tttgacaggg ttggggtgtc caaactgcat  79560
cgagtgcttc acttcccaag ggttgcagag catctaccac ctgcagaacc ttaccatcga  79620
ggtaaatgtc ccaggtcttt ccaaagggac ggaggacctg tctggaggca cagtgcactg  79680
actagggtga ctagtgggga aactcccaga gactcccacc agcaatcaga ttctgttctg  79740
aagtcagcag gattcggtaa tgtgaaggag actgggtaga caatcacatg tcccggtccc  79800
cggcagttac ctggagagct ttctctcttg ttagagcctc ctggtggccc agccaggcta  79860
cctttgattt cttaggcagg gttgtttcca ggacccaatg tgtgagaagt gtagaagcta  79920
agggggggaac agacctagaa agaatgaatg ggtctccaca tccagcctac acgtgagaca  79980
cagaacattc tgggttgaaa gtgggataga aatcttctgg aaggccctgc atcctgttac  80040
agcctagcca cacagactgc cttgatgtat ccatgagaca tgggtccagt gtgcaacagc  80100
tcagcccctc ctgccccagg gcccagtgtg caacagctca gcccctcctg ccccagggcc  80160
cagtgtgcat cagctcagcc cctcctgccc cagggcccag ggtgcaacag ctcagcccct  80220
cctgccccag ggcccagggt gcaacagctc agcccctcct gccccagggc ccagagtgca  80280
acagctcagc ccctcctgcc atgcctccca aaactgtttt ctagactctc acccaggcta  80340
agaggccata tttgtcacct acccaggaac tcaggctgga cacaaatatt tataagaggt  80400
tgtggggcta gagtctaaca cctgcattta tgggaccact gaccactacc tttcccatcc  80460
ttgagtcata cattaaccct tgtctcacca gagcttgaag ctaaaggatg tgcctggagt  80520
tagctgccaa ttaatggctt ccaagggaca cctgtggcca agagatgcat gggtggtctc  80580
ctaggtctcc attgctgttc tcgctgtgtc caggcctcag gctgatgagc aggccctcgt  80640
cactgtcccc tctgtcacct acacatgtca tctagctgtc ctagacaatt atgtgactag  80700
acattctgtg caggtgaccc tgatgctgtc cctaccctgt cacccacaca gtcaaggtct  80760
gataagtcag ctgccccctc agacagaggc ttcctagcag gtaggacacc cttgcaggtg  80820
tgagggacac acaactctgt agcttccctc ttgtaaccca aaggtgccca tcgctcttgc  80880
aggaccttgg ggctctgaag gtccctgacc agtaccgtat gaccatctgg aggggcctac  80940
aggacctgaa gcagagccat gactgcggcc agcaactgct acgctccagc agcaacgcgg  81000
ccaccatctc catcggcggc tctggcgagc tgcagcggca gcgggtcatg gaagccgtgc  81060
atttccgtgt gcgccacacc atcacgatcc ccaaccgtgg aggcgcaggt gcggtgacag  81120
gtcccgacga gtgggcggac tttggctttg acctgcctga ctgcaagtcc cgtaagcagc  81180
ccatcaaaga ggagttcaca gagacagaga gccactgagg aacgtacctt cttctcctgt  81240
ccttcctctg tgagaaactg ctcttggaag tgggacctgt tggctgtgcc cacagaaacc  81300
agcaaggacc ttctgccgga tgccattcct gaagggaagt cgctcatgaa ctaactccct  81360
cttgg                                                              81365
```

<210> SEQ ID NO 4
<211> LENGTH: 2586

<212> TYPE: DNA
<213> ORGANISM: homo sapiens

<400> SEQUENCE: 4
gattggggtt ttcccctccc atgtgctcaa gactggcgct aaaagttttg agcttctcaa 60
aagtctagag ccaccgtcca gggagcaggt agctgctggg ctccggggac actttgcgtt 120
cgggctggga gcgtgctttc cacgacggtg acacgcttcc ctggattggc agccagactg 180
ccttccgggt cactgccatg gaggagccgc agtcagatcc tagcgtcgag ccccctctga 240
gtcaggaaac attttcagac ctatggaaac tacttcctga aaacaacgtt ctgtccccct 300
tgccgtccca agcaatggat gatttgatgc tgtccccgga cgatattgaa caatggttca 360
ctgaagaccc aggtccagat gaagctccca gaatgccaga ggctgctccc cccgtggccc 420
ctgcaccagc agctcctaca ccggcggccc ctgcaccagc cccctcctgg cccctgtcat 480
cttctgtccc ttcccagaaa acctaccagg gcagctacgg tttccgtctg ggcttcttgc 540
attctgggac agccaagtct gtgacttgca cgtactcccc tgccctcaac aagatgtttt 600
gccaactggc caagacctgc cctgtgcagc tgtgggttga ttccacaccc ccgcccggca 660
cccgcgtccg cgccatggcc atctacaagc agtcacagca catgacggag gttgtgaggc 720
gctgccccca ccatgagcgc tgctcagata gcgatggtct ggcccctcct cagcatctta 780
tccgagtgga aggaaatttg cgtgtggagt atttggatga cagaaacact tttcgacata 840
gtgtggtggt gccctatgag ccgcctgagg ttggctctga ctgtaccacc atccactaca 900
actacatgtg taacagttcc tgcatgggcg gcatgaaccg gaggcccatc ctcaccatca 960
tcacactgga agactccagt ggtaatctac tgggacggaa cagctttgag gtgcgtgttt 1020
gtgcctgtcc tgggagagac cggcgcacag aggaagagaa tctccgcaag aaaggggagc 1080
ctcaccacga gctgccccca gggagcacta agcgagcact gcccaacaac accagctcct 1140
ctccccagcc aaagaagaaa ccactggatg gagaatattt caccettcag atccgtgggc 1200 gtgagcgctt cgagatgttc cgagagctga atgaggcctt ggaactcaag gatgcccagg 1260
ctgggaagga gccagggggg agcagggctc actccagcca cctgaagtcc aaaaagggtc 1320
agtctacctc ccgccataaa aaactcatgt tcaagacaga agggcctgac tcagactgac 1380
attctccact tcttgttccc cactgacagc ctcccacccc catctctccc tcccctgcca 1440
ttttgggttt tgggtctttg aacccttgct tgcaataggt gtgcgtcaga agcacccagg 1500
acttccattt gctttgtccc ggggctccac tgaacaagtt ggcctgcact ggtgttttgt 1560
tgtggggagg aggatgggga gtaggacata ccagcttaga ttttaaggtt tttactgtga 1620
gggatgtttg ggagatgtaa gaaatgttct tgcagttaag ggttagttta caatcagcca 1680
cattctaggt aggggcccac ttcaccgtac taaccaggga agctgtccct cactgttgaa 1740
ttttctctaa cttcaaggcc catatctgtg aaatgctggc atttgcacct acctcacaga 1800
gtgcattgtg agggttaatg aaataatgta catctggcct tgaaaccacc ttttattaca 1860
tggggtctag aacttgaccc ccttgagggt gcttgttccc tctccctgtt ggtcggtggg 1920
ttggtagttt ctacagttgg gcagctggtt aggtagaggg agttgtcaag tctctgctgg 1980
cccagccaaa ccctgtctga caacctcttg gtgaacctta gtacctaaaa ggaaatctca 2040
ccccatccca caccctggag gatttcatct cttgtatatg atgatctgga tccaccaaga 2100
cttgttttat gctcagggtc aatttctttt ttcttttttt tttttttttt tctttttctt 2160
tgagactggg tctcgctttg ttgcccaggc tggagtggag tggcgtgatc ttggcttact 2220
gcagcctttg cctccccggc tcgagcagtc ctgcctcagc ctccggagta gctgggacca 2280
caggttcatg ccaccatggc cagccaactt ttgcatgttt tgtagagatg gggtctcaca 2340
gtgttgccca ggctggtctc aaactcctgg gctcaggcga tccacctgtc tcagcctccc 2400
agagtgctgg gattacaatt gtgagccacc acgtccagct ggaagggtca acatctttta 2460
cattctgcaa gcacatctgc attttcaccc cacccttccc ctccttctcc cttttatat 2520 cccattttta tatcgatctc ttattttaca ataaaacttt gctgccacct gtgtgtctga 2580
ggggtg 2586

<210> SEQ ID NO 5
<211> LENGTH: 19144
<212> TYPE: DNA
<213> ORGANISM: homo sapiens

<400> SEQUENCE: 5
gattggggtt ttcccctccc atgtgctcaa gactggcgct aaaagttttg agcttctcaa 60
aagtctagag ccaccgtcca gggagcaggt agctgctggg ctccggggac actttgcgtt 120
cgggctggga gcgtgctttc cacgacggtg acacgcttcc ctggattggg taagctcctg 180
actgaacttg atgagtcctc tctgagtcac gggctctcgg ctccgtgtat tttcagctcg 240
ggaaaatcgc tggggctggg ggtggggcag tggggactta gcgagtttgg gggtgagtgg 300
gatggaagct tggctagagg gatcatcata ggagttgcat tgttgggaga cctgggtgta 360
gatgatgggg atgttaggac catccgaact caaagttgaa cgcctaggca gaggagtgga 420
gctttgggga accttgagcc ggcctaaagc gtacttcttt gcacatccac ccggtgctgg 480
gcgtagggaa tccctgaaat aaaagatgca caaagcattg aggtctgaga cttttggatc 540
tcgaaacatt gagaactcat agctgtatat tttagagccc atggcatcct agtgaaaact 600
ggggctccat tccgaaatga tcatttgggg gtgatccggg gagcccaagc tgctaaggtc 660
ccacaacttc cggacctttg tccttcctgg agcgatcttt ccaggcagcc cccggctccg 720
ctagatggag aaaatccaat tgaaggctgt cagtcgtgga agtgagaagt gctaaaccag 780
gggtttgccc gccaggccga ggaggaccgt cgcaatctga gaggcccggc agccctgtta 840
ttgtttggct ccacatttac atttctgcct cttgcagcag catttccggt ttctttttgc 900
cggagcagct cactattcac ccgatgagag gggaggagag agagagaaaa tgtcctttag 960
gccggttcct cttacttggc agagggaggc tgctattctc cgcctgcatt tctttttctg 1020
gattacttag ttatggcctt tgcaaaggca ggggtatttg ttttgatgca aacctcaatc 1080
cctccccttc tttgaatggt gtgccccacc ccgcgggtcg cctgcaacct aggcggacgc 1140
taccatggcg tgagacaggg agggaaagaa gtgtgcagaa ggcaagcccg gaggtatttt 1200
caagaatgag tatatctcat cttcccggag gaaaaaaaaa aagaatgggt acgtctgaga 1260
atcaaatttt gaaagagtgc aatgatgggt cgtttgataa tttgtcggaa aaacaatcta 1320
cctgttatct agctttgggc taggccattc cagttccaga cgcaggctga acgtcgtgaa 1380
gcggaagggg cgggcccgca ggcgtccgtg tggtcctccg tgcagccctc cggcccgagc 1440
cggttcttcc tggtaggagg cggaactcga attcatttct cccgctgccc catctcttag 1500
ctcgcggttg tttcattccg cagtttcttc ccatgcacct gccgcgtacc ggccactttg 1560
tgccgtactt acgtcatctt tttcctaaat cgaggtggca tttacacaca gcgccagtgc 1620
acacagcaag tgcacaggaa gatgagtttt ggcccctaac cgctccgtga tgcctaccaa 1680
gtcacagacc cttttcatcg tcccagaaac gtttcatcac gtctcttccc agtcgattcc 1740

```
cgaccccacc tttattttga tctccataac cattttgcct gttggagaac ttcatataga   1800
atggaatcag gctgggcgct gtggctcacg cctgcacttt gggaggccga ggcgggcgga   1860
ttacttgagg ataggagttc cagaccagcg tggccaacgt ggtgaatccc cgtctctact   1920
aaaaaataca aaaattagct gggcgtggtg ggtgcctgta atcccagcta ttcgggaggg   1980
tgaggcagga gaatcgcttg aacccgggag gcagaggttg cagtgagcca agatcgtgcc   2040
actacactcc agcctgggcg acaagaacga aactccgtct caaaaaaaag gggggaatca   2100
tacattatgt gctcattttt gtcgggcttc tgtccttcaa tgtactgtct gacattcgtt   2160
catgttgtat atatcagtat tttgctcctt ttcatttagt atagtccatc gattgtatat   2220
ccgtcctttt gatggccttt tgagttgttt cccatttgcg gttatgaaat aaagctgcta   2280
taaacattct tgtacaattc tttttgtgat catatgtttt cgtgtttctt ggagaaatac   2340
ttaggagggg aattgcgagt ttggaagtaa aaagtagctg tattttgaac tttttcagaa   2400
gctctgagtt ttccagagcg gttgtaccat tttacactcc aactagcaag gtatgggagt   2460
tattatggtt gtgccacagc cttccggaca ttaggtattg tcagtctttc taatgtggta   2520
tatccttgtg gttgtaattt acagttctct attgactaag gatgttcagc attttttcat   2580
gtgcctattg gccattcgta ttttgtttgt aaagtagctc ttcgagtctt ttacctgtta   2640
ttttggtttt ttgtttgttt ttattgttca gttgtgggac tgctttatac attctggata   2700
caagtccttt atcagatcca tgtgtcgtga atgttttctt ctgatctgtt gcttgcctat   2760
ttgtttgctt tacagagttt acagtatctt aagaggagtg gatttatctt ttttatgttc   2820
agtatttgcc ttgtcctgtt taggacatct tttttttttt ttttaacccc agggtcatga   2880
agatattatc ttacattttc ttttaggacc tttatggttg taagttttac agtaaggtcc   2940
ttgagccatt aattaattct taaaattaat tgtttatggt gtgaggtgta ggagtcagtc   3000
tctggtatct ttcctgtatg gaaatccagt tattctgtct ccacttgttg aaataggctt   3060
cctttctcta ctgaatgctt ttaattttaa ttattttaca gttggagtat agggctacca   3120
ttttagtgct attttctttt tttctttgtt aatttttgag acagggactc acactgttgc   3180
ccaggctaga gtacaatggc acaatcaagg cttactgcag cctcgaaccc ctgggctcaa   3240
gcagtcctct agcagcctca cgagtagctg ggattactcc accacaccca gctaactatt   3300
ttattttttt gtattgacag gatctcacta tgttgcccag gctggtctca aactgctggc   3360
ctcaagcttt catcccatct cggcctccca aagtgctggg attacaggtg tgagccacca   3420
tgcctgacct cttagtgcta ttttctattt atctcctctg ttctctgctc tctttaaacg   3480
ttggaggaag aaacagtacc catcttacac aaactcttca gaaaacagag gaacagactg   3540
ggcgcggtgg ctcatacctg taatctcagc actttggtac gctgaggcag gggatcattt   3600
gaggtcggga gttcgagacc agcctggcca acacggcgaa accccatctc tactaaaaat   3660
acaaaaagta gctaggcgtg gtgacacata cctgtaatgc cagttactca ggaggctgag   3720
gcacaagaat cccttgaacc tgggaagcgg aggttgcagt gagccgagat tgcgccactg   3780
cactccagcc tgggcaacag agtgagaccc tgtctcagaa aaaaaaagaa agaaagaaaa   3840
aatagaggaa tatttcccaa cttgttttcg aagccagcat aatcctggta ccaaaaccaa   3900
acaaggacat tataagaaaa gaaaatatag accaatattc ctgttagcat agacatgcaa   3960
cagctaacca attttagcaa accaaacctg gtaatataga aaaaaggata aataggccag   4020
tcgcggtggc tcacgcctgt aatcccagca ctttgggagg ctgaggcagg cagatcactt   4080
```

-continued

```
gaggtcagga gtttgagacc agcctgacca acatggtgaa accccgtttc taataaaaat   4140
acaaaaatca ggctgggcac ggtggctcac gcctgtaatc ccagcacttt gggaggccga   4200
ggtgggcaga tcacgaggtc aggagttcaa gaccagcctg accaatgtgg tgaaacgcca   4260
tctctactaa aaatacaaaa atcagccggt gtggtggcac ctgcctgtaa tcccagctac   4320
tcaggaggct gaggcagaat tgcttgaacc cgggaggcag aggttgcagt gagccaagat   4380
cgtgccactg cactccagcc tgggcgacag agcaagactt catctcaaaa aaaaaaaaaa   4440
attagctggg catggtggtg ggcacctgaa atcccagcta ctcgggagtc tgaggcagga   4500
gaatcgcttg aacccaggag gcagaagttg cactgagctg ggatcacacc attgcactcc   4560
agcctgggca acagagtgag actccatctc aaaaaaagaa aaagaaaaag gataaataca   4620
ttctaaccaa ataatgttta tctcatgatt gtagctgatt caacattcaa aaattggcct   4680
ggtgcagtag ctcaggcctg taatcccaac attttaggag gctgaggcag gaagatctct   4740
tgagcccagg atttcaagac cagcctgggc aacatagtca gactggtctt tactgggggg   4800
aaaaaaatca gtctgtgtaa ttcaccacat taacaaaggg aaacataaaa accctatgat   4860
catttcaaca gatgtagcaa aagcagttaa tgatattcaa cacatatgca tgattacaaa   4920
ccaaccaacc tcctagcaaa ctagggaaag gaaacttaac ctagtttgat aacagggcgt   4980
ccacagtcgg agttccacta gcagcataca taatggtaga aaactcagtg ctgccgggcg   5040
cggtggctca cgcctgtaat gccagcactt tgggaggcct aggcgggcgg atcacgaggt   5100
caggagatcg agactgtcct gactagcatg ctgaaacccc gtctctacta aaaatacaaa   5160
aacaaaaaat tagccgggca tggtggcggg cgcctatagt cccagctact cgggaggctg   5220
aggcgagaga atggcgtgaa cccgggaggc ggagcttgca gagcctagat cgtgccactg   5280
cactccagcc tgggtgacag agtgagactt cgtctcaaaa aaaaaaaaaa aaaaaaaaga   5340
aaagaaaact caacgctttt tcctctaaga tcaggaacta gaaaaggatt tgactctcac   5400
aacgttgata ccatactgga ggttttaacc aggcaagaaa aagaaataat gagggccggg   5460
tgcggtggct caggcctgta atcccagcac tttgggaagc cgagacgggt ggatcacgag   5520
gtcaggagat cgagaccatc ctggctaaca cggtgaaacc ctgtctctac taaatataca   5580
aaaaattagc cgggcgtagt ggcgggcgcc tgtagtccca gctactcggg aggctgaggc   5640
aggagaatgg cgtgaactca gggggcggag cttgcagtga gctgagatcg agccactgca   5700
ctccagcctg ggcgacagag caagactgtg tctcaaaaaa aaaaaaagaa aaagaaataa   5760
tgattagtgg cccgatgtct cacgcctata atcccagcac tttgggaggc cgaggtgggc   5820
agatcacctg aggtctggag ttggagacca gcctgacaaa gatggtgaaa cctcgtctct   5880
attaaaatat taaaaaaata gccaggcgtt ggccgggtac agtggctcat gcctgtaatc   5940
ccagcacttt gggaggccga ggtgggtgga tcacctgagg tcaggagttc aacaccagcc   6000
tggccaacat ggtgaaaccc catctctact aaaaatacaa aaattagccg ggcgtagtgg   6060
cgggcgcctg taatcccagc tacttgggag gcttaggcag gagaatcgct tgaacctggg   6120
aggcggaggt tgtagtgagc cgagattgca ccattgcact ccagcctggg tgacaaaagc   6180
aaaaactccg tctcaaaaaa aaaagaatta gccaggggta gtggtgaacg cctgtagtcc   6240
cagctactca ggaggcagag gcaggagaat cacttgaacc caggaggcag aggttgcagt   6300
gagccgagat tgtcccattg cactccagcc taggcgacaa gagcaaaatt ccatgtcaaa   6360
aaaaaaaaaa aaaaaggaaa gaaaaaaaat aacgattaga aaggaagaaa taaaacacat   6420
tcacagccag tatgattcta tacatacatg tcctaatggg gccaggcgtg gtggctcatg   6480
```

```
cctgtaatcc tagcactttt aggaggctga ggcaggtggc ttccctggga ccagcctggc   6540
caacatggtg aaaccccaac tctaataaaa atacaaaaaa tcagccaggc gtggtgacgg   6600
gcacctctaa tcccagctac tcaggaggct gaggcaggag aattgcttgg acctgggagg   6660
cagaggttgc agtgagccga gatcgcgcta ttgcactcca gcctgggcaa caagagtgaa   6720
actccggcag ggtgtggtgg cttacgcctg taatcccagc acttcgggag gctgaggcag   6780
gccgatcacc tgaggtcagg agtttgagac caacctaaca tggtgaaacc ccgtctctac   6840
taaaaataca agaattagct gggtgtagtg gtgggcgcct gtaatcccag ctacttggga   6900
ggctgagaca gaagaattgc ttgaacccag gaggtggagg ttgcagtgag ctgagatcat   6960
gccattgcac accacgccgg gcaacagagc gagattccgt ctcaaaaaaa aaaaaaaaga   7020
gtgaaactct atctcaaaaa aaaaaaaaag tcctaatgga aatccataa aaagctacca   7080
aaactaataa ataaatatag cagggttgca ggttacaggg caatatagtt atccctctat   7140
ctgtaggggc ttggttctgg gactcctcac acaccaaacc cacagatgtc taagtcccat   7200
atataagacg gtatagtatt tggatttaac ctacacatat cctcccatat agtttaaatt   7260
atctctagat tacttacatt acccccatac aatgaaaatg ctaatgtaca tgcaagtatg   7320
tatgtaagta cttgtactat attgtttagg gaatcactgg acatataggc cttcaagact   7380
gataccagca gccactgtta agattctggt caggcctgcc cctgtttggg gtctcagttg   7440
atctcattgc cttcccaccc agccaagggc acctgcattt ctcttggctc cctggccatt   7500
tggaaggcct agttcagcct ggcacatttg tatcctggcc cactgatgct ggtacccctg   7560
ggaaggtcct gctctgaaaa acacggagat tttagttgct actgaagatt tgagagataa   7620
agacagggag acctgtctgt agacctgtgt ccctccaagt gggattgaga ctttgggccc   7680
cccatttcag gacagcacct cctggcctgt tgactgaata gatccctgaa ggaggtgtac   7740
ttgcattaat ggagtggggg tgggagcagt accacagatc cgcactaaca atcacacagt   7800
tctctctaga ataataatat agaacaagtg aaatagaaca attgcagaaa gagctaacct   7860
ttgttgagct cttactgtgt gcccagcact ttcctcaact ctacatttcc cataatacac   7920
agagtactag gtaggccagg cttggtggct cacgcctgta atcccagcac tttaggaggc   7980
caagggggt ggatcacctg aggtcgggag ttcaagacca gcctgaccaa catggtgaaa   8040
ccccgtctct actagaagta caaaattagc caggtgtggt ggcacatgct tgtagtccta   8100
gctactcagc aggctgaggc aggagaatca tttgaatccg ggaggaggtt gcagtaagcg   8160
gagatagtgc cactgtactc cagcctgggc aataagagct gagactccgt ctcaaaataa   8220
aataaaataa aataaaataa aataaaataa aataaaaaaa gaaaagagcc tgccattaaa   8280
ggagctgttt ggtaggggat gttttgtcag tgcaaacaac agaaaagtgg gctgggcaca   8340
gtggttcatg cctgtaatcc cagcactttg ggaggccaag gcgggcggat cacctgaagt   8400
tgggagttca agaccagcct gaccaatatg gagaaacccc gtctctacta aaaatacaaa   8460
attagccggg cgcagtggcg catgcctgta atcccagcta ctcgggaggc tgaggcagga   8520
gaatcgcttg aacctgggag gcagaggttg cggtgagccg agatcgcacc attgcactcc   8580
agcctggacg agagcaaaac tctgtctcaa aaaaaaaaaa aaacagaaaa gtgtaacaaa   8640
cacttacagt aggcatgttt cttagcaaat ctgatgacaa atttggcata aagaaagaga   8700
gcatccctga aaaaaaaaaa aagaaaaaga aagagagcat cctgcctggg caacatagtg   8760
aaaccctgcc tctacaaaaa aactcaaaaa ttggccgggt gcagtggctc acacctgtaa   8820
```

-continued

```
tcccagcact ttgggagtcg gaggcgggag gatcacctga ggtcaggagt tcgaaaccag   8880
cctggccaac atggcaaaac cccatctcta ctaaaaatac aaaaaattaa tcaggcgcat   8940
tggtgggcgc ctgtaatccc agctactcag gaagttgagg caagaggatc gcttgaatct   9000
gggaggtgga ggttacagtg agtcgagatc acaccactgc actctagcct gggtgacagg   9060
gcgagactcc gtctccaaaa aaaaaaagaa aaagaaaaag actaaaaaat tagccaggca   9120
ggcctctgtg gtcccagcta cttgggaggc tgaggcagga gaatcactga gcccaggagt   9180
ccgaggctgt agtgagccat gattgcacca ctgtacccta gcttgggcaa caaagcaaga   9240
ccctgcctca aaagaaaaaa gaaagaaaga aagaacatgg cgggccaggc acagtggctc   9300
acacctgtaa tcccagcgct ttgagaggcc gaggcaggtg gatcacaagg tcaggagttc   9360
cacaccagcc tggccaacat ggtgaaaccc tgtctctact aaaaatacaa aaaatcagcc   9420
aggcatggtg gcaggggcct gtaatcccag ctactcggga ggctgaggca ggagaattgc   9480
ttgaaaccag aaggcagagg ttgcagtgag cctagactgc accactgcac tccagcctgg   9540
gcgaaaagag ccaaactcca tctcaaaaaa caaacaaaaa aacaaaacaa aagaaaacat   9600
ggcaaagcct ttgaaagctt gtctgggaga aggtgcgatg atagttgcat aacttcgtgc   9660
aagatgctgg tccacacagg ggctgcccct tgctctttct cgctctctta acctctcata   9720
taacaggctt gtgtgttatt cacatttatt gagcccaagc aggtgcaagg cattgtgatc   9780
taatactttg gtcagcaaga caacaagata gatcactgcc ctgcccttag gaagtgtata   9840
tgctattaga ggaaacagat aaaataaaca aggaaaagta tcagacaatg taagtgctat   9900
gagaatgcaa atgaggtgat gtgaattaaa ataggatgac ttaaagtctg cacgggaagg   9960
agcctacccc catgttcctg gctagccaag gaaccaccag ttgattagca gagaagggca  10020
gccagtctag ctagagcttt tggggaagag ggagtggttg ttaagagatg agattaaaga  10080
agccgagacg ggccattcgt gaggggtttg taatgcaggg ctgaggagtg tccgaagaga  10140
atgggcaggt gagcggtgag acagttgttc ttccagaagc tttgcagtga aaggaatcaa  10200
agaaatggag ccgtgtatca ggtggggaag ggtgggggcc aagggggtgt ccttccccat  10260
acagagattg caggctgaga atgactatat ccttgttaac aggaggtggg agcagggcac  10320
ggtagctcac acctgtaatc ttggcacttt aggaggctga ggcgggccga tcacctgaag  10380
taaggagttc gagaccagcc tggccaacat gcaaagccct gtctctacta aaaatacaaa  10440
aattagctgg gtgtggtggt actcgcctgt aatcccagct actcgggaga ctgaggcagg  10500
agaatggctt gaacccggaa ggtagaggtt gcagtgagct gagatcatgc cactgtgctc  10560
cagcctaggt gacagagaga gactccatct caaaaaaaaa aaaaaaatac aggaagggag  10620
ttgggaatag ggtgcacatt taggaagtct tggggattta gtggtgggaa ggttggaagt  10680
ccctctctga ttgtcttttc ctcaaagaag tgcatggctg gtgaggggtg gggcaggagt  10740
gcttgggttg tggtgaaaca ttggaagaga gaatgtgaag cagccattct tttcctgctc  10800
cacaggaagc cgagctgtct cagacactgg catggtgttg ggggaggggg ttccttctct  10860
gcaggcccag gtgacccagg gttggaagtg tctcatgctg gatccccact tttcctcttg  10920
cagcagccag actgccttcc gggtcactgc catggaggag ccgcagtcag atcctagcgt  10980
cgagccccct ctgagtcagg aaacattttc agacctatgg aaactgtgag tggatccatt  11040
ggaagggcag gcccaccacc cccaccccaa ccccagcccc ctagcagaga cctgtgggaa  11100
gcgaaaattc catgggactg actttctgct cttgtctttc agacttcctg aaaacaacgt  11160
tctggtaagg acaagggttg ggctggggac ctggagggct ggggacctgg agggctgggg  11220
```

```
ggctgggggg ctgaggacct ggtcctctga ctgctctttt cacccatcta cagtcccccct  11280
tgccgtccca agcaatggat gatttgatgc tgtccccgga cgatattgaa caatggttca  11340
ctgaagaccc aggtccagat gaagctccca gaatgccaga ggctgctccc cccgtggccc  11400
ctgcaccagc agctcctaca ccggcggccc ctgcaccagc cccctcctgg cccctgtcat  11460
cttctgtccc ttcccagaaa acctaccagg gcagctacgg tttccgtctg ggcttcttgc  11520
attctgggac agccaagtct gtgacttgca cggtcagttg ccctgagggg ctggcttcca  11580
tgagacttca atgcctggcc gtatccccct gcatttcttt tgtttggaac tttgggattc  11640
ctcttcaccc tttggcttcc tgtcagtgtt tttttatagt ttacccactt aatgtgtgat  11700
ctctgactcc tgtcccaaag ttgaatattc ccccttgaa tttgggcttt tatccatccc  11760
atcacaccct cagcatctct cctggggatg cagaactttt ctttttcttc atccacgtgt  11820
attccttggc ttttgaaaat aagctcctga ccaggcttgg tggctcacac ctgcaatccc  11880
agcactctca aagaggccaa ggcaggcaga tcacctgagc ccaggagttc aagaccagcc  11940
tgggtaacat gatgaaacct cgtctctaca aaaaaataca aaaaattagc caggcatggt  12000
ggtgcacacc tatagtccca gccacttagg aggctgaggt gggaagatca cttgaggcca  12060
ggagatggag gctgcagtga gctgtgatca caccactgtg ctccagcctg agtgacagag  12120
caagacccta tctcaaaaaa aaaaaaaaaa aagaaaagct cctgaggtgt agacgccaac  12180
tctctctagc tcgctagtgg gttgcaggag gtgcttacgc atgtttgttt ctttgctgcc  12240
gtcttccagt tgctttatct gttcacttgt gccctgactt tcaactctgt ctccttcctc  12300
ttcctacagt actcccctgc cctcaacaag atgttttgcc aactggccaa gacctgccct  12360
gtgcagctgt gggttgattc cacacccccg cccggcaccc gcgtccgcgc catggccatc  12420
tacaagcagt cacagcacat gacggaggtt gtgaggcgct gcccccacca tgagcgctgc  12480
tcagatagcg atggtgagca gctggggctg gagagacgac agggctggtt gcccagggtc  12540
cccaggcctc tgattcctca ctgattgctc ttaggtctgg cccctcctca gcatcttatc  12600
cgagtggaag gaaatttgcg tgtggagtat ttggatgaca gaaacacttt tcgacatagt  12660
gtggtggtgc cctatgagcc gcctgaggtc tggtttgcaa ctggggtctc tgggaggagg  12720
ggttaagggt ggttgtcagt ggccctccag gtgagcagta ggggggcttt ctcctgctgc  12780
ttatttgacc tccctataac cccatgagat gtgcaaagta aatgggttta actattgcac  12840
agttgaaaaa actgaagctt acagaggcta agggcctccc ctgcttggct gggcgcagtg  12900
gctcatgcct gtaatcccag cactttggga ggccaaggca ggcggatcac gaggttggga  12960
gatcgagacc atcctggcta acggtgaaac cccgtctcta ctgaaaaata caaaaaaaaa  13020
ttagccgggc gtggtgctgg gcacctgtag tcccagctac tcgggaggct gaggaaggag  13080
aatggcgtga acctgggcgg tggagcttgc agtgagctga gatcacgcca ctgcactcca  13140
gcctgggcga cagagcgaga ttccatctca aaaaaaaaaa aaaaaggcct cccctgcttg  13200
ccacaggtct ccccaaggcg cactggcctc atcttgggcc tgtgttatct cctaggttgg  13260
ctctgactgt accaccatcc actacaacta catgtgtaac agttcctgca tgggcggcat  13320
gaaccggagg cccatcctca ccatcatcac actggaagac tccaggtcag gagccacttg  13380
ccaccctgca cactggcctg ctgtgcccca gcctctgctt gcctctgacc cctgggccca  13440
cctcttaccg atttcttcca tactactacc catccacctc tcatcacatc cccggcgggg  13500
aatctcctta ctgctcccac tcagttttct tttctctggc tttgggacct cttaacctgt  13560
```

```
ggcttctcct ccacctacct ggagctggag cttaggctcc agaaaggaca agggtggttg  13620
ggagtagatg gagcctggtt ttttaaatgg gacaggtagg acctgatttc cttactgcct  13680
cttgcttctc ttttcctatc ctgagtagtg gtaatctact gggacggaac agctttgagg  13740
tgcgtgtttg tgcctgtcct gggagagacc ggcgcacaga ggaagagaat ctccgcaaga  13800
aaggggagcc tcaccacgag ctgcccccag ggagcactaa gcgaggtaag caagcaggac  13860
aagaagcggt ggaggagacc aagggtgcag ttatgcctca gattcacttt tatcaccttt  13920
ccttgcctct ttcctagcac tgcccaacaa caccagctcc tctccccagc caaagaagaa  13980
accactggat ggagaatatt tcacccttca ggtactaagt cttgggacct cttatcaagt  14040
ggaaagtttc cagtctaaca ctcaaaatgc cgttttcttc ttgactgttt tacctgcaat  14100
tggggcattt gccatcaggg ggcagtgatg cctcaaagac aatggctcct ggttgtagct  14160
aactaacttc agaacaccaa cttataccat aatatatatt ttaaaggacc agaccagctt  14220
tcaaaaagaa aattgttaaa gagagcatga aaatggttct atgactttgc ctgatacaga  14280
tgctacttga cttacgatgg tgttacttcc tgataaactc gtcgtaagtt gaaaatattg  14340
taagttgaaa atggatttaa tacacctaat ctaaggaaca tcatagctta gcctagcctg  14400
cttttttttt tttttttttt ggagacagag tctcactctg tcacccaggc tggagtgcag  14460
tggcgggatc tcggctcact gcaacctccg ccttctgggt tcaagcgatt ctcctgcctc  14520
agcccactga gtagctggga ttacaggcac ctgccccgac gcccagctaa tttttttgtta  14580
tttatttatt ttttttttta gtagagatga ggtttcacca tgttggccag gctagtctcg  14640
aactcctgac cttgtgatct gcctgccttg gcctcccaaa gtgctgggat tacaggcgtg  14700
agccaccgca cccggcctgc ctagcctact tttattttat ttttaatgga gacagcatct  14760
tgctctgttg cccaggctgg attacagtga tgtgatcata gctcattata ccctcctggg  14820
ctcaagcaat ccccctaact ctgcctcccc agtagctagg accacaggca tacaccacca  14880
tacccagcta atttttaaaa ttttttgtag atagatagag tctcactatg ttgcccaggc  14940
tggtctctag cctacttttt tgagacaagg tcttgctctg tcacccaggc tggatagagt  15000
gcagtagtgc agtcacagct cactgcagcc tccacctccc aggctccatc catcctccca  15060
gctcagcctc ccaagttgct tcaactacag gcctgcacca ccatgcctgg ctaattttta  15120
tttatttatt tttattttat tttattttat ttttttgaga ctcagtctca ctctgtcgcc  15180
caggctggag tgcagtggca tgatctcggc tcactgcaac ctctgcctcc tgggttcaag  15240
tgattctcct gcctcagcct cccgaatagc taggactaca agcgcctgct accacgccca  15300
gctaattttt gtatttttag tagagacagg gtttcaccat gttggccagg ctggtctcga  15360
acttctgacc atgtgatccg cccgcctcgg cctcccaaag tgctgggatt acaggtgtga  15420
gccaccacgc ccggctaatt tttatttatt tatttaaaga cagagtctca ctctgtcact  15480
caggctagag tgcagtggca ccatctcagc tcactgcagc cttgacctcc ctgggctccg  15540
gtgatttcac cctcccaagt agctaggact acaggcacat gccacgacac ccagctaatt  15600
ttttattttc tgtgaagtca aggtcttgct acgttgccca tgctggtatc aaacccctgg  15660
gctcaatcaa tccttccacc tcagcctccc caagtattgg ggttacaggc atgagctacc  15720
acactcagcc ctagcctact tgaaacgtgt tcagagcatt taagttaccc tacagttggg  15780
caaagtcatc taacacaaag cccttttttat agtaataaaa tgttgtatat ctcatgtgat  15840
ttattgaata ttgttactga aagtgagaaa cagcatggtt gcatgaaagg aggcacagtc  15900
gagccaggca cagcctgggc gcagagcgag actcaaaaaa agaaaaggcc aggcgcactg  15960
```

-continued gctcacgcct gtaatcccag catttcggga ggctgaggcg ggtggatcac ctgaggtcag 16020
gagttcaaga ccagcctagc caacatggtg aaaccccgtc tctactaaaa tacaaaaatt 16080
aaccgggcgt gatggcaggt gcctgtaatc ccagctactt gggaggctga ggcaggagaa 16140
tcgcttgaac caggaggcgg aggttgcagg gagccaagat ggcgccactg cactccagcc 16200
tgggcgatag agtgagactc cgtctcagaa aaaaaagaaa agaaacgagg cacagtcgca 16260
tgcacatgta gtcccagtta cttgagaggc taaggcagga ggatctcttg agcccaagag 16320
tttgagtcca gcctgaacaa catagcaaga catcatctct aaaatttaaa aaagggccgg 16380
gcacagtggc tcacacctgt aatcccagca ctttgggagg tggaggtggg tagatcacct 16440
gacgtcagga gttggaaacc agcctggcta acatggtgaa gccccatctc tactaaaaac 16500
acaaaaatta gccaggtgtg gtagcacacg cctgtagtcc cagctactcg ggaggctgag 16560
gcacaagaat cacttgaacc ccagaggcgg agattgcaat cagccaagat tgcaccattg 16620
cactcccgcc tgggcaacag agtgagaccc catctcaaaa taaataaata aatattttta 16680
aaagtcagct gtataggtac ttgaagtgca gtttctacta aatgcatgtt gcttttgtac 16740
cgtcataaag tcaaacaatt gtaacttgaa ccatctttta actcaggtac tgtgtatata 16800
cttacttctc cccctcctct gttgctgcag atccgtgggc gtgagcgctt cgagatgttc 16860
cgagagctga atgaggcctt ggaactcaag gatgcccagg ctgggaagga gccagggggg 16920
agcagggctc actccaggtg agtgacctca gccccttcct ggccctactc ccctgccttc 16980
ctaggttgga aagccatagg attccattct catcctgcct tcatggtcaa aggcagctga 17040
ccccatctca ttgggtccca gccctgcaca gacatttttt tagtcttcct ccggttgaat 17100
cctataacca cattcttgcc tcagtgtatc cacagaacat ccaaacccag ggacgagtgt 17160
ggatacttct ttgccattct ccgcaactcc cagcccagag ctggagggtc tcaaggaggg 17220
gcctaataat tgtgtaatac tgaatacagc cagagtttca ggtcatatac tcagccctgc 17280
catgcaccgg caggtcctag gtgacccccg tcaaactcag tttccttata tataaaatgg 17340
ggtaaggggg ccgggcgcag tggctcacga atcccacact ctgggaggcc aaggcgagtg 17400
gatcacctga ggtcgggagt ttgagcccag cctgaccaac atggagaaac cccatctcta 17460
ctaaaaatac aaaagtagcc gggcgtggtg atgcatgcct gtaatcccag ctacctactc 17520
gggaggctga ggcaggagaa tcgcttgaac ccgggaggca gaggttgcgg tgagctgaga 17580
tctcaccatt acactccagc ctgggcaaca agagtgaaac tccgtctcaa aaaagataaa 17640
taaagtaaaa tggggtaagg gaagattacg agactaatac acactaatac tctgaggtgc 17700
tcagtaaaca tatttgcatg gggtgtggcc accatcttga tttgaattcc cgttgtccca 17760
gccttaggcc cttcaaagca ttggtcaggg aaaaggggca cagaccctct cactcatgtg 17820
atgtcatctc tcctccctgc ttctgtctcc tacagccacc tgaagtccaa aaagggtcag 17880
tctacctccc gccataaaaa actcatgttc aagacagaag ggcctgactc agactgacat 17940
tctccacttc ttgttcccca ctgacagcct cccaccccca tctctccctc ccctgccatt 18000
ttgggttttg ggtctttgaa ccccttgcttg caataggtgt gcgtcagaag cacccaggac 18060
ttccatttgc tttgtcccgg ggctccactg aacaagttgg cctgcactgg tgttttgttg 18120
tggggaggag gatggggagt aggacatacc agcttagatt ttaaggtttt tactgtgagg 18180
gatgtttggg agatgtaaga aatgttcttg cagttaaggg ttagtttaca atcagccaca 18240
ttctaggtag gggcccactt caccgtacta accagggaag ctgtccctca ctgttgaatt 18300

```
ttctctaact tcaaggccca tatctgtgaa atgctggcat ttgcacctac ctcacagagt  18360

gcattgtgag ggttaatgaa ataatgtaca tctggccttg aaaccacctt ttattacatg  18420

gggtctagaa cttgacccc ttgagggtgc ttgttccctc tccctgttgg tcggtgggtt  18480

ggtagtttct acagttgggc agctggttag gtagagggag ttgtcaagtc tctgctggcc  18540

cagccaaacc ctgtctgaca acctcttggt gaaccttagt acctaaaagg aaatctcacc  18600

ccatcccaca ccctggagga tttcatctct tgtatatgat gatctggatc caccaagact  18660

tgttttatgc tcagggtcaa tttcttttt ctttttttt ttttttttc tttttctttg  18720

agactgggtc tcgctttgtt gcccaggctg gagtggagtg gcgtgatctt ggcttactgc  18780

agcctttgcc tccccggctc gagcagtcct gcctcagcct ccggagtagc tgggaccaca  18840

ggttcatgcc accatggcca gccaactttt gcatgttttg tagagatggg gtctcacagt  18900

gttgcccagg ctggtctcaa actcctgggc tcaggcgatc cacctgtctc agcctcccag  18960

agtgctggga ttacaattgt gagccaccac gtccagctgg aagggtcaac atcttttaca  19020

ttctgcaagc acatctgcat tttcacccca cccttcccct ccttctccct ttttatatcc  19080

catttttata tcgatctctt attttacaat aaaactttgc tgccacctgt gtgtctgagg  19140

ggtg                                                               19144
```

<210> SEQ ID NO 6
<211> LENGTH: 5572
<212> TYPE: DNA
<213> ORGANISM: homo sapiens

<400> SEQUENCE: 6

```
cctcccctcg cccggcgcgg tcccgtccgc ctctcgctcg cctcccgcct cccctcggtc     60

ttccgaggcg cccgggctcc cggcgcggcg gcggaggggg cgggcaggcc ggcgggcggt    120

gatgtggcgg gactctttat gcgctgcggc aggatacgcg ctcggcgctg ggacgcgact    180

gcgctcagtt ctctcctctc ggaagctgca gccatgatgg aagtttgaga gttgagccgc    240

tgtgaggcga ggccgggctc aggcgaggga gatgagagac ggcggcggcc gcggcccgga    300

gcccctctca gcgcctgtga gcagccgcgg gggcagcgcc ctcggggagc cggccggcct    360

gcggcggcgg cagcggcggc gtttctcgcc tcctcttcgt cttttctaac cgtgcagcct    420

cttcctcggc ttctcctgaa agggaaggtg gaagccgtgg gctcgggcgg gagccggctg    480

aggcgcggcg gcggcggcgg cacctcccgc tcctggagcg ggggggagaa gcggcggcgg    540

cggcggccgc ggcggctgca gctccaggga gggggtctga gtcgcctgtc accatttcca    600

gggctgggaa cgccggagag ttggtctctc cccttctact gcctccaaca cggcggcggc    660

ggcggcggca catccaggga cccgggccgg ttttaaacct cccgtccgcc gccgccgcac    720

cccccgtggc ccgggctccg gaggccgccg gcggaggcag ccgttcggag gattattcgt    780

cttctcccca ttccgctgcc gccgctgcca ggcctctggc tgctgaggag aagcaggccc    840

agtcgctgca accatccagc agccgccgca gcagccatta cccggctgcg gtccagagcc    900

aagcggcggc agagcgaggg gcatcagcta ccgccaagtc cagagccatt tccatcctgc    960

agaagaagcc ccgccaccag cagcttctgc catctctctc ctcctttttc ttcagccaca   1020

ggctcccaga catgacagcc atcatcaaag agatcgttag cagaaacaaa aggagatatc   1080

aagaggatgg attcgactta gacttgacct atatttatcc aaacattatt gctatgggat   1140

ttcctgcaga aagacttgaa ggcgtataca ggaacaatat tgatgatgta gtaaggtttt   1200

tggattcaaa gcataaaaac cattacaaga tatacaatct ttgtgctgaa agacattatg   1260
```

```
acaccgccaa atttaattgc agagttgcac aatatccttt tgaagaccat aacccaccac   1320
agctagaact tatcaaaccc ttttgtgaag atcttgacca atggctaagt gaagatgaca   1380
atcatgttgc agcaattcac tgtaaagctg gaaagggacg aactggtgta atgatatgtg   1440
catatttatt acatcggggc aaatttttaa aggcacaaga ggccctagat ttctatgggg   1500
aagtaaggac cagagacaaa aagggagtaa ctattcccag tcagaggcgc tatgtgtatt   1560
attatagcta cctgttaaag aatcatctgg attatagacc agtggcactg ttgtttcaca   1620
agatgatgtt tgaaactatt ccaatgttca gtggcggaac ttgcaatcct cagtttgtgg   1680
tctgccagct aaaggtgaag atatattcct ccaattcagg acccacacga cgggaagaca   1740
agttcatgta ctttgagttc cctcagccgt tacctgtgtg tggtgatatc aaagtagagt   1800
tcttccacaa acagaacaag atgctaaaaa aggacaaaat gtttcacttt tgggtaaata   1860
cattcttcat accaggacca gaggaaacct cagaaaaagt agaaaatgga agtctatgtg   1920
atcaagaaat cgatagcatt tgcagtatag agcgtgcaga taatgacaag gaatatctag   1980
tacttacttt aacaaaaaat gatcttgaca aagcaaataa agacaaagcc aaccgatact   2040
tttctccaaa ttttaaggtg aagctgtact tcacaaaaac agtagaggag ccgtcaaatc   2100
cagaggctag cagttcaact tctgtaacac cagatgttag tgacaatgaa cctgatcatt   2160
atagatattc tgacaccact gactctgatc cagagaatga accttttgat gaagatcagc   2220
atacacaaat tacaaaagtc tgaatttttt tttatcaaga gggataaaac accatgaaaa   2280
taaacttgaa taaactgaaa atggaccttt tttttttaa tggcaatagg acattgtgtc   2340
agattaccag ttataggaac aattctcttt tcctgaccaa tcttgtttta ccctatacat   2400
ccacagggtt ttgacacttg ttgtccagtt gaaaaaaggt tgtgtagctg tgtcatgtat   2460
ataccttttt gtgtcaaaag gacatttaaa attcaattag gattaataaa gatggcactt   2520
tcccgtttta ttccagtttt ataaaaagtg gagacagact gatgtgtata cgtaggaatt   2580
ttttcctttt gtgttctgtc accaactgaa gtggctaaag agctttgtga tatactggtt   2640
cacatcctac ccctttgcac ttgtggcaac agataagttt gcagttggct aagagaggtt   2700
tccgaagggt tttgctacat tctaatgcat gtattcgggt taggggaatg gagggaatgc   2760
tcagaaagga aataatttta tgctggactc tggaccatat accatctcca gctatttaca   2820
cacacctttc tttagcatgc tacagttatt aatctggaca ttcgaggaat tggccgctgt   2880
cactgcttgt tgtttgcgca ttttttttta aagcatattg gtgctagaaa aggcagctaa   2940
aggaagtgaa tctgtattgg ggtacaggaa tgaaccttct gcaacatctt aagatccaca   3000
aatgaaggga tataaaaata atgtcatagg taagaaacac agcaacaatg acttaaccat   3060
ataaatgtgg aggctatcaa caaagaatgg gcttgaaaca ttataaaaat tgacaatgat   3120
ttattaaata tgttttctca attgtaacga cttctccatc tcctgtgtaa tcaaggccag   3180
tgctaaaatt cagatgctgt tagtacctac atcagtcaac aacttacact tattttacta   3240
gttttcaatc ataatacctg ctgtggatgc ttcatgtgct gcctgcaagc ttcttttttc   3300
tcattaaata taaaatattt tgtaatgctg cacagaaatt ttcaatttga gattctacag   3360
taagcgtttt ttttctttga agatttatga tgcacttatt caatagctgt cagccgttcc   3420
acccttttga ccttacacat tctattacaa tgaattttgc agttttgcac atttttttaaa   3480
tgtcattaac tgttagggaa ttttacttga atactgaata catataatgt ttatattaaa   3540
aaggacattt gtgttaaaaa ggaaattaga gttgcagtaa actttcaatg ctgcacacaa   3600
```

```
aaaaaagaca tttgattttt cagtagaaat tgtcctacat gtgctttatt gatttgctat   3660

tgaaagaata gggttttttt tttttttttt tttttttttt ttaaatgtgc agtgttgaat   3720

catttcttca tagtgctccc ccgagttggg actagggctt caatttcact tcttaaaaaa   3780

aatcatcata tatttgatat gcccagactg catacgattt taagcggagt acaactacta   3840

ttgtaaagct aatgtgaaga tattattaaa aaggtttttt tttccagaaa tttggtgtct   3900

tcaaattata ccttcacctt gacatttgaa tatccagcca ttttgtttct taatggtata   3960

aaattccatt ttcaataact tattggtgct gaaattgttc actagctgtg gtctgaccta   4020

gttaatttac aaatacagat tgaataggac ctactagagc agcatttata gagtttgatg   4080

gcaaatagat taggcagaac ttcatctaaa atattcttag taaataatgt tgacacgttt   4140

tccatacctt gtcagtttca ttcaacaatt tttaaatttt taacaaagct cttaggattt   4200

acacatttat atttaaacat tgatatatag agtattgatt gattgctcat aagttaaatt   4260

ggtaaagtta gagacaacta ttctaacacc tcaccattga aatttatatg ccaccttgtc   4320

tttcataaaa gctgaaaatt gttacctaaa atgaaaatca acttcatgtt ttgaagatag   4380

ttataaatat tgttctttgt tacaatttcg ggcaccgcat attaaaacgt aactttattg   4440

ttccaatatg taacatggag ggccaggtca taaataatga cattataatg ggcttttgca   4500

ctgttattat ttttcctttg gaatgtgaag gtctgaatga gggttttgat tttgaatgtt   4560

tcaatgtttt tgagaagcct tgcttacatt ttatggtgta gtcattggaa atggaaaaat   4620

ggcattatat atattatata tataaatata tattatacat actctcctta ctttatttca   4680

gttaccatcc ccatagaatt tgacaagaat tgctatgact gaaaggtttt cgagtcctaa   4740

ttaaaacttt atttatggca gtattcataa ttagcctgaa atgcattctg taggtaatct   4800

ctgagtttct ggaatatttt cttagacttt ttggatgtgc agcagcttac atgtctgaag   4860

ttacttgaag gcatcacttt taagaaagct tacagttggg ccctgtacca tcccaagtcc   4920

tttgtagctc ctcttgaaca tgtttgccat acttttaaaa gggtagttga ataaatagca   4980

tcaccattct ttgctgtggc acaggttata aacttaagtg gagtttaccg gcagcatcaa   5040

atgtttcagc tttaaaaaat aaaagtaggg tacaagttta atgtttagtt ctagaaattt   5100

tgtgcaatat gttcataacg atggctgtgg ttgccacaaa gtgcctcgtt tacctttaaa   5160

tactgttaat gtgtcatgca tgcagatgga aggggtggaa ctgtgcacta aagtgggggc   5220

tttaactgta gtatttggca gagttgcctt ctacctgcca gttcaaaagt tcaacctgtt   5280

ttcatataga atatatatac taaaaaattt cagtctgtta aacagcctta ctctgattca   5340

gcctcttcag atactcttgt gctgtgcagc agtggctctg tgtgtaaatg ctatgcactg   5400

aggatacaca aaaataccaa tatgatgtgt acaggataat gcctcatccc aatcagatgt   5460

ccatttgtta ttgtgtttgt taacaaccct ttatctctta gtgttataaa ctccacttaa   5520

aactgattaa agtctcattc ttgtcaaaaa aaaaaaaaaa aaaaaaaaaa aa           5572
```

<210> SEQ ID NO 7
<211> LENGTH: 105338
<212> TYPE: DNA
<213> ORGANISM: homo sapiens

<400> SEQUENCE: 7

```
cctcccctcg cccggcgcgg tcccgtccgc ctctcgctcg cctcccgcct cccctcggtc     60

ttccgaggcg cccgggctcc cggcgcggcg gcggaggggg cgggcaggcc ggcgggcggt    120

gatgtggcgg gactctttat gcgctgcggc aggatacgcg ctcggcgctg ggacgcgact    180
```

-continued

```
gcgctcagtt ctctcctctc ggaagctgca gccatgatgg aagtttgaga gttgagccgc    240
tgtgaggcga ggccgggctc aggcgaggga gatgagagac ggcggcggcc gcggcccgga    300
gcccctctca gcgcctgtga gcagccgcgg gggcagcgcc ctcggggagc cggccggcct    360
gcggcggcgg cagcggcggc gtttctcgcc tcctcttcgt cttttctaac cgtgcagcct    420
cttcctcggc ttctcctgaa agggaaggtg gaagccgtgg gctcgggcgg gagccggctg    480
aggcgcggcg gcggcggcgg cacctcccgc tcctggagcg ggggggagaa gcggcggcgg    540
cggcggccgc ggcggctgca gctccaggga gggggtctga gtcgcctgtc accatttcca    600
gggctgggaa cgccggagag ttggtctctc cccttctact gcctccaaca cggcggcggc    660
ggcggctggc acatccaggg acccgggccg gttttaaacc tcccgtgcgc cgccgccgca    720
ccccccgtgg cccgggctcc ggaggccgcc ggcggaggca gccgttcgga ggattattcg    780
tcttctcccc attccgctgc cgccgctgcc aggcctctgg ctgctgagga gaagcaggcc    840
cagtcgctgc aaccatccag cagccgccgc agcagccatt acccggctgc ggtccagagc    900
caagcggcgg cagagcgagg ggcatcagct accgccaagt ccagagccat ttccatcctg    960
cagaagaagc cccgccacca gcagcttctg ccatctctct cctccttttt cttcagccac   1020
aggctcccag acatgacagc catcatcaaa gagatcgtta gcagaaacaa aaggagatat   1080
caagaggatg gattcgactt agacttgacc tgtatccatt tctgcggctg ctcctcttta   1140
cctttctgtc actctcttag aacgtgggag tagacggatg cgaaaatgtc cgtagtttgg   1200
gtgactataa catttaaccc tggtcaggtt gctaggtcat atattttgtg tttcctttct   1260
gtgtattcaa cctagggtgt gtttggctag acggaactct tgcctggttg caagtgtcaa   1320
gccaccgatt gctttcttag gctatctata tggtctcttc ctgagggcta ttgtccgtta   1380
atacagaata cagtacactg ttagtggatt agcgagctcg gtaatccggt ctcctaaatg   1440
aacaaaaaag tagacgcttt ttgaggttga gcatatttcg attaaatctt ggcttaggcc   1500
ctagatcaag ggtttagatc agaataaaat gaaaattagt gttgcacgta cgcatattgc   1560
atcagaatct tgcagtgatt gttttagttt cctgagttgc attgatagat tcttttaaaa   1620
tatgactgat ttgcataact ttagaagcag aatcattttc agtatatatg gtgcacattg   1680
agggcaaaaa gtagttttgt taatgtttaa acttaagtta cctacaactt tgaactgtat   1740
gtagaagttt tgtagtttga agtcaatagt gccataatat accttataag gcgttcttac   1800
tagatctttg ttatatttac ctttttctct ccctatgggg tgatgtagga tagtgcttga   1860
aatttgcact tcagtagcat ttaatgttca gtgctcttgt cataaacata gaatggatat   1920
tgagtagttt ctgatcccag atggtaatgt gtaggttcaa gggtattgtg tgtagcaagt   1980
gaagattgca gaaataaaac ttcagttcat gcttgaaatt taagtattgt tgtgatgcca   2040
gaattgctgc tcaccgtttt taggtttcag gtcctctgac accttttggt atcgttaatt   2100
ttactgattt gtgtagaatg tcagttgtat tttaccagct aatatctaga aatgctggca   2160
agaggggttt actccagctt tagattgtag gtatgttagc ttttttcata cagtgtatta   2220
aatttactga gtcagcttgc tgaataagac agaagcccaa gaattttaac agtgtgtagc   2280
tttagttgtc taaaagttag gccttcgggc ttcaaaagtt agtggtcatc gaaaagcatt   2340
aatctttgca gtttcaggta caacacattg gttttgatta gggatgggga tggggccctc   2400
tttttgcaga atggggaaag tattgacagg aattgagagc tattggtagg ccagtgtata   2460
aggtatgtga aaacagaatt aagttattgg tctgaagtga ctgaagcatt taggctctat   2520
```

-continued

```
caaggcctaa aatttggtaa tatgagtttg gtaatgcgaa ttgtggcagt ggacaatatt   2580
tagttaaaat tatgtaattg cataagtact agcacagtat ttttaataaa agttatttct   2640
tagcaaatgt cagttgcatt ttgtctaaag gtagagtgac actacagtgt ctatatgtcc   2700
tgctaaaaat tgtggggaat attttttttt aagacagcgt ttatatcggg agaggtttta   2760
ttccgttgga ttatgttagc tgcatataaa tgtgcacagt taattttgcc caagtttttg   2820
ttttgaaatg aatgtaaaac ttactgaaga agtagcttcc caaaatttag ttttctgtta   2880
agccaaaaat attattttaa aagagtattt gcaaattttg aagttgacat taattgagaa   2940
tgttactaag gctaaactgg acccgcttgc ccagaagata attatggaaa aattcttttg   3000
tgacttccaa agcagtctac tattagcatg aattactgac agtcatccaa atatatagga   3060
acaaaaaatt aaatgtttat gtaactttga aaaaaaagcc tttgaagaaa ataattgaat   3120
gctgtctggg agacagattt ctttcagcac ttaaagtaca taacacacta cttttacttt   3180
tcccacttga ttttaaatta tcagggttat taagacctta aaattatttt accaggtttt   3240
tacatgtgag ctgtgacatg actggcattt tctttgattt cagcgtatgt tggtctctac   3300
acatgaaatt tgtgtgactt aaaactttct ctaaaactgt acttttagtt atgatatgca   3360
tagaaagcag tatcaaatat tgcgtcaaat gactaataac acttaatttc tagagttgtg   3420
gttttattga gccaaaagtt gatatgaaaa aaagtcagta aggaaagtca gtgaagtgct   3480
tgcttttttg ataattgcac tcccaataat tttgatattc caacgtactt ggtttgcttg   3540
ttttcacgtt aatgttttct gtttattgga gtgggaaggc attaaaattg tcattgaaga   3600
ctttgtcttt gacatgttgt agtatttatt tcagtaacta acctgtgaaa agttaaattc   3660
ctttatgaaa gtagtgattg gagtattttt atctgataaa gaaagattaa taatgaagcc   3720
atttctccga ggaaaattga ggacaataat tcagttttaa aatattatcg caaaattaaa   3780
ttattctaaa aatttgttag tagggttata tgcttaatat tagtctgaaa tatagtgctg   3840
aatttgagac tatagaaaaa ttaagtgtat ttagggtatg tggaaacgtt aggcttctgt   3900
tgtattttta ttgtttggta gatttgcctc ttttcaaata aatgttcaca gggaatactt   3960
ttaacttgta gagagtacag tgactattga agttacctaa attacctcaa ggtaagtgat   4020
tactgaaatt aatcatgagg gttttaaaaa gtattctatt cacaacattt attttacatt   4080
gttttgtatc tgctaagtta tatttcctga aaaacatgac tggaccacct aattgctgta   4140
tgataactta caaacttcat ttttcatagt gcttattcaa gtgtaaagca caactgaaag   4200
gagtaatgta cagtttatat gaggaaaaag gaattttatt gctgccagtg taaaagtttg   4260
cacagcagta tagtcatcaa tgcagattta cattgcttat aatatactaa gtaaatacta   4320
aatgattaaa gataataaaa tatggtgagg tataaccacc ttcattttaa acttagtttt   4380
agaagatagt aaagaaagat tcctttatta cctttttaga attttatttt taataacatg   4440
ggaaaggcaa ctggtgatat tttaattttt gtatggaaca gtgcatctgc tttctcatag   4500
ccacataaaa tacataaact tcttagtgtt atgaaatggc ttacttttttg gaagtgaaga   4560
agtcttcaat tcttattttc taatgttatt ttgaaatttg cctccatttg ctgtttgttc   4620
atttggtgat agcgcaacac ttaaaaaaat attttaagcc gcttctgaag taatcacttc   4680
agtgactttt aatggaggag tatttgttat gggaaattca cttcacaaag ttttaacatt   4740
aattcacttg aagtaaacgt gctattttta aattttcatc tcaatctttt aagtaagacg   4800
aaagcttagg aaatcacttt tattattgat attgtgtgtg acttcagagt ttgtaaagag   4860
aattgtagaa gtgttgcatg catatgacaa ttttctgctt aattgaaatg tgaggcctct   4920
```

gccatactac aaggatttag cttccagaaa atgtaatatt aacatagctt aagaaatgta 4980
ttttttttt tctgtagaaa ccgttgggtt aaacaaacag ttcagaagtt ttattacatg 5040
gaacccatta gttcttaatc ttgttacctt tttcttcatt ttttctgtta aacttgattt 5100
tcacagtcag cattgaagaa ttcatcttgt ggcctgaatt cattaagaaa agatgttagg 5160
atttgttctg aagatagtga cttaggaaat ttgtgagact ggggtcagtc agttctgttt 5220
tacaattgct ttctatttgg tagctttgaa attaatttag ttgcttatca gagagaataa 5280
tgttgaggtt agactaacct taaattggta aggctttgct gagcaaactg ataactgtaa 5340
gtcttttata gggtgcatta ctgccacata tacgttcttc cataggtggt taaaagtata 5400
ttggtctgtg tttggtgatt ctctttgtac atattgagta tatgcattca ctaatgtaaa 5460
ataatttgcc aagaaaggtg aaattagtat attgtacttg actattcacc tttcccttag 5520
tttttgaat ttttttcatt ggttgcagag gaagtattag caatttaatt cttttaaaat 5580
aatttgcact ggaataaata agtatcggca aatataagaa gagtaacata atttaagggt 5640
gaattaattt tatttgggaa gttttagttc tgtatagtta aggcagattc ttcatttgca 5700
acagttgaca ttgggacatg tgtgaacatc ttcaaggtat taggacatct tcaaggcatt 5760
actttttggc agtgttgaga attttttttt tttttttttt tttttgaga tggaatctcg 5820
ctctatcgcc cagtctgggg tgcagtggca ggatctcggc tcactggaac ctctgcctcc 5880
caggttcagg cgattctcct gcctgaacct cccaagcagc tgggattata ggtgcatgcc 5940
accacgccca gatagttttt gtacttttag tagagatggg gttttaccac cttggccagg 6000
ctggtctcaa actccagacc tcaagtgatc cgcctgcctc ggcctcccaa aatgctggga 6060
ttacaggcgt gagccactgc gcctggccag tgttgagaat attgagagat ggatattgta 6120
gctgtacctg ccatcaaaag aattttcttg acctccacat agtgtgaaaa agaagactgt 6180
ttacacatta tattttaagt aattatacac ataattatta tcagtactca ccacttcaaa 6240
tatgaacagt gaatctaacc agtgtttgat ttctctgtgt gtgtatgtgt atacaaagtt 6300
agcaaacctt ttatcttaat atttattaaa aaacgaattt ttgtttcttt aaagaaaaga 6360
ctaccttaga gaatattgtt ctatagtttt taaatatggt cagatctatt ttaaattatg 6420
ttaaaatttt gagtattacg tttatctata cttttaagca tatatacatt gtttcatttt 6480
agattttagg gaggcagtgt gggctctgga gccagactgc ttgttttgta atcctggatc 6540
ttccatttag tagctggatg actttgagta ggttatttag attttctcaa tctattttat 6600
ctgtaaaatg gggatgataa tggaacctac cgcatacgtt tatcttgaat agtaagtgag 6660
ataataataa gtaatttcat ttagcatagt acctgccaca ttgtaaatac ttaaatggta 6720
gctactgctc tgaaaaactg taatttcagg ttatgtatgt agggaaatta tttgtatttt 6780
catttatggt gtatgattgt aactgaattt cctcagtttg ggccatgtta ggattttgtt 6840
tcaagttata agtgttttta aaaataaggg tattccttta ggaagtctgg gtatgacatg 6900
tctgtgattt tgctggttca tcacaaatgg gaaataaatc tctgctaact caaactgttg 6960
accaaagtaa aattaattat gccaatcaaa aactatttgc tttaaaatat aaaaggcaaa 7020
aacttcctat tagcataatg aagtagaatt tttaaacttt gttataatct taaattttct 7080
ttagtgttga agataggtca acttaactat catacatttt tattcacata aagtaaactc 7140
tgcctcaaat gtaataaact taatatgagt tatgtaaact ttggtcaata gaggtatatt 7200
ttttagcatt tccttttgaa aatttcagcc ttttgaggga gtcttgcaac tgaatgtcaa 7260
gttacattta ttacaataaa atggacactt aatataatct gtaatgcatt aacataatat 7320
gggaactttt aaagtattca gtctctgtat tattgagtcc tatttccaca tttggccagg 7380
attctcaata tgatttaggc ccaagacgtg ggaagaaaga agtaaagaac taaaggattt 7440
ttttcttcat ttttttaatt gaatatgggg aaagatggaa taagcttatc tgtccagtaa 7500
aggccattat gtgtacatag ggattattat ttttcccccc cttgggctgt actgatttcc 7560
cagatgtacc acagcactct tagtagtgaa gcacttgact tctagtgagt ggattttttg 7620
tgtgtgtgtt ttatattgca gagtgaatac actctgtctg atactatgtg actttctgat 7680
tatgtgattt ttatgcattt tatgtgtttt gtaaactagc tgtatttttg gtccatgtct 7740
aggttgtaga attgaattgt gcattttggc atctgagcac agctgagttt tctaaatcaa 7800
tctctctcct tgcacctagt ttttgcttta gatcactacc taagacttac tgttgattta 7860
atattagagc acttaagcat agctttgact tttatttcct ttgatttttg tagattttca 7920
ggctgaagta caataaggtt ctctgttctt tactagtaat tgcaaagatt gtattctgtg 7980
aattttattt gtttaatact tttgatcttt tgaagaggat gtaattattt aaggtattat 8040
gaaatgcatt gtgatttgaa ttagatactc tttggagatg gagttttgct gttgttgccc 8100
aggctggagt gcaatggtgt gatctcggct caccacagcc tccgcctcct gggttcaagc 8160
aattctcttg ccgcagcctc ccaagtagct ggaattacag gcatgcgcca ccacgcccgg 8220
ctaattttat attttttttt tcagtagaga tggggggttt ctccatgttg gtcaggctgg 8280
cctcgaactc ttgacctcag gtaatctgcc tgtctcagcc tgctaaagtg ctgagattac 8340
aggcatgagc cactgcgccc ggcctcagat actcttttaa ttagatgcgt ttaaaaattt 8400
aacccaccat tgctggcatg aatagatgta tttttagagt gattcataaa tatcgtatac 8460
atgtttaaag ttacaaactt tttgcttatt tcaaaatgca ggattctttt ccatttaaaa 8520
ttccctctct ttgtgagact tctttttgag tattctggtt actctaaact gattggagat 8580
gaaattagat agaattgaaa actgtacttt taaaatgaaa ttttggggat gtcattaagc 8640
ttgatttttt aggttttttt tttagtgtgt attataaatt attttacact gattgtcagc 8700
gataaaatgg aatgcctggg attttttaaa atttatttta ttcattttta taaggtaaaa 8760
acagtgtttt gctaggctta atttgaccat gttgtaaaat ttattgtata ccttgaaaga 8820
atcatttatg aaagatactg aattagctaa tatatactct gtcttatgta gtttttgatt 8880
aacaatacac tttttaaatc attagctcat ttgattttgc aaagaagaac aggtaaccta 8940
agaggcagac agaacaggca ttacttttat ttttctttct tttttatttt atttatttat 9000
ttatttattt attttttgca gcttaggaat tgtagctcca gtggaatcag tatcttgtta 9060
atggctagtg aaagactgag tctgaagaag gatgcaggac ttttttggca cttggtgcag 9120
tatttttccc attatgttac atgagtggtt cttaaacttc agtgtgttag aacaacctga 9180
agggcttatt aagctatgga ttgcttactc caccctcaga gtttctgatt cagtaggtct 9240
ggattgggac ctgagaattt ttatttctta gaagttttca agtgatgctg atgctggtgc 9300
tctggggatc acactttgag gaccaccaat gaacattatc tcccaccaag caaaccctta 9360
acatgttata ctcctttagg ttattagaat ttatacatgc attatttcat ttgacctgta 9420
aactctaagt aactttgcat ggaaaatgtt atcctgattt tatagacgag atagtgagtt 9480
tagaaaggca gtatggtgga atggagcata gatttggagt tggctagacc taaagtccag 9540
attaaatctc tgctcaaggc tgggcgtggt ggctcatgcc tgtaatccca gtgctttggg 9600
aggccagcgt tggcagattg cttgagtctg gaagttcgag accagtctgg gcaacatagg 9660

```
cagaccctgt ctctacaaaa aaaaatacaa aaattagtcg ggtgttatag tgcgcattgg   9720
tagtcccagc tactgaggag gctgaggtgg gatcacctga gactgggact ttgaggctgc   9780
attgagctgt gattgggaca ctgtactcct gcctgggtga cagagtgaga ccctctctca   9840
aaaataaata aataaataca tccccgctca gccacttatc agttacgtag atacactgcc   9900
taaccttagt gaaccctgtt tcgacaactc caaaatggga gtaaaaatcc taaacttgta   9960
cagtggtttt ttagttttgt taaaagtaca ggtgaggttt ttttcagagt attggttgcc  10020
atctgagagt gatccccttt cacctcctct aggactttta gcattttctg gagacatttt  10080
ggtggtcaca gctggggtgg tagagtgtgc tattggctag gggcttgaag ccagtgatgc  10140
tgcttaacat cctatatggc acaagacccc tccccatcaa caaagaatta tctagcccaa  10200
aatgctgtgt aaaatgtctg gtatataata agtataaatat ttgatgaaaa tcagtacctt  10260
tgcccccagg tgtgatattt aagaaggtca acttactaaa tcagtgatgg agttagtcct  10320
aacatctggg tgttctgact gctgctaggc cagtattctt tatatgataa taagaacttt  10380
gtccacagaa gatatcccta ataacaaaaa aggtttattt gaagaggact catgtgttct  10440
ttggctgatt gtgaaagtgt tgctttgaac ttctgttaga aaaggttgaa gatgttttcc  10500
gtaagtgttt ttaatactgt acgtagtatt cagaaggatg tttaattttt tttttaattt  10560
tgctagtagt ttttaaagta atccttttttc ctttaattat gtagttgttg aactgttggg  10620
agttactttt ctcttactat tttgttattt aatgtattct ttgaccttat gctttttttat  10680
tctaaagctg cttttattat agtcagatat gatgaagtta aatgtacaat gtaaaattgc  10740
aaatttccaa cgagctatac aaacttaaat atttctaagt aaagaaaata gggctgactc  10800
taaggttctt tgatccatgt gttgcattct tttctaggcc ctaaatttgc tatgccagcc  10860
tgttgaatta aagtgcttta tttatctaaa ttagaaactt gtattaaagt gaagttttag  10920
aaaaaaagaa acaaaatcgg aatggagttt taggttagcc cagagatggg aagatgccaa  10980
gaaggtagct ttagtggatt ctgaattttt tggttttgtt ttgtttttag ggcaggcaaa  11040
tgtaattaca aaagggttct aggaatagat tgctgtgatt ttttttctgt ttgcatgatt  11100
ttacagtttg ctttgcctct cacttttgaa tgcagaataa aatgtcaagg ccttattttt  11160
ttttaaattc ttaagaaatt taagatttga ctgttaattc cttttgaaat atgggatatt  11220
ttgagatacc aattatttaa gacaaatagg actcattgtt acaattcagt tgaataaggc  11280
ttatgatgtt tatttcagta tatgaatgaa aactatgtgc ttattgtact taagaaaatt  11340
tcttttatta aaaacatgac taaagagaat tttaaaaatc acccactgtc ctacttctct  11400
aaaacttaat gttttcatat tagcttccag ttttgttcat atgcatatac tttaaaacct  11460
agttcatggt gaacttaaga gggtgttctt tttaaaaaac aatttccatt gcactttgtc  11520
gttgccttaa ttaaatggtg aaatcatcag aaatatttat tttcctatac ttatacattt  11580
attaagcttg tttccatttt tttattttgt gattttttaa gtggatttaa gataacctaa  11640
acattagaga ggattttcat ggttttgatt catgaaatca taatgttata caaacctaac  11700
tgaagtgtta gagccttgaa gatttttccc ccgaattaca tatagtaact ctacttgtat  11760
ttaatactga aagcatattt tacttattta agtgagacaa agtaaaattt agctgaatac  11820
tttagatcta tcatttcctt ttcctgttgt aagaacatta cattgtgttg aaattaaagt  11880
ggatatagaa ggtaattaga ataaactgcc acatcatttt tatagtaaag tggtaataac  11940
actattgctt tctgtttttt taatcagaag gagtatgggc ttataatgat gttactgttc  12000
```

```
cctgaagcat attttgaatg atacggttta tatttgcaca gttgcccagg taatcattgt  12060
gatattaatt gatcaatttg ctatttattt gcgttttaaa tcagtactag tatttgtgct  12120
taaaaatttt gcatatgttt tatcagattt aatttttaag tgtcagatac taaaacaaat  12180
aaccttaact ttattaaatt ataatttttt atcatgaggt ggtattcatt tattcatata  12240
gttagaacaa aaaatattta aaatattgag gtagaaacaa attagtctct ttttaattaa  12300
aagccagatt acttgttaga gtaacatttt cccaaatgag gtaaaattgt tgcgactgtt  12360
aaacttaagg aaattttgat ctaggtgtgg tatataccttt cttgtggggt gctaatgaaa  12420
acagggatgg caaaaatatt ttgtttgtga gtgtatgcat ttatgctttt tgacaaccta  12480
agaaacactc ttacatctga gtatctttca tggactagct gtaggaaatc tatataaaat  12540
agcttagtat actgaaagta tgacatagtt ttacatatct agattgtggt tgtgattata  12600
tataatacta taaaatatgc taacgtgctg cttaataata ctatttggat ttttttaat  12660
actgaaaagg tcacacagat tgtgattatt gtgtagtgtc caagaactaa ggcctaccat  12720
ctgttactca aatgtatgaa aaagttaaga taatttagtg atataagtgg ttttgacacc  12780
actgtttttg gaataatcta attatgattt ttataaagac taatatcaaa ttttaaacgt  12840
ttgcaaaaat gaaacctaat agttatactg ttatttatat ttttctatta caatacagat  12900
actggctgag aactaaagat tgtgtaataa acgcctggcc ttcagtcatt tggttttttt  12960
tttccctcga ttgtttggat agttaactgg acatcatgtt ttaacttgag aaattaagtt  13020
atacaagatt ttgatatttt aaactagttt tcctaactgg ttgagatata taagaattta  13080
gtattacagg actcaatcag ggaactgatt taataagaat ttcttaaaaa tttgtttaaa  13140
tatttttcaa gttcttttct tcatcttcta caacttaatt cttgtctgta tgcaaatgag  13200
cttccccatt taaaatttg ctgttgcatt ttaggccact atagaagttg tttctttaat  13260
tttcactcac aagaatttgg tcttaccaaa ttgtgtaaat ctttaaaatt gtgtatttgg  13320
cttaatatta tagaatctga ttgatttaat ctaccttgtt tcatttagta tgttgacatt  13380
ttcttgagaa atttgttatg ccaaatgatt aacataataa tattttaagt ttagatatga  13440
ttttgaattt acattttcaa atgcaacttt gtgtctgtgg cctttttttt tttttttttt  13500
ttacgagaaa catcttgcca attttcagat taatctgtga ggaaagtaga ttggtttact  13560
agactcagtt tgtagacttt ggtgagaact gaattggagg ctatgaaaaa aatacctttt  13620
gggcctttct gaatagacat atatacataa attatatctc ttacattaag tgaggcacat  13680
atgtaggtga gatttttacc tgaatattaa aagtttaaaa gtcgttacct attctgttta  13740
cttaatagta tttaaagggt gtgagaggtg ttatgtgttt ctgtcccttg tttttattcc  13800
tatccctccc atctaactgt tggtactctt atcttcccag gtattaaact tgtatgtttt  13860
aaaagcttat ttacttgttg aaatggttaa cttaattagt tttttctttg aagtttcagc  13920
ctaaatattt tctgtttttt tatatgtcct ttaaatatga aaattctaca gctaatcata  13980
attagtaatt gtacttttc ccctattaca ataactggtt tcataataaa atggtatccc  14040
ttcaataaca agcatttata gtagtttatt aaaactaagg gtgttatcta ttcaaaccaa  14100
gcaatgcaga cttactgttg actctgttaa tatattttaa aattgcatat tactaaaatt  14160
taaaatatga ttttgactag tattttggtg tatgttattt tagatatttt gattatgcac  14220
tacttaagaa tgaattgtca agtatgatta taaagttgat ataatagtta accttcagtg  14280
ggaataggaa tcatttaata ttgttagata tttgtattat tagaacaatc tcctatgatt  14340
cttactaata tagtaatgaa tgacagacaa tatgttggct ttcatattta aaaattcaca  14400
```

-continued tgcatttcta gtttatgttt ttcttcgact aaaattctgc agcacttagg caaagctatt 14460
tttaccagtt ggaaaaaaag taagtcattt ccaaccaatt ttcctggctt gtagtataga 14520
ataaagagac ttgattttat tacattaaag ccaaatataa aatgatgcaa tctagcacac 14580
acttgtttgg aacttttctc ttttaaatat tcagattaag aggacgttga aaggtaaatt 14640
ttttttttt tttgagacgg agtctagctc tgtcacccag gctggagtgc actggcacga 14700
tttcggctta ctgcaagctc tgcctcccag gttcatgcca ttctcctgcc tcagcctccc 14760
gagtagctgg gactacaggc gcctaccacg gtggcgcccg gctaattttt tgtattttta 14820
gtagagacgg ggtttcaccg tgttagccag gatggtctcg atctcctgac ctcgtgatct 14880
gcctgcctcg gcctcccaaa gtgctgggat tacaggtaaa ttttgattgt tattagcaac 14940
tataaaagtt ttgcagttgg cttattggaa aaagaaaacc tccttgccgg agacggagac 15000
gcatttgtat tagaactttg ttttctgagt accttaccta tagtaggttt caaatattgg 15060
tgaattagtt gatggttagg tctgcataat tactgcgtat ggaaattctg gaaccctatt 15120
ttttcaaaat gcagctaatg ttgagagaat atgcactaaa tattactaga tctttgtttt 15180
tcaagatgct gatatccctt aacatcttct gcactttacc tgtttgaata tcttttttgc 15240
tgtaaaaatt agtggcctta tgtctttctg cataattata gagtagccaa aacctgtttt 15300
aggttaatca cctctggcaa aataaatgat aaaagcatag cttttgtaag cagaatgata 15360
ttacagaagt taacttataa atctaagtgt attaaagaca cttaggaaat ttatgataat 15420
gctgggtcag cattacagtt ttaacttttt acagtttttc atatgctttt tttgtgattt 15480
tgctgtagaa aattaacagt tggcatttgg cttagttcaa gtataatgct gttgacaagt 15540
atatctgaca cgtcattgaa ctaataatat ttttgaaagc tgataggtaa gttatatcta 15600
ttttgtttca ttcgtcatta gtgatcggtc ttagatgttt ttagcgagag caaaactgta 15660
gaggaatgtg tgtctgtgtg tgtatatgtg tgtgtgtgtg tgtgtatttt aacagcagga 15720
gagttctgaa acaggaaacc agtcttatca tattcatcca gagacctagg aagaaggtaa 15780
ttgtttggta tactcgttaa aaccagttgg ttgggcaact taaattttta gaggatcaca 15840
gatgtaggct tgagcagttg tagatagatg atttcttttt ttttctttct tttttctttt 15900
ttttttgaga tagagtctct ctctgtcatc caggctggag tgcggtggcg cgatcttggc 15960
ttactgcaac ctctgcctcc caggttcagg cgtttctcct gtctcagcct cctgagtagc 16020
tgggattaca ggcgcatgct gccatgcccg gctaattttt tgtattttag tagagacggg 16080
gtttcaccgt gttccccagg ctggtctcga actcctgagc tcaggcaatc tacccacctc 16140
ggcctcccaa agtgctggga ttacaggcgt gagccaccgt gtctggcgat agattatttc 16200
ataattaaca cctgctatga agaaaaattg attaaaatag ttgagaagtc tagtacactc 16260
tcagctaata tactaaatta tactatggat tttagagtat tgttaacatt atcagtgact 16320
tgatatcttc ctgaggttct aatttgctta actttaaata attggggttc agatcacctt 16380
gattgttccc ttaaagatta aattttgtaa aactgtgtgt aattttcctg tatctggttt 16440
ggatagcttt aaaaatggtt cttaagttta atgagttcaa ctgggaaaaa agttagttct 16500
attttagatg ttgtgtcact ggaaattatg tttccctgtt tgttatatgc acattattac 16560
aaagttgtaa tcaatgtttt catactgttc tctggtctgt ttttttcaca aatacacttt 16620
ttatttgtcg ccaggtactt atttttaaag ctatagaggt aatatttcat caggtgaggg 16680
taactaccat ggtttgtttg ctatactgtg ttagggttat tttcgttttt tttttctttt 16740

-continued

```
ataaactata gttgtgaata tgtttatgta gtttactttt ggtttattag aatatattgc  16800
tagagtggga ttacaggatt aaagagtgta cagtatttta gttttttttt ttttttaca   16860
agttgcagat ttgttgccaa atgaacgagt ttgtagtatt gctaacaagg agaagaatta  16920
ctagcaagtc ttgatgttac ttttgaagag tgtgatgatt gcatttagga agatatctaa  16980
acttctgttt caaagcaaaa agtatgtgca aatttcttac tcatgacaaa ttcatataat  17040
ataaaaacat gaaagttgtg aggtcaggtt gtttggagaa gtagaaaact tcagtagagt  17100
ttatagatag gcagtcttcc tttctggttt ggcactgaca gcagattaac tagaaagtgt  17160
tagaaggaac ctaaaattta tactaaagtc aatttaagtt aattaatata ccagaattcc  17220
ttcttttaca atttatttat aaaaacacca tattgagttg ccttgtaatg agacatttaa  17280
actaaattta aataacagaa ttcatgcacc atctaataac aaccccttat ttacaattat  17340
agagtccttt gcaattttat agatattttc atgtatccca tttggtcctt gaaacaatta  17400
atgaagaagt tacagcaagt ggtattatca ttattttaca gaagaacaaa acaaaaatat  17460
atgtggccca gagattgagt gatttacctg aggttatagg ctttagattg catagctgga  17520
agtagaacct tgttcttcta tattaaatga caatattcat taagtactta gcacaggatt  17580
tggtacctag taaatattta aatgttcctg tgttattcct gactattcct tctttattct  17640
taaaacgcca ttttttgagc actcttaata tttatagttc aaactttgta cctatgtacc  17700
tttttctctt tagaaaataa gatttcaggc tgcattaatt tgatctgtac aggaatgatt  17760
atatgtttta catattggga caaattgctc tttttttata taccttaagc tctagggtac  17820
atgtgcacaa catacagatt tgttacatat gtatacatgt gccatgttag tgtgctgcac  17880
ccattaactc atcacttaca ttaggtatat ctcctaatgc tatccctccc ccctccccat  17940
accccatgac aggccctggt gtgtgatgtt ccccaccctg tgtccaagtg ttctcattgt  18000
tcagttccca cctatgagtg agaacacgcg gtgtttggtt ttctgtcctt gcgatagttt  18060
gctcagaatg atggtttcta gcttcatcca tgtccctacc aaggacatga agctcatcct  18120
tttttatggc tgcatagtat tccatggtgt ctatgtgtca cattttctta atccagtcta  18180
tcattgatgg acatttgggt tggttccaag tctttgctat tgtgaatagt gctgcagtaa  18240
acatacatgt gcatgtgtct ttatagcagc atgatttata ctcctttggg tatataccca  18300
gtaatgggat tgctgggtca aatggtattt ctagttctag atcactgagg aattgccaca  18360
ctgacttgaa ctagtttaca gtcccaccaa cagtgtaaaa gtgttcctgt ttctccacat  18420
cctctccagc acctgttgtt tcctgacttt ttaatgatca ctattctaac tggtgtgaga  18480
tggtatctca ttgtggtttt gatttgcatt tctctgatgg ccagtgatga tgagcatttt  18540
ttcatgtgtc tgttcgctgc ataaatgtat tcttttgagt agtgtctgtt catatccttc  18600
gcccactttt tgatggggtt gtttgatttt ttcttggaag tttgtttaag ttctttgtag  18660
attctggata ttagcccttt gtcagatggg tagattgtaa aagttttctc ccattctcta  18720
ggttgcctgt tcactctcat ggtagtttct tttgctgtgc agaagctctt taggacaaat  18780
tgttcttaaa taatgaacag ttggcacttt ttcaactgga aaattcaagg aactgctctt  18840
tctgctttct gctcaatatg aatcttcaat ttagaaatga gagtccatca ttaacaattc  18900
aacatagctt attaatagga aaaaaaaacc tagtaacaaa tgtaaaatct ttgattaaat  18960
gagaaagtca tagaagttca tcagatttgt atttaaagca tgatttcatt agaaaagttg  19020
ataataagga tttaactgtg acataattgg aaaatacttg tttaaactta aaattttgaa  19080
aagaaatgta aatgtgatgt aacttatgaa tcagtggttg agtttctttt ttgctcacaa  19140
```

-continued

```
gaaccctaac tgtgtgttac ttgaaagcac tgatggaaat cagggaaaaa gctccagaag  19200
ttcctacgaa ataaaattaa atgataaagt cctggtatct gctaacttgc cttccattcc  19260
tgttatcttt tcttcttagt ctgacttcat taattctttc accctggcta ctggtttagc  19320
tcagtgtttt atgagccagg cagcttcaga ctttgctttt gatgctcttt gttcattacc  19380
tctaaagctg tattatcact ttcattttat cattaatgtt tcatgtatat gttatagttt  19440
catattgtta ctgcaacttt tacttagcta taatttaaaa aatatctgtg atctgtggaa  19500
ataattattc tatggcagaa aagtagttat tgcattttac tttataagtt gtttaaggat  19560
aagcatacct atatattaag cactacaaag aaacttttac aatggcttta tttttagcaa  19620
accatcatag ttaaaataag atttagtgta catgtcagga acacagtctt atgaaataag  19680
gtttagggag ctatttttag ttactatatc ctacttgaaa attgtagtta aatttctagc  19740
atataccccta ttaatttaga tgcaagtaca gatttgagat aaggtagata cattatttgg  19800
atgtcaactc ggaagttgtt caagaaaaga tattttgtta tttagatgta acttggaaca  19860
tatttctagt gtttcaagtc atgattgtat gcctagaaca ggcaataaaa atttacttag  19920
ctggtaaaac agccacatta tttcaaatat agtttagtta tattatggat taaattgatt  19980
tttgtggaca gactttagaa cttaattgct attaattaca ttttttcttt gggacggtat  20040
ttgttctttg gtgagaaagg attcttgtaa cacctaaatc aagactgtcc aaacatggca  20100
tatgcagttt accagtcaaa acaaactaat cacttaagat ctgtgtattt tgttttattt  20160
gaattatacc tcaattaaaa caaatttagc atgtttacac aaaggtgggg ggaaactgtc  20220
taatatatct gagatctgtt ggagctgggg tgaccatcca acttaggcaa gatagctagt  20280
accatgtatg catttctttt acctttctta ttgtatatac agtaatcact gatattatga  20340
gaaaaagaac tttttaataa ttcaggagat attttatcgc tagtatatat tgagtgctta  20400
ttatgtgcct tatatacttt ggactcattt aatcctcaac acaacaaccc tatgtagttc  20460
atactagaat tattcccatt taaagatggg gaaagtgatg tttagagagg ctaagtgact  20520
tgcccatggc caaagtatta gaactgggat ttgaacacag gtagcctgat tcctaaataa  20580
atgaccacta acattaaaaa gacataaaca tagaggtgtt tgttgcaatg ttagtcataa  20640
tacctaaaaa ttgtgaacta gttaaatgtc caatagtagt aaaatggttc attaaccatg  20700
gtacacccat caatataatg ttatattgtc atttaaaatt gtattcccaa gtttcgtatc  20760
aggaaaatat aataaatttt tgaaaaatgt aatgggatat attgtattta taatacagta  20820
atcactatgt aaccaacatt tttatttcca tcaaaaatta gttataaaga aatagaaatc  20880
taagaagttt aatagatatt accattgaac actagatttg tattagtatc ttttatattt  20940
atctctctca tttcctatat tggccatgtt tacttttaaa atagtaaaag tcataagctc  21000
tattttaaaa ataaatgtta gtttattaac ccaagaataa tagctaacta taaattcata  21060
tttgataaaa taaaaagatg acattcatca taagggatac atacctgtgc tagcatatgg  21120
catttttaaa atcacatgag taatttgtaa tcatcataga aatattagaa aatacaaata  21180
agcaaacaca tactgaaaat ttagtgttcc caaatctaaa acagagacac tgttttttttc  21240
ttttgggatt gtattttaga tatgttctta agttataata aagtaaatac ttaaaaggca  21300
aattgataca ttaaggattt caaagagtaa aactttttgt taagctttga tgttctttag  21360
aaagtttaga ttattccaca agtcactgtc gttgaaagaa aagtagttac agtggggtct  21420
tatgggataa ggcattacca tttgttcagt tgagagacag ctatcactat gttttaagca  21480
```

ttgttcatat attagctcat ttaatcctca tagcaacctt atatgatagg tacctttatt 21540
agccccattc tgcttaggaa gcaacagaaa gagtatgtat tttgcctaag gttgcacaat 21600
aagttaagct ggggttccaa ttctagcaag ttggttctag agtgtatgtt attaaccatt 21660
atgccgtagt gcctgcaagt agatctctag atgtcagaaa tactcatctt cctctggtta 21720
cctggttgtt ataaatcttt atgcttaata cttatgtcat tatatgtaaa tttcgtatta 21780
aacactcaac ttattcagaa gaatatcagg taagtgtagg ttaaggctgt tttctatcag 21840
aaatcattat atgtatatat attcctcagt tcttatgttg tttagttttt ctaaaatgtc 21900
aaattttata atatatggag aagtataaat gtatattaga aagattttgt ttatttgtgt 21960
aatttgtggc ataagaaata tttgcctcaa gatttggtgc ttgtttaggt agttgctggc 22020
attacttttg gaaatgtcag taaattttca tactgtcttg gaattttttc aatttttaca 22080
ttttattagt aaatgtaatt acaggttagt aaatcactta tttgaacctg tttcctttga 22140
aagttttata tttttatttg gaaatagaaa aaccttaatt tcctctcgtt gggcagtatg 22200
gtgtcaaaag cttgggcttt ggagcttcgt atataatctg ggttcaaatt ataacttact 22260
agttactaac ttgggcaaat tacccagtct ttttgactct caatttcttt gtctatgaaa 22320
tgtaatacta tttaggattg ttaggattaa atgagaatat atttggcata ctgtctggta 22380
catgatactt aacaggtact agttgtctac atctttctaa cttaggatgg atgccgatgt 22440
cttgggtaac atctcaaact ttatcagtaa ggaaggtgag aatctgaaga aaatgaaacc 22500
ttaaaaagat tgaattcctg gactccattt aaaggagtaa atagctcacg aacaagactt 22560
gctgctctgc aaagtcttcc atgttgatcc tggtctttga ctccttatct gtctgattaa 22620
attgaattcg ctgccgtggc atccttaaag ctggacctta ctttgtcagt cctgccttct 22680
ccatgttgct ttgtgtgtaa gcttcactgg actgtttgct ttttgctgat tattttatgt 22740
atttccatat gtctacttta gcctttgctt ggaatgttct aactgctctt gtttcttcct 22800
ctgtttactg gtttctgact taactcttaa ggattatcta atatattacc tacttggtga 22860
aggtttatct gtgtccccac agaattaatc cttccctctt taactcttaa gctatcttat 22920
tttttatcta atcgggtctt tggcacaatt ataggtctgt gtgtctgtct tccctaatag 22980
aataggaaag ccttgaggac agtagtcttt gcttacttag ccttatattc tcagtgcccc 23040
ttgtgcaaaa cgttcaatat atgtttgaat gattatgtga atgaaggagg gggccagctg 23100
aatttacttt aatgattatg taacacccat ttatgtatag ttatagactt gtctgaaatg 23160
agttaaatcc tttgcaacgt ttgctgctat gctttgaatg tctcttacaa aactcatgtt 23220
gaaatttaat tgccattgta atggtattaa gagatggaac ctttaagagg tgattagata 23280
atggtatctc tatccttatg aatggattaa tgctgtttga atggtagtgg atgagttatc 23340
ttgggagttt ggcctcctcc gtctcacatg cttccttacc ttctgccatg tggtaactca 23400
acacaaagat ccttgccaga tgctgatgcc atgctcttgg acttcccagt ctccagaacc 23460
gtgagccaaa tacatttctg ttcattctaa actacctgtt ttgtggtatt ctagtaaagc 23520
aacataaaat ttactaagaa aactggtacc aagagtgtga ttgttgccat aacaaatacc 23580
tgaaaatgtt caaatggctt gggttctggc tagagaagga tggaagagtt tggatgaaca 23640
ggctagaaaa agcctgtatt gctgagaata gagcattaag gacaattctg atgaggattc 23700
agaagaagag agctgtaggg aaaatctgga acttcttaga gagttgtcat cagttggtag 23760
aactataagt ggtaaaggtc tttctgatga tatctcagaa atgaagaaca agatactgga 23820
cactggagta aaggccatcc ttgttaaata gttgcaaaga acttggcgaa attatgttca 23880

-continued

```
tatcctaaga ctttatggaa tgcagaattt aagagtgatg aactaggata tgctgcagaa  23940
gaaataactc agcagcagag catttaggtt actggatggc tacttttaac cacttaaact  24000
aagctggggg aagggaatga cttgaagaca gaatttataa ttaaaagaga ggcagaatgg  24060
aaatacttgg aaaatttgca gcctggccat agtaaagaat gcaaaaggta tgtttaggag  24120
agcaaaccaa gggtgtggtc caggaaccat ttgctgaaga gattaatatt cctagaggag  24180
acccaagggc tatttatcaa gacagtggaa aaagacccca gaggcatttt ggagatcttt  24240
gaggctgcct gccccatcac aggcccagag ctctaggagg gcagaatggt ttgtggctca  24300
ggtggtcctt cacaagcttg ctgcccaggg ctacctcagc tccccatatt tcaacccagt  24360
gggccttggc tgtcctaggt ctggttcaga ggggcccagg tgtggcttag gctactgctg  24420
agtactcaaa tggtaaacct tggcagcgtc tatatggtgc taattctgca ggctcacagg  24480
atgaaagagc tgtgggagac atggctacca ccaccaggat ttcaaaggat gatggggata  24540
gtctgggaga gacttgccac aggcttggag cctctgaagg gtggaaatgt gggttggagt  24600
cactacagag agtccctact agggcattgc ataatggagc catggcagca ggcccaccac  24660
caaagcttca gaactgtaga gctacaagta tacagtgcca gcctgggaga acttcaggct  24720
tgagacccta acctgtgaaa gctgcatggg ctaagtacag caaagccatg gaggtggggc  24780
ttcccagggt ctattgggat gaaacgaatg tattttgtag gtgagaagga catgagtttt  24840
gaggcccagg ggcagaatgc tatggtttgg ttgtttcctt caaaactcat gttgaaactt  24900
cattgccatg tggcattatt atgaggtgga acctttcaga agtggttaca ttataagggc  24960
tttgccttca ttaatggatt aatgccatta ttgcaggtgt gggttagtta tctctggagt  25020
ttggccccct ttttctctat catgtgctca tgccctcttt tgccatgtga tgccttctac  25080
catgttatga tgcatccaga agactctcac cacatgcagc cccttgatct tagacttctc  25140
agcttctaga actgtgagtg aaataaactt cttttcttta taaattaccc cgtctgtggt  25200
attgtatagc agcagaaaat agacatcagc ctgaagttcc cccaggctgg cattaaatac  25260
taattattaa ttagtattta tagtgcaagg ataaattcaa gtttagccct ggttagaatg  25320
accacatttc aagggagggg ctttgtactt ctgtgcatat ctgtaaggat aaaaatctta  25380
atactattct cactgaaatt aatggtttag gttaggtaag gttgttagtg ctaataatta  25440
tttcttttaa taaaatattc ttagttgcgt tgttcaaaaa acatagatga tttgaattta  25500
tattttttgg ccaaaatata tttataattt tgagtaggaa ttccagagta ttggtagcta  25560
taaccacttt gggttccctg ccattgcttc tggtgcctca ttttttctga cgtcttccat  25620
tttcttacat ttgtcttcta aggtggagtt aagattactc agttaagatt atttcacttt  25680
aggcctctgc tgtcttctgc tttttttttt aaaatgaatg gatataatat cccaatacat  25740
tttgataatt gaacaacagc tacattttta agtgaggcta ctttcttcta attttttaaa  25800
tttatttttc tcagttttta aaaaaaatgt cagattggct aagagttggg gcagctttct  25860
tatgtgagag tagtagatga cagcaaatat ttgtgatgtt aaaatgataa tcctaatagt  25920
tttcttttag aatctttata ataaaaaccc tttgaggctg agggtgaatt tgtatgttcc  25980
taaagtgaca aaaaatgttc ttggggcata gtaatttaaa tcttagatgc ttttattagt  26040
ataatttttt ggtagaaatt tggcattaaa aaatgcatac agagcttttt ctacatacag  26100
ggcaagacag cattttgtca tggcaattag taaatagata attataaaac atctaatttt  26160
aagcaatttg ttacagaaac gatacaggta cattgtggca aaaatagaag atacaaaaca  26220
```

```
agcaaatatg agaaaaaata tacatgccac cacctatata tgacttttag tactttataa  26280
tcttttgtct atatatgtct atatggatat atacgtattc tttttatcca aatggtatta  26340
cattgtacat tctgttttga aacctgcctt ttttagtcat ttacatctac ttttccatct  26400
cagtaacttt tcatcttgtg taatgcccgg atcacattaa aatgtttcca attagctcaa  26460
aaatgtcctt tatggctggt ttggctaaaa cagtatccag gccagcattg cacctatgaa  26520
attggctgtt aggaatcttg tatctttaaa aatcaagggc agcaacccat cctcccgctt  26580
cccccacctc ccaccacccc cccacctttt ttttttctta aagatactgg cttgttgaag  26640
agagaatggg tcatgtccta caaactgtct gaatttgtcc agtttgctgt ctcatagtgt  26700
catttagctt gttttatcct atgtatttcc tgcaaattaa aatttgtatc tgaatccttg  26760
gtggatttga gttgaagatc cttaaccatc atagatgatg ctgtgtcctt tatattgcat  26820
gtcagaagtt acatgatctt tacttgattc atgatgagga gatggccact gaaattggac  26880
agtgacagtc ttttctgccc attgttcaat tatattcgtc tctttacatt agaaagtatt  26940
ttgggtagta gtattttggt gctgtaagaa agttcatttt ctcatcaacc actcacctat  27000
tggtttaaca ccatttgttg atctttgagt atatcagtaa tttcatcagg gtttgcaaaa  27060
taagacttta aattctattg ttttacatta ttaattgatg ttttttgata aggtagaact  27120
tgtgaaatgg gactatttgt ttgtctttaa atacagtctc tataggaaag acaaaataaa  27180
tacttaaatc tcactcttta ccatttttca aagtgaagaa ctattccgtt aaccacctca  27240
aaagatgata aataaaaagg gtatttttag ttgtttcaac tttttttttt tttttgagat  27300
ggggtcttac tctgttgccc aggctggtgt gctgtggtgc aatcatggta caccgaagcc  27360
tcagtctccc tgggctcaga tgattctccc acctcagcct gggactaaag gtgtacacca  27420
ccatggccag ccaatttttt tgtatttttt gtagagatgg ggttttgcca tattgcccag  27480
cctagcctca aactcctggg ctgaaggaat ccacccatct cagcctccca aagtgctagg  27540
attacagacg tgaccaacaa tatccggcct taactttttt cttttgagtg tctttataga  27600
ctcaaggact tttatttaat tcagggtgtt agtaccattt aaatgtttc tttgatgctc  27660
agattatcac agctagtcat ttggaccttt ataccacctc ctatgtccat ttgatatagg  27720
ccattaatct ctataagcct tcctccttct cttggaatga aaaggtatcc taggctcacc  27780
tgtaccttcc ctactccaga cctggcatta agtctttttc caaggagttt ggtacctttt  27840
agtttattat gatattagag atgaaaatct gtgttctagg aatgtttatt actgctagag  27900
tgatgttgct tttaggccat ttcagagaaa agacctagaa aacagatttt tacaaacatg  27960
aattcatact gatattttta gtttttttaca tgatttcttg attttacaat attatctgct  28020
ttcttaactt aaaattatga accttaaagt cattagcata acttctttgc ttatttctac  28080
aacataaaga aaatagtcct ggtgcggtgg ctcacactgt aatcccagca ctttgggaga  28140
ttgaggcagg tggattgctt gagctcagga gttcaagacc aacctgggca acatgatgaa  28200
accttgtctt tacaaaaaat tagctgggca tggtggcatg tgcttgtatt cccagctact  28260
caggaggctg aggtgggagg atcacctgag cccaggaggt caaggctcta gtgagccatg  28320
atcatgccac cacactccag cctgggtgac aaagtgagac cctgtttcag ggggaaaaaa  28380
aagataaaat agtttgagga ggctggatgt agtggctcat gcatgtcatc ctggcacttt  28440
gggaggtcaa ggtgggagga tggcttgagc ccaggagttt gagaccagcc tgtgccacat  28500
catgagacct ggtctctatt taaaaaaaaa aaaaaaagaa aatagtttga ggatatcaat  28560
aatgatatta ctagaatcag taaaactacc aaaagaagtt taaagtttct tcctagtgtt  28620
```

tttttgttct tagaatactt cctaccaaga agtgcagtaa aagtgcagtg tccaaatagc 28680
ccttgtaaca aaacctttct ctttctcctg ggtgccaatt tgacatttaa tcagttttgt 28740
ttctagcagt gttcaattta ttagattata agtctttttt ttctttatat tattctaaga 28800
tcaaaaatat ataaagatat acacaggagt cctgctgcta cctgttcttg ctatgctttt 28860
cccctttctt tccctttctc tgtgaagcag ccatttttat tagtttcttg tttatcactc 28920
atgcatgcat atgtttattg aggatgttga cattcaagca aatatatggg ttaacattct 28980
ttttgtcatc cctatacgaa agatataccc agtatactct attgggtggg tttttttcct 29040
taaaatattc agtagatctc tccagttagc acatagttat cttatagata gaacatatac 29100
atataacctt ttcttaaact atgctattaa aataatagct ttcagtaact tgataattat 29160
ttttggattg aaaatactac tgaaatcaac tcaatcatgt gaaagctgca gaaagaaaaa 29220
gacctagaaa aagggcattg gattaggtca actttgaatt ttatttggaa gataaatgag 29280
tccagaagtg agtgggcaga gattattgga gttggtcttg aaatgaggcg ttaggcagat 29340
tgactgggct ggtgtgaaag gtctgtcaga aaatcatgag attagattga ggtacctcaa 29400
aaaatgagag ctggtatgat gagtgggtaa gaatcataaa agcgtagagt gttgatgatt 29460
tttatagttt ataaatggtt cttgtgtgta gagttttgtt tttatgctag ctatagtctg 29520
taacataatt cactataatg ggcatgctaa atatccatga cagttgaccc ttgaacaaca 29580
cagagggtag gggcgcctac ccctgtgcag ttgaaaattc acatgtaact tttgactccc 29640
caaaacttaa tatttagcct atacttgact agaagtctta ctgatgacat aatgttcgtt 29700
aatacatatt ttatatatgt gtcagatagc atatttgtat aataaagtaa gctgcaggaa 29760
aaatattaaa atcataaaga agagaaaata tacttactat tcattaagtg gaagtggatc 29820
ctcataaagg tcttcatcct cactgccttc actttgagta ggccgaggag taggagagag 29880
aggaaaggtc agacttgctg tctcatgggt ggcagaggta gaagaaggtc cacatacaag 29940
tggtccgaca cagctcaaac cggttttgtt cattggccaa ctgtagtttg attgaaagta 30000
ataataaatg aagtttctgc ctcagttcag tattatcaag tcatagatag caagggctgg 30060
aagaaacctt agtagtaatc tctttgagtc taattatcat gtagaatagg aaattgcggt 30120
ctagaaaggt taagtgactt gtccaaatta cacaactagt tagagacata gccagctctt 30180
aaatctgact tccagatttt cactgtgtct tctttttct gtaacgtgtt gccttttta 30240
gccatgaaaa attagaagtt gaactcttgt cttttcaggc aggtgtcaat tttggggttt 30300
tgttttgatt tttggttttt gacataaagt actttagttc tgtgatgtat aaaccgtgag 30360
tttctgtttt tctcatatac ctgaatactg tccatgtgga agttaccttt tatctttacc 30420
agtattaaca cataaatggt tatacataaa tacattgacc accttttatt actccagcta 30480
tagtggggaa aactttcttt tcataactag ctaatgtttt aaaaagtatt cttttagttt 30540
gattgctgca tatttcagat atttctttcc ttaactaaag tactcagata tttatccaaa 30600
cattattgct atgggatttc ctgcagaaag acttgaaggc gtatacagga acaatattga 30660
tgatgtagta aggtaagaat gctttgattt tctatttcaa atattgatgt ttatattcat 30720
gttgtgtttt catttagaaa agatttctaa gccacagaaa aagatacttt gtgatgtaaa 30780
ctattattgt agtgctctat aatcattttt tggcttaccg tacctaatgg acttcagggg 30840
gatacagttc atttgataag aactgacctt atacattaca taatcaggta cttatgtgat 30900
atcatttcct ggactccata aaatgctggt caccaggttt aatacctgga ttccattaca 30960
gtgtgatttt tgtcttattt catagttggg gattaggctt aaaatcctag agtggattta 31020
ttcagttaaa tttattcaca ctaagatgta gatgactaat actgtatatt tttatgtaga 31080
ccaaatttta aggtaccact gtgcatatgt ataccaacta cctgaagaag tatttggttg 31140
gtacaagaga tatagaaagg aatcgctggg tgtaccaagg ctaatcagtt ttataatttt 31200
gcataatttt ctaactgcga ttatcattta gtttagaaca atttatttct caaggcccat 31260
gtaaatatta tttttaaaat atacagtctt aagaattcat ggcatatttt atgaaaggag 31320
gaattcatgt ctgatgtgca aatagtctta acatattttc taatttcaga gcaaaaatat 31380
atatgtatga ataaattaac tgtaaattgt cagtaggaac cttaagaatt cgtggcgtat 31440
tttatgaaag gaattcatgt ctgatgtgca aatagtctta acatatttgc taatttcaga 31500
gcaaaaatat atgtgtatta ataaatcaac tgtaaattgt cagtaagaac cttaatggct 31560
ttaaaagtta aaatttcagg tcaagcattg tggtgtgctc ctgtagtccc agctacttgg 31620
gaggctgagg tgggaggatc acttggcttg aacccccagg tagagggtag aggccagtct 31680
gggtaacaca gcgagaaccc atctcttaaa aaaaaagttt aagttgtgga ttatttcctt 31740
tacactcttt cattagtatc tttcctggag actttcaatt taaatacttg gtgcttatga 31800
caattagatg ttaaaatgga tgggaaagta ctttgtaact tataaagcat tatgcagatg 31860
tagactcctt ttataatagt tgtgtaagta tataagacaa cctacattct tcatgagcta 31920
gccataagtt ttagcaactt gctttgaacc acggtagatt tacaattttc tgtagtattg 31980
agttgtgttc atttagaatt ttgtaatatt tatattgaaa atcaaatttt tgtacctaca 32040
aaaactacaa aaaatccccc tagtttttat agtttctatt aaaattatag ctggtacata 32100
gggatgccag aaggactgtt taagaagctg aaaatagaga aatgaattta tcttctcata 32160
gttaggcagg gcacagtaga aggatgctta acattgcaag ctgatgggaa cagcaggttg 32220
atatagcttg tgataacact tctaaagaaa aagcaatgag ccatagaaaa aagaaaaaga 32280
tacattttga attaaggaag atggtgaatc tgggaagtga gcagtacagt caccagacgt 32340
gtatcctctc ctatggtaca gaagtgttta ttgggtctct ttatggcctg catgatatat 32400
cccacaagat gacctacttc acattatttt aattctgtat tcaactaagc actaattcaa 32460
cccagccaga ttagtactca taccaaaaaa gagtgaatac tctgaataga gggcaggttt 32520
tctgattatg gtgagaatat ctttgtggta aattaatctg gtgtgctagt ttttacgttg 32580
gtctcttctc agtgtcgtta gtcactgagg ctgattgatc atcttttagg ttactgataa 32640
agttcctgta cagctgattt tcagacctta gattgcaata acttcaccaa gaaaatactt 32700
cattgggaag cattttggtc cttccatttg attcataact cttaccttta tgcctctgaa 32760
ggaaaagatt tatacattca gcttgtaatt agtaatcaag actgaggttt agtctatcta 32820
gcttcacaat ctatctagtt tgttttgtct agccatatga tttcttcaaa tatgccattt 32880
cttaaaaaaa aatgttttat gtatcccgat taatatttag ccagtggttc ttttagccga 32940
tggatcttgt cacctcttat gatactatta atagcatgtc aacatgaaga attatctgct 33000
gaatataata gctatgctgt ccttgtttcc ttttgtctca ttcttttttg attgggggat 33060
aattggccaa taaagctttg atagcctcta ttgcccaggc ccctcctctt cttttatgag 33120
agaaaggatg aacagtgacc agaaataaag gtattgtttt tttctatcaa ctaaaatgga 33180
aataaataat tcctaagtaa tttgcctgtt aggattaaag tctccaagag aatggctgtg 33240
cctagtacct aagtgattaa tttccttgat tggttcacat tatattgagg atattagtaa 33300
tcagtagtga ttcctttttt ggttcaaaga tgatagtgtc acagtgaaaa atgtttttaa 33360

-continued aatttttgta tacttaattt ttctgttaac gaaagtattt tcagttggat ttttgtttgc 33420
cctctctatt agaatgccca aagaatattt aaaattttcc ttttctctta tactgcatat 33480
ttttcctgtg atttttcccc aaacggaaaa tactctgcag agattagact ttgttattgt 33540
tgtactacat cattgctttg actaaaataa actcagattg caaatacctt caagcttaca 33600
ttgctcagta tttttttttt tttttttttt tgagacggag tctcactctt gtcgcccagg 33660
ctggagtgca gtggtgccat ctcagctcac tgcaacctct gcctcctggg ttcaagcgat 33720
tctcctgcct cagcctgcgg agcagctggg attatagatg cccgccccca cgcccagctg 33780
atttttgtat ttgtagtaga gatggggttt taccttgttg gccagtctgg tctcaaactc 33840
ctgacctcgg gtgatccatc tgtctcggcc tctggaatta caggtgtgag ccgccacgcc 33900
tggctaaatt gatcagtatt atttaacttt gagggatatg atttgttatg gaatgcgaag 33960
ttttatactt gaggtactca gagtcctttt gagacaaata tttaacttct ccttttgagg 34020
ttaccgccta cgattgggaa ttaatgtaaa aaataagcca aaagaaagtg agggaaaagt 34080
gaaccaagct gtaatttttt tactcttttt tattgttgtt gttattgttg ctgtttttta 34140
ctatcttgat tgcaacagtt tggcttatat atatagcatt tggaattgac agtaagaaag 34200
ccacatctca tagaagctaa ctattcccaa attgtttttt tcttcttttc ctcttactac 34260
tgctgttttc ctcctttctt gctgctaagc tcttgtcctg acatgctggt aatatgaaac 34320
agtgttttat tcagataatt gattattctg taatatgtat gttaatcttt tttattacac 34380
tttaagtaat agggtacata tgcacaactt acagattcgt tacatatgta tacatgtgcc 34440
gtgttggttt gctgcaccca ttaactcgtc atttacatta ggtatttctc ctaatgttat 34500
ccctctccca accccccacc ccaggacagg ccccggtgtg tgatgttccc cgccctgtgt 34560
ccaagtgttc tcgttgttca gttgccacct gtgagtgaga acatgcggtg tttggttttc 34620
tgtccttgcg atagtttgct cagaatgatg gtttccagct tcatctatgt ccctacaaag 34680
gacgtgaagc tcatcctttt ttatggctgc atactactcc gtggtgtata tgtgccacat 34740
tttcttaatc cagtcagtca ttgatggaca tttgggttgg ttctaattct ttgctattgt 34800
gaatagtgct gcagtaaaca tacgtatgca tgtgtcttta tagtagcatg atttataatc 34860
ctttggatat atacccagta atggaattgc tgggtcaaat ggtatttcta gttctagatc 34920
cctgaggaat tgccacactg tcttccacaa tggttgaact agtttacagt cccaccaaca 34980
gtgtaaaaat gttcctgttc ctccacatcc tctccagcac ctgttgtttc ctgacttttt 35040
aatgatcgcc attctaactg gtgtgagatg gtatctcatt gtggttttga tttgcatttc 35100
tctgatggcc agtgatgatg agcatttttt catgtgtctg ttggctgcat aaatgtctat 35160
aaatgtcttc ttttggaaag tgtctgttca tatcctttgc ccactttttg atggggttgt 35220
ttgatttttt tcctgtaaat ttgtttaagt tctttgtaga ttctggatat tagccatttg 35280
tcagatgggt agattgcaga aattttcttc cattctatag gttgcctgtc cactctgatg 35340
gtagtttctt ttgctgtgca gaagctcttt agtttaatta gatcccattt gactattttg 35400
gcttttgttg ccattgcttt tggtgtttta gtcatgaagt ccttgcccat gcctatgtcc 35460
tgaatggtat tgcctaggtt tgcttctagg gtttttatgg ttttaggtct acatttaagt 35520
ctttaacatt taagtcttta atccatcttg aattaatttt tgtataaggt gtaaggaaat 35580
gatccaattt cagctttcta catatgacta gccagttttc ccagcaccat ttattaacta 35640
gggaaccctt tccccatttc ctgtttttgt caggtttgtc aaagatcaga tggttgtaga 35700

-continued

```
tgtgtcatgt tatttctgag ggctctgttc tgttccattg gtctatatct ctgttttggt  35760
accagtacca tgctgttttg gttactgtag ccttgtagta tagtttgaag tcaggtagtg  35820
tgatgcctcc agctttttc tttctgctta ggattgtctt ggcagtgcgg gctcttttt  35880
ggctccatat gaactttaaa gtagtttttt ccaattctgt gaagaaattt attggtagct  35940
tgatggggat ggcattgttt ctataaatta ccttgggcag tgtggccatt ttcacgatat  36000
tgattcttcc tacccatgag catggaatgt tcttccattt gtttgtgtca tcttttattt  36060
cgttgagcag tggtttgtag ttcttgaaca ggtccttcac atcccttgta agttggattc  36120
ctaggtattt tattctcttt gtagcagttg tgagtgggag ttcactcatg atttggctct  36180
ctgtctgtct gttattggtg tataagaatg cttgtgattt ttgcacattg attttgtatc  36240
ctgagacttt gctgaagttg cttatcagct gaaggagatt ttgggctgag acagtggggc  36300
tttctaaata tacaatcatg tcatctgcaa acagggacaa tttgacttcc tcttttccta  36360
attgaatacc ctttatttct ttctcttgcc tgattgccct ggccagaact tccaacactg  36420
tgttgaatag gagtggtgag agagggcgtc cctgtcttgt gccagttttc aaagggaatg  36480
cttccagttt ttgcccattc agtatgatac tggctgtggg tttgtcataa atagctctta  36540
ttattttgag atacgttcca tcaataccta atttattgag agtttttagc atgaagggct  36600
gttgaatttt gtcaaaggcc ttttctgcat ctattgagat aatcatgtgg tttttgtct  36660
ttggttctct ttatgtgatg gattatgttt attgatttgc gtatgttgaa ccagccttgc  36720
atcacaggga tgaagccaac ttgatcttgg tggataagct ttttgatgtg ctgctggatt  36780
cggtttgcca atattttatt gaggattttt gcattgatgt tcatcagggg tgttggtcta  36840
aaattctctt tttttgttgt gtctctgcca ggctttggta tcgggatggt gctggcctcc  36900
taaaatgagt tagggaggat tccctctttt tctatgaatt ggaatagttt cagaaggaat  36960
ggtaccagct cgtcttttta cctctggtag aattcggctg tgaatctgtc tggtcctgga  37020
ctttttcgg ttggtaggct attaattatt gcctcaattt cagagcctgt tactggtcta  37080
ttcagggatt caacttcttc ctggtttagt cttgggaggg tgtatatgtc caggaattta  37140
tccatttctt ctagattttc tagtttattt gcatagaggt gtttatagta ttctctgatg  37200
gtagtttgta tttctgtggg atcagtggtg atatcccctt tatcattttt tattgcatct  37260
atttgattct tctctctttt cttccttatt agtcttgcta gcagtctatc aattttgttt  37320
tttaaaaaaa ccagctcctg gattcattga tttttttttt gaagggtttt ttgtgtccta  37380
tctccttcaa ttctgctctg atcttagtta tttcttgcct tctgctagct tttgaatttg  37440
tttgctcttg catctctagt tgttttaatt gtgatattag ggtgttgatt ttagatcttt  37500
cctgctttct cttgtgggca tttagtgcta taaatttccc tgtatacact gctttaaatg  37560
tgtcccagag attctggtac gttgtgtctt tgttctcatt ggtttcaaag aacatcttta  37620
tttctgcctt catttgtta tttacccagt agtcattcag gagcaggttg atcagtttcc  37680
atgtagttgt gcagttttga gtgagtttct taatcctgag ttctaatttg attttactgt  37740
ggtctgagag acagtttgtt gtgattttta ttcttttaca tttgctgagg agtgagtgct  37800
ttacttccaa ctatgtggtc aattttggaa taagtgtgat gtggtgctga taagaatgta  37860
tattctgttg atttgggatg gagagttctg tagatgtcta ttaggtctgc ttggtgcaga  37920
gctgagttca aatcctggat atccttgtta accttctgtc tcgttgatct gtctcatatt  37980
gacagtgggg tgttaaaatc tcccgatatt aactgtgtgg gagtctaagt ctctttgtag  38040
gtcactcagg acttgcttta tgaatctagg tgctcctgta ttgggtgtat atatatttag  38100
```

gatagttagc tcttcttgtt gaattgatcc ctttaccatt atgtaatgcc cttctttgtc 38160
tcttttgatc tttgttggtt tacagtttgt tttattagag actaggattg caacccctgc 38220
tttttcttgc tttccatttg cttggtagat cttcctccat ccctttattt tgagcctgtg 38280
tgtgtgtctg catgtgagat acatctcctg aatacagcac actgatgggt cttgactctt 38340
tatccaattt gccagtcttt gtcttttaat tggggcattt accccattta catttaaggt 38400
taatattgtt atgtgtgaat ttgatcctgt cattgtgatg ttagctggtt attttgccca 38460
ttagttgatg tagtttcttc ctagcatcaa tggtctttac aatttggcat gtttttgcag 38520
tggctgatac cagttgttcc tttccatgtt tagtgcttcc ttcaggagct cttgtaaggc 38580
aggcctggta gtgacaaaat ctctcagcat ttgcttgtct gtaaaggttt ttatttctcc 38640
ttcccttatg aagcttagtt tggctggata tgaaattctg ggttgaaaat tcttttcttt 38700
aagaatgtag actattggcc cccactctct tctggcttgt agagtttcag cggagagatc 38760
tgctgttagt ctgatgggct tccctttgtg ggtaacccga cctttctctc tggctgccct 38820
ttacattttt tcctgcattt ccaccttggt gaatctaaca attatgtgtc ttggggttgc 38880
tcttctctag gagtatcttt gtggtggtct ctgtattccc tgaatttgaa tgttggcgtg 38940
ccttgctatg ttggggaagt tctcctggat aatatcctga agagtgtttt ccagcttggt 39000
tccattctcc ccgtcactgt caagtacacc aatcaaacgt agatttggtc ttttcacata 39060
gtcccatatt tcttggaggc tttgttcatt tctttttact gtttttctc taaacttctc 39120
ttcttgcttc atttcattca tttgatctgc aattactgat accctttctt ccacttgatc 39180
gaatcggctg ctgaagcttg tgcatgcgtc atgtagttct cgagccatga ttttcagctc 39240
catcaggtca tttatggtct tctgtacact gtttattcta gttagccatt tgtctaatct 39300
tttttcaaga tttttagctt ccttgcgatg ggtttgaaca tcctccttta gctcggagaa 39360
gtttgttact actgaccttc tgaagcctac ttctgtcaac tcgtcaaagt cattcttcat 39420
ccagctttgt tccattgctg gtgaggagct gtgatccttt ggaggagaag aggcactctg 39480
ggttttagaa ttttcagctt ttctgctctg ttttctcccc atctttgtgg ttttatctac 39540
ctttggtctt tgattatggt gacctacaga tggggttttg gtgtggatgt cctttttgtt 39600
aatgttgatg ctattccttt ctgtttgtta gttttccttc taacagtcag gtccctcagc 39660
tgtaggtctg ttggagtttg ctggaggtcc actccagaca ctgtctggat atcaccagtg 39720
gaggctgcag aacagcaaat attgcagaac agcaaatatt gctgccggag ccttcctctg 39780
gaagcttcgt cttgggggca cccggctgta tgaggtgtca gtcggcccct actgggaggt 39840
gtctcccagt taggctacaa gggggtcagg gacccacttg aggaggcagt ctgtccgttc 39900
tcagagctca aacactgtgc tggtagaact actgctctct tcagagctgt cagagaggga 39960
tgtttaagtc tgaggaagtt tctgctgcct tttgttcagc tatgccctgc ctccagaggt 40020
ggagtctaca gaggcaggca ggcctccttg agctgtggtg ggctccaccc agttggagct 40080
tcccaaccac tttacctact caagcctcag caatgatgga cgcccctccc ccagccaggc 40140
tgctgccttg aagttcaatt tggaactgct acgctagcag tgagcaaggc tctgtgggcg 40200
taggacctgc tgagccaggc acgggatata atctcctgtt gtgccatttg ctaagaccgt 40260
tggaaaagcg cagtatttgg gtggcagtgt cccaattttc ccggtatagt gtgtcacagc 40320
ttcccttggc ttggaaaggg acatcccccg accccttgtg cttcctgggt gaggcaatgc 40380
cccgccctgc ttcagctcac cctccgtggg ctgcacccac tttccaacca gtcccagtga 40440

-continued gaagaaccag gtacctcagt tggaaatgca gaaatcacct gtcttccgcg tggatcatgc 40500
tgggagctgc agacaggagc tgttcctatt tgaccatctt ggaatgccac cttttttttt 40560
tttttttttt ttttaaggca gtttcttgct ctgtcaccca ggctggggtg cagaggcatg 40620
atcacggctc actgcaacct ctgccttctg ggctcaagtg atcctcccac ctcagcctcc 40680
caagttgctg ggaccacagc cacgcatcac caggcctggc taatttttgt gtttttttgta 40740 gagatagggt ttcgctgtgt ttcccaggct ggtctcaaac tcctgcgctc aagcgatccg 40800
cctgcctcag cctcccaaag tgctgggatt acaggcatga gccactgcac ccggccaata 40860
tgtatgttaa tctcatccct caagctgata ctgaagtttt tcaatttatg ttatttggtg 40920
taaatctagg cagtctttaa caaaattggt gcttcatgtg tttaagaggc ataacttaag 40980
aattgtttgt ttcttataaa tcaggagaat ggaggtttaa tagaggtgaa ctgtctttct 41040
cactgcagaa cctttaatat gccactatgc attgtaaatc tcccaagagt gagattctag 41100
tatgatgctt ttcttttcct tttctgttct ttccctttcc ctctacctcc tttttctttt 41160
ctttgttggt ggcatgagtc ctatattata aggaaatgct tttagagtac agtcttctga 41220
tatatagtga tttttgaaaa agatttattt attgtcttgt tcactgtgag ctttttcccc 41280
catgtataag cagctgtgta atagattcaa gagcaccccc tcgccccttt ttttttgaga 41340
cagagtctcg ctcggtcact caggctggag tacggtggtg ctgtgatcat ggttcacctc 41400
gacttctggg ctccagcgat cctcccacct catcctctca agtagctggg accacaggcg 41460
tgtgtcaccg tacatggcta atttttctat ttttagtaga ggcagagttt cgccatgttt 41520
tccaggctgg tctcgaactc ctgaactcaa gcagtccacc tgtctcagcc tcccaaagtg 41580
ctgggattac aggcgtgagc ctccactccc agtctcaaat attcttttga aatatttgaa 41640
atatgttgat ctctcagtct ttcaacctta gttgtatgtt gattttcaat aaaaaggaag 41700
tatttgttgc cctaacatca gtattggcta ttcagtttaa aaaaggagtt aaagagatgt 41760
tatttatagg caggcttcaa aagaggaaag aatgatcagt ttcattctct gtttctagca 41820
tattctgact ccttctctca tattacctcg tttttcccac atttttttctt taataaagtg 41880 aaattcacat aacagctaac cattttaacc acggaaagtg tacattccgt ggcatttatt 41940
accttcacag tgttacctct acctttatca agtttcaaaa cattttatca ccccaaaaga 42000
aagccctgtt cttattgggt gcctcttgct tttttttttt tttttttttt taaatcttga 42060
gacggggtct tggtttgttt cccaggttgt agtgcaatgg ggcgatctca tctcattgca 42120
acctctgcct cccgagttca agcaattctc ctgcctcagc ctcccgtagc tgggactaca 42180
ggcacgcgcc acatgcctgg ctaatttttg tatttttagt agaaacgtgg tttcaccatg 42240
ttggccaggc tagccttgaa ctcctgacct taggtaatct gcctgccttg gcctcccaaa 42300
gtgctgggat tataggcgtg agccaccgtt ctggccacct cctacttctt tcattagtct 42360
taattcctta gtggatttga cagtgtttat attatctaca ccaatgcatt tttttgtatg 42420
ttaataatag gagatattta ttgggcattt atttacatac ttatttgcat gtgtaactgt 42480
tgtatagcca gtttatgtat ataatcttac taaatctcta cagtaaatct atccccattt 42540
catagatggt ttaaaagaag ttaacttccc caagcattac ttttagtaag tagtgagact 42600
gaaggttgag ttctggtctg tcagattccg aagttgtttc cttaggaacc atattatctt 42660
gtgtacaact cttgggctaa tcttgttaat attctttatt tgacctcaca ctgttgattc 42720
ataccatgtt taaaattgaa atacattacc tatatttaaa aattgagacc tcacataaaa 42780
agctatattt ctagctgctt ttgaaatttc gaaggatctt ccaacacttg gctgacattc 42840
ctgcgtgaca aaaatcagct ggagctgtgt aatgtccgac ctgtctctgt caatgaacag 42900
attattcatt gtcatttctc atctgttttt gagattgtaa ctttgattct gtataactca 42960
tagaattagt agttagacct atatatgtta gttattacat tatttgtata tgtacagact 43020
gctttagaca atattgtagt gttatatgtt aattttatca attaaaatgt gctataggat 43080
cattgtagag atcttgtctc taattaacag gattcataaa gagaaaacaa aggagagaaa 43140
catccagatt gaaaagacct acatagtgcc aagcacaata aaagaaaccc tatactaggc 43200
aaattattat gaaatttgtt ttaggacacc agaaataaag ataatatcta aaaacttttt 43260
agaatcgcct aggagggatt aggaatatga atagcatcta acttgttggc agtagaattg 43320
aaggtagaag gtggtaaaac atcaccttga aagttctgca ttcagcctag aattctgtat 43380
ccagttaaac catcaatcaa gtgtgaaagt aggggggaaaa actcaaggac taaaaaaatg 43440
tgctcatgaa gaacattttt tttggacatt acccagaaga tgtggttcaa caaaacaagg 43500
gaataaacca agaaaggaaa taaaagagct tcagtaaaca gagaatccca ctcagaagca 43560
acaaagaaga aagtcccagg atgacagctg tgacacaagc tgaaaagtta ccagttttgc 43620
ttggagcagg agattagaac ttccgggaaa ataatcaaat tgatagatgg atgttgaaat 43680
atttggagaa aaatgtaatg gattcttgca aaactgagca aattagaaaa aggaaacaat 43740
tattagcatt ggtggtttga gttaacccaa aattgtgatg ttgctatttt aggggaatta 43800
agataagtga aacacgtatg gaatactgct agttttgtaa gtctccttta ccatggcagg 43860
acatctgtag ttaataaatc tgtaagaagc agtattaaga ataatatttt aaaataccta 43920
attaaatagg aggaaaaaga atccgagtag ttgagggtga ttgcatctgg ggagaagcag 43980
gaataaaggt ttgaagataa atagggccag agatgagtaa ttttgttact gtgataatat 44040
attttatata tatgtgtatg tgtgtgcgtg tgtatatata tatatgagat atatctcata 44100
tatatgagat atatatgata tatatatgat atatatgata tatatatata aaacatacag 44160
ttcagtagca ttaacatcta gcattcagta catttacatt gttgtgcaat tgtcaccact 44220
gtccatctct agaacttttt cattatccca cactgacata ccacacccat taaataataa 44280
ctcctcattg ctcctcctgt tagtaccaac cattgttcta ctttcatctc tatgtatttg 44340
actattctag gtacctcgta taagcggaat cacgtgatat ctttttgtaa ctggcttatt 44400
tcactaacta tcttcgaggt tcatccatgt tgtagcagtt gttagcattt ccttcctttt 44460
aaaaggccga ataatattcc attgttatgt atataccata ttttgtttat ccatttattc 44520
atcaatagac acttttggct gttgtgaata atgctgctat gaatatgggt atgtaatacc 44580
tgtttgagta tctgctttca tttcttttgg atatgtaccc aaaagtgaga ttgctggatt 44640
gaatggtaat tctatattta aatttttgag aaaccaccat actgtttgat atactggctg 44700
cccaatttta cattaccacc agcaatacac tagggttccg aatttgccac atcctcacca 44760
tcgtgttgtt ttgtttatgt ttttttttaa taatagccat cctaatgggt gtgaagtctc 44820
attgtggttt taatttgcat tttcctaatg atcagcgata ttgaacattt gcacatgctt 44880
atttggtcat ttgtatatca gctttggagc aatgatgtct cttgaagcct tttgcccatt 44940
tatgaattga gtagtttggg atttttaaat tgtgttttag aagttctttg tatactctgg 45000
ctgggcacgg tggctcgtgc ctttgggagg ccgaggcagg tggatcacga ggttaggagt 45060
tcaagaccag actggctggt atagtgaaac cccatctcta ctaaaaatac aaaaaattagc 45120
tggtgtggtc gggcgtgatg gtgcacacct gtagtcccag ctgttgggga ggctgaggca 45180

-continued

```
ggagacttgc ttgaacccgg aaggtggggg ggttgcagtg agctgagatt gtgccactgc  45240
actcagcctg ggtgacagag cgagactctg tctcaaaaaa aaagaaaaag aagttctttg  45300
tattctctga atattaatcc cttattggat atgttatttg caaatatttt ctcccataaa  45360
gaatgggtta ctttttcact ctgttgattg tttcctttgc tgtgcaggag ctatttagct  45420
tgaaaaaatc caacttgtct gttttctttt gttgcctgta cctttggtgt cacattcaag  45480
aaataattgc caaattcata ccatgaaact ttcccccatg ttttctcctg aaggttttta  45540
tagttttagc tctcacattt aggtgtttga tccattttga gttaaatttt gtatataatg  45600
ttatgtaaga gtccagcttc acacttttgg atgtgaatat ctagttttcc cagcattatt  45660
tgttgaaaag agtgtctttt tccccattga atagtcttgg cactcttgtt gaaaattatt  45720
tgacaataga tgcaagggtt tatttttggg ctctctcgac tattctgtta gactatatgt  45780
ttgttttttt atgtcaggac caccctaatt ttagtactgt agctttatag taaaatttga  45840
aaccaggaag tatatgtctt gtgtatttat ttacttattt tttgaaatag catctggctc  45900
tgttgcccag gctggagtgc agtggcacaa tcttagctca ctgcaacctc cacatctgag  45960
gttcaagcaa tcctcccacc tcagcctcct gagtagctgg gattgtagac acataccacc  46020
atgctcagct agtttttgta tttcttgtag agacagggtt ttgccatatt gcccaggtgg  46080
gtctcgaact cctgagccca agcagtctgc cctcctcagt gtcccaaagt gttgcgatta  46140
caggtatgag ccaccgtgca tggccccaac ttcttatatt tcaagatggt tttggccctt  46200
cagggccctt tgtgagtttt aggatggatt tttttttaa cttttaagtt taggggtgca  46260
tgtgcaggtt tattacatag gtaaatttgt gtcaaggtgt tctgttgtat agattatttc  46320
atcacccagg tattaagcct agtacccatt agttattttt cctgagctcg cctcctccca  46380
cctggatttt tttttttatt tctaccagaa acattgttgg gattttggta gggattgtat  46440
tagtctgtag attgcattga atagtactga catcttaaca atattaagtc tttaaagcca  46500
tgaacaccag atgtctttcc atttatttac gtattctttc ttttctttca gcaatgtttt  46560
gtaattttca gtgtacaagt attttacctc cttggttaag ttaattccta agtattttat  46620
tcattctgat gatcttataa atctgttttc ttaatttcct ttcctaattg ttcattctta  46680
gggtatagaa acacaactga ttcttcgcac attaaatttg tgccctgctt cttcgcgggt  46740
ttgtttattc ttttttgtg tttgaaatcc ttgaggtttt ctgcatataa gattatatca  46800
tctgcaaatg agataatttt acttgttcct ttccaatttg agatgatttt tattcatttt  46860
cttaatgctc tctcatacat tcaatactat gttgaatgga agtggtgaaa gcaggcatcc  46920
tgtcttgttt ctgaccttat aggaaaagct ttcaattctt tgccattgac tatcatgtta  46980
gctatgggat ttttttttc cccccagata gagtctcgct gtgtcgccca ggctggagtg  47040
cagtggtgcg atctcggttc actgcaccct cctcctcccg ccaggttcaa gtgattctcc  47100
tgcttcagcc tcccaagtag ctgggattac aggtgtccac cactatgccc agctaatttt  47160
cgtattttta gtagaaacat ggtttcacca tgttggccaa gctggtctcg aactcttggc  47220
ctcaagtgat tcacctgcct cggcctccca tagtgctggg attatagtca gccaccatgc  47280
ctggccactg tgggattttt atatatggcc ttcattatgt tgtggtaatt tctttttatt  47340
cttagtttat tgagtgtttt tatcataaaa tcttgttgaa ttttttcaaa tattttttct  47400
gtgctagttg agatgaccat gtgatttgtt ttcttctttc tattaacatg atatattgtt  47460
tttcatatat tgagccattt ttgcatccca ggaataaatt ttacttggtc ttcgtgtata  47520
atccatttaa taagctgtgg aattcagttt gttggttctg tgttgaggac tttatatcaa  47580
```

tgttcctaag ggctactggt ctatagtttt cttttgtagt ttctttgact ttgctatcag 47640
ggcaatgctg gcctcattga atgtgttagg aagtgtttcc tcatccattt ttggcaaaac 47700
tttgggaaaa aacgatgttc tttaaatgtt tgatagaatt cacagataaa aaaatcacat 47760
ctagggcttt tgtctggaat ttttttattg ttattattga ttcagtcttg ttactagtta 47820
taggtctatt cagattttct ttttgtgtgt gtgattcagt attagtacat tttgtacttc 47880
tcgttatttc tccatttaat ctatattatc taatttgttg gcatacaatt gttcatagta 47940
ctgtcttctc tttttttaa acttctgtgc agttgatact aatgtcccta cttttatttc 48000
agattttagt aatttgaatc ttctttatct taatacaggt aaagctgggt caattgttaa 48060
aattttttca aagaaccagt tttggtttc attgattttt ctctgttatt tttctattat 48120
ttatatcctc tctaagcttt gttatttcct tcatcctgct agctttgggt ttattagttt 48180
gttctttttc tagttcctta agatttgaag ttggattatt gatttgagat cgttttcaat 48240
taaatgtgta caactacaaa tttccctctt aggactgctt ttgctgttct gtaatttttg 48300
gcatgttgtg tttttttgtt ttaatttatt tctaagtatt ttctaagttc ccttgtgatt 48360
tcttctgcgt ttaaccgtgt atttttttaat ttccacagtt ggtgaatttt ctacttttc 48420 ttcagttatt gattttattg attttcagtg gcatcctgtt gtgatagaag atactttatt 48480
tggttccctg tttttttttt aaaacagagt gttgctctgt cacccaggct ggagtgcagt 48540
ggtgcgatct tggctcactg caacatccac ctcctgggtt cgagcaattc tcctggtctc 48600
agcctcccca gtaggtagga ttacaggcac atgccaccat gcccagctaa tttttgtatt 48660
tttagtagag acagggtttc gccatgttgg ccaggatgat ctcgaactcc tgacttcaag 48720
tgatccaccc gccttggcct cccgaagtgc taggattata ggcgttagcc accttgtctg 48780
gcccagatcc tctattttct tgcctatatt ctgactgggt gtttttgtcc attattgaga 48840
gtagggtatc gaagtgtcca gctgttattt cagaactgtc tgtttacctt caattctgtc 48900 aatttttgc ttcatataat tgggtggtct cttattaggc atgtaaatgt ttttgattat 48960
tatatcttct tgctatattg acacttattg atgtgtaata tcttttttgt ctcaaccttg 49020
ttttgattta gtttgtctaa tattaatgta gctacctgca ctctcatttg gttattactt 49080
gtatagaatg tctttttaca tcccttattt gtgtctttgg atctgaaatg agtctcttgt 49140
agacagcata tacaatctct tgtagattgt gtttttctta tacattctgt caaactctgc 49200
cttttgattg aagagtttta tcatttacaa ttaaagtaat tattgataag gatttaactg 49260
ctgccatttt gctgtttatt ttctatatgc cttacagctt ttttgtccct catttcctgc 49320
cttactggca cttgtgttta gttgatattt tgtggtgaag tgttttaatt tccttgttat 49380
ttccttttgt ttatattctg ctattttctg tgtgtgtgtg tgtgtggttg ccattggggg 49440
tcacatttaa tgccctaaag ttataacact gcaatttcaa tttataccaa tttactttca 49500
atagcataca aaaattcagc tcataagatt cagtccctgc tcccttccag ttattgatgt 49560
cataaaatta catttttatg tattgtgtgt ctaaaagcgt agactaataa ttgtttttta 49620
atgcagtagt gtcttaattt gtggaaaaca aaaagtggag ttgtaaacca atgttacaat 49680
aatgctagct ttggtaattg ctcatgtatt tatcatttct cagatcttta tttcttaata 49740
cagcttcaag ttactgtcta gtctcctttt atttcagcct gaaagactca cttcagcgtt 49800
tcttgcagga caggtctggt gataatgaac tctctcagat tttgttaatc tggaaatgtc 49860
ttaatgtctt catttttaag gacatttttg ctggatatag tattctcagt tgacaggtat 49920
ttgtgtttat ttgtttgttt cctttcagga ttttaaatat atcatcccac tgccttctgt 49980
ccttcaagag ttctgatgag aaatctgctg atattgagga tccctttgta tgttacaagt 50040
tgcttctctc attccatgtt caggattctc tttttcata gtttgattat aatctatctc 50100
agtttttcct acttggatct ctgagttttt cctacttgga gttaattgag cttcttgaat 50160
atttatattc atgtctcatc aaatttggga agtttttgat taatatttct tcacataatc 50220
tttttgccc cttttctctc tttttattct gggattccca gagtgtgtat gtgttggtcc 50280
acttgatgat ggtgttccac aggtgtctta ggctcttgtc ttcaattttc cttcagtttt 50340
ttttttctgt tcctcagaca cgtggtattt tcagctgttc tgccttccaa gtttactgat 50400
tcttctgcct gcccaaattg gcttttgaat tcctctagta aatttttatt tcagtttttg 50460
tacttttcag ctccagcatt tattttttga tttttttatg ttttctcttt attgatattt 50520
caattttgtt ttttgacatt atccatatct tcctttagct ttttgagcac ctttcaacat 50580
ttgttttaaa gtctatgtct agtaagtgtc tgccatctga tcttctcagg cacagtttct 50640
gttaatttat ttttttcctt ttggcctata cttaatgttt tgcttggggt agtttttttt 50700
tttggtatgc tttgtgattt ttgttgttgt tgtcaaaaac tggaatttga atcttaaaga 50760
gtggtaactt tggaaattag atttttctct tttctctaag atgtgctatt ttgtttggtt 50820
tttttatttg ttgtagagta tttctatgct gggtgtaatc ttaagatctt ctcggcctgt 50880
gtttttccct gggcatgtgt agtgactttc taaattgccc tatgtatgca gttcttttgc 50940
agtagtatcc tccttaaatg tttggctcct aaaaggcaaa ataaataaat aaataaataa 51000
aaattaaaaa ttaaaaataa atcaaagggg tgaaatagct ctggatcttt aaatccctgg 51060
agcaattttt tcagccaatg gcagttaaat aatgatagtc tgcctctgtg tcacattttg 51120
atcagaagca gcaattagca atcagaacac agattcctga tatttggagg gcaaggtctt 51180
tgttgccaac cttgactctt acaaactgtg tgcagggtgc tctgggaaca tgtgcatggt 51240
tgcctgcttt gagagtgggt gatgggtagc cgcgacggca caaagagctg aaattgactc 51300
aaactaactg atttaccatt caagtctttc cttagaaact gaaaacctga atagactcca 51360
gagttccaga atcacagatt ctgcttacag tcgtctaggt ggggagatgg gttcctggta 51420
cttctgattc tgccatcttt ctttgactaa tttttttttt ttgttcttga gatggagtct 51480
tactctgttg cccgcccagg ctggagtaca gtagcatgac ctcggctcac tgcaacctct 51540
gcctcccggg ttcaggcaat tctcctgcct cagcttccca agtagctgga attacaggcg 51600
tgcaccacca tgcctggcta attttttgta tttttagtag agacagggtt tcaccatgtt 51660
ggccaggcta gtctcgaact cctgacctca ggtgatcaac ccgcctcagc ctcccaaagt 51720
gctaggatta caggtgtgag ccactgcacc cagctcttag acaaattttt tattccaaac 51780
ttttttattt ttatcatttg aaaggtatat gtttattatt ttgtcaaaaa taattttaaa 51840
acgtattctt gaagcttatt tagatctgtt tcataggaac tgtgaagaaa gtaaagaatt 51900
taaaaaatga agacagattt tctcaccctg cttatgggtg cttctcgtgc tagccttttg 51960
caagtgtcgg gaagtgtaac ctgcaggagg catcagggct ttgggcctgc atggtctgag 52020
tgctgccctg tgagtttcag aaggcgcagc aacctgtata cctgaaagcc atctctgctg 52080
gggcaggtac ctagtgtccc cacctacctg ggtcgtagtc aggccctggg caagcctgct 52140
atgcttttcc ttccctaatc cctcaggggt gggatagaga gcacagtggc ctcccaggga 52200
ggtagaagct gctccagact aacaatcaga gctgccagtt cttaatcccc aagaccgcca 52260
gacttcacaa agacataccg aggtctgtgc tgtcagtgcc ccactactac actcccttaa 52320

```
gtagccccac attcttgtgc ttgtttcttt tttctgctct ctttccttgc ccaggtaaga  52380
ggtctgccca taagggatat tttgcagcat gtgaagcttt ttaaaaagtt aggcttattg  52440
aagtataatt tacacacaaa gtacaaaaaa aaaaagactg tgttctcaaa tctgtgagtc  52500
attaatgggt ttagatgttt atatattgaa attattggaa gtaaggtatg tttatattag  52560
aaagatttgt agtctagatt atccaagttt tgggagtatt acctctctgc ttttgtttat  52620
ctactttttt agtctctact ttccaagtat ctataggcaa attttcccat ttccctttgg  52680
aaagtgctgt tttcttgctt tttttccgcc tttccattgt gtcagactta taaggcaatc  52740
agccaactgt gggcatgaaa tccttgggag gaaagagaag gaagtgggag gggcagccat  52800
ggtgaatgtt tccctaagtt atagtcaagt tctttgagag aacataacct catccccttt  52860
ttaaactgtt gtaatacttt cttttaaata gattgtttat tctcctgcaa gtctcacagt  52920
tgttcacagt ggtaggtaag aaatcataaa gttcaaatat taaagggagc tcacaaaaga  52980
gcatggtttc accagccctc actaaaaaca aaattatggg aaaatgctgt aaaagaaacc  53040
agaattcttg gttgcaaatg atagaaagtg actctgattt acctaatcag aaaggaattt  53100
ttaaaaaagt attaggtagg tcatagtttg acaacaagac ttggaagata ggtggaagct  53160
aagggaagca agacatggcc ccaaggtttc aacaggagca atctgcttag gactttgctg  53220
cttggacact tggtgtaata gctgctgcca ctatgcctcg aaactggtga ctctgctcat  53280
taactcacct cctctggtga tctctaggaa taatctctga ctctcctgta ccttgtcctc  53340
actaggattc ggtatccacg gcaaaaagat ctattaatag ttggtatcag gcctgtacat  53400
gtgttaagag aaagatgagg aaagaagtat ctgcttctaa tctcttgaaa ttatctccaa  53460
attgaaatgg tattttggtt gcctaacagc ctgaagatga caaatatccc ctacaaattt  53520
ctcctatttt accctcttcc taactatatc tgtaatttaa agtttcacat attcttttga  53580
aaattgtttt cattgtttac ccacttttta agaaaagcaa atgggaacat actaccactg  53640
tttggcccct ttcaaaaatt ttatatctga ggaatcttcc atattgttgt ggacatctac  53700
ctacctgatt cttttattaa ctacctttta tttcatttta tgatcatgct atcattaata  53760
ggcccctatg atgaatatat aagttgtttc cagttttttt tttgtcattg agaacagttc  53820
acatatgtat cttgttgtct tttccaagta tatctttaag gcaaattctt agcagtggag  53880
ttgctaggtc cattgcgtct atggtttaaa ctagtgcctt caaaaatggt attttatata  53940
ctcactgttt aagagtgctt cttccttcta tccccactaa ctttggcaaa ctgaatagtt  54000
tcaaacttta actttttata gcttgttggc aaaaaatggt atcttgttat ttgatcgtgt  54060
ttttttaatt gtgaggttta gcgacttttt gatgtattgg tcttatgtac tttctggtgt  54120
gtgtgtatgt atatactgac cctattttca acttattttt cttttagttt gtttgtattt  54180
tccttaatga ttttcaggaa accaatttta ttctttcttc agacagttgt ctaatgttct  54240
gcttctcttg ccatttgaat tttgtgacta caaaattcag atgaaacaat aatagcataa  54300
agaacttggt gggttatctt ttgttttgca ttattgattg tttattaaga aatattcttt  54360
aaaagtcacc ttgcttaaat tagcaagtag gaaatgcttt caataaagag aactgtcatg  54420
tacccactac tccttactta ctgaatcatc ttcttttgga tagagaagat aaaagtgaaa  54480
agggaattta agagttcctg ccttttttcct tgtctttagc attatatagc tgtttaatgt  54540
gtgggagtct aatttctttt ttctttcttg agacaaagtc tcactctgtt gcccaggctg  54600
gagtgcagtg gcacagtctt ggctcactgc aacctctgcc tcccaggttc aagcaattct  54660
```

cctgccttag cctcctgagt agctgggact acaggcatgt gccaccatgc ccggctaatt 54720
tttgtatttt tagtagatat gggacttcac catgttggcc aggctggtct tgaactcctg 54780
acctctagtg atctgcctgc tttggcctcc caaagtgctg ggattacagg catgagccac 54840
tgcacctggc ctaatttttt tattgttctt tttggtgtga acattctccc ctcctccaag 54900
ccttttgttt ttactatttt catgttcctt tatatgtgct gctgttttgt ttcatctgta 54960
attatctctc atcccctttt ttggctatta taatatatat atgtacgttt tgaatctgag 55020
ctttgaaggt aaattcactg cagctgtgtt ggttgatttt agataatttg tgtatttcct 55080
cctttgtctt ttttaaactg gagtcatttg tagttgttta tacagaattt tagtttttaa 55140
aaccacaagt ctttcattat aggttgagtt atgaattcat agcctgttat ttaaatgaag 55200
cttttgaaat ctgttttact gatctgtatc atatctaact acgccagtat ttccttcctt 55260
gtctgacgtg aactctaaaa ttatgtgaac actttctccc tgtttcctgg catttccact 55320
caaacttgtt cctcattctt agttagaaat atatccagaa ttgtagtttc tttctaatct 55380
aatgacagaa gcaaattaat caagcatggc aagaatttat tggaaaactg catgtagttg 55440
aaaatatgtt tagtatatat tttgacagct gtgaagtctc taatttttac tgtacctttt 55500
ctctgttcca attttatgct ctattctaag gatgtaccca tttctactac ctgactaggg 55560
agcatgtgta ttgtatccca gcagattttt tttttcatag atagatatcc tttagatatc 55620
tgttatccag tgtaggtagc cactagccac atgtagctat cattatgttt aaatgtaaat 55680
aaaataaaat aaatttactg agttgttttt gctagctaca tttcttgtgc tcagtagcta 55740
catgtggctt gtgattactg tattaagaca gcacagatac agaacatttt cattattgca 55800
aaagttctgt tagacagtgc tgttctatac agtgtcattc tgcctctcat tctaaaaagt 55860
tctaattcct gaagttgatg tactctttct gttgctgtcc tctagcttaa tcaaaataaa 55920
tttgagtctt tttaaaggta ggttgcattt tacatactga tatttctaaa tcagaggcta 55980
tttatattac ttttttttata ttacttttaa aaattagctt tattggagta taatttacat 56040
gcaataaaat ctacccattt taaatgtacg gttcattgac ttttgagaaa tacacacaca 56100
cacacacaca cacacacacc ttcttgtaaa cacacacctt cttgtaaaca caacaaccaa 56160
gatttagaac actcgcttta tgaaaagttt ccctcatgcc catttgtagt cagtccccaa 56220
acctggtttc aggcaatctc tgatctgctt tctatatgct ttgcctatac taggattaca 56280
tataaataca gtcatatagc atgtattcct ttttgtgtct ggcttctttc ttttagtata 56340
atatttttga aatttatccc tgttgttact agtatcaata atttgttctt ttttattgct 56400
gactaatatt acattgtatg gatatgacat ttctttatta gtgtggtggg catttgagtt 56460
gttttcagtt tgggtctgtt atgaacaaag ctgctgtaag cattcatgtg caagactttt 56520
gtggacatat atttttgttt ctgtttattc aatacctttg agtagaattg ttgggtcaca 56580
tgatgtagat cagttgaaca gagtagattc cagaaaagtt cacatacaca tttcttgaca 56640
aaggtgctga gattattcat gggaaaagga taatctttta aacaaataat actggaacaa 56700
tagagaaaac aaagtgaacc ttgactttta tgtcttatca tatacaaaaa ttaatttgaa 56760
gtggattgtt gacctaaatg taaaagtaaa atttaaaaat ataaaacttc tagatgaaaa 56820
cataggagaa aatctctgtg acttttggtt taaagatttc ttagacagta catataaaat 56880
taactatata aggaaaaaat ggacaaattt gactttatca acattaaaaa tttctgctca 56940
ttgaaagact caaaatgaaa aggcaagcag ttttggagaa aatatttgca atacatatat 57000
ctgaaaaagg acttgaatgt ataatatata cataaagatg ctcttacaac ttcataatga 57060
gaaaataacc ccataaagag aagggcaggc cgggtgcagt ggctcatgcc tataatgcca 57120
gcacttttgg aggctgaggt gggtgaattg cttgagccca ggagtttgag accagcctgg 57180
gcaacatggt gaaacccagt ctctacaaaa taaaaaaata caagaaatta gctgggcatg 57240
atggcatgca cctgtagtcc tagctgtttg ggaggctgag gtgggaggat agcttgagcc 57300
tgggaggcgg aggctgcagt gagctgtgat cgcaccgctg cacgcttgcc tgagcaacac 57360
agtgagatcc tgtctcaaaa caaacaaaca aaaaaaaaaa caaaaaatgg aaacagaaat 57420
tttacaaaag aagatatata gatggccagt aggcatatga aaagatgttt aaaatcagtc 57480
atcagggaaa tgaaaattta aacgtaatga gatagctcat atttactgga atggctcaaa 57540
aagggcttac aggaattggc aaagacatag attaactgga actcttatgc atgttggtta 57600
gagcacaaaa tgatatgatt tcttgggaga aatatttggc agtttttaag attatttttg 57660
atagccttct gaatttctta gtgagttata ggtcagttct gccactgttt ctttcttttc 57720
tttctttctt tctttccttc cttcccttcc ttcccttcct tgcctgtctt gcctgccttc 57780
cttgccttgc ctgccttgcc ttcctttctt cctttcttcc ctttcttttc tttcttttct 57840
tttttttttt aaaggagtct cgttttgttg cccaggctgg agtgcagtgg cacgatcttg 57900
gctcactgca acctccacct cccgggttca agcaattctc cctgcctcag cttccccaat 57960
agctgggatt acaggcgcgt tccaccatac ttggctaatt tttttaattt tggcagaggc 58020
agggtttcac tgtgttggcc aggctagtct cgaacacctg acctcaagtg atctgcccgc 58080
cttggcctcc cagagtactg ggattacagg tgtgagccac tgcgcctggc ctggcactgt 58140
ttatttcttt tccctccagt tttataccta tttagagaga ttagattttc ttgagtacta 58200
ggaatcacta tttttgagca gaattattca aaactgttat tattttttct ttaacttgag 58260
gcaatgtagg agaaagcagt actgtgcagg tgaaagttac aaacaagaac attttaaaca 58320
agatagttac tttccatgta ttggatacgt aacagaatta attctaataa ccatcctgaa 58380
gatggtcagg aggcattagt taagaattga aatgtttgga gcttgcctgt gttgatggga 58440
ttaaggcagg gatgatttat gtgtaaattt atgcgttagt aacagcagta accgctgtag 58500
ttacactagg gttctaagag caaatgttga ttaaacatga atgtagcagg agtgataagg 58560
tttggctctg tgtccccacc caaatctcat gtggagttgt gatcctcagt gttggaggag 58620
gggcttggta ggaggtgatt ggatcatggg agtggtttgt aatggtttta gcactatcac 58680
cctagagctg tctcgcgaaa gagttctcct gagatctgct tgtatataag tgtgtagcac 58740
ctcccctctt tgctctctct cttcctccta ctcctgccgc ggggacgtgc ttgctttccc 58800
ttggccttct gccatgattg taagtttcct gaggcctctg attaaacctt tcttcttcta 58860
aaagattacc cagtctcagg tagttcttta tagcagtgtg agaatggact aatacaaggg 58920
gaaatatata tggttaccaa atagcgaatt agccatggga aaaagtagca aataaataat 58980
tattttactt tttcagatgc taatttttct tttcgtttat tttaggattg gtgggagctg 59040
tccaatgtcc ttaggctgtt ttccaaatga gataccaaaa gctagttctc catcgggttt 59100
ctcaggctgc tagaagcatt cattattatg gttgtcatta cttcgagttc tgttgccgct 59160
atgcccacag tagtatttgt tacataacag gtgcttgata aatatttgct aaatgaattt 59220
ttggaaaata caatctgcca cacctttctt ctacagttta caatcttctg ttgagatcat 59280
ccgatagatt ttttttctta gatattgtac ttttgaggcc tcaaattgct gtcttttgta 59340
ttttctatgt ctgcagagac tttccatctt tcactcattg tattcattgt tttttaacat 59400

```
ctttgtacat atttatagta actgttttaa agtcactgtc tgttaattca aacatctggt  59460
tcatcttgga gtctgattct attgcctgct ctttttcttt tgtaataggt catgtttttc  59520
tgctttgcct gtctagtaaa ttttaatcgt atgttgaaat gtagggagtt tggattgtta  59580
cttcctttaa gggtgctgag tttcattttg tcaggcattt aaattgatag ttgatttagt  59640
attgtcaggt ttggttctct ttgttaaagc aggcattttt cagatttgtc ttttgtccta  59700
gggcatggtt tttaacttca aggttgccct ttccaatgtc tcagctaagt atctggggtg  59760
ttccatgagg tctcttccac tttgcctagg ccagaactcc agcttctccc agtattatat  59820
ttcgttacct ctggcgtcat ctccgttatg ctttcagatc ctgcgcatag acagcccagc  59880
ccccagccaa ggacctgaga tgaaatccat acaaaattct tagtcccttg ctccacaaac  59940
tccaacagcc ttagcagtct aatctcttcc tgtttacctc agtgaaatct gtgttccact  60000
tgagttccat ttccttctgt atcagagaag agccaccatg ctgaaagcaa ggggcactat  60060
gtttctttgt tcttaaggat ggtagcctat ctgcaacaac tgtagtgtga tataaaaata  60120
tataatttat gttgctgaca gttacaaata ctgcttgcag tactttgtaa cataattttt  60180
cagattcaag ttcatatact cttttttttcc acatcaccac acacatattt tcagacttcc  60240
tcctcatcct tcttcttgcc agtagttgta ttataattcc tgccagtagt tacattataa  60300
ttttggttat atcaatattg agtttttatg ggattataac tagataaatg ccattcatag  60360
ttaagtgata gagtatattg tgactttttt cctgcatgtt ttattttttc tggacttcac  60420
agttgtctct cttttttttta aaaaaattag ttttcaatgt tcttagcttt aattcataaa  60480
ctcacccccta attgtataaa tctctcaaca tgtttaagca catttggcat tatatcaatt  60540
ttatcttttc caggtgcctt ctaatctgtc ccagtctgga ctaattgttc ttcctggctt  60600
gctgtatggc tgtctactca agatgtccct tcaccatcat tctagggatt cccttttcct  60660
ctcttgtggg ttagattctt cagttcttgg agactgtcat cttctttcat ggtttcccac  60720
tcttgttttg gcggagcaca tctttagtaa cttcctgaca aagtgtatgg tttgagattt  60780
cgctgatttt aaaatgccct tattatatag tcacacttga tttatagtct gtcttggtat  60840
agaattctag gctgagaaga gttttccctc aaaatcagaa ggttttgccc aattgttttt  60900
tagctgctag tattgctgtt aaaaaggata atgtcatttt gattctagat tcttttatga  60960
aacctgtttc ttctctggca gcttttagga tcttctgttt ctttggtatt cagaaatttc  61020
atgagatatg tgtgcttcta ttttggtctt attttcatct gttttgccag gtactcatgc  61080
aactttccag tttgaaaact cacatccttc actttgagt attttcttg agttatgtct  61140
tcggtttctt ctcagtgttc tctgtttctg gaactcctaa aatatattta acatcctgaa  61200
ctcttagttt ttgtttagtc ttctgatttt catttgtctt tttattctgt atattctgtt  61260
aattcctcgg cttcatggtc ttctagccct tcttttgcct atcttatggg gttgaggatt  61320
aaacagttta tatacctgag gtgcttagga tatgtctgtc atatagtaag tgcttgtgtt  61380
agctgtaatt gttgtttact ttcataactg tcttgaggga aaggtctttg gtcttgattc  61440
tttgacttct tggctgtaca tgaccttgga cgagttatgt aatctctttg agacctacct  61500
ccctcttctg tatagtgtta ataagctcta gctctcagat gtttgtgagg gtcgaatgga  61560
gtatatatgt gaaaatgttt aataccttttg tacagaatta atagttagta cgtggatctt  61620
tcaaatatca aaagttttca gtttgatggg aaaatgatgt ctgaattttc agggttattt  61680
ttaagagtac ttgattatga ctgtcttgta aatctctatg agctaggtat acttgcacta  61740
aatgctaatg ctttttaaag aagttatgtc ttaatattca gtctcattat gttaggttga  61800
```

agatagaaga ttatgaaaat attctctgaa aagctctggt tttacttcag attgtataaa 61860
tctgtgtaat gtaataatta tttaagaatg acatgattac tactctaaac ccatagaagg 61920
ggtatttgtt ggattattta ttttcactta aatggtattt gagattagga aaaagaaaat 61980
ctgtcttttg gtttttcttg atagtattaa tgtaatttca aatgttagct catttttgtt 62040
aatggtggct ttttgtttgt ttgtttttgtt ttaaggtttt tggattcaaa gcataaaaac 62100
cattacaaga tatacaatct gtaagtatgt tttcttattt gtatgcttgc aaatatcttc 62160
taaaacaact attaagtgaa agttatctgc ttgttagagt gaggtagagt taaagataca 62220
ttttaacaga attgtattcc taaaccgatt aagtcaagaa gtccaagagc attgttagat 62280
catttagaaa gtgtagtgat gaggtaaaac attgttggca cagattcatg ttacttgatc 62340
tgctttaaat gacttggcat ctagcccata tttgagccca taaccgtgtg gtaatttgaa 62400
gtgtaattca cagtagagct tctgttaaag cactaatagc atcttccatg gaggtatact 62460
tcagagtgaa tataattttg tttatcctgt gtctctagag ctattgactg aaaaagctgt 62520
tagggcattc tctaactgta catcacctaa gttatttaaa attgctgaat taggtggctt 62580
gtcttgtcta ggacagagtt ttaaggactg cccacctgat tgatagagct agttgacctt 62640
atctttaact ttttgttttt cttttgactt tgggagtaga gatgtgaaaa ggtaaaaagg 62700
aaggaaggaa gagaaaactt aactcttttt gcccatgaag actgtttttc cttctcaaaa 62760
tattgactat tttctgattt gtaaaaatcg gcacataaaa cgtgttattt tttacttgac 62820
ttttatcttt cccatgtgat atctataaat tatagatagg aaaaatttat ctgtaattta 62880
gtgatctttc tagtgtgata aaacgtcaga agtactgaga gtggagtgga cattgatatt 62940
gttactctca gtaagttttc actgattttt ctcagagtca tgaaggaaca aacgtttgtt 63000
aagtccttat cacttattag ataacacaaa acatgttggg ggggtgtgta cagaggtgag 63060
taagatgtag ctcccattct caagtcgctt acattctaat gtaaaaggta gacaaagcat 63120
tacagaagaa gtaactctgc tatagaaggt tgcaatgaag agaacattgg aaacactaat 63180
tttaccttat aaagaaggtt tcataaagga aggcaagttt gagctggggt gaaaaggacc 63240
agtaagggtt gactttcaag ccaaggagag gaggggaagt gatgttacag gccaaaggaa 63300
tggcattgta agaagcttgt tggcataaaa gtgtttagaa tatggcagcg aattcattat 63360
catcagattg tggtgtctgt atgttggggg tgggagagaa ttgtggtggc aataggcaac 63420
aagataaaag aaagtaaaag gtgttatgga aacttaatgg gtccagctta caaatgatct 63480
atgcatttag ggtctttct cttttcctga taaacctctc ctacaaagag ccttgttgcg 63540
gataccatag tgtttctttg gaggaaaata aaaactacaa agctttgtat tttttgcaca 63600
actggattca gaatataagt aataaaaaag gacaagaact ttcaaaagct agaagccatt 63660
aaactgagtc acttcagggt tagactatca gaactgggga tttagaaagt ctcagaatgg 63720
aaatcgaagg acaccaaaga caaattcggc ctttttcaaa attttattct agtttaacat 63780
attcaaagaa agggaaggaa attcttttca ttcctgtgtg tagtgacttc ctgctttaag 63840
aacttaggac ttcagctgta ctatcagtat tgtaggccac ttaacattat tatggttaaa 63900
gttggcattg gagagagcct aggaacctaa ctgcctgttt gtttttatat ttccaaccat 63960
tggattccca agttaatgaa gtctgtttat tagttgaggg tagctcttaa tgcatatatt 64020
ttaatgcccc ttccccacat ggaatcataa gctttcagaa ctggagagta cctgaaagag 64080
atcatttagt ccaaccttct cattttacag atggggaatc tgaggcctag agaagttaag 64140

-continued

```
tgagttgaac aaggtcacac aggtacatat ggtagccgac catccactgt ttatgccaat  64200
attcccttta cgttttgctt ttttgcttgt tcgttttaac ctctccaaat tttactgact  64260
tcagaagttt ctagaactaa gttatagcat gttttgagtt ctaatgtcac tttccgatct  64320
tctttacctt ttttctacct ctgtttgtat ttctggttct ggttaagtga gtctggtaag  64380
cagcaggtgt tctattttat ttcttttatt tttaggatag tattacatgt gatatatatg  64440
tctttgcaaa catacataat ttgaagatct taaaatattt gcactaggca tacccacatt  64500
taatagtatg ttaaatcttt tatagcaatt atgatataca tgggtgaaga agagttccta  64560
atatggcctt tctgattaac tgtatctgtt tatatctgtg ttttcttcag gcattcataa  64620
cattaagcaa attcaggtgt actgttactt aattgaatta atcagtttgt tttgtacaag  64680
tatattttat ttttgttcct tgttgtataa tctggtagga atggggaagg ggagatagtg  64740
aataaagaga tgtatacttc ttgcctttga ggaatttaag ttttcactgt ataccaattt  64800
tttaaaggta tttactatat ttcagtgcat attttatttg acatacttta tcattttgtg  64860
gtaaaccttt agctttacta attttcatct attaagtttt cttttgtaag atggtgatag  64920
cttcatcaaa gagagtaaag aagagacctg cctacctagc tgattctatg gcaaatctca  64980
cttctctgga agcttttcct gttaatctta ttccttcagt ttctgcctct tgtttcataa  65040
aaactcattc tttaaatgct tattcatttc tcttgtctca tataaaccaa tatgaggtac  65100
tggtatcttt tgagttttag ttataaggaa gcataaatgg ttaaatttaa atggctaaac  65160
cccatttgcc atttgtgtat ctttaatttt agtttgttga gagacttatc actaccaaac  65220
cacaaagaat ttaaaagaaa ctgtcagtag gtataggtgg aaggagggca tttatcagag  65280
atttaattt aagaagaaag tcttcatcct tatcctacca acccccattc cctgagcata  65340
tttatcatta ctagtcccag catatttgct cccatatttc ctatgcttac ctgtgaagat  65400
tttcataact ttttccttgc tttttactgt cactgttggt tctgtgattt atgacagata  65460
ctgctcttgt aggaatgctg gctttgactg aaatttgtta ctgcttttgt atttaaaact  65520
tttttttat tataagtaga attatggaac agtagtagaa aaagtttgac ttttgtaatc  65580
agagatactg agcttgagtt ctggctcttt catttgtata ctgttatttg gggcaagttt  65640
tttaatgctc ttaagtctta gctttctcat atataaaatg gagataataa cagttatcac  65700
gtgattgtga ggatgaaaca aaaaaaagtg gaaactcttt gtaaggtgtg ttcatctggt  65760
tgacacttag tagtcattac ttccactttc cgtccatata gtcctcttaa cagtaatatt  65820
tgagaggcat ttttattaaa gcagtcttaa ggagtgttcg tcaaaccaca tgttctggga  65880
tcctgagaaa gtaggggaag tttagagaac tgaagctgca caaaactaat gtttattttc  65940
tgttgtgttg tcctgagacc agcttcttag attgtgtttc ctagtcctac atctctgatt  66000
ccttataaaa tattccatta tgaattcttc actattgaca atttctcccc ttttatctta  66060
aaagtaccaa agaaagtgta aaatgtgact gtcttgtcag tcctcttttt cctgtttttc  66120
atgtcagtgg gtatgaaatt actagcaagg atgcatatat gtgcatatgt cattactaaa  66180
tgcattttct ttctagaaaa actcaatata ctaaattgta ctaaaaagga aaagcttgtt  66240
ttgttttgag tggtagtatg aaagttgttt tattttaggt ctgaccagtt agaaaccaat  66300
ggattgtagt ttatttataa ttagttaaac cttcatgtga atttggtttt gaattacctt  66360
taaggtagag aagaaactat atagatgttt ttcagggttt ctaaatgtac aatacaggtt  66420
cacaatcact tatttgaaac tcttggggcc aagtatgttt ccattttcag aaattttagt  66480
tttcaaaagg tagcacagat aaatatactt ttacataaac accccagtgg ggtgtgggtc  66540
```

```
agtacctgaa atgaaatgtt ttactcttcg ctctaagtgt attaaatatt atgtacaatc  66600
ttattacttc agatcaggat ttgctgtagt tgagtttgcc ataaaactta agagaaaatt  66660
ttagatgttt tgaacttttg ggatattgaa attgcaggtt aaggagctat ggacctttat  66720
ttgttttaaa atgctaagag tttattttaa gtaattttta aaaaatttgt tttgcatagt  66780
agttggagtt accagggtac tgctaaccac actgatatgt aagatctctt tctgagcctt  66840
ttattgtttg taaacatggc ctgttaatca ttagaaagcc agtacatact aacatatcac  66900
tgctattaag acaaatatta gcatactcta gtaatgacaa gtcagcattt tactattctg  66960
tattgatttt acttattctt tcattactct catactgtaa ttaaaacttg caatctgaga  67020
gactgttgaa aaaggtgatc gttggctttt caacagggag taaggtctgg tttaaaaaaa  67080
aattagtaag catttggcca agtagattaa caacattcag tttttcttta ctgtccttat  67140
gcttttacta tttttaacat atatcttttt gaagaatagt ttgagaatta tgtatgctta  67200
actatgagat acagatacta ttgaaactag tcagttgttt ataggtactt gtaaaattaa  67260
aaatatattc caatagcatg cagatttttc atagaggaaa tttgaaagca tggaagcacc  67320
tgaatttaca gtactctgta ttagtggcat cacaagtttt taagcaaatg tattagctct  67380
aattgcatac acttaatctt ttaagctttg gttttattat tataatatgg gggtgataac  67440
agtatctact taatagaatt cttgttatta catgaaataa ttaatgttaa acacagcata  67500
atatgtgtca cattataaag attcaggcaa tgtttgttag tattagtact tttttttctt  67560
cctaagtgca aaagataact ttatatcact tttaaacttt tcttttagtt gtgctgaaag  67620
acattatgac accgccaaat ttaattgcag aggtaggtat gaatgtactg tactatgttg  67680
tataacttaa acccgataga ctgtatctta ctgtcataac aataatgagt catccagatt  67740
atcgagtgag atacatattt aagaattatc tttaaaaatt tcaaaaattt taattttact  67800
gttgtgtttt aggaaaaagt attgcataaa gctattaata ttgtcaggaa gactaaagtg  67860
cagcatagac taagaattag gaaaattcct agactaaaaa tagtataagg agagggttta  67920
cctactattt gaggcagttg gtctaatagt aagcaatcac agggagaaag cagaactact  67980
taactcttct gtgttgagga atgacataaa aggtaggaaa ggatataaca aatgttgata  68040
agaggagtct gatggatgag aggagggaac tgctttaaat gagtttctac ttcagacata  68100
agttaattct cagagcccac aaaaactttc acttttattt gtgaaataca actcagttct  68160
catggcttaa cactttaaac catgagaaaa ctgaagagtt gagaagcttg gcagatgctg  68220
ctgtgatagt caaaaagaaa gtgggtgcca tgagctacta ttgatgtatt tgccattgat  68280
ccctcctgaa aatctagaat ggactttcag acaaatggtt tgaaaattct aaatcactaa  68340
tgattgagat ttagtatagg tttactaaga acgggttttt tttgtttttg tttttggtgg  68400
atttaggctg ttgcttacta agcaaagcag gctttagttg aggtttatct tgctttaaac  68460
agatatttaa cagattttcc tggaggtttt tgtgtaccac tgggaaaatg aagttaggca  68520
gatgactaag tgaaagctgt cctgctgact ccttataatg atagtcattg tctaccagaa  68580
gatctctcct gtcacaccaa aggataattg attatatcct gtaccatatt atgagtcacc  68640
tgattggaga tataagacat acttctcaca tatttagatg acacaggtta gtacattgaa  68700
tatcagccag ggtttttaag gatcttaata gagtggaact aaggtagaaa ctattaagag  68760
caattaatag tgatatatct atagtcctgt ttctaaacaa gttttttttaa aaacctcaac  68820
tctgactata gtgaacagag aagtcttgga ctcttacaat tcatgtgaga agacctgaaa  68880
```

-continued

```
ctttgataac aattatatac attttgtgag taatttcttt ggtgtatgcc ttcacatatc  68940
tctggtatgt gacctatgct gcagtccatt gagcatagat tcccagaatg tattctcctg  69000
cagaaaatgg aggaaaataa tacttggctt ccctaatgat tacatgtgta tacaacacta  69060
acatttgcaa gaccaccttt aaataacaca cttagcattt ttattttatg aaatgtaata  69120
tgtagttctt tgcatagttt atcctattag taatctattc tgtctttgga atatgttttg  69180
tgatgatgaa ataaatacta taaatagtat tattcctttt gcattgagag tcctgacgaa  69240
atgtccatgt gacagttcat tttgggttta gctctacctc taatatgtga cctatgctac  69300
cagtccgtat agcgtaaatt cccagaatat atcctcctga ataaaatggg ggaaaataat  69360
acctggcttc cttaatgatt atatttaaga cttatcaaga gactattttc tatttaacaa  69420
ttagaaagtt aagcaataca ttatttttct ctggaatcca gtgtttcttt taaatacctg  69480
ttaagtttgt atgcaacatt tctaaagtta cctacttgtt aattaaaaat tcaagagttt  69540
ttttttctta ttctgaggtt atctttttac cacagttgca caatatcctt ttgaagacca  69600
taacccacca cagctagaac ttatcaaacc cttttgtgaa gatcttgacc aatggctaag  69660
tgaagatgac aatcatgttg cagcaattca ctgtaaagct ggaaagggac gaactggtgt  69720
aatgatatgt gcatatttat tacatcgggg caaatttttta aaggcacaag aggccctaga  69780
tttctatggg gaagtaagga ccagagacaa aaaggtaagt tattttttga tgtttttcct  69840
ttcctcttcc tggatctgag aatttattgg aaaacagatt ttgggtttct ttttttcctt  69900
cagttttatt gaggtgtaat tgacaagtaa aaattatata taaatacaat gtataatatg  69960
atgttttgat gtatgtgtat atacattgtg aaatgattac tacagtcaaa ctacttaaca  70020
tattcatcac ctcacataat tattattctc cccccagggt gaaagcattt aagatctaca  70080
agctacaatt ttcaattata caatgttatt attaactata gtcactatgc tgtccagtag  70140
agcttcagat cttgttcatc ttgtgttcct ccctccccac cctcagtccc tggaaaacag  70200
gttttaaaga tagttgctaa tccttatttc ttctaaattt ttaaatcagt tgctgcctca  70260
atttctatat gagaaatgac tgattgattt catttttctg ttcacgctac cattttcata  70320
tcatactagc acatgttacc cattaactgt attgcagatt tggtctcaca aaattcttct  70380
aaaataacat ttttaaaaag catattaatc aaaaataagc tttatatttc tgaagcttgt  70440
ttgagcatag aatgcctttg gataaaatac cattacctag taaagtgtga acttttataa  70500
tccataaaaa ttattctttt ataagaatat tcataaatgt agttagatta atagaagatt  70560
ctcgattctt tgatcagaaa actaaggact atattgaaaa atcagtgaca aatttaattc  70620
ttatagtaca tctgaaagaa aaaagaaaac tcttgggaga acttttacag tgatttaatt  70680
ttgctgttga tatatttctt tgggtggtaa gtatggcaaa acatgttaaa atttaatgca  70740
aagagatttt gtacattttt ccatctctaa gaaggacaaa gcctaagccc ctccagatag  70800
atagaaaaac tcatttagag agttctcctt catgttaatc taatttcttc ttaattcagc  70860
tgtaaaacag aaatagaatg atcgtattaa tcatttaaag ctgtgtaatt gcatagattc  70920
cttgttcctt taccccctct tatatcttgt ttcctatcct ttgtgacttt ttttgcatta  70980
tatataagga tgccgaaata ctgtttattg ttgatagttt acaaaattga atcttacatt  71040
agtgcataat tttggtgaat gttgaagatt atggtagatt gccttacatt tctgcatatt  71100
gtttgcacct tggaatgata gcactggcat gaattataga gctgaggatc taaagatttt  71160
tactttgatt tatcccatta tcatctgcag ggaaacaatt gcttttactg attaaaaatg  71220
caggctgggc acagcggctc acgcctgtaa tcccagtact ttgggaggcc gaggcgggcg  71280
```

```
gatcacaagg tcaagagatc gagaccatcc tggccaacca acatggtgaa acctcatctc  71340
tactaaaaat acaaaaatta gctgggtgtg gtggcgcgtg cctgtaatcc cagctactca  71400
ggatgctgag gcaggagaat cgcttgaacc cgggaggtgg aggttgcagt gagccgagac  71460
tgtgccactg cactccagcc tggtgataga gggagactcc atctcaaaaa aaaaaaaaaa  71520
tgcagtagca aaagcgatgg tagaaattta aaacagagtt gatgagcagc atatattttg  71580
gtagtggaaa aaaaggtaaa aaattttttg taataaaata gaaaaatttt gtaatgtgga  71640
ggcgcagaac actagattta agccaggggg tcttaaattg tgttacattc cttttaaagt  71700
ctgatggaag gtataaatgt tctcccctca aaaaatgtgc atagtgtaca taaaattttg  71760
cagtttttat tacattgaaa tatattcttt tagacagaat gtaaaagaac cttcatgaaa  71820
actatgtcac tttttttatgc aaaaaccagt ggctactaca tgagagcaat gaataaatct  71880
aagtggtaca aattaaccaa aattaagctt tagttctgtt caatactaaa ttttaatgaa  71940
aagactgcta tttaactttt aaaataacaa gttgaaacta tgctctttga ctttgacttt  72000
gcaactttta tatgatcttt gatatccaat cagtgttgac tttggtaaaa agtgctgaaa  72060
atgctatttt acaaaagaaa gaagagtaaa tggaatctgt agattctatt gcctgatgaa  72120
agtagacgtg tcaagaaata agaattctcc aaggctcttc agataaattc atgtttcatc  72180
attttctttg ccttcaagtt actgagatca tttttggcaa gatctgtatc attaatgctg  72240
tgttaggaaa gaaaagatta tgactccaca ttttactttc aaggttgaag agttaaactg  72300
tttaaaaaga gtgtatgtta tcctgtaaac agcagtatca ggctgtagaa tttgtcttct  72360
gaaagcaggg aacttatata tagcaaagaa cttcatagtg ctcccatttc ttgacaaaac  72420
ctctcgagaa gctcttgatt gaaagtcttg gctttcatga atctggcagc tttcacaata  72480
gtggattttt catgacaaat catcttacac agggaattat tcaagggttg gcacttgaaa  72540
cagtagaata ctttcacaac aagagataag atttctttca ggattgatga cagtcttgca  72600
ccctagcgca tactgatgaa gagagcagtg ggtgaccatg acatggagag cttctgtctt  72660
taccagtgcc ccaatatcag atgtgttgtc tggcagtaag gtgtactgtc tgcctacaga  72720
atactgaggt ttcttcagga gaagtttttt ggtaaagaaa ctttaccatt ttgaaagtgt  72780
taatgttttc tgaagcttcc aaaaagattc caaaatggga atgtttcctt gattgtgtca  72840
ccatgcttgc atttgatgaa aacttgtagc cggctatact gagaaatcat atctgaagaa  72900
aggtggtact tccaatcttt ttgtgaccta ctttattatt gttttttaa tgtcagggtt  72960
ttttttggaa tggagaaaag tatttgatag aggtattgca acagtcttat tcttcttcat  73020
gctacaagta tatttgactc tttctaagat acttgccttc actgttcaac tgtgtgactt  73080
tttgtttgtt tagcattaca atcaatatcc tagtaggatg atttaatcaa tgatttttaa  73140
ttggaacaaa tagtttttgt aatggtctag gcttttccaa cttaactgtg ctctcacatg  73200
tggtctcttt ttctccctct ttcctccttc ttatacactc tcacccacac acatatgcat  73260
acataccctg tctgatgtat ctgcttcttc agaatagttg gctgtgctct gctgatgatg  73320
agaacttgcc atttaagaag gacttgggat agtccatgtc atcatgttca gggataaaag  73380
taaaacccaa gggcatttaa actttattgt attttatttt ctgtttccag tccaaattaa  73440
atccaagaga aggctccata atcaaaaagt aaggacatat tttaaatttg ccaatgggaa  73500
gatattctag tcattacagt ctggtaatac tatcaattct gtttctcttc agaggtgagg  73560
ggagactatt tgatgaaatc gtaagtcctg tagggtgttg tgaaataggg ccagaatgaa  73620
```

agatagcaag aatagtgtta tgaaaataaa atgcaaagtt tataatatca tgtggtaaaa 73680
tgtaatagta tttacttcat cagtagaact gctctagtag ctgtatattc tccatccttg 73740
cataggttgg aatatccccc aagtgaaaag agattgatgg gctaatagtt aatagaaaat 73800
ggagatctgt acatacagtg ttaagaatgt agatattaaa attgttatat ttagctgtta 73860
cataatatta agactcagag ttaagtaatt tcactgaaat tgattgcttt ttgtgtcttg 73920
gagtcaaaat aaataactga aatctactat acttggctca tgcttaatta atatacttag 73980
accatatttc ggatgaatta ttcacagaat ctaaaggagt atcctcgtgt tcttaccttc 74040
tttatccctg tgtttattta aaaaggcaaa aaaaatggag cagatgctgt tggttgacca 74100
tattttactg aacagtagca tttgtgttta ggttgaaaca gcattagaaa actagatacg 74160
gattaaagtc agtggtaggt tttttttttt ttttcttcca ggaatgtttc ttatagatga 74220
tcaaacaggc acaggaaggg gaagtgttgt gatcaatatt atccagttaa tattagcatt 74280
cagaggaaaa tttgagtcct ctgatacact gttaaatttc tttctatact atcaagtcca 74340
caaatcctgg aactgcaaaa gaattttgag actgttcaaa ataattaatc tctgtatagg 74400
ctcaggcttt cctgcaaggt tatgaaatgc tgataaaatt ggtcttattt tgaaaggctc 74460
ctcagcttat acctttcctt acaaatgctt ccttacaaat gctaaagcat ttaatgactc 74520
ctgacttaaa gggaatttgg acagattgag gttgttggtc ttggaaatat aatactgcag 74580
gcttctgtaa aatacttgaa atgtaattgt tttaaaactt tcaaagatac cacttgtttg 74640
cctgttggtt agaatactgg tgaaataatt tttaatcttt tatgaataac taatttcatc 74700
ataagaaaac ttagctaagc atggtaaagc tgttgttata caactgtgga attcttcctg 74760
aggagtaact atcttataat aaatgtagtt gattatctaa agtagtttta ttcttggaat 74820
atctcataat aggtttattc tcttcttgtc agtatttcct tgtagattga gcctgtggat 74880
ttgcattttt gtaattgtga atcaccatta taggagatac atgcatttta tctacttttc 74940
agtttgtatg gggttaactt tattagaatt atctttaatg ttattttgct tatatcctta 75000
attttaatta tagacaaaca ttaagaagct ggagaaaatt atgttctagt gacatttata 75060
tagaagaaga atcttttttc cccctttctt ttttgaaggg agatgaggca gtcatatttt 75120
ggtaaagaat ttgtagactt tgcagaggtc tcttcaaaat aatctggctc agagtcttga 75180
catatcctca gcagacatgg tgcaaattag atggcagagt ggtgggtaca agttgaccat 75240
aaaataacgc attaggttag taatgcccaa ataatacttt gggttttcag tgttgcagag 75300
aagtcagaca actgatagtt attataaaga aaaatgttct gagagtgagg taaccgctta 75360
agggaaggaa gcctccttct gtcttattca ctaatttaca agaagataat tgtgttacac 75420
ttccttagga gtcattcatt tgtatatttg acacttttgc tttatgaaca tgtgaagatt 75480
attcaaaagt aagctgttgg tgattttttt cttccaagaa agcatgccac agggcaactt 75540
ctagggttgg ttctcatcta gtcctgtgct ccacactatc tgcatctgca cttaagtttc 75600
aatattagat aactcacatg tttaaactat gaagaaagag ttaaaacatc ctgagaatgc 75660
tagtaagtat gtatttttga aaggacttcc aaaatttgag tttaaagagg taaactcctt 75720
ttacatgaca aagttactta gaaacactac tgctgtttcc ctctcccttg ccttctccct 75780
gtcccatgca tacccccagc tgtgttccag aatgatggca cataaagtaa acattcatat 75840
ttatttccct ttttttgttt tttttttttt tttttttttt tgcttgtttg ttttgttttt 75900
ttgtttgaga cagtctcact caatcaccca ggctggagtg cagtggcaac atctcagctc 75960
actgcaacct ctacctcctg agttcaagcg attctcctgc ctcagcctcc cgagcagctg 76020
ggattacagg cgcctgcccc cacgcctggc taatttttgt atttttagta gagatggggt 76080
ttcgccatgt tggccagact ggtcttgaac tcttgacctc aagtgatccg cccacctcgg 76140
cctcccaaag tgctgagatt acaggcatga gtcactgtgc ctggcctctt attttttctt 76200
tggttaaact tttagggaaa aagtttgagc tgcttttaat tttctttttg tttttaaata 76260
aattattaaa gtttctctat gttaggaact cttgtgtaca tgagttcatt gagcttattc 76320
ttaataaaga caaatcttct agaaataata gttgtatctt taaatgatct caaggaaaat 76380
gtttggtttc tctggggaat gaattttcat gacctaatct taaatcaggt tattttttct 76440
agcctgttta ctaaatttct acatgttata acctaatgaa attttcttac ttcctcttta 76500
tttaaaacaa actataatta ctgtcttttt aaaaatcttc caatgtggcg ttcttatttt 76560
tcttaacatt tgaattttcc tgggccaaac catgttacta tgatacacat tatttaaggc 76620
tgttatataa tacagtaaaa ttgtagaact ttcatacctt gaaggatctt agcaattatt 76680
taattcaaac ccattctaac atagatgata aaacagattt gcagggttgg gcacggtggc 76740
tcatacctat attcccagca ctttgggaga ctcaagcggg aagattgctt gagcccagga 76800
gttcaagacc agcttgggca acatagtgag aggctgtctc tacaaaaaaa tatttaaaaa 76860
atagccgggc atggtgtcac gtgcctgtag ttccagctgc ttgggaggct gaggtgggag 76920
gattgccaga gcctgggagg ttgaggctgc agtgagccat gatcacacca cagcactcta 76980
gcctagagcc tccctgtgtg gcaggctcta cacttcagat aggcaacaga tcgagacctt 77040
gtttcacaaa acgaacagat ctgcaaagat caacctgtcc taagtcatat aatctctttg 77100
tgtaataata aaaaccccat cttctaacct taaacctggt atttttttct acgaaactat 77160
gttctgcagt ccaaattatt tttctttatt attttgaatc ctaaagtaga aatagaaact 77220
tagaaaaata aaaagcaact cctttatgac atatgaggac tttttcagtt ttaaataaga 77280
aaaacccaac tcaaagtagc ttaaataaaa ggagacattt tttgacttac ataacctaaa 77340
agctctggcc tggatctagg tgctcaacag atctcaagag tatctctctt attctctctc 77400
cctcccttac cctcctcctc ttttctctct tctgtatata tgttattttc aaacaggctc 77460
tcacaagtag tggcaagata tagttcctaa tagcttcagg tttgcattct acctacttta 77520
gcaactatga tgagaagaga gctacaattt gagcaaaaat ttgtagggtg agttctgatt 77580
tccctggatt gaggcacatg cctattattc ctgaaccaaa tattctgtcc agggaatgga 77640
attctctggg gcatgtatct aaagctgaag tgtagagcct gccacacagg gataataata 77700
gttttccaaa gaaaaatcaa ggaggggaaa gaatgttgga aagagaaaaa aatatcagtt 77760
gtctgcttca catttgttct caataattag tttcatagaa gtgaaatact gtgtaacacc 77820
ctaaacttta gagattcttc gtagacagga aaaataagaa ctcaatgaag ttgtgacttc 77880
attcaaatca cgtagtttat atacatgcta ttagtaaaac ccaggacagc tgagtacaag 77940
ttttaccctt atattcacat tgaggtccag atcctggttt tgaatgagat aattacgtgc 78000
agtcggactg ttttctgatc ctaaaaatag agacaataat atctatcttg taaagttatg 78060
gtagtgttaa agatatataa aatgttggca agtaccttaa tatacaataa ctactgctat 78120
atgttgtcat tgtaataata atcatatttc ttcctttgtt gaattgcttt cctgtagtaa 78180
tcttattgtg atcatcctga aacatagatt tccgagcttc aagcaaacac tattatgttg 78240
aaaaatctac attatttcta agtttagcag tgccagtgga aagtttattg aaatagaaaa 78300
ttactttttt aactgaggag tgtagattgt gaattcgtga ttcatcttct taggagatga 78360

-continued

```
tcggaatatt gataaatatt gatgcataga atatgaacaa aacattacat atcttgtgct  78420
gtgatattaa agtagtattc tgttctggta gtagtatggc agtattttag gtctgaaaga  78480
tgtacataat ctgtactttg aagtctgttt tttaagagat taatcacaag agatttacat  78540
aaaacaacta aggttaaaaa taaatggtgg attagagata catcaggcaa atttcaattt  78600
caaaagcaga tgacagaatc tcagtatcag ggtagcattt aaagcaaaaa gcattaaact  78660
ggatcaaaaa tgtcatttta catcaacaca gggtacactc caggtaaaga cttaacagtt  78720
atgaacgaat gtgctaaaca tcaaaatgta ttaagtaaaa gctgaaagaa atgaagaata  78780
attggtagaa aagcaatgat aggaatcctt aatgtacttc aaaaggcacg aagtaagaag  78840
gtacagtcat gtaccacata atgatgtttg agtcaacacc tgacctggta tacgacaatg  78900
gtcctataaa attataatgg agctaaaaag cttctatcac ctagtgatgt tgaagccgtt  78960
gcaatgcaat gtatcactca catgtttgtg gtaatgctgg tgtaagcaaa cttactgtac  79020
tgtcagttgt ataaaagcat agcacagtta tgttcagcac ataatacttt ataatgataa  79080
acgaatatgt tactagttta cgtgtttaca gtactattat tttagcatgt gcttctgctt  79140
attaaaaaat gttaactata aaataatctt taggcagatc ctacaggagg tattccagat  79200
aaaggcatta ttgtcatagg agatggcagc tccatggatg ttattgcccc ttaagacctt  79260
ccagtgggac aagatgtata ggtggaagac agtgatattg atgatcctga ccttgtagag  79320
gccaaggcta aagtatgtat ttattagttt ttaacaagag tttaaaaagt aaaaaaaaaa  79380
aataaattta aaaatagaaa aaatcttaat aaggatacaa agaaaaaatg tttttgtgta  79440
gctgtgtaat atgtttttgt tttaagttaa atgttacaaa agagtcagag ttaaattttt  79500
ttatatttat aaagtgaaaa agttataaaa tgctaaggtt aatttactga agaaagaaaa  79560
aatttttaaa cagatttaga gtagcatgtt tataaaatct acagtagttt acagtaatat  79620
cctaggcctt cacattaact caccactcac ccactgactc acccagagca gcttccaatc  79680
ctgtaagctc cattcgtggt aagtgcccta tacaggtgta caatttttat atcctttata  79740
ccatttttac tgaacctttt ctgtctttta gatacacaaa taacattgtg ttacagttgc  79800
ctatgatatt gaatacagta acttactgta caagtttgta gcataggagc tgtatcatat  79860
agcctgggtg tgtagtgaac tataccatct aggcttgtgt aagtatattt tatgacacag  79920
tgatgaaatc atccagatac agtttctctt aagcaacaca taactgtata tatatatata  79980
taggtggctt taataataaa ataatgaaat atatttcttt ttttctgtca ttgacaaaac  80040
aattaccagt cttactaatt agatcaactg caaaacaaaa tctcactcaa aaataaaaat  80100
atgtaagtcc cattccttga ttacaattca ttagaactgg agatttttaa aaatgtttaa  80160
atttatatgg aaatataaaa tcatgtttta aataattttt gattcaatga ggaaatgtaa  80220
atttagaact aaagattaat aactagagat ttataaaggc aaaaatgtta atgaattagg  80280
aaacagtaaa ccatttgaac taatctaaat actgattgca tgaaaatgcc aataaaatca  80340
atacatattt ttaaaagcca gtcaaggata aaagaaaaga gggaaactaa aagtgagaca  80400
ttaagtatga gaaaggagat aaaactaaag tgtggaggtg atgttaaaaa ttatattcag  80460
gtctgtgcta atcattttgg aaatttcagt gagaagtggg caattttcag tgaatatatc  80520
attgtaaatg ctttgaggag agacaaaatc tgaatagacc ctgcaataat gaaaatgtct  80580
aggagccctc aagaaatacc tggtttaaat tgcatttcag gtggctggtt atcacacctt  80640
gaagtatcaa gtaattatgt tatctaaatt ggaccaggtg ttagaaaaat atgtgagact  80700
tcacaggtgg ctgcttatgt agcccttata ccttaatctg ataaaggtag catatattta  80760
```

aaaagagaga aaaccagaag gtacaattta gggaaaatta aatacttcta tttggccaaa 80820
gtaagagtac attcaaggga attgtgagag gtaagagtgg aaacagaggt tggagctgta 80880
tttttatgct gtgattgaat tacagtgtgt gataaatatt gctcttattt gggtagatta 80940
ccatttaaca ttttgaatta attggtaatt ggattaatct taacttttaa aaaactaatc 81000
tgagagtggt ataaaggata gattacagaa tggataaagg gtgataaatc agttggctat 81060
ggcaaaattg caggaagaaa ctgaaatagg ccacagaaaa ctgaaactga cattttgagt 81120
agtatttcag aatcaagatc tggattttgg caactgaata gatgcgtagg aatcaaagat 81180
gagtatacta aatgaactta atctatgatt tgtctgtcat tttattgtgt accattagtg 81240
tgtatgcatg tatgtatgtg ccaggtagtt aataggctga ctgtgtctct tagctccact 81300
ctgctgcctg ggcctttgcc atagtgctgg agttccctca cttctctttt ctgtaaccct 81360
attatattac tgctgtctct cagctgtgtt tcattcctca agcagaaaga agatgggagg 81420
atcatatagt agttgactag aagctgtgga gtttgagtgc tgggattata tctagttcca 81480
ttacttatga agattatatc tagttccatt acttcacctc atctataaaa tggtttacca 81540
atagtaccta ccttacatgg ttttatgagt attaaattat gtatttctaa agacatttag 81600
aacaatacaa agaatatagt gtgggctcaa taagtgacga tggtgttagt tattagaagg 81660
ccatcgagtg ctggagaaaa taattgaata tcattgatgg aaataaagga agttttccac 81720
gttaaaaagc ttcggttttt ggaaatgtgt gttttcagta tttctgagat taccaggtag 81780
aaattccagc cagatgttgg aattctgcac tggcagttgg gaataaagtc atgttaaagg 81840
agataagttt tggagttatt gtgtaaaatt ggtaaagcac tggaatagat tggtttgaca 81900
gaggggaaac tctttttgag ataggcctat atttagggac aagagaagag acaaccaata 81960
agggttgaaa gaaaccttga gagagtaagt cctatgacag aagcagggaa gtttcagaat 82020
gattgcagaa agatcagcca ggctcttcct gttctccatc gtggtgcagg atcaaggtga 82080
aaaggataac cccatgcagg aattttgcat ctgcaggctc cgcttcaaca tctgtttagg 82140
agaaagtgga gacagactga cctgagtaac taaggtcttg gaacagctta caggtcagaa 82200
ccaggtgttt tccaaagcta gatatactgt tagcgccttt ggcaacagaa gaaatgaaaa 82260
gactgttgtc tgctgcacag ttcgaggggc caaggcagac gaaatcctgg agaatgatct 82320
aaaggtgcag gagtgtgagt taagaaaaaa taacttctca gatactggaa actttggttt 82380
tgggacccag gaacacattg atctgggtat cagatatgac ccaagcattg atgtctacag 82440
cctggacttc tatgtggtgc tggaaaagcc aggtttcatc attgcaggta agaagtgcgg 82500
gacaggcttc attggtgcca aatagaatca gcaaagagga ggccatgcgc tggttccagc 82560
agaagtatga tgggatcatc cttcctggca aataaattct catttctacc caaaagggta 82620
ataaaaagtt ttcagtgaaa tgtttaaaaa aaaaataaaa aaaagatcag ccagcagcca 82680
ggatgggatt gtgaaaacag caggaaatta gttgttgaca aagcattaat gaccattaag 82740
aaatcagcct cggctgggca tggtggctca tccctgtaat cgtaacactt tgggaggcca 82800
aggcagattt cttgagtcca ggagttgaga ccagcctagg caacatggca aaaccctcgt 82860
tcctccttaa taaataaata aatgaataaa taaacaagca agcaagcagg gcttggtgtt 82920
aggcgcctgt actcctagct actcgggagg ctgagggggt tgaacctggg aggcaaaggt 82980
tgcagtgagc caagattgca ctactgcact ccagcctggg tgacagagtg agaccatggc 83040
acccccctcc ccttcaaaaa gaaatcagcc tcataatcaa tttctctgga ttaaggagta 83100

-continued

```
agagcgtctc aagatttgct gtttatagag agggaggcta atagtttgag agagatacag  83160
aatctaggga gagtgtgggt ttttggtctt tcagttgttt gccagccttg gataaagaat  83220
gaagattact tgagcatatt atttagagac aagtggagag aataaaggca catgccagat  83280
aggagataat taataaagca cttgtccaaa atagaaactt gttgaacagg aagagacgtc  83340
aagtataagg agattttaag atgggagaag ggaattttga gtgtttgtat tggatgacct  83400
cagggttccc agtaaagcag gagctgaatt catcgaaggt gatgtgttgg tcaggatcaa  83460
gagagaggtt gggagaacaa agtgctaaaa tcgttgtggt caagagttta aaaagtgtat  83520
accagaagag ttattgagtg ataggggttt gaaataggca aagctgtagg aaagggggct  83580
ggaaggaata ttaggaggaa cactaaatat acttctgagg tctacctcct ggtctgtgaa  83640
cataaaggag ctgaaagagt aatggctgaa gttctttagt ttagctaaag ttttttagct  83700
aaagctagaa ttgttgaaag ttgtatttga ggaaaaaaag ttaaggatac agttgaccgt  83760
tcgataatgt agcccactgt tgaccagaag ccctacccac aacataaaca ggcaataaca  83820
catattttgt atgtgtatta tatagtatat tcttaacaat aaagtaaact agagaaaaga  83880
acatgtatca agaaaatcat aaggaagaga aaacacattt acagtactgt actgtattta  83940
ttggtaccat acatttatgt tgctgtttac aagatgaagc atctgtctga aatggccagc  84000
agctacagct gtacctatct actgtacata tcaagcaagt cactttattc ttataatgtc  84060
tatgacttct ttctttgaaa gcgcttccat catcactgtt ggcacttcat atgggtctca  84120
tggtgttaag gtttacggca ttgcactaga cacaatgaaa actacacaag agggccgggc  84180
acggtggctc acgcctgtaa tcccagcact ttgggaggcc gaggcgggcg gatcatgagg  84240
tcaggagatt gagaccatcc tggctaacac agtgaaaccc tgtctctatt aaaaataaaa  84300
aaattagcca ggcatggtgg cacgtgcctg taatcccagc taatcgggag gctgaggcag  84360
gagaatcgct ttttcccaga aggcgtaggt tgcagtgagc cgagatcgtg ccactgcact  84420
ccagcctgga tgatagaggg agactctgtc gcaaaaaaaa agaaaagaaa aagaaaagaa  84480
aagaaaaaca cacaagagcc gtgagagaga tagcttttga ttgcaataca caatttactg  84540
gagagatgag ctgatcatac agagatgatt agtgtcacac agtgttttaa acagattctt  84600
gcaaccctgg agttcactgc agtagcaaca gaagttagct atgagatttt aacagtagta  84660
tagtatgtac tacagttaat attaggtagc tatgatttaa tgctgcatct ttgcatttgt  84720
ttacatttat cttgactaca agtggtatta tgtctggtct taaggtttgt gtgcatatgt  84780
tttgatgaat tttaactttt tataataggt ttgtgtatat tttatggcag taaatgataa  84840
aacagactaa tctacatata ttttatgtag tcatgacata aacctaactt tttcttaact  84900
ttttgatatt tctagtctat gtgtttcatc tgcaggtttt ttcaaattgt tgaaatctct  84960
gaaaaatttt attgaaaaaa aatccatata tgtaagtgga cccacacatt tcaaacctgt  85020
gttcaagggt cagctgtgta aataattttc ctcaaaatta aagtggaaaa ggagagttac  85080
tactagtaga aagtagaact gtacccttgg gcaggggtgt gtgtgtgtag ttaaagatca  85140
atttaactta aaaggtcttg gttagagaat aaaaactggc ccttattagc tttaatttac  85200
atgaaaaatg aaaaatttta ggccaggcac agtggctcag gcctgtaatc ccttaacttt  85260
gggagaccaa ggggagtgga tcacttgagg tcaggagttc aagacagcct ggccaacatg  85320
ctgactcacc cttccctact gaaaatacaa aagttagcca ggcgcagtgg ccatccctac  85380
agtgctagct actcgggagg ctgaggcagg agaattgctt gaacccggga ggcaaggttg  85440
cggtgagctg agatcgcacc actgcactcc agactgggtg acagagcgag actccatctc  85500
```

aaaaaaaaaa aaaaaaaaaa aagatttgaa aacagagtat tttttaatct gcaagagctt 85560
tacagccttt tattcatatg tataagcttt taaagatgac taaaatttta gtgtggactt 85620
tccactcatt ggaaatccta tattgcaggt gttaattcaa ttttagtgag tgtgcatcat 85680
ggctcagaga gataggacta gaatgaggag gtcacattgg agactctgaa acagatacat 85740
gtgagcctcc caacttttta atatttgtta atctagaagt gttgaatttt gggtgctgac 85800
aaggcagcag gtagataaga attgcaaagt taagaaaata gactgtaata ttgatggtaa 85860
actaattgat taaattttaa aatgtacttt tccatgtttt tctttgaatt gtcagtaatt 85920
ttgtttcaac tggtattcat acatagatta ttcacccaat gttgacaact agtagattta 85980
tatatttttt atgttgccta tcctttttttg ggtaaggatt aacagaatgt ataatcacct 86040
acattatagg tacactacta atcacttgct acttgaaaaa acctaaagct ttgaaatctt 86100
tttattattg cacacaaact tatgccaaaa atggagataa agagaaaaat gtcatccact 86160
aaaccccaac aaataatgtt gacaatgtgg tctactcgta gactcgcatt gacttaattt 86220
ttttaaatct tattgcatat tttgactaga taataaatgc atatggttaa aaaattcaca 86280
tggttcaaaa aagtacacct cccactcatc ttccatgtga tatttccttt ctgcttagca 86340
attctgtatt tatcttgcta aacatgaatg acagttgttt gctgaaatta cattaaatgt 86400
gacgtaataa aatcattgta agtttacatt ttttaacttt aataattttt aatgttttaa 86460
tgaagagtat gaagagtagt agtactgctc ttcaaagtac tactacttta ccttaccttt 86520
tactgttttg ttaagaaaat taggccgggc gcagtggctc acgcctgtaa tcccagcact 86580
ttgggaggcc gagacgggcg gatcacgagg tcaggagatc gagaccatcc tggctaacac 86640
ggtgaaaccc cgtctctact aaaaatacaa aaattagccg ggcatggtgg tgcgcgcctg 86700
tagtcccagc tacacgggag gctgaggcag gagaatggcg tgaacccggg aggcagagct 86760
tgcagtgagc cgagatcgca ccactgcact ccagcctggg cgacagagcg aaactccgtc 86820
tcaaaaaaaa aaaaaaaaaa aagaaaaaag aaaattatat agaaataaaa ttccagctat 86880
tccaaaactg caccttgaat acaggtacag aattgctaaa accgtgtacc attttgtagt 86940
tttagcatgc ttttgtgtaa ctgcatctgg tgtttgatcc tcatgagagc cctgttaagg 87000
aagggtacat attattgtcc tcattttcct tcgaaaacac atcagagttt gtattttgac 87060
tgtcagcatt caaatacaag tcttttattt ataaaatttt ggtctttata ctgtggctaa 87120
aaatcttaaa tcacttgtca tgatttgaaa tggtttatac cgattttttt tgacatttat 87180
acacacatac acatattttt aaattgtcta taataaaatc atgctcatct ttgaaaaaat 87240
attaggagta ctacagtgga tacctacata cttgctattc agcatacctg gtttttttgtt 87300
tgtttttttga gacagtcttc tctgtggtcc aggttggagt gcagtggcac gatctcagct 87360
cattgcaacc tccgtctccc aggctcaagt gattgtcctg cctcagcctc ccaagtagct 87420
gggactgcag gtacacatca ccacgcccag ctaatttttt gtatttttgg tagagacggg 87480
gtttcaccat gttggccagg ctggtctcca actcctgacc tcaagtgatc agcccacctc 87540
ggcctcccag agtgctggga ttacaggttg tgagccactg cacctggcct gtttttaaat 87600
tcacataaat atgttttata tttttcatta gggagaagaa ggttgtgtct acaattttta 87660
agacattggg gagatttaga tgccagtagt aacttaaaag agaaataatt gcaaattctt 87720
tttcctcttg agtatacttt catttaaggt acagtgttct gtaagttact tttaccgtta 87780
aacttcttaa tgttgcttat tgtttgtctt acatttttag gttggatttt tcttaagtca 87840

```
catgtctaat aaaaaaaacc cttaaatacc tcatttattc gtcttcgtta gtgaatgcat  87900
tgttgtacat attagatttt tctctttaga taactcagct tcccctatta agtgccacat  87960
gtattacaaa attttattta tgttttattg tttaataaac tcttgagaac tagatacatt  88020
ttaatcattt gtaatactta cattttctaa aacacttcat ttttccctgg tttcttcaac  88080
aaagagatgc atgtagtaca aggatagctt tacctgtgtt agaagattgt ttcacacatt  88140
tacatcaact gcatagtcct gtttttgttg ggccctaatg ccagcatcac tttttgctac  88200
tgctgtttct gccttaaagg caatatgcct ctgtctagtt tgctgattct gatactcttt  88260
cccctggaaa gtaggtaatc aagtttgtga ggagctgtgt gtttaaggag tccataaatc  88320
cttgtgggga gccctaggtg tatagagcat agctgtaggg cagaggcctt tgacacttat  88380
tctggatatg cagtggcctt tgcctatggg gttcatgggt cagagcgctg ttgtgacctt  88440
tgaataaatg ggttgttatg ataattgttt taagggagga gagttattct gatatccttt  88500
gtattgatat tgctcttatt tattattgag ctggatttaa gtattaatca tttaaggtca  88560
aatttctaat gtatatatgt tcttaaatgg ctacgaccca gttaccatag caatttagtg  88620
aaataactat aatggaacat tttttttcaa tttggcttct cttttttttc tgtccaccag  88680
ggagtaacta ttcccagtca gaggcgctat gtgtattatt atagctacct gttaaagaat  88740
catctggatt atagaccagt ggcactgttg tttcacaaga tgatgtttga aactattcca  88800
atgttcagtg gcggaacttg cagtaagtgc ttgaaattct catccttcca tgtattggaa  88860
cagttttctt aaccatatct agaagtttac ataaaaattt agaaagaaat ttaccacatt  88920
tgaaatttat gcaggagact atatttctga agcatttgaa caaattaatt agctttgttg  88980
ttcaactcat tgggctaaag aagccaaaag caatgggttt taatgtagtc gaagccaaat  89040
tatatttatg aaagaaatat tctgtgttat aaccaccaaa tacagcccaa ttctgactag  89100
atgatggaag aacctgtccc atcagaggtc cagcatgagg tccagcagag gtccaccaga  89160
ggagttcagc aatttgctgc tcttagggca gggatcaatt ccttaatatc ttaggaagac  89220
taggtattga cagtaatggt gacaaagcaa tgaaaaggaa aggaagaagt gataagacgt  89280
ggcagcaagc tgaagtatga tgagtaaaga ataggaatca aagtatgtgg agtgttagag  89340
aaaacctgga tttagatcca gattctagtc ctatctctgt cattaatcta ttgcgtaacc  89400
ctgagcatat catctacctc tctttgagtt tgcttgtcaa taaaatgaag agactttgaa  89460
atctgagact tcctggataa gtactaaata cagattatgt cactgatgtc tgcctctatt  89520
tatttctccc ttttacccta atctctataa gtctacctca gtcatcctga tcctattcta  89580
cttctctgat gttgttgtca gataggtgtg atcatcctca tcagatcttt tctgtattct  89640
tagagacaga taactttatc aaagaccaca gatttattag tatagcatgt taaagtcttc  89700
taaagagtct cattgatgct cttttcatct cagtacaatt tttaaaactg ctgaatgcaa  89760
ggtactgagc tgttggaagt gactgacaga tgaatgtaac agattcatag agaaggaaaa  89820
aggaagaaaa actcatgctc ttcctatagt attgatatca gtgtaagagc caagagaaag  89880
gtataaagta tcatgcagat attaagggaa agaaaacatt cactttagta atctttcctc  89940
attttctagt ttcctcttat gtactatgat ttaatactgt agtaaagttt taataaaata  90000
tgagctatat gtaattaagt gggaggttgt ggggctaggc acgaggctca cacgtgtaac  90060
cccagcactt tgggaggctg aggcaggcgg atcgcttgat ctcaggagtt cgagaccagc  90120
ctggacaaca aggtgaaacc ccatctctac taaaaacaca aaaattagct gggcatagtg  90180
gcacacacct gtagtcccag cttcttggga ggctgaggca ggagaatcgc ttgaatccag  90240
```

gaggcagagg ttgcagttag ccgagatcat gccactgcac tgcagcctgg acatcggagc 90300
aagactttgt cttagaaata aataaataaa tataaaataa aataaatggg aagttgtgta 90360
tataaattat aaatgctaca ttcagaaaag cttttgaagg ttgtcagaca gtttcttaaa 90420
ggaagttcac cagttcttta ttgaacattg aagaaaacat acagtttaga ctggcattaa 90480
aactgaaaga agtggccaga cgcagtggta gacgcagtgg ttcacgcctg taatcccagc 90540
actttgggag gtcaaggtgg atggatcacc tgaggtcagg agtttgagat caggctggcc 90600
gacatggtga aaccctgtct ctactaaaaa tacaaaaatt agccaggcat ggtgatgcgt 90660
gcctgtagtc ccagctactt gggaggctga ggcaggagaa ttgcttgaag ccgaaggtgg 90720
aggttgcagt gagccgagat tgcgtcattg cactccagcc agggcggtaa gagtgaggct 90780
ccgtcttaaa aaaaaaataa gtaaataaat taaaaactac tgaaagaagt attacaggca 90840
atgggaaata gcttgagtgg aagtgcagca gaaggaaaaa gctggacaag aatgtagtgt 90900
cagagaatag gtatggaacg tgtgagtgac tgttagagga tcttgaatgg ggataacaga 90960
cttgatttca taaatactga gatgtcatga taatacttga ggactaaacc atgttttaag 91020
gacagttgta tgcaaagttg taatcgcaag aggaaaaaat agtggaaaag aaaccagtaa 91080
taaaacttgc cttaatgcag gtatgctaag acaatcaaat gggatttcat taatttttta 91140
tttgccattt atagccaaag attttgtaaa agttttgagc ccagtcaggt gaaatagtct 91200
cagaaagaaa gaaaagtgaa tctgagactt ggagacatta atgttgatat tttggtttta 91260
aacgtgtttt aaatccggta aaagtgagct tctcacatga caatattcag tgggtacttg 91320
ggagtatggg ttcgaatcta ggtaggagat atatcgatat tttgggcatc atcaggaaag 91380
ggagagtagt taagcctttc atataaataa tggtgtggcg tttgggcatg ggaagtcttg 91440
gaggaaagga agaaaaggag agggtgagga ctgagataag aatggcaact tgggtttagg 91500
aagaagaaga ggaatcaatg tagagaacag atagtgctga aaaatacagc atcttctgta 91560
gggattggca gctttttctt gatttttgtc ttaatatttc taagagatgg aaaaagctac 91620
tatattctag acatttaaca gggttaaaaa tgttactaaa agatgatcaa tgtggttttc 91680
attcaagact ataacaatat gtatatatcc aaggaaattt aattctgact taaaaaaatt 91740
gttttgcttg tatagattta gggacacaag tgtaattttg ttacatgcat agagtgtata 91800
gtttcaagtc agggctttta ggttgtccat catctgaata atatacattg tacccattaa 91860
gtaatttctc atcttctact caccgtttca agtctccact atttatcatt ccattcttta 91920
cattctgatt ttcatttact aggtgtatta gtctgttttt gcattgcttt aaagaaatac 91980
ctgagactga gtattaaaca ggtttaacct gttttcttta tgaattcttc tttaattggc 92040
tcatggttct gcacgctgta cagaaagcat agcagcatct gcttctgggg aggcctcagg 92100
aagcctccaa tcatggctga aggcaaaagg ggagcatggt gagaatggga gcaagaaaga 92160
gaaggagtgg tggggagaag gtgccaccca cttttaaatg ccagctcact taccaccaag 92220
aggatggccc aagccattca tgtgggatct gcccccatga ttcaagcttc ttccaccagg 92280
ccccacctct agcactgggg attacaattc aacctgagat ttgggaggga aagatatcca 92340
aactatatca ctaggtctgg atcttgttat ttattttttg gaacatagtc atatatatcc 92400
aaggatatat attgtagaag tccacagaac catactaata ttggacttct gcttagttag 92460
gtcttatcta tctgaaacat gatattcata ttgcagagaa gattattttc tttagtgatt 92520
gaggaaatct ttactactta tacattttta atataatact ataatatttg aagatgcaca 92580

```
ttttagatgt agtttaattg aaacctggaa atactattaa tttgcttttt aaagtcctaa  92640
aatcaggatt atcagattct gaattaatgg agtttaaatc aaaaagatta caaggcagtt  92700
tttcagtttt attctggtta attttatcac agctttggaa tcctactttg tttatttgct  92760
tcttgaagtt agatttccca gtgaaatttc agtatcacat aaagtcttat gaaatggctc  92820
attgcacttt gaactttgag tcaaggaagt gaaatttatt gatagattgt tggtgtaata  92880
tttatcctgt ttgtggtagc ttttttgaat aataagtgtc ttagaagacc atgttggagt  92940
agcctgcatg cttttatcaa acatattaat tatgtgatgg ctgatactgc tttagatatt  93000
acatagaaat agtagtaggt gtttactaaa ctggaaattt catttaactt ggtttagctt  93060
tgccttgttc tcagtcacat tgataaaaat gtaagacttt tgtttatctt ttagaataat  93120
gacacctttt ggtgctgaga attttttgtt ttatatatat atatatatat acgtaatata  93180
aatacaaaat atatttaaat atgtataata tttctcatac actttatgta actttgtgtt  93240
cctgtttctc tattatcttg gcatgttttc ttcaaatggc acttcttaac ctcctaaggt  93300
taataaattt ctttgtaatg gacttttgtt ttctaattcc tcagcgtatg acaaatgaat  93360
tatactttgt caaattattt aggtaacttt cagtttttga agtcctggga tcataacatt  93420
catcagtctt taatttctgt cattaaggtc attagctata aatgaattta tgagtagatt  93480
taaaaaataa aacatacaat ccttccctta acacactttc ccaccatttg gttcaactgc  93540
tagtgtaaaa gcatgatgaa ttttgagaag ttatatttta ccagttactt tattttttac  93600
cagttattta aaacagacat gagccaaagc cagaatactt gttaatgaaa atgaggtgtt  93660
ttggaggaaa ggaaggttgt gctgcagttt ttacttgaaa tctgttacat ttctttacag  93720
aaatttcaaa tctcttgttt cctgttatga tggtggcatt atataccttt aaaatgtgag  93780
ctataggaaa atgaatgatg gttaattttt taataaatat ttagacttgt gtttttgaaa  93840
tttttataa cattgttata ggttttatcc tctttctctt gtgaacatgt agtgatttgt  93900
attttgtgat ctttgccgca tgctagagac ttaagaatac tatagcaaat atctgtcttc  93960
tttacattta aaaatttttc gtgactactc cctgttgata tctgtcttaa aagttacttt  94020
tgatgtagtt cacaaatgta ccagataatt atttcatcgt ttttaatgct taaagttttt  94080
atttgtatta ggatttttag tatgatttta atgttaaagt tttgaagtta ctctgccact  94140
agaagtctaa ttttgggact tactattcat gaaataggaa ttgactttta tataagtaat  94200
aggaccttat tttgaaggtt caaactggag aaaatcttac attgtttata tttttatttc  94260
atttatttca gttgatttgc ttgagatcaa gattgcagat acagaatcca tatttcgtgt  94320
atattgctga tattaatcat taaaatcgtt tttgacagtt tgacagttaa aggcatttcc  94380
tgtgaaataa tactggtatg tatttaacca tgcagatcct cagtttgtgg tctgccagct  94440
aaaggtgaag atatattcct ccaattcagg acccacacga cgggaagaca agttcatgta  94500
ctttgagttc cctcagccgt tacctgtgtg tggtgatatc aaagtagagt tcttccacaa  94560
acagaacaag atgctaaaaa aggtttgtac tttactttca ttgggagaaa tatccaaaat  94620
aaggacagat taaaagctat attttatttt atgacatgta aggaactata atttgttttc  94680
tattagatct gcaggtgttt tgcttactct ggcattggtg agacattata agggtaaata  94740
atcctgtttg aaggaaaagg ccttatggca ttgtaacatg agaggaattt ttcttaacaa  94800
ggatggttaa ctgagaagaa attagcatgg gaccaatatt ttaaaaattt tggtctatag  94860
gtagaaatga gatctgttct gtggtcttat gtagtgacac aaaccacttt ttctccattt  94920
tggcttatgt ttctttttct ttcctttttt ttttttttcc tttttgttag agacagggtc  94980
```

-continued

```
ttgttctatt gcccaggctg agtagctaag actacaagca tgtgccacca cacccagcta  95040
atttttttta tttttatttt tgtagggaca gggtctcact atgttgccca ggctggtctc  95100
aaactcctgg gcacaagcag tcctcacgct ttggcatccc aaagagttgg aattacaggt  95160
gtgcgccatc atgcctggcc ttaacgtttc ttaagacttg attattttct atttagcttc  95220
tgtggattta ctgattaatt ttttaactag gagagaaatc agtatgaaga ggaagtaata  95280
aagaatgaaa acatggtatt taaatgtgca ggtttagaaa gttaatgaag tttgaatttg  95340
attgatctgt atttagagaa ggcaacgtct tattatttta aaaccaacta tccgccctgt  95400
gcggtggctc acgcctgtaa ttccagcact ttgggaggct gaggtgggca gatcagctga  95460
ggtcaggagt tcgagaccag cctggccaac atggttaaac cccatctcta ctaaaaatac  95520
aaaaaaatta gccgggtgtg gtggcaggcg cctgttttcc cagctactca ggaggcttga  95580
ggcaggataa ttgctgaacc cgagaggcgg aggttgcagt aagccaagaa tgcaccattg  95640
tactccagcc tgggcaacaa gagtgaaact ccatctcaaa aaaaaagaaa aaaaaaacaa  95700
caactatctt catttaaaat attaaatgtg aatatttaaa gtgagactaa ggtgcaacat  95760
ttttagatag taatgaagaa aaggactaac tttgtagtgt tgctgccttg ttaaacatac  95820
tagatagcat attgccaatc tttaaacatt ctcaatgata ggatttattt actttttctg  95880
atttttagct tttcttttga aagaaaataa gaggaagttt catttactgc aaaattttaa  95940
atgctgcttt gatgtatcag tagagatata attttccttt atccagaatc caagtagctg  96000
gaaaaaaaaa tcaaaatatg ctgaactttt ttttttttag ccagaaaccc atttcctatc  96060
gtctgtacaa ataaaagtta aatatatctc aataacttag aaaaattatt ttttgataat  96120
ccaggaagta ttagcaactg ttttaaaatt aagataacta gtaagtttta tttagctttc  96180
aaaaataggc atctacatca tcatctctgc ataccttttag gaatttccta attcttattt  96240
cccttcatct gtactttaac acatgcaaaa ttgaaggtta gattaaatat tttatgattta  96300
tttgtttatc cttgactaca taaatttcca ttttattgat tttccctgcc ttatttaaga  96360
atatgctatg attaaaacac aaaaaatttt agtataaccc atatatatat agaattcacc  96420
tttttgttat ttaaatatta ttggcttatt ttcttctaag taaaatacaa ttactggcta  96480
aaataattga aataagcaaa aaaaaaattt taaagacctt gtatacaaga ttactttgcc  96540
aggtactgtt aaaagatgca atgacattta agacgtaaca tccttaagga tcttattttc  96600
tgggggataa aaaactttaa gataaattag aataaaagat ttaaatggca ttttaaggta  96660
ccaggtacca gataagatgt cacaaggctg tatatcatta attgccaaat gatttataca  96720
ggccagattt ctttgttggt caatagaggt ttaaagtgat gaacttctgt tgtgtttttt  96780
tattaagaag gtattatctt attagtaaga agtgattttt tttaagaaca agcattttat  96840
aacatcaaaa gaaatcagta gtactctttc ctaccccctc atatttattc tgaaagtatt  96900
caagcattat attgtcatgt aagaaactgg agcttctcat gtttgtattg ctgtagaagt  96960
aaacatgtat ttgccatgcg tcatcaggga agttgcactc accgtccaag aacttttgtt  97020
aaagtaaatc ttggaatagg tagctcattt gaaatgtaga aaaaattaaa tccatatctg  97080
aattttgttt atatgtatgt acacgtaaac taaaaacgta tttaaagcta gtattagatg  97140
agaaaagagg tttttttact taaaatttta aggcaaaagt agtttatctt agatcttgtg  97200
agattgtatt tttggtttaa aatttgagaa tttgagtgaa gaaaaatcat gtgaatgaaa  97260
atgcaacaga taactcagat tgccttataa tagtctttgt gtttaccttt attcagaata  97320
```

```
tcaaatgata gtttattttg ttgacttttt gcaaatgttt aacataggtg acagattttc  97380
ttttttaaaa aaataaaaca tcattaatta aatatgtcat ttcatttctt tttcttttct  97440
ttttttttt ttttaggaca aaatgtttca cttttgggta aatacattct tcataccagg  97500
accagaggaa acctcagaaa aagtagaaaa tggaagtcta tgtgatcaag aaatcgatag  97560
catttgcagt atagagcgtg cagataatga caaggaatat ctagtactta ctttaacaaa  97620
aaatgatctt gacaaagcaa ataaagacaa agccaaccga tacttttctc caaattttaa  97680
ggtcagttaa attaaacatt ttgtgggggt tgttgacttg tatgtatgtg atgtgtgttt  97740
aattctagga gtacagctga tgaagaactt gcttgacaag tttttaactt atgtattatt  97800
tcgaagcagt gtttacgtag cagtaacatg aaagtttcta ataaaatacc caatgtacac  97860
agcgtcaaaa aagctgcatt tttccttttc ctaattcttc gttgtttgct gaaatctggg  97920
gcaaaggtgc gggagggggc taaatgactg ggatatgaag taggaatggg agaggaaaga  97980
aatagatggg aactcagtca tttgggaatg attcatatgg aatgttttta ctgcttccac  98040
tcctgtctgc cttccaattt attctcaatc cctcagagtg atcttaaaaa tagacttgat  98100
tgtgtcactt ctgtttacac tttataagga ccttgtgttt tttttttac catgacctac  98160
aaggcccagc ataatttagc acagggctac ctcctacatc agcactagtc accttctctc  98220
cttgtttctt gagattcagt catactggtc tttcttcagt tcttcaaaat gctaagcttc  98280
tgcctcttct agtctttcca gttattttcc ttctccctgt accttttcat ctcagccttt  98340
tcccctgacc ttccatagct atcttcatat ttccagcctt agcttcaatc tcatattctc  98400
tgaagtcctt tgattgtcct cccgttattc ttttttaaa aatcctattt ccttatattg  98460
tatcttagaa ttatttggtt tgtttcattt ttgcctatgt gtgatatatg tatttctaca  98520
taggtatata tatctactta tagacaagaa ttcttcagat taaaaaaatc tgatttgtaa  98580
acattcccaa gtggttgttt accatttttt tcttccccct tcctatttct tattctacct  98640
gattttcccc tgttcattca ccacactcgt ttctttctct tttttactct ctcttaattt  98700
ttcattcaat ttttataaca tgtaataaat ctaactgtag cgtctgagta ttaagaatat  98760
tgctagtaat acttcacctg taatcccagc actttgggag gctaaggcag gcggatcact  98820
tgaggcccag gagtttaaga ccagccggcc aatatggcga aaccctatct gcactacaaa  98880
tacaaaaatt agctgggcat ggtgtcgcac acctgtaatc ccagctactt gggaggctga  98940
ggcacaagaa ttgcttgagc ctgtgagatg gaggttgcag tgagccgaga tcacaccagt  99000
gcacgtgcac ttcagcctgg gcaacagagc aagactctgt cttaaaaaaa aaaaaaaaaa  99060
aaaaatatat acacacacac acacacacac acacacacac acacactatt actaccaata  99120
tacatacata tatgtatgta tgtatgtatg tatattggta gtaatagtaa tacttgggcc  99180
cctgcacgtt ttaagtgaaa atagatctaa tattaaatgt ctttagccct taaatttttt  99240
ttaagtgttc agaagtttcc ctttaaaaaa atttttaata tataataatt gtacatattt  99300
atgggataca gagtgatatt ttcatgtatg cagtgtgtga tgatcaaatc aggataatta  99360
gcatatggat cacctcaaac atttgtcatt tctttgtgtt aggaacattc aaaattctgt  99420
cttctagcta tttgaaaata tacagtaaat tattgttgac tagttacagt tctatagaac  99480
actataattt attcctcctg tgtgtaattt tttatctttt aaccaacatc tccctatcct  99540
cccctcccac tccctttccc ggcctctaat aaccacactc ttatgagctc aactttttta  99600
gcttccatat atgagtgaga acatacggta tttatctttc tgtacctgac ttattttact  99660
taacatcatg tcctccgggc tagacattct ctttagaatc cacaggtttc ctttcttttc  99720
```

tctaaatctg cattttgctc agccattaac ttttaaaatg tctttttccc tttagtttta 99780
ttgttttcta ttttaatatt gcaagatgtt ttatatttgt gattacaaat aaaaactcca 99840
ttattagtaa acaaatacaa tgtcatatag tagtaagtgc tataaaaaat agacaggata 99900
gaaagtaatc ttggtttgta tgttttttgt tttttagcaa agatgattag agaaggccca 99960
accaagcaga taacatttaa gcagaggcct aaatcatata agtgagttat acaaatatct 100020
gggaaaagag ttaagagtac agatgcaaaa gcccttagac aagagaatga gcttggtata 100080
tctgaagagt ggataagtca ttttgactga aacagagtgg acaagaaaac cagtccaagt 100140
gtaaagacac tagtgtgtgt tcagcatagg aaggatgtaa tctgaatttt gtgtttaata 100200
ttccctgtgt tcatgctttc aaaatacaga tgagtgagga aagtagggag aaggggtaat 100260
aaaggaagct gagagatcag ttaagaggta cttgaatagt ttagtaaaga tgagagaaga 100320
tgtttgcttc ttgttgcccc tcactgctta gaatagtggc agtgaagggt aacaagaagc 100380
tgtcagatta acttaaagag tttactgatg cagtggatgt tggttgtaag agaagaattg 100440
ataatgactc ttggataata ggggagggag gggctgtcaa tataatataa tgaagaaggg 100500
atttgaagtc atttctgatt taaatctcac atccactacc tacttttaat agatatgtag 100560
cctttaacaa gttccctaac ctttctgggc cttagctacc tccccttgga aatggaaata 100620
cctaacatgt aaggttgttt tgacagttat tttcactagg catgtaaagg cacttgactc 100680
tctgttatag accactgtat tatgttaatg tccctctcct tcctcccttt aggtaaagtt 100740
tttagggcta ataaatccca aatatcaatg ttgatcagta gtttgtgttt gtgtagtgtt 100800
gtttatatca aaaactacat tgaagccggg cacagtggtt cacgcctaaa atcgcaacac 100860
tttgggaggc caaggtgggc ctcccacctt gaactaagga gtttgagacc agcctgggca 100920
acatggtgaa atcccatctc tacaaaaaat ataaaagcta gctgggtgtg gtggcatgca 100980
cctgtagtcc tagctacttg ggaggctgag gttgatcctg ggagtttgag cctgcagtga 101040
gctgtgaaga tgccactgca ctctagtctg ggtgacagag caagaccctg tctcaaaaac 101100
acacacacac acacacacac acacaaagaa atacattgat ttttcacata ggtagtaaga 101160
gaaacattct ttttgaactc agctgtttgt gaattgaatt ttgtaattca aatgctatat 101220
tatgtaaact attgatgact ttcaatctgc atttattttg tataattatt tagttaatat 101280
ttgccactta tattccttaa aaaataaaat tgaggttggg cgtggtggct cacacttgta 101340
atcccagcac tttgggaggc tgaggcaggc agattgcctg agctcaggag tttgagatca 101400
gcctgggcaa catcatgaac cccatttcta ctaaaataca aaaaattatc tgggcatggt 101460
ggtgtacacc tgtagcccta gctgtttggg aggctaaggc acgagaattg cttgaacccg 101520
ggaggcagag gttgcagtga gccaagatca tgccactgca ctccagcttg gcaacagagc 101580
aagactcttg tctccagaaa taaaaataaa taaattgtat taacatcctg atagtttatc 101640
tgtttagtac ctagcaagaa agaaaatgtt gaacatctta agaagagggt catttaaaag 101700
gcctcttaaa gatcatgttt gttacagtgc ttaaaaatta atatgttcat ctgcaaaatg 101760
gaataaaaaa tctgttaaaa atatatttca ctaaatagtt taagatgagt catatttgtg 101820
ggttttcatt ttaaattttc tttctctagg tgaagctgta cttcacaaaa acagtagagg 101880
agccgtcaaa tccagaggct agcagttcaa cttctgtaac accagatgtt agtgacaatg 101940
aacctgatca ttatagatat tctgacacca ctgactctga tccagagaat gaaccttttg 102000
atgaagatca gcatacacaa attacaaaag tctgaatttt tttttatcaa gagggataaa 102060
acaccatgaa aataaacttg aataaactga aaatggacct ttttttttt aatggcaata 102120
ggacattgtg tcagattacc agttatagga acaattctct tttcctgacc aatcttgttt 102180
taccctatac atccacaggg ttttgacact tgttgtccag ttgaaaaaag gttgtgtagc 102240
tgtgtcatgt atataccttt ttgtgtcaaa aggacattta aaattcaatt aggattaata 102300
aagatggcac tttcccgttt tattccagtt ttataaaaag tggagacaga ctgatgtgta 102360
tacgtaggaa ttttttcctt ttgtgttctg tcaccaactg aagtggctaa agagctttgt 102420
gatatactgg ttcacatcct accccctttgc acttgtggca acagataagt ttgcagttgg 102480
ctaagagagg tttccgaagg gttttgctac attctaatgc atgtattcgg gttaggggaa 102540
tggagggaat gctcagaaag gaaataattt tatgctggac tctggaccat ataccatctc 102600
cagctattta cacacacctt tctttagcat gctacagtta ttaatctgga cattcgagga 102660
attggccgct gtcactgctt gttgtttgcg catttttttt taaagcatat tggtgctaga 102720
aaaggcagct aaaggaagtg aatctgtatt ggggtacagg aatgaacctt ctgcaacatc 102780
ttaagatcca caaatgaagg gatataaaaa taatgtcata ggtaagaaac acagcaacaa 102840
tgacttaacc atataaatgt ggaggctatc aacaaagaat gggcttgaaa cattataaaa 102900
attgacaatg atttattaaa tatgttttct caattgtaac gacttctcca tctcctgtgt 102960
aatcaaggcc agtgctaaaa ttcagatgct gttagtacct acatcagtca acaacttaca 103020
cttattttac tagttttcaa tcataatacc tgctgtggat gcttcatgtg ctgcctgcaa 103080
gcttcttttt tctcattaaa tataaaatat tttgtaatgc tgcacagaaa ttttcaattt 103140
gagattctac agtaagcgtt ttttttcttt gaagatttat gatgcactta ttcaatagct 103200
gtcagccgtt ccaccctttt gaccttacac attctattac aatgaatttt gcagttttgc 103260
acatttttta aatgtcatta actgttaggg aattttactt gaatactgaa tacatataat 103320
gtttatatta aaaaggacat ttgtgttaaa aaggaaatta gagttgcagt aaactttcaa 103380
tgctgcacac aaaaaaaaga catttgattt ttcagtagaa attgtcctac atgtgcttta 103440
ttgatttgct attgaaagaa tagggttttt tttttttttt tttttttttt ttttaaatgt 103500
gcagtgttga atcatttctt catagtgctc ccccgagttg ggactagggc ttcaatttca 103560
cttcttaaaa aaaatcatca tatatttgat atgcccagac tgcatacgat tttaagcgga 103620
gtacaactac tattgtaaag ctaatgtgaa gatattatta aaaaggtttt tttttccaga 103680
aatttggtgt cttcaaatta taccttcacc ttgacatttg aatatccagc cattttgttt 103740
cttaatggta taaaattcca ttttcaataa cttattggtg ctgaaattgt tcactagctg 103800
tggtctgacc tagttaattt acaaatacag attgaatagg acctactaga gcagcattta 103860
tagagtttga tggcaaatag attaggcaga acttcatcta aaatattctt agtaaataat 103920
gttgacacgt tttccatacc ttgtcagttt cattcaacaa tttttaaatt tttaacaaag 103980
ctcttaggat ttacacattt atatttaaac attgatatat agagtattga ttgattgctc 104040
ataagttaaa ttggtaaagt tagagacaac tattctaaca cctcaccatt gaaatttata 104100
tgccaccttg tctttcataa aagctgaaaa ttgttaccta aaatgaaaat caacttcatg 104160
ttttgaagat agttataaat attgttcttt gttacaattt cgggcaccgc atattaaaac 104220
gtaactttat tgttccaata tgtaacatgg agggccaggt cataaataat gacattataa 104280
tgggcttttg cactgttatt atttttcctt tggaatgtga aggtctgaat gagggttttg 104340
attttgaatg tttcaatgtt tttgagaagc cttgcttaca ttttatggtg tagtcattgg 104400
aaatggaaaa atggcattat atatattata tatataaata tatattatac atactctcct 104460
tactttattt cagttaccat ccccatagaa tttgacaaga attgctatga ctgaaaggtt 104520
ttcgagtcct aattaaaact ttatttatgg cagtattcat aattagcctg aaatgcattc 104580
tgtaggtaat ctctgagttt ctggaatatt ttcttagact ttttggatgt gcagcagctt 104640
acatgtctga agttacttga aggcatcact tttaagaaag cttacagttg ggccctgtac 104700
catcccaagt cctttgtagc tcctcttgaa catgtttgcc atacttttaa aagggtagtt 104760
gaataaatag catcaccatt ctttgctgtg gcacaggtta taaacttaag tggagtttac 104820
cggcagcatc aaatgtttca gctttaaaaa ataaaagtag ggtacaagtt taatgtttag 104880
ttctagaaat tttgtgcaat atgttcataa cgatggctgt ggttgccaca aagtgcctcg 104940
tttaccttta aatactgtta atgtgtcatg catgcagatg gaaggggtgg aactgtgcac 105000
taaagtgggg gctttaactg tagtatttgg cagagttgcc ttctacctgc cagttcaaaa 105060
gttcaacctg ttttcatata gaatatatat actaaaaaat ttcagtctgt taaacagcct 105120
tactctgatt cagcctcttc agatactctt gtgctgtgca gcagtggctc tgtgtgtaaa 105180
tgctatgcac tgaggataca caaaaatacc aatatgatgt gtacaggata atgcctcatc 105240
ccaatcagat gtccatttgt tattgtgttt gttaacaacc ctttatctct tagtgttata 105300
aactccactt aaaactgatt aaagtctcat tcttgtca 105338

<210> SEQ ID NO 8
<211> LENGTH: 1675
<212> TYPE: DNA
<213> ORGANISM: homo sapiens

<400> SEQUENCE: 8
gttgcagcct gctgcgcgcc caggggtccc gcgggttttc gggcgcaggg tggcgcccgc 60
ggcaggcggc ggccatgaac ttctccgagg tattcaagct ctccagctta ctctgcaagt 120
tctccccgga cggcaagtac ctggcttcct gtgtccagta ccggttagtg gtccgggatg 180
tgaacaccct tcagatcctt cagctgtaca cgtgcctaga ccagatccag cacatcgagt 240
ggtcggcaga ctcgctcttc atcctgtgcg ccatgtacaa gcgagggctg gtgcaggtct 300
ggtctttaga gcagcccgaa tggcactgca aaatagacga gggctcagcc gggctggtgg 360
cctcgtgctg gagcccggac gggcgccaca ttctcaacac cacggaattc catctgcgga 420
taaccgtctg gtccttgtgc acaaaatccg tgtcttacat caaataccccg aaagcttgtc 480 tgcagggaat caccttcacc agggacggcc gctacatggc gctggcagaa cggcgcgact 540
gcaaagatta cgtgagcatc ttcgtctgca gtgattggca gctcctgcgg cattttgata 600
cggacaccca ggatctcaca gggattgagt gggccccaaa cggctgtgtg ctggcagtgt 660
gggacacctg cttggagtac aagattctgc tgtactcatt ggatggccgg ttgttgtcca 720
cgtacagcgc ttacgagtgg tccctgggca tcaagtctgt ggcctggagc cccagcagtc 780
agttcctggc agttgggagc tatgatggaa aggtgcgcat ccttaatcac gtgacttgga 840
aaatgatcac ggagtttggg catcctgcag ccattaatga tcccaagata gtggtgtata 900
aggaggccga gaagagccca cagctgggac tgggctgcct ctccttcccg ccgccccggg 960
ccggggccgg ccctctcccg agctcagaga gtaaatatga gatcgcctct gtcccagtct 1020
ccttacagac actgaaacct gttaccgaca gagcaaaccc gaaaatgggc ataggaatgc 1080
tggcatttag tcctgacagc tacttcctgg cgacaaggaa cgacaacatt cccaatgccg 1140
tctgggtctg ggacattcag aagctgaggc tgttcgcggt gctcgagcag ctgtccccag 1200
tgcgcgcgtt tcagtgggac ccgcagcagc cgcggctggc catctgcacg ggaggcagca 1260
ggctctacct gtggtcccca gcgggctgca tgtcggtgca ggtgcctggg gaaggcgact 1320
ttgcagtgct ctctctgtgc tggcatttaa gcggagactc gatggccctc ctcagcaagg 1380
atcacttctg cctctgcttc ctggagacag aggcagtggt cggcacagcc tgcagacagc 1440
tgggcggcca cacgtagcag cggtgcacta acgtgtgcag aaacagggct actctgtgtt 1500
tccagtgtgg gaaaaaacac agcttcacca ggaggttctc cactgtggtg gtctggattc 1560
agtgattgat tctatttttc tatagcaaag catttttgta aatatgtatg gtataaaact 1620
gtagttttat tatttaaaat aaatacttgc tgatttaaaa aaaaaaaaaa aaaaa 1675

<210> SEQ ID NO 9
<211> LENGTH: 518
<212> TYPE: DNA
<213> ORGANISM: homo sapiens

<400> SEQUENCE: 9
gcaagagggc tgccaacgct actaatcaga catgctgggt ccacagggct gtccccaaac 60
tggaaagaag tcctagaaaa tagatgattc ttcctaaaac gtaaattgga tcatgcctct 120
cccccaacag tctcatgcct atggaaggga atcctgtccc ccaaggggtt ctccctcctg 180
tctcctccaa gaaccaggca gtgtggggtg gggcagcagg acccagggtc tcggagctgg 240
ggcctcccca gcctcacttg gggcctccaa ggctaagttc tgtgacctcc agggcccaag 300
agtgagttcc tctggctgct ccagaaagtg aagagagaag agccaacccc ggctcgggcc 360
acgagccccg aggcactgac cacagccaga gcaggcctgc tggaagctcc gtccctgctg 420
cagatccctg cgccacatga tatcagcaat tgctgcaatt tcgccctaag tactcttgtt 480
tcccctaata atccacgttt catctccaca ataaacat 518

<210> SEQ ID NO 10
<211> LENGTH: 759
<212> TYPE: DNA
<213> ORGANISM: homo sapiens
<220> FEATURE:
<221> NAME/KEY: misc_feature
<222> LOCATION: (457)..(457)
<223> OTHER INFORMATION: n is a, c, g, t or u

<400> SEQUENCE: 10
cactacaggg aacggcccag gaacccatcc acccgtcccc agctctcatc actctgacct 60
ctggcttttt gtttcctggg gcatttcaca gcaaattcca cctatgagac cgtctcatcc 120
gtaatacacc agtacatgct tccagcagct tggtgacatg aaaggacctc cgtggctggc 180
cttactccct gtggatgcca cagctgcagg atcctggggc cccaacagaa gccggtgaag 240
gaagagttcc tgctccagca gaacaaaact gccctttgcc cagaaatcct gcaaactgag 300
gctggacgac ttgaaatact catcagcgag attaccacga agcccaggtg cgagggaccc 360
tcacgcctgt tgctgcgtgg gccgcccaga catcgccaga gaccaaaccg cagaagatgc 420
tcggagccca acatctacaa acctgccccg ccacggnccc caggctcaga aactggtttt 480
tagtcagctc caatgattag cttttttttt tttctctttg gttcccatag aaatgcctct 540
tcaaagcatt atgggacaac acacccaccc agtttctgta ccggtggagc ttctggggga 600
agtttcagga ctaggaacac acagggcggc tcaggacaca ttcaccccaa agtatgactg 660
tggagaccag aatacgccac ccctaaatat gactatagga gaccagaata cgtaccccaa 720
aatatgcctg tggagaccag aatagccacc caaatatcc 759

<210> SEQ ID NO 11
<211> LENGTH: 25892
<212> TYPE: DNA
<213> ORGANISM: Mus musculus

<400> SEQUENCE: 11
gtacttccgg ccgctgcctg gggcggttgc gggaggtact tcggagccgg gctggcccgg 60
gctggccgtg gccatgaact tctcggagtc attcaagctc tcgggcctgc tctgcaggtt 120
ctccccggac ggcaagtacc tggtgagctg cggcgcgctg ggcggaacct aagtgtgggc 180
gcgcgacttg tgcacggggc cggggcgggc cgaagggggg cgggaagggg gcccgagccg 240
ggcggccgcg gggactcagg ctggacttag ggggcggggt gggaggtggg agagggaggc 300
aggcagaggg gtttcagccc agatgaggga gaaccagatg attagagaga acgaacctga 360
agccgaagag ggatccaggc cagccaggct gggggatcct ggcaggtgac cagggtggag 420
aaagaggacg tggagcagag tggggatgga gttggggttg ctattctggc aggtggtcag 480
ggttaggaag gaggtcttgg agcaggtggc cagggctggg tgggtgccag gctcccggct 540
ccagtttccc ttcatcaaag ttggataaga tgactctgct ttcacacatt tgagggcaca 600
ggggatggca gctcattgct attttgtatg ttttctgtga gcgagctggt taaacggggc 660
cctcctttgt gaaactcgtc ataagcaaat ggtttaaata actagctttc attgccaggg 720
ttggatgtta gctgtctatt ctttgggtgg cagaatagtg ttcagatggg tgtttcaagg 780
tacgccaaca tgaccattgt gcatttgtag aaggctgacg ttaggaagcc atcagggaaa 840
actcaagtct tattttaaaa aactgtggtt ccgtgccagt cgggtagctt ggctagtaac 900
ggtacctgcc accaaacctg atgacctgag tcccagctct aggacccact taatggaagg 960
agagaactgt ctcctgcatg ttgtcctctg gcctccacat aagccgtaac tagtgcctga 1020
cccttctcac atacaaatgc aatcctaatt tttaacaagt tttctttgat taatctatca 1080
ttctcttttt aactgactga taccattgat tgattgattg actgattgac agggtttctc 1140
tgtagctctg accaggttgg ccttgaactc aaagatctgc cccttgtctc ctgagtgctg 1200
ggattaacgg agcatgccac catgcctggc tgtcttgatt ctcagttcac acccctgctg 1260
tgtttgtcca ggcttttgag acatccttta ccctccttat acacatcatc ctaacaatgt 1320
aggaagtgtc agggtaggac ctgcttagca gggaaaggta ctgccatgca agcccgagga 1380
cttgagctcc ggctcgggaa cccacgtaaa ggtgggagga gaccatcagc ctcgcacaca 1440
ttgatacatt ttaccttttt ccaagtgcct ccagagacta aggttgcttt acggttctga 1500
aagtctcagt gaacagcaaa gaagttgcat ttgggttagc tgatatttgt gcttgccgct 1560
catcaaaata tcgtggagct cttaataatt gtttctttca agttttgtcc taaatcctga 1620
gcagagcgag tccatgtttc cagtgttggt gtcttaagtg attcctaagg aatccattgt 1680
aacaggttac tgctcaccaa actctaatgt gagaacacaa gccctttgat aggtcctcct 1740
tctgatctgc acttgccctc ttgctctctt tccacagaag acaaatgtgg cttcattaaa 1800
aaaaaaagag tctgtgtgtg tgtgtgtgtg tgtgtgagtg agagagagag agagacagag 1860
acagagacag agagacagag atagaaacag agagatgcta caacacacgt gtagagggca 1920
gaggacaacc cccagtgtta ttccttacct tccaccttgt ttgagacaag gtctcttgct 1980
cttcactgca taaagcaggc tagctggccc acatgtacct gcctcagcct cccctctgcc 2040
tcccctctgc ctcctcatag aaactaggat tttaaacagt ttttaggatt aacacagttt 2100

-continued

```
tatgtggctt ctgtgcatcc aaacctgttt ctgaggcaag tgcaagtttt tggcttttag   2160
acaatggcat aatatgcaaa gctggcctca gactcagaaa gtagttgagc acctccctag   2220
tacagtgatt acaagtgtgc accatcactc ccaagtagta aaaaaataca cacacacaca   2280
cacacacaca cacacacaca ggctttttga gacagtttct ctgtgtagcc ccagctgtcc   2340
tggaactcac tcagtagagg gaggctggcc tcaaactcag ggatctgccc acctctgact   2400
tctgagtgct gggattaaag gagtgcacca cccccatctt taaatttact tgtacagatg   2460
gctcagcggg taagagcact gactgctcac ccaaaggtcc tgagttcaaa tccccgcaac   2520
cacttggtgg ctcacaacca cccgtaatga gatctgatgc cctcttctgg tgcatctgaa   2580
gacagctaca gtgtacttac tatataataa taaataaatc tttaaaaaaa tttacttgta   2640
caaatttgtg ggttagagta tgataatttg gttaatatat actgtgtgga acttttaaac   2700
ttttgaatgc tccacctttt atctttttct aactcatttt gcaatgagac ccataagttt   2760
tggtccacat gaagctaagt gtgtcgaaca ggaggggagg agctggccat tgaggcaagg   2820
ctccctgctg tagaagagat gctatcccgt gctgtctgcc tcacttttta ggcttcctgt   2880
gtccagtacc gattagtgat ccgggatgtg acgacccttc agatccttca gttgtacaca   2940
tgcctggacc agatccagca catagagtgg tctgcagact ccctcttcat cctgtgtgcc   3000
atgtacaggc gggggcttgt gcaggtttgt accaccatgt attagtagag tgtatagatg   3060
ggtgctacat gtctgtgggc cttgaacagg catgtgccac ttacatatat gatgtgtgta   3120
ggcaggcaca tgccacatat acataagact cacataagtg tgtctcatgt gtaactaact   3180
ggtctggcgc tgtttctgta gcagagttag aattaggaaa cgtttccagg agtgtgacta   3240
ggaaggagtc caggtgtttg caccccttctt tcaggtttag gggaaatgc aatgagactc   3300
aaggttgcct tcttttctta tgtgtaattt atttatttta tgtgcattgg tgttttatct   3360
gtatgcattt ctgtgtgatg gtgtcaggtc tcagagttac cgatagctgt gagctgcagt   3420
acgggggctg ggaattgaac ggggtcatca ggaagagcag tcagtgctct cggctgctga   3480
ggcatctctc cagcccccag atatgctttc ttttaaaatg taatgctctc taatagttta   3540
atccaaacac ttttgatgtg gaaaaacaaa caaacaccac caaaacagta aattgttctc   3600
agtctttgag catgattttt cttttttttt tttttttaaa gatttattta ttggttatat   3660
gtaagtacac tgtagctgtc ttcagacact ccagaagagg gcgtcagatc tcgttacaga   3720
tggttgtgag ccaccatgtg gttgctggga tttgaactcc ggaccttcag aagaacagtt   3780
gggtgctctt acccactgag ccatctcacc agccccgagc atgatttttc tgagcgggag   3840
gtatttgcaa tggcagtgga acaacttgga cagggttcta ggaagttcta gaaggttcta   3900
gaaggccgtg ttccagtatt cactaagcct aactaatgag gtcacaggga tgggcacatg   3960
agcagaccct tcaaaggtgc actgcagtga agtcaccagg aagtgtggct tgtagccact   4020
gggccatctg aggtagcatg gtgtatatcc tctccctcag agaggcctcc tgcgtggtac   4080
agctatttgc actcctctgt gtttctttta tgaatcaagg tctggtcact cgagcagcca   4140
gaatggcact gcaagatcga cgagggctct gcggggctgg tcgcttcctg ctggagtcca   4200
gatggccgcc acatcctgaa cacaaccgaa tttcatgtaa gctggccaaa cgtagcccac   4260
tctgttcttc gcctaaaata gcctgggaat gtgaaagtct ggttctggag cagtattcag   4320
gccagagttc ataaacagta taatttttaa actctatttt aaagaaaaat aggacattaa   4380
aaggagttgg caagatggct cagtgggtat ggctcttgct accaagcctt gccacatggt   4440
ggagggtaag aacgacagat gccccaaagt tagagtaaca agggaaaatg tatgtcttct   4500
```

gtaatgggct gttacaggct gcagtgctca tgctgacatc ttaaagggac aggtgctcat 4560
gttgacatct taaagggaca ggtgctcatg ttgacatctt aaagggacag gtgctcatgt 4620
tgacatctta aagggacatt tggcctgggc ttttggctgc atatttgagt gttttctaga 4680
ccactttggc cagcaatctt catgcttatg gagttctgca gaccagagtc cagcttccag 4740
atctcataga cttgggctca gtccctccgt taatggccca aaggaaaggt tacccactgc 4800
agaatttata aactgttttt taatgtactt ttttattcag cagctgtgtt acactcactg 4860
aaatggaaag gaacatttgg acagagagta gactgtacag actgcctctg tacactgtta 4920
acctactgct aggtcatagc cactgtgcct gtgacattaa agtgaatggc aacatcctgt 4980
gtggaggaat atgtcacagc aaggggaccc tgaaaaatat accctccctt tttgttgtat 5040
tgagatggga tctcactgtg tagccttgac tggcctggaa cgcactatgt agactaggct 5100
tgcctcaaac tcagagagct gcctgcctct gcttcttgac tactgggagt aaagtagcca 5160
ccagtcctat cttattccaa gcctttagat tttagcttct aaaagtccca cagacttcat 5220
ttaccaccag ctatgctcag tagtcaggag gtgaccctgt gcgcatgaca gattcgtaga 5280
gtggacacat aactgagagt catatgttcc cgctcacaac agttagatcg ctgtgtactc 5340
ttctgggggc aggaagtcca cgtgagggtg ctgcaagatg gagagaggcc cagctcccat 5400
gagacaaggg gaagacgatt gaattgtgtg gctggtgtct gtctggtccg tggaagacac 5460
tcccctgcac acgcacactt cccagagcac ctccaggcct tgagaggctg ccagcctcca 5520
gagggcacct ttgactgcat tgcacaaaag ccattttcac ctttttttgga gagtcttggg 5580
gtccccgatg catatgacac tgtgcggttt acagcagctc acaggttaca ttgcctgtac 5640
aagggccctc ctagccggca tagctgctgc tcttgttcct tgtgaggaaa ggctctctgg 5700
ggcacactca cctgccgtct gctgctgggc atgagttgtg aggcaccagt ggctttggcc 5760
tttcttatgc acctcttcta gtgtctggat ccttccaggc tagtgcaggt gggtgtgtgc 5820
gcagcttcca ggctagtgca ggtgggtgtg tgcgcagctt ccaggctagt gcaggtgggt 5880
atgcgcagct tcccgagggt ttgcatcagg atttgaagtg gcgagacgtt gcagcatcgt 5940
ggggcttttg aaaatctcag ttactctcca ctttatattt tgaggcaatg tctcttactt 6000
gaacccagag ctccccagtt ctgcagttca gctagcttcc tgtccctggg gtcatagaca 6060
ggtcaccgca caccctgggg tgtgcaggag tgctggggtt ccagactcac ttgagcagta 6120
aggcttcccc ggagatttcc ccagccccac actgtgtgtg tgggctcagt tgtcacctgg 6180
cgaatggaga catttgctct catggctgct ctgtgtgggt gcactgaagt aaactgcaca 6240
tgagtgtgcg gtgtgggtcc atgtttatgt attccagctt taagactctt tgtgaagatg 6300
ggaagcatcc taacccttct ctcccctttc cctggcagct gcgaatcacg gtctggtccc 6360
tgtgcaccaa atctgtatct tacatcaagt atcccaaggc ctgccagcag ggtgagtctg 6420
tctttacaca gtccttgtaa ctgttctgag agtgtgcact tagagcagat agaggagcta 6480
cagcagcacc tctcccccca gcctccatca ctgtgcaccc ctcccccagc ctccatcact 6540
gtgcacccct cccccagcct ccatcactgt gcacccctcc cccagcttcc atcactgtgc 6600
accccctccc cccagcctct atcactgtgc acctctcccc cagcctccat cactgtgcac 6660
ccctccccca gcctccatca ctgtgtaccc ctccccccag cctccatcac tgtgcacccc 6720
tcccccagcc tccatcactg tgcacacctc ccccagcctc catcactgtg cacacctccc 6780
ccagcctcca tcactgtgca ccccccttccc ccagcctcta tcactgtgta ccccctctcc 6840

-continued

```
cagcctccat cactgtgcac cccctccccc agcctccatc actgtgtacc cccccagcct   6900
ccatcactgt gcaccccctc cccccaagcc tccatcactg tgcacccccct cccccaaagc   6960
ctccatcact gtgcaccccc tcccccaaag cctccatcac tgtgcacccc ctcccccagt   7020
ctccatcact gtgtacccct cccccaaagc ctccatcact gtgcaccccc tccccccaag   7080
cctccatcac tgtgtacccc tcccccaaag cctccatcac tgtgccatcc tctgtgctcc   7140
ttcctgtgtg tctgtgagat tccctccatg ccatttcttt gacaacagga tgctgtaaaa   7200
agtagacagg cattgtcctg ggaggagaac ctttaccttc attcacacag ggcactcagc   7260
ttgcctttgg tgcctagctg tcagcttcac ttcactaact ttttttagtc aagatttatt   7320
tttaggatgt gtgtgtgtgt gtgtatgtgt gtgtgtgtgt ataagagaga gagagaggtg   7380
tatctgtgtg tgtatgtgca tgcatatgtg tgtctgtgtg catgtatgtg tgtgagagag   7440
agggagaggg agaggaagag atgtgtatct gtgtgtgtct atgtgtctgt atgcatgtgt   7500
gtgtgtgtat aggtgtaggt ataggtgtgt atgtctgtct gcgtgcatgt gtgtgtgtat   7560
gtgtgtgtgt gtgtgtgcgt gtggtgtatg ggtaatgtga atgcaagttg aagttacagg   7620
tgatagtgag ctgcttgttc tgggttctgg gatcagtttt caggaaaagc agcacttttt   7680
aaaaaagatt tatttatatt atacataagt acactgtagc tgttttcaga catgccagaa   7740
gagggcgtca gatctcatta caggtggttg ggagccacca tctggttgct gggatttgaa   7800
ctcaggacct cagtgcccct acctgctgag ccctcgccag cccacagcac aagtctttat   7860
ccagtgagcc atctccagct cagctcacta gctcttctgt cgggatggca tgctgtctgt   7920
cacctctgag catctcagaa cagggaaagg aggaaggctg ggccgagtgc atggggtgac   7980
gggtggtcat gccacccacc tgccccaaac ccagaaacta acagtagagg gcacacagta   8040
ggggcacaca gaggggcacg aagtaggggc acacataggc atgctcttgt ttgtttgttg   8100
ccacaaggac aatatgtcta atgttgcaga tcacattaga ctgatggcat cgtaagtctg   8160
ttgtgggttt tgtgtcttaa gtgctactgg atctaaagaa cagtctggcc ctgggtgcag   8220
gtggtcctca agtctgttat ctgaagtgtt cttgtcattc ttgaggcctt gaccgcaggc   8280
cttttacagt aatgcagggc tggaaaaaag ttacttaatg tttttaagta agattgtccc   8340
gaatattctt tacaacttta gttatttgaa atgacaagtt caaaaggtga ctcagcatct   8400
ttcagaggac tctaggtcac tgcccagcac ccaggtcagg aggctcacaa ctgcctgtag   8460
cttcagctcc gacggaatgg gactcttccg tcctcggcgc gcacccctgc aggctgtgtg   8520
tatacctata cacagatgta cacacatcca tacactaatt aaaaataaaa gcgaaaacga   8580
aatgcagtga cacagctgac tcagtgtata aagtgcttgt ggagcatgag aacgggagtt   8640
caaatctcca gacctacaat aaaggccagg tacagaggca gaagtctgtg atcccagcac   8700
ccccacatca agatgggagg tggaaactaa gaattccaga agcttgcagg ccagctagac   8760
tggcatgtgc agttgcaaac aaaagatctg tctcaaacaa ggtggatgag caatatagac   8820
gcccaaggtt gtcctcttag ccctcataca tacatatgca tggcacatgt gcctaaattc   8880
acacacatgg accaccacca ccacacacac acaactgcaa gctgggtttt gaccatcagg   8940
tatgcctgta gttccctttg tgaaacatgg ccctctgctg tgtttcacaa agtgacattt   9000
gtgactcttt aagaatcagg tccttgggtt tgattctgta taatcacccg cctcacctgc   9060
aagagggata agggctctgc ttgtcagagt cctacgtgac aatgtcttgc tcatgggaag   9120
atgagaagga cacatttccg gggcggggcg gggagagctc gctcccccct tgtccctttt   9180
aaaaagtccc tgatgtgctc cagtcctttc ccacacttgg ttccatctgg ttccagttta   9240
```

-continued

```
ccatctctct ccacaggact aactttcacc agggatggcc gctacctggc cttagcagag   9300
aggcgggact gcagggacta tgtcagcatc tttgtgtgca gtgactggca gctcctccgg   9360
gtaaggccat cctctgctgc tggctgggaa aaggggtaga actagcgttc ctggtgatcc   9420
cagaggctgt tgcagcccct ggggtagaca gaatgatggg gttcccatgg ccagaggaca   9480
ggggccctgt gtgtgactcc aagcagtgca cactacgtgt gatctagact ccctggtgca   9540
tgcacacttg gtgcacagta gaagttagca tgttgacatg aactttgaac cctctttctc   9600
cataagggaa ttcctccctg ggaggaatgc agttttgttg gcctgggtaa aatgtctcag   9660
gagccgtgac actgagcaaa tgctctctgt gcccacaagc ttcagtgtca gagtgttaga   9720
gagacatctg aaggggcgcc ctgggaagca gggtgcgggt gggcaggggt ccatggggat   9780
gagggcatgc ggccttgccc agcatggttg gcacactgtg tgcactcacc agaacaacac   9840
acagatactt tgtctgttgc tgcatataaa atgatacatg aaccaaaagc attagttaga   9900
aaataaatgc actacttgtc taaggacatg ttttccaact gtcatgtttt ttttctcatc   9960
tggaagcact ttgacacaga cacccaggat ctcacaggga tcgagtgggc cccgaatggc  10020
tgtgtactgg ccgcgtggga cacctgcttg gaggtatagc acatgaccag cagcacagtc  10080
cctttcagga atgttcacct gcaggtacct gtgtgctcag tgcatcgagc tgctgggtgc  10140
tggcgtgccg cacgcagggc ctgtgactgt gtcaatgtct catctgcagt acaaggttct  10200
gctgtactcc ttggacggcc gcctgctgtc agcatactgt gcctatgaat ggtccctggg  10260
catcaagtct gtggcttgga gccccagcag tcagttcctg gccattggga gctacgatgg  10320
aaaggtagga agtggctcag ggctcaggcc aactcgacga gctgtaggac acctgcagcc  10380
cgtgagctac ctgcatgtca ttctcacggt tccttcccca ggtgcgcctc ctaaatcacg  10440
tgacctggaa gatgataact gagtttgggc atcctgcaac cattaacaac cccaagacag  10500
taagtctgca tacgcttcca cccgagcacc gtggtctccc gggtgcaggg agccgccctt  10560
gaccctcctt agttgctgtg atgttgtctt ccctgttctg cccctcatgc cctccttggt  10620
gaagggcatt tggagtccag gctcgtccgt ggactgatcc tgtcctagcc ggatgctcat  10680
catgctctgc cctcggcaga tccctgggag agtgagctga ggaatcctga gcgtgggcca  10740
tcctgccaga gcagggcaca ccgcaggcag agaggccggg agagctggtc tgtatggact  10800
gcagctaggg cggcccaggc ccaggcccag gggtgcagag ttgaaggcag gttctgaagc  10860
tcagaggtgc tgagtccgct gtcttctgtc agtgctgaag ctcagtagtg ctgagtcctc  10920
tgtcttctgt cagtgctgaa gctcagtagt gctgagtcct ctgtcttctg tcagtgctga  10980
agctcagtag tgctgagtcc tctgtcttct gtcagtgctg aagctcagga gtgctgagtc  11040
ctctgtcttc tgtcagtgct gaagctcagt agtgctgagt cctctgtctt ctgtcagtgc  11100
tgaagctcag tagtgctgag tcctctgtct tctgtcagtg ctgaagctca ggagtgctga  11160
gtcctctgtc ttctgtcagt gctgaagctc aggagtgctg agtcctctgt cttctgtcag  11220
tgctgaagct cagtagtgct gagtcctctg tcttctgtca gtggtctgga ccaaggacag  11280
gtttctgctt cccttggaca aggagggcca gggccatggc ccggggctca gttagctgcc  11340
ccaaagccta tgtctgcaga accctgtagg aaggagaagc taggtggagg ctgggcttta  11400
gtcagggtgc tcctcctgta acagtggttg aaccttagag atgacagagt acaggctggc  11460
cgtgcaggct gccaaggttt gcctgtggtt caagcgcctg tctcccccac gtgtgcactg  11520
gtggtttctc tgcctgggac tgcggagtac cccactaacc taagcgtgtg agtgaacttt  11580
```

gtgtcaccgg gtcagaggac ccggggacac gatcaaccta gttaaagtag aacgggttca 11640
ttttggctcc taatttctga ggtttcagtc catggtccct tcaccattta ctttgggtag 11700
cacattgtgg tggggacaaa tggcagagca gagctgacct tcagctgctc tggccaagaa 11760
gcagagagga aggacaggtg aggtcccaat gtggccttca aagtcatgct cccagtggcc 11820
cgggcctgta aggtccatgc tagcaccaag tctgtcaggc ctggccgttt gctactccac 11880
aggctcgctg ccaccactgt cctctcctgg cctacttttc tcctgtgcac acacaggcca 11940
ctgccgaatc gctgtgacat agctcaccat gtaaacatag ccatgtgctc agagccctct 12000
ctaaaggaca gcctggccag cagtactgcg gtggcagctg caaagggtca gacttggccg 12060
ccgcctcttc ccagcgacct ccgtgtgggg cacatagata ggttgggcca ccttccactg 12120
gctctcgtca cagactgcta gcagccacat cattgttttt caggttgtgt ataaggaagc 12180
tgagaagagc ccactgctgg ggttgggcca cctgtccttc ccgccgcccc gagcaatggc 12240
tggtgccctc tctacctcag agagcaaatg taagcagcag agggctgtgt cctccatggg 12300
agaaagcttg tttttctct cttaaatgag aatcctctgt ccacgtgaat ctcagaggct 12360
gcttgttttg ggtgtggaag atgttaagat gggggtctca atcctgcagt gtagagaccg 12420
caggtgttct cctgtgaagc ctgcctttcc tccctgctct gcagtccctg aaggagtgag 12480
gggacatcag ctgtgcagca cccgcttgga gggggggagg cagccaggct gtaggttgct 12540
catgctggct tgtgcttact tattttctgt tgggtgatag ttctttgatt cccagctgga 12600
aaggggtagc cacctgtgcc ccgagacgct ggaaatgggt ggacagaact gccaggtgtc 12660
caagtagtgg ggactagctc agaaagcagg gcttcagagc agggctgtat cctgcactgg 12720
aactgttgtc cccagggaac ctgtgaacgt gcctctcacc acagctgtcc tcttaatccc 12780
tcctgtgctt ctctgcagtg tgtttccttc cctctctttg ccctctcccc ttaaccagtg 12840
cccttagccc gtcccccgtc gtgttgcaga tgagatcgcc tcgggaccag tttccttgca 12900
gactctgaag ccagtagctg acagagcgaa cccgaggatg ggtgtaggga tgctggcttt 12960
cagctctgac agctacttcc tggcatcaag aaatggtcag tgccacactc atttcgtagg 13020
cagggtcagc tgctcgcggc cctttgaggc ggagagtaga gatgaaccga gaagcaaagg 13080
ggcagctgtg tgctcctctc cctggttcct gcagaaatgg gcgttcagca cagcagctcc 13140
tttctgcaca gcagctcctt gcccatggcc tggccgcctg gctgctccct cctgcactcc 13200
tcactgtgca agaacagggc ttacctctag ttttgtttgc attttttggg gggggtgcct 13260
ctgtgttttt aatagtttat ctcctttata tactttgtat cttgaccaca gcctccctcc 13320
ttcctcgcct cccagtccca cccatacaaa tccttcccca ttgccctgtc ccctcctcct 13380
cagaggaggc gccctccccc cacccccacc ctggggcagg actaagcaca cttctcccac 13440
tgaggcccaa ctcggcagtc caggtagggg aaagggatcc aggggcaggg gctggaccta 13500
ggcctccaca ctgtaggaaa tgtacagttg gtcttcttgt gggctcccta acaagtgaag 13560
tggggggctg tcttgtttgc attttgtaca tctacagatg taaaaaccac aggaagaaga 13620
ggtgtggctt tggcaggcca tgtctttgtt ctgggtgctg gtccctgaga acagccagag 13680
ggctggcagt gccagcactg acatgtgtcc cgtctctgct tccttgcaga caatgtcccc 13740
aatgctgtct ggatctggga cattcaaaag ctgaagctgt ttgtggtact agagcatatg 13800
tctccagtgc gctcatttca gtgggaccca cagcagccga ggctggccat ctgcacagga 13860
ggaagcaagg tgtacctgtg gtccccagca ggctgcgtgt cggtgcaggt gcctggggaa 13920
ggtaagcgta agccagcaca tgctggcctc agacaggctg acctgcttaa acctattgcc 13980

-continued

```
acgtgtcatg catgggaaag atgcccttct gcatcctgta ggaccttgcc cagattgtgt  14040
gcctcacagg aactggctgt ccttaaggtt tactggcttt gtcttcagcc ctggggtgac  14100
cagactcctc actcacccgc aggcccggt ctctaaccct ctggctgcct gtctctctag  14160
gtgactttcc agtgctcgga ctgtgctggc acttaagtgg ggattccttg gccctcctta  14220
gtaaggacca cttctgtctc tgcttcctgg agaccaagga gagggttggc acagcctacg  14280
aacagcggga cggcatgcct aggacctgag tggaaaccaa ggcagtagac tgctgattcc  14340
aacgtgagct aacggctgca caggttctcc agatgggatg ggctattctg cccagttttc  14400
tgtaaatatg tataaagtta tgtaaagtag gtatttgcta atccattgaa cagtggtggt  14460
tgttttcttc aaggccttag ctcacagacc caaggtcttg ggaggataaa gaatcctgaa  14520
gtaaggactc aagcctgcct catggccttg cagactctga agccagtagc gaacccgagg  14580
atgggtgtag ggatgctggc tttcagctct aacagctact tcctggcatc aagaaatggt  14640
cagtgccaca ctcattcgta ggcagggtca gcattccctg aggggttttc tgtcagtggg  14700
ctttggaaca aggtggacta atgtcagact ggccagccct cctgcagctg gatgtactca  14760
gaagtgcccc gcacctgtgc ctgtccccgt gtgagctgta aatcccacaa cagttgggca  14820
ggtctctggc cttacaagtg aattctgcag agaggcctgg gtcactgcct ggtagagtgg  14880
aagagctcag cccacccaaa cctctctatc tctagtaagt gccttgaaag cagacagacc  14940
agtatgtctg tactggtgac cagggttccc accaggactg cacacttgtg tatctgagtt  15000
tctgtaaaga ggaccatgct cacaagggtc ctcagtcagc cagacttcag tcctcaagac  15060
agtctttggc actcctgatt ctgtgacaat aacttcaaaa aggagcaact ccatttggtt  15120
taaatgtctt tactagaaca aaagcacagg ctgaaaacag gtgcatctga ggtcaccttt  15180
cctcttggat aggccatggc attccggtca catccatgcc ggttaactaa agcgagaggt  15240
atagagtgac aggccagcat ctacagtgca ctggcaaggc tagaacgaca gcagcaagct  15300
gtgtgtggct ggcgtgtcaa agctcagcag tgctcagtga gctctaggat gctcgtctgt  15360
ttatagcatg cacttttaaa acccaactat tcagtccctt ttaaacagag acaggatgat  15420
agaaacccac caccatgact tccggaaggg gctagcttat gttatgagag taaccttttg  15480
ggcctaggaa aactgctgta ttaacacaac ctggattaat ttataaagtg tgattctaag  15540
tcagacacat tcacagaaag gcaggttcac caggagctgc caggcagact gtctttctta  15600
gtgactggct gctggctgct actgtattta gctttttttaa aaaacgggct gaattttaaa  15660
atacagcact tgagagttaa tatataggga gagttaaata tgtgcagaag ccgctcactg  15720
tactcagctg tatgcaacag tctacacagc acaagtgggt ggacattgtg ctcggcatgc  15780
tggagggaga acgtggcgtt acagaaggaa cacagtggta tgggggcagc tgaatctgcc  15840
tttgtaagat tgtgttgcca agatgtccaa tatccaacta aatatacata atccacttga  15900
ctattctaat cggatacatg ccctccttcc ctccagccag tgggtggcat gaggtggcac  15960
agggagtccc caccaccttg gtttccggga cgcagctgtc tagaagccta tcttgcccct  16020
ggtcatggag tagcccagct tggcttcatt gttgatgaag gacatgagcc ccacgtaggt  16080
ctcgatgagg agggggcgct ccagcaccag cacggtattc gcctgccctg gcagtgggct  16140
ctccttctgg gccttcttga cagcttggat caggagagcc ttgaagcttt ccaactttga  16200
agagaataaa catggagcct taacctcatg ccaagacagc agtactggga aacgaggatt  16260
ctgagttcaa atcctcccaa ataccacata gtgatgacat caccaatgac aggttgggcc  16320
```

-continued ctatgagctg tgtcatcagg tggttcatca tgtacaaaca tcatgaaggg acctgcctta 16380
agtccaacct agagagtacc agtctatctc taaagatgca gtcaggagat tcggcagcct 16440
gagacaaggt actgccagtg ccaacaggtg gaaaatcttt tttacagacg cacatgctct 16500
ggagtgcacc tcactaagca ggtgatgctg taattgcaca cgctgcctgc actggtgtgc 16560
tgtgcactga ctgacaggta gcatcacaga tggaggaatt catgaggact atgatgtcac 16620
caagtgacag ggctttctca gccctactct aactgtgcag aatgctcagc gctccctcag 16680
cacctctcct gggaacttcc agagtacctg tgtcaccagc agcacctgcc aagccccgcc 16740
agtactgtgg gcttttccca tgctcgctca cccacccagt ccagactgag catcctgcaa 16800
tgggatggtg actctgttct taaacagcac cacctagctt cctactgtgg aactgcacct 16860
ccagggttca cactgacagt ggccttggcc tgcttacatg gcacagagac gctgtcttct 16920
cgtccatgcc agccattggg tgttctatga aggtggcata gggcatgttt gtagaccagg 16980
ggttccatct gttgatgaag gaagggcggc tctgcttgtc ccactgaatg cgaaccccaa 17040
agccttctct cctgatgggg gagggggaga aagccttgct taccacagga atacaacatt 17100
gcattcagta tcagggatgg ctggggaacc tgtgacctag tgtaacaatg gcctccacta 17160
acagcttcac acacttccaa agcgtaacaa gttaatgagc ctcctttgca gcctatgaaa 17220
ccggcacaca gtccaacctg gcctaattat ggccgtgttt gttcttaatg ttactgaatg 17280
atgcttaagt tagtagccat tagcttcctg gagtccctag tcaaataatt cttttatagc 17340
aagccaacca gtctctgaag gctgttaggt gttttgcgat gtatcgaatt tttagtaata 17400
ctgagcacat gccctgtgtc tccctcctgc tggagttaaa actcccagac tccctacata 17460
gcttatgaca gtgggctctg attccatgta tcttaacggt atttaaatga atggttttta 17520
gtggggacag agtggccgac tgtgccagca tccctttcaa ggaggtactg agcaacccgg 17580
aaatcaccag cctctactta aaggtccttt ccactggttc ttcaagatga gacctttacc 17640
tcacaagaga gtgggtcaat accacttaca ggatccgctg gggccctgcc gtgtagtgcg 17700
ctggtgcacc tacttgttga gcgacttcgg aggaaactgg aattctccac aggagatggt 17760
gtctaccgcg ctgagcgcca ccctgaccac ctgctggcac tgaaggctga tgaagtcata 17820
tttgcagatg agcagcgact ggtcggtgac cagcaccagc cgctccttct cgttgttcca 17880
gtggtccacc ctggagagga gaggggccgc ccatcaccaa gagccccgcc tgcccccgcc 17940
cgcccccgcc cagtgtcccc gcagtcccct cgcgccggct tactcggtca gcagccacac 18000
cccctggatc tcgccgtcct ccacgggccg taccacggcg cggatctcct cgaccgcctg 18060
ctcgatggtg ccgggccgga acacgaagta ctccttgacg cgggcgcggc gtgtagggtc 18120
gtggacgttc agcggccaca acgtctggcg cagcggtgtg cccgccccag gccggcccgc 18180
acccgcgtcc tcgccggccg ccagcaccgc cgtggggctc gtgcccgccg agtccaccgt 18240
gtcccgcagc tgcagcatcg cgccgccacc ggcagcctcc accgacggcc gccgccccgg 18300
cgtccgcccg gccgcgcccc gccctccctc gttcgccttg tgattggttg agtcctgcag 18360
agcccgcctt ccggacccgc ctccagctcc gtcgactgcg tctcgcgatt ggctttcccc 18420
taagctgtct tctgcaattg ggtctaaagt gctgccgttc atgattacgg cggcccctcc 18480
tgggccggaa gctgccgcca cgcgcggagc cacttcctgt ttacaggaag ggcgagttaa 18540
aaaaaaaaaa aatgccggtc gggggttcct ggctgagaac ggggaaaggg acgccatgga 18600
ctcgcgcgga agggggcact tgggggctcg tgcgtagggc gttgccccga cagtgtgtcc 18660
tcgcttggct ccgtgccctt caccttcggg cttacggtgc acttcgggcg gaggtgtgcg 18720
gcgcacttag gaggtgtgca tgcctgggga gtgtgaaagt gtgggcatgg gtgtgtgcgc 18780
gtctgaggat tgtgaaagcg tgggaatggg tgtgtgcgcg tctgaggatt gtggacactg 18840
tgtcggggca cctcagatag aggcttctca ggagtgtgct gcactccttg ggcgtggtca 18900
ccttgggagt gtgggtttat agggtgtgtg cacactggag ataggagtgt gtgcaggtca 18960
gaggtggctg tcagagggtt ctttatattg ggcatgatac gcacaagtaa gctaccatgt 19020
caccgaagag tgctgctggg gcggggggtg gggggagttg gaaggaaacg ccgtaggatg 19080
ctcttgggcc ctgcagcttc tccctgggac agaagccatg cgagatgtcc ctgagttcct 19140
gctcccacgg gggtgccagc agtgtgcctg ggttgatgga gctaatggac cgctatgata 19200
gtgtggccca aaagtctttt ctaacagtca ccaagacata ggttagactc atcagtgaat 19260
gacagcccaa gatacagctc aggcctgtag tctgtctcct gaccgttgtg agggctcctt 19320
agcctgctgg accttttaca gtgtggcttc gtcagagaat ccagtccaat gaggtctccg 19380
ggacactggt gggagcagcc acgatgacgt gaattcccac agaggttcct gagaccgctg 19440
tggatgtgaa gagtgtgctg aaagctgaca gagaaagggg agatgaatag ataagtgcat 19500
ataaggcaat aagccaggga tggagaggtg gctcagcagt taagaacact ggctgcgccg 19560
ggcgtggtgg cgcacgcctt taatcccagc actcgggagg cagaggcagg cagatttctg 19620
agttccaggc cagcctggtc tacatagtga gttccaggac agccagggct acacagagaa 19680
accctgtctc gaaaaaaacc aaaaaaaaaa aaaaaaaaaa tcaaggaggc ttctaccttt 19740
agggctggta agatggctca gttggtaaga gcacccgact gctcttccga aggtccaaag 19800
ttcaaatccc agcaaccaca tggtggctca caaccacccg taatgagatc tgatgccctc 19860
ttctggtgca tctgaagaca gctacagtgt acttacatat aataaataaa taaataaatc 19920
tttaaaaaaa aaaacaaaaa acactggctg ctcttccaaa ggactggggt tcaatcccca 19980
gcacccacat ggcagctcac gactcttaac tccaggatcc aataccctta cacagactta 20040
tatgcagaca aaacaccaat gcacataaga ataatgttta ataacacaaa taagcaaatg 20100
tcaagtttgt ggcatgcatg aatcctaggt gtgagagaga aacatcatct atttctggct 20160
cagcctttct tatacaacac aggactacct tgccctaagg tggcaccaca tgaaatgggc 20220
agagcccccc cccccatatt actcaccaat taagaaaatg ttacagccgg gcgtggtggc 20280
acacgcctat aatcccagca ctcaggaggc agaggcaggt ggatttctga tactggcact 20340
tagagcctct cattcaaagg atcacggcta agcaggtgct ctgtatctgt ccggagcaga 20400
ggggacgagc agcaggtgtc cgctctgaaa cctggcttct acagaagtgt aaatccttta 20460
ctaccgtgag gagtctccag tatccacact gtgaataaac accattatat cttacgtgag 20520
gctgccagga cagaccacag actggcttgc tggaagtaac cgaagcatgt agtgaggttg 20580
ctgagaccag acggccagaa ccacagtgtg tgtgcatgtg cgcttgcatg tgcatgtatg 20640
tgtgtccttc tgatacctga gggcacatgt cttcctttgc ctttccagcc tcccgtgttg 20700
tcagccatgc tggatgtccc tcagcctgtg gctgcctctc cccgttggct gactttccat 20760
agtcatcgtc gctttctcat ttgtaaggat tcctgacgtt ggcacaggcc tgccctaacg 20820
gccccctttt gacctgatca tgttcacaga ctattttcca aagatggtga gagtcatgga 20880
gactggttgg gacttgcgtg tatcattaac aggtacataa ttcaactggt gtgtgtgtgg 20940
gggggggag ggtgtttcgg gcaggtgcaa gcgatgaagc atttagatga cctccacgtg 21000
tgcacacagg tcacggcggg ggcaaggagc aagacatgat gactgtgact agggagtaag 21060
gtattggggg cccagagctt gggttggtcc tgaggtccac tagccgttgc cagggatttt 21120
caagaggctg ttcccaaagt ggtcagcaga tggcgcaact acccacacat ggcctccctg 21180
ggagatcaca gtttggcagg tatgggatgt tttcaagtcc tagatgaagc tgttatcttt 21240
ctgtagaaga ctcagaagct cagctataac aagcagattc ttgccttaat ttcctgatgc 21300
tgtgacttag cattttggga actcagcggg ccctcctttt tgaagtgctg agaatggatc 21360
ccaggcctcc cacatgctct gccacttgag atgcttcctc taagactgag ccccaccttt 21420
gatacctgtg agaatcctga gcacgctggg gtgggttctc agagctgcat ggggctcctc 21480
cagagctggt accacacaca cacacacaca cacacacgga ggattgttgt gtgtgtggtc 21540
cttccagagc cagctgcact ttgggtcgtg cacagggtgt gcaccgctgg aagtttgcct 21600
caggaggcaa tcctcgcact gccccaagct ctgcgattgt tgtgcttccc atgttaacct 21660
cggtcactga gtcaaagaat ccacaacaga tgcagaggta actttgaaag agaaccgggt 21720
tcccagactg gagaggtggc tcagcaggca aaggtctttg ctgccaccct gatgaccaga 21780
gttcaattcc tgggtcccac acagtggaag gagagaagaa actcatgtag attgtccttt 21840
gacctccaca cactctgaga catacgtata tacacacatg agttaaatgc acacacagac 21900
gggactagag aaagagcaca gctcctacca cccagcccca tcttggcagt tgtctccctg 21960
atgtcccctc tcacatctcc ctctctgttc tcctacaggg acccattctg ataatccaga 22020
atgatctgat ctgagacccc ctctctcagt aacttcacca aagaccccgt ttccaaatca 22080
ggccccacgg ggggatgtgg gcatgaggac atgggctttc ctagggaagc tatgcaattc 22140
agatgtgcca tctccccaga tgtgaacaga taccatccct gcttgcagtg atgggtaaat 22200
atcccataca cttgccatcc caggccttcc tccctgaccc ccctgtggta aagggtagat 22260
atacagtgat gggtggaggc ctgggatggg ccaggccagg cctatgctgg gaaaccacat 22320
ggtggctgga cggcagtctg ctgtgtagcg ttatatcggc ttgatactgg ctagagtcat 22380
tggggaaacc tcagttgaga aaatagcccc caccagacag gcctgtgggc aaacttatgt 22440
aacattttct tttcttttct tttcttttat ttatttattt atttatttat tttggttttt 22500
cgagacagtg tttctctgta tagccctggc tgtcctggaa ctcactctgt agaccaggct 22560
ggcctcgaac tcagaaatcc gcctgcctct gcctcctgag tgctgggatt ataggcgtgt 22620
gccaccacgc ccggctgtaa cattttctta attggtgagt aatatggggg gggggggctc 22680
tgcccatttc atgtggtgcc accttagggc aaggtagtcc tgtgttgtat aagaaaggct 22740
gagccagcct tgggaggtaa tgcagtggtg agcagaatct ctctacggcc tctgcttcag 22800
ttcctgcctt caaattcctg cctcgagttc ctggcctgac ttccctcagt gatggactct 22860
gacctgagag ttgtaagaag aaataaatct ttcctcttct aatcactttc gatcatggtg 22920
tttcatcaca gcagtgaaaa cagaaactaa gacagtagct agatacccat tgaagctgga 22980
caggctggat gctcagttac tgagcaggag ccagcctcca gggacatagt taggtttcat 23040
gtcatgctca aggtcaggat agagtgagtg gtataggcca ggcagctggc cgccaacagg 23100
gccaagccta agccctgggc aaaatcctat gccctgaccc cgtagtgagc cttagcccat 23160
gtgagtcagc gtacttaggg gccttccatt ttggcttctc tctcacagca gggttggagc 23220
tttagaaatg gatgtgggaa tgggcgaacc acaggcttgt aaatggatcg tttgtcgttt 23280
agatggggca ttgcatgtgt gctttgctct ccagagacta tccccatctg tctcttgagt 23340
tttgccaaat tctgctcacc cctaatgatg ccatctgccc aaacaggtga ctgtggtcac 23400
cacactgcac ctgaggacct gatgatactt taggtgtctg tttctctttt gctttttgag 23460

-continued

```
agagagagtc ttaacatgtt gcacaggtca gcctccaaac tccgatcctt ctgcctcagc  23520
ctccttggtg gagtactggg atcaaagaca ggcgtggctc ttgggctgtg agccaacctt  23580
tggtatcact taggctagcc tctcacctgt tagaagctga catgaaaact cagacaaaac  23640
actagattgt cctcttggga tggtggcctt cggctcagca gctgatgtcc ctgtggctgc  23700
tggggtactt tgggtttctg tctggagggc tatctcttcc agctctgaga tgcgtcaggc  23760
tggagagcag gcagccagca tggttctggg aaaggaggga gcggtttgct ttggaaatta  23820
gcgctgtggt tcgagctctc ctcttcccca cattattttc cctccagcca aagacgattc  23880
taattatttc cagtagagaa tgagacaagg acagcgaaaa gtatcgtctg ctcggggaac  23940
aacggtgaag gccttaatcc atgccactgg gagagacagg cagagctctg tgaattcaag  24000
gctaaactgg tctctacagt gagcttgagc acagccaagg ctagtggagg tgtgggggga  24060
gtgcttttta ggaaaatgag agcagttgtt ctccaagtgt gaaaaaaatg gaactgcagc  24120
ctcgcctctt gtctccttgg gatgaactgc caagcaaagt ccaacccaga gtgtcatcag  24180
ggttgtgact cagtgacatt ttagcacact gctggtggaa gccacggcgg cagggtggac  24240
ggaggaaggg aaaatcctag gagatcctag gaggtgggtg ctgtagccac gggttctggc  24300
ctggtgtgaa taccactcaa ttcgtgaaaa ctcaggacta aataaataaa tatatgtgtg  24360
ggccaggcat ggtggcacat gcctttaatc tttagcattc aggagtcaga ggcaggtgga  24420
tcttttagtt caaggccaga atggtctaca gaaagagttc caaggcagcc agagctatat  24480
agagaaaccc tgtctcaaaa aacaaaaaca aaaaaacaac gaaatgtttg tgtgtggtgt  24540
attaatgttt tgctttaata aatatatttg tgtttcacat gatgctcaat gtccacagag  24600
gctcagaaga ggacattgga tccctaggaa ttagagttac agagcattga gtgactggcc  24660
atgtgggtgc tgggaatcaa acccaggtcc tctaggagag cagtcagtgc tcttaaccac  24720
tgatttatct ttccagactc aagggcaaat tcgatcttta ccctgtgaat gggatgatca  24780
gaccctaaag tggaatgtga cacgtgacct attttcaata aaggatagaa ctgatggccc  24840
accctcctcc tgaagccagc actgtggttc gtcaatatgc ccaagcccac aagagggcgc  24900
catgccaaca gtccagttcc tgcagatatc ctgaggttct tgacagcaca tttaaggcag  24960
ttgcagctaa attccaaagt aactaaaagg aactggatag attaacctct aaattaattt  25020
ggaacaatga ccaagaattg ccattataag accaacaaga ttcctcggca ggtaaaagtg  25080
actgttgaca agcctaatga cctgggtttg acccccgtgg cacacatcat agaggaaaag  25140
gaccagttcc atcaagttgt cctctgatcc ctacacgtgc acagcggcac atgtgatacc  25200
caataaatga atgagtctaa taaaaaaatt taaaagtatc tgcagggaaa accaagtaac  25260
ggatttctca gacctatgga tacagctatg taaagccaat acccagagtt atatcaggaa  25320
ggtctcagtg gccagctctt gctctgtctt gttccagcaa ggaaggacaa ctgacacaac  25380
aattctagat gcagtcattg gaaacaccca gaagcgggtg ctgcatgtgt tgagctagga  25440
gagaatatga tatcagtagt atcctggtga ccagctagcc attcgtcctc tccctgaatg  25500
gcagacaggg atggactccg agtgagaaaa tacacacaac agattgaaca acagagcaag  25560
cagccacctt cctgagccaa gtgccttatg cattttcaca ggcatgttta catgaggaca  25620
ttatcatgca agtacttgat gaacccggag tgcgctctcc ccctcgactc gcccctgcac  25680
ttatttctga gtgatgggga gacaagccga gtgcacacct cgtggaattg agccgccctg  25740
ttgaccatgt tgtgactgtc actccagccc gtgagacaat ttgaaataat catgtccaac  25800
```

cagctgtcgt aatttgttag ctgtaaagtt gcaatatgct tgctgtgagt tacagaactg 25860
tattaaatac attgtcattt gattcctagt tt 25892

<210> SEQ ID NO 12
<211> LENGTH: 279
<212> TYPE: DNA
<213> ORGANISM: Mus musculus

<400> SEQUENCE: 12
atggagagag cagacataca tctccggtgc aggtaccctg ctcagaccaa gccggagcca 60
gcctactggc agcccattct ctccggcaaa gctagacaca atatgagcaa ttgctgcgat 120
ttctccataa gtgctcttgt ttcccctaat aattcacgtt tcatctccac aataaacatt 180
gttagaactc ttctctgggc tttaaatata cataattgct ccccgtgcca gtaaaaggta 240
ttaattccat ttatgcattc cataaacttt taggataac 279

<210> SEQ ID NO 13
<211> LENGTH: 1982
<212> TYPE: DNA
<213> ORGANISM: homo sapien

<400> SEQUENCE: 13
gtcccggctc cgcgggttcc gtgggtcgcc cgcgaaatct gatccgggat gcggcggccc 60
aatcggaagg tggaccgaaa tcccgcgaca gcaagaggcc cgtagcgacc cgcggtgcta 120
aggaacacag tgctttcaaa agaattggcg tccgctgttc gcctctcctc ccgggagtct 180
tctgcctact cccagaagag gagggaagca caggtgggtt tctttagctc tgcgtcggat 240
ccctgagaac ttcgaagcca tcctggctga ggctaatctc cgctgtgctt cctctgcagt 300
atgaagactt tggagactca accgttagct ccggactgct gtccttcaga ccaggaccca 360
gctccagccc atccttctcc ccacgcttcc ccgatgaata aaaatgcgga ctctgaactg 420
atgccaccgc ctcccgaaag gggggatccg ccccggttgt ccccagatcc tgtggctggc 480
tcagctgtgt cccaggagct acgggagggg gacccagttt ctctctccac tcccctggaa 540
acagagtttg gttcccctag tgagttgagt cctcgaatcg aggagcaaga actttctgaa 600
aatacaagcc ttcctgcaga agaagcaaac gggagccttt ctgaagaaga agcgaacggg 660
ccagagttgg ggtctggaaa agccatggaa gatacctctg ggaacccgc tgcagaggac 720 gagggagaca ccgcttggaa ctacagcttc tcccagctgc ctcgatttct cagtggttcc 780
tggtcagagt tcagcaccca acctgagaac ttcttgaaag gctgtaagtg ggctcctgac 840
ggttcctgca tcttgaccaa tagtgctgat aacatcttgc gaatttataa cctgcccca 900 gagctgtacc atgaggggga gcaggtggaa tatgcagaaa tggtccctgt ccttcgaatg 960
gtggaaggtg ataccatcta tgattactgc tggtattctc tgatgtcctc agcccagcca 1020
gacacctcct acgtggccag cagcagccgg gagaacccga ttcatatctg ggacgcattc 1080
actggagagc tccgggcttc ctttcgcgcc tacaaccacc tggatgagct gacggcagcc 1140
cattcgctct gcttctcccc ggatggctcc cagctcttct gtggcttcaa ccggactgtg 1200
cgtgtttttt ccacggcccg gcctggccga gactgcgagg tccgagccac atttgcaaaa 1260
aagcagggcc agagcggcat catctcctgc atagccttca gcccagccca gcccctctat 1320
gcctgtggct cctacggccg ctccctgggt ctgtatgcct gggatgatgg ctcccctctc 1380
gccttgctgg gagggcacca agggggcatc acccacctct gctttcatcc cgatggcaac 1440
cgcttcttct caggagcccg caaggatgct gagctcctgt gctgggatct ccggcagtct 1500
ggttacccac tgtggtccct gggtcgagag gtgaccacca atcagcgcat ctacttcgat 1560
ctggacccga ccgggcagtt cctagtgagt ggcagcacga gcggggctgt ctctgtgtgg 1620
gacacggacg ggcctggcaa tgatgggaag ccggagcccg tgttgagttt tctgccccag 1680
aaggactgca ccaatggcgt gagcctgcac cctagcctgc ctctcctggc cactgcctcc 1740
ggtcagcgtg tgtttcctga gcccacagag agtggggacg aaggagagga gctgggcctt 1800
cccttgctct ccacgcgcca cgtccacctt gaatgtcggc ttcagctctg gtggtgtggg 1860
ggggcgccag actccagcat ccctgatgat caccagggcg agaaagggca gggaggaacg 1920
gagggaggtg tgggtgagct gatataaaaa ggtttttatg ataaaaaaaa aaaaaaaaaa 1980
aa 1982

<210> SEQ ID NO 14
<211> LENGTH: 789
<212> TYPE: DNA
<213> ORGANISM: homo sapiens
<220> FEATURE:
<221> NAME/KEY: misc_feature
<222> LOCATION: (9)..(9)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (30)..(30)
<223> OTHER INFORMATION: n is a, c, g, t or u

<400> SEQUENCE: 14
taaacgggna aagatgcctt nctttttaan cctaattgaa ttttaaatgt ccttttgaca 60
caaaaaggta tatacatgac acagctacac aacctttttt caactggaca acaagtgtca 120
aaaccctgtg gatgtatagg gtaaaacaag attggtcagg aaaagagaat tgttcctata 180
actggtaatc tgacacaatg tcctattgcc attaaaaaaa aaaggtccat tttcagttta 240
ttcaagttta ttttcatggt gttttatccc tcttgataaa aaaaaattca gacttttgta 300
atttgtgtat gctgatcttc atcaaaaggt tcattctctg gatcagagtc agtggtgtca 360
gaatatctat aatgatcagg ttcattgtca ctaacatctg ttgttacaga agtttaactt 420
gctagcctcc ggatttgacg gctcctctac tgcctttgag aagtacagtt tcaccttaaa 480
ttttggagaa aacgttcacg ttgactttgt ctttattttc ttacggcaag acaatttttt 540
gttataagta agttcctata cttcccttgc atttatttta caccctccta tatctgtcaa 600
tctttatcta tttttttgtt taacaataaa cccactaatt tccctacttt ttcttccaac 660
gttatccacc tatcacctgg atcataaata atgtttttct tccccataag ttcaaaactt 720
tttccccctc tttttttcca cccctctttt tgattcttcg caataaacct ttatttgttt 780
tctccccac 789

<210> SEQ ID NO 15
<211> LENGTH: 467
<212> TYPE: DNA
<213> ORGANISM: homo sapiens

<400> SEQUENCE: 15
aagaaatggc atatttgaag aaatcatatg gctagacaaa acaaactaga tagattgtga 60
agctagatag actaaacctc agtcttgatt actaattaca agctgaatgt ataaatcttt 120

```
tccttcagag gcataaaggt aagagttatg aatcaaatgg aaggaccaaa atgcttccca      180

atgaagtatt ttcttggtga agttattgca atctaaggtc tgaaaatcag ctgtacagga      240

actttatcag taacctaaaa gatgatcaat cagcctcagt gactaacgac actgagaaga      300

gaccaacgta aaaactagca caccagatta atttaccaca aagatattct caccataatc      360

agaaaacctg ccctctattc agagtattca ctcttttttg gtatgagtac taatctggct      420

gggtcgaatt agtgcttagt tgaatacaga attaaaataa tgtgaag                    467
```

```
<210> SEQ ID NO 16
<211> LENGTH: 21
<212> TYPE: DNA
<213> ORGANISM: artificial
<220> FEATURE:
<223> OTHER INFORMATION: targets natural antisense

<400> SEQUENCE: 16

gcctccttat acaccactat c                                                 21

<210> SEQ ID NO 17
<211> LENGTH: 20
<212> TYPE: DNA
<213> ORGANISM: artificial
<220> FEATURE:
<223> OTHER INFORMATION: targets natural antisense

<400> SEQUENCE: 17

gtgctggatc tggtctaggc                                                   20

<210> SEQ ID NO 18
<211> LENGTH: 19
<212> TYPE: DNA
<213> ORGANISM: artificial
<220> FEATURE:
<223> OTHER INFORMATION: targets natural antisense

<400> SEQUENCE: 18

accactgcct ctgtctcca                                                    19

<210> SEQ ID NO 19
<211> LENGTH: 27
<212> TYPE: DNA
<213> ORGANISM: artificial
<220> FEATURE:
<223> OTHER INFORMATION: targets natural antisense

<400> SEQUENCE: 19

cugcucuggc uguggucagu gccucgg                                           27

<210> SEQ ID NO 20
<211> LENGTH: 27
<212> TYPE: DNA
<213> ORGANISM: artificial
<220> FEATURE:
<223> OTHER INFORMATION: targerts natural antisense

<400> SEQUENCE: 20

auucccuucc auaggcauga gacuguu                                           27

<210> SEQ ID NO 21
<211> LENGTH: 27
<212> TYPE: DNA
<213> ORGANISM: artificial
<220> FEATURE:
<223> OTHER INFORMATION: targets natural antisense
```

-continued

<400> SEQUENCE: 21
ccaagcugcu ggaagcaugu acuggug 27

<210> SEQ ID NO 22
<211> LENGTH: 27
<212> TYPE: DNA
<213> ORGANISM: artificial
<220> FEATURE:
<223> OTHER INFORMATION: targets natural antisense

<400> SEQUENCE: 22
agacggucuc auagguggaa uuugcug 27

<210> SEQ ID NO 23
<211> LENGTH: 21
<212> TYPE: DNA
<213> ORGANISM: artificial
<220> FEATURE:
<223> OTHER INFORMATION: targets natural antisense

<400> SEQUENCE: 23
gatgtatgtc tgctctctcc a 21

<210> SEQ ID NO 24
<211> LENGTH: 20
<212> TYPE: DNA
<213> ORGANISM: artificial
<220> FEATURE:
<223> OTHER INFORMATION: targets natural antisense

<400> SEQUENCE: 24
ggcttggtct gagcagggta 20

<210> SEQ ID NO 25
<211> LENGTH: 21
<212> TYPE: DNA
<213> ORGANISM: artificial
<220> FEATURE:
<223> OTHER INFORMATION: targets natural antisense

<400> SEQUENCE: 25
cctgcaccgg agatgtatgt c 21

<210> SEQ ID NO 26
<211> LENGTH: 21
<212> TYPE: DNA
<213> ORGANISM: artificial
<220> FEATURE:
<223> OTHER INFORMATION: targets natural antisense

<400> SEQUENCE: 26
ccggagatgt atgtctgctc t 21

<210> SEQ ID NO 27
<211> LENGTH: 21
<212> TYPE: DNA
<213> ORGANISM: artificial
<220> FEATURE:
<223> OTHER INFORMATION: targets natural antisense

<400> SEQUENCE: 27
gcccaccacc tcattattcc c 21

<210> SEQ ID NO 28

<211> LENGTH: 20
<212> TYPE: DNA
<213> ORGANISM: artificial
<220> FEATURE:
<223> OTHER INFORMATION: targets natural antisense

<400> SEQUENCE: 28
ccagtcccaa gtccagcaga 20

<210> SEQ ID NO 29
<211> LENGTH: 20
<212> TYPE: DNA
<213> ORGANISM: artificial
<220> FEATURE:
<223> OTHER INFORMATION: targets natural antisense

<400> SEQUENCE: 29
gcctccgtga actcctcctt 20

<210> SEQ ID NO 30
<211> LENGTH: 20
<212> TYPE: DNA
<213> ORGANISM: artificial
<220> FEATURE:
<223> OTHER INFORMATION: targets natural antisense

<400> SEQUENCE: 30
gttccgccca ccacctcatt 20

<210> SEQ ID NO 31
<211> LENGTH: 21
<212> TYPE: DNA
<213> ORGANISM: artificial
<220> FEATURE:
<223> OTHER INFORMATION: targets natural antisense

<400> SEQUENCE: 31
ggagcaagaa cuuucugaat t 21

<210> SEQ ID NO 32
<211> LENGTH: 21
<212> TYPE: DNA
<213> ORGANISM: artificial
<220> FEATURE:
<223> OTHER INFORMATION: targets natural antisense

<400> SEQUENCE: 32
ccaaucagcg caucuacuut t 21

<210> SEQ ID NO 33
<211> LENGTH: 21
<212> TYPE: DNA
<213> ORGANISM: artificial
<220> FEATURE:
<223> OTHER INFORMATION: targets natural antisense

<400> SEQUENCE: 33
ccaccaauca gcgcaucuat t 21

<210> SEQ ID NO 34
<211> LENGTH: 27
<212> TYPE: DNA
<213> ORGANISM: artificial
<220> FEATURE:
<223> OTHER INFORMATION: targets natural antisense

<400> SEQUENCE: 34
uucauaacuc uuaccuuuau gccucug 27

<210> SEQ ID NO 35
<211> LENGTH: 27
<212> TYPE: DNA
<213> ORGANISM: artificial
<220> FEATURE:
<223> OTHER INFORMATION: targets natural antisense

<400> SEQUENCE: 35
auucugacac cacugacucu gauccag 27

<210> SEQ ID NO 36
<211> LENGTH: 27
<212> TYPE: DNA
<213> ORGANISM: artificial
<220> FEATURE:
<223> OTHER INFORMATION: targets natural antisense

<400> SEQUENCE: 36
auuaccaguu auaggaacaa uucucuu 27

<210> SEQ ID NO 37
<211> LENGTH: 25
<212> TYPE: DNA
<213> ORGANISM: artificial
<220> FEATURE:
<223> OTHER INFORMATION: targets natural antisense

<400> SEQUENCE: 37
gaggcacuga ccacagccag agcag 25

<210> SEQ ID NO 38
<211> LENGTH: 25
<212> TYPE: DNA
<213> ORGANISM: artificial
<220> FEATURE:
<223> OTHER INFORMATION: targets natural antisense

<400> SEQUENCE: 38
cagucucaug ccuauggaag ggaat 25

<210> SEQ ID NO 39
<211> LENGTH: 25
<212> TYPE: DNA
<213> ORGANISM: artificial
<220> FEATURE:
<223> OTHER INFORMATION: targets natural antisense

<400> SEQUENCE: 39
ccaguacaug cuuccagcag cuugg 25

<210> SEQ ID NO 40
<211> LENGTH: 25
<212> TYPE: DNA
<213> ORGANISM: artificial
<220> FEATURE:
<223> OTHER INFORMATION: targets natural antisense

<400> SEQUENCE: 40
gcaaauucca ccuaugagac cguct 25

<210> SEQ ID NO 41
<211> LENGTH: 21
<212> TYPE: DNA

<213> ORGANISM: artificial
<220> FEATURE:
<223> OTHER INFORMATION: targets natural antisense

<400> SEQUENCE: 41
acctctggag ctctctggaa c 21

<210> SEQ ID NO 42
<211> LENGTH: 25
<212> TYPE: DNA
<213> ORGANISM: artificial
<220> FEATURE:
<223> OTHER INFORMATION: targets natural antisense

<400> SEQUENCE: 42
tatgatggaa aggtgcgcat cctta 25

<210> SEQ ID NO 43
<211> LENGTH: 25
<212> TYPE: DNA
<213> ORGANISM: artificial
<220> FEATURE:
<223> OTHER INFORMATION: targets natural antisense

<400> SEQUENCE: 43
cttccctgga ttggcagcca gactg 25

<210> SEQ ID NO 44
<211> LENGTH: 25
<212> TYPE: DNA
<213> ORGANISM: artificial
<220> FEATURE:
<223> OTHER INFORMATION: targets natural antisense

<400> SEQUENCE: 44
atatgcagaa atggtccctg tcctt 25

<210> SEQ ID NO 45
<211> LENGTH: 25
<212> TYPE: DNA
<213> ORGANISM: artificial
<220> FEATURE:
<223> OTHER INFORMATION: targets natural antisense

<400> SEQUENCE: 45
gaggcauaaa gguaagaguu augaa 25

<210> SEQ ID NO 46
<211> LENGTH: 25
<212> TYPE: DNA
<213> ORGANISM: artificial
<220> FEATURE:
<223> OTHER INFORMATION: targets natural antisense

<400> SEQUENCE: 46
ggaucagagu caguggugu agaat 25

<210> SEQ ID NO 47
<211> LENGTH: 25
<212> TYPE: DNA
<213> ORGANISM: artificial

-continued

```
<220> FEATURE:
<223> OTHER INFORMATION: targets natural antisense

<400> SEQUENCE: 47

gagaauuguu ccuauaacug guaat                                   25
```